United States Patent
Wagner et al.

(10) Patent No.: US 9,006,387 B2
(45) Date of Patent: Apr. 14, 2015

(54) ANTI-VIRAL COMPOUNDS

(71) Applicant: AbbVie, Inc., North Chicago, IL (US)

(72) Inventors: Rolf Wagner, Antioch, IL (US); John K. Pratt, Kenosha, IL (US); Dachun Liu, Waukegan, IL (US); Michael D. Tufano, Chicago, IL (US); David A. DeGoey, Salem, WI (US); Warren M. Kati, Gurnee, IL (US); Charles W. Hutchins, Green Oaks, IL (US); Pamela L. Donner, Mundelein, IL (US); John T. Randolph, Libertyville, IL (US); Christopher E. Motter, Oak Creek, IL (US); Lissa T. Nelson, Highland Park, IL (US); Sachin V. Patel, Round Lake, IL (US); Mark A. Matulenko, Libertyville, IL (US); Ryan G. Keddy, Beach Park, IL (US); Tammie K. Jinkerson, Pleasant Prairie, WI (US); Todd W. Rockway, Grayslake, IL (US); Clarence J. Maring, Palatine, IL (US); Douglas K. Hutchinson, Antioch, IL (US); Charles A. Flentge, Salem, WI (US); David A. Betebenner, Libertyville, IL (US); Kathy Sarris, Mundelein, IL (US); Kevin R. Woller, Antioch, IL (US); Seble H. Wagaw, Evanston, IL (US); Jean C. Califano, Whitefish Bay, WI (US); Wenke Li, Gurnee, IL (US); Daniel D. Caspi, Evanston, IL (US); Mary E. Bellizzi, North Chicago, IL (US); Yi Gao, Vernon Hills, IL (US); Allan C. Krueger, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/180,886

(22) Filed: Feb. 14, 2014

(65) Prior Publication Data

US 2014/0315792 A1    Oct. 23, 2014

Related U.S. Application Data

(62) Division of application No. 12/813,301, filed on Jun. 10, 2010, now Pat. No. 8,691,938.

(60) Provisional application No. 61/186,291, filed on Jun. 11, 2009, provisional application No. 61/242,836, filed on Sep. 16, 2009, provisional application No. 61/243,596, filed on Sep. 18, 2009.

(51) Int. Cl.
| | |
|---|---|
| *C07K 16/00* | (2006.01) |
| *A61K 38/00* | (2006.01) |
| *C07K 5/06* | (2006.01) |
| *C07D 401/14* | (2006.01) |
| *C07D 403/14* | (2006.01) |
| *C07D 417/14* | (2006.01) |
| *C07C 33/26* | (2006.01) |
| *C07C 205/19* | (2006.01) |

(52) U.S. Cl.
CPC ............ *C07K 5/06* (2013.01); *C07D 401/14* (2013.01); *C07D 403/14* (2013.01); *C07D 417/14* (2013.01); *C07C 33/26* (2013.01); *C07C 205/19* (2013.01)

(58) Field of Classification Search
None
See application file for complete search history.

(56) References Cited

U.S. PATENT DOCUMENTS

2004/0034189 A1* 2/2004 Cho et al. .............. 528/394

* cited by examiner

*Primary Examiner* — Thomas S Heard
*Assistant Examiner* — Jeanette Lieb
(74) *Attorney, Agent, or Firm* — Xu Zhang

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

9 Claims, No Drawings

ANTI-VIRAL COMPOUNDS

This application is a divisional of U.S. patent application Ser. No. 12/813,301 filed Jun. 10, 2010, which claims the benefit from U.S. Provisional Application Ser. No. 61/186,291 filed Jun. 11, 2009, U.S. Provisional Application Ser. No. 61/242,836 filed Sep. 16, 2009, and U.S. Provisional Application Ser. No. 61/243,596 filed Sep. 18, 2009; all of these applications are incorporated herein by reference in their entireties.

FIELD

The present invention relates to compounds effective in inhibiting replication of Hepatitis C virus ("HCV"). The present invention also relates to compositions comprising these compounds and methods of using these compounds to treat HCV infection.

BACKGROUND

HCV is an RNA virus belonging to the *Hepacivirus* genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY

The present invention features compounds of Formulae I, $I_A$, $I_B$, $I_C$ and $I_D$, and pharmaceutically acceptable salts thereof. These compounds and salts can inhibit the replication of HCV and therefore are useful for treating HCV infection.

The present invention also features compositions comprising the compounds or salts of the present invention. The compositions can also include additional therapeutic agents, such as HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features compounds having Formula I, and pharmaceutically acceptable salts thereof,

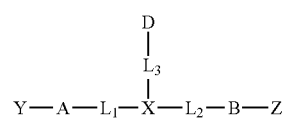

wherein:
  X is $C_3$-$C_{12}$carbocycle or 3- to 12-membered heterocycle, and is optionally substituted with one or more $R_4$;
  $L_1$ and $L_2$ are each independently selected from bond; or $C_1$-$C_6$alkylene, $C_2$-$C_6$alkenylene or $C_2$-$C_6$alkynylene, each of which is independently optionally substituted at each occurrence with one or more $R_L$;
  $L_3$ is bond or $L_S$-K-$L_S$'-, wherein K is selected from bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B$')—, —N($R_B$)SO$_2$N($R_B$')—, or —N($R_B$)S(O)N($R_B$')—;
  A and B are each independently $C_3$-$C_{12}$carbocycle or 3- to 12-membered heterocycle, and are each independently optionally substituted with one or more $R_4$;
  D is $C_3$-$C_{12}$carbocycle or 3- to 12-membered heterocycle, and is optionally substituted with one or more $R_4$; or D is hydrogen or $R_4$;
  Y is selected from -T'-C($R_1R_2$)N($R_S$)-T-$R_D$, -T'-C($R_3R_4$)C($R_6R_7$)-T-$R_D$, -$L_K$-T-$R_D$, or -$L_K$-E;
  $R_1$ and $R_2$ are each independently $R_C$, and $R_5$ is $R_B$; or $R_1$ is $R_C$, and $R_2$ and $R_5$, taken together with the atoms to which they are attached, form a 3- to 12-membered heterocycle which is optionally substituted with one or more $R_4$;
  $R_3$, $R_4$, $R_6$, and $R_7$ are each independently $R_C$; or $R_3$ and $R_6$ are each independently $R_C$, and $R_4$ and $R_7$, taken together with the atoms to which they are attached, form a 3- to 12-membered carbocycle or heterocycle which is optionally substituted with one or more $R_4$;
  Z is selected from -T'-C($R_8R_9$)N($R_{12}$)-T-$R_D$, -T'-C($R_{10}R_{11}$)C($R_{13}R_{14}$)-T-$R_D$, -$L_K$-T-$R_D$, or -$L_K$-E;
  $R_8$ and $R_9$ are each independently $R_C$, and $R_{12}$ is $R_B$; or $R_8$ is $R_C$, and $R_9$ and $R_{12}$, taken together with the atoms to which they are attached, form a 3- to 12-membered heterocycle which is optionally substituted with one or more $R_4$;

$R_{10}$, $R_{11}$, $R_{13}$, and $R_{14}$ are each independently $R_C$; or $R_{10}$ and $R_{13}$ are each independently $R_C$, and $R_{11}$ and $R_{14}$, taken together with the atoms to which they are attached, form a 3- to 12-membered carbocycle or heterocycle which is optionally substituted with one or more $R_A$;

T and T' are each independently selected at each occurrence from bond, $-L_S-$, $-L_S-M-L_S'-$, or $-L_S-M-L_S'-M'-L_S''-$, wherein M and M' are each independently selected at each occurrence from bond, $-O-$, $-S-$, $-N(R_B)-$, $-C(O)-$, $-S(O)_2-$, $-S(O)-$, $-OS(O)-$, $-OS(O)_2-$, $-S(O)_2O-$, $-S(O)O-$, $-C(O)O-$, $-OC(O)-$, $-OC(O)O-$, $-C(O)N(R_B)-$, $-N(R_B)C(O)-$, $-N(R_B)C(O)O-$, $-OC(O)N(R_B)-$, $-N(R_B)S(O)-$, $-N(R_B)S(O)_2-$, $-S(O)N(R_B)-$, $-S(O)_2N(R_B)-$, $-C(O)N(R_B)C(O)-$, $-N(R_B)C(O)N(R_B')-$, $-N(R_B)SO_2N(R_B')-$, $-N(R_B)S(O)N(R_B')-$, $C_3$-$C_{12}$carbocycle or 3- to 12-membered heterocycle, and wherein said $C_3$-$C_{12}$carbocycle and 3- to 12-membered heterocycle are each independently optionally substituted at each occurrence with one or more $R_A$;

$L_K$ is independently selected at each occurrence from bond, $-L_S-N(R_B)C(O)-L_S'-$ or $-L_S-C(O)N(R_B)-L_S'-$; or $C_1$-$C_6$alkylene, $C_2$-$C_6$alkenylene or $C_2$-$C_6$alkynylene, each of which is independently optionally substituted at each occurrence with one or more $R_L$; or $C_3$-$C_{12}$carbocycle or 3- to 12-membered heterocycle, each of which is independently optionally substituted at each occurrence with one or more $R_A$;

E is independently selected at each occurrence from $C_3$-$C_{12}$carbocycle or 3- to 12-membered heterocycle, and is independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or $-L_S-R_E$, wherein two adjacent $R_A$, taken together with the atoms to which they are attached and any atoms between the atoms to which they are attached, can optionally form carbocycle or heterocycle;

$R_B$ and $R_B'$ are each independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_B$ or $R_B'$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_C$ is independently selected at each occurrence from hydrogen, halogen, hydroxy, mercapto, amino, carboxy, nitro, oxo, phosphonoxy, phosphono, thioxo, formyl or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_C$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_E$ is independently selected at each occurrence from $-O-R_S$, $-S-R_S$, $-C(O)R_S$, $-OC(O)R_S$, $-C(O)OR_S$, $-N(R_SR_S')$, $-S(O)R_S$, $-SO_2R_S$, $-C(O)N(R_SR_S')$, $-N(R_S)C(O)R_S'$, $-N(R_S)C(O)N(R_S'R_S'')$, $-N(R_S)SO_2R_S'$, $-SO_2N(R_SR_S')$, $-N(R_S)SO_2N(R_S'R_S'')$, $-N(R_S)S(O)N(R_S'R_S'')$, $-OS(O)-R_S$, $-OS(O)_2-R_S$, $-S(O)_2OR_S$, $-S(O)OR_S$, $-OC(O)OR_S$, $-N(R_S)C(O)OR_S'$, $-OC(O)N(R_SR_S')$, $-N(R_S)S(O)-R_S'$, $-S(O)N(R_SR_S')$ or $-C(O)N(R_S)C(O)-R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_L$ is independently selected at each occurrence from halogen, nitro, oxo, phosphonoxy, phosphono, thioxo, cyano, $-O-R_S$, $-S-R_S$, $-C(O)R_S$, $-OC(O)R_S$, $-C(O)OR_S$, $-N(R_SR_S')$, $-S(O)R_S$, $-SO_2R_S$, $-C(O)N(R_SR_S')$ or $-N(R_S)C(O)R_S'$; or $C_3$-$C_6$carbocycle 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; wherein two adjacent $R_L$, taken together with the atoms to which they are attached and any atoms between the atoms to which they are attached, can optionally form carbocycle or heterocycle;

$L_S$, $L_S'$ and $L_S''$ are each independently selected at each occurrence from bond; or $C_1$-$C_6$alkylene, $C_2$-$C_6$alkenylene or $C_2$-$C_6$alkynylene, each of which is independently optionally substituted at each occurrence with one or more $R_L$; and $R_S$, $R_S'$ and $R_S''$ are each independently selected at each occurrence from hydrogen; $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_S$, $R_S'$ or $R_S'$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

A and B preferably are independently selected from $C_5$-$C_6$carbocycle (e.g., phenyl), 5- to 6-membered heterocycle (e.g., pyridinyl or thiazolyl), or 8- to 12-membered bicycles such as

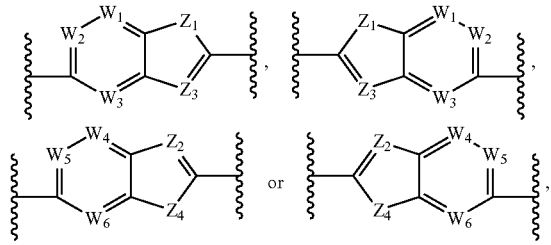

where $Z_1$ is independently selected at each occurrence from O, S, NH or $CH_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from $C_5$-$C_6$carbocycle, 5- to 6-membered heterocycle,

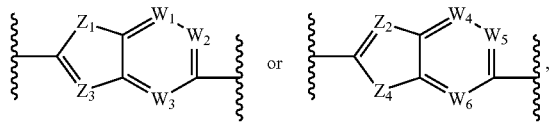

and is optionally substituted with one or more $R_A$; B is selected from $C_5$-$C_6$carbocycle, 5- to 6-membered heterocycle,

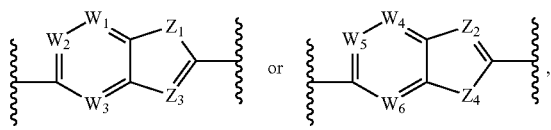

and is optionally substituted with one or more $R_A$; where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from phenyl (e.g., 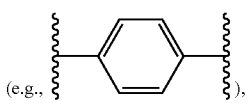), pyridinyl (e.g., ), thiazolyl

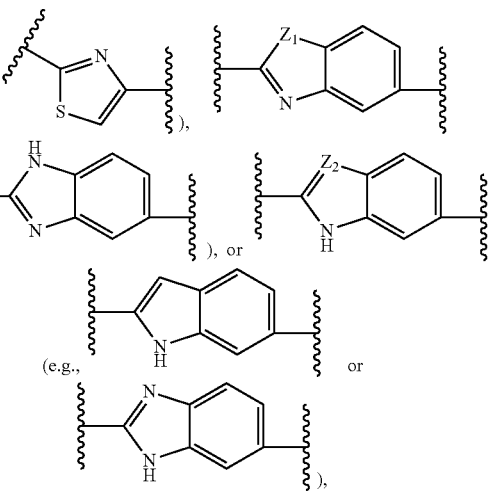

and is optionally substituted with one or more $R_A$; and B can be selected from phenyl (e.g., 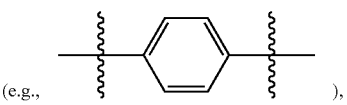 [SMILES: *c1ccc(*)cc1]), pyridinyl (e.g., 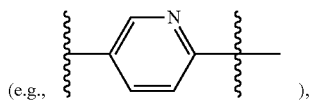), thiazolyl (e.g., 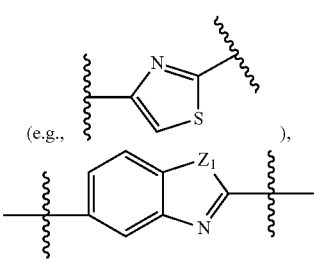

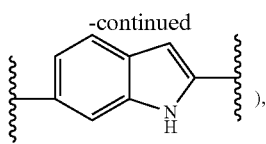

and is optionally substituted with one or more $R_A$. Highly preferably, both A and B are phenyl (e.g., both A and B are

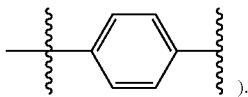 [SMILES: *c1ccc(*)cc1]

Also highly preferably, A is

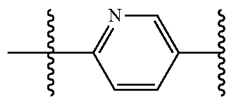

and B is

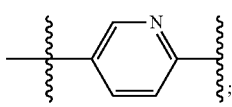

or A is

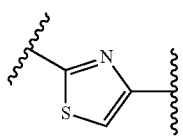 [SMILES: *c1csc(*)n1]

and B is

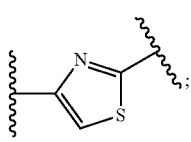 [SMILES: *c1csc(*)n1]

or A is

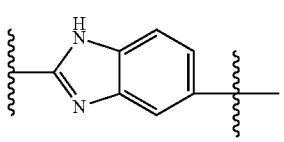 [SMILES: *c1ccc2[nH]c(*)nc2c1]

and B is

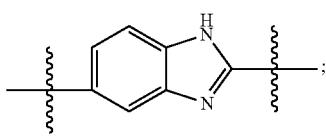 [SMILES: *c1ccc2[nH]c(*)nc2c1]

or A is

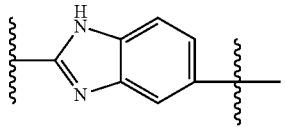 [SMILES: *c1ccc2[nH]c(*)nc2c1]

and B is

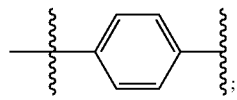

or A is

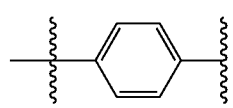

and B is

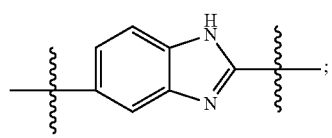

wherein each A and B is independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle (e.g., phenyl), 5- to 6-membered heterocycle (e.g., pyridinyl, pyrimidinyl, thiazolyl), or 6- to 12-membered bicycles (e.g., indanyl, 4,5,6,7-tetrahydrobenzo[d]thiazolyl, benzo[d]thiazolyl, indazolyl, benzo[d][1,3]dioxol-5-yl), and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

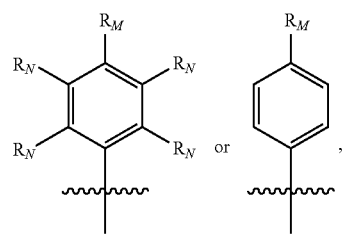

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

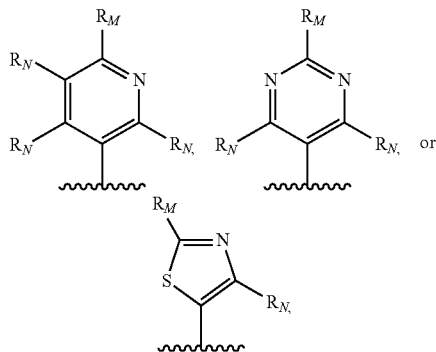

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

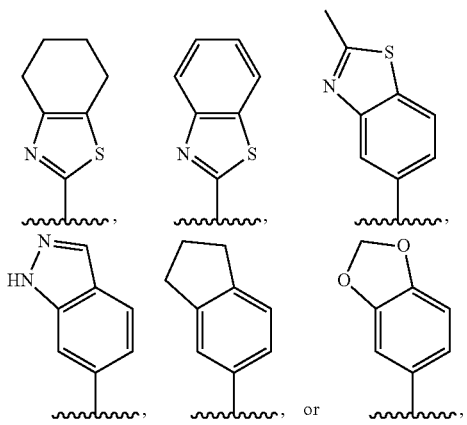

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)O$C_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$ (e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

X preferably is $C_5$-$C_6$carbocycle, 5- to 6-membered heterocycle, or 6- to 12-membered bicycles, and is optionally substituted with one or more $R_A$. X can also be $C_5$-$C_6$carbocycle or 5- to 6-membered heterocycle which is optionally substituted with one or more $R_A$, wherein two adjacent $R_A$ on X, taken together with the ring atoms to which they are attached, optionally form a 5- to 6-membered carbocycle or heterocycle. Also preferably, X is

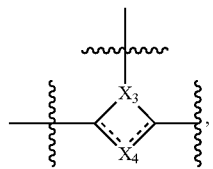

wherein $X_3$ is C(H) or preferably N and is directly appended to -$L_3$-D; $X_4$ is $C_2$-$C_4$alkylene, $C_2$-$C_4$alkenylene or $C_2$-$C_4$alkynylene, each of which optionally contains one or two heteroatoms selected from O, S or N; and X is optionally substituted with one or more $R_A$, and two adjacent $R_A$ on X, taken together with the ring atoms to which they are attached, can optionally form a 5- to 6-membered carbocycle or heterocycle. In addition, X can be

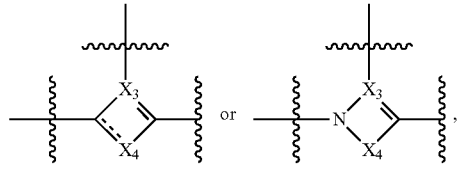

or wherein $X_3$ is C and is directly linked to -$L_3$-D, $X_4$ is $C_2$-$C_4$alkylene, $C_2$-$C_4$alkenylene or $C_2$-$C_4$alkynylene each of which optionally contains one or two heteroatoms selected from O, S or N, and X is optionally substituted with one or more $R_A$, and two adjacent $R_A$ on X, taken together with the ring atoms to which they are attached, optionally form a 5- to 6-membered carbocycle or heterocycle.

For instance, X can be

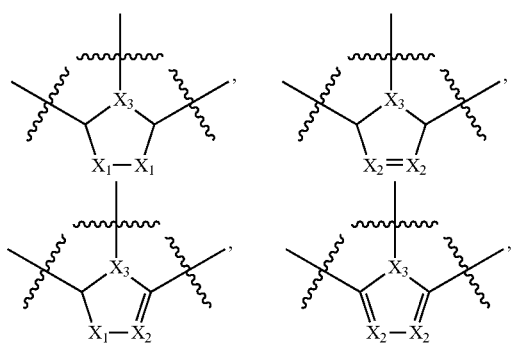

-continued

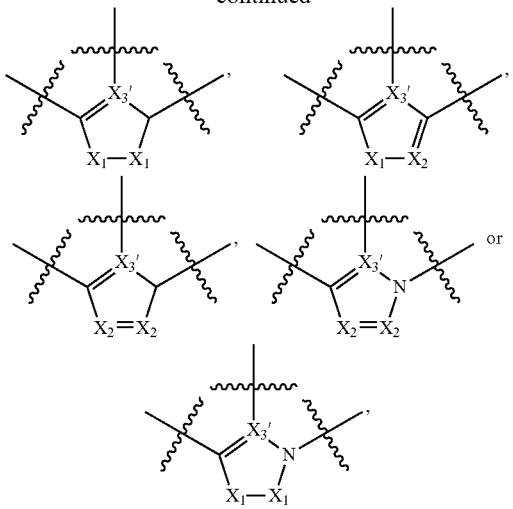

wherein $X_1$ is independently selected at each occurrence from $CH_2$, O, S or NH, $X_2$ is independently selected at each occurrence from CH or N, $X_3$ is N and is directly linked to -$L_3$-D, and $X_3'$ is C and is directly linked to -$L_3$-D; and X is optionally substituted with one or more $R_A$, and two adjacent $R_A$ on X, taken together with the ring atoms to which they are attached, optionally form a 5- to 6-membered carbocycle or heterocycle. For another example, X is

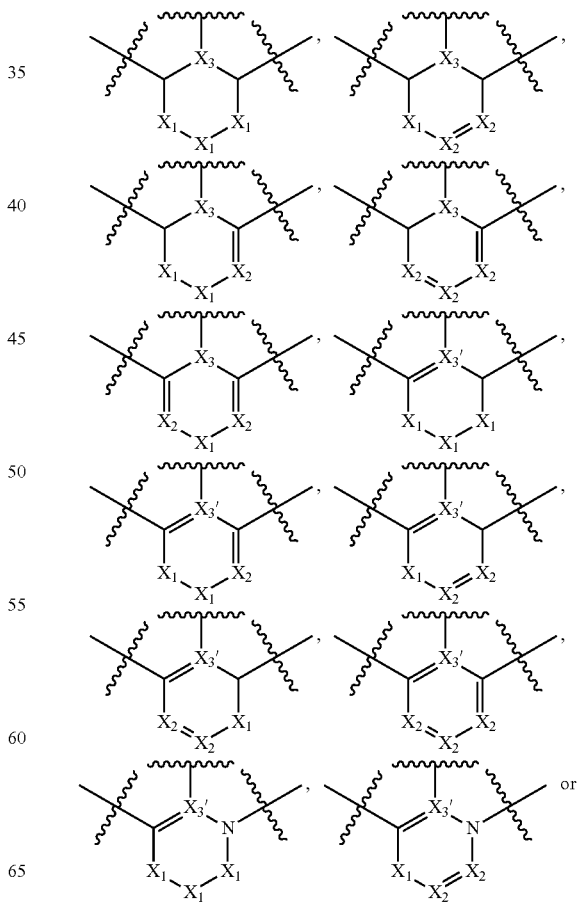

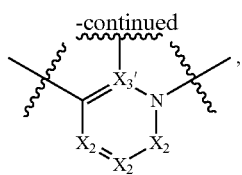

wherein $X_1$ is independently selected at each occurrence from $CH_2$, O, S or NH, $X_2$ is independently selected at each occurrence from CH or N, $X_3$ is N and is directly linked to -$L_3$-D, and $X_3'$ is C and is directly linked to -$L_3$-D; and wherein X is optionally substituted with one or more $R_A$, and two adjacent $R_A$ on X, taken together with the ring atoms to which they are attached, optionally form a 5- to 6-membered carbocycle or heterocycle.

Highly preferably, X is

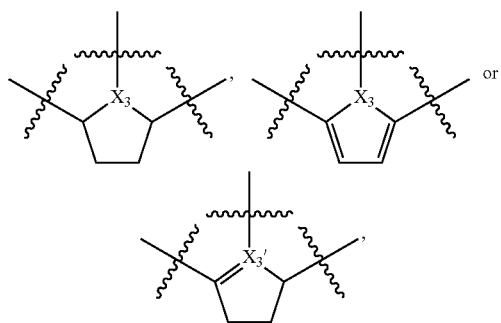

wherein $X_3$ is C(H) or N and is directly linked to -$L_3$-D, $X_3'$ is C and is directly linked to -$L_3$-D, and wherein X is optionally substituted with one or more $R_A$, and two adjacent $R_A$ on X, taken together with the ring atoms to which they are attached, optionally form a 5- to 6-membered carbocycle or heterocycle. More preferably, $X_3$ is N.

Non-limiting examples of X include:

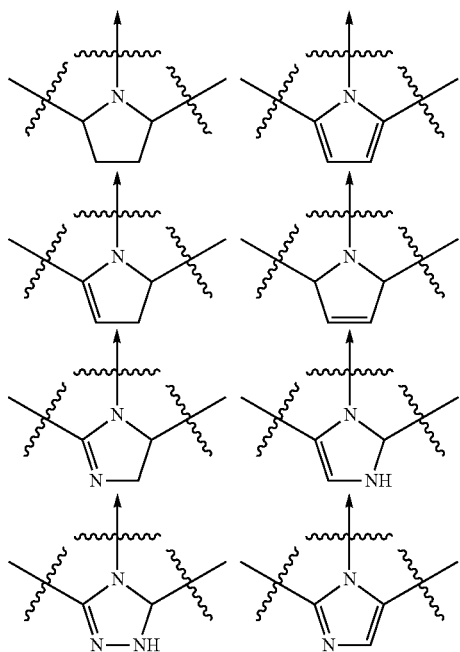

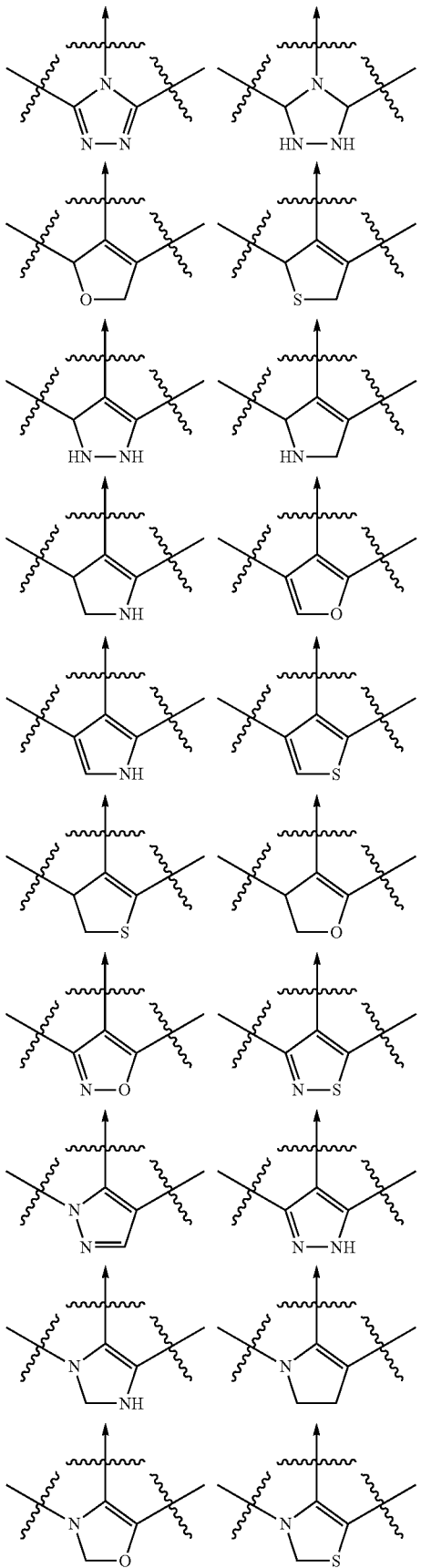

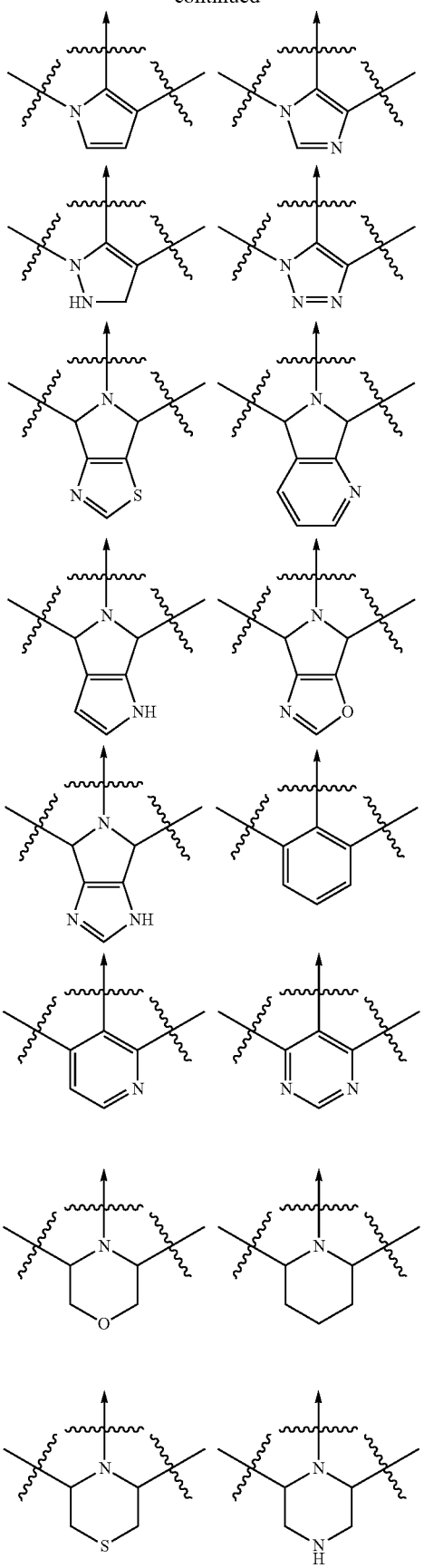

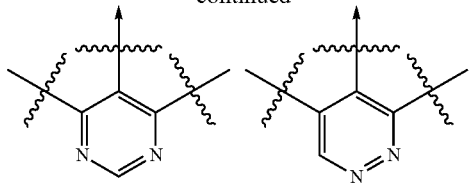

wherein "→" indicates the covalent attachment to -L₃-D. Each X can be optionally substituted with one or more $R_A$, and two adjacent $R_A$ on X, taken together with the ring atoms to which they are attached, optionally form a 5- to 6-membered carbocycle or heterocycle.

Non-limiting examples of preferred X include the following pyrrolidine rings, each of which is optionally substituted with one or more $R_A$:

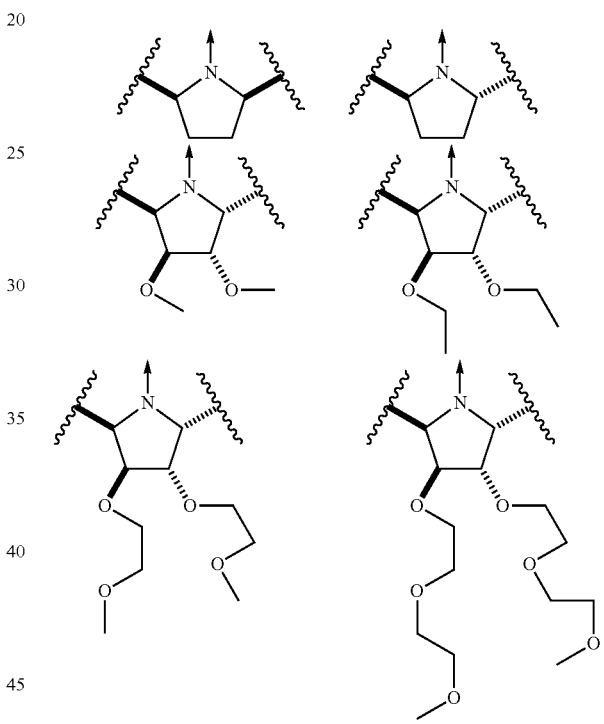

As shown, the relative stereochemistry at the 2- and 5-positions of the above pyrrolidine ring may be either cis or trans. The stereochemistries of optional substituents $R_A$ at the 3- or 4-positions of the pyrrolidine may vary relative to any substituent at any other position on the pyrrolidine ring. Depending on the particular substituents attached to the pyrrolidine, the stereochemistry at any carbon may be either (R) or (S).

Non-limiting examples of preferred X also include the following pyrrole, triazole or thiomorpholine rings, each of which is optionally substituted with one or more $R_A$:

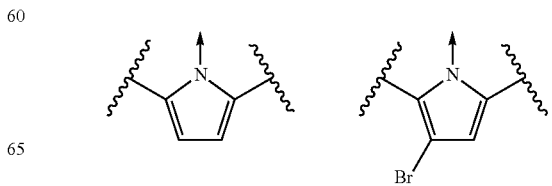

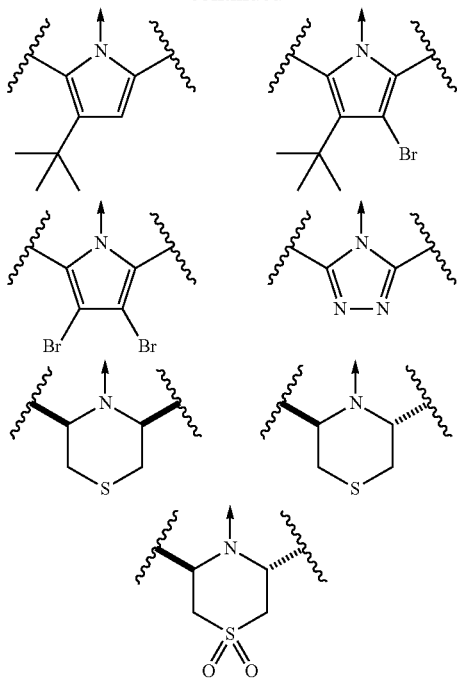

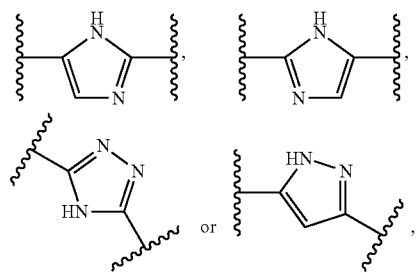

As shown, the relative stereochemistry at the 3- and 5-positions of the thiomorpholine ring may be either cis or trans. Depending on the particular substituents attached to the thiomorpholine, the stereochemistry at any carbon may be either (R) or (S).

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more $R_L$. Highly preferably, $L_1$, $L_2$ and $L_3$ are bond.

Y is preferably selected from -$L_S$-C($R_1R_2$)N($R_5$)-T-$R_D$, -$L_S$-C($R_3R_4$)C($R_6R_7$)-T-$R_D$, -G-C($R_1R_2$)N($R_5$)-T-$R_D$, -G-C($R_3R_4$)C($R_6R_7$)-T-$R_D$, —N($R_B$)C(O)C($R_1R_2$)N($R_5$)-T-$R_D$, —N($R_B$)C(O)C($R_3R_4$)C($R_6R_7$)-T-$R_D$, —C(O)N($R_B$)C($R_1R_2$)N($R_5$)-T-$R_D$, C(O)N($R_B$)C($R_3R_4$)C($R_6R_7$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

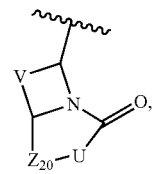

and is optionally substituted with one or more $R_A$ (e.g., one or more chloro or bromo). E preferably is a 7- to 12-membered bicycle (such as

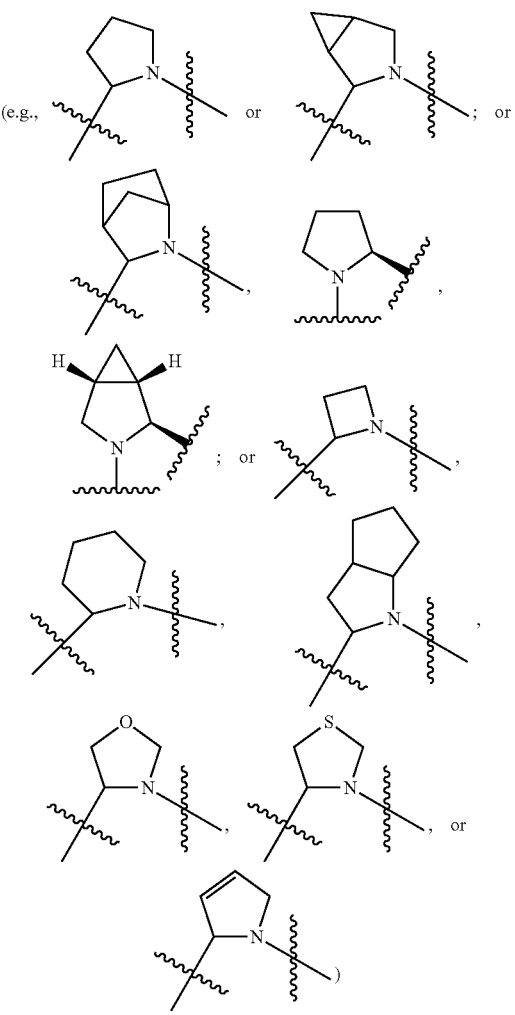

wherein U is independently selected at each occurrence from —(CH$_2$)— or —(NH)—; V and $Z_{20}$ are each independently selected from $C_1$-$C_4$alkylene, $C_2$-$C_4$alkenylene or $C_2$-$C_4$alkynylene, in which at least one carbon atom can be independently optionally replaced with O, S or N), and is optionally substituted with one or more $R_A$. More preferably, $R_1$ is $R_C$, and $R_2$ and $R_5$, taken together with the atoms to which they are attached, form a 5- to 6-membered heterocycle or 6- to 12-membered bicycle which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_3$ and $R_6$ are each independently $R_C$, and $R_4$ and $R_7$, taken together with the atoms to which they are attached, form a 5- to 6-membered carbocycle/heterocycle or 6- to 12-membered bicycle

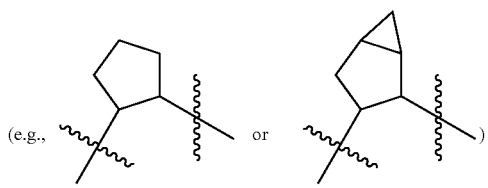 [SMILES: *C1CCCC1* ; *C1CC2CC2C1*]

(e.g., [structure] or [structure])

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Y can also be selected from -M-C($R_1R_2$)N($R_5$)—C(O)-$L_Y$'-M'-$R_D$, -M-C($R_1R_2$)N($R_5$)-$L_Y$'-M'-$R_D$, -$L_S$-C($R_1R_2$)N($R_5$)—C(O)-$L_Y$'-M'-$R_D$, -$L_S$-C($R_1R_2$)N($R_5$)-$L_Y$'-M'-$R_D$, -M-C($R_3R_4$)C($R_6R_7$)—C(O)-$L_Y$'-M'-$R_D$, -M-C($R_3R_4$)C($R_6R_7$)-$L_Y$'-M'-$R_D$, -$L_S$-C($R_3R_4$)C($R_6R_7$)—C(O)-$L_Y$'-M'-$R_D$, or -$L_S$-C($R_3R_4$)C(R)C($R_6R_7$)-$L_Y$'-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$')—, —N($R_B$)S(O)— or —N($R_B$)S(O)$_2$—, and $L_Y$' preferably is $C_1$-$C_6$alkylene which is optionally substituted with one or more $R_L$. $L_Y$', for example, is a $C_1$-$C_6$alkylene such as, but not limited to,

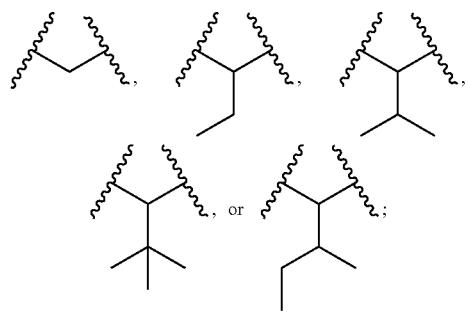

and the optional $R_L$ is a substituent such as, but not limited to phenyl, —SMe, or methoxy. Any stereochemistry at a carbon within the group $L_Y$' can be either (R) or (S). More preferably, $R_1$ is $R_C$, and $R_2$ and $R_5$, taken together with the atoms to which they are attached, form a 5- to 6-membered heterocycle or 6- to 12-membered bicycle

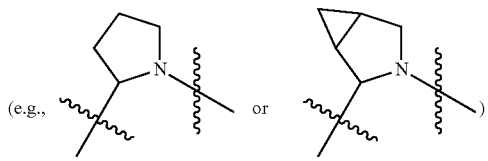 [SMILES: *C1CCCN1* ; *C1C2CC2CN1*]

which is optionally substituted with one or more $R_A$ (e.g., one or more hydroxy); and $R_3$ and $R_6$ are each independently $R_C$, and $R_4$ and $R_7$, taken together with the atoms to which they are attached, form a 5- to 6-membered carbocycle/heterocycle or 6- to 12-membered bicycle

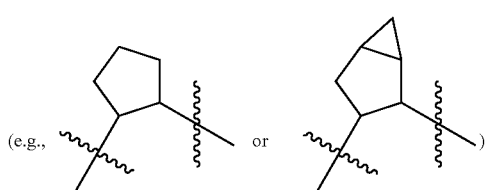 [SMILES: *C1CCCC1* ; *C1CC2CC2C1*]

or which is optionally substituted with one or more $R_A$.

Also preferably, Y is selected from —N($R_B$)CO—C($R_1R_2$)N($R_S$)—C(O)-$L_Y$'-N($R_B$)C(O)O—$R_D$, —N($R_B$)CO—C($R_1R_2$)N($R_S$)—C(O)-$L_Y$'-N($R_B$)C(O)—$R_D$, —N($R_B$)CO—C($R_1R_2$)N($R_S$)—C(O)-$L_Y$'-N($R_B$)S(O)$_2$—$R_D$, —N($R_B$)CO—C($R_1R_2$)N($R_S$)—C(O)-$L_Y$'-N($R_BR_B$')—$R_D$, —N($R_B$)CO—C($R_1R_2$)N($R_5$)—C(O)-$L_Y$'-O—$R_D$, —N($R_B$)CO—C($R_1R_2$)N($R_5$)—C(O)-$L_Y$'-$R_D$, —N($R_B$)CO—C($R_1R_2$)N($R_5$)—$R_D$, -$L_S$-C($R_1R_2$)N($R_5$)—C(O)-$L_Y$'-N($R_B$)C(O)O—$R_D$, -$L_S$-C($R_1R_2$)N($R_5$)—C(O)-$L_Y$'-N($R_B$)C(O)—$R_D$, -$L_S$-C($R_1R_2$)N($R_5$)—C(O)-$L_Y$'-N($R_B$)S(O)$_2$—$R_D$, -$L_S$-C($R_1R_2$)N($R_5$)—C(O)-$L_Y$'-N($R_BR_B$')—$R_D$, -$L_S$-C($R_1R_2$)N($R_5$)—C(O)-$L_Y$'-O—$R_D$, -$L_S$-C($R_1R_2$)N($R_5$)—C(O)-$L_Y$'-$R_D$, -$L_S$-C($R_1R_2$)N($R_5$)—$R_D$, —N($R_B$)CO—C($R_3R_4$)C($R_6R_7$)—C(O)-$L_Y$'-N($R_B$)C(O)O—$R_D$, —N($R_B$)CO—C($R_3R_4$)C($R_6R_7$)—C(O)-$L_Y$'-N($R_B$)C(O)—$R_D$, —N($R_B$)CO—C($R_3R_4$)C($R_6R_7$)—C(O)-$L_Y$'-N(R)S(O)$_2$—$R_D$, —N($R_B$)CO—C($R_3R_4$)C($R_6R_7$)—C(O)-$L_Y$'-N($R_BR_B$')—$R_D$, —N($R_B$)CO—C($R_3R_4$)C($R_6R_7$)—C(O)-$L_Y$'-O—$R_D$, —N($R_B$)CO—C($R_3R_4$)C($R_6R_7$)—(O)-$L_Y$'-$R_D$, —N($R_B$)CO—C($R_3R_4$)C($R_6R_7$)—RD, -$L_S$-C($R_3R_4$)C($R_6R_7$)—C(O)-$L_Y$'-N($R_B$)C(O)O—$R_D$, -$L_S$-C($R_3R_4$)C($R_6R_7$)—C(O)-$L_Y$'-N($R_B$)C(O)—$R_D$, -$L_S$-C($R_3R_4$)C($R_6R_7$)—C(O)-$L_Y$'-N($R_B$)S(O)$_2$—$R_D$, -$L_S$-C($R_3R_4$)C($R_6R_7$)—C(O)-$L_Y$'-N($R_BR_B$')—$R_D$, -$L_S$-C($R_3R_4$)C($R_6R_7$)—C(O)-$L_Y$'-O—$R_D$, -$L_S$-C($R_3R_4$)C($R_6R_7$)C(O)-$L_Y$'-$R_D$, or -$L_S$-C($R_3R_4$)C($R_6R_7$)—$R_D$, wherein $L_Y$' preferably is $C_1$-$C_6$alkylene which is optionally substituted with one or more $R_L$. $R_1$ may be $R_C$, and $R_2$ and $R_5$, taken together with the atoms to which they are attached, may form a 5- to 6-membered heterocycle or 6- to 12-membered bicycle

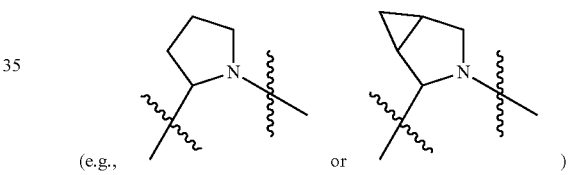

which is optionally substituted with one or more $R_A$; and $R_3$ and $R_6$ may be each independently $R_C$, and $R_4$ and $R_7$, taken together with the atoms to which they are attached, may form a 5- to 6-membered carbocycle/heterocycle or 6- to 12-membered bicycle

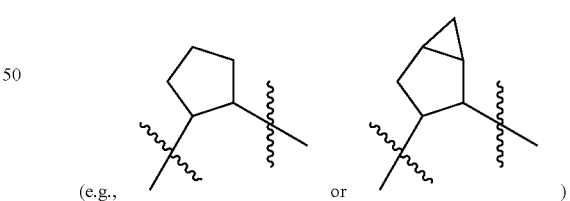

which is optionally substituted with one or more $R_A$.

Highly preferably, Y is selected from —N($R_B$")CO—C($R_1R_2$)N($R_5$)—C(O)-$L_Y$-N($R_B$")C(O)-$L_S$-$R_E$ or —C($R_1R_2$)N($R_5$)—C(O)-$L_Y$-N($R_B$")C(O)-$L_S$-$R_E$, or Y is -G-C($R_1R_2$)N($R_5$)—C(O)-$L_Y$-N($R_B$")C(O)-$L_S$-$R_E$, wherein $L_Y$ is $C_1$-$C_6$alkylene optionally substituted with one or more $R_L$, and $R_B$" is each independently $R_B$. $R_B$" and $R_1$ are each preferably hydrogen or $C_1$-$C_6$alkyl, and $R_2$ and $R_5$, taken together with the atoms to which they are attached, preferably form a 5- to 6-membered heterocycle or 6- to 12-membered bicycle (e.g., 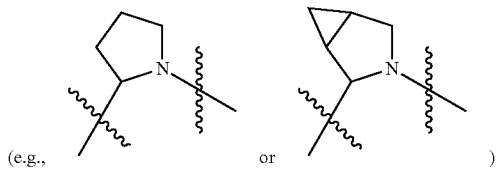 [SMILES: *C1CCCN1* ; *C1C2CC2CN1*] or )

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)). Preferably, $L_Y$ is $C_1$-$C_6$alkylene substituted with one or more $R_L$ such as a $C_3$-$C_6$carbocycle 3- to 6-membered heterocycle which is optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Highly preferably, $L_Y$ is a $C_1$-$C_6$alkylene such as, but not limited to,

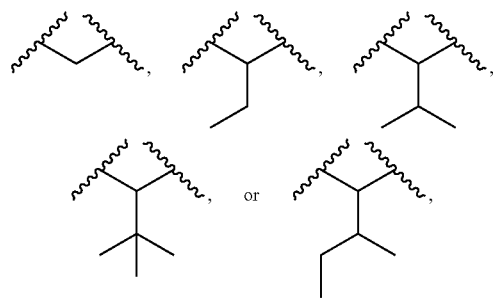

(stereochemistry at a carbon within the group $L_Y$ can be either (R) or (S)), $L_Y$ is optionally substituted with one or more $R_L$ (e.g., one or more phenyl or methoxy), G preferably is

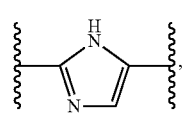

$R_B{''}$ is hydrogen; —C($R_1R_2$)N($R_5$)— is

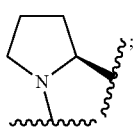 [SMILES: *[C@@H]1CCCN1*]

$L_S$ is a bond; and $R_E$ is methoxy.

Non-limiting examples of preferred Y include:

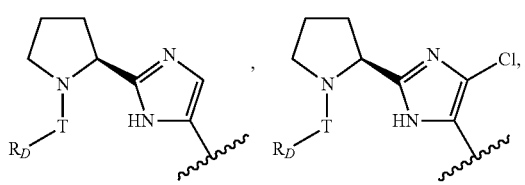

-continued

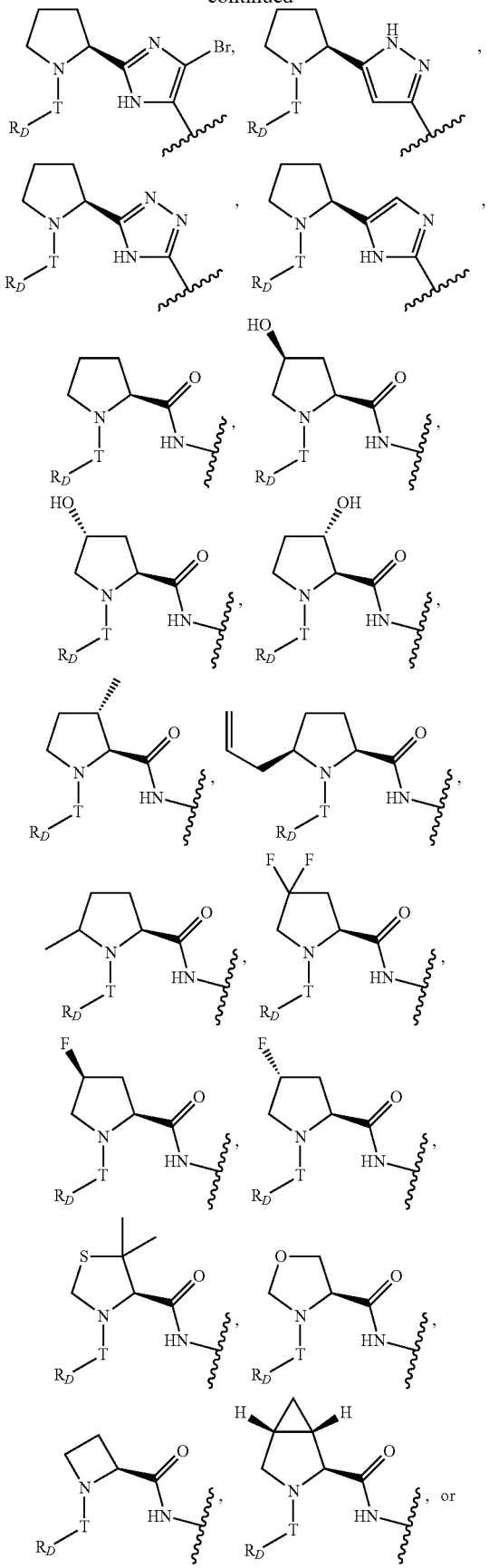

-continued

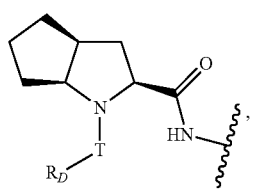

wherein T and $R_D$ are as defined herein. T, for example, can be $-L_S-M-L_S'-M'-L_S''-$ where $L_S$ is a bond; M is C(O); $L_S'$ is $C_1-C_6$alkylene such as, but not limited to,

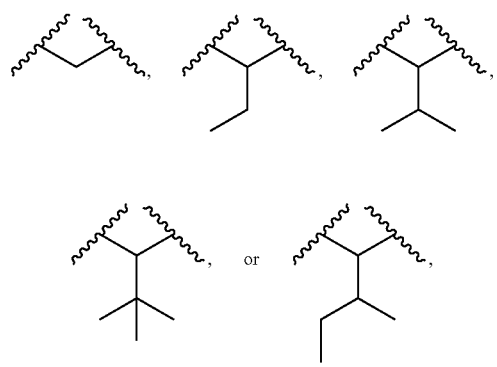

where $L_S'$ is optionally substituted with one or more $R_L$; $R_L$ is a substituent such as, but not limited to phenyl or methoxy; M' is —NHC(O)— or —NMeC(O)—; and $L_S''$ is a bond. Any stereochemistry at a carbon within the group $L_S'$ can be either (R) or (S). $R_D$, for example is methoxy. T-$R_D$ includes, but is not limited to:

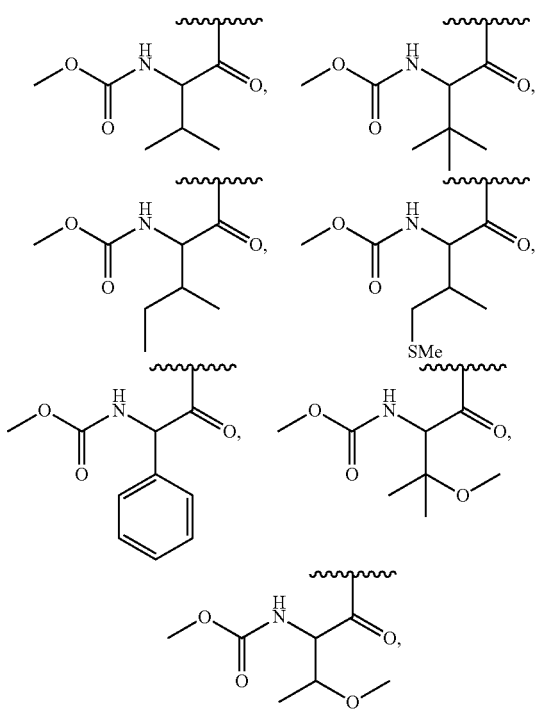

T-$R_D$ may also include certain stereochemical configurations; thus T-$R_D$ includes, but is not limited

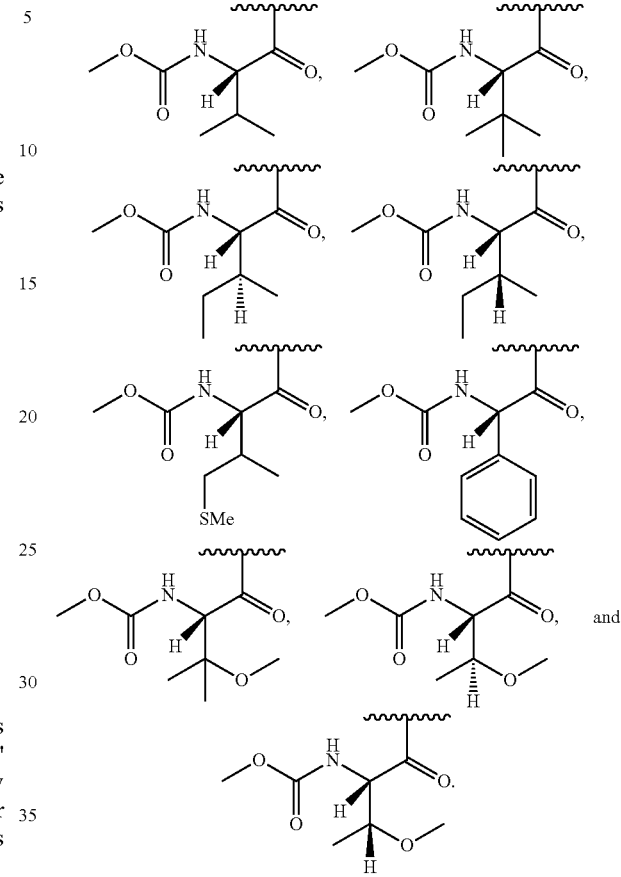

Non-limiting examples of preferred Y also include:

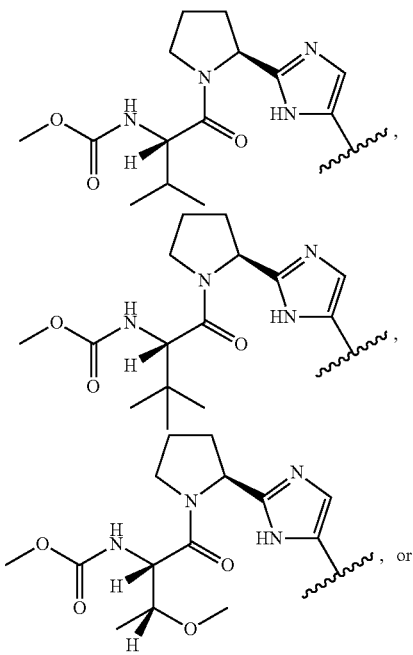

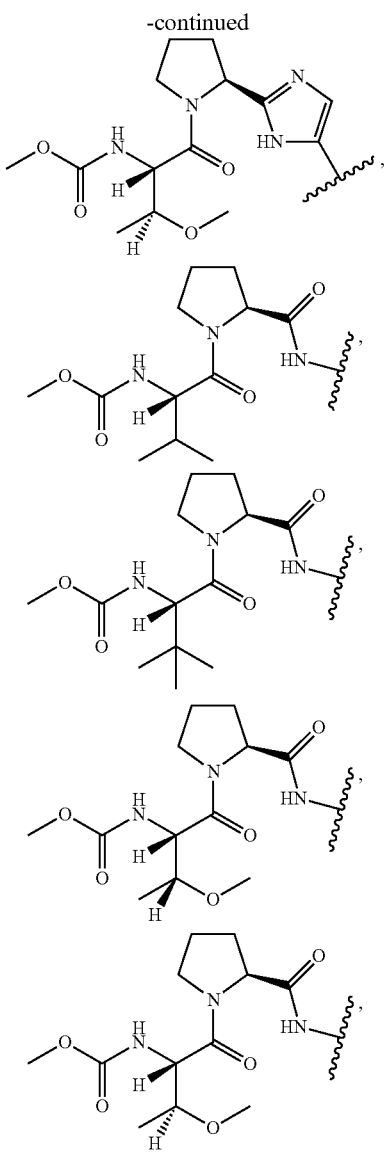

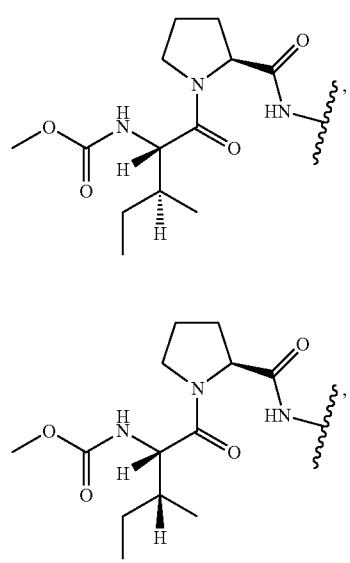

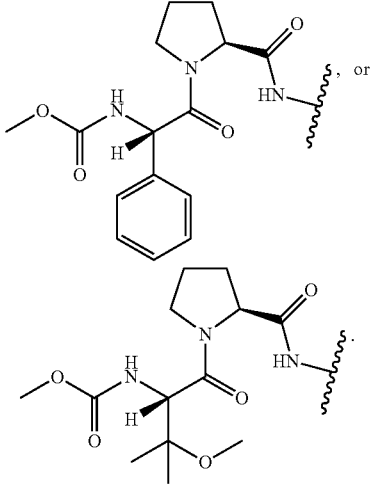

Z is preferably selected from -$L_S$-C($R_8R_9$)N($R_{12}$)-T-$R_D$, -$L_S$-C($R_{10}R_{11}$)C($R_{13}R_{14}$)-T-$R_D$, -G-C($R_8R_9$)N($R_{12}$)-T-$R_D$, -G-C($R_{10}R_{11}$)C($R_{13}R_{14}$)-T-$R_D$, —N($R_B$)C(O)C($R_8R_9$)N($R_{12}$)-T-$R_D$, —N($R_B$)C(O)C($R_{10}R_{11}$)C($R_{13}R_{14}$)-T-$R_D$, —C(O)N($R_B$)C($R_8R_9$)N($R_{12}$)-T-$R_D$, C(O)N($R_B$)C($R_{10}R_{11}$)C($R_{13}R_{14}$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

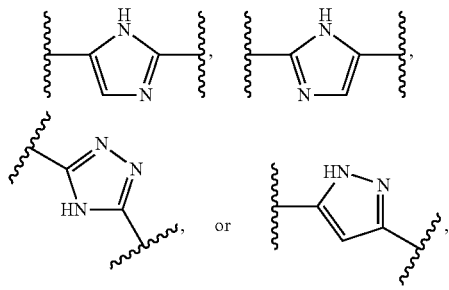

and is optionally substituted with one or more $R_A$ (e.g., one or more chloro or bromo). E preferably is a 8- to 12-membered bicycle (such as

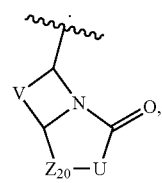

wherein U is independently selected at each occurrence from —(CH$_2$)— or —(NH)—; and V and $Z_{20}$ are each independently selected from $C_1$-$C_4$alkylene, $C_2$-$C_4$alkenylene or $C_2$-$C_4$alkynylene, in which at least one carbon atom is independently optionally replaced with O, S or N), and is optionally substituted with one or more $R_A$. More preferably, $R_S$ is $R_C$, and $R_9$ and $R_{12}$, taken together with the atoms to which they are attached, form a 5- to 6-membered heterocycle or 6- to 12-membered bicycle

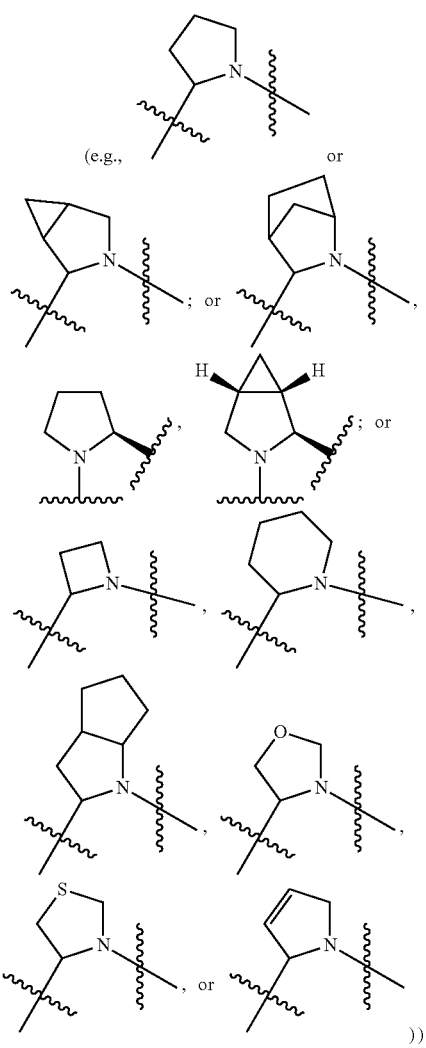

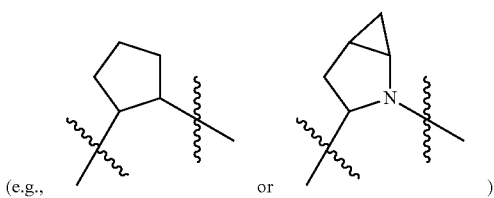 [SMILES: *C1CCCC1* ; *C1CC2CC2N1*]

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Z can also be selected from -M-C($R_8R_9$)N($R_{12}$)—C(O)-$L_Y'$-M'-$R_D$, -M-C($R_8R_9$)N($R_{12}$)-$L_Y'$-M'-$R_D$, -$L_S$-C($R_8R_9$)N($R_{12}$)—C(O)-$L_Y'$-M'-$R_D$, -$L_S$-C($R_8R_9$)N($R_{12}$)-$L_Y'$-M'-$R_D$, -M-C($R_{10}R_{11}$)C($R_{13}R_{14}$)C(O)-$L_Y'$-M'-$R_D$, -M-C($R_{10}R_{11}$)C($R_{13}R_{14}$)-$L_Y'$-M'-$R_D$, -$L_S$-C($R_{10}R_{11}$)C($R_{13}R_{14}$)—C(O)-$L_Y'$-M'-$R_D$, or -$L_S$-C($R_{10}R_{11}$)C($R_{13}R_{14}$)-$L_Y'$-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B'$)—, —N($R_B$)S(O)— or —N($R_B$)S(O)$_2$—, and $L_Y'$ preferably is $C_1$-$C_6$alkylene which is optionally substituted with one or more $R_L$. $L_Y'$, for example, is a $C_1$-$C_6$alkylene such as, but not limited to,

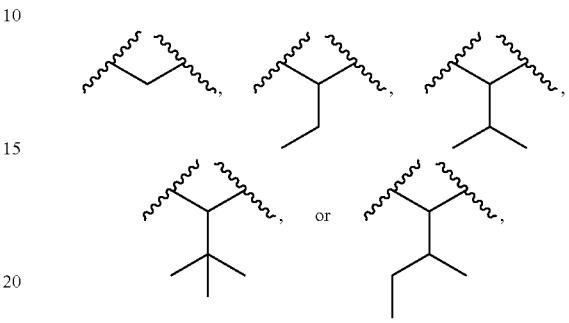

and the optional $R_L$ is a substituent such as, but not limited to phenyl, —SMe, or methoxy. Any stereochemistry at a carbon within the group $L_Y'$ can be either (R) or (S). More preferably, $R_8$ is $R_C$, and $R_9$ and $R_{12}$, taken together with the atoms to which they are attached, form a 5- to 6-membered heterocycle or 6- to 12-membered bicycle

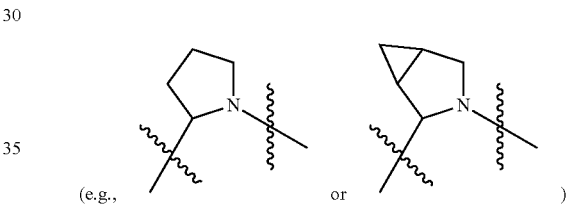

which is optionally substituted with one or more $R_A$ (e.g., one or more hydroxy); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle

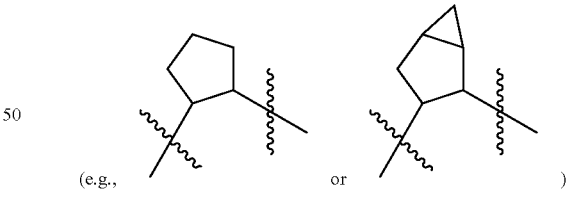

which is optionally substituted with one or more $R_A$.

Also preferably, Z is selected from —N($R_B$)CO—C($R_8R_9$) N($R_{12}$)—C(O)-$L_Y'$-N($R_B$)C(O)O—$R_D$, —N($R_B$)CO—C ($R_8R_9$)N($R_{12}$)—C(O)-$L_Y'$-N($R_B$)C(O)—$R_D$, —N($R_B$)CO—C($R_8R_9$)N($R_{12}$)—C(O)-$L_Y'$-N($R_B$)S(O)$_2$—$R_D$, —N($R_B$) CO—C($R_8R_9$)N($R_{12}$)—C(O)-$L_Y'$-N($R_BR_B'$)—$R_D$, —N($R_B$) CO—C($R_8R_9$)N($R_2$)—C(O)-$L_Y'$-O—$R_D$, —N($R_B$)CO—C ($R_8R_9$)N($R_{12}$)—C(O)-$L_Y'$-$R_D$, —N($R_B$)CO—C($R_8R_9$)N ($R_{12}$)—$R_D$, -$L_S$-C($R_8R_9$)N($R_{12}$)—C(O)-$L_Y'$-N($R_B$)C(O)O—$R_D$, -$L_S$-C($R_8R_9$)N($R_{12}$)—C(O)-$L_Y'$-N($R_B$)C(O)—$R_D$, -$L_S$-C($R_8R_9$)N($R_{12}$)—C(O)-$L_Y'$-N($R_B$)S(O)$_2$—$R_D$, -$L_S$-C($R_8R_9$) N($R_{12}$)—C(O)-$L_Y'$-N($R_BR_B'$)—$R_D$, -$L_S$-C($R_8R_9$)N($R_{12}$)—C (O)-$L_Y'$-O—$R_D$, -$L_S$-C($R_8R_9$)N($R_{12}$)—C(O)-$L_Y'$-$R_D$, -$L_S$-C $(R_8R_9)N(R_{12})$—$R_D$, —$N(R_B)CO$—$C(R_{10}R_{11})C(R_{13}R_{14})$—C(O)-$L_Y$'-$N(R_B)C(O)O$—$R_D$, —$N(R_B)CO$—$C(R_{10}R_{11})C(R_{13}R_{14})$—C(O)-$L_Y$'-$N(R_B)C(O)$—$R_D$, —$N(R_B)CO$—$C(R_{10}R_{11})C(R_{13}R_{14})$—C(O)-$L_Y$'-$N(R_BR_B')$—$R_D$, —$N(R_B)CO$—$C(R_{10}R_{11})C(R_{13}R_{14})$—(O)-$L_Y$'-O—$R_D$, —$N(R_B)CO$—$C(R_{10}R_{11})C(R_{13}R_{14})$—C(O)-$L_Y$'-$R_D$, —$N(R_B)CO$—$C(R_{10}R_{11})C(R_{13}R_{14})$—$R_D$, -$L_S$-$C(R_{10}R_{11})C(R_{13}R_{14})$—C(O)-$L_Y$'-$N(R_B)C(O)O$—$R_D$, -$L_S$-$C(R_{10}R_{11})C(R_{13}R_{14})$—C(O)-$L_Y$'-$N(R_B)C(O)$—$R_D$, -$L_S$-$C(R_{10}R_{11})C(R_{13}R_{14})$—C(O)-$L_Y$'-$N(R_B)S(O)_2$—$R_D$, -$L_S$-$C(R_{10}R_{11})C(R_{13}R_{14})$—C(O)-$L_Y$'-$N(R_BR_B')$—$R_D$, -$L_S$-$C(R_{10}R_{11})C(R_{13}R_{14})$—C(O)-$L_Y$'-O—$R_D$, -$L_S$-$C(R_{10}R_{11})C(R_{13}R_{14})$—C(O)-$L_Y$'-$R_D$, or -$L_S$-$C(R_{10}R_{11})C(R_{13}R_{14})$—$R_D$, wherein $L_Y$' preferably is $C_1$-$C_6$alkylene which is optionally substituted with one or more $R_L$. $R_8$ may be $R_C$, and $R_9$ and $R_{12}$, taken together with the atoms to which they are attached, may form a 5- to 6-membered heterocycle or 6- to 12-membered bicycle

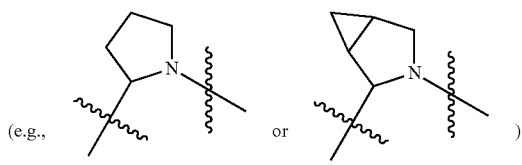 [SMILES: *C1CCCN1* ; *C1C2CC2CN1*]

(e.g., or )

which is optionally substituted with one or more $R_4$; and $R_{10}$ and $R_{13}$ may be each independently $R_C$, and $R_{11}$ and $R_{14}$, taken together with the atoms to which they are attached, may form a 5- to 6-membered carbocycle/heterocycle or 6- to 12-membered bicycle

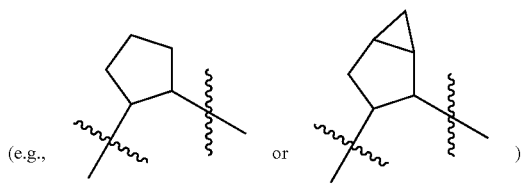 [SMILES: *C1CCCC1* ; *C1CC2CC2C1*]

(e.g., or )

which is optionally substituted with one or more $R_4$.

Highly preferably, Z is selected from —$N(R_B")CO$—$C(R_8R_9)N(R_{12})$—C(O)-$L_Y$-$N(R_B")C(O)$-$L_S$-$R_E$ or —$C(R_8R_9)N(R_{12})$—C(O)-$L_Y$-$N(R_B")C(O)$-$L_S$-$R_E$, or Z is -G-$C(R_8R_9)N(R_{12})$—C(O)-$L_Y$-$N(R_B")C(O)$-$L_S$-$R_E$, wherein $L_Y$ is $C_1$-$C_6$alkylene optionally substituted with one or more $R_L$, and $R_B"$ is each independently $R_B$. $R_B"$ and $R_8$ are each preferably hydrogen or $C_1$-$C_6$alkyl, and $R_9$ and $R_{12}$, taken together with the atoms to which they are attached, preferably form a 5- to 6-membered heterocycle or 6- to 12-membered bicycle

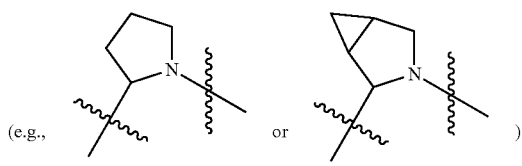 [SMILES: *C1CCCN1* ; *C1C2CC2CN1*]

(e.g., or )

which is optionally substituted with one or more $R_4$ (such as, but not limited to hydroxy, halo (e.g., fluoro), $C_1$-$C_6$alkyl (e.g., methyl), or $C_2$-$C_6$alkenyl (e.g., allyl)). Preferably, $L_Y$ is $C_1$-$C_6$alkylene substituted with one or more $R_L$ such as a $C_3$-$C_6$carbocycle 3- to 6-membered heterocycle which is optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Highly preferably, $L_Y$ is a $C_1$-$C_6$alkylene such as, but not limited to,

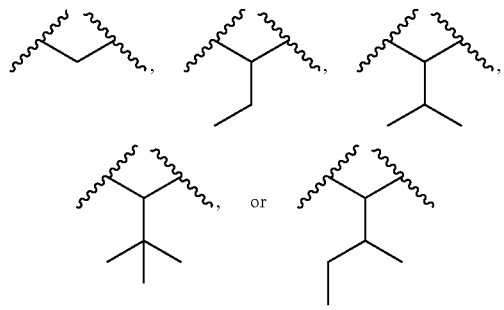

(stereochemistry at a carbon within the group $L_Y$ can be either (R) or (S)); $L_Y$ is optionally substituted with one or more $R_L$ (e.g., one or more phenyl or methoxy); G preferably is

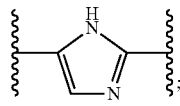 [SMILES: *c1cnc(*)[nH]1]

$R_B"$ is hydrogen; —$C(R_8R_9)N(R_{12})$— is

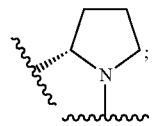

$L_S$ is a bond; and $R_E$ is methoxy.

Non-limiting examples of preferred Z include:

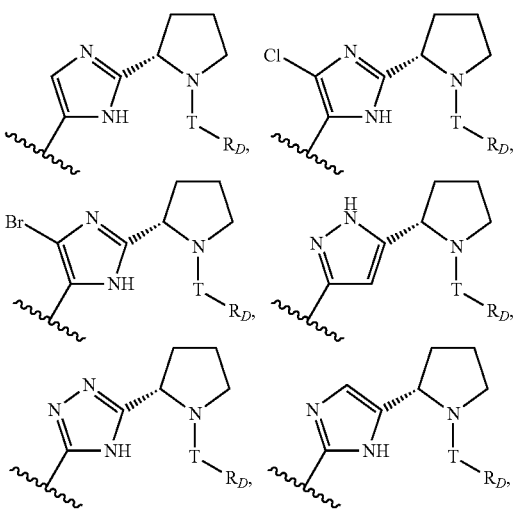

-continued

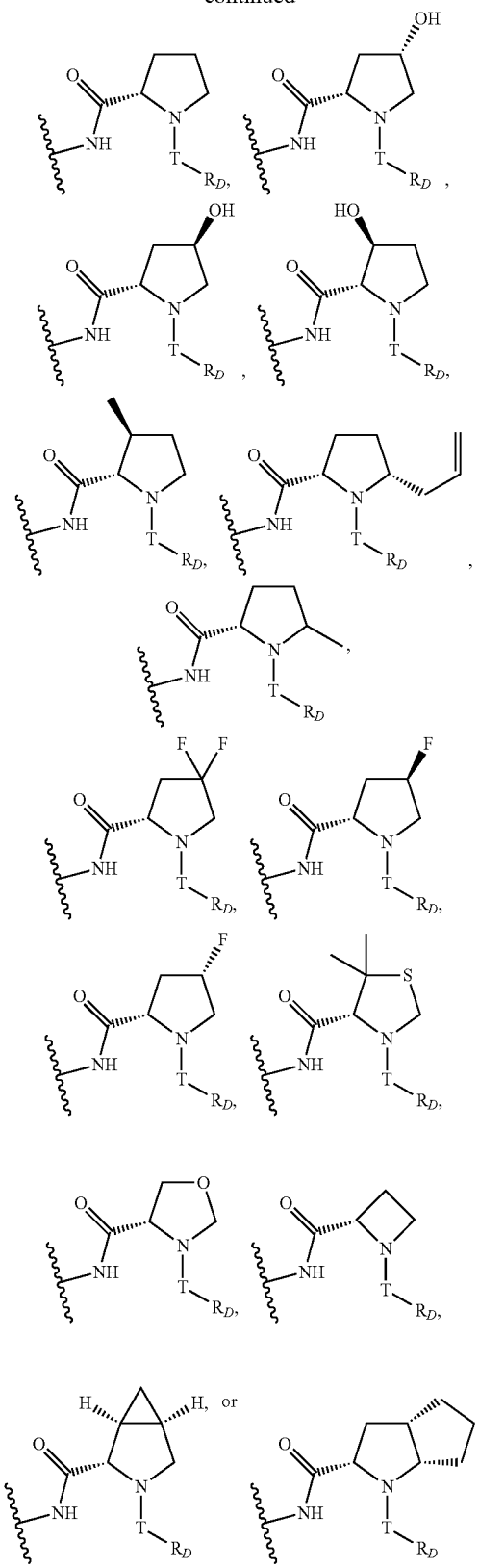

wherein T and $R_D$ are as defined herein. T, for example, can be -$L_S$-M-$L_S'$-M'-$L_S''$- where $L_S$ is a bond; M is C(O); $L_S'$ is $C_1$-$C_6$alkylene such as, but not limited to,

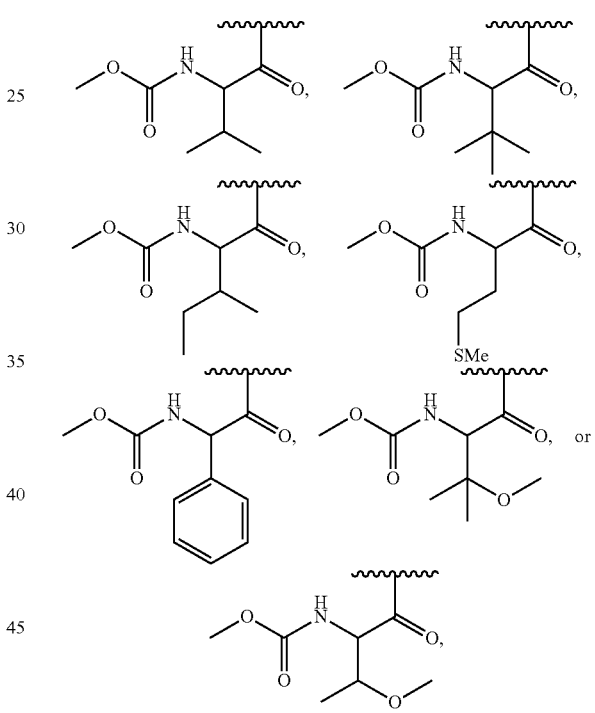

where $L_S'$ is optionally substituted with one or more $R_L$; the optional $R_L$ is a substituent such as, but not limited to phenyl or methoxy; M' is —NHC(O)— or —NMeC(O)—; and $L_S''$ is a bond. Any stereochemistry at a carbon within the group $L_S''$ can be either (R) or (S). $R_D$, for example is methoxy. T-$R_D$ includes, but is not limited to:

T-$R_D$ may also include certain stereochemical configurations; thus T-$R_D$ includes, but is not limited to:

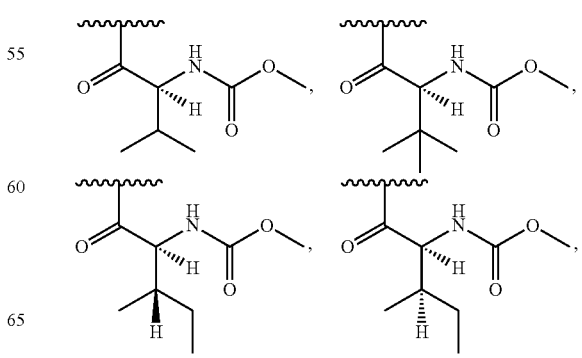

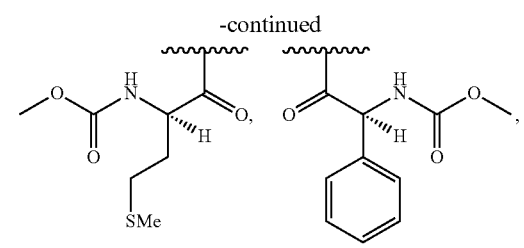
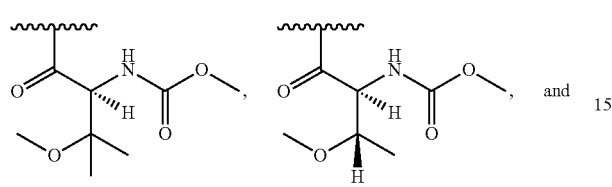 and
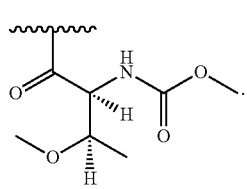
Non-limiting examples of preferred Z also include:
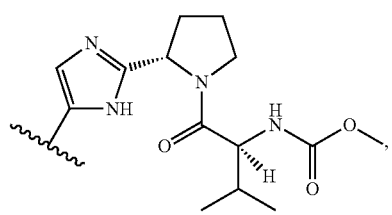
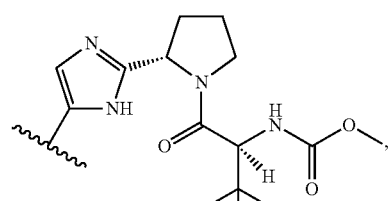
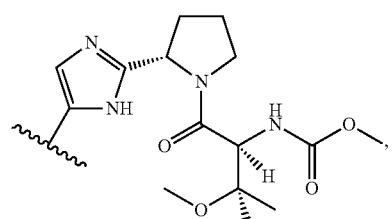
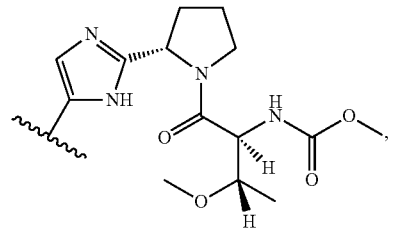
-continued
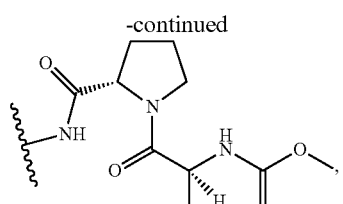
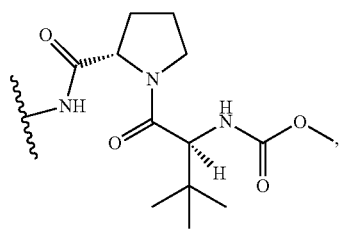
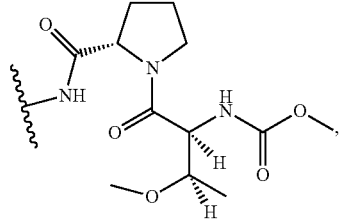
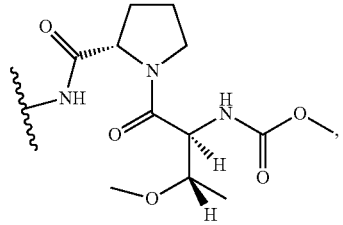
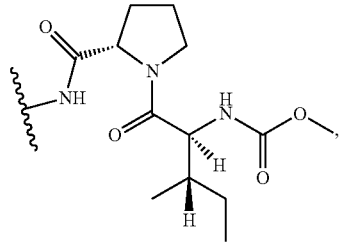
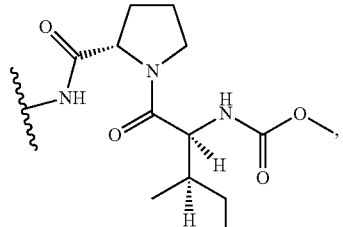
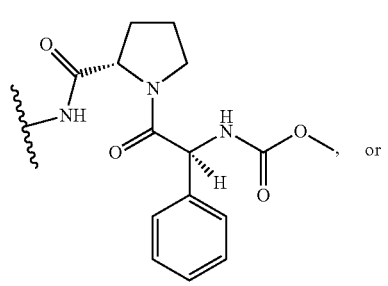 or -continued

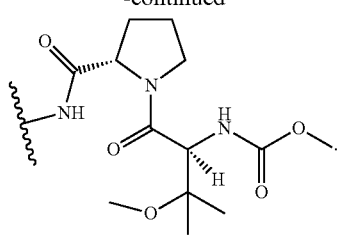

T can be, without limitation, independently selected at each occurrence from —C(O)-L$_S$'-, —C(O)O-L$_S$'-, —C(O)-L$_S$'-N(R$_B$)C(O)-L$_S$"-, —C(O)-L$_S$'-N(R$_B$)C(O)O-L$_S$"-, —N(R$_B$)C(O)-L$_S$'-N(R$_B$)C(O)-L$_S$"-, —N(R$_B$)C(O)-L$_S$'-N(R$_B$)C(O)O-L$_S$"-, or —N(R$_B$)C(O)-L$_S$'-N(R$_B$)-L$_S$"-. Preferably, T is independently selected at each occurrence from —C(O)-L$_S$'-M'-L$_S$"- or —N(R$_B$)C(O)-L$_S$'-M'-L$_S$"-. More preferably, T is independently selected at each occurrence from —C(O)-L$_S$'-N(R$_B$)C(O)-L$_S$"- or —C(O)-L$_S$'-N(R$_B$)C(O)O-L$_S$"-.

T can also be, for example, -L$_S$-M-L$_S$'-M'-L$_S$"- where L$_S$ is a bond; M is C(O); L$_S$' is C$_1$-C$_6$alkylene (e.g., 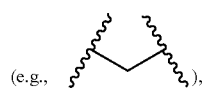), where L$_S$' is optionally substituted with R$_T$; the optional R$_T$ is a substituent selected from —C$_1$-C$_6$alkyl, —C$_2$-C$_6$alkenyl, —C$_1$-C$_6$alkyl-OH, —C$_1$-C$_6$alkyl-O—C$_1$-C$_6$alkyl, 3- to 6-membered heterocycle (e.g., tetrahydrofuranyl), or C$_3$-C$_6$carbocyclyl (e.g., phenyl, cyclohexyl); M' is —NHC(O)—, —N(Et)C(O)— or —N(Me)C(O)—; and L$_S$" is a bond. R$_D$ preferably is hydrogen, —C$_1$-C$_6$alkyl (e.g., methyl), —O—C$_1$-C$_6$alkyl (e.g., methoxy, tert-butoxy), methoxymethyl, or —N(C$_1$-C$_6$alkyl)$_2$ (e.g., —NMe$_2$).

T-R$_D$ can be, without limitation,

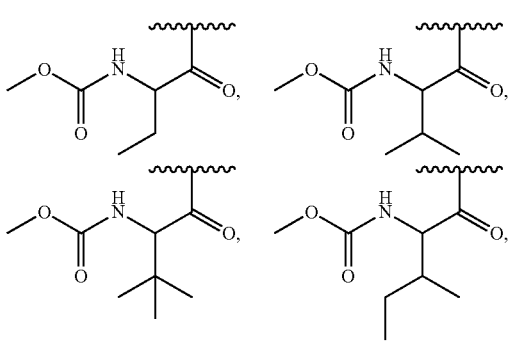

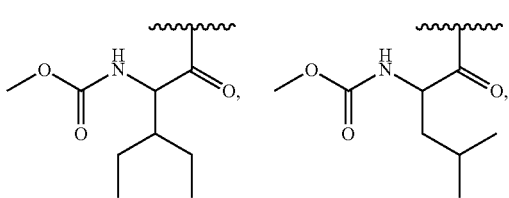

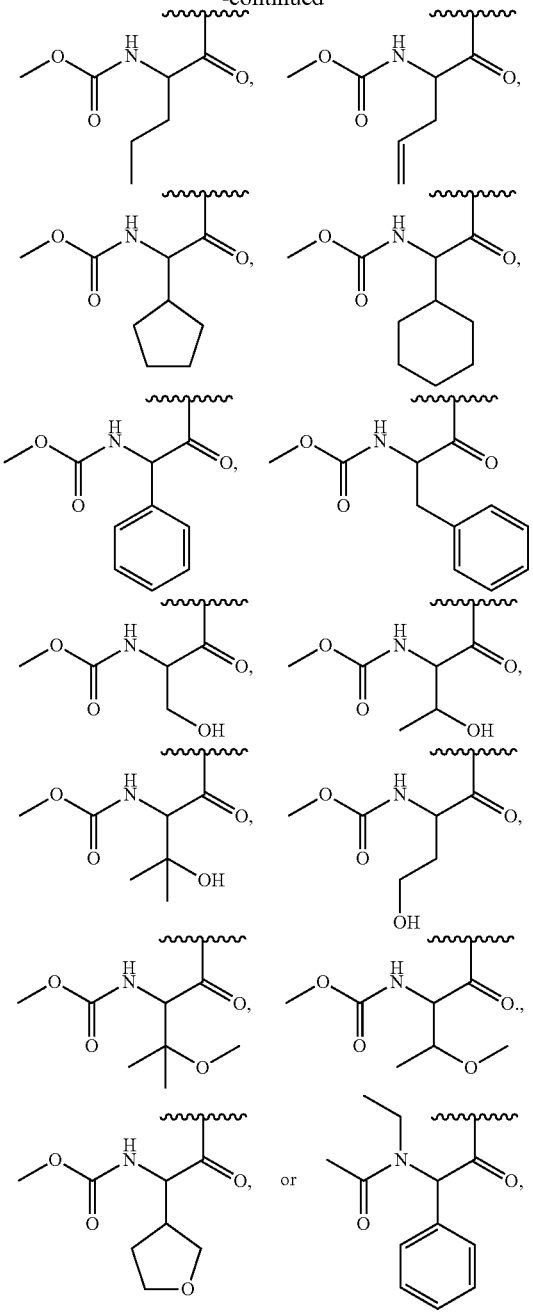

wherein the stereochemistry at a carbon within the group T-R$_D$ can be either (R) or (S).

T can also be, without limitation, -L$_S$-M-L$_S$'- where L$_S$ is a bond; M is C(O); L$_S$' is C$_1$-C$_6$alkylene (e.g., 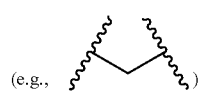)

where L$_S$' is optionally substituted with R$_T$; the optional R$_T$ is a substituent selected from —C$_1$-C$_6$alkyl, —C$_1$-C$_6$alkyl-OH, —C$_1$-C$_6$alkyl-O—C$_1$-C$_6$alkyl, or a C$_3$-C$_6$carbocyclyl (e.g., phenyl, cyclohexyl). R$_D$, for example is —OH; —OC(O)Me; —NH(C$_1$-C$_6$alkyl) (e.g., —NHMe, —NHEt); —N(C$_1$-

C$_6$alkyl)$_2$ (e.g., —NMe$_2$, —NEt$_2$); a 3- to 10-membered heterocyclyl (e.g., pyrrolidinyl, imidazolidinyl, hexahydropyrimidinyl, morpholinyl, piperidinyl) optionally substituted with one or more halogen, oxo; C$_3$-C$_{10}$carbocycle (e.g., cyclopentyl) optionally substituted with —OH; —C$_1$-C$_6$alkyl (e.g., isopropyl, 3-pentyl) optionally substituted with —OH; or NHR$_T$ where R$_T$ is a 3- to 6-membered heterocyclyl (e.g., thiazolyl, pyrimidinyl). T-R$_D$ includes, but is not limited to:

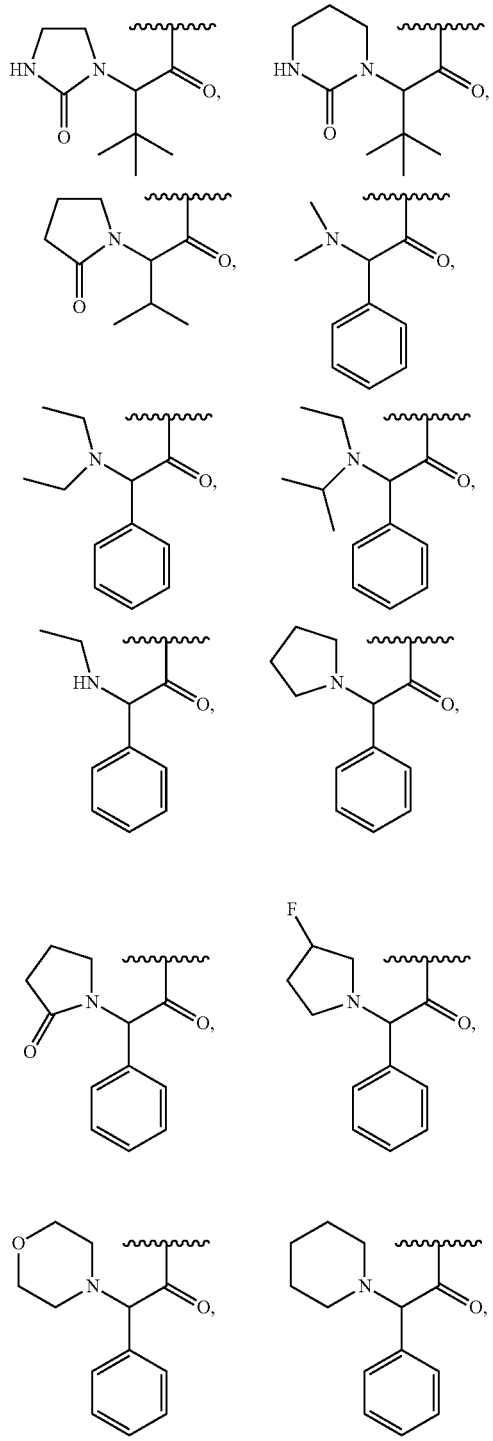

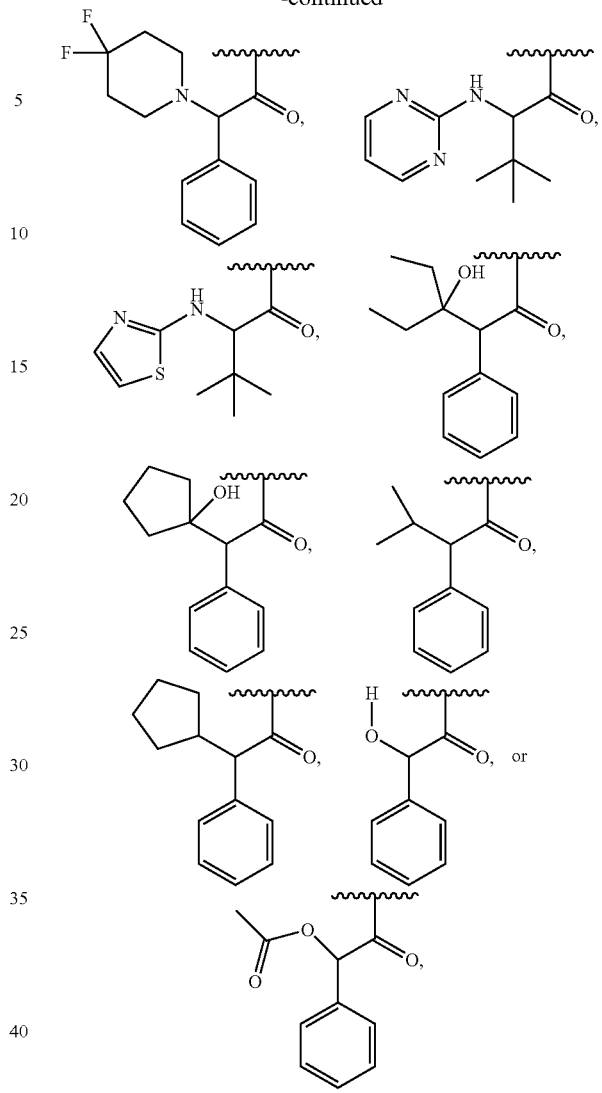

-continued wherein the stereochemistry at a carbon within the group T-R$_D$ can be either (R) or (S).

For each compound of Formula I, L$_K$ can also be independently selected at each occurrence from a bond; -L$_S$'-N(R$_B$)C(O)-L$_S$-; -L$_S$'-C(O)N(R$_B$)-L$_S$-; or C$_1$-C$_6$alkylene, C$_2$-C$_6$alkenylene, C$_2$-C$_6$alkynylene, C$_3$-C$_{10}$carbocycle or 3- to 10-membered heterocycle, each of which is independently optionally substituted at each occurrence with one or more substituents selected from halogen, R$_T$, —O—R$_S$, —S—R$_S$, —N(R$_S$R$_S$'), —OC(O)R$_S$, —C(O)OR$_S$, nitro, oxo, phosphonoxy, phosphono, thioxo, formyl or cyano, wherein L$_S$ and L$_S$' are as defined above.

For Formula I as well as Formulae I$_A$, I$_B$, I$_C$ and I$_D$ described below, including each and every embodiment described thereunder, R$_A$ preferably is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S'$), -$L_A$-S(O)$R_S$, -$L_A$-SO$_2$$R_S$, -$L_A$-C(O)N($R_S R_S'$), -$L_A$-N($R_S$)C(O)$R_S'$, -$L_A$-N($R_S$)C(O)N($R_S' R_S''$), -$L_A$-N($R_S$)SO$_2$$R_S'$, -$L_A$-SO$_2$N($R_S R_S'$), -$L_A$-N($R_S$)SO$_2$N($R_S' R_S''$), -$L_A$-N($R_S$)S(O)N($R_S' R_S''$), -LA-OS(O)—$R_S$, -LA-OS(O)$_2$—$R_S$, -LA-S(O)$_2$O$R_S$, -LA-S(O)O$R_S$, -$L_A$-OC(O)O$R_S$, -$L_A$-N($R_S$)C(O)O$R_S'$, -$L_A$-OC(O)N($R_S R_S'$), -$L_A$-N($R_S$)S(O)—$R_S'$, -$L_A$-S(O)N($R_S R_S'$) or -$L_A$-C(O)N($R_S$)C(O)—$R_S'$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$, or Y and Z, or Y-A- and Z—B—, or -A-$L_1$- and —B-$L_2$-, can be the same or different. In some instances, Y-A-$L_1$- is identical to Z—B-$L_2$-. In some other instances, Y-A-$L_1$- is different from Z—B-$L_2$-.

In one embodiment, A and B are each independently 5- or 6-membered carbocycle or heterocycle (e.g., phenyl such as

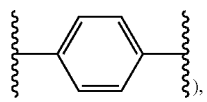 [SMILES: *c1ccc(*)cc1]

), and are each independently optionally substituted with one or more $R_A$. X is 5- or 6-membered carbocycle or heterocycle or 6- to 12-membered bicycle (e.g., 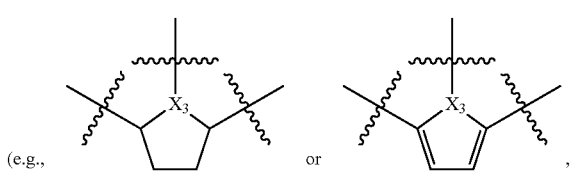 , wherein $X_3$ is N and is directly linked to -$L_3$-D) and is optionally substituted with one or more $R_A$. Specific examples of X are described hereinabove. D is $C_5$-$C_6$carbocycle or 5- to 6-membered heterocycle (e.g., phenyl), and is optionally substituted with one or more $R_A$. Preferably, D is

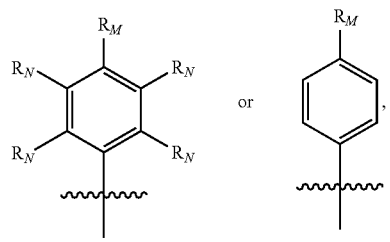

or wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1 R_2$)N($R_5$)-T-$R_D$, or —N($R_B$)C(O)C($R_3 R_4$)C($R_6 R_7$)-T-$R_D$, and Z is —N($R_B$)C(O)C($R_8 R_9$)N($R_{12}$)-T-$R_D$, or —N($R_B$)C(O)C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g., 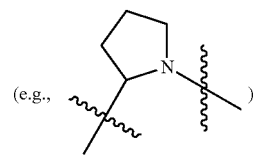 [SMILES: *C1CCCN1*] )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., 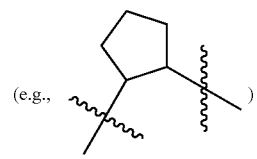 [SMILES: *C1CCCC1*] )

which is optionally substituted with one or more $R_A$. $R_8$ is $R_C$, and $R_9$ and $R_{12}$, taken together with the atoms to which they are attached, form a 5- to 6-membered heterocyclic ring (e.g., 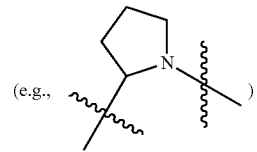 [SMILES: *C1CCCN1*] )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

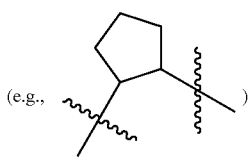 [SMILES: *C1CCCC1*]

which is optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —CH$_2$—) and optionally substituted with one or more substituents selected from $R_L$. T can also be, without limitation, selected from —C(O)-$L_Y'$-$L_S''$-, —C(O)-$L_Y'$-O-$L_S''$-, —C(O)-$L_Y'$-N($R_B$)-$L_S''$-, or C(O)-$L_1$-N($R_B$)S(O)$_2$-$L_S''$-. In some cases, at least one of Y and Z is, or both Y and Z are independently,

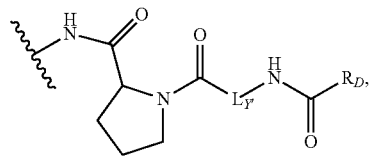

wherein non-limiting examples of $R_D$ include (1) —O—$C_1$-$C_6$alkyl, —O—$C_2$-$C_6$alkenyl, —O$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y'$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another embodiment, A is

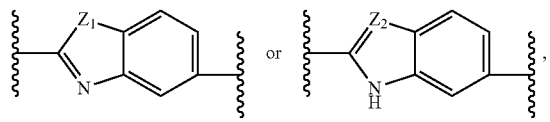

and is optionally substituted with one or more $R_A$; B

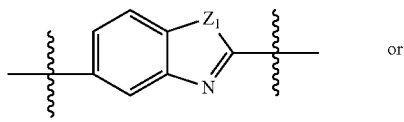

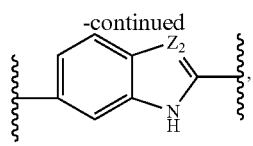

and is optionally substituted with one or more $R_A$. $Z_1$ is independently selected at each occurrence from O, S, NH or CH$_2$; and $Z_2$ is independently selected at each occurrence from N or CH. X is 5- or 6-membered carbocycle or heterocycle or 6- to 12-membered bicycle

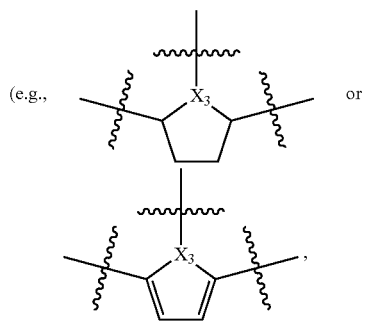

wherein $X_3$ is N and is directly linked to -$L_3$-D) and is optionally substituted with one or more $R_A$. Specific examples of X are described hereinabove. D is $C_5$-$C_6$carbocycle or 5- to 6-membered heterocycle (e.g., phenyl), and is optionally substituted with one or more $R_A$. Preferably, D is

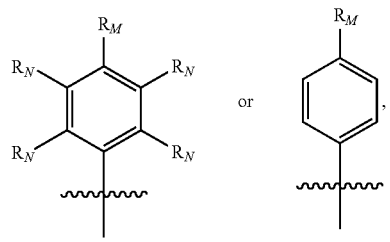

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -$L_S$-C($R_1R_2$)N($R_5$)-T-$R_D$ or -$L_S$-C($R_3R_4$)C($R_6R_7$)-T-$R_D$, and Z is -$L_S$-C($R_8R_9$)N($R_{12}$)-T-$R_D$ or -$L_S$-C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring

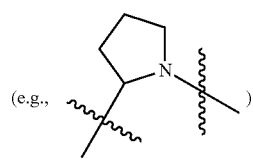 [SMILES: *C1CCCN1*]

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., 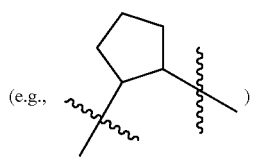 [SMILES: *C1CCCC1*])

which is optionally substituted with one or more $R_A$. $R_8$ is $R_C$, and $R_9$ and $R_{12}$, taken together with the atoms to which they are attached, form a 5- to 6-membered heterocyclic ring (e.g., 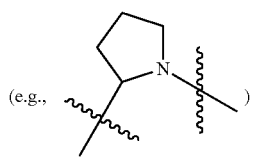 [SMILES: *C1CCCN1*])

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 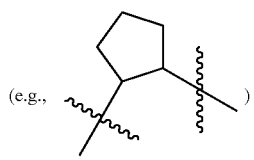 [SMILES: *C1CCCC1*])

which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is independently $C_1$-$C_6$alkylene (e.g., —$CH_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, at least one of Y and Z is, or both Y and Z are independently,

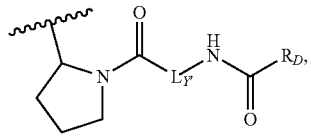

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In still yet another embodiment, A and B are each independently 5- or 6-membered carbocycle or heterocycle (e.g., A and B are each independently phenyl, such as

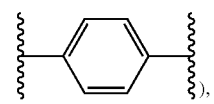 [SMILES: *c1ccc(*)cc1]), and are each independently optionally substituted with one or more $R_A$. X is 5- or 6-membered carbocycle or heterocycle or 6- to 12-membered bicycle (e.g., 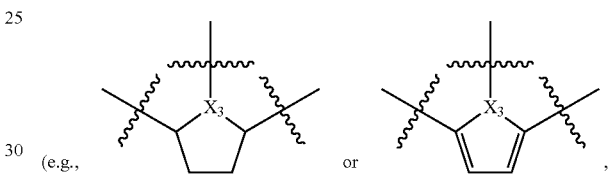, wherein $X_3$ is N and is directly linked to -$L_3$-D) and is optionally substituted with one or more $R_A$. Specific examples of X are described hereinabove. D can be, for example, $C_5$-$C_6$carbocycle or 5- to 6-membered heterocycle (e.g., phenyl), and is optionally substituted with one or more $R_A$. Preferably, D is

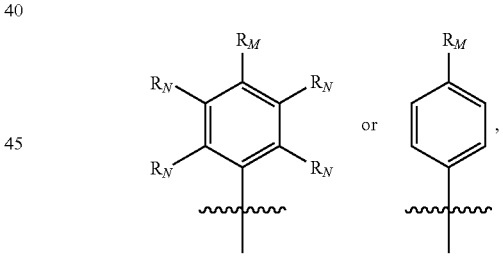

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -G-C($R_1R_2$)N($R_5$)-T-$R_D$ or -G-C($R_3R_4$)C($R_6R_7$)-T-$R_D$, and Z is -G-C($R_8R_9$)N($R_{12}$)-T-$R_D$ or -G-C($R_{10}R_{11}$)C($R_{13}R_{14}$)-T-$R_D$. G is independently $C_5$-$C_6$carbocycle or 5- to 6-membered heterocycle, such as

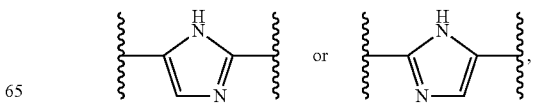

and is independently optionally substituted with one or more $R_A$. $R_1$ is $R_C$, and $R_2$ and $R_5$, taken together with the atoms to which they are attached, form a 5- to 6-membered heterocyclic ring (e.g., 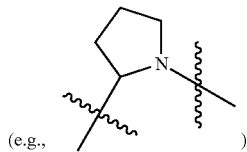 [SMILES: *C1CCCN1*] )

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g., 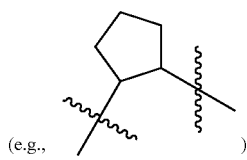 [SMILES: *C1CCCC1*] )

which is optionally substituted with one or more $R_A$. $R_8$ is $R_C$, and $R_9$ and $R_{12}$, taken together with the atoms to which they are attached, form a 5- to 6-membered heterocyclic ring (e.g., 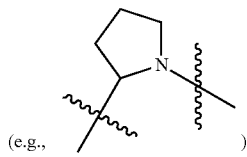 [SMILES: *C1CCCN1*] )

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g., 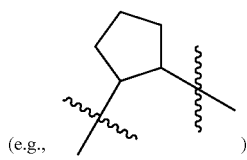 [SMILES: *C1CCCC1*] )

which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, at least one of Y and Z is, or both Y and Z are independently,

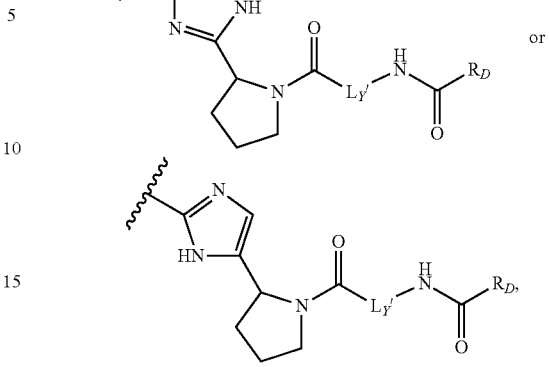

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In yet another embodiment, A and B are each independently 5- or 6-membered carbocycle or heterocycle (e.g., A and B are each independently phenyl, such as

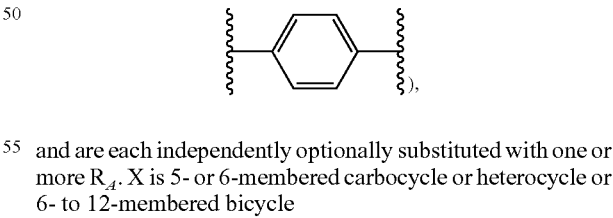

and are each independently optionally substituted with one or more $R_A$. X is 5- or 6-membered carbocycle or heterocycle or 6- to 12-membered bicycle (e.g., 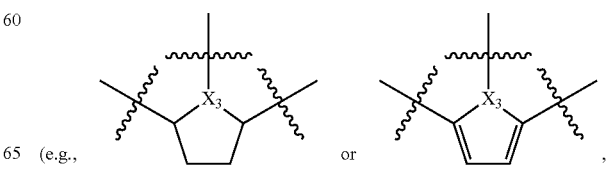 , wherein $X_3$ is N and is directly linked to -$L_3$-D) and is optionally substituted with one or more $R_A$. Specific examples of X are described hereinabove. D can be, for example, $C_5$-$C_6$carbocycle or 5- to 6-membered heterocycle (e.g., phenyl), and is optionally substituted with one or more $R_A$. Preferably, D is

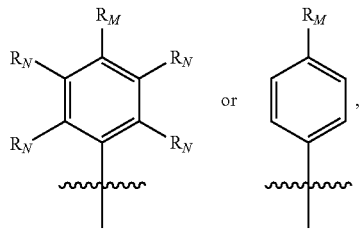

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1R_2$)N($R_5$)-T-$R_D$ or —N($R_B$)C(O)C($R_3R_4$)C($R_6R_7$)-T-$R_D$, and Z is -G-C($R_8R_9$)N($R_{12}$)-T-$R_D$ or -G-C($R_{10}R_{11}$)C($R_{13}R_{14}$)-T-$R_D$; or Y is -G-C($R_1R_2$)N($R_5$)-T-$R_D$ or -G-C($R_3R_4$)C($R_6R_7$)-T-$R_D$, and Z is —N($R_B$)C(O)C($R_8R_9$)N($R_{12}$)-T-$R_D$ or —N($R_B$)C(O)C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring

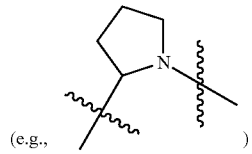 [SMILES: *C1CCCN1*]

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring

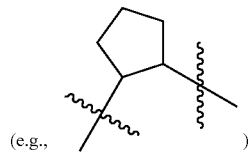 [SMILES: *C1CCCC1*]

which is optionally substituted with one or more $R_A$. $R_8$ is $R_C$, and $R_9$ and $R_{12}$, taken together with the atoms to which they are attached, form a 5- to 6-membered heterocyclic ring

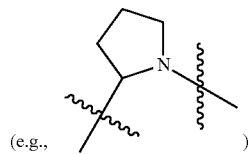 [SMILES: *C1CCCN1*]

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring

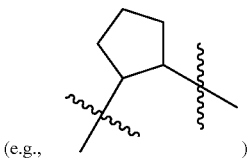 [SMILES: *C1CCCC1*]

which is optionally substituted with one or more $R_A$. G is independently $C_5$-$C_6$carbocycle or 5- to 6-membered heterocycle, such as

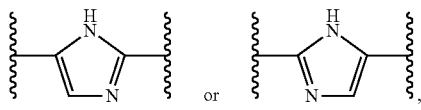

and is independently optionally substituted with one or more $R_A$. T is preferably independently selected at each occurrence from —C(O)-$L_{Y'}$-N($R_B$)C(O)-$L_S''$- or —C(O)-$L_{Y'}$-N($R_B$)C(O)O-$L_S''$-. $L_{Y'}$ is each independently $L_S'$ and, preferably, is each independently $C_1$-$C_6$alkylene (e.g., —$CH_2$—) and optionally substituted with one or more substituents selected from $R_L$. T can also be, without limitation, selected from —C(O)-$L_{Y'}$-$L_S''$-, —C(O)-$L_{Y'}$-O-$L_S''$-, —C(O)-$L_{Y'}$-N($R_B$)-$L_S''$-, or —C(O)-$L_{Y'}$-N($R_B$)S(O)$_2$-$L_S''$-. In some cases, Y is

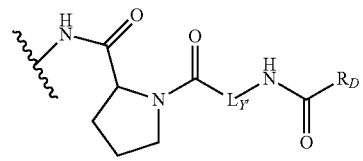

as described above, and Z is

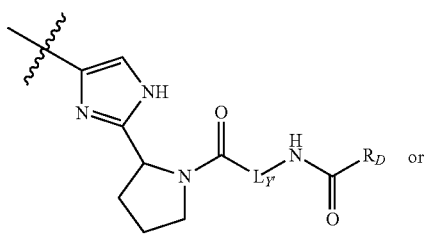

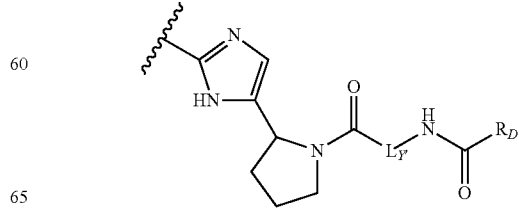

as described above. In some other cases, Y is

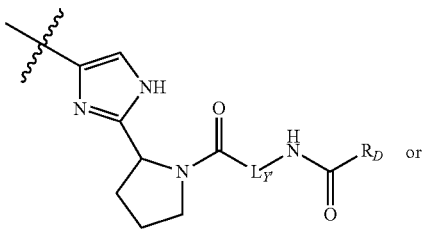

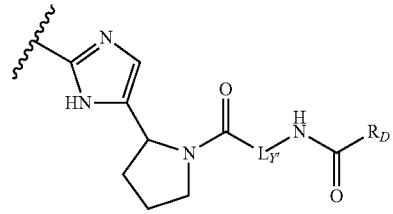

as described above, and Z is

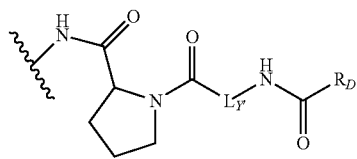

as described above.

In still another embodiment, A is 5- or 6-membered carbocycle or heterocycle (e.g., phenyl such as

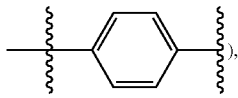

and B is

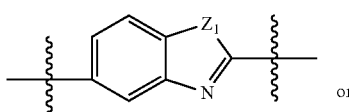

(e.g.,

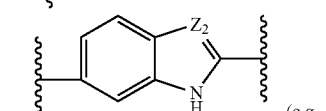

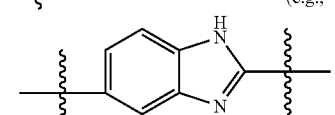, or 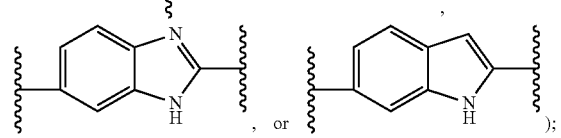);

or A is

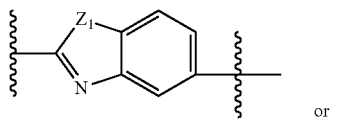

or

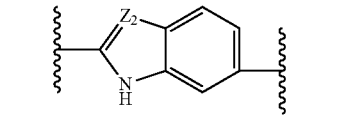

(e.g., 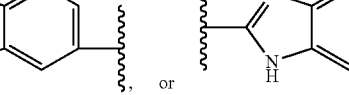

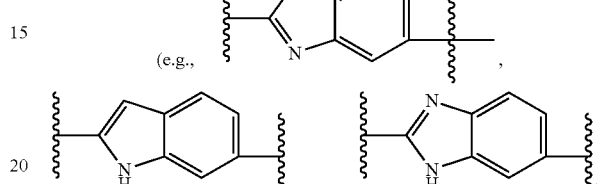), and B is 5- or 6-membered carbocycle or heterocycle (e.g., phenyl such as

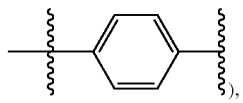

A and B are each independently optionally substituted with one or more $R_A$. $Z_1$ is independently selected at each occurrence from O, S, NH or $CH_2$; and $Z_2$ is independently selected at each occurrence from N or CH. X is 5- or 6-membered carbocycle or heterocycle or 6- to 12-membered bicycle

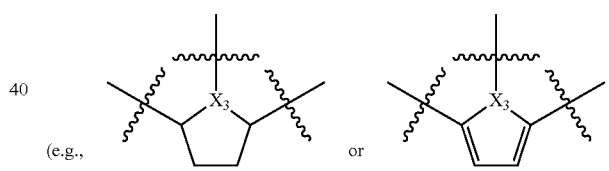

(e.g., 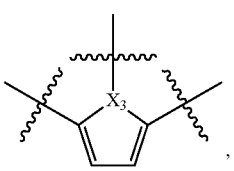 or , wherein $X_3$ is N and is directly linked to -$L_3$-D) and is optionally substituted with one or more $R_A$. Specific examples of X are described hereinabove. D is $C_5$-$C_6$carbocycle or 5- to 6-membered heterocycle (e.g., phenyl), and is optionally substituted with one or more $R_A$. Preferably, D is

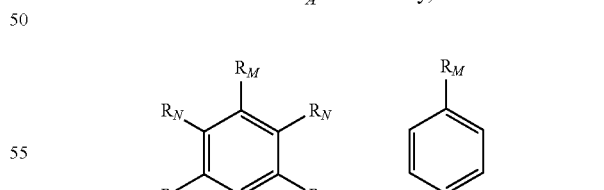

or 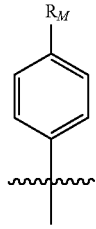, wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. When A is 5- or 6-membered carbocycle or heterocycle (e.g., phenyl such as

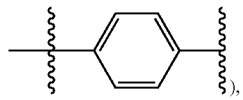

Y is —N(R$_B$)C(O)C(R$_1$R$_2$)N(R$_5$)-T-R$_D$, —N(R$_B$)C(O)C(R$_3$R$_4$)C(R$_6$R$_7$)-T-R$_D$, -G-C(R$_1$R$_2$)N(R$_5$)-T-R$_D$ or -G-C(R$_3$R$_4$)C(R$_6$R$_7$)-T-R$_D$, and Z is -L$_S$-C(R$_8$R$_9$)N(R$_{12}$)-T-R$_D$ or -L$_S$-C(R$_{10}$R$_{11}$)C(R$_{13}$R$_{14}$)-T-R$_D$. When B is 5- or 6-membered carbocycle or heterocycle (e.g., phenyl such as

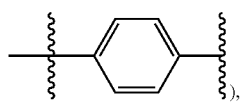

Y is -L$_S$-C(R$_1$R$_2$)N(R$_5$)-T-R$_D$ or -L$_S$-C(R$_3$R$_4$)C(R$_6$R$_7$)-T-R$_D$, and Z is —N(R$_B$)C(O)C(R$_8$R$_9$)N(R$_{12}$)-T-R$_D$, —N(R$_B$)C(O)C(R$_{10}$R$_{11}$)C(R$_{13}$R$_{14}$)-T-R$_D$, -G-C(R$_8$R$_9$)N(R)N(R$_{12}$)-T-R$_D$ or -G-C(R$_{10}$R$_{11}$)C(R$_{13}$R$_{14}$)-T-R$_D$. R$_1$ is R$_C$, and R$_2$ and R$_5$, taken together with the atoms to which they are attached, form a 5- to 6-membered heterocyclic ring

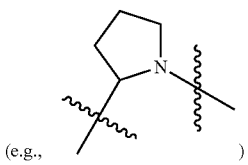 [SMILES: *C1CCCN1*]

which is optionally substituted with one or more R$_A$; R$_3$ and R$_6$ are each independently R$_C$, and R$_4$ and R$_7$, taken together with the atoms to which they are attached, form a 5- to 6-membered carbocyclic or heterocyclic ring

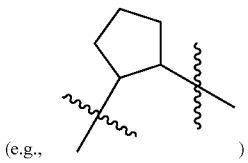 [SMILES: *C1CCCC1*]

which is optionally substituted with one or more R$_A$. R$_8$ is R$_C$, and R$_9$ and R$_{12}$, taken together with the atoms to which they are attached, form a 5- to 6-membered heterocyclic ring

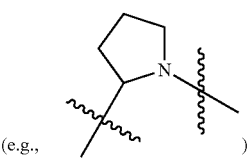 [SMILES: *C1CCCN1*]

which is optionally substituted with one or more R$_A$; and R$_{10}$ and R$_{13}$ are each independently R$_C$, and R$_{11}$ and R$_{14}$, taken together with the atoms to which they are attached, form a 5- to 6-membered carbocyclic or heterocyclic ring

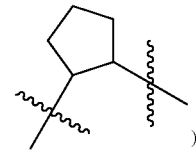

which is optionally substituted with one or more R$_A$. G is independently C$_5$-C$_6$carbocycle or 5- to 6-membered heterocycle, such as

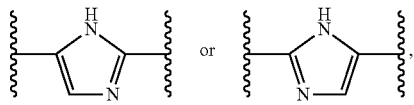 [SMILES: *c1cnc(*)[nH]1 ; *c1cnc(*)[nH]1]

and is independently optionally substituted with one or more R$_A$. T is preferably independently selected at each occurrence from —C(O)-L$_Y$'-N(R$_B$)C(O)-L$_S$"- or —C(O)-L$_Y$'-N(R$_B$)C(O)O-L$_S$"-. L$_Y$' is each independently L$_S$' and, preferably, is each independently C$_1$-C$_6$alkylene (e.g., —CH$_2$—) and optionally substituted with one or more substituents selected from R$_L$. T can also be, without limitation, selected from —C(O)-L$_Y$'-L$_S$"-, —C(O)-L$_Y$'-O-L$_S$"-, —C(O)-L$_Y$'-N(R$_B$)-L$_S$"-, or —C(O)-L$_Y$'-N(R$_B$)S(O)$_2$-L$_S$"-. In some cases when A is 5- or 6-membered carbocycle or heterocycle (e.g., phenyl such as

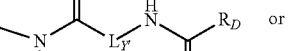

Y is

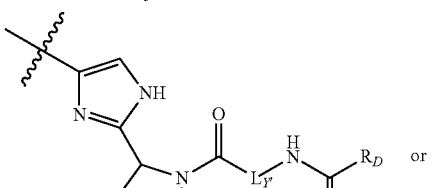

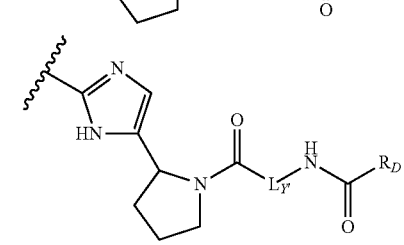

as described above, and Z is

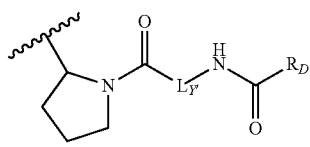

as described above. In some other cases when B is 5- or 6-membered carbocycle or heterocycle (e.g., phenyl such as

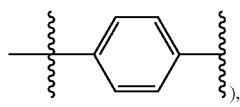 [SMILES: *c1ccc(*)cc1]

Y is

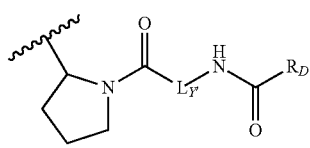

as described above, and Z is

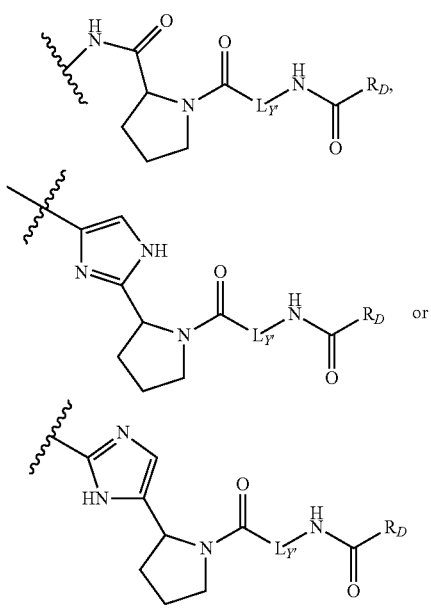

described above.

In another aspect, the present invention features compounds of Formula $I_A$ and pharmaceutically acceptable salts thereof.

$I_A$

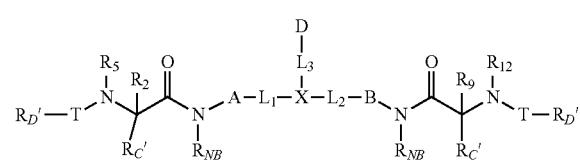

wherein:

$R_{NB}$ is each independently selected from $R_B$;
$R_C'$ is each independently selected from $R_C$;
$R_D'$ is each independently selected from $R_D$;
$R_2$ and $R_5$, taken together with the atoms to which they are attached, form a 3- to 12-membered heterocycle which is optionally substituted with one or more $R_4$;
$R_9$ and $R_{12}$, taken together with the atoms to which they are attached, form a 3- to 12-membered heterocycle which is optionally substituted with one or more $R_4$;
A, B, D, X, $L_1$, $L_2$, $L_3$, T, $R_A$, $R_B$, $R_C$, and $R_D$ are as described above in Formula I.

In this aspect, A and B preferably are independently selected from $C_5$-$C_6$carbocycle or 5- to 6-membered heterocycle, and are each independently optionally substituted with one or more $R_A$. More preferably, at least one of A and B is phenyl (e.g., 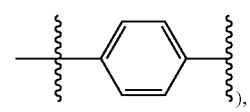), and is optionally substituted with one or more $R_A$. Highly preferably, both A and B are each independently phenyl (e.g., 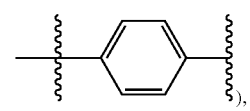), and are each independently optionally substituted with one or more $R_A$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

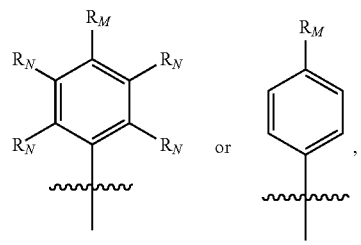

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

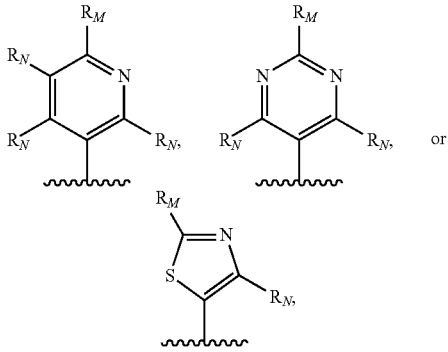

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

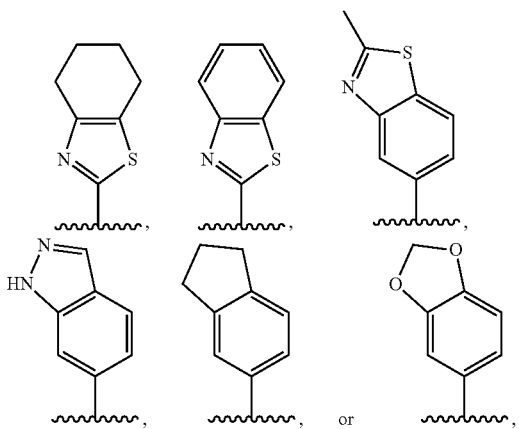

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C($CF_3$)$_2$—OH, —C($CH_3$)$_2$—CN, —C($CH_3$)$_2$—$CH_2$OH, or —C($CH_3$)$_2$—$CH_2 NH_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N($CH_2 CH_2$OMe)$_2$); —N($C_1$-$C_6$alkyl)($C_1$-$C_6$alkylene-O—$C_1$-$C_6$alkyl) (e.g. —N($CH_3$)($CH_2 CH_2$OMe)); —O—$C_1$-$C_6$alkyl (e.g., —O-Me, —O-Et, —O-isopropyl, —O-tert-butyl, —O-n-hexyl); —$C_1$-$C_6$haloalkyl (e.g., —OCF$_3$, —OCH$_2$CF$_3$); —O—$C_1$-$C_6$alkylene-piperidine (e.g., —O—$CH_2 CH_2$-1-piperidyl); —N($C_1$-$C_6$alkyl)C(O)O$C_1$-$C_6$alkyl (e.g., —N($CH_3$)C(O)O—$CH_2 CH$($CH_3$)$_2$), —N($C_1$-$C_6$alkyl)SO$_2 C_1$-$C_6$alkyl (e.g., —N($CH_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$ (e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

X preferably is $C_5$-$C_6$carbocycle, 5- to 6-membered heterocycle, or 6- to 12-membered bicycles

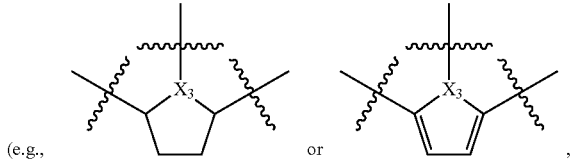

(e.g., or , wherein $X_3$ is N and is directly linked to -$L_3$-D), and is optionally substituted with one or more $R_4$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —$CH_2$— or —$CH_2CH_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

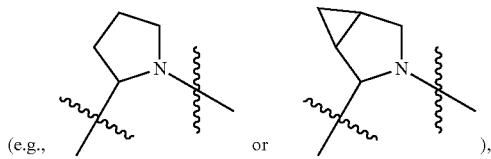 [SMILES: *C1CCCN1* ; *C1C2CC2CN1*]

(e.g., or ), which is optionally substituted with one or more $R_4$.

$R_9$ and $R_{12}$, taken together with the atoms to which they are attached, preferably form a 5- to 6-membered heterocycle or 6- to 12-membered bicycle

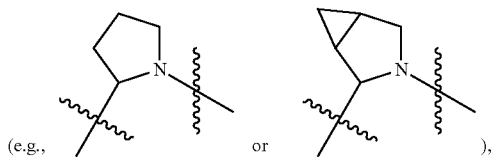

(e.g., or ), which is optionally substituted with one or more $R_4$.

-T-$R_D$' can be, without limitation, independently selected at each occurrence from —C(O)-$L_Y$'-, —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$"-$R_D$', wherein $L_Y$' is each independently $L_S$' and, preferably, is each independently $C_1$-$C_6$alkylene (e.g., —$CH_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —$CH_2$—) and optionally substituted with one or more substituents selected from $R_L$.

$R_{NB}$ and $R_C$' are preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, -$L_A$-SO$_2 R_S$, -$L_A$-C(O)N($R_S R_S$'), -$L_A$-N($R_S$)C(O)$R_S$', -$L_A$-N($R_S$)C(O)N($R_S R_S$"), -$L_A$-N($R_S$)SO$_2 R_S$', -$L_A$-SO$_2$N($R_S R_S$'), -$L_A$-N($R_S$)SO$_2$N($R_S$'$R_S$"), -$L_A$-N($R_S$)S(O)N($R_S$'$R_S$"), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S'$ and $L_S''$ preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A, B, and D are each independently phenyl, and are each independently optionally substituted with one or more $R_A$. Preferably, D is

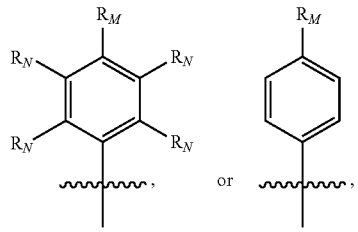

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D'$ is independently selected at each occurrence from —C(O)-$L_{Y'}$-N($R_B$)C(O)-$L_S''$-$R_D'$ or —C(O)-$L_{Y'}$-N($R_B$)C(O)O-$L_S''$-$R_D'$, wherein $L_{Y'}$ is $C_1$-$C_6$alkylene (e.g., —CH$_2$—) and optionally substituted with one or more substituents selected from $R_L$, and $L_S''$ preferably is bond. -T-$R_D'$ can also be, without limitation, selected from —C(O)-$L_{Y'}$-$L_S''$-$R_D'$, —C(O)-$L_{Y'}$-O-$L_S''$-$R_D'$, C(O)-$L_{Y'}$-N($R_B$)-$L_S''$-$R_D'$, or —C(O)-$L_{Y'}$-N($R_B$)S(O)$_2$-$L_S''$-$R_D'$.

In still another aspect, the present invention features compounds of Formula $I_B$ and pharmaceutically acceptable salts thereof:

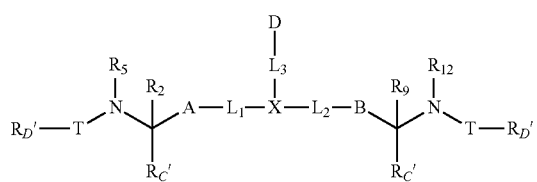

$I_B$ wherein:
$R_C'$ is each independently selected from $R_C$;
$R_D'$ is each independently selected from $R_D$;
$R_2$ and $R_5$, taken together with the atoms to which they are attached, form a 3- to 12-membered heterocycle which is optionally substituted with one or more $R_A$;
$R_9$ and $R_{12}$, taken together with the atoms to which they are attached, form a 3- to 12-membered heterocycle which is optionally substituted with one or more $R_A$;
A, B, D, X, $L_1$, $L_2$, $L_3$, T, $R_A$, $R_C$, and $R_D$ are as described above in Formula I.

In this aspect, A and B preferably are independently selected from 8- to 12-membered bicycles such as

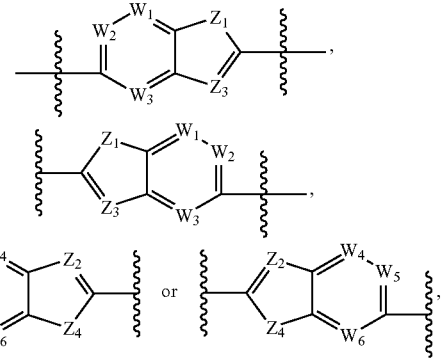

where $Z_1$ is independently selected at each occurrence from O, S, NH or CH$_2$, $Z_2$ is independently selected at each occurrence from N or CH, $Z_3$ is independently selected at each occurrence from N or CH, $Z_4$ is independently selected at each occurrence from O, S, NH or CH$_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from

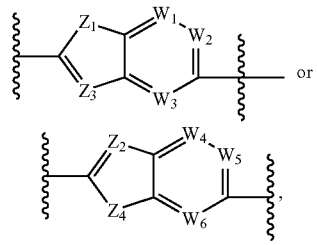

and is optionally substituted with one or more $R_A$; B is selected from

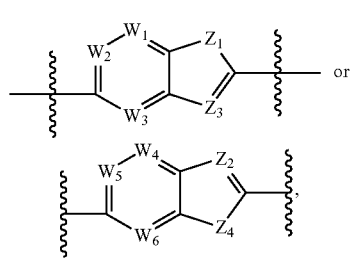

and is optionally substituted with one or more $R_M$ where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from

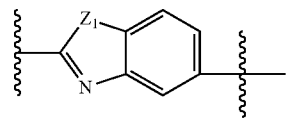

-continued

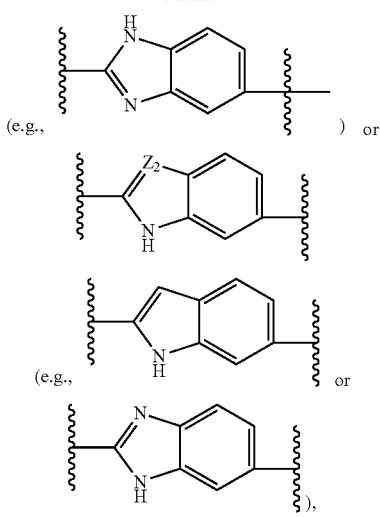

and is optionally substituted with one or more $R_A$; and B can be selected from

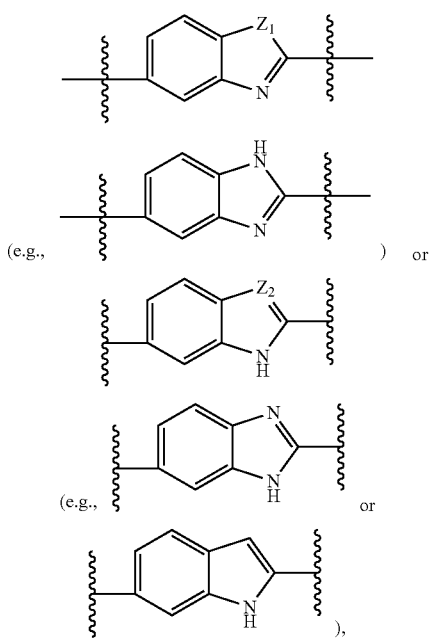

and is optionally substituted with one or more $R_A$.

Also preferably, A is

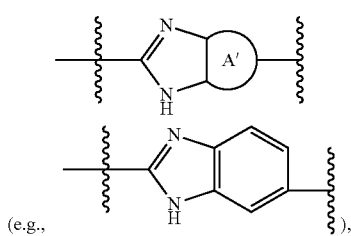

and B is

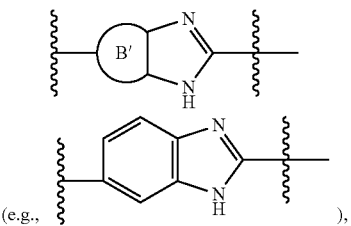

wherein A' and B' are independently selected from $C_5$-$C_6$carbocycle or 5- to 6-membered heterocycle, and A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

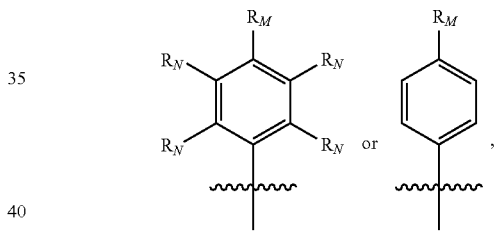

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

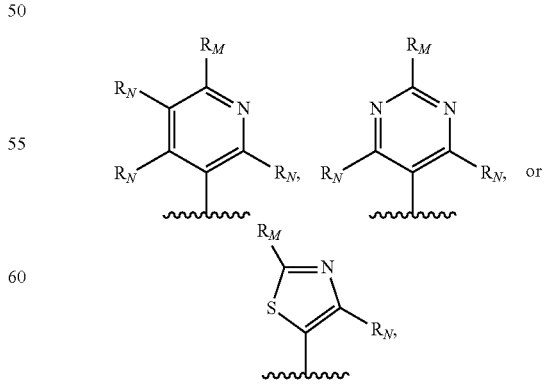

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

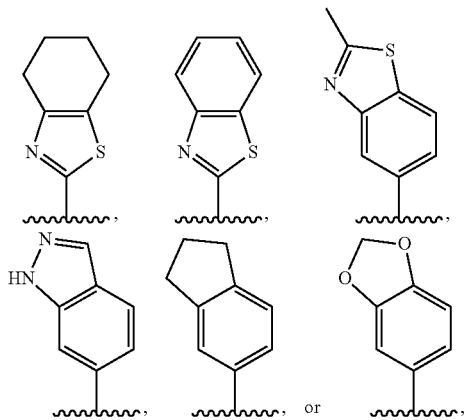

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)OC$_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$ (e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, CF$_3$).

X preferably is $C_5$-$C_6$carbocycle, 5- to 6-membered heterocycle, or 6- to 12-membered bicycles (e.g., 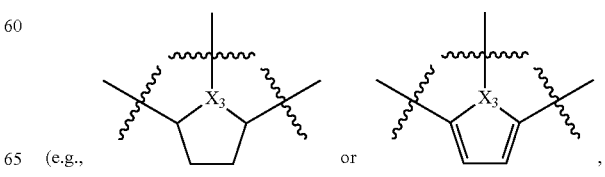

wherein $X_3$ is N and is directly linked to -$L_3$-D), and is optionally substituted with one or more $R_A$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

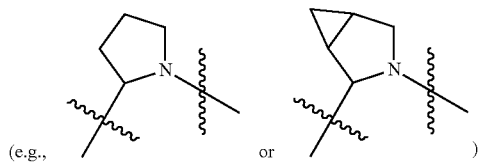 [SMILES: *C1CCCN1* ; *C1C2CC2CN1*]

which is optionally substituted with one or more $R_A$. $R_9$ and $R_{12}$, taken together with the atoms to which they are attached, preferably form a 5- to 6-membered heterocycle or 6- to 12-membered bicycle

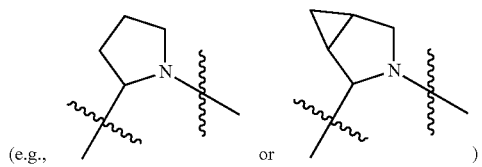 [SMILES: *C1CCCN1* ; *C1C2CC2CN1*]

which is optionally substituted with one or more $R_A$.

-T-$R_D$' can be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$"-$R_D$', wherein $L_Y$' is each independently $L_S$ and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_C$' is preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, -$L_A$-SO$_2 R_S$, -$L_A$-C(O)N($R_S R_S$'), -$L_A$-N($R_S$)C(O)$R_S$', -$L_A$-N($R_S$)C(O)N($R_S$'$R_S$"), -$L_A$-N($R_S$)SO$_2 R_S$', -$L_A$-SO$_2$N($R_S R_S$'), -$L_A$-N($R_S$)SO$_2$N($R_S$'$R_S$"), -$L_A$-N($R_S$)S(O)N($R_S$'$R_S$"), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A is

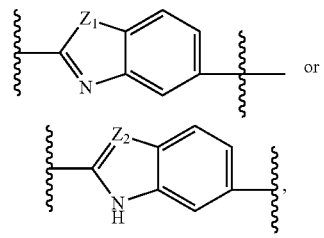

and is optionally substituted with one or more $R_A$; B is

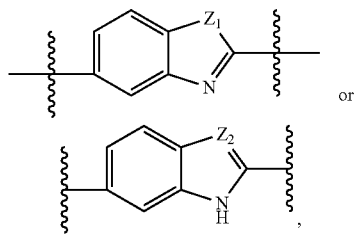

and is optionally substituted with one or more $R_A$; and D is $C_5$-$C_6$carbocycle or 5- to 6-membered heterocycle (e.g., phenyl), and is optionally substituted with one or more $R_A$. Preferably, D is

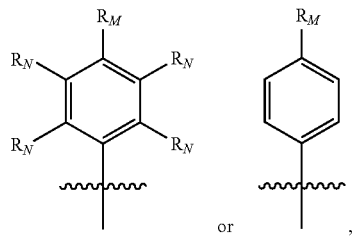

herein $R_M$ and $R_N$ are as defined above. $Z_1$ is independently selected at each occurrence from O, S, NH or $CH_2$; and $Z_2$ is independently selected at each occurrence from N or CH. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —$CH_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'.

In yet another aspect, the present invention further features compounds of Formula $I_C$ and pharmaceutically acceptable salts thereof.

$I_C$

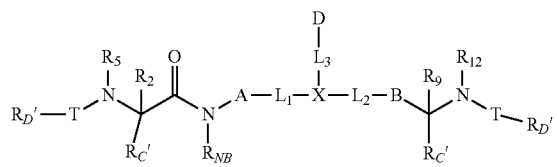

wherein:
$R_{NB}$ is $R_B$;
$R_C$' is each independently selected from $R_C$;
$R_D$' is each independently selected from $R_D$;
$R_2$ and $R_5$, taken together with the atoms to which they are attached, form a 3- to 12-membered heterocycle which is optionally substituted with one or more $R_A$;

$R_9$ and $R_{12}$, taken together with the atoms to which they are attached, form a 3- to 12-membered heterocycle which is optionally substituted with one or more $R_A$;
A, B, D, X, $L_1$, $L_2$, $L_3$, T, $R_A$, $R_B$, $R_C$, and $R_D$ are as described above in Formula I.

In this aspect, A preferably is $C_5$-$C_6$carbocycle or 5- to 6-membered heterocycle, and is optionally substituted with one or more $R_A$; and B preferably is 8- to 12-membered bicycle (such as

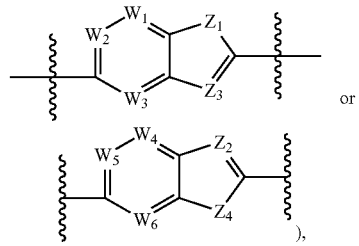

and is optionally substituted with one or more $R_A$. $Z_1$ is O, S, NH or $CH_2$; $Z_2$ is N or CH; $Z_3$ is N or CH; $Z_4$ is O, S, NH or $CH_2$; and $W_1$, $W_2$, $W_3$, $W_4$, $W_5$ and $W_6$ are each independently selected from CH or N.

More preferably, A is phenyl (e.g., 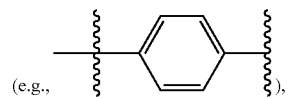), and is optionally substituted with one or more $R_A$; and B is

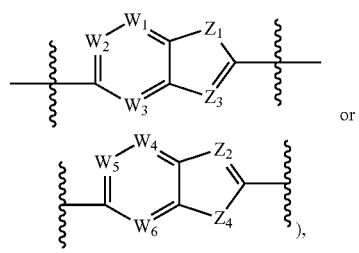

and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, B can be

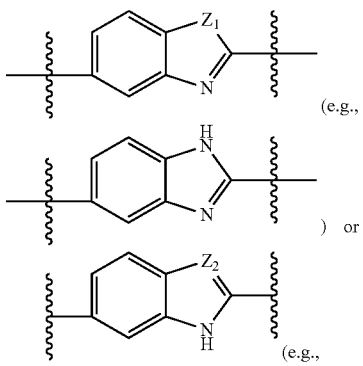

-continued

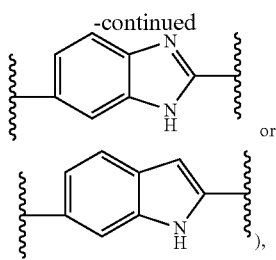 or

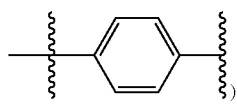), and is optionally substituted with one or more $R_A$.

Also preferably, A is $C_5$-$C_6$carbocycle (e.g., phenyl such as

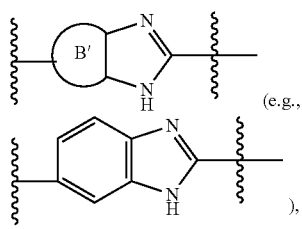)

or 5- to 6-membered heterocycle; and B is

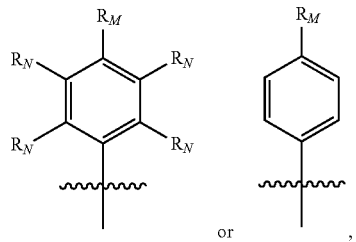 (e.g., ), wherein B' is selected from $C_5$-$C_6$carbocycle or 5- to 6-membered heterocycle. A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

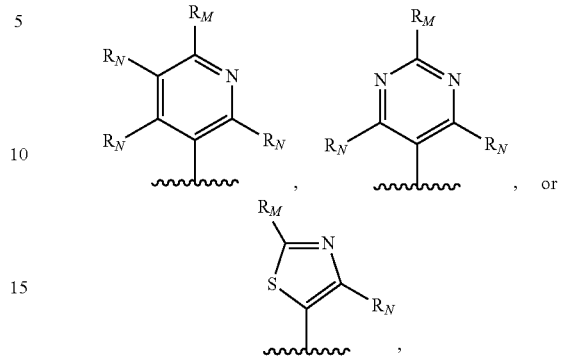

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

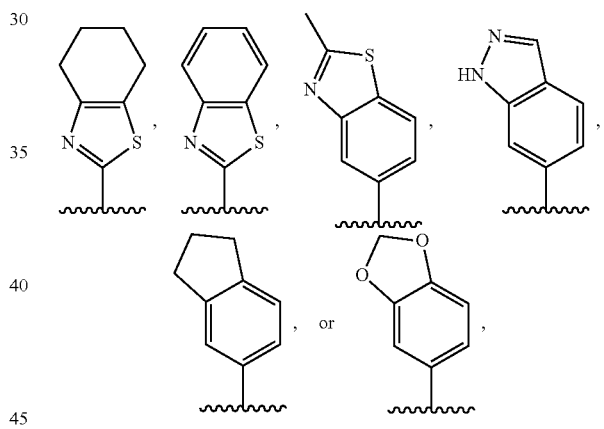

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is $-L_S-R_E$, wherein $L_S$ is a bond or $C_1-C_6$alkylene, and $R_E$ is $-N(R_SR_S')$, $-O-R_S$, $-C(O)R_S$, $-C(O)OR_S$, $-C(O)N(R_SR_S')$, $-N(R_S)C(O)R_S'$, $-N(R_S)C(O)OR_S'$, $-N(R_S)SO_2R_S'$, $-SO_2R_S$, $-SR_S$, or $-P(O)(OR_S)_2$, wherein $R_S$ and $R_S'$ can be, for example, each independently selected at each occurrence from (1) hydrogen or (2) $C_1-C_6$alkyl optionally substituted at each occurrence with one or more halogen, hydroxy, $-O-C_1-C_6$alkyl or 3- to 6-membered heterocycle; or $R_M$ is $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3-C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl, $C_2-C_6$haloalkynyl, $-C(O)OR_S$, or $-N(R_SR_S')$. More preferably, $R_M$ is halogen (e.g., fluoro, chloro, bromo, iodo), hydroxy, mercapto, amino, carboxy, or $C_1-C_6$alkyl (e.g., methyl, isopropyl, tert-butyl), $C_2-C_6$alkenyl or $C_2-C_6$alkynyl, each of which is independently optionally substituted at each occurrence with one or more substituents selected from halogen, hydroxy, mercapto, amino, cyano, or carboxy. For example $R_M$ is $CF_3$, $-C(CF_3)_2-OH$, $-C(CH_3)_2-CN$, $-C(CH_3)_2-CH_2OH$, or $-C(CH_3)_2-CH_2NH_2$. Also preferably $R_M$ is $-L_S-R_E$ where $L_S$ is a bond and $R_E$ is $-N(R_SR_S')$, $-O-R_S$, $-N(R_S)C(O)OR_S'$, $-N(R_S)SO_2R_S'$, $-SO_2R_S$, or $-SR_S$. For example where $L_S$ is a bond, $R_E$ is $-N(C_1-C_6$alkyl$)_2$ (e.g., $-NMe_2$); $-N(C_1-C_6$alkylene-O$-C_1-C_6$alkyl$)_2$ (e.g. $-N(CH_2CH_2OMe)_2$); $-N(C_1-C_6$alkyl)$(C_1-C_6$alkylene-O$-C_1-C_6$alkyl) (e.g. $-N(CH_3)(CH_2CH_2OMe)$); $-O-C_1-C_6$alkyl (e.g., $-O-Me$, $-O-Et$, $-O$-isopropyl, $-O$-tert-butyl, $-O$-n-hexyl); $-O-C_1-C_6$haloalkyl (e.g., $-OCF_3$, $-OCH_2CF_3$); $-O-C_1-C_6$alkylene-piperidine (e.g., $-O-CH_2CH_2$-1-piperidyl); $-N(C_1-C_6$alkyl)$C(O)OC_1-C_6$alkyl (e.g., $-N(CH_3)C(O)O-CH_2CH(CH_3)_2$), $-N(C_1-C_6$alkyl)$SO_2C_1-C_6$alkyl (e.g., $-N(CH_3)SO_2CH_3$); $-SO_2C_1-C_6$alkyl (e.g., $-SO_2Me$); $-SO_2C_1-C_6$haloalkyl (e.g., $-SO_2CF_3$); or $-S-C_1-C_6$haloalkyl (e.g., $SCF_3$). Also preferably $R_M$ is $-L_S-R_E$ where $L_S$ is $C_1-C_6$alkylene (e.g., $-CH_2-$, $-C(CH_3)_2-$, $-C(CH_3)_2-CH_2-$) and $R_E$ is $-O-R_S$, $-C(O)OR_S$, $-N(R_S)C(O)OR_S'$, or $-P(O)(OR_S)_2$. For example $R_M$ is $-C_1-C_6$alkylene-O$-R_S$ (e.g., $-C(CH_3)_2-CH_2-OMe$); $-C_1-C_6$alkylene-C(O)OR_S$ (e.g., $-C(CH_3)_2-C(O)OMe$); $-C_1-C_6$alkylene-N(R_S)C(O)OR_S'$ (e.g., $-C(CH_3)_2-CH_2-NHC(O)OCH_3$); or $-C_1-C_6$alkylene-P(O)(OR_S)_2$ (e.g., $-CH_2-P(O)(OEt)_2$). Also more preferably $R_M$ is $C_3-C_6$carbocycle or 3- to 6-membered heterocycle, each of which is independently optionally substituted with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl, $C_2-C_6$haloalkynyl, $-C(O)OR_S$, or $-N(R_SR_S')$. For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1-C_6$alkyl which is optionally substituted with one or more substituents selected from halogen, hydroxy, mercapto, amino or carboxy (e.g., tert-butyl, $CF_3$).

X preferably is $C_5-C_6$carbocycle, 5- to 6-membered heterocycle, or 6- to 12-membered bicycle (e.g., 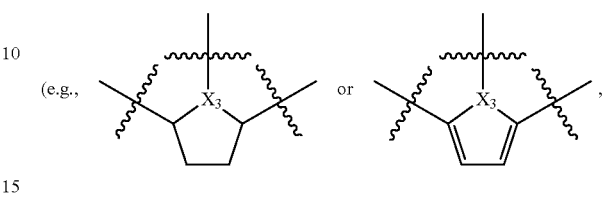

wherein $X_3$ is N and is directly linked to $-L_3-D$), and is optionally substituted with one or more $R_A$. Non-limiting examples of X are described hereinabove.

$L_1$ and $L_2$ are preferably independently bond or $C_1-C_6$alkylene, $L_3$ is preferably selected from bond, $C_1-C_6$alkylene or $-C(O)-$, and $L_1$, $L_2$, and $L_3$ are each independently optionally substituted with one or more $R_L$. More preferably, $L_1$, $L_2$ and $L_3$ are each independently bond or $C_1-C_6$alkylene (e.g., $-CH_2-$ or $-CH_2CH_2-$), and are each independently optionally substituted with one or more $R_L$. Highly preferably, $L_1$, $L_2$ and $L_3$ are bond. $L_1$ and $L_2$ can be the same or different.

$R_2$ and $R_5$, taken together with the atoms to which they are attached, preferably form a 5- to 6-membered heterocycle or 6- to 12-membered bicycle (e.g., 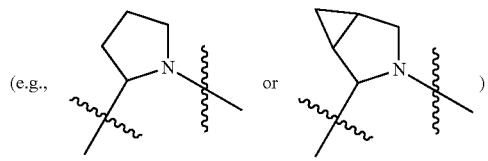 [SMILES: *C1CCCN1* ; *C1C2CC2CN1*] )

which is optionally substituted with one or more $R_A$. $R_9$ and $R_{12}$, taken together with the atoms to which they are attached, preferably form a 5- to 6-membered heterocycle or 6- to 12-membered bicycle (e.g., 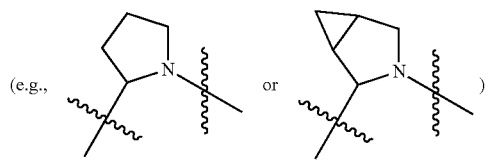 [SMILES: *C1CCCN1* ; *C1C2CC2CN1*] )

which is optionally substituted with one or more $R_A$.

$-T-R_D'$ can be, without limitation, independently selected at each occurrence from $-C(O)-L_{Y'}-R_D'$, $-C(O)O-L_{Y'}-R_D'$, $-C(O)-L_{Y'}-N(R_B)C(O)-L_S''-R_D'$, $-C(O)-L_{Y'}-N(R_B)C(O)O-L_S''-R_D'$, $-N(R_B)C(O)-L_{Y'}-N(R_B)C(O)-L_S''-R_D'$, $-N(R_B)C(O)-L_{Y'}-N(R_B)C(O)O-L_S''-R_D'$, or $-N(R_B)C(O)-L_{Y'}-N(R_B)-L_S''-R_D'$, wherein $L_{Y'}$ is each independently $L_S'$ and, preferably, is each independently $C_1-C_6$alkylene (e.g., $-CH_2-$) and optionally substituted with one or more substituents selected from $R_L$. Preferably, $-T-R_D'$ is independently selected at each occurrence from $-C(O)-L_{Y'}-M'-L_S''-R_D'$ or $-N(R_B)C(O)-L_{Y'}-M'-L_S''-R_D'$. More preferably, $-T-R_D'$ is independently selected at each occurrence from $-C(O)-L_{Y'}-N(R_B)C(O)-L_S''-R_D'$ or $-C(O)-L_{Y'}-N(R_B)C(O)$ O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_{NB}$ and $R_C$' are preferably hydrogen, and $R_D$' preferably is independently selected at each occurrence from $R_E$. More preferably, $R_D$ is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, -$L_A$-SO$_2 R_S$, -$L_A$-C(O)N($R_S R_S$'), -$L_A$-N($R_S$)C(O)$R_S$', -$L_A$-N($R_S$)C(O)N($R_S$'$R_S$"), -$L_A$-N($R_S$)SO$_2 R_S$', -$L_A$-SO$_2$N($R_S R_S$'), -$L_A$-N($R_S$)SO$_2$N($R_S$'$R_S$"), -$L_A$-N($R_S$)S(O)N($R_S$'$R_S$"), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$') or -$L_A$-C(O)N($R_S$)C(O)—$R_S$', wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

In one embodiment of this aspect, A is phenyl, and is optionally substituted with one or more $R_A$; and B is

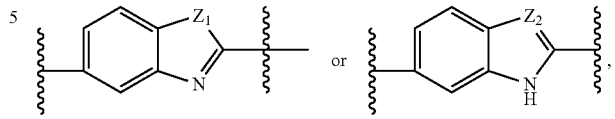

and is optionally substituted with one or more $R_A$, wherein $Z_1$ is O, S, NH or CH$_2$; and $Z_2$ is N or CH. D is $C_5$-$C_6$carbocycle or 5- to 6-membered heterocycle (e.g., phenyl), and is optionally substituted with one or more $R_A$. Preferably, D

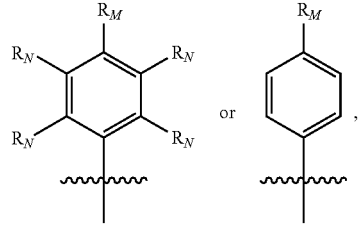

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'.

In yet another aspect, the present invention features compounds of Formula $I_D$ and pharmaceutically acceptable salts thereof.

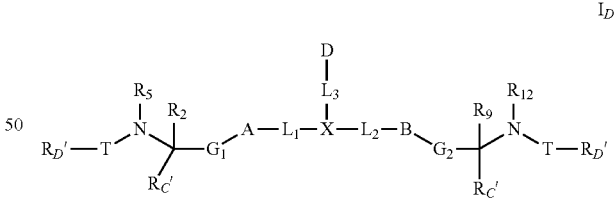

$I_D$ wherein:
  $G_1$ and $G_2$ are each independently selected from $C_5$-$C_6$carbocycle or 5- to 6-membered heterocycle, and are each independently optionally substituted with one or more $R_A$;
  $R_C$' is each independently selected from $R_C$;
  $R_D$' is each independently selected from $R_D$;
  $R_2$ and $R_5$, taken together with the atoms to which they are attached, form a 3- to 12-membered heterocycle which is optionally substituted with one or more $R_A$;
  $R_9$ and $R_{12}$, taken together with the atoms to which they are attached, form a 3- to 12-membered heterocycle which is optionally substituted with one or more $R_A$;

A, B, D, X, $L_1$, $L_2$, $L_3$, T, $R_A$, $R_C$, and $R_D$ are as described above in Formula I.

In this aspect, A and B preferably are independently selected from $C_5$-$C_6$carbocycle or 5- to 6-membered heterocycle, and are each independently optionally substituted with one or more $R_A$. More preferably, at least one of A and B is phenyl

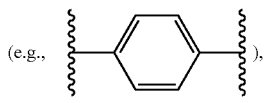

and is optionally substituted with one or more $R_A$. Highly preferably, both A and B are each independently phenyl

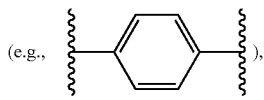

and are each independently optionally substituted with one or more $R_A$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

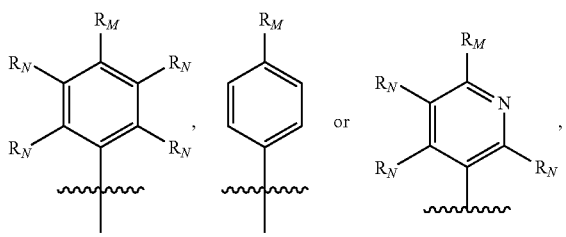

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

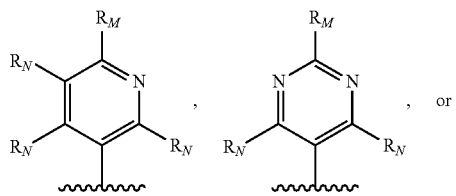

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

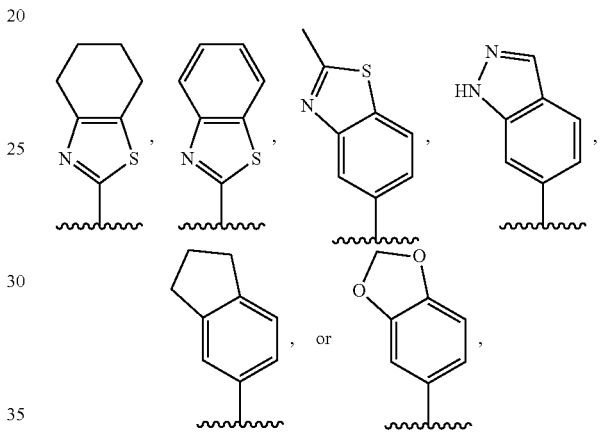

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)$OR_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C($CF_3$)$_2$—OH, —C($CH_3$)$_2$—CN, —C($CH_3$)$_2$—$CH_2$OH, or —C($CH_3$)—$CH_2NH_2$. Also preferably $R_M$ is -$L_S$-$R_E$ where $L_S$ is a bond and $R_E$ is —N($R_S R_{S'}$), —O—$R_S$, —N($R_S$)C(O)$OR_S'$, —N($R_S$)$SO_2 R_S'$, —$SO_2 R_S$, or —$SR_S$. For example where $L_S$ is a bond, $R_E$ is —N($C_1$-$C_6$alkyl)$_2$ (e.g., —$NMe_2$); —N($C_1$-$C_6$alkylene-O—$C_1$-$C_6$alkyl)$_2$ (e.g. —N($CH_2 CH_2 OMe$)$_2$); —N($C_1$-$C_6$alkyl)(C(—$C_1$-$C_6$alkylene-O—$C_1$-$C_6$alkyl) (e.g. —N($CH_3$)($CH_2 CH_2 OMe$)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —$OCF_3$, —$OCH_2 CF_3$); —O—$C_1$-$C_6$alkylene-piperidine (e.g., —O—$CH_2 CH_2$-1-piperidyl); —N($C_1$-$C_6$alkyl)C(O)O$C_1$-$C_6$alkyl (e.g., —N($CH_3$)C(O)O—$CH_2 CH(CH_3)_2$), —N($C_1$-$C_6$alkyl) $SO_2 C_1$-$C_6$alkyl (e.g., —N($CH_3$)$SO_2 CH_3$); —$SO_2 C_1$-$C_6$alkyl (e.g., —$SO_2 Me$); —$SO_2 C_1$-$C_6$haloalkyl (e.g., —$SO_2 CF_3$); or —S—$C_1$-$C_6$haloalkyl (e.g., $SCF_3$). Also preferably $R_M$ is -$L_S$-$R_E$ where $L_S$ is $C_1$-$C_6$alkylene (e.g., —$CH_2$—, —C($CH_3$)$_2$—, —C($CH_3$)$_2$—$CH_2$—) and $R_E$ is —O—$R_S$, —C(O)$OR_S$, —N($R_S$)C(O)$OR_S'$, or —P(O)($OR_S$)$_2$. For example $R_M$ is —$C_1$-$C_6$alkylene-O—$R_S$ (e.g., —C($CH_3$)$_2$—$CH_2$—OMe); —$C_1$-$C_6$alkylene-C(O)$OR_S$ (e.g., —C($CH_3$)$_2$—C(O)OMe); —$C_1$-$C_6$alkylene-N($R_S$)C(O)$OR_S'$ (e.g., —C($CH_3$)$_2$—$CH_2$—NHC(O)$OCH_3$); or —$C_1$-$C_6$alkylene-P(O)($OR_S$)$_2$ (e.g., —$CH_2$—P(O)($OEt$)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)$OR_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

X preferably is $C_5$-$C_6$carbocycle, 5- to 6-membered heterocycle, or 6- to 12-membered bicycles

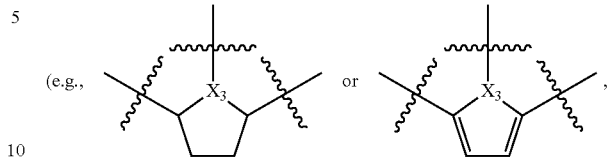

(e.g., or , wherein $X_3$ is N and is directly linked to -$L_3$-D), and is optionally substituted with one or more $R_A$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —$CH_2$— or —$CH_2 CH_2$—), and are each independently optionally substituted with one or more $R_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle

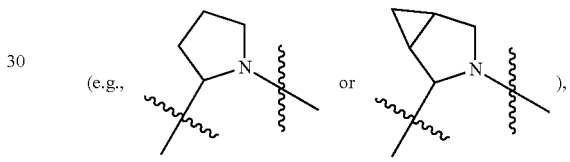

(e.g., or ), which is optionally substituted with one or more $R_A$.

$R_9$ and $R_{12}$, taken together with the atoms to which they are attached, preferably form a 5- to 6-membered heterocycle or 6- to 12-membered bicycle

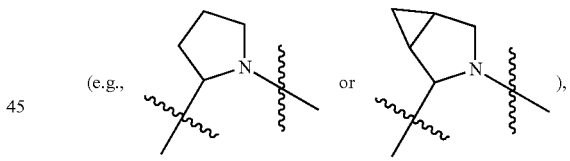

(e.g., or ), which is optionally substituted with one or more $R_A$.

$G_1$ and $G_2$ preferably are each independently selected from

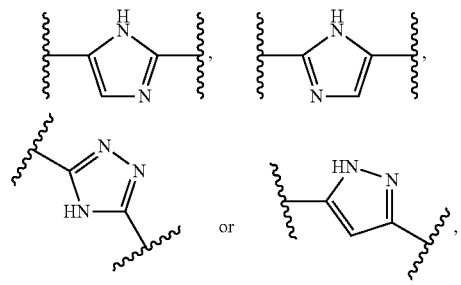

and are each independently optionally substituted with one or more $R_A$ (e.g., one or more chloro or bromo). More preferably, $G_1$ is

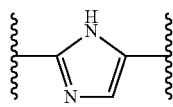 [SMILES: *c1cnc(*)[nH]1]

(including any tautomer thereof), and G$_2$ is

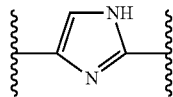 [SMILES: *c1c[nH]c(*)n1]

(including any tautomer thereof), and each G$_1$ and G$_2$ is independently optionally substituted with one or more R$_A$ (e.g., one or more chloro or bromo).

-T-R$_D$' can be, without limitation, independently selected at each occurrence from —C(O)-L$_Y$'-, —C(O)O-L$_Y$'-R$_D$', —C(O)-L$_Y$'-N(R$_B$)C(O)-L$_S$"-R$_D$', —C(O)-L$_Y$'-N(R$_B$)C(O)O-L$_S$"-R$_D$', —N(R$_B$)C(O)-L$_Y$'-N(R$_B$)C(O)-L$_S$"-R$_D$', —N(R$_B$)C(O)-L$_Y$'-N(R$_B$)C(O)O-L$_S$"-R$_D$', or —N(R$_B$)C(O)-L$_Y$'-N(R$_B$)-L$_S$"-R$_D$', wherein L$_Y$' is each independently L$_S$' and, preferably, is each independently C$_1$-C$_6$alkylene (e.g., —CH$_2$—) and optionally substituted with one or more substituents selected from R$_L$. Preferably, -T-R$_D$' is independently selected at each occurrence from —C(O)-L$_Y$'-M'-L$_S$"-R$_D$' or —N(R$_B$)C(O)-L$_Y$'-M'-L$_S$"-R$_D$'. More preferably, -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$'. Highly preferably, -T-R$_D$' is independently selected at each occurrence from —C(O)-L$_Y$'-N(R$_B$)C(O)—R$_D$' or —C(O)-L$_Y$'-N(R$_B$)C(O)O—R$_D$', wherein L$_Y$' preferably is each independently C$_1$-C$_6$alkylene (e.g., —CH$_2$—) and optionally substituted with one or more substituents selected from R$_L$.

R$_C$' is preferably hydrogen, and R$_D$' preferably is independently selected at each occurrence from R$_E$. More preferably, R$_D$' is independently selected at each occurrence from C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, C$_3$-C$_6$carbocycle or 3- to 6-membered heterocycle; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

R$_A$ preferably is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl; or -L$_A$-O—R$_S$, -L$_A$-S—R$_S$, -L$_A$-C(O)R$_S$, -L$_A$-OC(O)R$_S$, -L$_A$-C(O)OR$_S$, -L$_A$-N(R$_S$R$_S$'), -L$_A$-S(O)R$_S$, -L$_A$-SO$_2$R$_S$, -L$_A$-C(O)N(R$_S$R$_S$'), -L$_A$-N(R$_S$)C(O)R$_S$', -L$_A$-N(R$_S$)C(O)N(R$_S$'R$_S$"), -L$_A$-N(R$_S$)SO$_2$R$_S$', -L$_A$-SO$_2$N(R$_S$R$_S$'), -L$_A$-N(R$_S$)SO$_2$N(R$_S$'R$_S$"), -L$_A$-N(R$_S$)S(O)N(R$_S$'R$_S$"), -L$_A$-OS(O)—R$_S$, -L$_A$-OS(O)$_2$—R$_S$, -L$_A$-S(O)$_2$OR$_S$, -L$_A$-S(O)OR$_S$, -L$_A$-OC(O)OR$_S$, -L$_A$-N(R$_S$)C(O)OR$_S$', -L$_A$-OC(O)N(R$_S$R$_S$'), -L$_A$-N(R$_S$)S(O)—R$_S$', -L$_A$-S(O)N(R$_S$R$_S$') or -L$_A$-C(O)N(R$_S$)C(O)—R$_S$', wherein L$_A$ is bond, C$_1$-C$_6$alkylene, C$_2$-C$_6$alkenylene or C$_2$-C$_6$alkynylene.

More preferably, R$_A$ is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

Highly preferably, R$_A$ is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

L$_S$, L$_S$' and L$_S$" preferably are each independently selected at each occurrence from bond; or C$_1$-C$_6$alkylene, C$_2$-C$_6$alkenylene or C$_2$-C$_6$alkynylene.

A and B can be the same or different. Likewise, L$_1$ and L$_2$ can be the same or different.

In one embodiment of this aspect, A, B, and D are each independently phenyl, and are each independently optionally substituted with one or more R$_A$; and G$_1$ is

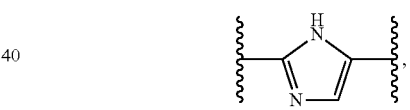

G$_2$ is

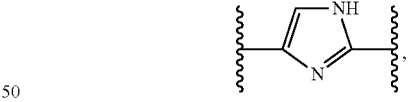

and each G$_1$ and G$_2$ is independently optionally substituted with one or more R$_A$ (e.g., one or more chloro or bromo). Preferably, D is

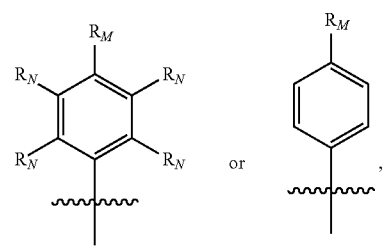

wherein $R_M$ and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'.

The present invention also features the compounds of Formulae I, $I_A$, $I_B$, $I_C$ and $I_D$ as described herein (including each embodiment described herein) or salts thereof, except that D is $C_3$-$C_{12}$carbocycle or 3- to 12-membered heterocycle which is substituted with J and optionally substituted with one or more $R_A$, where J is $C_3$-$C_{12}$carbocycle or 3- to 12-membered heterocycle and is optionally substituted with one or more $R_A$, or J is —SF$_5$. Preferably, D is $C_5$-$C_6$carbocycle, 5- to 6-membered heterocycle or 6- to 12-membered bicycle and is optionally substituted with one or more $R_A$, and J is $C_3$-$C_6$carbocycle or 3- to 6-membered heterocycle and is optionally substituted with one or more $R_A$. More preferably, D is $C_5$-$C_6$carbocycle or 5- to 6-membered heterocycle and is optionally substituted with one or more $R_A$, and J is $C_3$-$C_6$carbocycle or 3- to 6-membered heterocycle and is optionally substituted with one or more $R_A$. Highly preferably, D is phenyl substituted with J and optionally substituted with one or more $R_A$, where J is $C_3$-$C_6$carbocycle or 3- to 6-membered heterocycle and is optionally substituted with one or more $R_A$. Preferred $R_A$s are as described above. In one embodiment, D is

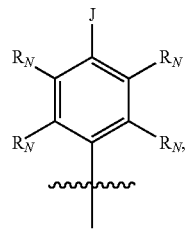

wherein each $R_N$ is independently selected from $R_D$ and preferably is hydrogen, and J is as defined above and preferably is $C_3$-$C_6$carbocycle or 3- to 6-membered heterocycle optionally substituted with one or more $R_A$. In another embodiment, D is

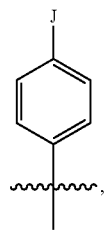

and J is $C_3$-$C_6$carbocycle or 3- to 6-membered heterocycle and is optionally substituted with one or more $R_A$.

Moreover, the present invention features the compounds of Formulae I, $I_A$, $I_B$, $I_C$ and $I_D$ as described herein (including each embodiment described herein, as well as where D is $C_3$-$C_{12}$carbocycle or 3- to 12-membered heterocycle substituted with J and optionally substituted with one or more $R_A$ as described hereinabove) or salts thereof, except that X is optionally substituted with one or more $R_A$'. Specific examples of X are as described above, such as

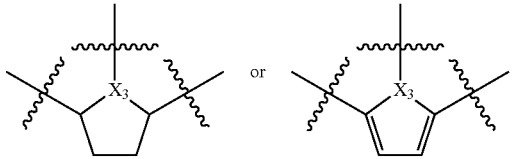

wherein $X_3$ is N and is directly linked to -$L_3$-D. Each $R_A$' is independently $R_A$; or $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is optionally substituted with one or more $R_L$. $R_A$ is as defined above. In one embodiment, each $R_A$' is independently $R_A$; or $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is optionally substituted with one or more substituents selected from halogen, hydroxy, mercapto, amino, carboxy, nitro, oxo, phosphonoxy, phosphono, thioxo, formyl or cyano. In another embodiments, each $R_A$' is independently selected from $R_A$; or $C_1$-$C_{10}$alkyl, $C_2$-$C_{10}$alkenyl or $C_2$-$C_{10}$alkynyl, each of which contains 0, 1, 2, 3, 4 or 5 O and is optionally substituted with one or more $R_L$. In a further embodiment, each $R_A$' is independently selected from $C_1$-$C_{10}$alkyl, $C_2$-$C_{10}$alkenyl or $C_2$-$C_{10}$alkynyl, each of which contains 0, 1, 2 or 3 O and is optionally substituted with one or more substituents selected from halogen, hydroxy, mercapto, amino, carboxy, nitro, oxo, phosphonoxy, phosphono, thioxo, formyl or cyano.

In another aspect of the invention, each $R_A$' is independently $R_A$ or —($R_X$—$R_Y$)$_N$—($R_X$—$R_Y$'), wherein N is 0, 1, 2, 3, 4; each $R_X$ is independently O, S or N($R_B$); each $R_Y$ is independently $C_1$-$C_6$alkylene, $C_2$-$C_6$alkenylene or $C_2$-$C_6$alkynylene each of which is optionally substituted with one or more substituents selected from halogen, hydroxy, mercapto, amino, carboxy, nitro, oxo, phosphonoxy, phosphono, thioxo, formyl or cyano; and $R_Y$' is independently $C_1$-$C_6$alkyl, $C_2$-$C_6$alkenyl or $C_2$-$C_6$alkynyl each of which is optionally substituted with one or more substituents selected from halogen, hydroxy, mercapto, amino, carboxy, nitro, oxo, phosphonoxy, phosphono, thioxo, formyl or cyano. $R_A$ and $R_B$ are as defined above. In one embodiment, each $R_X$ is O. For example, each $R_A$' is selected from —(O—$C_1$-$C_6$alkylene)$_N$-(O—$C_1$-$C_6$alkyl), wherein N preferably is 0, 1, 2 or 3.

In addition, the present invention features the compounds of Formulae I, $I_A$, $I_B$, $I_C$ and $I_D$ as described herein (including each embodiment described herein, as well as where D is $C_3$-$C_{12}$carbocycle or 3- to 12-membered heterocycle substituted with J and optionally substituted with one or more $R_A$ as described hereinabove, or where X is optionally substituted with one or more $R_A$' as described herein above), wherein:

$R_E$ is independently selected at each occurrence from —O—$R_S$, —S—$R_S$, —C(O)$R_S$, —OC(O)$R_S$, —C(O)OR$_S$, —N($R_S R_S$'), —S(O)$R_S$, —SO$_2 R_S$, —C(O)N($R_S R_S$'), —N($R_S$)C(O)$R_S$', —N($R_S$)C(O)N($R_S$'$R_S$"), —N($R_S$)SO$_2 R_S$', —SO$_2$N($R_S R_S$'), —N($R_S$)SO$_2$N($R_S$'$R_S$"), —N($R_S$)S(O)N($R_S$'$R_S$"), —OS(O)—$R_S$, —OS(O)$_2$—$R_S$, —S(O)$_2$OR$_S$, —S(O)OR$_S$, —OC(O)OR$_S$, —N($R_S$)C(O)OR$_S$', —OC(O)N($R_S R_S$'), —N($R_S$)S(O)—$R_S$', —S(O)N($R_S R_S$'), —P(O)(OR$_S$)$_2$, or —C(O)

$N(R_S)C(O)$—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$, or —$N(R_SR_S')$; and $R_S$, $R_S'$ and $R_S''$ are each independently selected at each occurrence from hydrogen; $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —O—$C_1$-$C_6$alkyl, —O—$C_1$-$C_6$alkylene-O—$C_1$-$C_6$alkyl, or 3- to 6-membered carbocycle or heterocycle; or 3- to 6-membered carbocycle or heterocycle; wherein each 3- to 6-membered carbocycle or heterocycle in $R_S$, $R_S'$ or $R_S'$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibuytl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer, and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The invention encompasses each conformational isomer of these compounds and mixtures thereof.

Certain compounds of the invention may also exist in zwitterionic form and the invention encompasses each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., A, B, D, X, $L_1$, $L_2$, $L_3$, Y, Z, T, $R_A$ or $R_B$'). Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$carbocyclyl$C_1$-$C_6$alkyl refers to a $C_3$-$C_6$carbocyclyl appended to the parent molecular moiety through a $C_1$-$C_6$alkyl group.

Unless otherwise specified, when a linking element links two other elements in a depicted chemical structure, the leftmost-described component of the linking element is bound to the left element in the depicted structure, and the rightmost-described component of the linking element is bound to the right element in the depicted structure. To illustrate, if the chemical structure is -$L_S$-M-$L_S$'- and M is —N($R_B$)S(O)—, then the chemical structure is -$L_S$-N($R_B$)S(O)-$L_S$'-.

If a linking element in a depicted structure is a bond, then the element left to the linking element is joined directly to the element right to the linking element via a covalent bond. For example, if a chemical structure is depicted as -$L_S$-M-$L_S$'- and M is selected as bond, then the chemical structure will be -$L_S$-$L_S$'-. If two or more adjacent linking elements in a depicted structure are bonds, then the element left to these linking elements is joined directly to the element right to these linking elements via a covalent bond. For instance, if a chemical structure is depicted as -$L_S$-M-$L_S$'-M'-$L_S$''-, and M and $L_S$' are selected as bonds, then the chemical structure will be -$L_S$-M'-$L_S$''-. Likewise, if a chemical structure is depicted as -$L_S$-M-$L_S$'-M'-$L_S$''-, and M, $L_S$' and M' are bonds, then the chemical structure will be -$L_S$-$L_S$''-.

When a chemical formula is used to describe a moiety, the dash(s) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple bonds. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—H(CH(CH$_2$CH$_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom. Where a carbocycle group is a divalent moiety linking two other elements in a depicted chemical structure (such as A in Formula I), the carbocycle group can be attached to the two other elements through any two substitutable ring atoms. Likewise, where a carbocycle group is a trivalent moiety linking three other elements in a depicted chemical structure (such as X in Formula I), the carbocycle group can be attached to the three other elements through any three substitutable ring atoms, respectively.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group. Where a heterocycle group is a divalent moiety that links two other elements in a depicted chemical structure (such as A in Formula I), the heterocycle group can be attached to the two other elements through any two substitutable ring atoms. Likewise, where a heterocycle group is a trivalent moiety that links three other elements in a depicted chemical structure (such as X in Formula I), the heterocycle group can be attached to the three other elements through any three substitutable ring atoms, respectively.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl"), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5, 2-oxadiazinyl), morpholinyl, azepinyl, oxepinyl, thiepinyl, thiomorpholinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl" or indazolyl), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, 4,5,6,7-tetrahydrobenzo[d]thiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may also be, without limitation, a spiro ring system, such as, for example, 1,4-dioxa-8-azaspiro[4.5]decanyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

═════ in a chemical formula refers to a single or double bond.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., Design of Prodrugs, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, Protecting Groups in Chemical Synthesis ($3^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The compounds of the present invention can be prepared using a variety of methods. As a non-limiting example, the compounds of the present invention can be prepared according to Scheme I starting from compounds of Formula II (e.g., n=0 to 8), Formula V ($X_4$ can be, for example, O or $NR_A$, where $R_A$ is as described hereinabove and is preferably H or $R_E$ as defined above such as $C_1$-$C_6$alkyl, 3- to 12-membered carbocycle or heterocycle, —C(O)$R_S$, —C(O)O$R_S$, —C(O)N($R_S R_S$'), —$SO_2$N($R_S R_S$'), —S(O)$_2$O$R_S$, —S(O)O$R_S$, —S(O)N($R_S R_S$'), or a suitable protecting group such as Boc or Fmoc), or Formula VIII (E can be, for example, 3- to 7-membered carbocycle or heterocycle and is optionally substituted with one or more $R_A$), wherein A, B, D, Y, Z and $R_A$ are as described above. The 1,4-diketones II, V, and VIII can be reduced to the 1,4-diols using the methods described below, and the resultant racemic, enantiomerically enriched, or meso 1,4-diols may be converted to the dimesylates III, VI, or IX, or alternatively to ditriflates, ditosylates, or dihalides by the methods described below. The dimesylates III, VI, and IX, ditriflates, ditosylates, or dihalides may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under the conditions described below to give the compounds of the invention. $L_1$ and $L_2$ can be readily introduced to Formulae II, V and VIII, as appreciated by those skilled in the art in light of the present invention. Likewise, $D-L_3-NH_2$ can be used instead of $D-NH_2$, as appreciated by those skilled in the art.

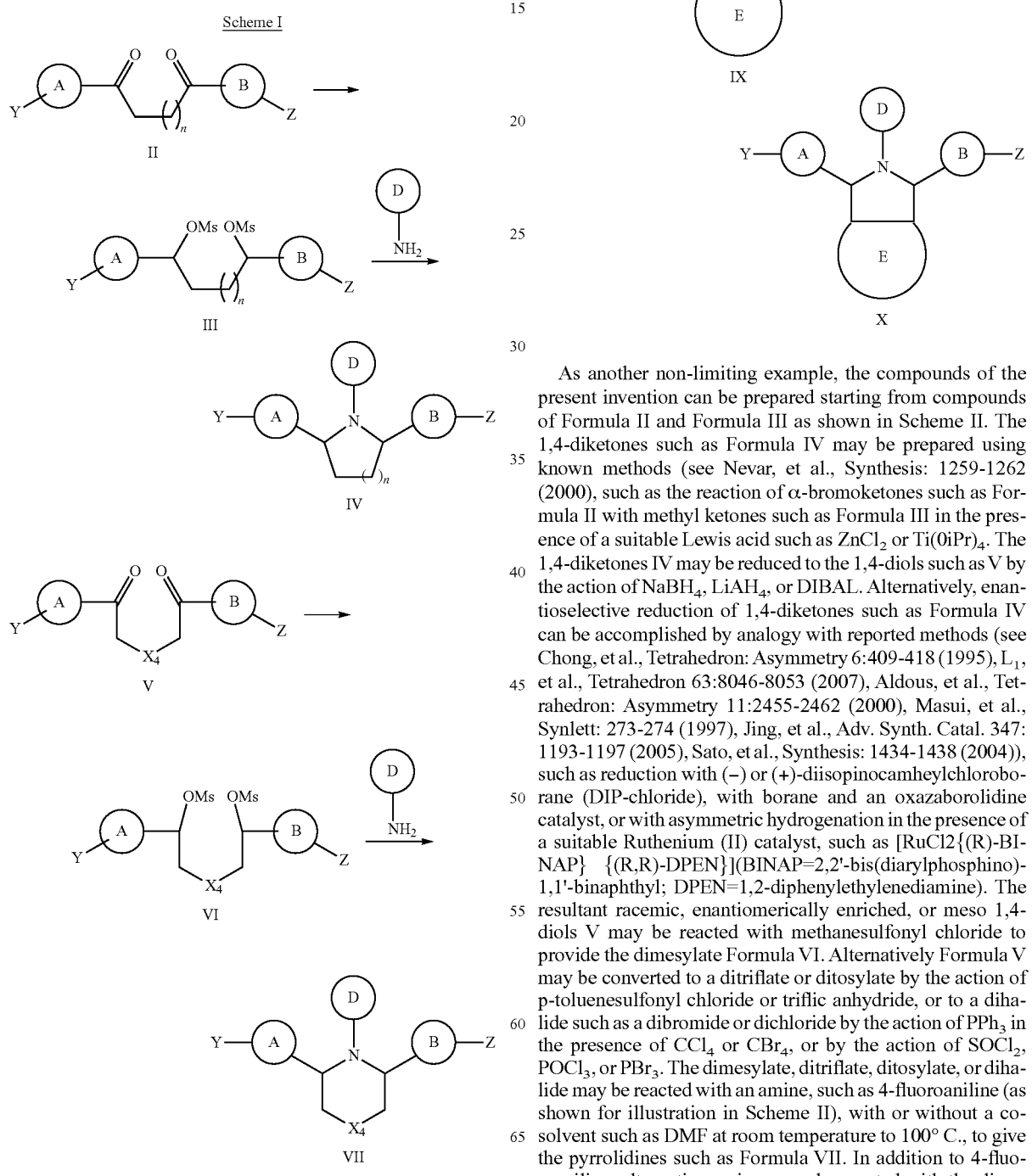

As another non-limiting example, the compounds of the present invention can be prepared starting from compounds of Formula II and Formula III as shown in Scheme II. The 1,4-diketones such as Formula IV may be prepared using known methods (see Nevar, et al., Synthesis: 1259-1262 (2000), such as the reaction of α-bromoketones such as Formula II with methyl ketones such as Formula III in the presence of a suitable Lewis acid such as $ZnCl_2$ or $Ti(OiPr)_4$. The 1,4-diketones IV may be reduced to the 1,4-diols such as V by the action of $NaBH_4$, $LiAH_4$, or DIBAL. Alternatively, enantioselective reduction of 1,4-diketones such as Formula IV can be accomplished by analogy with reported methods (see Chong, et al., Tetrahedron: Asymmetry 6:409-418 (1995), $L_1$, et al., Tetrahedron 63:8046-8053 (2007), Aldous, et al., Tetrahedron: Asymmetry 11:2455-2462 (2000), Masui, et al., Synlett: 273-274 (1997), Jing, et al., Adv. Synth. Catal. 347: 1193-1197 (2005), Sato, et al., Synthesis: 1434-1438 (2004)), such as reduction with (−) or (+)-diisopinocamheylchlorborane (DIP-chloride), with borane and an oxazaborolidine catalyst, or with asymmetric hydrogenation in the presence of a suitable Ruthenium (II) catalyst, such as [RuCl2{(R)-BINAP} {(R,R)-DPEN}](BINAP=2,2'-bis(diarylphosphino)-1,1'-binaphthyl; DPEN=1,2-diphenylethylenediamine). The resultant racemic, enantiomerically enriched, or meso 1,4-diols V may be reacted with methanesulfonyl chloride to provide the dimesylate Formula VI. Alternatively Formula V may be converted to a ditriflate or ditosylate by the action of p-toluenesulfonyl chloride or triflic anhydride, or to a dihalide such as a dibromide or dichloride by the action of $PPh_3$ in the presence of $CCl_4$ or $CBr_4$, or by the action of $SOCl_2$, $POCl_3$, or $PBr_3$. The dimesylate, ditriflate, ditosylate, or dihalide may be reacted with an amine, such as 4-fluoroaniline (as shown for illustration in Scheme II), with or without a co-solvent such as DMF at room temperature to 100° C., to give the pyrrolidines such as Formula VII. In addition to 4-fluoroaniline, alternative amines may be reacted with the dimesylate Formula VI, including but not limited to aniline, 3,5-difluoroaniline, 3,4-difluoroaniline, 3-fluoroaniline, 4-trifluoromethylaniline, 4-chloroaniline, heteroaryl amines, alkyl amines, cycloalkyl amines, substituted benzylamines, or allylamine. The dinitro Formula VII may be reduced to the diamino Formula VIII using Fe in the presence of $NH_4Cl$, HCl, or acetic acid, or by treatment with a hydride reducing agent, such as sodium borohydride (with or without the addition of a transition metal salt, such as $BiCl_3$, $SbCl_3$, $NiCl_2$, $Cu_2Cl_2$, or $CoCl_2$) in a solvent such as ethanol or THF. Alternatively, Formula VII can be reduced to the product Formula VIII by hydrogenation in the presence of a suitable catalyst, such as a palladium or platinum catalyst or Raney nickel. The diamine Formula VIII may be reacted with a suitably protected proline acid (Boc is shown, although Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base such as Hunig's base, pyridine, 2,6-lutidine, or triethylamine, to give Formula IX. Removal of the Boc protecting groups to give X may be accomplished by treatment with an acid, such as TFA, HCl, or formic acid. Compounds of the present invention may be prepared by coupling of Formula X with an acid of choice using the standard peptide coupling reagents and conditions described above. Alternately, diamine VIII may be reacted with an N-substituted proline in the presence of a peptide coupling reagent such as EDAC/HOBT, PyBOP, HATU, $T_3P$, or DEBPT, in a solvent such as THF, DMF, dichloromethane, or DMSO, with or without the addition of an amine base such as Hunig's base, pyridine, 2,6-lutidine, or triethylamine, to directly give compounds of the present invention (Formula XI).

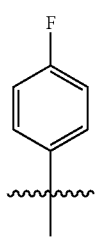 [SMILES: *c1ccc(F)cc1]

in each Formula within Scheme II can be replaced with

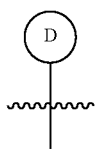

where D is defined above, and such compounds can be readily prepared according to the process described in Scheme II (including making compound XI directly from compound VIII).

Scheme II

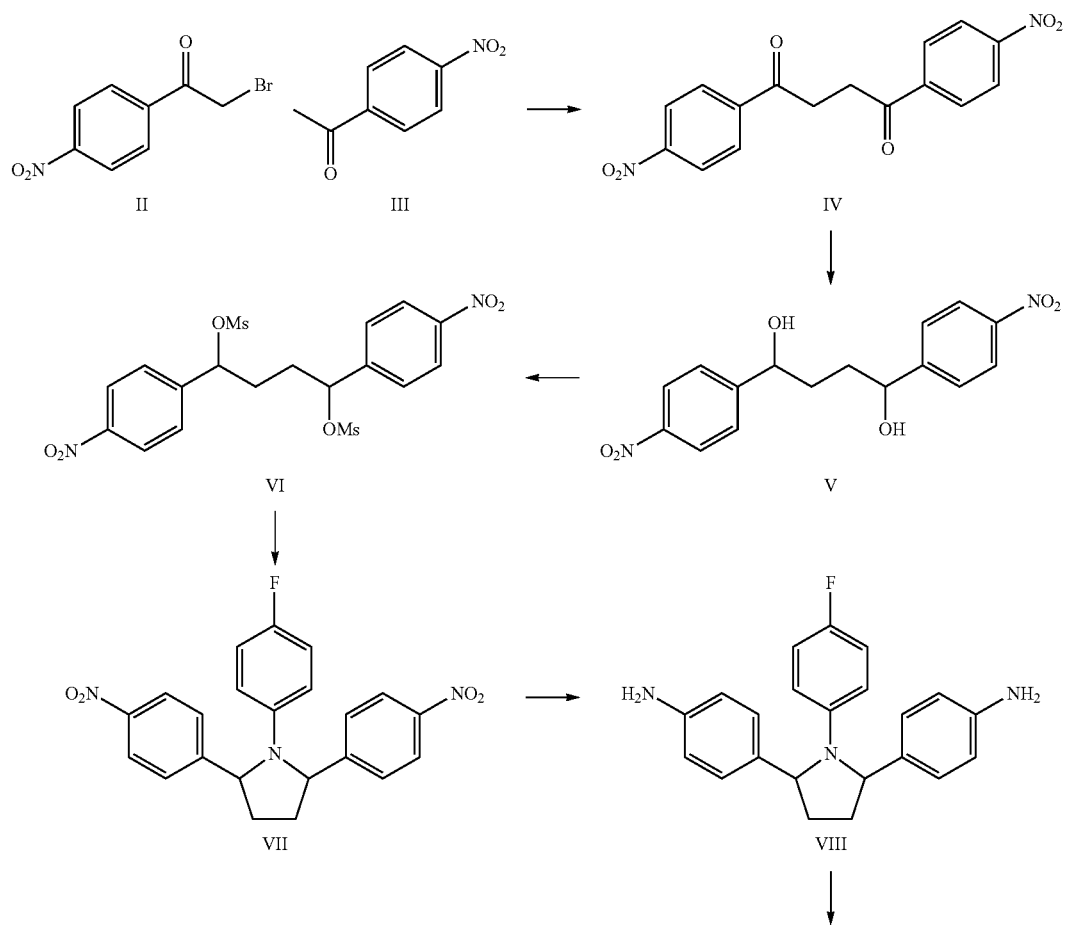

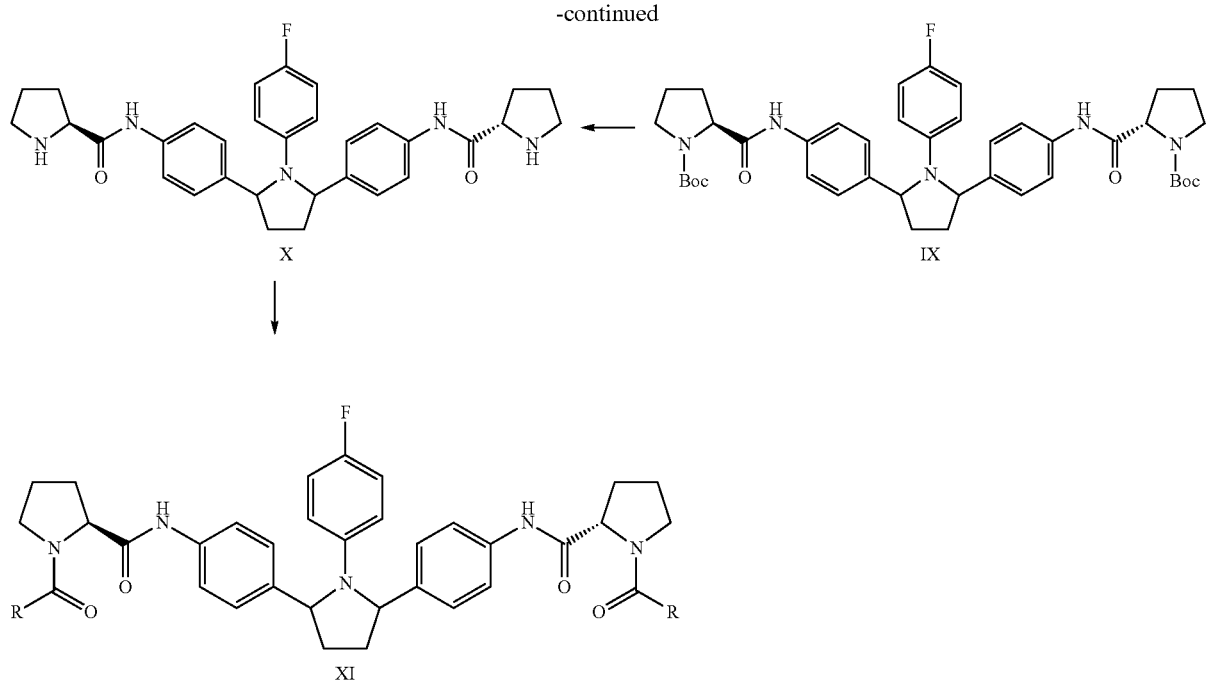

-continued

As yet another non-limiting example, the compounds of the present invention can be prepared starting from compounds of Formula II and Formula III as shown in Scheme III, where A, B, D, Y, and Z are as described above, using conditions similar to those described above for the preparation of IV in Scheme II. Similarly, the resulting 1,4-diketone IV may be reduced to the 1,4-diols V using the methods described above for Scheme II. The resultant racemic, enantiomerically enriched, or meso 1,4-diols V may be converted to the dimesylate VI or alternatively to a ditriflate, ditosylate, or dihalide by the methods described above. The dimesylate VI, ditriflate, ditosylate, or dihalide may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under the conditions described above the give the compounds of the invention. Alternatively, compounds such as VIII, where R is a group such as allyl, 4-methoxybenzyl, or 2,4-dimethoxybenzyl, may be treated with reagents useful for the removal of the R group (rhodium catalyst such as Rh(Ph$_3$P)$_3$Cl for R=allyl, treatment with an acid such as TFA or HCl for R=4-methoxybenzyl or 2,4-dimethoxybenzyl, hydrogenolysis with a Pd catalyst for R=substituted benzyl) to generate compounds such as IX. Amine IX may be reacted with an aryl halide or triflate such as X (iodide shown for illustration) employing the Buchwald-Hartwig reaction in the presence of a palladium catalyst (such as Pd(OAc)$_2$ or Pd$_2$(dba)$_3$) and a phosphine ligand (such as triphenylphosphine or XantPhos) and a base (such as sodium bis(trimethylsilyl)amide, potassium tert-butoxide, or K$_3$PO$_4$) to give the compounds of the present invention. Alternatively, the compounds of the present invention may be obtained by reaction of IX with an aldehyde or ketone through reductive amination in the presence of a hydride reducing agent, such as sodium borohydride or sodium cyanoborohydride (with or without the addition of an acid, such as acetic acid) in a solvent such as ethanol, toluene, THF, or dichloromethane. Alternatively the reductive amination may be conducted through the use of hydrogenation in the presence of a suitable catalyst, such as a palladium or platinum catalyst or Raney nickel. Alternatively, amine IX may react with electrophilic reagents, such as alkyl halides, or with aryl electrophiles (suitably electron deficient aryl and heteroaryl halides and triflates) through nucleophilic aromatic substitution reactions to give the compounds of the present invention.

Scheme III

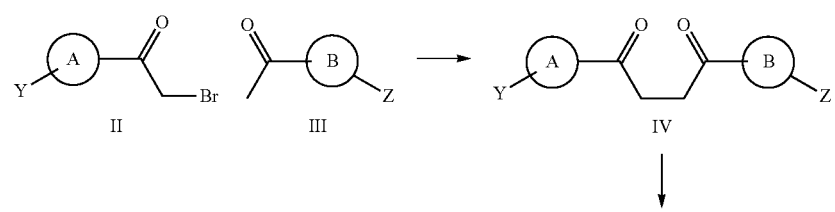

-continued

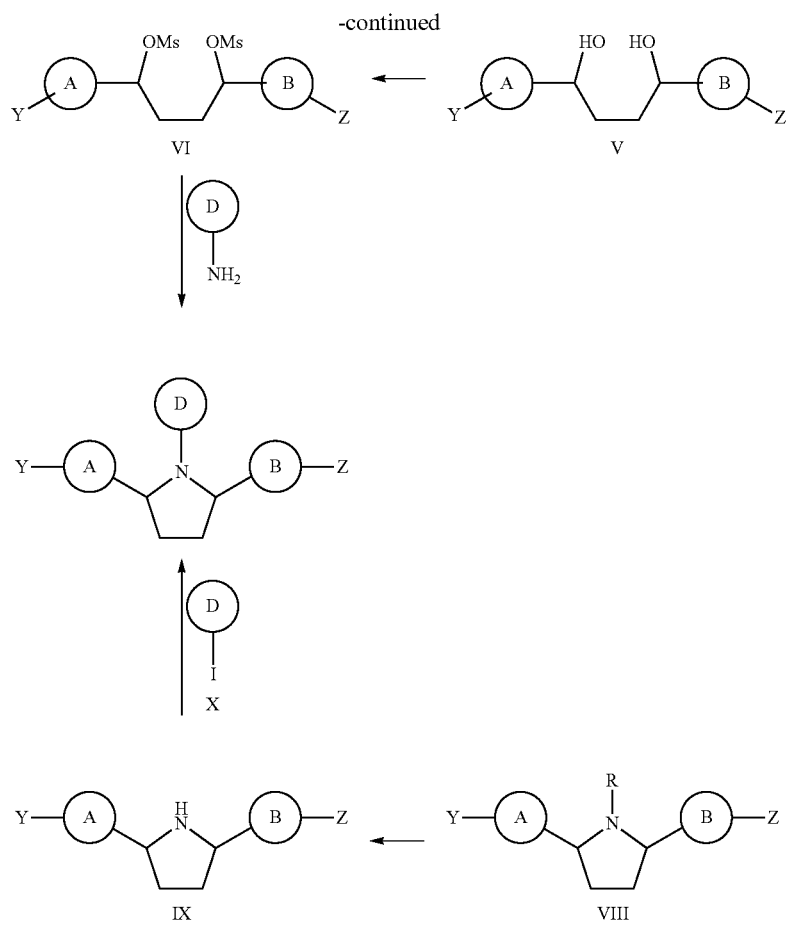

R = allyl or substitued benzyl

As a further non-limiting example, the compounds of the present invention can be prepared starting from compounds of Formula II and Formula III as shown in Scheme IV, where $X_5$ in Formula II and Formula III represents a halogen (e.g., Cl, Br, or F) or a nitro group. The 1,4-diketones such as IV may be prepared using known methods described above for the preparation of IV for Scheme II. The 1,4-diketones IV may be reduced to the 1,4-diols such as V by the action of $NaBH_4$, $LiAlH_4$, or DIBAL. Alternatively, enantioselective reduction of 1,4-diketone such as IV can be accomplished by the methods described above for the preparation of V for Scheme II. The resultant racemic, enantiomerically enriched, or meso 1,4-diols V may be reacted with methansulfonyl chloride to provide the dimesylate VI. Alternatively V may be converted to a ditriflate or ditosylate by the methods described above for Scheme II. The dimesylate, ditriflate, ditosylate, or dihalide may be reacted with an amine including but not limited to aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine to give VII. When $X_5$ in Formula VII is nitro, the nitro groups may be reduced to the tetramino product IX using Fe in the presence of $NH_4Cl$, HCl, or acetic acid, or with a hydride reducing agent, such as sodium borohydride (with or without the addition of a transition metal salt, such as $BiCl_3$, $SbCl_3$, $NiCl_2$, $Cu_2Cl_2$, or $CoCl_2$) in a solvent such as ethanol or THF. Alternatively, VII ($X_5$=nitro) can be reduced to the product IX by hydrogenation in the presence of a suitable catalyst, such as a palladium or platinum catalyst or Raney nickel. Alternatively, compounds VII where $X_5$=halogen may be reacted with ammonia (R=H) or an amine bearing a suitable protecting group (R=substituted benzyl such as 4-methoxybenzyl or 2,4 dimethoxybenzyl or R=allyl). The resulting products VIII may be treated with a reagent useful for the removal of the R protecting group (rhodium catalyst such as $Rh(Ph_3P)_3Cl$ for R=allyl, treatment with an acid such as TFA or HCl for R=4-methoxybenzyl or 2,4-dimethoxybenzyl, hydrogenolysis with a Pd catalyst for R=substituted benzyl) to give the product IX. Formula IX may be reacted with a suitably protected proline acid (Boc is shown, although Cbz, Troc, or Fmoc may be substituted) in the presence of a peptide coupling reagent, such as EDAC/HOBT, PyBOP, HATU, or DEBPT, in a solvent such as THF, DMF, dichloromethane, or DMSO, with or without the addition of an amine base, such as Hunig's base, pyridine, 2,6-lutidine, or triethylamine, to give X as a mixture of the amide products. Conversion to the benzimidazole compound XI may be accomplished by heating X in acetic acid (50-100° C.). Alternatively, XI may be prepared by reaction of IX with an aldehyde, followed by treatment with an oxidant, such as $Cu(OAc)_2$ or $MnO_2$ (see Penning, et al., Bioorg. Med. Chem. 16:6965-6975 (2008). After removal of the Boc protecting groups from XI (accomplished by treatment with an acid, such as TFA, HCl, or formic acid), the compounds of the present invention may be prepared by coupling of the resulting diamine XII with an acid of choice using the standard peptide coupling reagents and conditions described above for Scheme II.

99
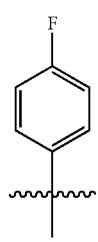
100
in each Formula within Scheme IV can be replaced with
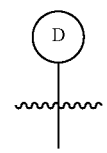
where D is defined above, and such compounds can be readily prepared according to the process described in Scheme IV.
Scheme IV
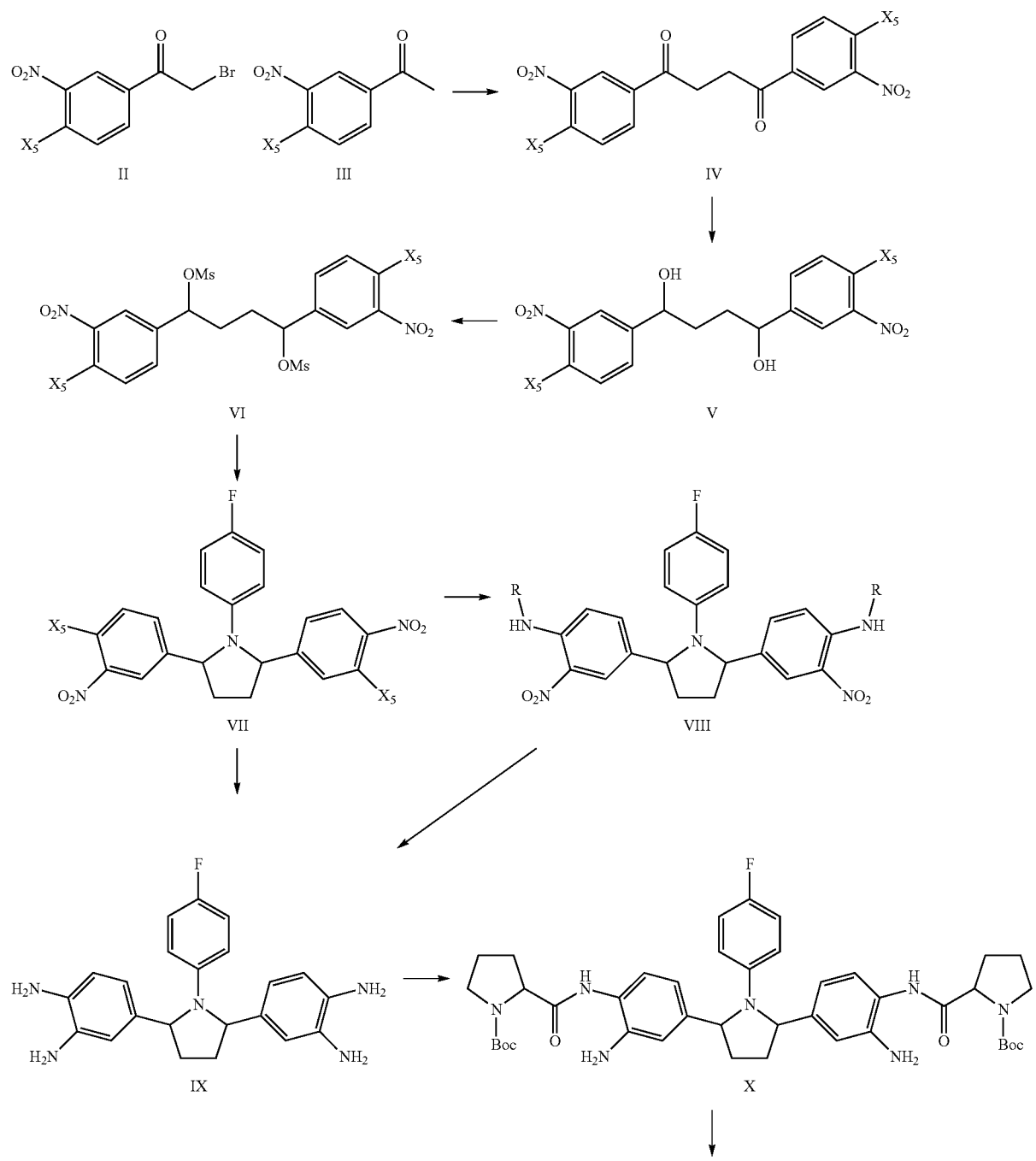

-continued

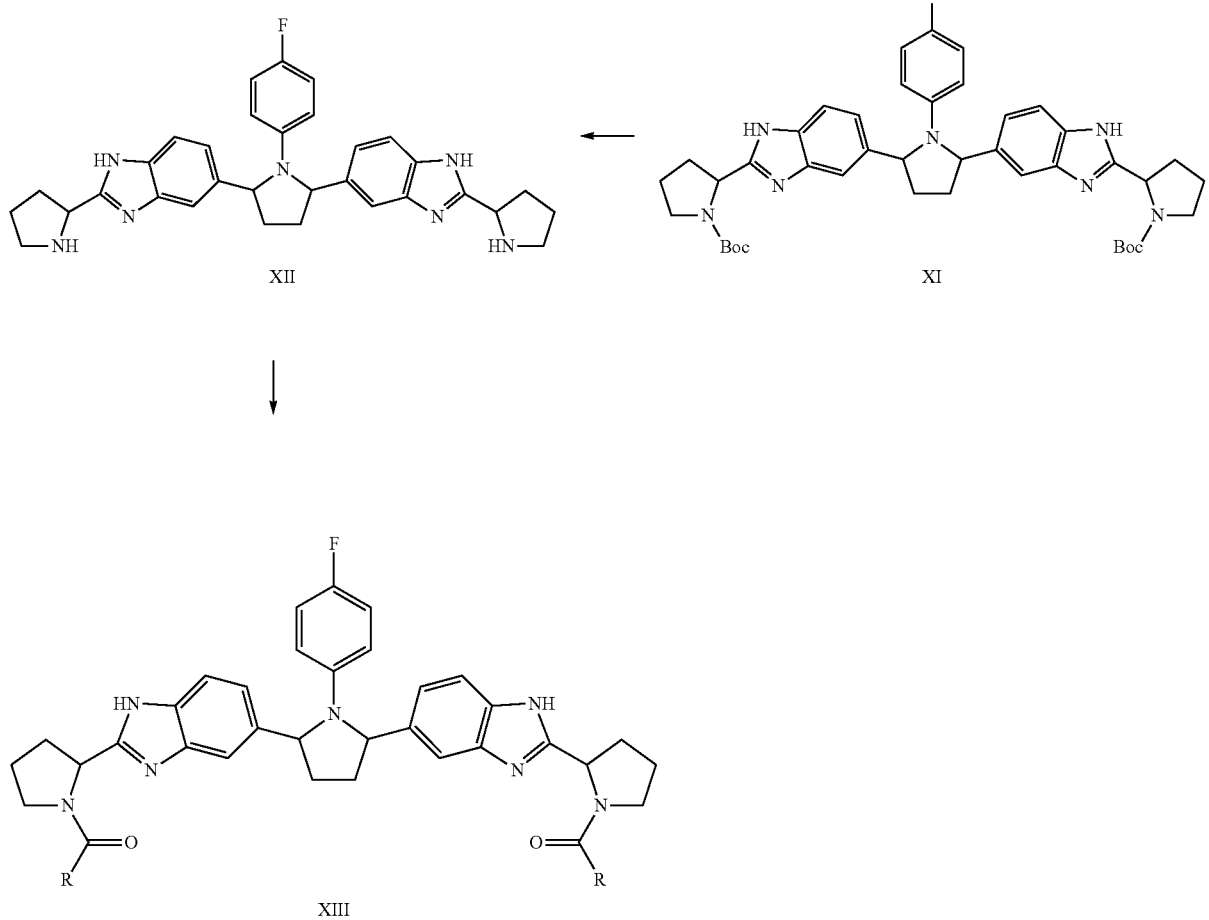

$X_5$ = halogen or $NO_2$

Alternatively IX in Scheme IV may be prepared from a compound of Formula II as shown in Scheme V. Compound VIII from Scheme II may be treated with an acylating agent such as acetyl chloride or acetic anhydride to give compound II (Scheme V). Nitration of compound II to provide III may be accomplished using known methods, such as treatment with nitric acid or potassium nitrate in the presence of an acid such as sulfuric acid or treatment with $NO_2BF_4$. Removal of the acetamide protecting group may be accomplished by treatment with Boc anhydride in the presence of DMAP to give IV, followed by sequential treatment of IV with hydroxide (such as NaOH, KOH, or LiOH) to remove the acetyl group and a strong acid such as TFA or HCl to remove the Boc protecting group. The nitro groups in V may be reduced to amino groups using the methods described above for Scheme IV.

in each Formula within Scheme V can be replaced with

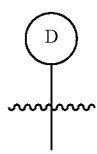

where D is defined above, and such compounds can be readily prepared according to the process described in Scheme V.

Scheme V

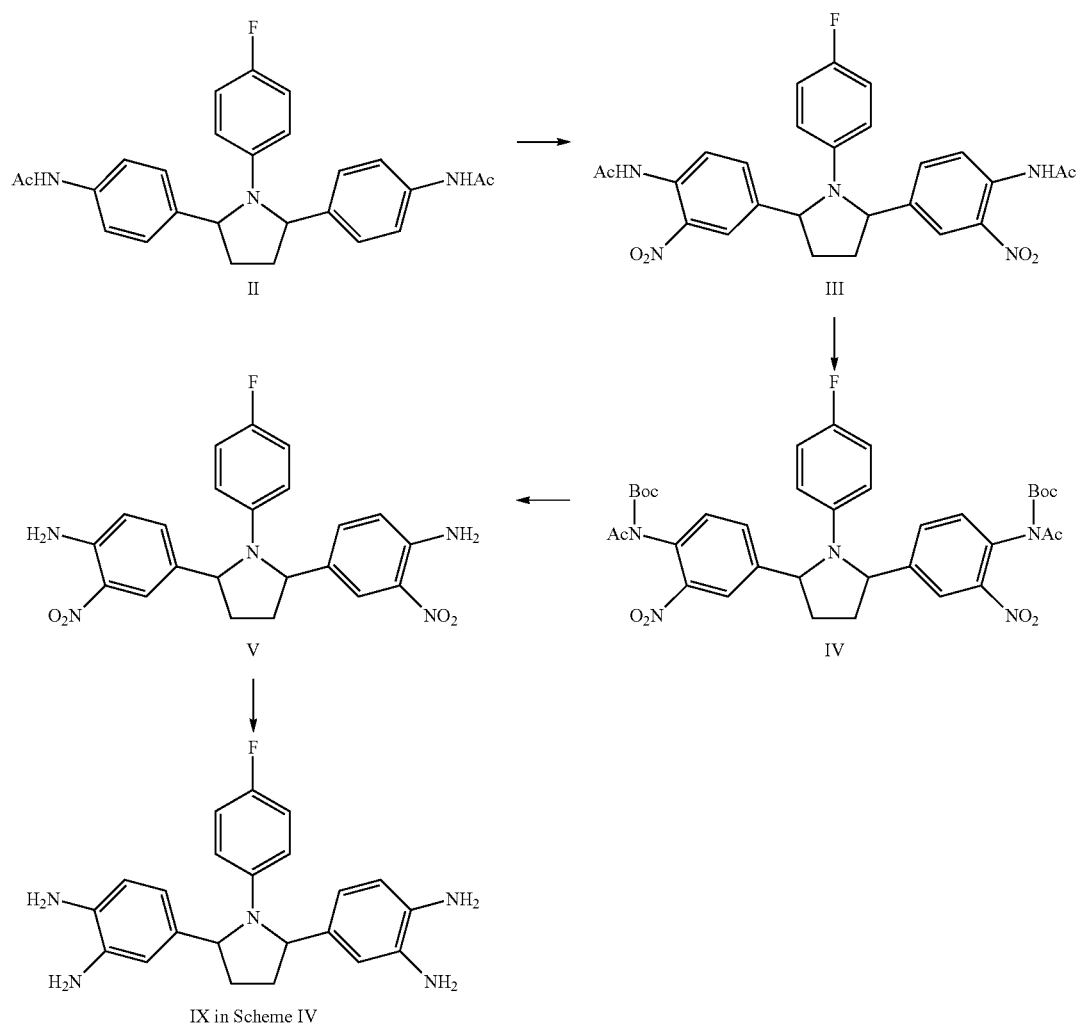

As still another non-limiting example, the compounds of the present invention can be prepared starting from compounds of Formula II as shown in Scheme VI, where A, B, D, Y, and Z are as described above. A 1,4-diketone compound of Formula II (prepared as described in Scheme III) may be reacted with an amine, including but not limited to, aniline, 3,5-difluoroaniline, 3,4-difluoroaniline, 4-fluoroaniline, 3-fluoroaniline, 4-trifluoromethylaniline, 4-chloroaniline, heteroaryl amines, alkyl amines, cycloalkyl amines, substituted benzylamines, or allylamine, under acid catalyzed conditions, such as acetic acid, TFA, formic acid or HCl, to give the compounds of the invention.

Scheme VI

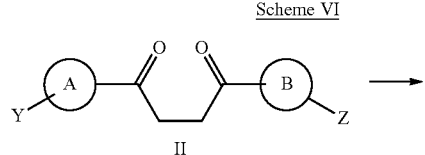

-continued

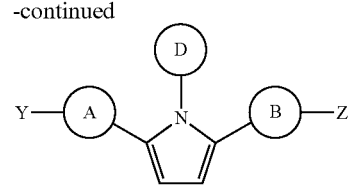

As a further non-limiting example, the compounds of the present invention can be prepared from a compound of Formula II as shown in Scheme VII. A compound of Formula II, where $R_X$ is a halogen, such as bromo, chloro, or iodo, or a triflate or a nonaflate may be converted to a boronic acid or ester such as Formula III, where R is hydrogen, methyl, ethyl, or a cyclic pinacolate ester. For example a compound of Formula II can be transformed to a compound of III by treatment with pinacol-borane in the presence of a catalyst such as, for example, tris(dibenzylidineacetone)palladium (0), and a ligand such as, for example, tri-t-butylphosphine, in solvents such as, for example, tetrahydrofuran, dioxane, or toluene at temperatures ranging from ambient to about 130° C. Alternatively, compound II can be reacted with bis(pinacolato)diboron in the presence of a catalyst such as, for example, Combiphos-Pd6 (CombiPhos Catalysts, Inc. (NJ, USA), dichloro[1,1'-bis(diphenylphosphino)ferrocene]palladium (II) dichloromethane adduct, or palladium acetate in the presence of a ligand such as, for example, 2-dicyclohexylphosphino-2',4',6'-triisopropylbiphenyl (XPhos), and a base such as, for example, potassium acetate in solvents such as, for example, toluene, dioxane, tetrahydrofuran, dimethylformamide or dimethyl sulfoxide at temperatures from about 60 to about 130° C. to give compound III. Alternatively, a compound of Formula II may be reacted with an organolithium reagent, such an n-BuLi, sec-BuLi, or t-BuLi, followed by reaction with trimethyl borate or triethyl borate, to give a compound of Formula III.

A compound of Formula III in Scheme VII can be coupled with a compound of Formula IV, where $R_Y$ is a halogen, such as bromo, chloro or iodo, under Suzuki reaction conditions to provide a compound of Formula V. Such conditions include, for example, use of a palladium catalyst such as, for example, tris(dibenzylidineacetone)palladium (0), palladium acetate, bis(triphenylphosphine)palladium (II) chloride, tetrakis(triphenylphosphine)palladium, or dichloro[1,1'-bis(diphenylphosphino)ferrocene]palladium (II) dichloromethane adduct; base such as, for example, potassium carbonate, potassium phosphate, potassium t-butoxide, sodium carbonate, cesium carbonate, or cesium fluoride; and solvent such as, for example, toluene, ethanol, water, or tetrahydrofuran, or mixtures thereof heated in the temperature range from about 40 to about 130° C.

Removal of the Boc protecting groups from V may be accomplished by treatment with an acid, such as TFA, HCl, or formic acid. Compounds of the present invention such as VI may be prepared by coupling the resulting amino compounds with an acid of choice using the standard peptide coupling reagents, such as EDAC/HOBT, PyBOP, HATU, or DEBPT, in a solvent such as THF, DMF, dichloromethane, or DMSO, with or without the addition of an amine base such as Hunig's base, pyridine, 2,6-lutidine, or triethylamine. Each $R_Z$ is independently $-L_Y'-M'-R_D$ (e.g., $-L_Y-N(R_B")C(O)-L_S-R_E$), and D, $L_3$, $R_1$, $R_2$, $R_5$, $L_Y$, $R_B"$, $L_S$, $R_E$, $L_Y'$, M' and $R_D$ are as defined above.

Scheme VII

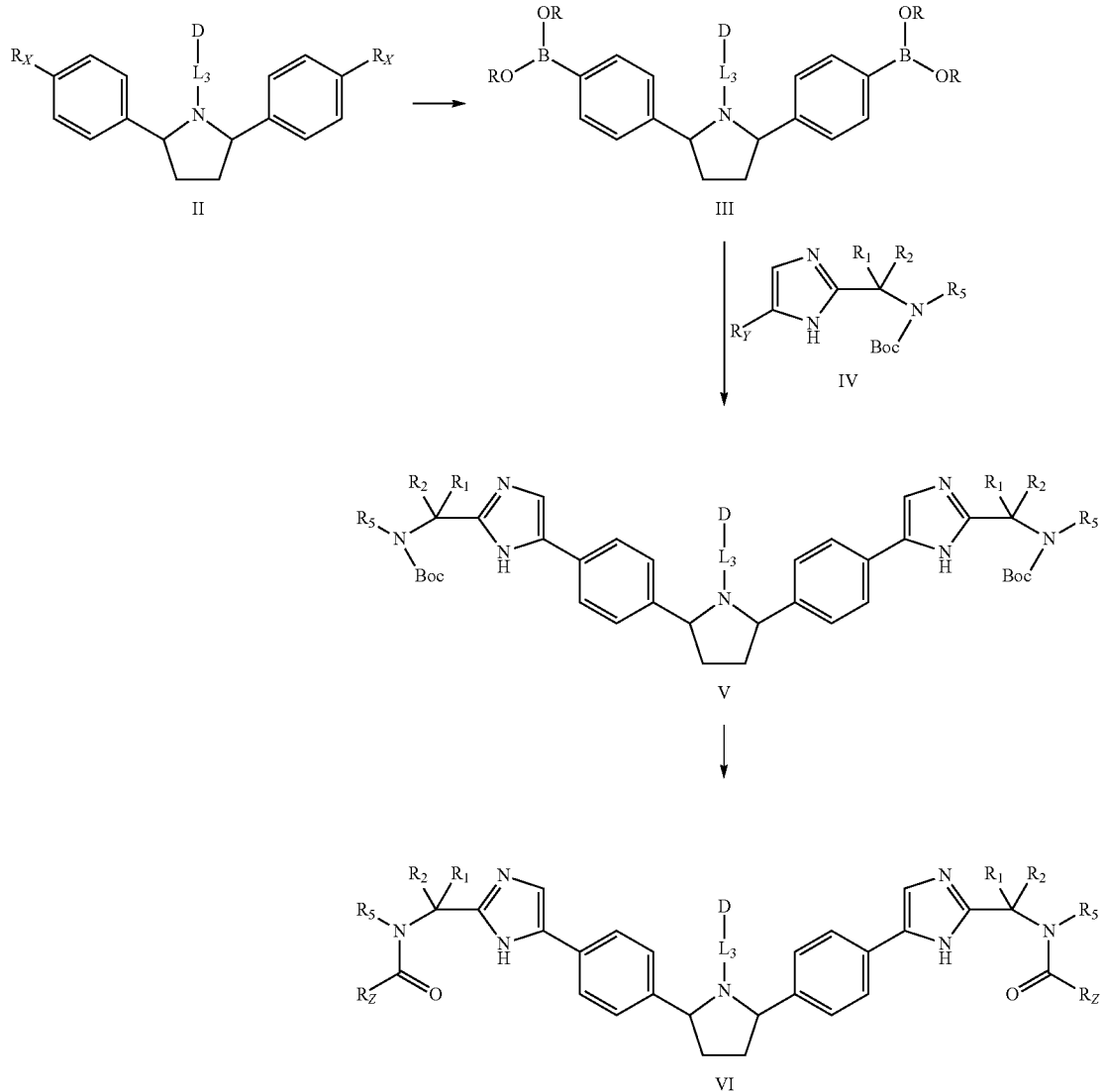

As another non-limiting example, the compounds of the present invention can be prepared according to Scheme VIII starting from the compound of Formula II, initially cleaving the diol in oxidative fashion followed by subsequent acid hydrolysis of the acetonide. This dialdehyde intermediate is then treated with an aryl boronate or aryl boronic acid (compound IV where A and Y are as described previously, or compound VII) and aniline III (where W is $R_M$ or J, and $R_M$ and J are as defined above) resulting in the formation of Formula V or Formula VIII respectively. Formula V can be derivatized by deprotonating the hydroxyl groups with a strong base such as sodium hydride, butyl lithium, or potassium hydride, followed by alkylation with $R_S$-halogen. Alternatively Formula VIII can be deprotonated with a strong base (e.g., sodium hydride) and alkylated with $R_S$-halogen as well, followed by acid hydrolysis of the phenol protecting groups. The sulfonylation of the phenols with nonafluorobutylsulfonyl fluoride in the presence of a neutralizing agent such as potassium carbonate in a polar aprotic solvent such as DMF, followed by heating provides a compound of Formula IX. Boronate of Formula X is produced by heating Formula IX with bis(pinacolato)diboron in the presence of X-phos and a palladium catalyst, such as Pd2(dba)3 and a base such as potassium acetate in an organic solvent such as dioxane. Formula X is further derivatized to final product by heating a suitably substituted heteroarylhalide in the presence of a palladium catalyst such as PdCl2(dppf) in the presence of a base such as sodium carbonate in a mixture of toluene and ethanol. $R_S$ is as defined above.

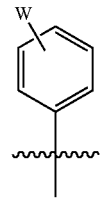

in each Formula within Scheme VIII can be replaced with

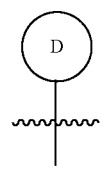

where D is defined above, and such compounds can be readily prepared according to the process described in Scheme VIII.

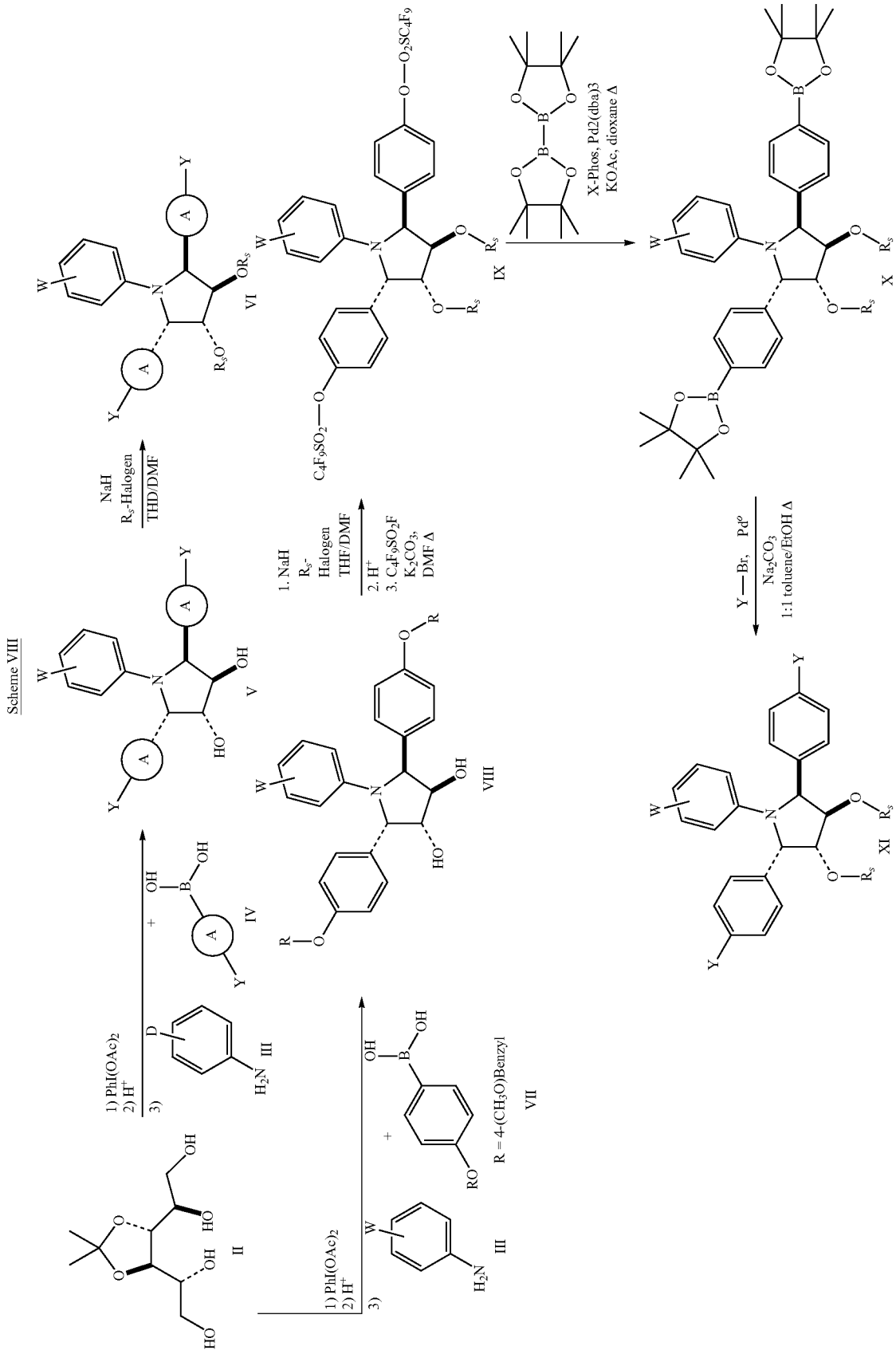

As yet another non-limiting example, the compounds of the present invention can be prepared according to Scheme IX starting from the compounds of Formula II and Formula III. Formula III carboxylic acid is activated towards coupling using reagents such as isobutylchloroformate, DCC, EDAC, or HATU in the presence of an organic base, such as diisopropylethylamine. Upon activation, dianiline of Formula II is added to the reaction, with the isolation of an intermediate amide, which is heated in acetic acid, preferably at 60° C., to yield the compound of Formula IV. The benzimidazole of Formula IV is treated with SEM-Cl in the presence of a base in an aprotic solvent such as THF, yielding two protected benzimidazole regioisomers V. The boronate esters VI are produced by heating Formula V with bis(pinacolato)diboron in the presence of a palladium catalyst, such as PdCl2(dppf), X-Phos, and a base such as potassium acetate in an organic solvent such as dioxane. Heating yields both benzimidazole regioisomers VI. Diol VII is cleaved in oxidative fashion followed by subsequent acid hydrolysis of the acetonide. This dialdehyde intermediate is then treated with an aryl boronate VI and aniline VIII (where W is $R_M$ or J, and $R_M$ and J are as defined above) resulting in the formation of the 3 benzimidazole regioisomers of Formula IX. Formula X is produced by deprotonating the hydroxyl groups with a strong base such as sodium hydride, butyl lithium, or potassium hydride, followed by alkylation with $R_S$-halogen, followed by acid hydrolysis of the pyrollidine and benzimidazole protecting groups, preferably by treatment with mineral acid, such as hydrochloric acid in an alcoholic solvent such as methanol. The carboxylic acid $R_Z$—COOH is activated towards coupling using reagents such as isobutylchloroformate, DCC, EDAC, or HATU in the presence of an organic base, such as diisopropylethylamine. Upon activation, Formula X is added to the reaction, with the isolation of Formula XI.

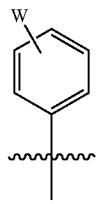

in each Formula within Scheme IX can be replaced with

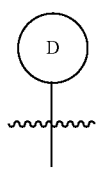

where D is defined above, and such compounds can be readily prepared according to the process described in Scheme IX.

Scheme IX

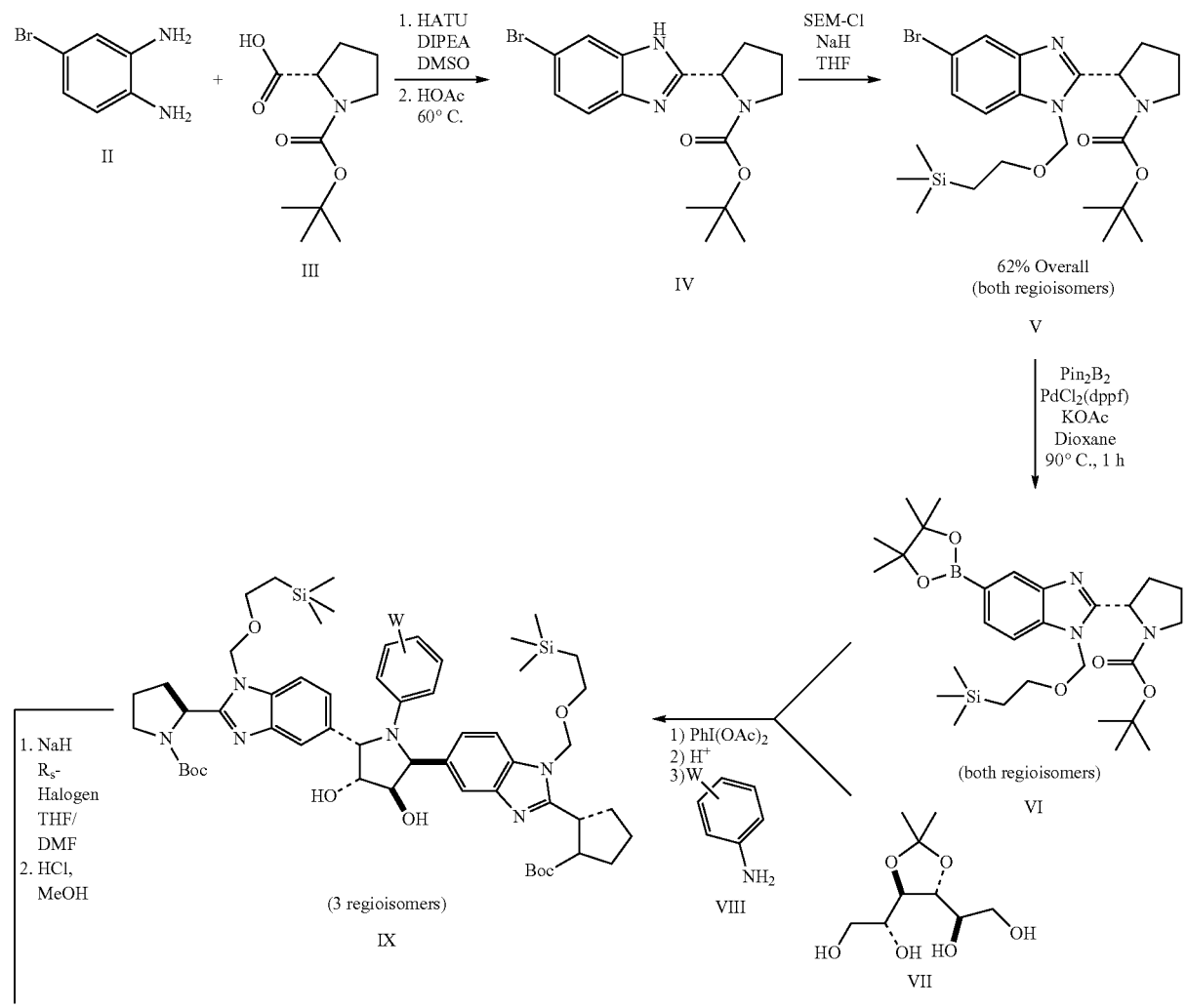

-continued

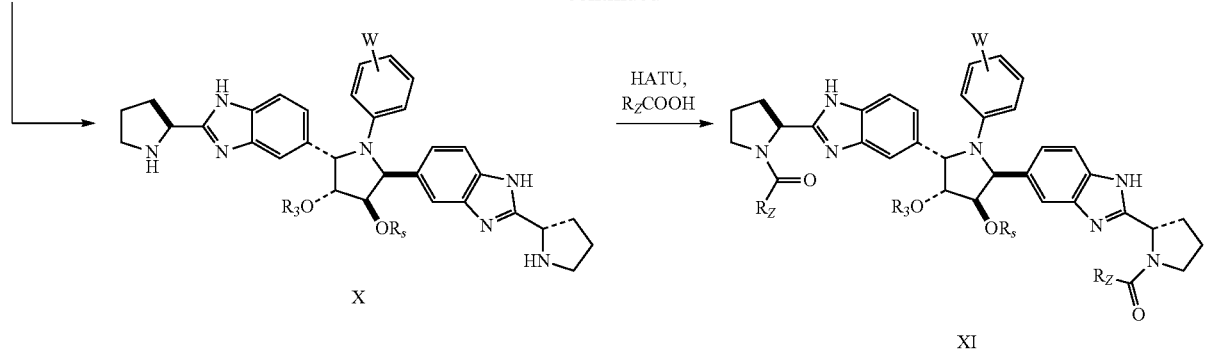

Compounds of the invention of general formula (8), where $R_{20}$ is $-L_S'-M'-L_S''-R_D$ and D is as described above, can be prepared according to the methods of Scheme X. The bromoalkylketone (1) can be reacted with an arylalkylketone (2) using the Lewis acid mediated conditions, described above in Scheme II, to give the diaryldiketone (3). The diketone (3) can be converted to the bisboronate (4) by reaction with bis(pinacolato)diborane in the presence of a base such as potassium acetate, a catalyst such as $PdCl_2(dppf)\text{-}CH_2Cl_2$, in a solvent such as DMSO, dimethoxyethane or dioxane with heating to between 60-100° C. Bisboronate (4) can be converted to the intermediate (5) by Suzuki reaction using, in analogous fashion, the Suzuki conditions described in Scheme VII. The intermediate (5) can be converted to (6) by reaction with an amine $D\text{-}NH_2$ under the analogous conditions described in Scheme VI. For example, reaction of (5) with $D\text{-}NH_2$ in the presence of an acid such as, but not limited to, TFA, in a solvent such as, but not limited to, toluene and with heating up to 110° C. can provide intermediates of general structure (6). Compounds (6) can be converted to compounds of general formulas (7) and then (8) using, in analogous fashion, the methods described in Scheme VII.

Scheme X

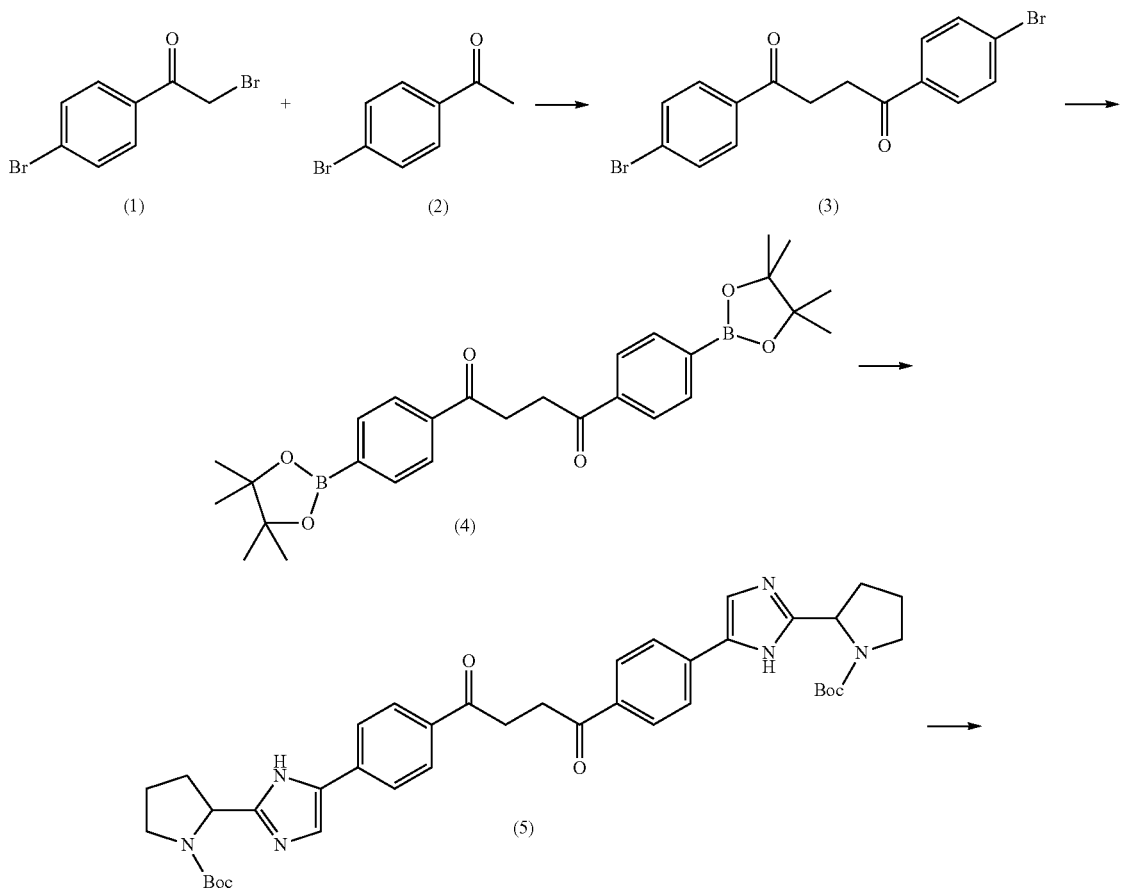

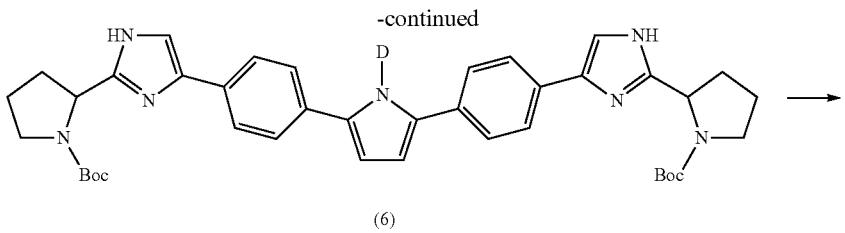

(6)

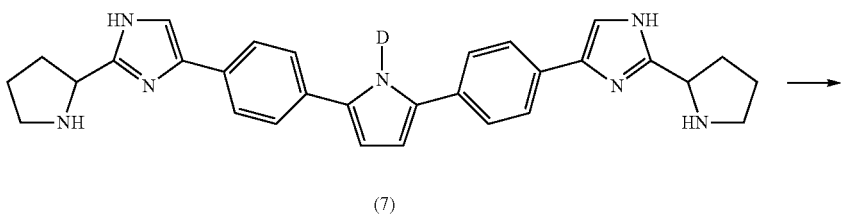

(7)

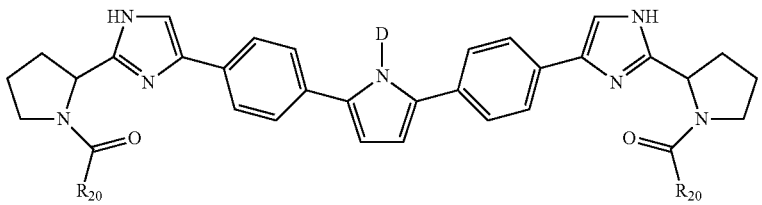

(8)

The intermediates (6) can also be prepared using the route depicted in Scheme XI. The intermediate (3) can be reacted with an amine D-NH$_2$ using, in analogous fashion, the conditions described in Schemes VI and X to provide intermediates (9), which can be converted to (10) using, analogously, conditions as described above in Scheme X; and (10), in turn, can be converted to compounds (6) using the Suzuki reaction conditions described in Scheme VII.

-continued

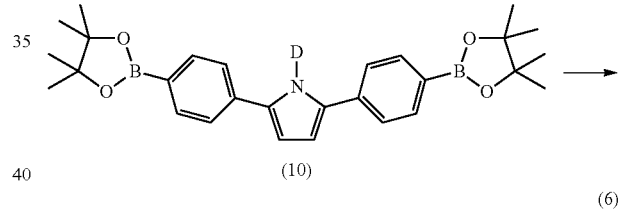

(10)

(6)

Compounds of the invention of general formula (15), where R$_{20}$ is -L$_S$'-M'-L$_S$"-R$_D$ and D is as described above, can be prepared according to the methods of Scheme XII. Compounds (11) can prepared according to the procedures to convert (3) to (9), using general conditions as described in Scheme VI, such as by reacting an appropriate nitrophenyldiketone with an amine D-NH$_2$ with heating in acetic acid to temperature of about 70° C. The compounds (11) can be converted to (12) using the reduction conditions described in Scheme II. Compounds (12) can be converted sequentially to compounds of general formulae (13), (14) and (15) by using, in analogous fashion, the methods described above in Scheme II.

Scheme XI (3) ⟶

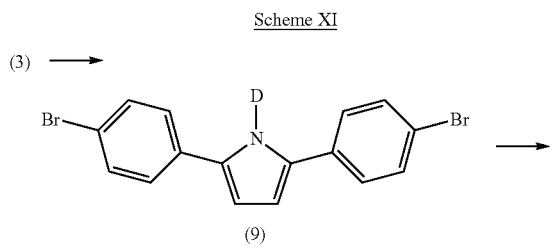

(9)

Scheme XII

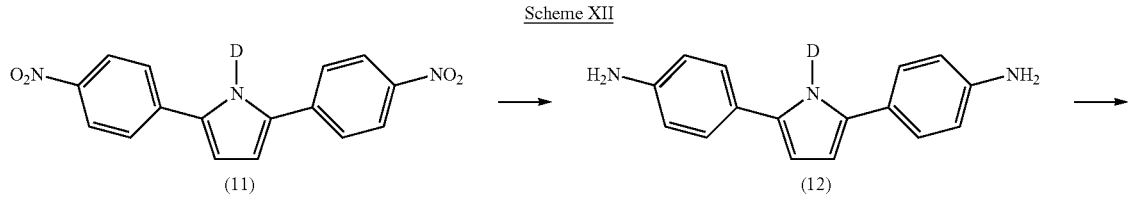

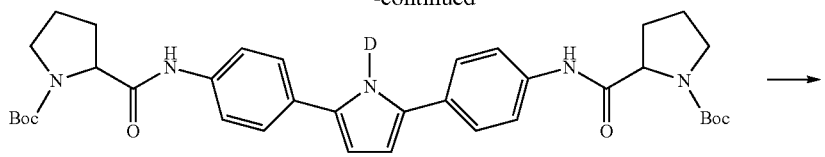

(13)

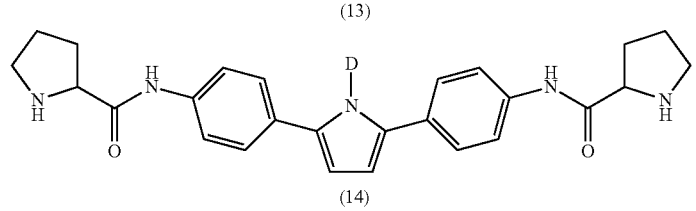

(14)

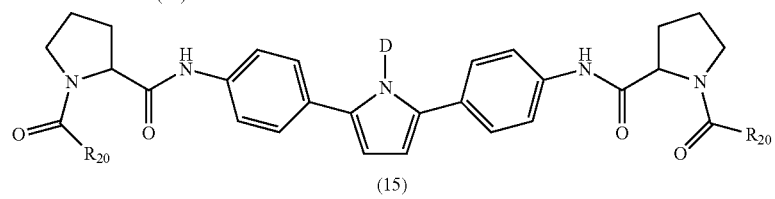

(15)

Compounds of general formula (19), where D is as described above, can be prepared according to the methods of Scheme XIII. Compounds of general formula (16) can be converted to compounds of general formula (17) using a Buchwald reaction with tert-butyl-2-carbamoylpyrrolidine-1-carboxylate. This Buchwald reaction can be conducted in the presence of a base (e.g., cesium carbonate), a palladium catalyst (e.g., tris(dibenzylideneacetone)dipalladium(0)), a phosphine ligand (e.g., 4,5-bis(diphenylphosphino)-9,9-dimethylxanthene) in solvent such as dioxane with heating to about 80-120° C. The intermediate (17) can be reduced to (18) and cyclized to (19) using, in analogous fashion, the conditions described generally in Scheme IV. Compounds (19) can be further reacted as illustrated in Scheme IV to provide compounds of the invention.

Scheme XIII

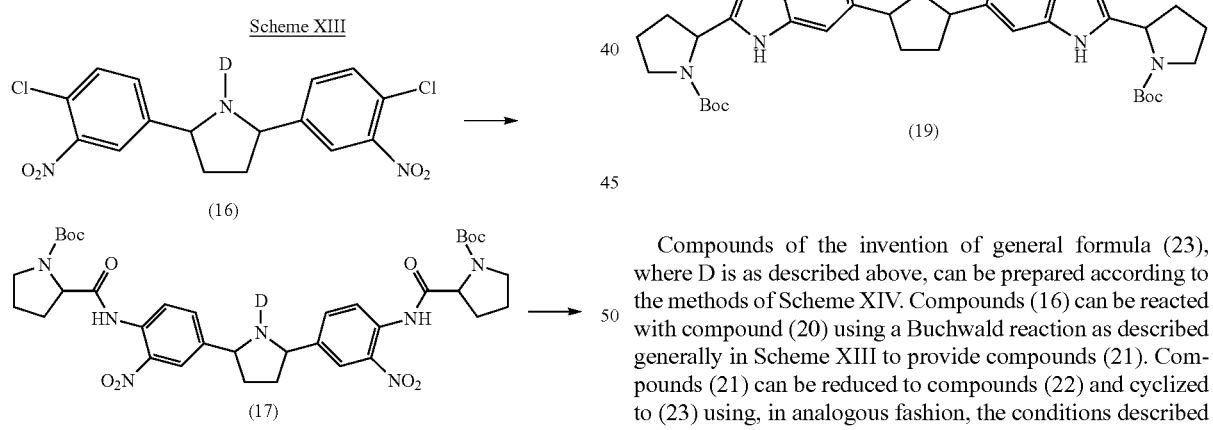

Compounds of the invention of general formula (23), where D is as described above, can be prepared according to the methods of Scheme XIV. Compounds (16) can be reacted with compound (20) using a Buchwald reaction as described generally in Scheme XIII to provide compounds (21). Compounds (21) can be reduced to compounds (22) and cyclized to (23) using, in analogous fashion, the conditions described generally in the foregoing Schemes.

Scheme XIV

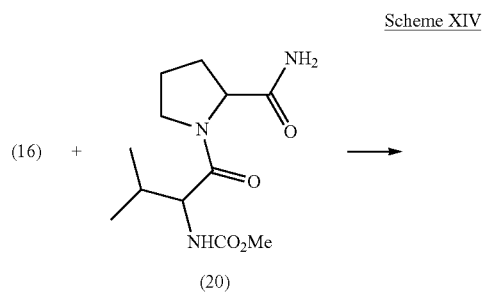

-continued

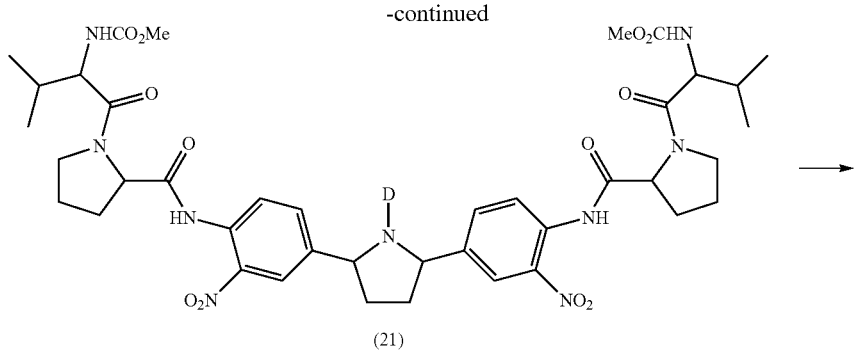

(21)

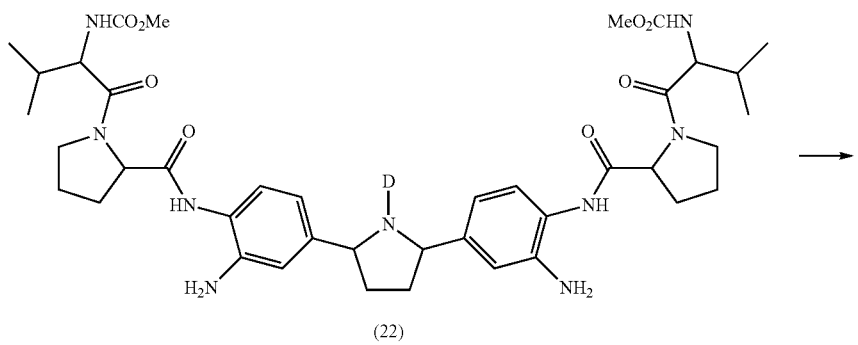

(22)

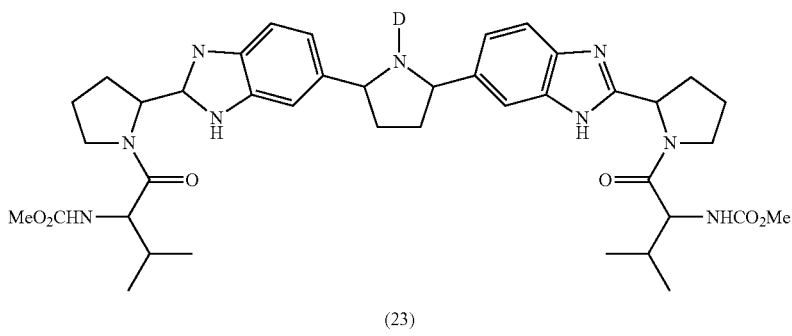

(23)

Compounds of the invention of general formula (29), where $R_{20}$ is -$L_S$'-M'-$L_S$''-$R_D$ and D is as described above, can be prepared according to the methods of Scheme XV. Compounds of formula (24) can be converted to compounds of formula (25) (Sonogashira reaction) by reaction with trimethylsilylacetylene, a palladium catalyst (e.g., bis(triphenylphosphine)palladium(II)chloride), a copper catalyst (e.g., copper(I)iodide), and a base (e.g., triethylamine) wherein an amine base can also be used as solvent. The compounds (25) can be desilylated to compounds (26) by reaction with a fluoride source (e.g., tetrabutylammonium fluoride) in a solvent such as THF. Compounds (26) can be converted to compounds (27) by formation of the dianion of (26) with n-butyllithium and subsequent reaction with a Weinreb amide (e.g., N-(tert-butoxycarbonyl)-L-proline-N'-methoxy-N'-methylamide). This reaction can be conducted in an appropriate solvent such as THF or dimethoxyethane. Compounds (27) can be converted to compounds (28) by reaction with hydrazine in a solvent such as ethanol. The compounds (28) can be converted to compounds (29) using the methods described generally in the foregoing Schemes.

Scheme XV

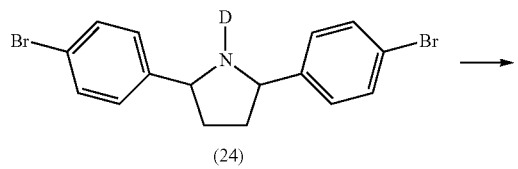

(24)

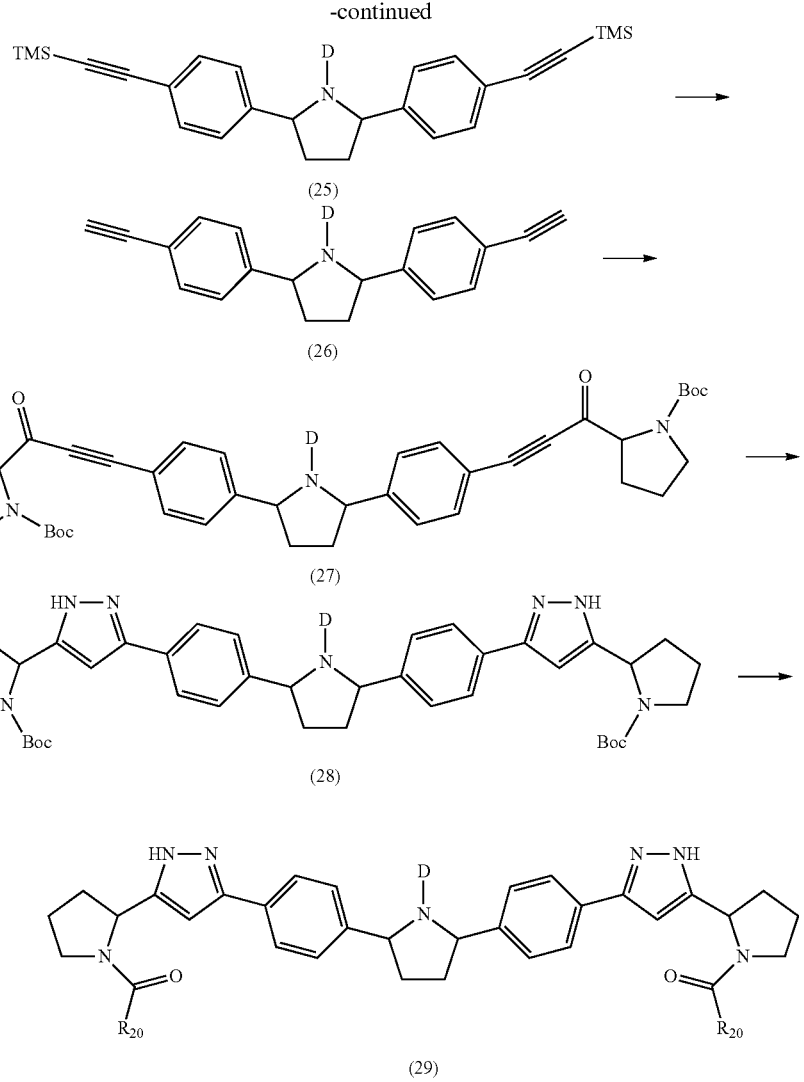

Compounds of the invention of general formula (34), where $R_{20}$ is -$L_S'$-M'-$L_S''$-$R_D$ and D is as described above, can be prepared according to the methods of Scheme XVI. Compounds (24) can be converted to compounds (30) by reaction of (24) with CO(g) under pressure (ca. 60 psi) in the presence of a palladium catalyst (e.g., PdCl$_2$(dppf)) in methanol as solvent and with heating to around 100° C. Compounds (30) can be converted to compounds (31) by reaction with hydrazine in a solvent such as methanol with heating to about 60-80° C. Compounds (31) can be converted to compounds (32) by reaction with N-Boc-2-cyano-pyrrolidine in the presence of a base (e.g. potassium carbonate) in a solvent such as butanol and with heating to around 150° C. with irradiation in a microwave reactor. Compounds (32) can be deprotected to compounds (33) and acylated to (34) using, in analogous fashion, the conditions described generally in the foregoing Schemes.

Scheme XVI

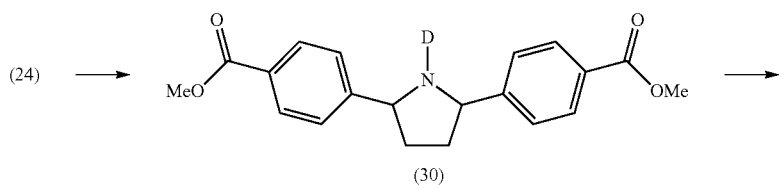

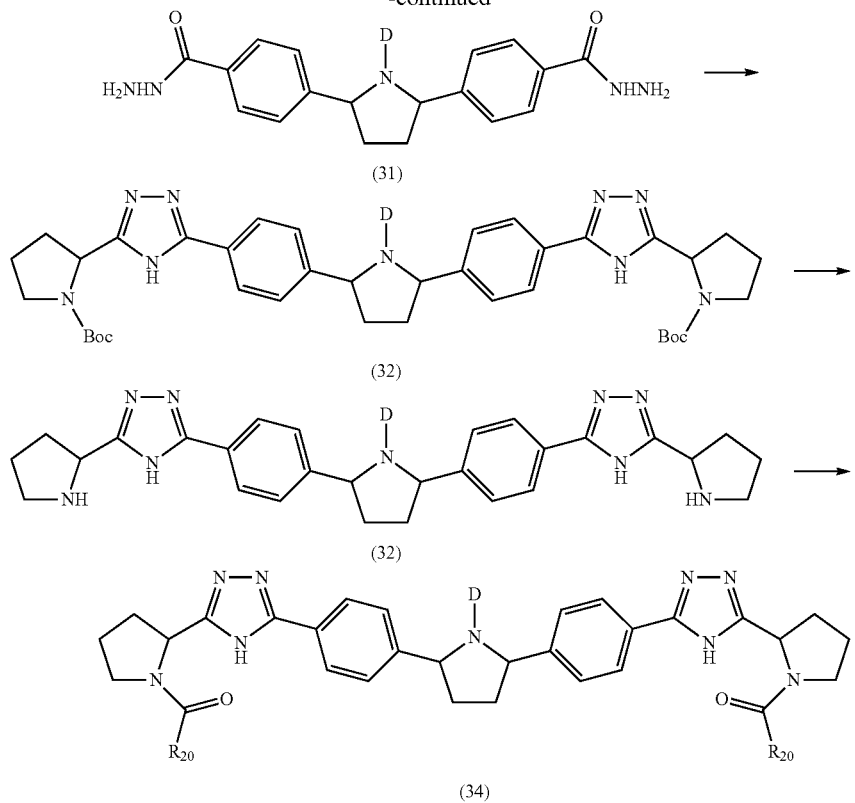

Compounds of the invention of general formula (38), where R$_{20}$ is -L$_S$'-M'-L$_S$''-R$_D$ and D is as described above, can be prepared according to the methods of Scheme XVII. Compounds of formula (24) can be converted to compounds (35) by reaction with CuCN in a solvent such as DMF and with heating to about 160° C. with microwave irradiation. Compounds (35) can be converted to compounds (36) by reaction with HCl(g) in anhydrous methanol at 0° C. with warming to room temperature. Compounds (36) can be converted to compounds (37) by reaction with NH$_3$(g) in anhydrous methanol at 0° C. with warming to room temperature. Compounds (37) can be converted to compounds (38) by reaction with (41) in THF in the presence of a base (e.g., potassium carbonate).

Scheme XVII

(24) ⟶

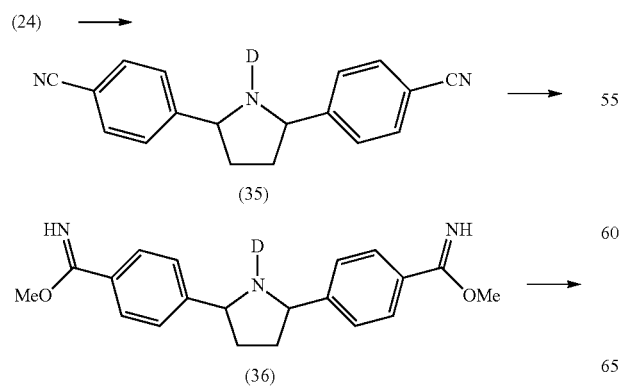

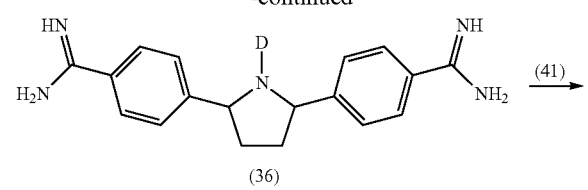

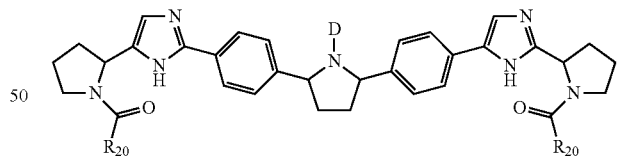

Compounds of formula (41), where R$_{20}$ is -L$_S$'-M'-L$_S$''-R$_D$, can be prepared using the methods of Scheme XVIII. Compounds (39) can be converted to compounds (40) by sequential reaction of (39) with isobutylchloroformate in THF at 0° C. followed by diazomethane. Compounds (40) can be converted to compounds (41) by reaction with HBr in acetic acid.

Scheme XVIII

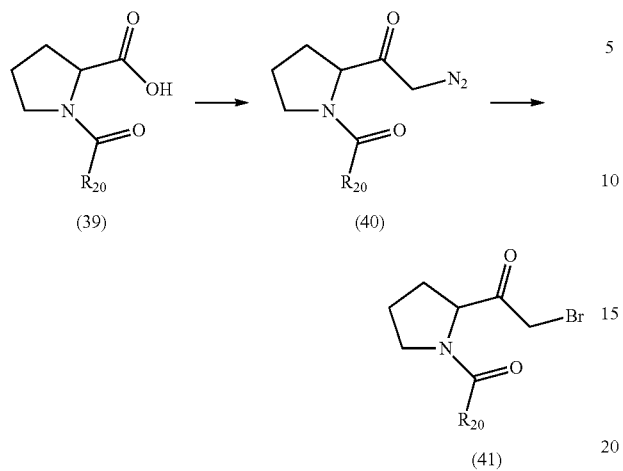

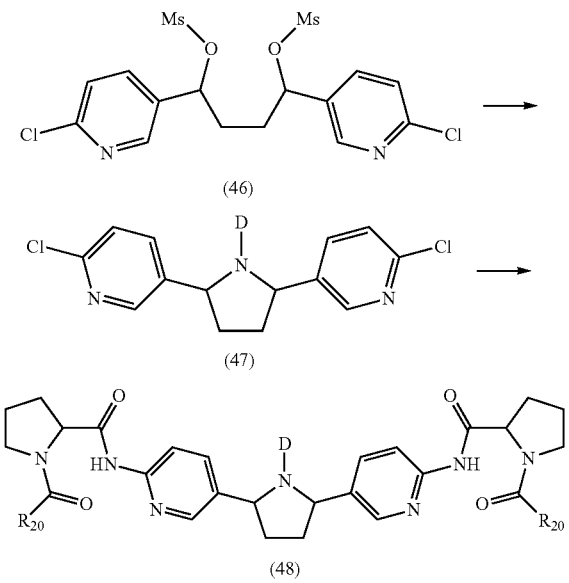

Compounds of the invention of general formula (48), where $R_{20}$ is $-L_S'-M'-L_S''-R_D$ and D is as described above, can be prepared according to the methods of Scheme XIX. Compound (42) can be reacted with compound (43) using, in analogous fashion, the Lewis acid mediated conditions described above in Scheme II to provide compound (44). Compound (44) can be converted sequentially to the diol (45), the mesylate (46) and the cyclic intermediate (47) using, in analogous fashion, the conditions of Scheme II. Compounds (47) can be converted to compounds (48) by reaction with (20) under Buchwald conditions such as those referred to Scheme XIV and described in Scheme XIII.

Scheme XIX

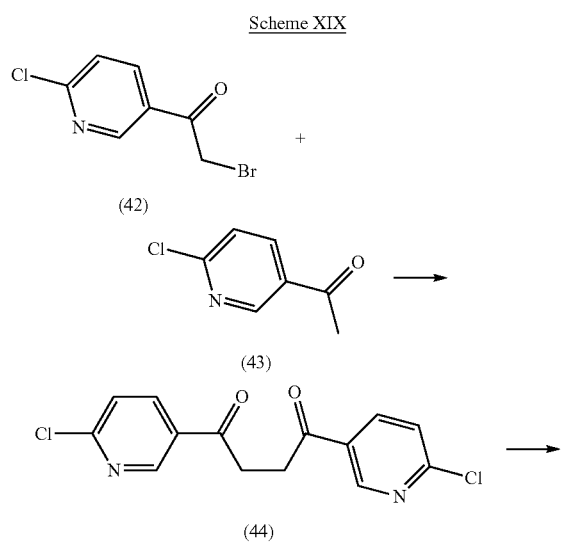

Compounds of the invention of general formula (55), where $R_{20}$ is $-L_S'-M'-L_S''-R_D$ and D is as described above, can be prepared according to the methods of Scheme XX. Diethyl meso-2,5-dibromoadipate (49) can be reacted with an amine $D-NH_2$ in a solvent such as THF, dioxane, or dimethoxyethane with heating from 50-100° C. to give compounds (50). Compounds (50) can be converted to (51) by alkaline hydrolysis with a base (e.g., NaOH, KOH) in an alcohol (e.g., methanol, ethanol) and water mixture for solvent. Compounds (51) can be converted to (52) by reaction first with oxalylchloride, and treatment of the intermediate acid chloride with diazomethane at 0° C. Compounds (52) can be converted to (53) by reaction with aqueous HBr. Compounds (53) can be converted to compounds (54) by reaction with thiourea in ethanol or like solvent. Compounds (54) can be converted to compounds (55) using, in analogous fashion, the conditions described above in Scheme II.

Scheme XX

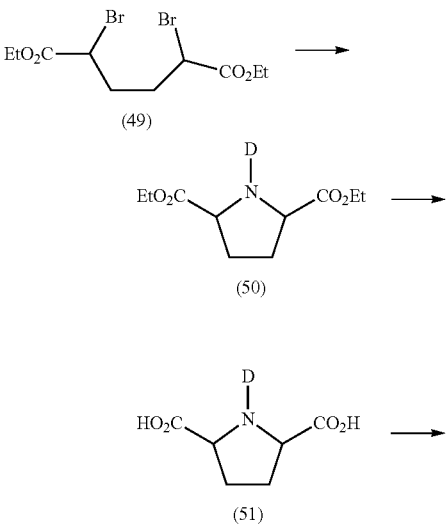

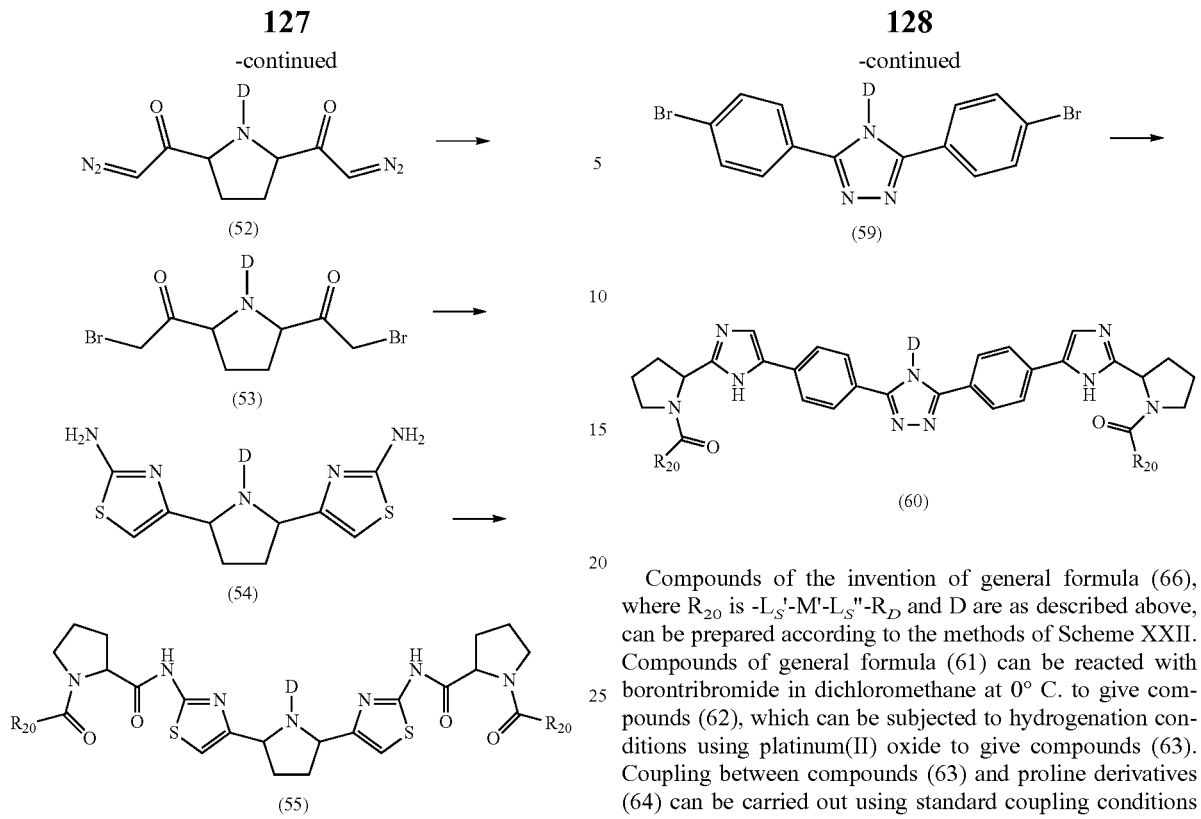

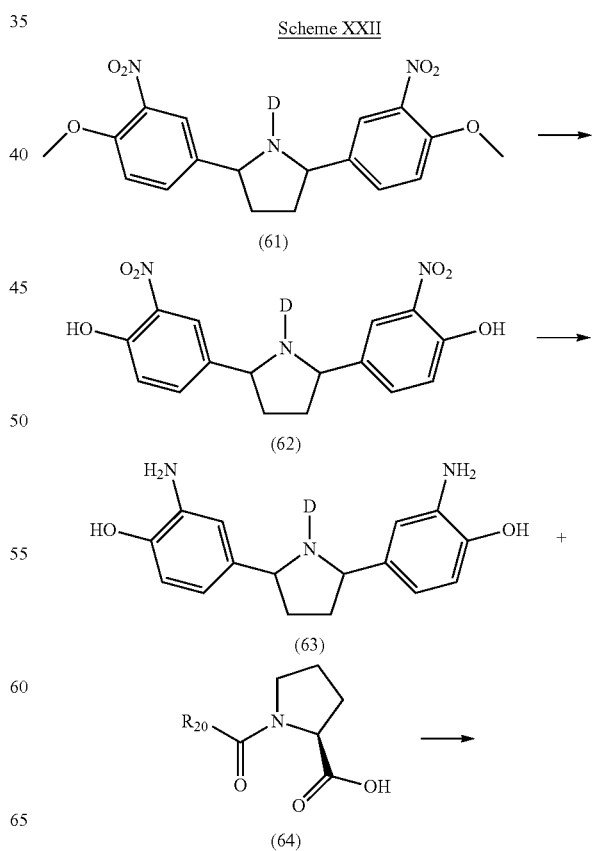

Compounds of the invention of general formula (60), where $R_{20}$ is -$L_S$'-M'-$L_S$"-$R_D$ and D is as described above, can be prepared according to the methods of Scheme XXI. Compound (56) can be reacted with compound (57) in pyridine with heating to about 135° C. to form compound (58). Compound (58) can be converted to compounds (59) by reaction of an amine D-NH$_2$ with POCl$_3$ followed by addition of (58) and heating at about 200° C. in 1,2-dichlorobenzene. Compounds (59) can be converted to compounds (60) using, in analogous fashion, the conditions described above in Scheme VII.

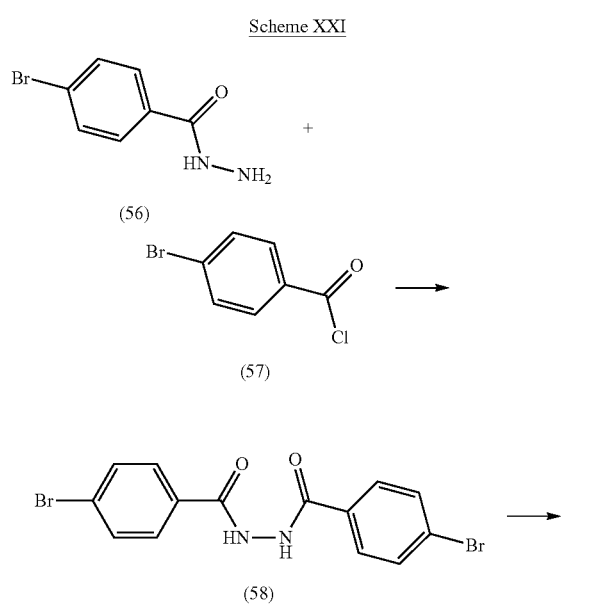

Compounds of the invention of general formula (66), where $R_{20}$ is -$L_S$'-M'-$L_S$"-$R_D$ and D are as described above, can be prepared according to the methods of Scheme XXII. Compounds of general formula (61) can be reacted with borontribromide in dichloromethane at 0° C. to give compounds (62), which can be subjected to hydrogenation conditions using platinum(II) oxide to give compounds (63). Coupling between compounds (63) and proline derivatives (64) can be carried out using standard coupling conditions described above to give compounds (65), which can be converted to (66) by the action of diethylazodicarboxylate and triphenylphosphine in THF.

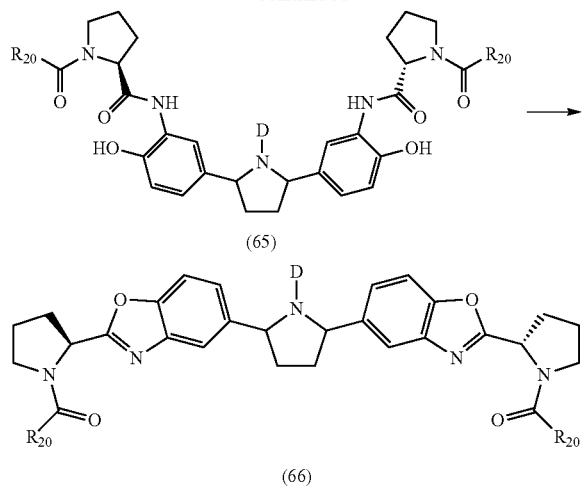

(65)

(66)

Compounds of the invention of general formula (74), where $R_{20}$ is -$L_S$'-M'-$L_S$''-$R_D$ and D is as described above, can be prepared according to the methods of Scheme XXIII. Compound (67) can be converted to (68) by reduction of the nitro group using tin(II) chloride in ethanol. Compound (69) can be made from (68) by peptide coupling with Boc-proline, followed by heating of the resulting amide in acetic acid at 80° C. Compound (69) can be reacted with SEM-Cl and diisopropylethylamine in dichloromethane to give (70), which can be coupled with (71) using a palladium catalyst such as PXPd using a base such as cesium fluoride in a solvent such as N,N-dimethylformamide at 100° C. to give (72). Compound (72) can be converted to (73) by reaction with Selectfluor® in a mixture of THF and water, followed by hydrogenation using 3% Pt on carbon in ethylacetate and then reduction using sodium borohydride in methanol. Compound (73) can be reacted with methanesulfonyl chloride and triethylamine in dichloromethane at −10° C., followed by addition of an amine ($H_2$N-D) to give an intermediate that can be converted to (74) by deprotection using 4N HCl in 1,4-dioxane and then coupling with $R_{20}CO_2H$ using peptide coupling procedures described above.

Scheme XXIII

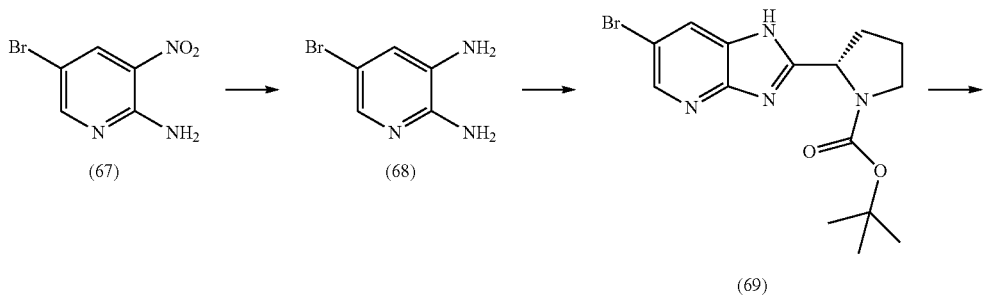

(67)          (68)          (69)

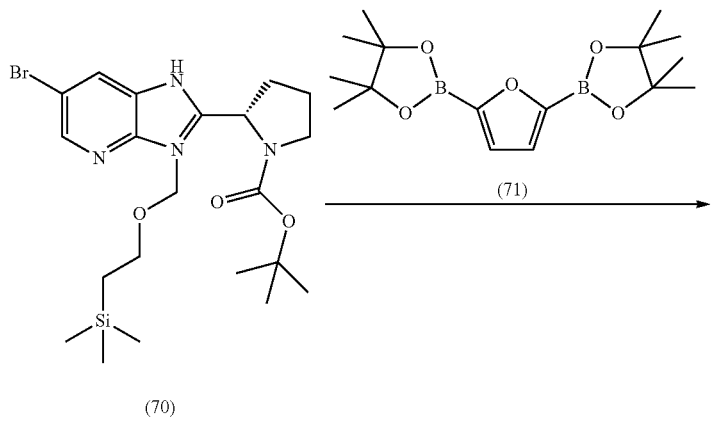

(70)

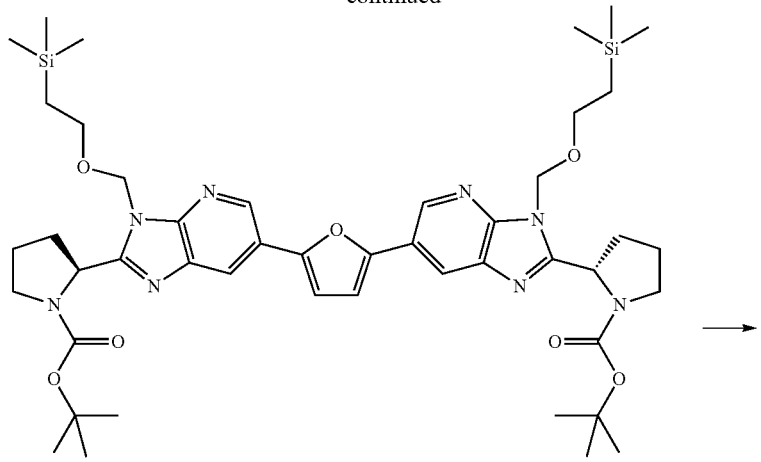

(72)

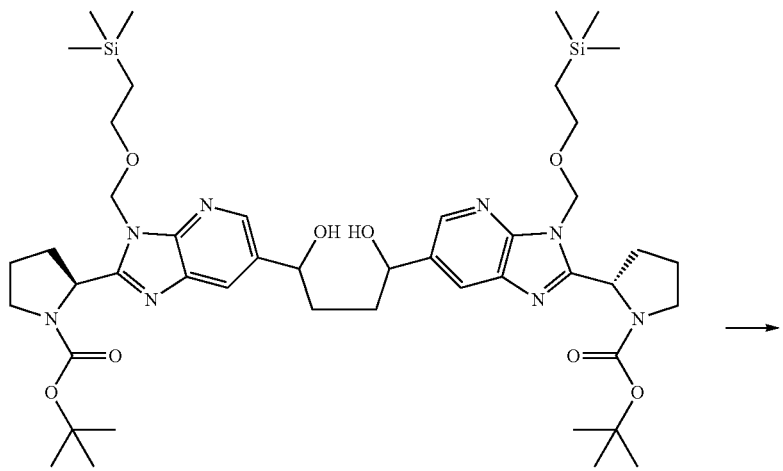

(73)

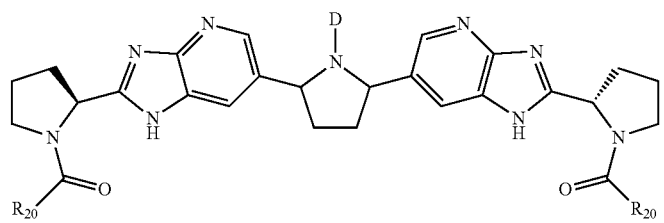

(74)

Compounds of the invention of general formula (81), where $R_{20}$ is -$L_S'$-$M'$-$L_S''$-$R_D$ and D is as described above, can be prepared according to the methods of Scheme XXIV. Compound (75) can be converted to (76) using $SnCl_2$ in ethanol. Coupling of (76) with (64) using peptide coupling procedures described above to give an amide that can be heated in acetic acid at 100° C. to give (77). Compound (77) can be reacted with SEM-Cl and diisopropylethylamine in dichloromethane to give (78), which can be reacted with (71) as described above to give (79). Compound (79) can be converted to (80) using Selectfluor® in a mixture of THF and water, followed by hydrogenation with Pt on carbon in ethylacetate and reduction with sodium borohydride in methanol. Compound (80) can be converted to compounds (81) by mesylation with methanesulfonyl chloride and triethylamine at temperatures less than 0° C., followed by reaction with primary amine $H_2N$-D and deprotection using 4N HCl in 1,4-dioxane.

Scheme XXIV
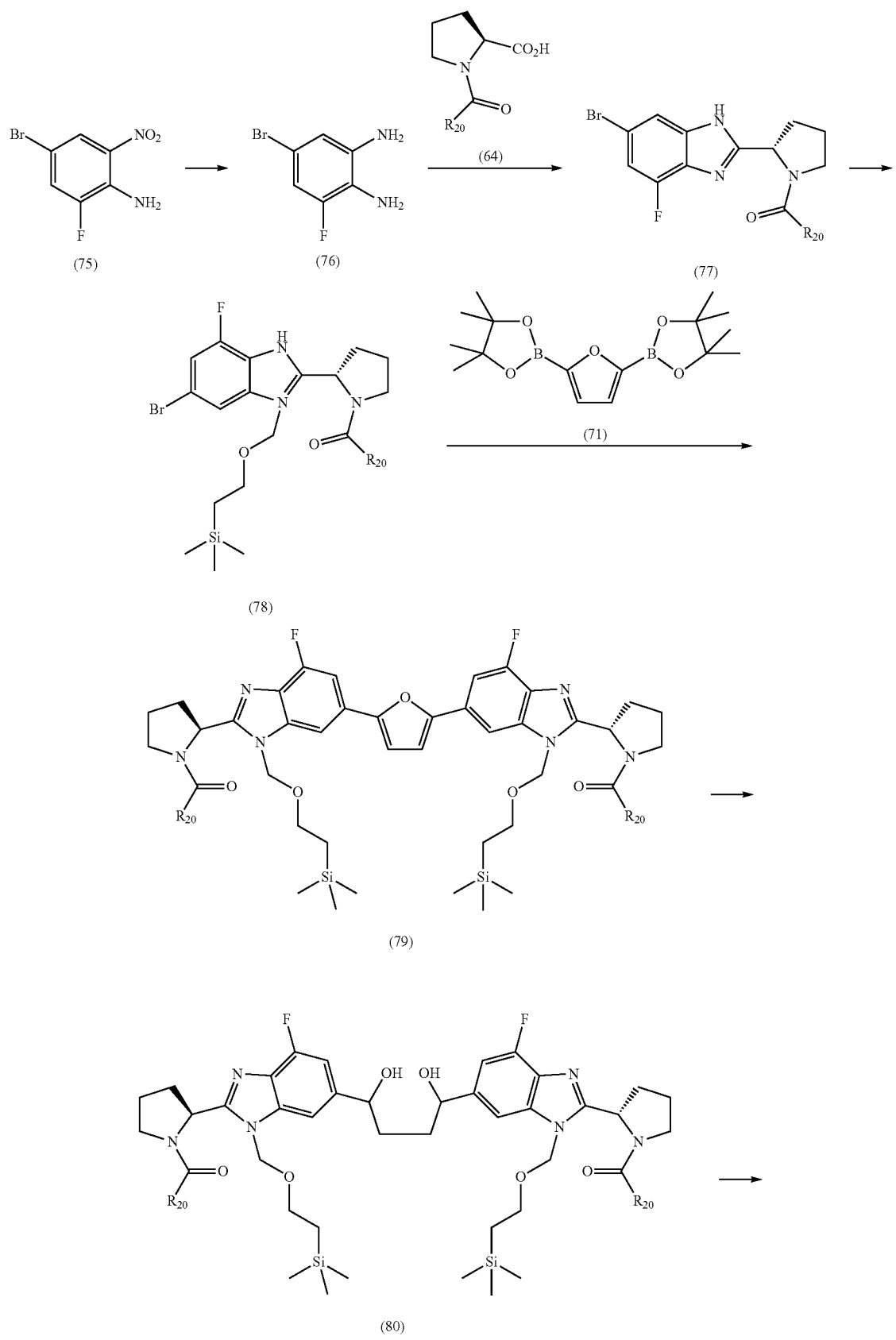

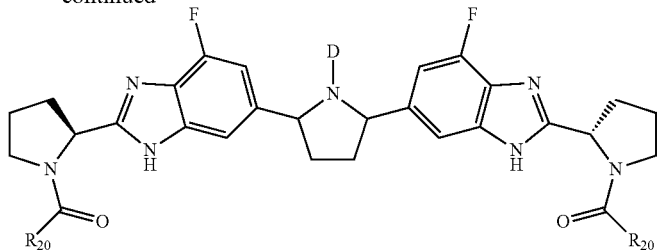

(81)

Certain amines, D-NH$_2$, in the foregoing Schemes are represented by formula (84), and may be prepared according to the general method shown in Scheme XXV, wherein R$_N$ is as defined above (e.g., halogen, alkyl, haloalkyl) and R$_M$ is —N(R$_S$R$_S$') (e.g., —NEt$_2$), heterocyclyl (e.g., pyrrolidin-1-yl, piperidin-1-yl, etc.), or —OR$_S$ (e.g., —O-t-butyl, —O-isopropyl, etc.). Fluoronitrobenzenes (82) can be reacted with an appropriate amine in the presence of dibasic potassium phosphate in a solvent such as DMSO optionally with heating to give intermediates (83), wherein R$_M$ is —N(R$_S$R$_S$') (e.g., —NEt$_2$) or heterocyclyl (e.g., pyrrolidin-1-yl, piperidin-1-yl, etc.). Fluoronitrobenzenes (82) can also be reacted with alkali metal alkoxides (e.g., potassium tert-butoxide) to give intermediates (83), wherein R$_M$ is —OR$_S$ (e.g., —O-t-butyl, —O-isopropyl, etc.). Intermediates (83) may be converted to (84) using well-known nitro reduction conditions. For example, (83) can be converted to (84) by catalytic hydrogenation using palladium on carbon. Alternatively, (83) can be converted to (84) by reaction with iron/ammonium chloride in THF/methanol/water as solvent. Other conditions for effecting nitro reduction include those described in the foregoing schemes and those generally known to one skilled in the art.

Scheme XXV

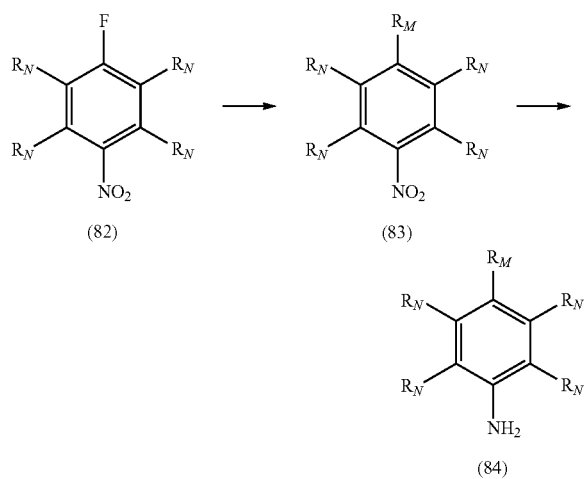

In the foregoing Schemes, compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemistry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —NH$_2$ or —OH) is not compatible with the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

Other compounds of the invention can be similarly prepared according to the above-described schemes as well as the procedures described in following examples, as appreciated by those skilled in the art. It should be understood that the above-described embodiments and schemes and the following examples are given by way of illustration, not limitation. Various changes and modifications within the scope of the present invention will become apparent to those skilled in the art from the present description.

Example compounds below were named using either ChemDraw version 9.0 or ACD version 12 (ACD v12). Final compounds for Examples 1-50 were named using ChemDraw unless otherwise indicated as being named using ACD v12. Final compounds after Example 50 were named using ACD v12. Intermediates were named using ChemDraw, unless otherwise indicated as being named using ACD v12.

Certain compounds in the Examples below were purified using reverse-phase HPLC. Purification was conducted using either a C18 or C8 reverse-phase column. Compounds were eluted using a gradient of about 10-100% acetonitrile in 0.1% aqueous TFA; about 60-100% methanol in 10 mM aqueous ammonium acetate; or about 10-95% methanol in 10 mM aqueous ammonium acetate. For purifications conducted with TFA, the product thus obtained may be in the form of a TFA salt. Compounds may be characterized as the TFA salt or as the free base following neutralization, extraction and isolation.

Certain compounds in the Examples below were purified using normal phase silica gel chromatography including traditional flash chromatography or an automated purification

137 system (e.g., Isco Combi-Flash, Analogix Intelliflash) using pre-packed silica gel columns (55 or 35 μm silica gel, Isco gold columns)

Typical solvents for silica gel chromatography include: Ethyl acetate in hexanes, Diethyl ether in hexanes, THF in hexanes, Ethyl acetate in methylene chloride, Methanol in methylene chloride, Methanol in methylene chloride with NH$_4$OH, Acetone in hexanes, and Methylene chloride in hexanes.

Example 1

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

138 mL) and extracted with ethyl acetate (3×50 ml). The combined organic layers were dried over Na$_2$SO$_4$, filtered and concentrated. The resulting residue was triturated with dichloromethane to give an orange solid that was collected by filtration and dried to give the title compound (2.0 gm, 61% yield).

Example 1B 1,4-Bis(4-nitrophenyl)butane-1,4-diol

To a solution of the product from Example 1A (1.0 g, 3.05 mmol) in anhydrous THF (30 ml) at 0° C. was added sodium borohydride (0.357 g, 9.44 mmol). The resulting mixture was stirred at 50° C. overnight. The cooled mixture was poured into water, extracted with ethyl acetate, dried over Na$_2$SO$_4$, filtered and concentrated in vacuo. The resulting solid was triturated with dichloromethane to give a tan solid that was collected by filtration and dried to give the title compound (0.82 gm, 81% yield).

Example 1C 1,4-Bis(4-nitrophenyl)butane-1,4-diyl dimethanesulfonate

To a solution of the product from Example 1B (0.80 g, 2.407 mmol) in dry CH$_2$Cl$_2$ (25 ml) at 0° C. was added

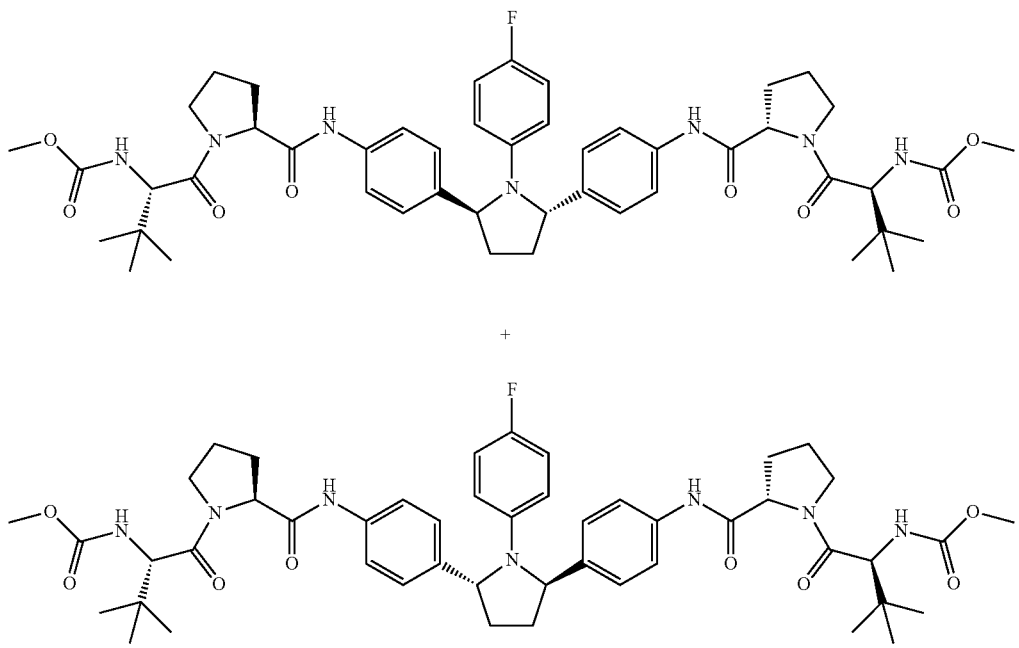

Example 1A 1,4-Bis(4-nitrophenyl)butane-1,4-dione

Anhydrous zinc(II) chloride (2.73 g, 20.00 mmol) was stirred in dry benzene (15 ml) while diethylamine (1.558 ml, 15.00 mmol) and t-butanol (1.435 ml, 15.00 mmol) were added, and the resulting mixture was stirred at room temperature for 90 min to give a cloudy solution. To this mixture was added 2-bromo-1-(4-nitrophenyl)ethanone (2.44 g, 10.00 mmol) and 1-(4-nitrophenyl)ethanone (2.477 g, 15.00 mmol), and the resulting mixture was stirred at room temperature overnight. The mixture was poured into water (50 triethylamine (1.007 ml, 7.22 mmol), followed by dropwise addition of methanesulfonyl chloride (0.469 ml, 6.02 mmol). The resulting mixture was stirred at 0° C. for 30 min, during which time the starting material slowly went into solution. After stirring an additional 1 h at 0° C., a precipitate began to form. Saturated aq NH$_4$Cl (4 ml) was added, and stirring was continued at room temperature for 20 min. The mixture was washed with water (2×10 ml), and the organic layer was treated with hexanes (10 ml) to give an orange solid that was collected by filtration to give the title compound (0.75 gm, 64% yield).

Example 1D

1-(4-Fluorophenyl)-2,5-bis(4-nitrophenyl)pyrrolidine

The product from Example 1C (0.6 gm, 1.228 mmol) and 4-fluoroaniline (2.0 ml, 20.82 mmol) were combined and stirred at 50° C. overnight. The resulting mixture was partitioned between 0.2 N HCl (50 ml) and ethyl acetate (3×50 ml), and the combined organic layers were dried over $Na_2SO_4$, filtered and concentrated in vacuo. The crude product was purified by chromatography on silica gel using a solvent gradient of 0-40% ethyl acetate in hexane to give the title compound as a mixture of cis and trans isomers (0.5 gm, 100% yield).

Example 1E

4,4'-(1-(4-Fluorophenyl)pyrrolidine-2,5-diyl)dianiline

To a solution of the product from Example 1D (0.501 g, 1.23 mmol) in ethanol (5 ml) and THF (5.00 ml) was added iron powder (0.412 g, 7.38 mmol) and a solution of ammonium chloride (0.197 g, 3.69 mmol) in water (1.0 ml). The resulting mixture was stirred at 80° C. for 45 min. The mixture was cooled, filtered through celite, washed with ethanol, and concentrated in vacuo. The crude product was purified by chromatography on silica gel using a solvent gradient of 0-100% ethyl acetate in hexanes to give the title compound as a mixture of cis and trans isomers (0.135 gm, 32%).

Example 1F

(2S,2'S)-tert-Butyl 2,2'-(4,4'-(1-(4-fluorophenyl)pyrrolidine-2,5-diyl)bis(4,1-phenylene))bis(azanediyl)bis(oxomethylene)dipyrrolidine-1-carboxylate To a mixture of the product from Example 1E (0.13 gm, 0.374 mmol), (S)-1-(tert-butoxycarbonyl)pyrrolidine-2-carboxylic acid (0.201 gm, 0.935 mmol) and HATU (0.356 gm, 0.935 mmol) in DMSO (3 ml) was added Hunig's base (0.196 ml, 1.123 mmol), and reaction mixture was stirred at room temperature for 90 min. The mixture was poured into water and extracted by ethyl acetate. The organic extract was dried over $Na_2SO_4$, filtered and concentrated in vacuo to give a crude product that was purified by column chromatography on silica gel, eluting with a solvent gradient of 5-100% ethyl acetate in hexane to give title compound (0.28 gm, 100%).

Example 1G

(2S,2'S)—N,N'-(4,4'-(1-(4-Fluorophenyl)pyrrolidine-2,5-diyl)bis(4,1-phenylene))dipyrrolidine-2-carboxamide To the product from Example 1F (0.28 gm, 0.377 mmol) in $CH_2Cl_2$ (2.0 ml) was added TFA (2.0 ml). The reaction mixture was stirred at room temperature for 45 min and concentrated in vacuo. The residue was partitioned between 3:1 $CH_2Cl_2$:2-PrOH and saturated aq. $NaHCO_3$. The organic layer was dried over $Na_2SO_4$, filtered and concentrated to give the title compound (0.195 gm, 95% yield).

Example 1H

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and

Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate To a mixture of the product from Example 1G (0.03 gm, 0.055 mmol), (S)-2-(methoxycarbonylamino)-3,3-dimethylbutanoic acid (0.0262 gm, 0.138 mmol) and HATU (0.0526 gm, 0.138 mmol) in DMSO (0.5 ml) was added Hunig's base (0.029 ml, 0.166 mmol), and the resulting mixture was stirred at room temperature for 90 min. The mixture was poured into water (2 ml) and extracted by ethyl acetate (2×2 ml), and the combined organic layers were concentrated and subjected to HPLC purification on a semi-prep C18 reverse-phased column using a gradient of 10-100% acetonitrile in 0.1% aq TFA. The trans-substituted pyrrolidine isomer was the first of 2 stereoisomers to elute, providing the title compound as a 1:1 mixture of diastereomers (0.014 gm, 29% yield): 1H NMR (TFA salt) (400 MHz, DMSO-D6) δ ppm 0.93-1.01 (m, J=4.99 Hz, 18H) 1.62-1.68 (m, 2H) 1.81-1.93 (m, 6H) 1.94-2.04 (m, 2H) 2.09-2.20 (m, 2H) 3.54 (s, 6H) 3.59-3.69 (m, 2H) 3.73-3.81 (m, 2H) 4.18-4.24 (m, 2H) 4.43 (dd, J=7.81, 5.42 Hz, 2H) 5.16 (d, 2H) 6.20 (dd, J=9.05, 4.39 Hz, 2H) 6.78 (t, J=8.89 Hz, 2H) 7.09 (d, J=8.89 Hz, 2H) 7.12 (d, 4H) 7.50 (d, J=8.02 Hz, 4H) 9.99 (s, 2H). The title compound showed an $EC_{50}$ value of less than about 0.1 nM in HCV 1b-Con1 replicon assays in the presence of 5% FBS. The 1b-Con1 replicon assay is described below.

Example 2

Dimethyl (2S,2'S)-1,1'-((2S,2'S)-2,2'-(4,4'-((2S,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

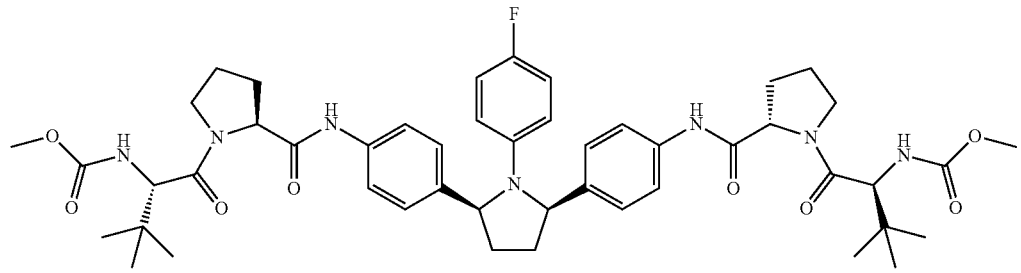

To a mixture of the product from Example 1G (0.03 gm, 0.055 mmol), (S)-2-(methoxycarbonylamino)-3,3-dimethylbutanoic acid (0.0262 gm, 0.138 mmol) and HATU (0.0526 gm, 0.138 mmol) in DMSO (0.5 ml) was added Hunig's base (0.029 ml, 0.166 mmol), and the resulting mixture was stirred at room temperature for 90 min. The mixture was poured into water (2 ml) and extracted by ethyl acetate (2×2 ml), and the combined organic layers were concentrated and subjected to HPLC purification on a semi-prep C18 reverse-phased column using a gradient of 10-100% acetonitrile in 0.1% aq TFA. The cis-substituted pyrrolidine isomer was the second of 2 stereoisomers to elute, providing the title compound (0.018 gm, 37% yield): 1H NMR (TFA salt) (400 MHz, DMSO-D6) δ ppm 0.93-1.01 (m, J=3.04 Hz, 18H) 1.75-1.94 (m, 6H) 1.94-2.05 (m, 2H) 2.11-2.22 (m, 2H) 2.31-2.35 (m, 1H) 3.54 (s, 6H) 3.61-3.70 (m, 2H) 3.74-3.83 (m, 2H) 4.22 (d, J=8.78 Hz, 2H) 4.46 (dd, J=8.02, 5.42 Hz, 2H) 4.65 (t, 2H) 6.34 (dd, 2H) 6.86 (t, J=8.89 Hz, 2H) 7.08 (d, 2H) 7.43 (d, J=7.81 Hz, 4H) 7.60 (d, J=8.57 Hz, 4H) 10.05 (s, 2H). The title compound showed an $EC_{50}$ value of less than about 0.1 nM in HCV 1b-Con1 replicon assays in the presence of 5% FBS.

Example 3

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

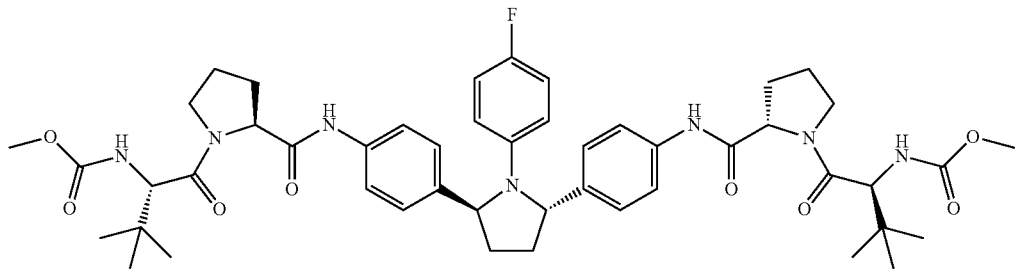

The product from Example 1H was purified by chiral chromatography on a Chiralpak AD-H semi-prep column eluting with a 1:1 mixture of hexanes:(2:1 IPA:EtOH). The title compound was the first of 2 stereoisomers to elute. 1H NMR (400 MHz, DMSO-D6) δ ppm 0.97 (s, 18H) 1.61-1.67 (m, J=5.64 Hz, 2H) 1.79-1.92 (m, 6H) 1.93-2.04 (m, J=5.86 Hz, 2H) 2.07-2.20 (m, J=6.51 Hz, 2H) 3.54 (s, 6H) 3.59-3.69 (m, 2H) 3.71-3.83 (m, 2H) 4.21 (d, J=8.89 Hz, 2H) 4.43 (dd, J=7.97, 5.37 Hz, 2H) 5.15 (d, J=6.51 Hz, 2H) 6.20 (dd, 2H) 6.78 (t, J=8.95 Hz, 2H) 7.13 (d, J=8.57 Hz, 4H) 7.50 (d, J=8.57 Hz, 4H) 9.99 (s, 2H). The title compound showed an $EC_{50}$ value of less than about 0.1 nM in HCV 1b-Con1 replicon assays in the presence of 5% FBS.

Example 4

Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

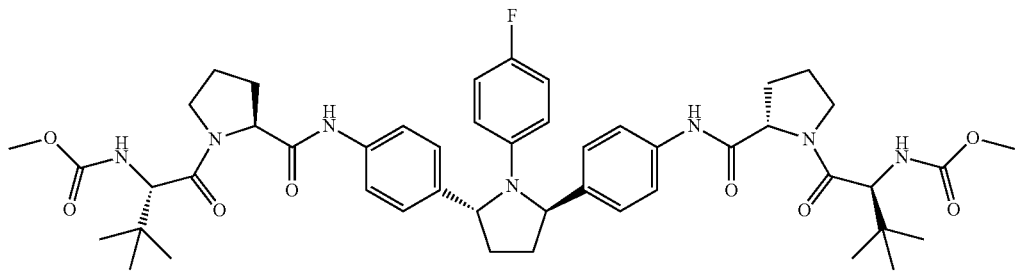

The product from Example 1H was separated by chiral chromatography on a Chiralpak AD-H semi-prep column eluting with a 1:1 mixture of hexanes:(2:1 IPA:EtOH). The title compound was the second of 2 stereoisomers to elute. 1H NMR (400 MHz, DMSO-D6) δ ppm 0.96 (s, 18H) 1.64 (d, J=5.53 Hz, 2H) 1.78-1.93 (m, 6H) 1.94-2.06 (m, 2H) 2.09-2.21 (m, 2H) 3.54 (s, 6H) 3.59-3.69 (m, 2H) 3.72-3.83 (m, 2H) 4.20 (d, J=8.89 Hz, 2H) 4.43 (dd, J=7.92, 5.42 Hz, 2H) 5.16 (d, J=6.29 Hz, 2H) 6.20 (dd, J=9.16, 4.39 Hz, 2H) 6.77 (t, J=8.95 Hz, 2H) 7.12 (d, J=8.57 Hz, 4H) 7.50 (d, J=8.57 Hz, 4H) 9.99 (s, 2H). The title compound showed an $EC_{50}$ value of less than about 0.1 nM in HCV 1b-Con1 replicon assays in the presence of 5% FBS.

Example 5

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(1-oxobutane-2,1-diyl)dicarbamate and Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(1-oxobutane-2,1-diyl)dicarbamate 4.86-4.91 (m, 4H) 4.96 (d, J=6.61 Hz, 2H) 6.17-6.25 (m, 2H) 6.47 (d, J=8.35 Hz, 4H) 6.74 (t, 2H) 6.82 (d, J=8.35 Hz, 4H).

Example 5B (2S,2'S)-tert-Butyl 2,2'-(4,4'-((2S,5S)-1-(4-fluorophenyl)pyrrolidine-2,5-diyl)bis(4,1-phenylene))bis(azanediyl)bis(oxomethylene)dipyrrolidine-1-carboxylate and (2S,2'S)-tert-Butyl 2,2'-(4,4'-((2R,5R)-1-(4-fluorophenyl)pyrrolidine-2,5-diyl)bis(4,1-phenylene))bis(azanediyl)bis(oxomethylene) dipyrrolidine-1-carboxylate The product from Example 5A (50 mg, 0.144 mmol) was subjected to the conditions described in Example 1F to give the title compound as a 1:1 mixture of diastereomers (105 mg, 98%): 1H NMR (400 MHz, DMSO-D6) δ ppm 1.34 (d, 18H) 1.66 (d, J=5.10 Hz, 2H) 1.74-1.89 (m, 6H) 2.07-2.23 (m, 2H) 4.15-4.25 (m, 2H) 5.18 (d, J=3.47 Hz, 2H) 6.18-6.25 (m, 2H) 6.78 (t, J=8.95 Hz, 2H) 7.14 (d, J=8.24 Hz, 4H) 7.51 (t, J=8.29 Hz, 4H) 9.92 (d, 2H).

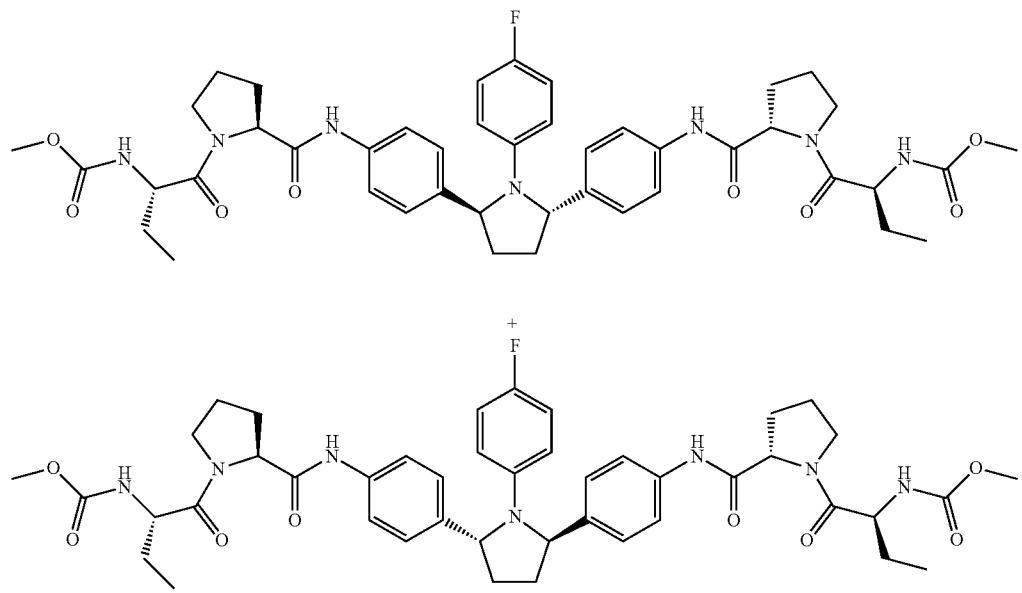

Example 5A 4,4'-((2S,5S)-1-(4-Fluorophenyl)pyrrolidine-2,5-diyl)dianiline and 4,4'-((2R,5R)-1-(4-Fluorophenyl) pyrrolidine-2,5-diyl)dianiline The product from Example 1E was purified by column chromatography on silica gel, eluting with a solvent gradient of 0-100% ethyl acetate in hexanes. The title compound eluted as the first of 2 stereoisomers and was obtained as a racemic mixture of trans diastereomers. 1H NMR (400 MHz, DMSO-D6) δ ppm 1.57 (d, J=5.64 Hz, 2H) 2.36-2.42 (m, 2H)

Example 5C (2S,2'S)—N,N'-(4,4'-((2S,5S)-1-(4-Fluorophenyl) pyrrolidine-2,5-diyl)bis(4,1-phenylene))dipyrrolidine-2-carboxamide and (2S,2'S)—N,N'-(4,4'-((2R,5R)-1-(4-Fluorophenyl)pyrrolidine-2,5-diyl)bis(4,1-phenylene))dipyrrolidine-2-carboxamide The product from Example 5B was subjected to the conditions described in Example 1G to give the title compound as a 1:1 mixture of diastereomers.

Example 5D

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(1-oxobutane-2,1-diyl)dicarbamate and Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(1-oxobutane-2,1-diyl) dicarbamate To a mixture of the product from Example 5C (0.102 g, 0.188 mmol), (S)-2-(methoxycarbonyl amino)butanoic acid (0.064 g, 0.395 mmol) and HATU (0.150 g, 0.395 mmol) in

Example 6

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-hydroxy-3-methyl-1-oxobutane-2,1-diyl)dicarbamate and Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-hydroxy-3-methyl-1-oxobutane-2,1-diyl)dicarbamate

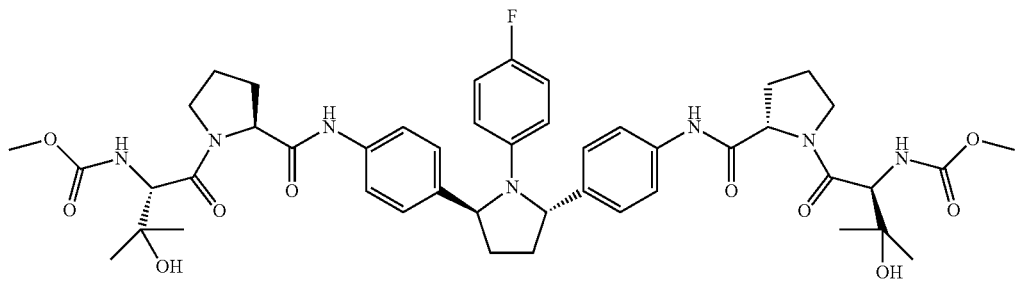

+

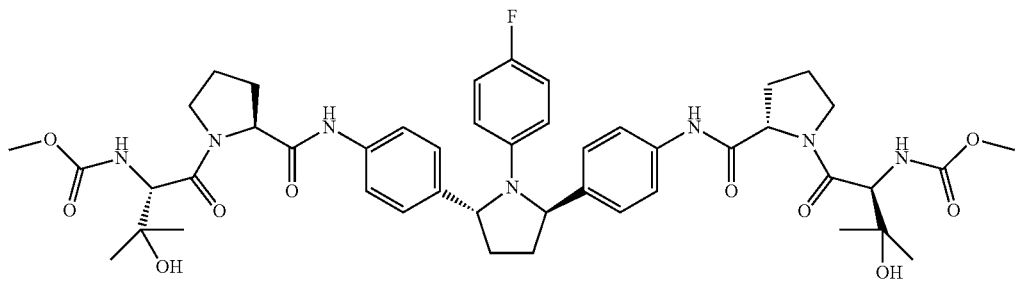

DMSO (2 ml) was added Hunig's base (0.099 ml, 0.565 mmol), and the reaction was stirred at room temperature for 45 min. The reaction mixture was partitioned between water and ethyl acetate, and the organic layer was dried over $Na_2SO_4$, filtered and concentrated in vacuo. The crude product was purified by column chromatography on silica gel using a solvent gradient of 0-4% MeOH in dichloromethane to give the title compound as a 1:1 mixture of stereoisomers (0.158 gm, 94% yield): 1H NMR (400 MHz, DMSO-D6) δ ppm 0.86-0.96 (m, 6H) 1.53 (d, J=4.34 Hz, 2H) 1.59-1.73 (m, 2H) 1.80-1.96 (m, J=6.29 Hz, 4H) 1.96-2.06 (m, 2H) 2.08-2.20 (m, 2H) 3.52 (s, 6H) 3.67-3.79 (m, 2H) 4.12-4.23 (m, 2H) 4.42 (dd, J=8.13, 4.66 Hz, 2H) 5.16 (d, J=6.40 Hz, 2H) 6.20 (dd, J=9.22, 4.45 Hz, 2H) 6.77 (t, J=8.89 Hz, 2H) 7.12 (d, J=7.59 Hz, 4H) 7.30 (dd, J=7.59, 3.25 Hz, 2H) 7.50 (d, J=8.24 Hz, 4H) 8.16 (s, 2H) 9.95 (s, 2H). The title compound showed an $EC_{50}$ value of from about 0.1 to about 1 nM in HCV 1b-Con1 replicon assays in the presence of 5% FBS.

To a mixture of the product from Example 5C (0.1 g, 0.185 mmol), (S)-3-hydroxy-2-(methoxycarbonyl amino)-3-methylbutanoic acid (0.074 g, 0.388 mmol) and HATU (0.147 g, 0.388 mmol) in DMSO (2 ml) was added Hunig's base (0.097 ml, 0.554 mmol), and the reaction mixture was stirred at room temperature for 45 min. The reaction mixture was partitioned between water and ethyl acetate, and the organic layer was dried over $Na_2SO_4$, filtered and concentrated in vacuo. The crude product was purified by column chromatography on silica gel using a solvent gradient of 0-4% MeOH in dichloromethane to give the title compound as a 1:1 mixture of stereoisomers (0.162 gm, 97% yield): 1H NMR (400 MHz, DMSO-D6) δ ppm 1.15 (d, J=10.19 Hz, 12H) 1.64 (d, J=5.64 Hz, 2H) 1.87-1.98 (m, 6H) 2.09-2.22 (m, 2H) 3.55 (s, 6H) 3.58-3.66 (m, 2H) 3.66-3.74 (m, 2H) 3.83-3.92 (m, 2H) 4.37 (s, 2H) 4.44-4.50 (m, 2H) 5.07 (s, 2H) 5.11 (s, 2H) 5.17 (d, J=6.18 Hz, 2H) 6.15-6.28 (m, 2H) 6.78 (t, J=8.89 Hz, 2H) 7.13 (d, J=8.13 Hz, 4H) 7.51 (d, J=7.81 Hz, 4H) 8.11-8.23 (m, 2H) 9.67 (d, J=9.11 Hz, 2H). The title compound showed an $EC_{50}$ value of less than about 0.1 nM in HCV 1b-Con1 replicon assays in the presence of 5% FBS.

Example 7

Dimethyl (2S,2'S,3R,3'R)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methoxy-1-oxobutane-2,1-diyl)dicarbamate and Dimethyl (2S,2'S,3R,3'R)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methoxy-1-oxobutane-2,1-diyl)dicarbamate

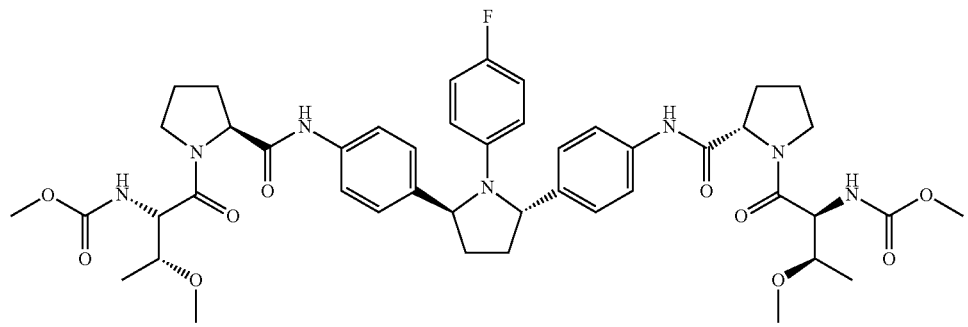

+

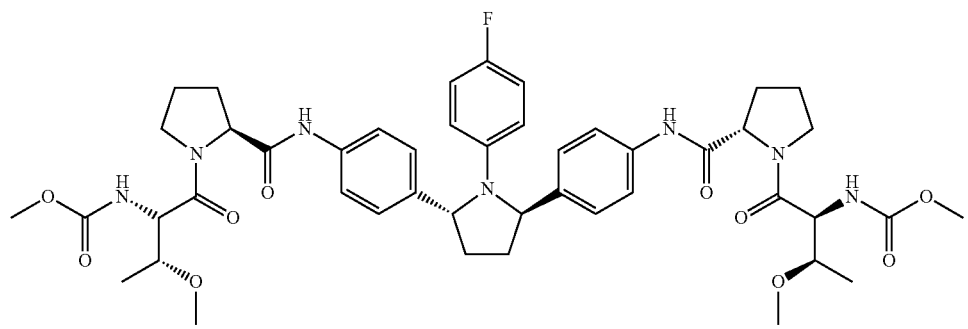

To a mixture of the product from Example 5C (0.025 gm, 0.046 mmol), (2S,3R)-3-methoxy-2-(methoxycarbonylamino)butanoic acid (0.01941 gm, 0.102 mmol) and HATU (0.0439 gm, 0.115 mmol) in DMSO (0.2 ml) was added Hunig's base (0.024 ml, 0.138 mmol). The mixture was stirred at room temperature for 2 hr, and was then poured into water and extracted with ethyl acetate. The organic phase was dried over Na$_2$SO$_4$ filtered and concentrated in vacu, and the crude product was purified by chromatography on silica gel using a solvent gradient of 0-5% MeOH in CH$_2$Cl$_2$ to give the title compound (0.040 gm, 93% yield): 1H NMR (400 MHz, DMSO-D6) δ ppm 1.09-1.31 (m, 6H) 1.64 (d, J=5.10 Hz, 2H) 1.83-1.93 (m, J=12.42, 12.42 Hz, 4H) 1.93-2.03 (m, 2H) 2.11-2.19 (m, 2H) 3.10-3.18 (m, J=6.94 Hz, 2H) 3.24 (d, J=4.99 Hz, 6H) 3.42-3.49 (m, J=10.84, 6.72 Hz, 2H) 3.53 (s, 6H) 3.58-3.70 (m, 2H) 3.79-3.89 (m, 2H) 4.26 (t, J=7.10 Hz, 2H) 4.41 (dd, J=7.97, 4.93 Hz, 2H) 5.16 (d, J=6.29 Hz, 2H) 6.20 (dd, J=9.11, 4.34 Hz, 2H) 6.78 (t, J=8.95 Hz, 2H) 7.12 (d, 4H) 7.33 (dd, J=7.70, 3.47 Hz, 2H) 7.50 (d, J=8.13 Hz, 4H) 9.95 (s, 2H). The title compound showed an EC$_{50}$ value of from about 0.1 to about 1 nM in HCV 1b-Con1 replicon assays in the presence of 5% FBS.

Example 8 dimethyl (2S,2'S,3R,3'R)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methoxy-1-oxobutane-2,1-diyl)dicarbamate

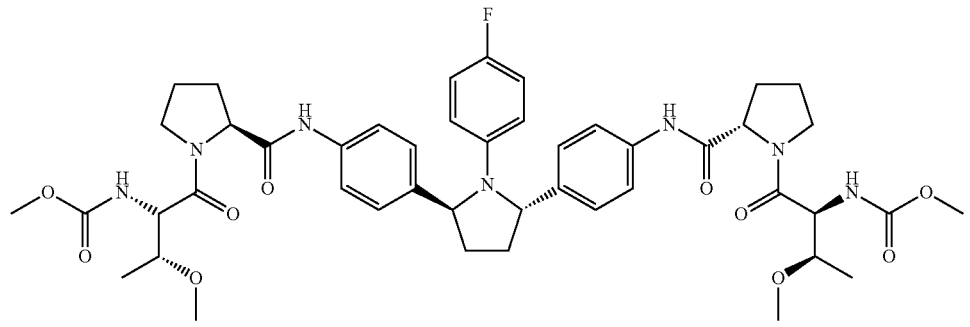

The product from Example 7 was purified by chiral chromatography on a Chiralpak AD-H semi-prep column eluting with a 1:3 mixture of hexanes:(1:1 IPA:EtOH). The title compound was the first of 2 stereoisomers to elute. 1H NMR (400 MHz, DMSO-D6) δ ppm 1.13 (d, J=6.18 Hz, 6H) 1.64 (d, J=5.64 Hz, 2H) 1.82-1.93 (m, 4H) 1.95-2.04 (m, 2H) 2.10-2.19 (m, 2H) 3.25 (s, 6H) 3.44-3.48 (m, 2H) 3.53 (s, 6H) 3.62-3.71 (m, 2H) 3.79-3.87 (m, 2H) 4.26 (t, J=7.75 Hz, 2H) 4.41 (dd, J=7.92, 4.99 Hz, 2H) 5.16 (d, J=6.51 Hz, 2H) 6.20 (dd, J=9.16, 4.39 Hz, 2H) 6.78 (t, J=8.89 Hz, 2H) 7.13 (d, J=8.57 Hz, 4H) 7.34 (d, J=7.92 Hz, 2H) 7.50 (d, J=8.57 Hz, 4H) 9.95 (s, 2H). The title compound showed an $EC_{50}$ value of less than about 0.1 nM in HCV 1b-Con1 replicon assays in the presence of 5% FBS.

Example 9 dimethyl (2S,2'S,3R,3'R)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methoxy-1-oxobutane-2,1-diyl)dicarbamate The product from Example 7 was purified by chiral chromatography on a Chiralpak AD-H semi-prep column eluting with a 1:3 mixture of hexanes:(1:1 IPA:EtOH). The title compound was the second of 2 stereoisomers to elute. 1H NMR (400 MHz, DMSO-D6) δ ppm 1.12 (d, J=6.18 Hz, 6H) 1.64 (d, J=5.64 Hz, 2H) 1.82-1.93 (m, 4H) 1.95-2.06 (m, 2H) 2.10-2.21 (m, 2H) 3.24 (s, 6H) 3.42-3.48 (m, 2H) 3.53 (s, 6H) 3.61-3.73 (m, 2H) 3.78-3.88 (m, 2H) 4.26 (t, J=7.75 Hz, 2H) 4.41 (dd, J=7.92, 4.99 Hz, 2H) 5.16 (d, J=6.18 Hz, 2H) 6.20 (dd, 2H) 6.78 (t, J=8.89 Hz, 2H) 7.13 (d, J=8.46 Hz, 4H) 7.33 (d, J=7.81 Hz, 2H) 7.49 (d, J=8.46 Hz, 4H) 9.95 (s, 2H). The title compound showed an $EC_{50}$ value of from about 0.1 to about 1 nM in HCV 1b-Con1 replicon assays in the presence of 5% FBS.

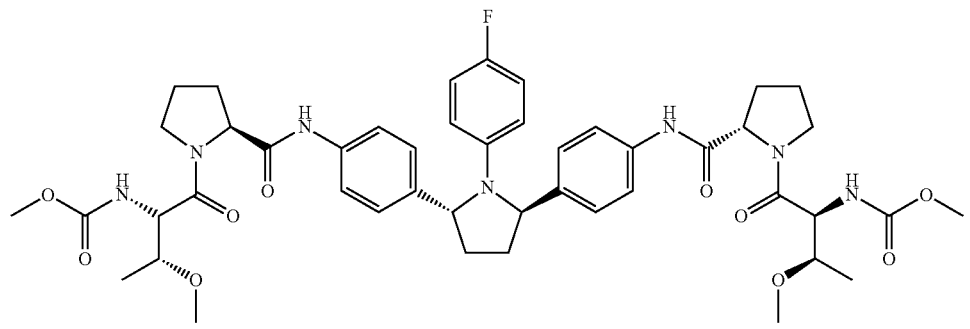

Example 10

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl) dicarbamate and Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl) dicarbamate

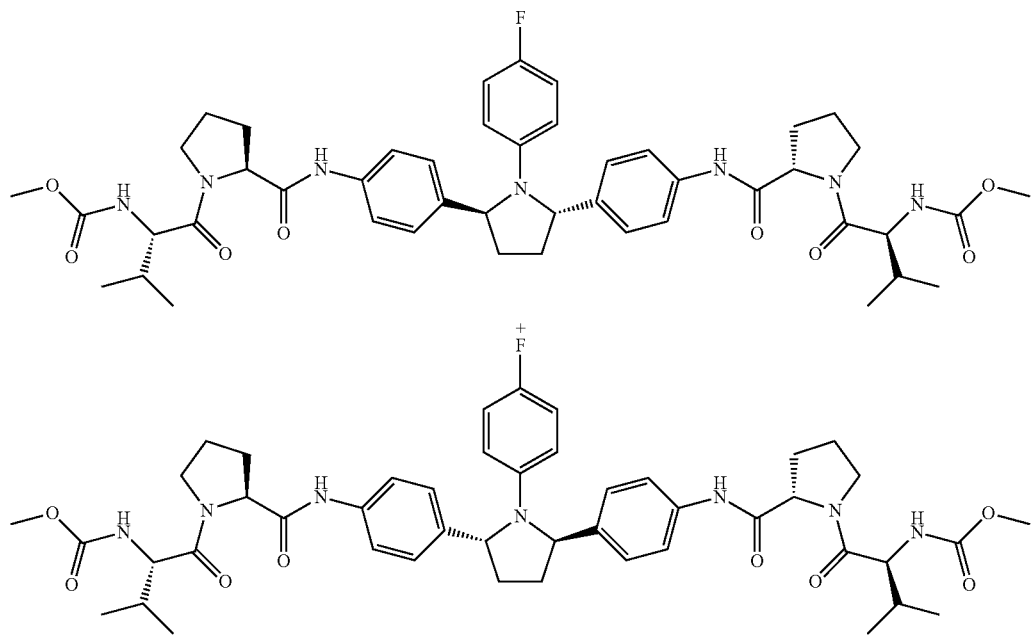

To a mixture of the product from Example 1G (0.030 g, 0.055 mmol), (S)-2-(methoxycarbonylamino)-3-methylbutanoic acid (0.024 g, 0.14 mmol) and HATU (0.052 g, 0.14 mmol) in DMSO (0.3 ml) was added Hunig's base (0.024 ml, 0.166 mmol), and the resulting mixture was stirred at room temperature for 90 min. The mixture was partitioned between water and ethyl acetate, and the organic layer was concentrated and subjected to HPLC purification on a semi-prep C18 reverse-phased column using a gradient of 10-100% acetonitrile in 0.1% aq TFA. The trans-substituted pyrrolidine isomer was the first of 2 stereoisomers to elute, providing the title compound as a 1:1 mixture of diastereomers (9 mg, 16%): 1H NMR (TFA salt) (400 MHz, DMSO-D6) δ ppm 0.85-0.96 (m, 12H) 1.64 (d, J=5.75 Hz, 2H) 1.82-1.92 (m, 6H) 1.95-2.06 (m, 2H) 2.08-2.20 (m, 2H) 3.52 (s, 6H) 3.57-3.68 (m, 2H) 3.74-3.86 (m, J=5.86 Hz, 2H) 4.02 (t, J=8.35 Hz, 2H) 4.42 (dd, J=7.92, 4.88 Hz, 2H) 5.16 (d, J=6.18 Hz, 2H) 6.20 (dd, J=9.16, 4.39 Hz, 2H) 6.77 (t, J=8.89 Hz, 2H) 7.12 (dd, J=8.51, 1.68 Hz, 4H) 7.31 (dd, J=8.24, 3.36 Hz, 2H) 7.50 (d, J=7.26 Hz, 4H) 9.99 (s, 2H). The title compound showed an $EC_{50}$ value of less than about 0.1 nM in HCV 1b-Con1 replicon assays in the presence of 5% FBS.

Example 11

Dimethyl (2S,2'S)-1,1'-((2S,2'S)-2,2'-(4,4'-((2S,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl) dicarbamate

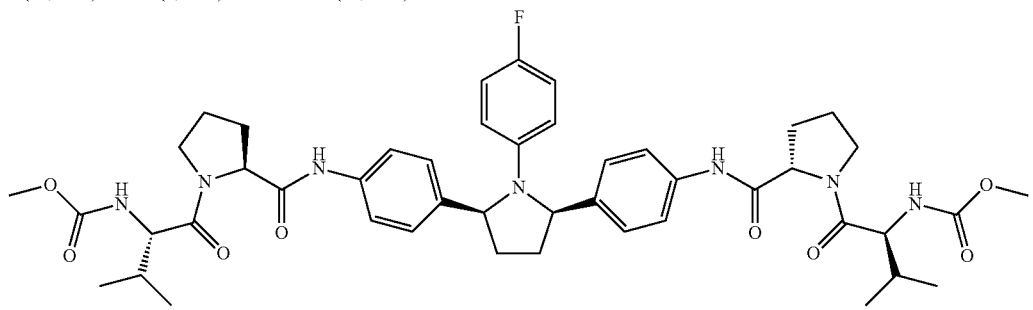

To a mixture of the product from Example 1G (0.030 g, 0.055 mmol), (S)-2-(methoxycarbonylamino)-3-methylbutanoic acid (0.024 g, 0.14 mmol) and HATU (0.052 g, 0.14 mmol) in DMSO (0.3 ml) was added Hunig's base (0.024 ml, 0.166 mmol), and the resulting mixture was stirred at room temperature for 90 min. The mixture was partitioned between water and ethyl acetate, and the organic layer was concentrated and subjected to HPLC purification on a semi-prep C18 reverse-phased column using a gradient of 10-100% acetonitrile in 0.1% aq TFA. The cis-substituted pyrrolidine isomer was the second of 2 stereoisomers to elute, providing the title compound (11 mg, 20%): 1H NMR (TFA salt) (400 MHz, DMSO-D6) δ ppm 9.35 (s, 2H) 8.26 (s, 2H) 7.77-7.83 (m, 4H) 7.68-7.73 (m, 4H) 7.01 (t, J=8.95 Hz, 2H) 6.61-6.71 (m, 2H) 6.23 (d, J=8.35 Hz, 2H) 4.87-4.97 (m, 2H) 4.67-4.78 (m, 2H) 4.42-4.52 (m, 2H) 3.99-4.09 (m, 2H) 3.87-3.97 (m, 2H) 3.84 (s, 6H) 1.22 (dd, J=6.78, 2.11 Hz, 6H) 1.15 (dd, J=6.72, 2.06 Hz, 6H). The title compound showed an $EC_{50}$ value of less than about 0.1 nM in HCV 1b-Con1 replicon assays in the presence of 5% FBS.

Example 12

Dimethyl (2S,2'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl) dicarbamate

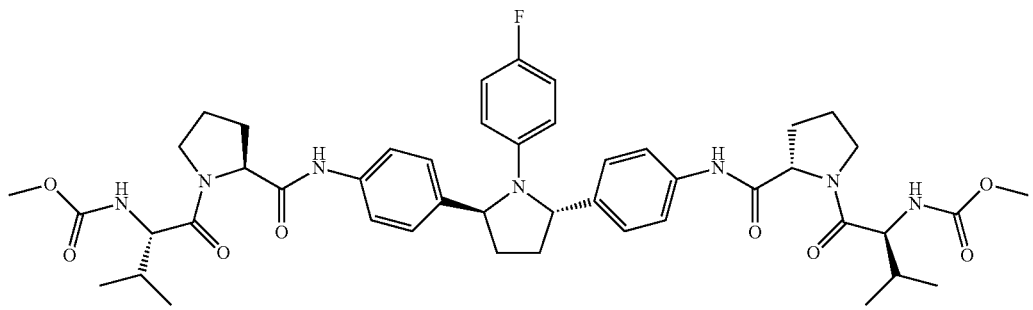

The product from Example 10 was separated by chiral chromatography on a Chiralpak AD-H semi-prep column eluting with a 1:1 mixture of hexanes:(2:1 2-PrOH:EtOH). The title compound eluted as the first of 2 stereoisomers. 1H NMR (400 MHz, DMSO-D6) δ ppm 0.84-0.97 (m, 12H) 1.64 (d, J=5.64 Hz, 2H) 1.88 (s, 6H) 1.95-2.05 (m, 2H) 2.08-2.19 (m, 2H) 3.52 (s, 6H) 3.58-3.66 (m, 2H) 3.76-3.85 (m, 2H) 4.02 (t, J=8.51 Hz, 2H) 4.42 (dd, J=8.02, 4.88 Hz, 2H) 5.15 (d, J=6.51 Hz, 2H) 6.20 (dd, J=9.16, 4.39 Hz, 2H) 6.78 (t, J=8.89 Hz, 2H) 7.13 (d, J=8.46 Hz, 4H) 7.31 (d, J=8.35 Hz, 2H) 7.50 (d, J=8.46 Hz, 4H) 9.99 (s, 2H). The title compound showed an $EC_{50}$ value of less than about 0.1 nM in HCV 1b-Con1 replicon assays in the presence of 5% FBS.

Example 13

Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl) dicarbamate

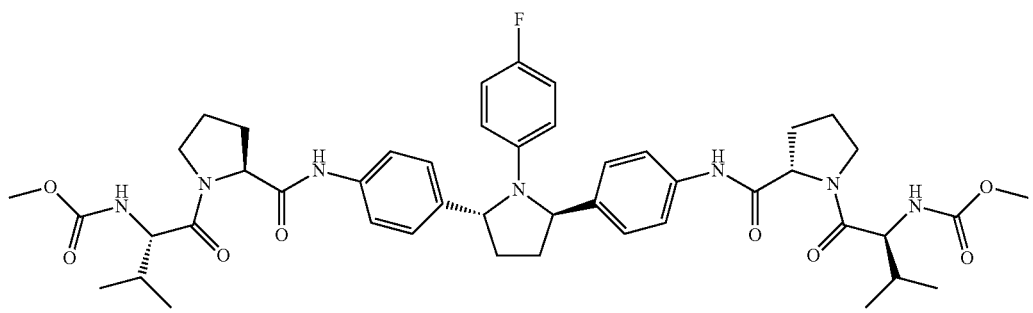

The product from Example 10 was separated by chiral chromatography on a Chiralpak AD-H semi-prep column eluting with a 1:1 mixture of hexanes:(2:1 2-PrOH:EtOH). The title compound eluted as the second of 2 stereoisomers. 1H NMR (400 MHz, DMSO-D6) δ ppm 0.82-0.97 (m, 12H) 1.65 (d, 2H) 1.80-2.05 (m, 8H) 2.08-2.20 (m, 2H) 3.52 (s, 6H) 3.57-3.68 (m, 2H) 3.76-3.87 (m, 2H) 4.01 (t, 2H) 4.42 (dd, 2H) 5.16 (d, J=6.40 Hz, 2H) 6.20 (dd, J=9.22, 4.45 Hz, 2H) 6.77 (t, J=8.95 Hz, 2H) 7.12 (d, J=8.57 Hz, 4H) 7.30 (d, J=8.35 Hz, 2H) 7.50 (d, J=8.46 Hz, 4H) 9.98 (s, 2H). The title compound showed an $EC_{50}$ value of less than about 0.1 nM in HCV 1b-Con1 replicon assays in the presence of 5% FBS.

Example 14

Dimethyl (1S,1'S)-2,2'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-((R)-tetrahydrofuran-3-yl)ethane-2,1-diyl)dicarbamate and Dimethyl (1S,1'S)-2,2'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-((R)-tetrahydrofuran-3-yl)ethane-2,1-diyl)dicarbamate To a mixture of the product from Example 5C (0.013 g, 0.024 mmol), HATU (0.02275 gm, 0.060 mmol), and (S)-2-(methoxycarbonylamino)-2-((R)-tetrahydrofuran-3-yl)acetic acid (0.0107 gm, 0.053 mmol) in DMSO (0.200 ml) was added Hunig's Base (0.013 ml, 0.072 mmol). The reaction was stirred at room temperature for 2 hr, poured into water, and extracted with ethyl acetate. The organic extract was dried over $Na_2SO_4$, filtered and concentrated in vacuo, and the crude material was purified on a semi-prep C18 reverse-phased column using a gradient of 10-100% acetonitrile in 0.1% aq TFA to give the title compound (6.9 mg, 28% yield): 1H NMR (TFA salt) (400 MHz, DMSO-D6) δ ppm 1.61-1.77 (m, 4H) 1.80-1.94 (m, 6H) 1.93-2.06 (m, 2H) 2.08-2.21 (m, 2H) 3.44 (dd, J=8.46, 6.29 Hz, 2H) 3.53 (s, 6H) 3.56-3.68 (m, 8H) 3.68-3.77 (m, 2H) 3.80-3.90 (m, 2H) 4.23 (t, J=8.84 Hz, 2H) 4.43 (dd, J=8.02, 4.77 Hz, 2H) 5.16 (d, J=6.29 Hz, 2H) 6.20 (dd, J=9.11, 4.45 Hz, 2H) 6.77 (t, J=8.95 Hz, 2H) 7.13 (d, J=8.57 Hz, 4H) 7.50 (d, J=8.57 Hz, 4H) 7.60 (d, J=7.92 Hz, 2H) 9.98 (s, 2H). The title compound showed an $EC_{50}$ value of from about 0.1 to about 1 nM in HCV 1b-Con1 replicon assays in the presence of 5% FBS.

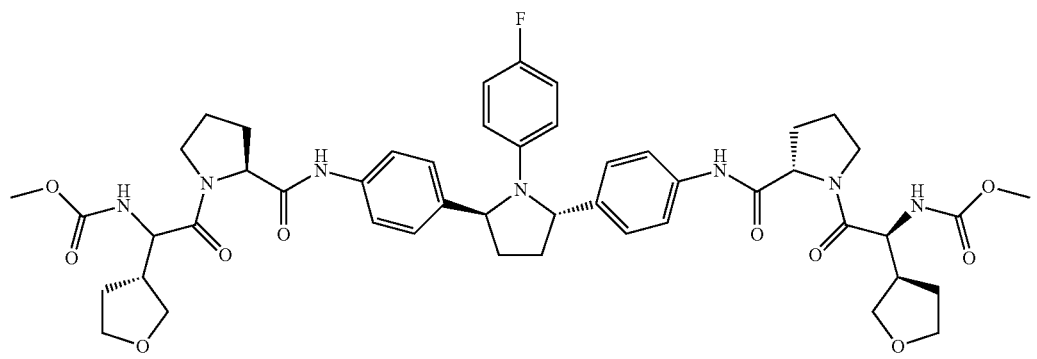

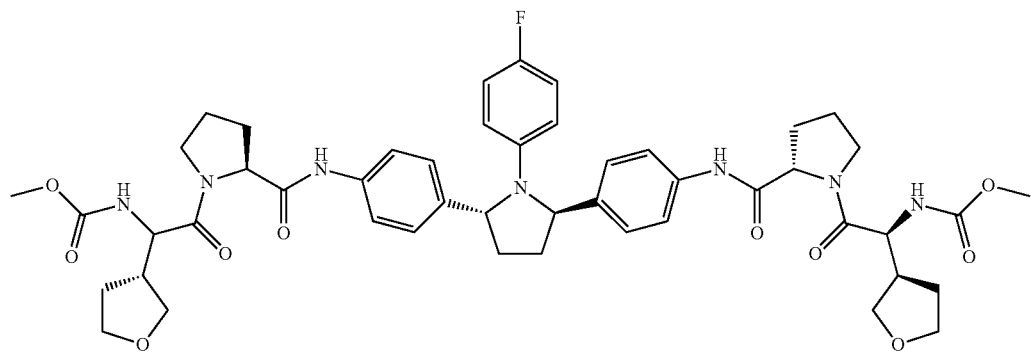

Example 15

Dimethyl (1S,1'S)-2,2'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-((R)-tetrahydrofuran-3-yl)ethane-2,1-diyl)dicarbamate

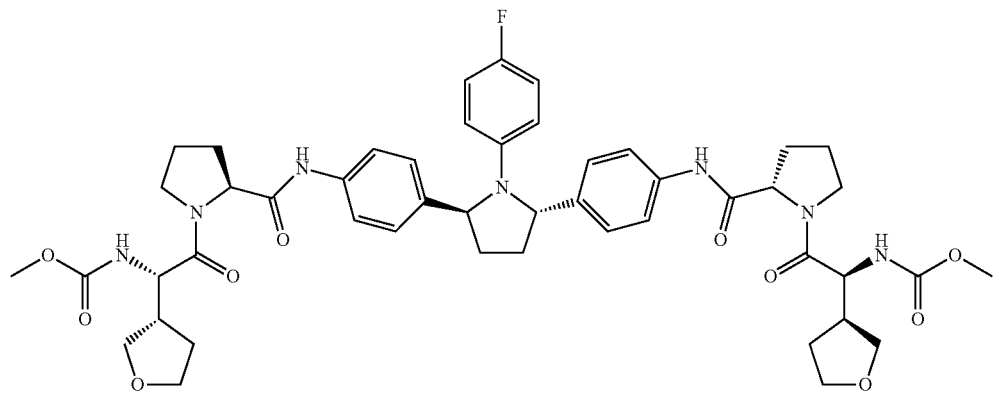

The product from Example 14 was separated by chiral chromatography on a Chiralpak AD-H semi-prep column eluting with a 2:3 mixture of hexanes:(1:1 2-PrOH:EtOH). The title compound eluted as the first of 2 stereoisomers. 1H NMR (400 MHz, DMSO-D6) δ ppm 1.59-1.78 (m, 4H) 1.79-1.94 (m, 6H) 1.94-2.05 (m, 2H) 2.09-2.23 (m, J=5.10 Hz, 2H) 3.44 (dd, J=8.35, 6.40 Hz, 2H) 3.53 (s, 6H) 3.57-3.73 (m, 8H) 3.71-3.80 (m, 2H) 3.81-3.89 (m, 2H) 4.23 (t, J=8.78 Hz, 2H) 4.43 (dd, J=7.97, 4.83 Hz, 2H) 5.16 (d, J=6.07 Hz, 2H) 6.16-6.24 (m, 2H) 6.78 (t, J=8.89 Hz, 2H) 7.13 (d, J=8.57 Hz, 4H) 7.50 (d, J=8.46 Hz, 4H) 7.60 (d, J=8.02 Hz, 2H) 9.98 (s, 2H). The title compound showed an $EC_{50}$ value of less than about 0.1 nM in HCV 1b-Con1 replicon assays in the presence of 5% FBS.

Example 16

Dimethyl (1S,1'S)-2,2'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-((R)-tetrahydrofuran-3-yl)ethane-2,1-diyl)dicarbamate

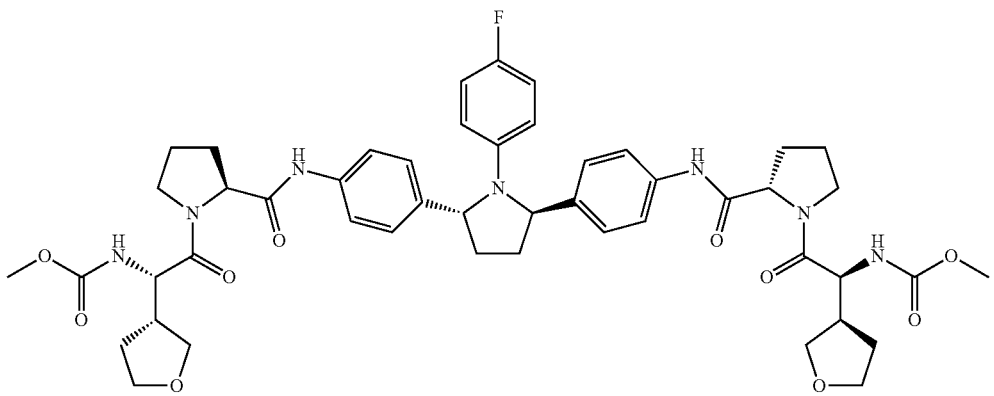

The product from Example 14 was separated by chiral chromatography on a Chiralpak AD-H semi-prep column eluting with a 2:3 mixture of hexanes:(1:1 2-PrOH:EtOH). The title compound eluted as the second of 2 stereoisomers. 1H NMR (400 MHz, DMSO-D6) δ ppm 1.61-1.77 (m, 4H) 1.80-1.94 (m, 6H) 1.93-2.06 (m, 2H) 2.08-2.21 (m, 2H) 3.44 (dd, J=8.46, 6.29 Hz, 2H) 3.53 (s, 6H) 3.56-3.68 (m, 8H) 3.68-3.77 (m, 2H) 3.80-3.90 (m, 2H) 4.23 (t, J=8.84 Hz, 2H) 4.43 (dd, J=8.02, 4.77 Hz, 2H) 5.16 (d, J=6.29 Hz, 2H) 6.20 (dd, J=9.11, 4.45 Hz, 2H) 6.77 (t, J=8.95 Hz, 2H) 7.13 (d, J=8.57 Hz, 4H) 7.50 (d, J=8.57 Hz, 4H) 7.60 (d, J=7.92 Hz, 2H) 9.98 (s, 2H). The title compound showed an $EC_{50}$ value of from about 0.1 to about 1 nM in HCV 1b-Con1 replicon assays in the presence of 5% FBS.

Example 17

(R,2S,2'S)—N,N'-(4,4'-((2S,5S)-1-(4-Fluorophenyl)pyrrolidine-2,5-diyl)bis(4,1-phenylene))bis(1-((R)-2-phenyl-2-(piperidin-1-yl)acetyl)pyrrolidine-2-carboxamide) and (R,2S,2'S)—N,N'-(4,4'-((2R,5R)-1-(4-Fluorophenyl)pyrrolidine-2,5-diyl)bis(4,1-phenylene))bis(1-((R)-2-phenyl-2-(piperidin-1-yl)acetyl)pyrrolidine-2-carboxamide)

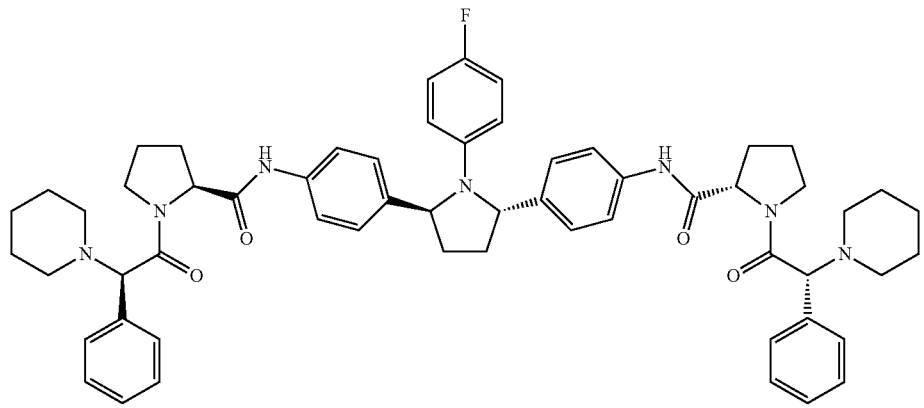 [SMILES: O=C(Nc1ccc([C@@H]2CC[C@@H](c3ccc(NC(=O)[C@@H]4CCCN4C(=O)[C@@H](c4ccccc4)N4CCCCC4)cc3)N2c2ccc(F)cc2)cc1)[C@@H]1CCCN1C(=O)[C@@H](c1ccccc1)N1CCCCC1]

To a mixture of (R)-2-phenyl-2-(piperidin-1-yl)acetic acid TFA salt (0.0455 mg, 0.137 mmol), the product from Example 1G (0.030 gm, 0.055 mmol), and HATU (0.0526 gm, 0.138 mmol) in DMSO (0.300 ml) was added Hunig's base (0.029.0 ml, 0.166 mmol), and the resulting mixture was stirred at rt for 2 hr. The mixture was partitioned between water and ethyl acetate, the organic layer was dried over $Na_2SO_4$, filtered and concentrated in vacuo. The crude product was subjected to HPLC purification on a semi-prep C18 reverse-phased column using a gradient of 10-100% acetonitrile in 0.1% aq TFA (8.3 mg, 11%): 1H NMR (TFA salt) (400 MHz, DMSO-D6) δ ppm 1.20-1.42 (m, 4H) 1.61-2.02 (m, 16H) 2.62-2.81 (m, 4H) 3.01-3.23 (m, J=9.32 Hz, 4H) 3.87-3.98 (m, 2H) 4.40-4.47 (m, J=8.24 Hz, 2H) 5.14-5.24 (m, 2H) 5.50 (d, J=8.78 Hz, 2H) 6.23 (dd, J=8.89, 4.34 Hz, 2H) 6.75-6.84 (m, 2H) 7.16 (d, J=7.81 Hz, 4H) 7.48-7.59 (m, 12H) 7.62 (d, J=3.69 Hz, 4H) 9.89 (s, 2H) 10.17 (s, 2H). The title compound showed an $EC_{50}$ value of from about 0.1 to about 1 nM in HCV 1b-Con1 replicon assays in the presence of 5% FBS.

Example 18

(R,2S,2'S)—N,N'-(4,4'-((2S,5R)-1-(4-fluorophenyl)pyrrolidine-2,5-diyl)bis(4,1-phenylene))bis(1-((R)-2-phenyl-2-(piperidin-1-yl)acetyl)pyrrolidine-2-carboxamide)

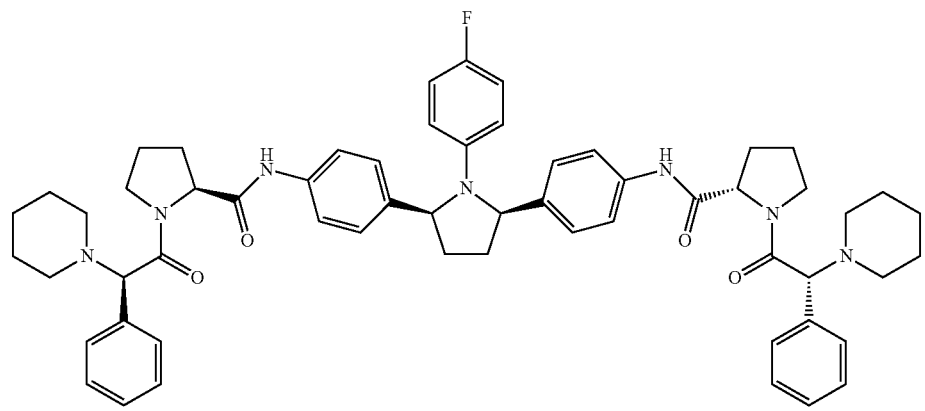 [SMILES: O=C(Nc1ccc([C@H]2CC[C@@H](c3ccc(NC(=O)[C@@H]4CCCN4C(=O)[C@@H](c4ccccc4)N4CCCCC4)cc3)N2c2ccc(F)cc2)cc1)[C@@H]1CCCN1C(=O)[C@@H](c1ccccc1)N1CCCCC1]

To a mixture of (R)-2-phenyl-2-(piperidin-1-yl)acetic acid TFA salt (0.0455 mg, 0.137 mmol), the product from Example 1G (0.030 gm, 0.055 mmol), and HATU (0.0526 gm, 0.138 mmol) in DMSO (0.300 ml) was added Hunig's base (0.029.0 ml, 0.166 mmol), and the resulting mixture was stirred at rt for 2 hr. The mixture was partitioned between water and ethyl acetate, the organic layer was dried over Na$_2$SO$_4$ filtered and concentrated in vacuo. The crude product was subjected to HPLC purification on a semi-prep C18 reverse-phased column using a gradient of 10-100% acetonitrile in 0.1% aq TFA (8.7 mg, 12%): 1H NMR (TFA salt) (400 MHz, DMSO-D6) δ ppm 1.22-1.43 (m, 4H) 1.62-2.03 (m, J=80.02 Hz, 16H) 2.08-2.18 (m, 2H) 2.62-2.85 (m, 4H) 3.04-3.24 (m, 4H) 3.88-3.99 (m, 2H) 4.41-4.52 (m, 2H) 4.64-4.72 (m, 2H) 5.52 (d, J=8.24 Hz, 2H) 6.36 (dd, J=9.05, 4.50 Hz, 2H) 6.88 (t, J=8.89 Hz, 2H) 7.41-7.68 (m, 18H) 9.89 (s, 2H) 10.23 (s, 2H). The title compound showed an EC$_{50}$ value of less than about 0.1 nM in HCV 1b-Con1 replicon assays in the presence of 5% FBS.

Example 19

Dimethyl (2S,2'S)-1,1'-((2S,2'S)-2,2'-(4,4'-(1-(4-fluorophenyl)-1H-pyrrole-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate the residue purified by column chromatography (gradient elution from 30% to 50% EtOAc:hexanes) to provide 1.09 g (77%) of the title compound.

Example 19C (2S,2'S)-tert-Butyl 2,2'-(4,4'-(1-(4-fluorophenyl)-1H-pyrrole-2,5-diyl)bis(4,1-phenylene))bis(azanediyl) bis(oxomethylene)dipyrrolidine-1-carboxylate To a solution of Example 19B (1.09 g, 3.17 mmol) in DMF (15.87 mL) at rt was added HATU (2.66 g, 6.98 mmol), (S)-1-(tert-butoxycarbonyl)pyrrolidine-2-carboxylic acid (1.503 g, 6.98 mmol), and Hunig's base (2.218 mL, 12.70 mmol). Stirring was continued overnight. The mixture was partitioned between water and EtOAc added. Organic phase washed with brine, dried (Na$_2$SO$_4$) and concentrated. Residue purified by column chromatography (gradient elution from 20% to 50% EtOAc/hexanes). MS (ESI; M+H) m/z=738.

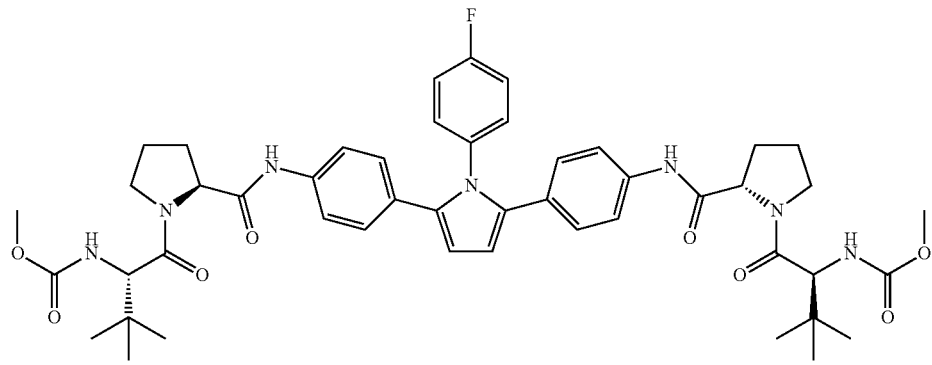 [SMILES: COC(=O)N[C@H](C(=O)N1CCC[C@H]1C(=O)Nc1ccc(-c2ccc(-c3ccc(NC(=O)[C@@H]4CCCN4C(=O)[C@@H](NC(=O)OC)C(C)(C)C)cc3)n2-c2ccc(F)cc2)cc1)C(C)(C)C]

Example 19A 1-(4-Fluorophenyl)-2,5-bis(4-nitrophenyl)-1H-pyrrole

To a slurry of the product from Example 1A (1.5 g, 4.57 mmol) in acetic acid (22.85 mL) was S added 4-fluoroaniline (4.33 ml, 45.7 mmol). The mixture was heated to 70° C. for 24 h. After cooling to rt the mixture was diluted with water and ether and stirred vigorously, filtered and dried to provide 1.67 g (91%) of the title compound.

Example 19B 4,4'-(1-(4-Fluorophenyl)-1H-pyrrole-2,5-diyl)dianiline

To a solution of example 19A (1.017 g, 2.496 mmol) in ethanol (15 mL) and THF (15 mL) was added iron powder (0.836 g, 14.98 mmol) followed by ammonium chloride (0.401 g, 7.49 mmol) and water (3.75 mL). Reaction mixture was refluxed for 45 minutes. Slurry filtered through celite, washed with ethanol, combined filtrate was concentrated and

Example 19D (2S,2'S)—N,N'-(4,4'-(1-(4-Fluorophenyl)-1H-pyrrole-2,5-diyl)bis(4,1-phenylene))dipyrrolidine-2-carboxamide To the product from Example 19C (100 mg, 0.136 mmol) in CH$_2$Cl$_2$ (2.0 mL) was added TFA (1.0 mL) and the reaction was stirred 1 h. Mixture concentrated, the residue was partitioned between water and 25% IPA-CHCl$_3$ and neutralized with NaHCO$_3$. The organic layer was dried over Na$_2$SO$_4$, filtered and concentrated to give the title compound as a white solid used without further purification. MS (DCI; M+H) m/z=538.

Example 19E

Dimethyl (2S,2'S)-1,1'-((2S,2'S)-2,2'-(4,4'-(1-(4-fluorophenyl)-1H-pyrrole-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate To a mixture of the product from Example 19D (0.073 g, 0.136 mmol) in CH$_2$Cl$_2$ (10 mL) at rt was added Hunig's base (0.070 mL, 0.407 mmol). To this was then added (S)-2-methoxycarbonylamino-3,3-dimethyl-butyric acid (0.054 g, 0.285 mmol) followed by HATU (0.114 g, 0.299 mmol). Mixture stirred for 2 hrs then washed with saturated NaHCO$_3$ and the organic phase concentrated and the residue purified by column chromatography (1% gradient elution from 0% to 3% MeOH—CH$_2$Cl$_2$) to provide the desired compound as a light tan solid. MS (ESI; M+H) m/z=881; 1H NMR (400 MHz, DMSO-D6) δ ppm 0.96 (s, 18H), 1.81-1.89 (m, 4H), 1.95-2.00 (m, 2H), 2.11-2.16 (m, 2H), 3.53 (s, 6H), 3.61-3.65 (m, 2H), 3.75-3.79 (m, 2H), 4.20 (d, J=8.85 Hz, 2H), 4.39-4.42 (m, 2H), 6.39 (s, 2H), 6.96 (d, J=8.69 Hz, 4H), 7.07-7.10 (m, 4H), 7.17 (dd, J=8.70, 8.70 Hz, 2H), 7.41 (d, J=8.70 Hz, 4H), 10.01 (br s, 2H). The title compound showed an EC$_{50}$ value of less than about 0.1 nM in HCV 1b-Con1 replicon assays in the presence of 5% FBS.

Example 20

Dimethyl (2S,2'S)-1,1'-((2S,2'S)-2,2'-(4,4'-((2S,5S)-1-phenylpyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and Dimethyl (2S,2'S)-1,1'-((2S,2'S)-2,2'-(4,4'-((2R,5R)-1-phenylpyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate Example 20B (2S,2'S)-tert-Butyl 2,2'-(4,4'-(1-phenylpyrrolidine-2,5-diyl)bis(4,1-phenylene))bis(azanediyl)bis(oxomethylene)dipyrrolidine-1-carboxylate The product from Example 20A (19 mg, 0.049 mmol) was subjected to the conditions described in Example 1E. The crude product was subjected to the conditions described in Example 1F to give the title compound (33 mg, 93%).

Example 20C

Dimethyl (2S,2'S)-1,1'-((2S,2'S)-2,2'-(4,4'-((2S,5S)-1-phenylpyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and Dimethyl (2S,2'S)-1,1'-((2S,2'S)-2,2'-(4,4'-((2R,5R)-1-phenylpyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate The product from Example 20B (30 mg, 0.041 mmol) was subjected to the conditions described in Example 1G, and the crude product was subjected to the conditions described in Example 1H. The crude product was subjected to HPLC

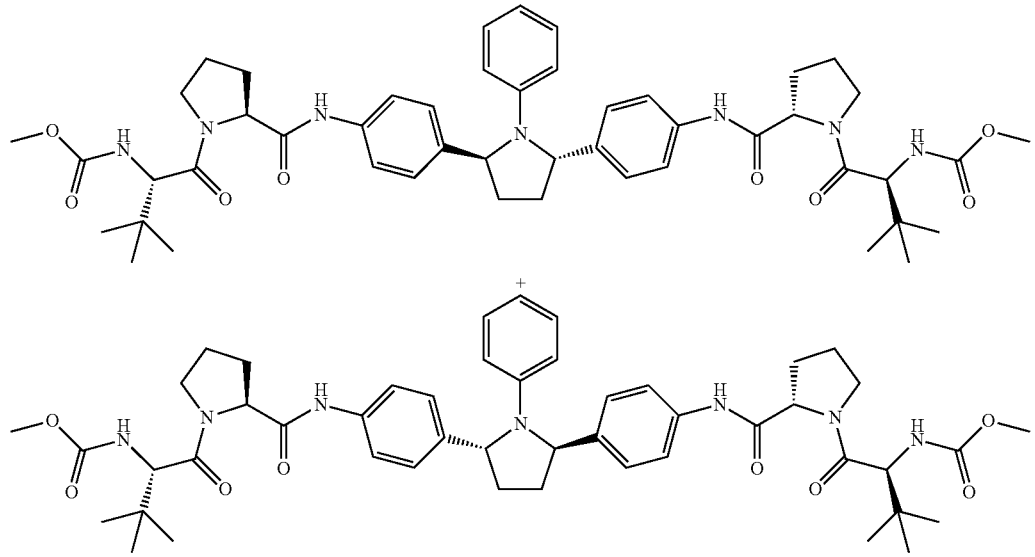

Example 20A 2,5-Bis(4-nitrophenyl)-1-phenylpyrrolidine

A mixture of the product from Example 1C (50 mg, 0.102 mmol) and aniline (0.2 ml, 2.19 mmol) were stirred at rt for 48 h. The mixture was partitioned between 1N aq. HCl and ethyl acetate, and the organic layer was dried over Na$_2$SO$_4$, filtered and concentrated in vacuo. The crude product was purified by column chromatography on silica gel using a solvent gradient of 0-50% ethyl acetate in hexanes. The title compound was obtained as a yellow solid (19 mg, 48%).

purification on a semi-prep C18 reverse-phased column using a gradient of 10-100% acetonitrile in 0.1% aq TFA. The trans-substituted pyrrolidine isomer was the first of 2 stereoisomers to elute, providing the title compound as a 1:1 mixture of diastereomers (7 mg, 19%): 1H NMR (TFA salt) (400 MHz, DMSO-D6) δ ppm 0.95 (d, J=5.31 Hz, 18H) 1.59-1.67 (m, 2H) 1.79-1.91 (m, 4H) 1.91-2.02 (m, 2H) 2.08-2.17 (m, 2H) 3.52 (s, 6H) 3.58-3.68 (m, 2H) 3.71-3.82 (m, 2H) 4.19 (d, J=9.00 Hz, 2H) 4.42 (dd, 2H) 5.17 (d, J=5.64 Hz, 2H) 6.24 (d, J=8.35 Hz, 2H) 6.39 (t, J=7.37 Hz, 2H) 6.90 (t, J=7.92 Hz, 2H) 7.07 (d, 2H) 7.11 (d, 4H) 7.48 (d, J=8.24 Hz, 4H) 9.98 (s, 2H). The title compound showed an EC$_{50}$ value of less than about 0.1 nM in HCV 1b-Con1 replicon assays in the presence of 5% FBS.

Example 21

Dimethyl (2S,2'S)-1,1'-((2S,2'S)-2,2'-(4,4'-((2S,5R)-1-phenylpyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl) dicarbamate

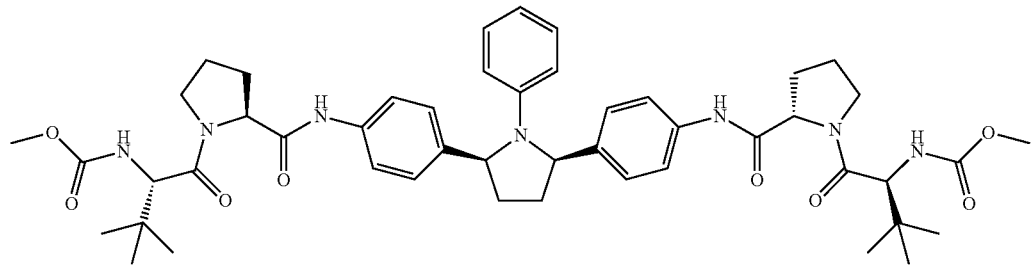

The product from Example 20B (30 mg, 0.041 mmol) was subjected to the conditions described in Example 1G, and the crude product was subjected to the conditions described in Example 1H. The crude product was subjected to HPLC purification on a semi-prep C18 reverse-phased column using a gradient of 10-100% acetonitrile in 0.1% aq TFA. The cis-substituted pyrrolidine isomer was the second of 2 stereoisomers to elute, providing the title compound (8.5 mg, 24%): 1H NMR (TFA salt) (400 MHz, DMSO-D6) δ ppm 0.96 (d, J=3.25 Hz, 18H) 1.74-1.91 (m, 6H) 1.93-2.03 (m, 2H) 2.10-2.20 (m, 2H) 3.53 (s, 6H) 3.58-3.69 (m, 2H) 3.72-3.83 (m, 2H) 4.20 (d, J=8.89 Hz, 2H) 4.45 (dd, J=7.97, 5.37 Hz, 2H) 4.68 (t, J=5.20 Hz, 2H) 6.37 (d, J=8.24 Hz, 2H) 6.56 (t, J=7.26 Hz, 2H) 6.98 (t, J=7.92 Hz, 2H) 7.07 (d, 2H) 7.42 (d, J=8.02 Hz, 4H) 7.58 (d, J=8.57 Hz, 4H) 10.03 (s, 2H). The title compound showed an $EC_{50}$ value of less than about 0.1 nM in HCV 1b-Con1 replicon assays in the presence of 5% FBS.

Example 22

Dimethyl (1R,1'R)-2,2'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-phenylethane-2,1-diyl) dicarbamate and Dimethyl (1R,1'R)-2,2'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(2-oxo-1-phenylethane-2,1-diyl) dicarbamate

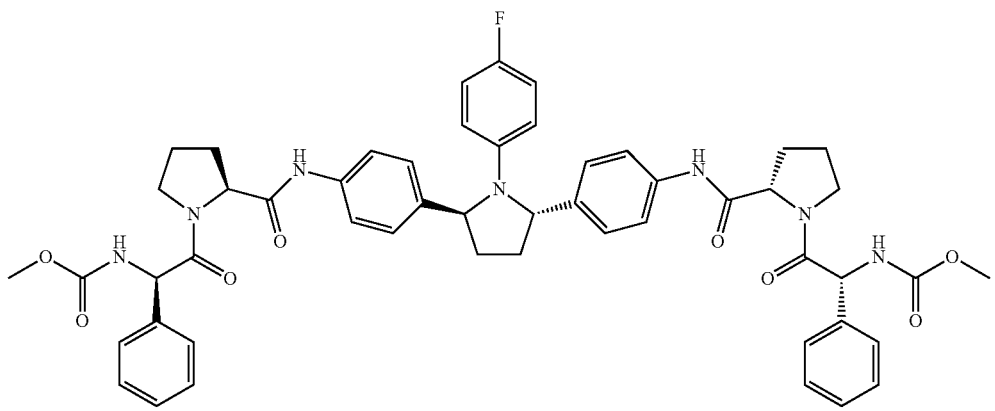

+

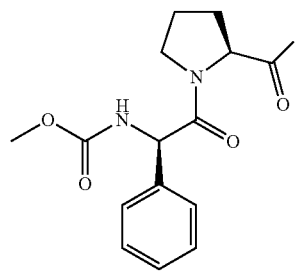

The product from Example 5C (25 mg, 0.046 mmol) was subjected to the conditions described in Example 5D, substituting (R)-2-(methoxycarbonylamino)-2-phenylacetic acid for (S)-2-(methoxycarbonyl amino)butanoic acid, to give the title compound as a 1:1 mixture of diastereomers (42 mg, 48%): 1H NMR (400 MHz, DMSO-D6) δ ppm 9.83 (s, 2H) 7.67 (d, J=7.81 Hz, 2H) 7.51-7.57 (m, 4H) 7.29-7.44 (m, 8H) 7.15 (d, J=8.46 Hz, 4H) 6.74-6.83 (m, 2H) 6.17-6.28 (m, J=9.00, 4.34 Hz, 2H) 5.48 (d, J=7.81 Hz, 2H) 5.12-5.24 (m, 1H) 4.33-4.43 (m, J=8.13 Hz, 2H) 3.75-3.87 (m, 2H) 3.54 (s, 6H) 1.73-2.05 (m, 8H) 1.62-1.70 (m, 2H). The title compound showed an EC$_{50}$ value of less than about 0.1 nM in HCV 1b-Con1 replicon assays in the presence of 5% FBS.

Example 23

Dimethyl (2S,2'S)-1,1'-((2S,2'S)-2,2'-(4,4'-((2S,5S)-1-(4-(trifluoromethyl)phenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and Dimethyl (2S,2'S)-1,1'-((2S,2'S)-2,2'-(4,4'-((2R,5R)-1-(4-(trifluoromethyl)phenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

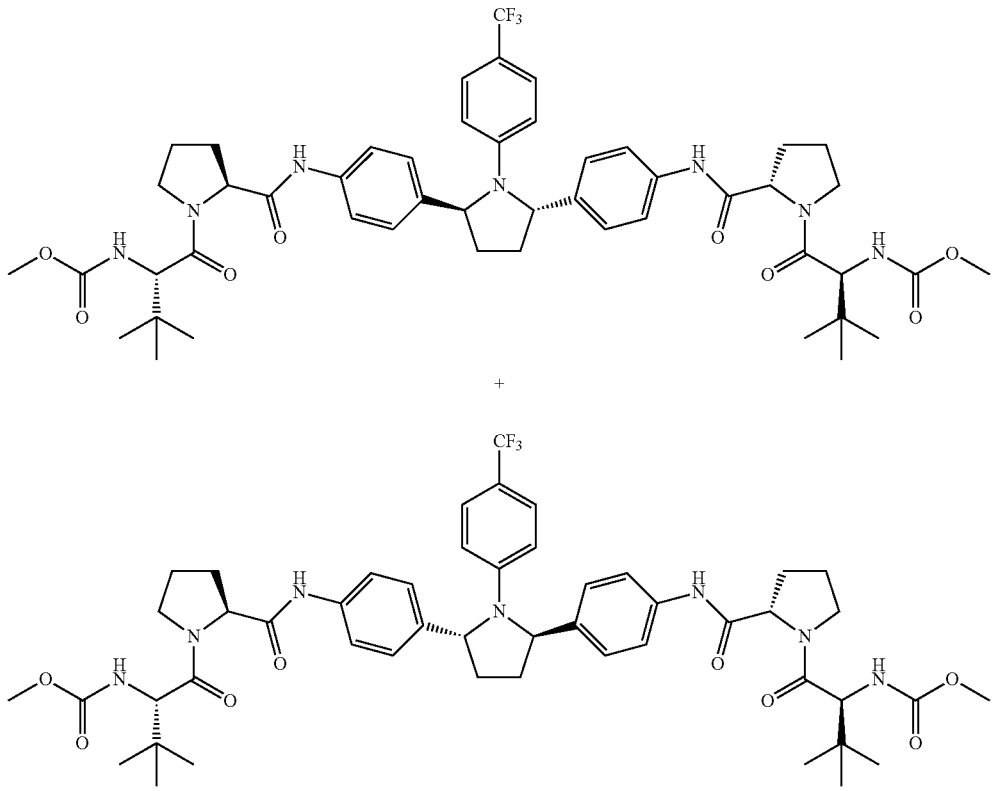

Example 23A 4,4'-((2S,5S)-1-(4-(Trifluoromethyl)phenyl)pyrrolidine-2,5-diyl)dianiline and 4,4'-((2R,5R)-1-(4-(Trifluoromethyl)phenyl)pyrrolidine-2,5-diyl)dianiline The product from Example 1C (0.74 g, 1.5 mmol) was subjected to the conditions described in Example 1D, substituting 4-(trifluoromethyl)aniline for 4-fluoroaniline. The product thus obtained was subjected to the conditions described in Example 1E to give the title compound as a racemic mixture of trans-substituted pyrrolidine stereoisomers (0.10 g, 17%).

Example 23B (2S,2'S)—N,N'-(4,4'-((2S,5S)-1-(4-(Trifluoromethyl)phenyl)pyrrolidine-2,5-diyl)bis(4,1-phenylene))dipyrrolidine-2-carboxamide and (2S,2'S)—N,N'-(4,4'-((2R,5R)-1-(4-(Trifluoromethyl)phenyl)pyrrolidine-2,5-diyl)bis(4,1-phenylene))dipyrrolidine-2-carboxamide The product from Example 23A (0.95 g, 0.24 mmol) was subjected to the conditions described in Example 1F to give a solid (0.166 g, 88%), which was dissolved in 4M HCl in 1,4-dioxane (2 ml), and the resulting mixture was stirred at rt for 30 min. The resulting mixture was concentrated and dried in vacuo to give an HCl salt of the title compound as a 1:1 mixture of stereoisomers.

Example 23C

Dimethyl (2S,2'S)-1,1'-((2S,2'S)-2,2'-(4,4'-((2S,5S)-1-(4-(trifluoromethyl)phenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate and Dimethyl (2S,2'S)-1,1'-((2S,2'S)-2,2'-(4,4'-((2R,5R)-1-(4-(trifluoromethyl)phenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate The product from Example 23B (58 mg, 0.083 mmol) was subjected to the conditions described in Example 1H to give the title compound as a colorless solid (30 mg, 39%): 1H NMR (free base) (400 MHz, DMSO-D6) δ ppm 10.03 (s, 2H) 7.52 (d, J=8.46 Hz, 4H) 7.25 (d, J=8.89 Hz, 2H) 7.14 (d, J=7.48 Hz, 4H) 7.06-7.11 (m, 2H) 6.36 (d, J=8.35 Hz, 2H) 5.23-5.33 (m, 2H) 4.39-4.48 (m, 2H) 4.21 (d, J=8.46 Hz, 2H) 3.71-3.82 (m, 2H) 3.58-3.69 (m, 2H) 3.54 (s, 6H) 2.08-2.21 (m, 2H) 1.93-2.06 (m, 2H) 1.76-1.94 (m, 4H) 1.61-1.73 (m, 2H) 0.96 (m, 18H). The title compound showed an $EC_{50}$ value of less than about 0.1 nM in HCV 1b-Con1 replicon assays in the presence of 5% FBS.

Example 24

Dimethyl (2S,2'S,3S,3'S)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxopentane-2,1-diyl)dicarbamate and Dimethyl (2S,2'S,3S,3'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxopentane-2,1-diyl)dicarbamate

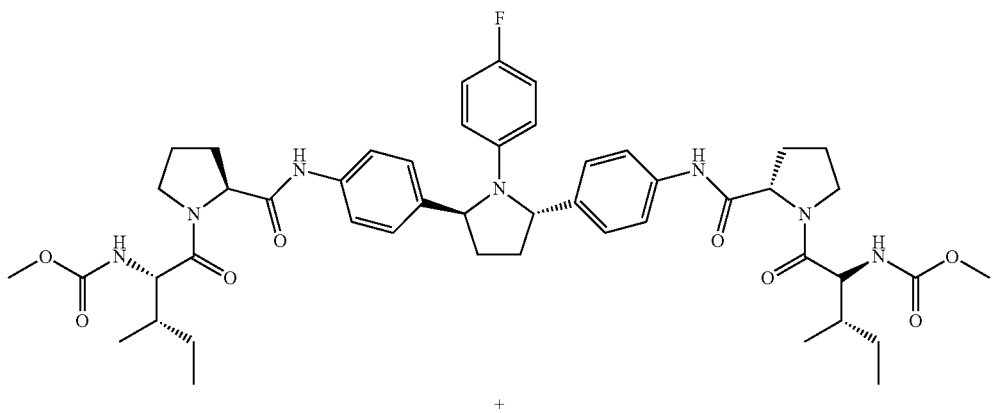

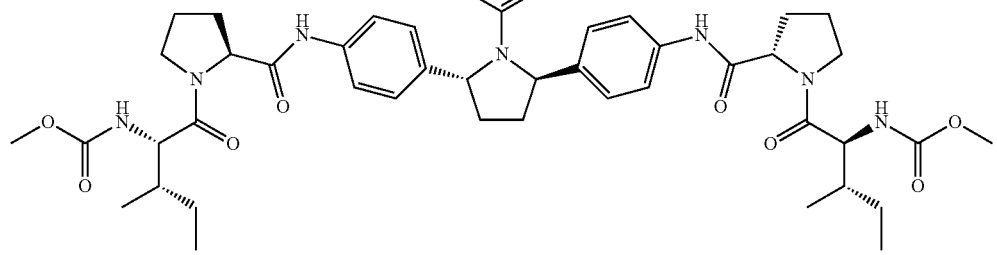

The product from Example 1G (20 mg, 0.037 mmol) was subjected to the conditions described in Example 1H, substituting (2S,3S)-2-(methoxycarbonylamino)-3-methylpentanoic acid (15.4 mg, 0.081 mmol) for (S)-2-(methoxycarbonylamino)-3,3-dimethylbutanoic acid. The title compound was obtained as a 1:1 mixture of diastereomers (13.5 mg, 41%) after silica gel chromatography (0-5% MeOH/CH$_2$Cl$_2$): 1H NMR (free base) (400 MHz, DMSO-D6) δ ppm 9.99 (s, 2H) 7.50 (dd, J=8.46, 1.52 Hz, 4H) 7.36 (dd, J=8.35, 3.04 Hz, 2H) 7.13 (dd, J=8.62, 1.79 Hz, 4H) 6.78 (t, J=8.89 Hz, 2H) 6.20 (dd, J=9.16, 4.39 Hz, 2H) 5.16 (d, J=6.29 Hz, 2H) 4.43 (dd, J=7.92, 4.77 Hz, 2H) 4.02-4.13 (m, 2H) 3.77-3.89 (m, 2H) 3.57-3.67 (m, 2H) 3.52 (s, 6H) 2.08-2.21 (m, J=14.96 Hz, 2H) 1.94-2.05 (m, 2H) 1.81-1.93 (m, J=5.42 Hz, 4H) 1.60-1.79 (m, 4H) 1.42-1.57 (m, 2H) 1.04-1.18 (m, 2H) 0.89 (t, J=6.51 Hz, 6H) 0.76-0.85 (m, 6H). The title compound showed an EC$_{50}$ value of less than about 0.1 nM in HCV 1b-Con1 replicon assays in the presence of 5% FBS.

Example 25

Dimethyl (2S,2'S,3R,3'R)-1,1'-((2S,2'S)-2,2'-(4,4'-((2S,5S)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxopentane-2,1-diyl)dicarbamate and Dimethyl (2S,2'S,3R,3'R)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3-methyl-1-oxopentane-2,1-diyl)dicarbamate

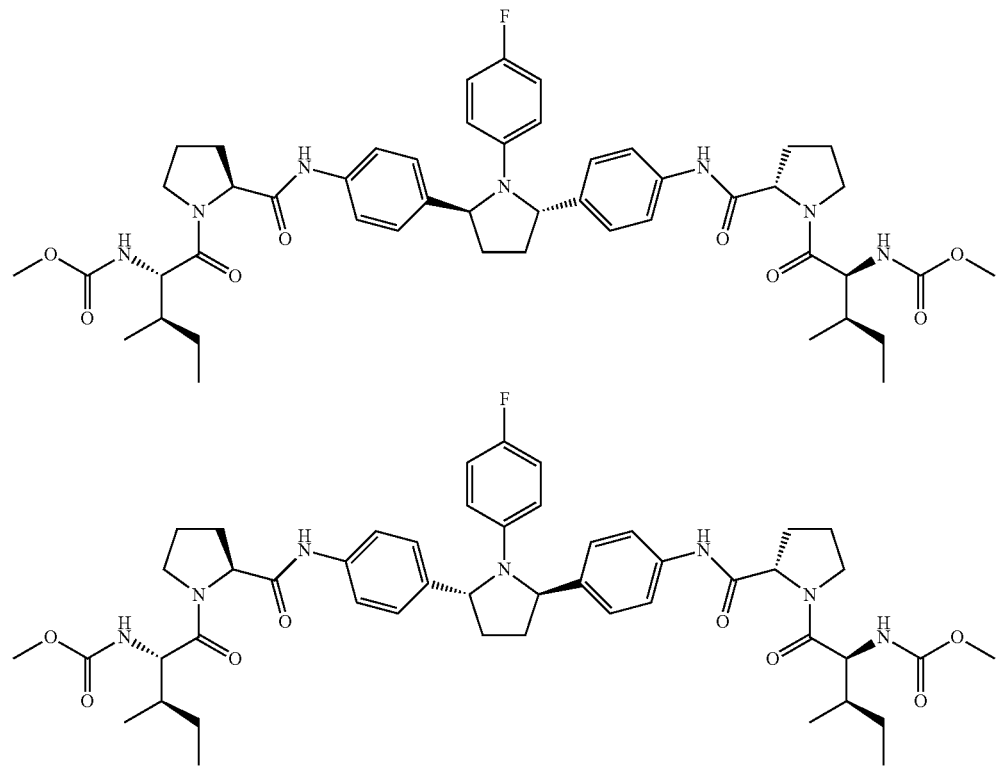

The product from Example 1G (25 mg, 0.046 mmol) was subjected to the conditions described in Example 1H, substituting (2S,3R)-2-(methoxycarbonylamino)-3-methylpentanoic acid (19.2 mg, 0.102 mmol) for (S)-2-(methoxycarbonylamino)-3,3-dimethylbutanoic acid. The title compound was obtained as a 1:1 mixture of diastereomers (20.5 mg, 50%) after silica gel chromatography (0-5% MeOH/CH$_2$Cl$_2$): 1H NMR (free base) (400 MHz, DMSO-D6) δ ppm 9.96 (s, 2H) 7.49 (d, J=8.35 Hz, 4H) 7.14 (t, J=7.43 Hz, 4H) 6.77 (t, J=8.89 Hz, 2H) 6.20 (dd, J=9.11, 4.45 Hz, 2H) 5.16 (d, J=6.40 Hz, 2H) 4.38-4.48 (m, 2H) 4.18-4.28 (m, 2H) 3.69-3.82 (m, 2H) 3.55-3.64 (m, 2H) 3.52 (s, 6H) 2.09-2.20 (m, 2H) 1.95-2.05 (m, 2H) 1.72-1.95 (m, 6H) 1.58-1.70 (m, J=5.64 Hz, 2H) 1.40-1.55 (m, 2H) 1.06-1.18 (m, 2H) 0.79-0.91 (m, 12H). The title compound showed an EC$_{50}$ value of less than about 0.1 nM in HCV 1b-Con1 replicon assays in the presence of 5% FBS.

Example 26 dimethyl (2S,2'S)-1,1'-((2S,2'S)-2,2'-(4,4'-(4,4'-(1-(4-tert-butylphenyl)-1H-pyrrole-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate aq. citric acid (30 mL), poured reaction into a separatory funnel with Et$_2$O (550 mL) and 10% (w/v) aq citric acid, separated layers, and washed organic phase with water and brine. Dried the organic phase over anhydrous Na$_2$SO$_4$, filtered, and concentrated to afford a yellow oil (9.4 g), which was used directly in the next reaction.

Example 26B (S)-tert-butyl 2-(1H-imidazol-2-yl)pyrrolidine-1-carboxylate

The product from Example 26A (20 g, 100 mmol) was dissolved in methanol (50.2 mL) and ammonium hydroxide (50.2 mL) was added. To this solution glyoxal (40% in water, 24.08 mL, 211 mmol) was added, dropwise, over 10 min. The reaction was stirred at room temperature overnight. Reaction was concentrated under reduced pressure, diluted with 50 mL of water, and then extracted with ethyl acetate. Washed organic layer with brine, dried (Na$_2$SO$_4$) and concentrated to a tan solid. Solid was treated with ether and concentrated. The solid was then triturated with 2:1 diethyl ether:hexanes (150

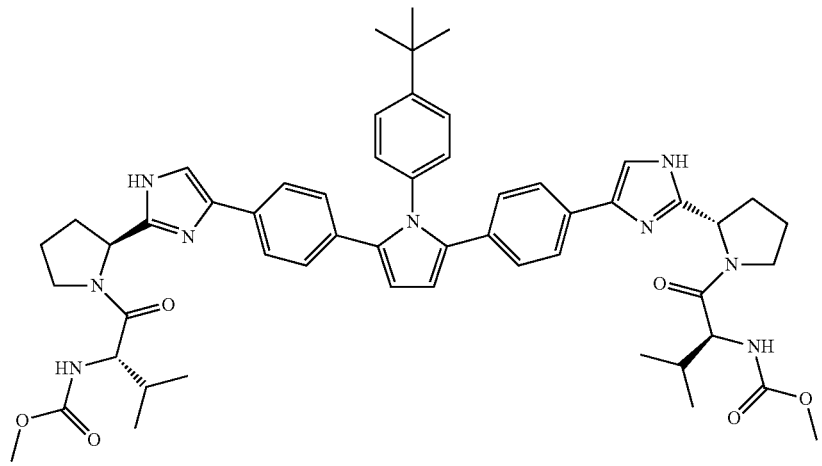

Example 26A (S)-tert-butyl 2-formylpyrrolidine-1-carboxylate

To an oven-dried 500-mL 3-neck flask purged with nitrogen was added oxalyl chloride (5.32 mL, 60.8 mmol) and anhydrous dichloromethane (125 mL), and the solution cooled to −78° C. A solution of anhydrous DMSO (7.30 mL, 103 mmol) in anhydrous dichloromethane (25 mL) was added dropwise from a constant-pressure addition funnel over 20-min period. A solution of (S)-tert-butyl 2-(hydroxymethyl)pyrrolidine-1-carboxylate (9.41 g, 46.8 mmol) in anhydrous dichloromethane (50 mL) was added dropwise from a constant-pressure addition funnel over 20-min period, then stirred reaction mixture at −78° C. for 30 min. Added triethylamine (32.6 mL, 234 mmol) dropwise via syringe over a 5-min period and stirred the thick white mixture in an ice-water bath for 30 min. Quenched reaction with 10% (w/v)

mL) to afford 17 g of solid, which was used directly in the next reaction.

Example 26C (S)-tert-butyl 2-(4,5-dibromo-1H-imidazol-2-yl)pyrrolidine-1-carboxylate N-bromosuccinimide (108 mmol) was added to a cold (0° C.) solution of the product from Example 26B (12.05 g, 50.8 mmol) in dichloromethane (200 mL). Let stir in ice bath for 2 h and then concentrated, dissolved in ethyl acetate (250 mL) washed with water (3×150 mL), brine (1×100 mL), dried (MgSO$_4$) and concentrated to very dark residue, chased with dichloromethane/hexanes (1:1) to get brown solid (~19 g). Triturated solid with ether (~100 mL), filtered to isolate a tan solid (13.23 g, 65% yield).

Example 26D (S)-tert-butyl 2-(5-bromo-1H-imidazol-2-yl)pyrrolidine-1-carboxylate or (S)-tert-butyl 2-(4-bromo-1H-imidazol-2-yl)pyrrolidine-1-carboxylate Dissolved the product from Example 26C (6.25 g, 15.82 mmol) in dioxane (200 mL) and water (200 mL) in a 1 L round bottom flask equipped with a condenser and glass stopper, added a solution of sodium sulfite (22.38 g, 174 mmol) in water (200 mL), and heated at reflux with heating mantle for 16 h. Reaction was reddish-amber homogeneous solution. Cooled reaction to room temperature, removed dioxane and some water by rotary evaporation, extracted with dichloromethane, washed the combined organic extracts with brine (50 mL), dried over anhydrous $Na_2SO_4$, filtered, and concentrated by rotary evaporation, co-evaporating with 2:1 hexanes/dichloromethane (100 mL) to give a beige foam (4.38 g). Dissolved foam in dichloromethane (2 mL), added hexanes (2 mL), applied solution to column, and purified by silica gel flash chromatography eluting with 30% to 80% ethyl acetate/hexanes to afford the title compound as a white solid (3.48 g).

Example 26E 1,4-bis(4-bromophenyl)butane-1,4-dione

To a solution of zinc(II) chloride (19.62 g, 144 mmol) in benzene (108 mL) were added diethylamine (11.16 mL, 108 mmol) and 2-methylpropan-2-ol (10.32 mL, 108 mmol) and the mixture was stirred at room temperature for 2 h. 2-bromo-1-(4-bromophenyl)ethanone (20.0 g, (72 mmol) and 1-(4-bromophenyl)ethanone (21.48 g, 108 mmol) were added in one portion, and the mixture was stirred overnight (18 h). Quenched with 5% $H_2SO_4$ (500 mL) and stirred vigorously to induce precipitation of the product, which was collected by vacuum filtration and washed with benzene, water, methanol, then dichloromethane, successively. The product was dried under vacuum to give the title compound as a white solid (11.15 g, 39.1% yield).

Example 26F 2,5-bis(4-bromophenyl)-1-(4-tert-butylphenyl)-1H-pyrrole

To a solution of the product from Example 26E (4.00 g, 10.10 mmol) in toluene (40 mL) was added 4-tert-butylaniline (1.81 g, 12.12 mmol) followed by TFA (2.30 g, 20.20 mmol). Mixture heated to 110° C. for 2 h. Mixture cooled to room temperature and water and diethyl ether were added. Stirred for 15 min, filtered, washed with water and diethyl ether and dried to provide the title compound as a white solid (4.61 g; 90% yield).

Example 26G 1-(4-tert-butylphenyl)-2,5-bis(4-(4,4,5,5-tetramethyl-1,3,2-dioxaborolan-2-yl)phenyl)-1H-pyrrole To a solution of the product from Example 26F (2.32 g, 4.56 mmol) in DMSO (26 mL) at room temperature were added bis(pinacolato)diborane (2.54 g, 10.02 mmol), potassium acetate (5.00 g, 36.4 mmol) and $PdCl_2$(dppf) (744 mg, 0.91 mmol). The mixture was degassed and heated to 85° C. After 4 h, the mixture was cooled to room temperature, diluted with dichloromethane and washed with water followed by brine. The organic phase was dried ($Na_2SO_4$) and concentrated. The residue was taken up in 20% ethyl acetate: hexanes and filtered through a short plug of silica gel (elution with 20% ethyl acetate:hexanes) and concentrated to afford the title compound as a light yellow solid (1.62 g; 59% yield).

Example 26H (2S,2'S)-tert-butyl 2,2'-(4,4'-(4,4'-(1-(4-tert-butylphenyl)-1H-pyrrole-2,5-diyl)bis(4,1-phenylene))bis(1H-imidazole-4,2-diyl))dipyrrolidine-1-carboxylate A mixture of the product from Example 26D (664 mg, 2.10 mmol), the product from Example 26G (1.48 g, 2.45 mmol), 2 M sodium carbonate (1400 µL, 2.80 mmol), and Pd(dppf)Cl2 (51.2 mg, 0.070 mmol) in DME (2800 µL) was subjected to microwave irradiation at 140° C. for 20 min. The mixture was diluted with ethyl acetate, then washed with water and brine, and dried over $Na_2SO_4$. The product was purified on silica gel eluted with 30 to 70% ethyl acetate:hexanes to provide the title compound (140 mg; 24% yield).

Example 26I (2S,2'S)-4,4'-(4,4'-(1-(4-tert-butylphenyl)-1H-pyrrole-2,5-diyl)bis(4,1-phenylene))bis(2-(pyrrolidin-2-yl)-1H-imidazole)

To a solution of the product from Example 26H (135 mg, 0.164 mmol) in dichloromethane (2 mL) at room temperature was added TFA (0.60 mL). After 3 h, the solvent was removed and the residue partitioned between water and 25% isopropyl alcohol:$CHCl_3$; neutralized with $NaHCO_3$. The organic phase was dried ($Na_2SO_4$), filtered and concentrated. Residue used directly in the next S reaction (98 mg; 96% yield).

Example 26J

Dimethyl (2S,2'S)-1,1'-((2S,2'S)-2,2'-(4,4'-(4,4'-(1H-(4-tert-butylphenyl)-1H-pyrrole-2,5-diyl)bis(4,1-phenylene))bis(1H-imidazole-4,2-diyl))bis(pyrrolidine-2, -diyl))bis(3-methyl-1-oxobutane-2,1-diyl) dicarbamate To a solution of the product from Example 26I (98 mg, 0.158 mmol) in DMF (2 mL) at room temperature was added (S)-2-(methoxycarbonylamino)-3-methylbutanoic acid (61 mg, 0.347 mmol), EDAC (66 mg, 0.347 mmol) and 1-hydroxybenzotriazole hydrate (53 mg, 0.347 mmol). After 3 h, the mixture was transferred to a separatory funnel with ethyl acetate and water. The organic phase was concentrated and the residue purified by chromatography (1% gradient elution from 0% to 4% methanol:dichloromethane) to provide the desired material as a light yellow solid (70 mg; 30% yield).

$^1$HNMR (MeOH-d4; 400 MHz): δ 7.55-7.30 (m, 6H), 7.25-6.96 (m, 8H), 6.45 (s, 2H), 5.12 (dd, J=5.43, 5.43 Hz, 2H), 4.20 (d, J=7.26 Hz, 2H), 4.02-3.90 (m, 2H), 3.85-3.80 (m, 2H), 3.64 (s, 6H), 2.36-1.93 (m, 10H), 1.31 (s, 9H), 0.97-0.86 (m, 12H). The title compound showed an $EC_{50}$ value of less than about 0.1 nM in HCV 1b-Con1 replicon assays in the presence of 5% FBS.

Example 27 dimethyl (2S,2'S)-1,1'-((2S,2'S)-2,2'-(4,4'-(4,4'-((2S,3R,4R,5S)-1-(4-fluorophenyl)-3,4-dimethoxypyrrolidine-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate

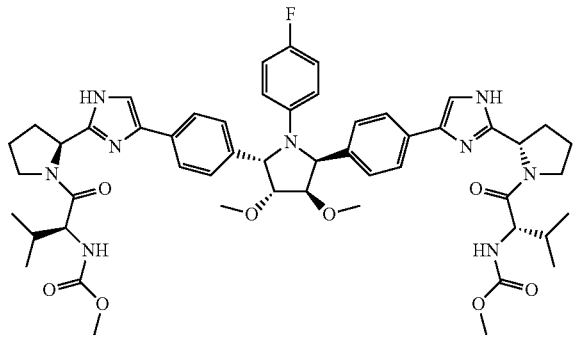 [SMILES: COC(=O)N[C@H](C(=O)N1CCC[C@H]1c1nc(-c2ccc([C@H]3[C@@H](OC)[C@H](OC)[C@H](c4ccc(-c5c[nH]c([C@@H]6CCCN6C(=O)[C@@H](NC(=O)OC)C(C)C)n5)cc4)N3c3ccc(F)cc3)cc2)c[nH]1)C(C)C]

Example 27A (2S,3R,4R,5S)-2,5-bis(4-bromophenyl)-1-(4-fluorophenyl)pyrrolidine-3,4-diol A solution of 3,4-O-isopropylidene-D-mannitol (2.24 g, 10.08 mmol) in 2:1 methanol-dichloromethane (45 mL) was treated with iodobenzene diacetate (7.95 g, 24.19 mmol) followed by stirring at room temperature for 5 h. The mixture was concentrated by rotary evaporation and the residue was dissolved in 0.1M aq. sulfuric acid solution (20.6 mL) followed by stirring at room temperature for 18 h. The mixture was adjusted to pH 6 by addition of solid sodium bicarbonate. The mixture was then sequentially treated with 4-fluoroaniline (1.96 mL, 20.16 mmol), 4-bromophenylboronic acid (3.64 g, 18.14 mmol), and absolute ethanol (40 mL). The mixture was then heated in an oil bath (110° C.) at reflux for 20 h. The dark brown mixture was cooled to room temperature and concentrated in vacuo. The residue was taken up in ethyl acetate (100 mL), washed with water (50 mL), 0.33M aq. potassium phosphate tribasic solution (2×50 mL), and brine (50 mL). The organic phase was dried over anhydrous sodium sulfate, filtered, and the filtrate concentrated by rotary evaporation to a dark reddish-brown oil. Dissolved oil in dichloromethane-hexanes, concentrated in vacuo, and dried in vacuo to give a dark brown foam. Purification by silica gel flash chromatography eluting with a step gradient of 10% to 15% ethyl acetate/dichloromethane afforded pure product as a yellow solid (1.216 g, 24%).

Example 27B (2S,3R,4R,5S)-2,5-bis(4-bromophenyl)-1-(4-fluorophenyl)-3,4-dimethoxypyrrolidine Dissolved the product of Example 27A (237 mg, 0.467 mmol) in a mixture of THF (3 mL) and DMF (1 mL) under a nitrogen atmosphere and cooled to 0° C. Added 60% sodium hydride dispersion in mineral oil (56.1 mg, 1.402 mmol) in portions and stirred the mixture at 0° C. for 15 min. Then added neat iodomethane (65 L, 1.028 mmol), removed the cooling bath, and stirred the reaction at room temperature for 14.5 h. Diluted the reaction in ethyl acetate (50 mL), washed with saturated aq. ammonium chloride solution (25 mL), water (2×25 mL), and brine (25 mL). Dried the organic phase over anhydrous sodium sulfate, filtered, and concentrated the filtrate by rotary evaporation. The yellow residue was purified by silica gel flash chromatography eluting with 30% hexanes/dichloromethane to afford the title compound as a white foam (206 mg, 82%).

Example 27C (2S,3R,4R,5S)-1-(4-fluorophenyl)-3,4-dimethoxy-2,5-bis(4-(4,4,5,5-tetramethyl-1,3,2-dioxaborolan-2-yl)phenyl)pyrrolidine Charged a nitrogen-purged flask with the product of Example 27B (204 mg, 0.381 mmol), bis(pinacalato)diboron (242 mg, 0.953 mmol), potassium acetate (112 mg, 1.143 mmol), and anhydrous dioxane (2 mL). Sparged the mixture with nitrogen for 30 min, added 1,1'-bis(diphenylphosphino)ferrocene-palladium (II) dichloride dichloromethane complex (31.1 mg, 0.038 mmol), sparged the mixture again with nitrogen for 5 min, and heated in an oil bath at 85° C. for 6 h. The reaction was vacuum filtered through a small bed of celite 545, the collected solids were thoroughly washed with 5% methanol/dichloromethane, and the filtrate concentrated in vacuo, chasing the residue with dichloromethane/hexanes to give a tan solid. Purification by silica gel flash chromatography eluting with 5% ethyl acetate/dichloromethane afforded the title compound as a salmon-colored solid (238 mg, 99%).

Example 27D (2S,2'S)-tert-butyl 2,2'-(4,4'-(4,4'-((2S,3R,4R,5S)-1-(4-fluorophenyl)-3,4-dimethoxypyrrolidine-2,5-diyl)bis(4,1-phenylene))bis(1H-imidazole-4,2-diyl))dipyrrolidine-1-carboxylate A nitrogen-purged 5-mL microwave tube was charged with the product of Example 27C (237 mg, 0.377 mmol), the product from Example 26D (298 mg, 0.941 mmol), and a mixture of absolute ethanol (1.5 mL) and toluene (1.5 mL). Sonicated to obtain a cloudy orange mixture, added 1M aq sodium carbonate (0.941 mL, 0.941 mmol), and sparged with nitrogen for 20 min. Added 1,1'-bis(diphenylphosphino)ferrocene-palladium (II) dichloride dichloromethane complex (30.8 mg, 0.038 mmol), sparged the mixture again with nitrogen for 5 min, sealed the reaction tube with an aluminum crimp cap, and heated in a microwave reactor with stirring at 100° C. for 1 h. Cooled reaction to room temperature, diluted in ethyl acetate (75 mL), washed with water (2×25 mL) and brine (25 mL), dried the organic phase over anhydrous magnesium sulfate, filtered, and concentrated the filtrate by rotary evaporation to a dark yellow solid. Purification by silica gel flash chromatography eluting with 4% methanol/dichloromethane afforded the title compound as a yellow solid (221 mg, 69%).

Example 27E (S)-4,4'-(4,4'-((2S,3R,4R,5S)-1-(4-fluorophenyl)-3,4-dimethoxypyrrolidine-2,5-diyl)bis(4,1-phenylene))bis(2-((S)-pyrrolidin-2-yl)-1H-imidazole)

A solution of the product of Example 27D (147.5 mg, 0.174 mmol) in anhydrous dichloromethane (2 mL) under nitrogen was treated with TFA (1 mL) and stirred at room temperature for 30 min. The solvent was removed in vacuo and chased with 1:10 dichloromethane-hexanes (3×50 mL) to afford a pale yellow solid (193 mg). The solid TFA salt was dissolved in anhydrous methanol (15 mL), treated with dry Amberlite IRA-400(OH) resin (1.66 g, previously washed 10 g of wet resin (Supelco) with deionized water (3×25 mL) and methanol (3×25 mL), then dried in vacuo), and stirred for 2 h at room temperature. The mixture was then vacuum filtered, the collected resin washed thoroughly with methanol, the filtrate concentrated by rotary evaporation, and the residue chased with 1:10 dichloromethane-hexanes to afford the title compound as a light yellow solid (94 mg, 0.145 mmol, 83%).

Example 27F dimethyl (2S,2'S)-1,1'-((2S,2'S)-2,2'-(4,4'-(4,4'-((2S,3R,4R,5S)-1-(4-fluorophenyl)-3,4-dimethoxypyrrolidine-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate In an oven-dried round bottom flask, dissolved the product of Example 27E (92 mg, 0.142 mmol) in a mixture of DMF (1 mL) and DMSO (1 mL) under nitrogen and cooled the solution to 0° C. Added sequentially (S)-2-(methoxycarbonylamino)-3-methylbutanoic acid (53.5 mg, 0.305 mmol), EDAC (61.1 mg, 0.312 mmol), 1-hydroxybenzotriazole hydrate (47.8 mg, 0.312 mmol), and N-methylmorpholine (47 μL, 0.426 mmol). Removed the cooling bath and stirred at room temperature for 15 h. Diluted the reaction with ethyl acetate (50 mL), washed with saturated aq. sodium bicarbonate solution (25 mL), water (2×25 mL), and brine (25 mL). The organic phase was dried over anhydrous magnesium sulfate, filtered, and the filtrate concentrated by rotary evaporation. Purification by silica gel flash chromatography eluting with 5% methanol/dichloromethane afforded the title compound as a pale yellow solid (78 mg, 56%). $^1$H NMR (400 MHz, DMSO-d6) δ ppm 0.86 (dd, J=17.67, 6.72 Hz, 12H), 0.97-1.37 (m, 3H), 1.41-2.29 (m, 11H), 3.53 (s, 6H), 3.69-3.86 (m, 4H), 4.04 (q, J=8.02 Hz, 2H), 4.12-4.23 (m, 2H), 5.07 (d, J=3.80 Hz, 2H), 5.35-5.48 (m, 2H), 6.31 (dd, J=9.16, 4.39 Hz, 2H), 6.74 (t, J=8.89 Hz, 2H), 7.12-7.71 (m, 12H), 11.53-12.31 (m, 2H); MS (ESI+) m/z 963 (M+H)+. The title compound showed an $EC_{50}$ value of less than about 0.1 nM in HCV 1b-Con1 replicon assays in the presence of 5% FBS.

Example 28 dimethyl (2S,2'S)-1,1'-((2S,2'S)-2,2'-(5,5'-((2R,5R)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate and dimethyl (2S,2'S)-1,1'-((2S,2'S)-2,2'-(5,5'-((2S,5S)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate

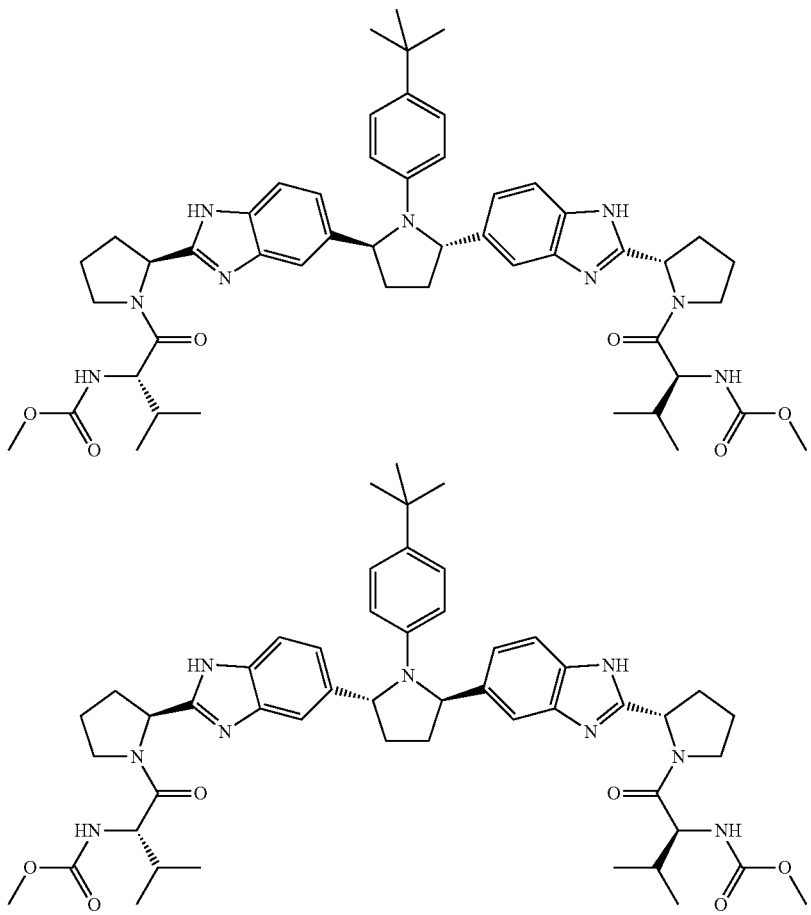

Example 28A 1,4-bis(4-chloro-3-nitrophenyl)butane-1,4-dione

Zinc chloride (27.4 g, 201 mmol), diethylamine (15.6 mL, 151 mmol) and t-butanol (14.4 mL, 151 mmol) were combined in benzene (151 mL) at room temperature under a nitrogen atmosphere and stirred for 2 h. 1-(4-chloro-3-nitrophenyl)ethanone (30.1 g, 151 mmol) and 2-bromo-1-(4-chloro-3-nitrophenyl)ethanone (28 g, 101 mmol) were added. The mixture was stirred vigorously for 20 h, S and the solid product was collected by filtration and rinsed with benzene, water, methanol, and dichloromethane. The solid was dried in a vacuum oven.

Example 28B 1,4-bis(4-chloro-3-nitrophenyl)butane-1,4-diol

The product of Example 28A (5.75 g, 14.48 mmol) was dissolved in ethanol (150 mL) at room temperature and treated with sodium borohydride (1.21 g, 31.9 mmol) portionwise over 5 minutes. The solution was heated at 70° C. for 1 h and then cooled to room temperature, quenched with water, extracted into ethyl acetate, dried over sodium sulfate, and concentrated to dryness to give 4.81 g (83%) of an off-white solid.

Example 28C 1,4-bis(4-chloro-3-nitrophenyl)butane-1,4-diyl dimethanesulfonate The product of Example 28B (4.81 g, 11.99 mmol) and triethylamine (5.85 mL, 42.0 mmol) were dissolved in dichloromethane (80 mL) at room temperature and treated with methanesulfonyl chloride (2.34 mL, 30.0 mmol) dropwise over 10 minutes. The resulting solution was stirred for 2 h then concentrated to dryness and used directly in the next step.

Example 28D 1-(4-tert-butylphenyl)-2,5-bis(4-chloro-3-nitrophenyl)pyrrolidine The product from Example 28C (6.6 g, 11.84 mmol) was slurried in DMF (30 mL) and 4-t-butyl aniline (18.7 mL, 118 mmol) was added and the solution was heated at 55° C. for 2 h then cooled and poured into water and extracted into dichloromethane. The organics were concentrated and the residue was purified by chromatography on silica gel 120 g column, eluting with 0-5% ethyl acetate/hexanes to give 4.41 g (72%) of a thick oil.

Example 28E 4,4'-(1-(4-tert-butylphenyl)pyrrolidine-2,5-diyl)bis(N-(4-methoxybenzyl)-2-nitroaniline)

The product from Example 28D (4.41 g, 8.57 mmol) was combined, neat, with p-methoxy benzylamine (8.93 mL, 68.6 mmol) and heated at 145° C. for 1 h. The mixture was diluted with dichloromethane and filtered. The filtrate was washed with 0.5 M HCl, then NaHCO₃ soln, then brine, concentrated and purified by chromatography on silica gel with an 80 g column, eluting with 0-50% ethyl acetate/hexanes to give 4.13 g (67%) of an orange foamy solid.

Example 28F 4,4'-(1-(4-tert-butylphenyl)pyrrolidine-2,5-diyl)bis(N1-(4-methoxybenzyl)benzene-1,2-diamine)

The product from Example 28E (2 g, 2.79 mmol) was dissolved in a mixture of THF (15 mL), ethanol (15 mL), and ethyl acetate (5 mL) then platinum oxide (0.254 g, 1.12 mmol) was added via THF slurry. The flask was evacuated and purged with nitrogen twice, then evacuated and opened to hydrogen balloon. The mixture was stirred at room temperature for 20 h, then filtered through celite, concentrated, and purified by chromatography on silica gel with an 80 g column, eluting with 0-40% ethyl acetate/dichloromethane to give the first peak of trans product 0.508 g (28%).

Example 28G (2S,2'S)-tert-butyl 2,2'-(5,5'-(1-(4-tert-butylphenyl)pyrrolidine-2,5-diyl)bis(2-(4-methoxybenzylamino)-5,1-phenylene)bis(azanediyl)bis(oxomethylene))dipyrrolidine-1-carboxylate The product from Example 28F (0.422 g, 0.643 mmol) and diisopropylethylamine (0.674 mL, 3.86 mmol) were dissolved in DMSO (6 mL) at room temperature and treated with S-Boc-proline (0.319 g, 1.48 mmol) followed by HATU (0.514 g, 1.35 mmol). The solution was stirred for 1 h at room temperature then diluted with water and the solid product was filtered off and purified by chromatography on silica gel with a 40 g column, eluting with 0-50% ethyl acetate in dichloromethane to give 0.565 g (84%) of a yellow solid.

Example 28H (2S,2'S)-tert-butyl 2,2'-(5,5'-(1-(4-tert-butylphenyl)pyrrolidine-2,5-dine-2,5-yl)bis(2-amino-5,1-phenylene)bis(azanediyl)bis(oxomethylene))dipyrrolidine-1-carboxylate The product from Example 28G (0.565 g, 0.538 mmol) was dissolved in dichloromethane (5 mL) and water (0.25 mL) at room temperature and treated with DDQ (0.244 g, 1.076 mmol) portionwise over 2 minutes. The mixture was diluted with sodium bicarbonate solution, extracted into dichloromethane, concentrated and purified by chromatography on silica gel with a 40 g column, eluting with 0-15% methanol/dichloromethane to give 0.355 g (81%) of a yellow solid.

Example 28I (2S,2'S)-tert-butyl 2,2'-(5,5'-(1-(4-tert-butylphenyl)pyrrolidine-2,5-diyl)bis(1H-benzo[d]imidazole-5,2-diyl))dipyrrolidine-1-carboxylate The product from Example 28H was dissolved in neat acetic acid (3 mL) and heated at 72° C. for 2 h. The solution was concentrated and then poured into water and adjusted pH to ~7-8 with sodium bicarbonate. The product was extracted into dichloromethane, concentrated and purified by chromatography on silica gel with a 40 g column, eluting with 0-5% methanol/dichloromethane to give 0.185 g (55%) of a light yellow solid.

Example 28J (S)-5,5'-(1-(4-tert-butylphenyl)pyrrolidine-2,5-diyl) bis(2-((S)-pyrrolidin-2-yl)-1H-benzo[d]imidazole)

The product from Example 28I (0.204 g, 0.264 mmol) was dissolved in THF (2 mL) at room temperature and treated with 4 M hydrochloric acid in dioxane (2 mL). The mixture was concentrated to dryness and used directly in the next step.

Example 28K dimethyl (2S,2'S)-1,1'-((2S,2'S)-2,2'-(5,5'-((2R,5R)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate and dimethyl (2S,2'S)-1,1'-((2S,2'S)-2,2'-(5,5'-((2S,5S)-1-(4-tert-butylphenyl)pyrrolidine-2,5-diyl)bis(1H-benzo[d]imidazole-5,2-diyl))bis(pyrrolidine-2,1-diyl))bis(3-methyl-1-oxobutane-2,1-diyl) dicarbamate The product from Example 28J (0.150 g, 0.261 mmol) and diisopropylethylamine (0.365 mL, 2.09 mmol) were dissolved in DMSO (3 mL) at room temperature and treated with (S)-2-(methoxycarbonylamino)-3-methylbutanoic acid (0.105 g, 0.601 mmol) followed by HATU (0.204 g, 0.536 mmol). The solution was stirred for 1 h at room temperature then diluted with water and the solid product was filtered off and purified by chromatography on silica gel with a 12 g column, eluting with 0-8% methanol in dichloromethane to give 0.143 g (60%) of a yellow solid. $^1$H NMR (400 MHz, DMSO-D6) δ ppm 0.75-0.92 (m, 12H) 1.07 (s, 9H) 1.64-1.76 (m, 2H) 1.85-2.04 (m, 6H) 2.12-2.26 (m, 4H) 2.43 (dd, J=7.75, 4.07 Hz, 2H) 3.53 (s, 6H) 3.76-3.87 (m, 4H) 4.04 (dd, J=11.49, 6.51 Hz, 2H) 5.12 (t, J=7.59 Hz, 2H) 5.35 (d, J=3.25 Hz, 2H) 6.25 (d, J=8.46 Hz, 2H) 6.85-6.96 (m, 2H) 7.07 (t, J=7.97 Hz, 2H) 7.19 (s, 1H) 7.28 (d, J=8.35 Hz, 3H) 7.38 (dd, J=8.19, 1.90 Hz, 1H) 7.46 (d, J=8.13 Hz, 1H) 11.97-12.09 (m, 2H). The title compound showed an $EC_{50}$ value of less than about 0.1 nM in HCV 1b-Con1 replicon assays in the presence of 5% FBS.

Example 29 dimethyl (2S,2'S)-1,1'-((2S,2'S)-2,2'-(5,5'-((2R,5R)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate and dimethyl (2S,2'S)-1,1'-((2S,2'S)-2,2'-(5,5'-((2S,5S)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate

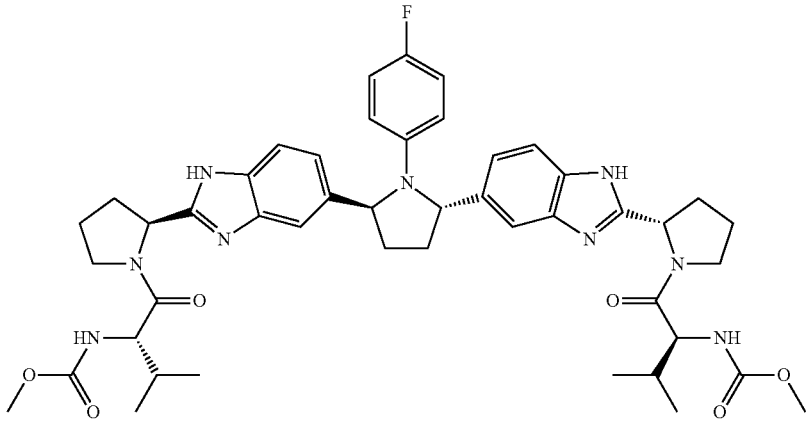

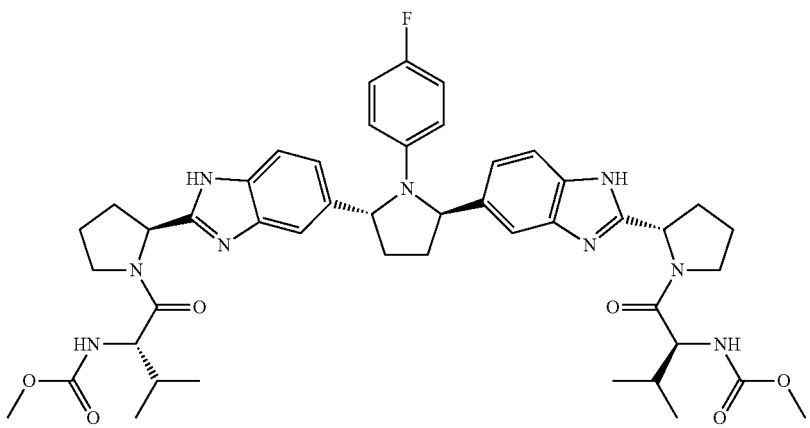

Example 29A 2,5-bis(4-chloro-3-nitrophenyl)-1-(4-fluorophenyl)pyrrolidine

The product from Example 28C (2.9 g, 5.2 mmol) and 4-fluoroaniline (5.0 mL, 52.0 mmol) were combined, neat, and heated at 45° C. for 20 h then cooled and poured into water and extracted into dichloromethane. The organics were concentrated the residue was purified by chromatography on silica gel with a 120 g column, eluting with 0-5% ethyl acetate/hexanes to give 0.59 g (24%) of a thick oil.

Example 29B 4,4'-(1-(4-fluorophenyl)pyrrolidine-2,5-diyl)bis(N-(4-methoxybenzyl)-2-nitroaniline)

The product from Example 29A (0.88 g, 1.86 mmol) was combined with 4-methoxy benzylamine (3.64 mL, 28.0 mmol) and heated at 145° C. for 1 h in a microwave reactor. The mixture was diluted with dichloromethane and filtered. The filtrate was concentrated and purified by chromatography on silica gel with a 330 g column, eluting with 0-60% ethyl acetate/hexanes to give 0.79 g (62%) of an orange foam solid.

Example 29C 4,4'-(1-(4-fluorophenyl)pyrrolidine-2,5-diyl)bis(2-nitroaniline)

The product from Example 29B (0.78 g, 1.15 mmol) was dissolved in dichloromethane (10 mL) at room temperature and treated with TFA (1.8 mL, 23.0 mmol) for 3 h. The residue was concentrated and partitioned between dichloromethane and sodium bicarbonate solution. The organics were concentrated and purified by chromatography on silica gel with a 40 g column, eluting with dichloromethane to give 0.218 g (43%) of the trans isomer.

Example 29D 4,4'-(1-(4-fluorophenyl)pyrrolidine-2,5-diyl)dibenzene-1,2-diamine The product from Example 29C (0.218 g, 0.50 mmol) was dissolved in DMF (5 mL) then platinum oxide (0.226 g, 0.99 mmol) was added via THF slurry. The flask was evacuated and purged with nitrogen twice, then evacuated and opened to hydrogen balloon. The mixture was stirred at room temperature for 20 h. The solution was taken on to the next step without purification.

Example 29E (2S,2'S)-tert-butyl 2,2'-(5,5'-(1-(4-fluorophenyl)pyrrolidine-2,5-diyl)bis(2-amino-5,1-phenylene))bis(azanediyl)bis(oxomethylene)dipyrrolidine-1-carboxylate The crude DMF solution of the product from Example 29D was treated with diisopropylethylamine (0.296 mL, 1.70 mmol) and S-Boc-proline (0.192 g, 0.89 mmol) followed by HATU (0.322 g, 0.85 mmol). The solution was stirred for 1.5 h at room temperature then diluted with water and the solid product was filtered off and purified by chromatography on silica gel with a 12 g column, eluting with 0-3% methanol in dichloromethane to give 0.235 g (72%) of a yellow solid.

Example 29F (2S,2'S)-tert-butyl 2,2'-(5,5'-(1-(4-fluorophenyl)pyrrolidine-2,5-diyl)bis(1H-benzo[d]imidazole-5,2-diyl))dipyrrolidine-1-carboxylate The product from Example 29E was dissolved in neat acetic acid (2 mL) and heated at 60° C. for 1 h. The solution was concentrated then poured into water and adjusted pH to ~7-8 with sodium bicarbonate. The product was extracted into dichloromethane, concentrated and purified by chromatography on silica gel with a 12 g column, eluting with 0-20% ethyl acetate in dichloromethane to give 0.124 g (55%) of a light yellow solid.

Example 29G (S)-5,5'-(1-(4-fluorophenyl)pyrrolidine-2,5-diyl)bis(2-((S)-pyrrolidin-2-yl)-1H-benzo[d]imidazole)

The product from Example 29F (0.120 g, 0.163 mmol) was dissolved in dichloromethane (2 mL) at room temperature and treated with TFA (1 mL). The mixture was concentrated to dryness, dissolved in 25% ISOPROPYL ALCOHOL/dichloromethane and washed with sodium bicarbonate solution. The resulting solids were filtered off and dried and the organics were concentrated and dried to give the title compound (0.062 g 72% yield) of an off-white solid.

Example 29H dimethyl (2S,2'S)-1,1'-((2S,2'S)-2,2'-(5,5'-((2R,5R)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate and dimethyl (2S,2'S)-1,1'-((2S,2'S)-2,2'-(5,5'-((2S,5S)-1-(4-fluorophenyl)pyrrolidine-2,5-diyl)bis(1H-benzo[d]imidazole-5,2-diyl))bis(pyrrolidine-2, -diyl))bis(3-methyl-1-oxobutane-2,1-diyl)dicarbamate The product from Example 29G (0.062 g, 0.116 mmol) and diisopropylethylamine (0.101 mL, 0.58 mmol) were dissolved in DMSO (2 mL) at room temperature and treated with (S)-2-(methoxycarbonylamino)-3-methylbutanoic acid (0.051 g, 0.289 mmol) followed by HATU (0.092 g, 0.243 mmol). The solution was stirred for 1 h at room temperature then diluted with water and the S solid product was filtered off and purified by chromatography on silica gel with a 12 g column, eluting with 0-7% methanol in dichloromethane to give 0.021 g (21%) of a yellow solid. $^1$H NMR (400 MHz, DMSO-D6) δ ppm 0.78-0.90 (m, 12H) 1.70 (s, 2H) 1.87-2.03 (m, 6H) 2.13-2.26 (m, 4H) 2.54-2.62 (m, 2H) 3.54 (s, 6H) 3.82 (s, 4H) 4.03-4.11 (m, 2H) 5.09-5.18 (m, 2H) 5.32-5.42 (m, 2H) 6.28 (dd, J=8.89, 4.34 Hz, 2H) 6.70-6.80 (m, 2H) 7.01-7.10 (m, 2H) 7.20 (d, J=9.32 Hz, 1H) 7.27-7.34 (m, 3H) 7.38 (dd, J=8.13, 2.71 Hz, 1H) 7.45 (d, J=8.02 Hz, 1H) 12.03 (s, 2H). The title compound showed an $EC_{50}$ value of less than about 0.1 nM in HCV 1b-Con1 replicon assays in the presence of 5% FBS.

Example 30 dimethyl (2S,2'S)-1,1'-((2S,2'S)-2,2'-(5,5'-((2S,5S)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate

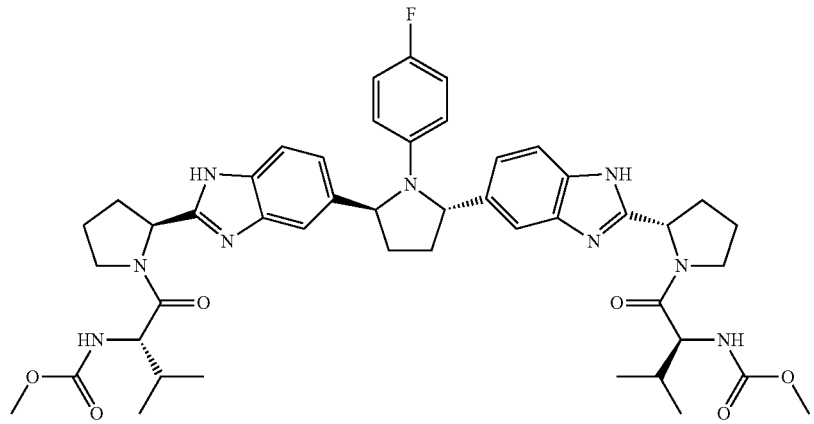

The product from Example 29H was purified by chiral chromatography on a Chirapak IA column eluting with a mixture of hexane/EtOH/MeOH/1,2 Dichloroethane/diethylamine (25/25/25/25/0.1). $^1$H NMR (400 MHz, DMSO-D6) δ ppm 0.75-0.89 (m, 12H) 1.64-1.73 (m, 2H) 1.85-2.03 (m, 6H) 2.12-2.24 (m, 4H) 2.81-2.90 (m, 2H) 3.52 (s, 6H) 3.76-3.87 (m, 4H) 4.01-4.09 (m, 2H) 5.08-5.16 (m, 2H) 5.34 (q, J=6.65 Hz, 2H) 6.26 (dd, J=9.05, 4.50 Hz, 2H) 6.67-6.78 (m, 2H) 7.03 (t, J=8.02 Hz, 2H) 7.20 (s, 1H) 7.24-7.32 (m, 3H) 7.36 (d, J=8.13 Hz, 1H) 7.44 (d, J=7.92 Hz, 1H) 12.01-12.07 (m, 2H). The title compound showed an $EC_{50}$ value of less than about 0.1 nM in HCV 1b-Con1 replicon assays in the presence of 5% FBS.

Example 31 dimethyl (2S,2'S)-1,1'-((2S,2'S)-2,2'-(5,5'-((2R,5R)-1-(4-fluorophenyl)pyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate

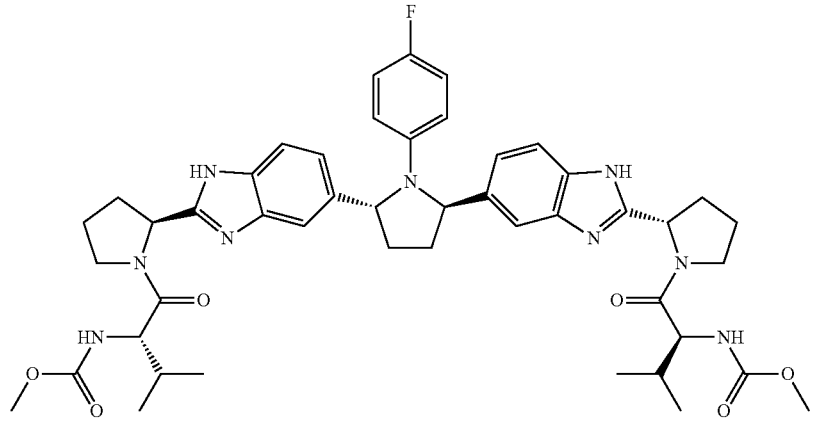

The product from Example 29H was purified by chiral chromatography on a Chirapak IA column eluting with a mixture of hexane/EtOH/MeOH/1,2 Dichloroethane/diethylamine (25/25/25/25/0.1). $^1$H NMR (400 MHz, DMSO-D6) δ ppm 0.74-0.93 (m, 12H) 1.69 (t, J=9.65 Hz, 2H) 1.82-2.06 (m, 6H) 2.09-2.26 (m, 4H) 3.04-3.23 (m, 2H) 3.52 (s, 6H) 3.73-3.90 (m, 4H) 4.06 (t, J=8.46 Hz, 2H) 5.05-5.21 (m, 2H) 5.29-5.44 (m, 2H) 6.21-6.32 (m, 2H) 6.67-6.86 (m, 2H) 7.05 (t, J=8.78 Hz, 2H) 7.18 (s, 1H) 7.23-7.33 (m, 3H) 7.37 (d, J=8.13 Hz, 1H) 7.45 (d, J=8.02 Hz, 1H) 12.04 (d, J=14.96 Hz, 2H). The title compound showed an $EC_{50}$ value of less than about 0.1 nM in HCV 1b-Con1 replicon assays in the presence of 5% FBS.

Example 32

(1R,4R)-1,4-bis(4-nitrophenyl)butane-1,4-diol

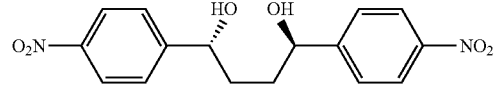

To (S)-(−)-α,α-diphenyl-2-pyrrolidinemethanol (2.71 g, 10.70 mmol) was added THF (80 mL) at 23° C. The very thin suspension was treated with trimethyl borate (1.44 g, 13.86 mmol) over 30 seconds, and the resulting solution was mixed at 23° C. for 1 h. The solution was cooled to 16-19° C., and N,N-diethylaniline borane (21.45 g, 132 mmol) was added dropwise via syringe over 3-5 min (caution: vigorous H₂ evolution), while the internal temperature was maintained at 16-19° C. After 15 min, the H₂ evolution had ceased. To a separate vessel was added the product from Example 1A (22.04 g, 95 wt %, 63.8 mmol), followed by THF (80 mL), to form an orange slurry. After cooling the slurry to 11° C., the borane solution was transferred via cannula into the dione slurry over 3-5 min. During this period, the internal temperature of the slurry rose to 16° C. After the addition was complete, the reaction was maintained at 20-27° C. for an additional 2.5 h. After reaction completion, the mixture was cooled to 5° C. and methanol (16.7 g, 521 mmol) was added dropwise over 5-10 min, maintaining an internal temperature <20° C. (note: vigorous H₂ evolution). After the exotherm had ceased (ca. 10 min), the temperature was adjusted to 23° C., and the reaction was mixed until complete dissolution of the solids had occurred. Ethyl acetate (300 mL) and 1 M HCl (120 mL) were added, and the phases were partitioned. The organic phase was then washed successively with 1 M HCl (2×120 mL), H₂O (65 mL), and 10% aq. NaCl (65 mL). The organics were dried over MgSO₄, filtered, and concentrated in vacuo. Crystallization of the product occurred during the concentration. The slurry was warmed to 50° C., and heptane (250 mL) was added over 15 min. The slurry was then allowed to mix at 23° C. for 30 min and filtered. The wet cake was washed with 3:1 heptane:ethyl acetate (75 mL), and the orange, crystalline solids were dried at 45° C. for 24 h to provide the title compound (15.35 g, 99.3% ee, 61% yield), which was contaminated with 11% of the meso isomer (vs. dl isomer).

Example 33

(1S,4S)-1,4-bis(4-nitrophenyl)butane-1,4-diol

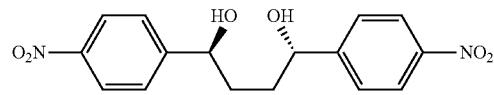 [SMILES: O=[N+]([O-])c1ccc([C@@H](O)CC[C@H](O)c2ccc([N+](=O)[O-])cc2)cc1]

The product from Example 1A (30 g, 95 wt %, 91.4 mmol) was subjected to the conditions described in Example 32, substituting (R)-(−)-α,α-diphenyl-2-pyrrolidinemethanol for (S)-(−)-α,α-diphenyl-2-pyrrolidinemethanol, to give the title compound (20.14 g, >99.55 ee, 61% yield) which was contaminated with 9.7% of the meso isomer (vs. dl isomer).

Example 34

Dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate and Dimethyl (2S,2'S)-1,1'-((2S,2'S)-2,2'-(4,4'-((2R,5R)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate

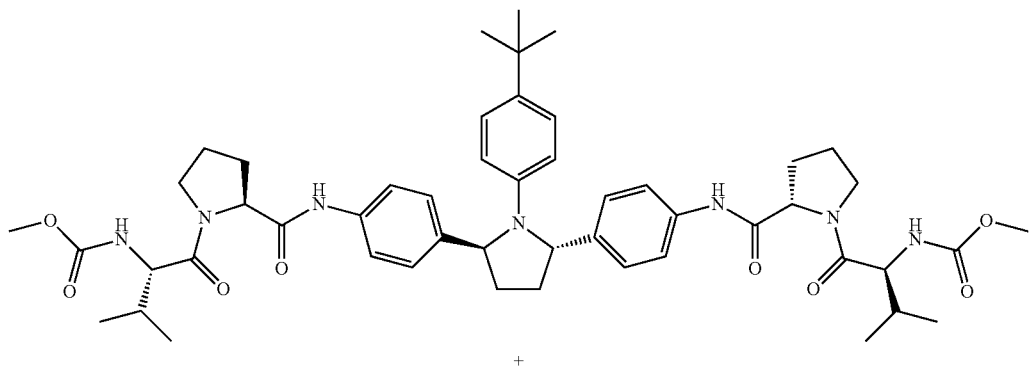

+

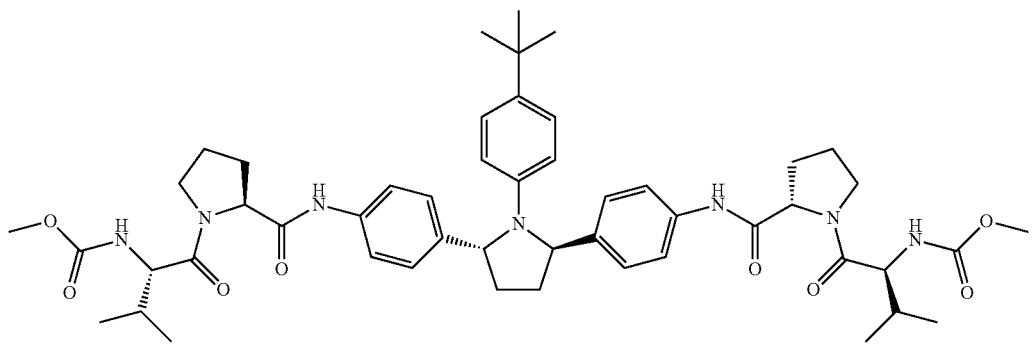

Example 34A

1-(4-tert-butylphenyl)-2,5-bis(4-nitrophenyl)pyrrolidine

The product from Example 1C (3.67 g, 7.51 mmol) and 4-tert-butylaniline (11.86 ml, 75 mmol) in DMF (40 ml) was stirred under nitrogen at 50° C. for 4 h. The resulting mixture was diluted into ethyl acetate, treated with 1M HCl, stirred for 10 minutes and filtered to remove solids. The filtrate organic layer was washed twice with brine, dried with sodium sulfate, filtered and evaporated. The residue was purified by chromatography on silica gel eluting with ethyl acetate in hexane (5% to 30%) to give a solid. The solid was triturated in a minimal volume of 1:9 ethyl acetate/hexane to give a light yellow solid as a mixture of trans and cis isomers (1.21 g, 36%).

Example 34B

4,4'-((2S,5S)-1-(4-tert-butylphenyl)pyrrolidine-2,5-diyl)dianiline and 4,4'-((2R,5R)-1-(4-tert-butylphenyl)pyrrolidine-2,5-diyl)dianiline To a solution of the product from Example 34A (1.1 g, 2.47 mmol) in ethanol (20 ml) and THF (20 ml) was added PtO$_2$ (0.22 g, 0.97 mmol) in a 50 ml pressure bottle and stirred under 30 psi hydrogen at room temperature for 1 h. The mixture was filtered through a nylon membrane and evaporated. The residue was purified by chromatography on silica gel eluting with ethyl acetate in hexane (20% to 60%). The title compound eluted as the first of 2 stereoisomers (trans isomer, 0.51 g, 54%).

Example 34C

(2S,2'S)-tert-Butyl 2,2'-(4,4'-((2S,5S)-1-(4-tert-butylphenyl)pyrrolidine-2,5-diyl)bis(4,1-phenylene))bis(azanediyl)bis(oxomethylene)dipyrrolidine-1-carboxylate and (2S,2'S)-tert-Butyl 2,2'-(4,4'-((2R,5R)-1-(4-tert-butylphenyl)pyrrolidine-2,5-diyl)bis(4,1-phenylene))bis(azanediyl)bis(oxomethylene)dipyrrolidine-1-carboxylate To a mixture of the product from Example 34B (250 mg, 0.648 mmol), (S)-1-(tert-butoxycarbonyl)pyrrolidine-2-carboxylic acid (307 mg, 1.427 mmol) and HATU (542 mg, 1.427 mmol) in DMSO (10 ml) was added Hunig's base (0.453 ml, 2.59 mmol). The reaction mixture was stirred at room temperature for 1 h. The mixture was partitioned with ethyl acetate and water. The organic layer was washed with brine, dried with sodium sulfate, filtered and evaporated. The residue was purified by chromatography on silica gel eluting with ethyl acetate in hexane (10% to 50%) to give the title compound (500 mg, 99%).

Example 34D

(2S,2'S)—N,N'-(4,4'-((2S,5S)-1-(4-tert-butylphenyl)pyrrolidine-2,5-diyl)bis(4,1-phenylene))dipyrrolidine-2-carboxamide and (2S,2'S)—N,N'-(4,4'-((2R,5R)-1-(4-tert-butylphenyl)pyrrolidine-2,5-diyl)bis(4,1-phenylene))dipyrrolidine-2-carboxamide To the product from Example 34C (498 mg, 0.638 mmol) in dichloromethane (4 ml) was added TFA (6 ml). The reaction mixture was stirred at room temperature for 1 h and concentrated in vacuo. The residue was partitioned between 3:1 CHCl$_3$:isopropyl alcohol and saturated aq. NaHCO$_3$. The aqueous layer was extracted by 3:1 CHCl$_3$:isopropyl alcohol again. The combined organic layers were dried over Na$_2$SO$_4$, filtered and concentrated to give the title compound (345 mg, 93%).

Example 34E

Dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate and

Dimethyl (2S,2'S)-1,1'-((2S,2'S)-2,2'-(4,4'-((2R,5R)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate The product from Example 34D (29.0 mg, 0.050 mmol), (S)-2-(methoxycarbonylamino)-3-methylbutanoic acid (19.27 mg, 0.110 mmol), EDAC (21.09 mg, 0.110 mmol), HOBT (16.85 mg, 0.110 mmol) and N-methylmorpholine (0.027 ml, 0.250 mmol) were combined in DMF (2 ml). The reaction mixture was stirred at room temperature for 3 h. The mixture was partitioned with ethyl acetate and water. The organic layer was washed with brine twice, dried with sodium sulfate, filtered and evaporated. The residue was purified by chromatography on silica gel eluting with ethyl acetate in hexane (50% to 80%) to give a solid. The solid was triturated with ethyl acetate/hexane to give the title compound (13 mg, 29%). $^1$H NMR (400 MHz, DMSO-D6) δ ppm 0.85-0.95 (m, 12H) 1.11 (s, 9H) 1.59-1.65 (m, 2H) 1.79-2.04 (m, 8H) 2.10-2.18 (m, 2H) 2.41-2.46 (m, 2H) 3.52 (s, 6H) 3.57-3.67 (m, 2H) 3.76-3.86 (m, 2H) 4.00 (t, J=7.56 Hz, 2H) 4.39-4.46 (m, 2H) 5.15 (d, J=7.00 Hz, 2H) 6.17 (d, J=7.70 Hz, 2H) 6.94 (d, J=8.78 Hz, 2H) 7.13 (d, J=7.37 Hz, 4H) 7.30 (d, J=8.20 Hz, 2H) 7.50 (d, J=8.24 Hz, 4H) 9.98 (s, 2H); (ESI+) m/z 895 (M+H)+. The title compound showed an EC$_{50}$ value of less than about 0.1 nM in HCV 1b-Con1 replicon assays in the presence of 5% FBS.

Example 35

Dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate

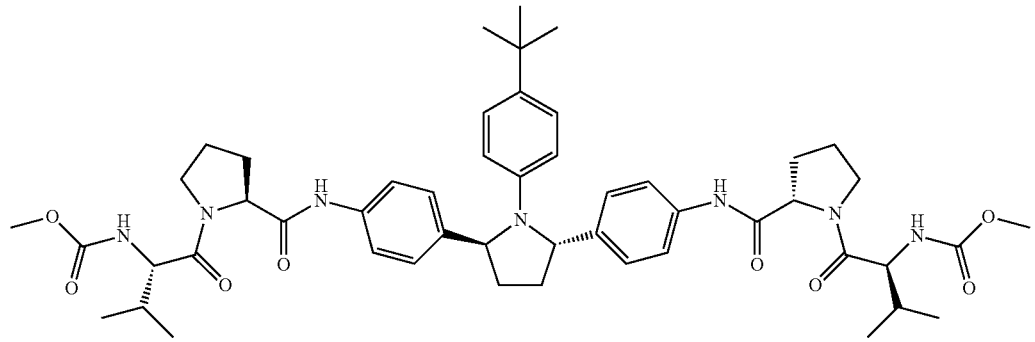

The product from Example 34E was purified by chiral chromatography on a Chiralpak AD-H semi-prep column eluting with a 2:1 mixture of hexane:(2:1 isopropyl alcohol:EtOH). The title compound was the first of the 2 diastereomers to elute. $^1$H NMR (400 MHz, DMSO-D6) δ ppm 0.88 (d, J=6.61 Hz, 6H) 0.93 (d, J=6.72 Hz, 6H) 1.11 (s, 9H) 1.63 (d, J=5.42 Hz, 2H) 1.80-2.04 (m, 8H) 2.09-2.19 (m, 2H) 2.44-2.47 (m, 2H) 3.52 (s, 6H) 3.59-3.66 (m, 2H) 3.77-3.84 (m, 2H) 4.02 (t, J=8.40 Hz, 2H) 4.42 (dd, J=7.86, 4.83 Hz, 2H) 5.14 (d, J=6.18 Hz, 2H) 6.17 (d, J=8.67 Hz, 2H) 6.94 (d, J=8.78 Hz, 2H) 7.13 (d, J=8.46 Hz, 4H) 7.31 (d, J=8.35 Hz, 2H) 7.50 (d, J=8.35 Hz, 4H) 9.98 (s, 2H). The title compound showed an $EC_{50}$ value of less than about 0.1 nM in HCV 1b-Con1 replicon assays in the presence of 5% FBS.

Example 36

Dimethyl (2S,2'S)-1,1'-((2S,2'S)-2,2'-(4,4'-((2R,5R)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate The product from Example 34E was purified by chiral chromatography on a Chiralpak AD-H semi-prep column eluting with a 2:1 mixture of hexane:(2:1 isopropyl alcohol:EtOH). The title compound was the second of 2 diastereomers to elute. $^1$H NMR (400 MHz, DMSO-D6) δ ppm 0.87 (d, J=6.51 Hz, 6H) 0.92 (d, J=6.72 Hz, 6H) 1.11 (s, 9H) 1.63 (d, J=5.53 Hz, 2H) 1.82-2.04 (m, 8H) 2.09-2.18 (m, 2H) 2.41-2.47 (m, 2H) 3.52 (s, 6H) 3.58-3.67 (m, 2H) 3.75-3.84 (m, 2H) 4.02 (t, J=7.26 Hz, 2H) 4.43 (dd, J=7.92, 4.88 Hz, 2H) 5.14 (d, J=6.18 Hz, 2H) 6.17 (d, J=8.78 Hz, 2H) 6.94 (d, J=8.67 Hz, 2H) 7.12 (d, J=8.46 Hz, 4H) 7.31 (d, J=8.35 Hz, 2H) 7.49 (d, J=8.46 Hz, 4H) 9.98 (s, 2H). The title compound showed an $EC_{50}$ value of less than about 0.1 nM in HCV 1b-Con1 replicon assays in the presence of 5% FBS.

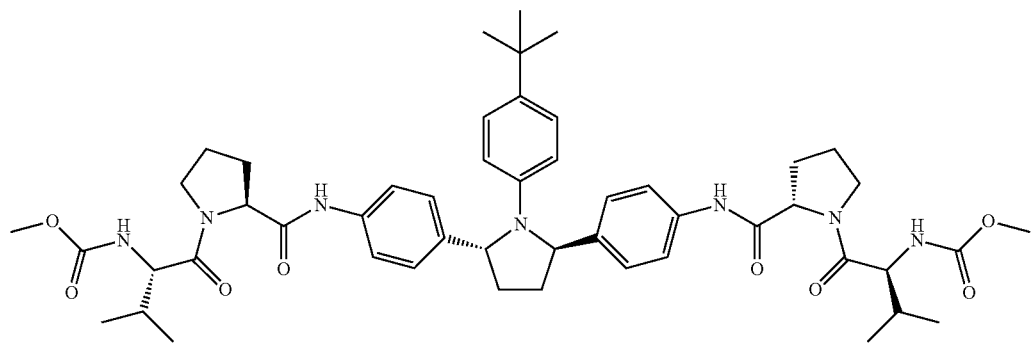

Example 37

Dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate

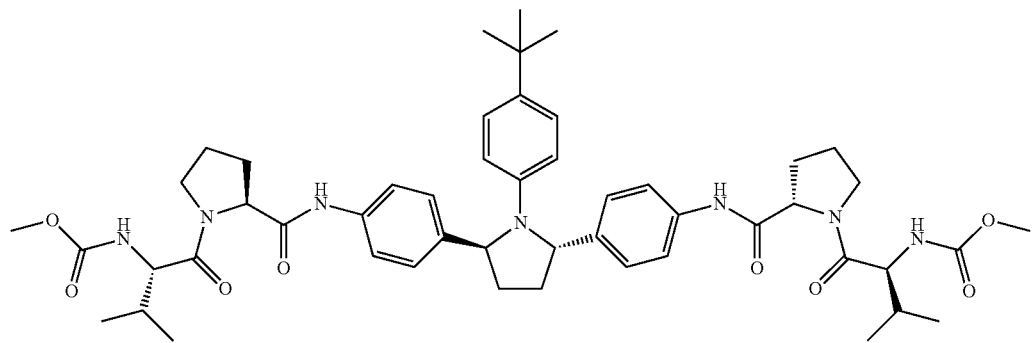

Example 37A (S)-2,5-dioxopyrrolidin-1-yl 2-(methoxycarbonylamino)-3-methylbutanoate To a mixture of (S)-2-(methoxycarbonylamino)-3-methylbutanoic acid (19.66 g, 112 mmol) and N-hydroxysuccinimide (13.29 g, 116 mmol) was added ethyl acetate (250 ml), and the mixture was cooled to 0-5° C. Diisopropylcarbodiimide (13.88 g, 110 mmol) was added and the reaction mixture was stirred at 0-5° C. for about 1 hour. The reaction mixture was warmed to room temperature. The solids (diisopropylurea by-product) were filtered and rinsed with ethyl acetate. The filtrate was concentrated in vacuo to an oil. Isopropyl alcohol (200 ml) was added to the oil and the mixture was heated to about 50° C. to obtain a homogeneous solution. Upon cooling, crystalline solids formed. The solids were filtered and washed with isopropyl alcohol (3×20 ml) and dried to give the title compound as a white solid (23.2 g, 77% yield).

Example 37B (S)-1-((S)-2-(methoxycarbonylamino)-3-methylbutanoyl)pyrrolidine-2-carboxylic acid To a mixture of L-proline (4.44 g, 38.6 mmol), water (20 ml), acetonitrile (20 ml) and DIEA (9.5 g, 73.5 mmol) was added a solution of the product from Example 37A (10 g, 36.7 mmol) in acetonitrile (20 mL) over 10 minutes. The reaction mixture was stirred overnight at room temperature. The solution was concentrated under vacuum to remove the acetonitrile. To the resulting clear water solution was added 6N HCl (9 ml) until pH~2. The solution was transferred to a separatory funnel and 25% NaCl (10 ml) was added and the mixture was extracted with ethyl acetate (75 ml), and then again with ethyl acetate (6×20 ml), and the combined extracts were washed with 25% NaCl (2×10 ml). The solvent was evaporated to give a thick oil. Heptane was added and the solvent was evaporated to give a foam, which was dried under high vacuum. Diethyl ether was added and the solvent was evaporated to give a foam, which was dried under high vacuum to give the title compound (10.67 g) as a white solid.

The compound of Example 37B can also be prepared according to the following procedure:

To a flask was charged L-valine (35 g, 299 mmol), 1N sodium hydroxide solution (526 ml, 526 mmol) and sodium carbonate (17.42 g, 164 mmol). The mixture was stirred for 15 min to dissolve solids and then cooled to 15° C. Methyl chloroformate (29.6 g, 314 mmol) was added slowly to the reaction mixture. The mixture was then stirred at rt for 30 min. The mixture was cooled to 15° C. and pH adjusted to ~5.0 with concentrated HCl solution. 100 mL of 2-methyltetrahydrofuran (2-MeTHF) was added and the adjustment of pH continued until the pH reached ~2.0. 150 mL of 2-MeTHF was added and the mixture was stirred for 15 min. Layers were separated and the aqueous layer extracted with 100 mL of 2-MeTHF. The combined organic layer was dried over anhyd $Na_2SO_4$ and filtered, and $Na_2SO_4$ cake was washed with 50 mL of 2-MeTHF. The product solution was concentrated to ~100 mL, chased with 120 mL of IPAc twice. 250 mL of heptanes was charged slowly and then the volume of the mixture was concentrated to 300 mL. The mixture was heated to 45° C. and 160 mL of heptanes charged. The mixture was cooled to rt in 2 h, stirred for 30 min, filtered and washed with 2-MeTHF/heptanes mixture (1:7, 80 mL). The wetcake was dried at 55° C. for 24 h to give 47.1 g of Moc-L-Val-OH product as a white solid (90%).

Moc-L-Val-OH (150 g, 856 mmol), HOBt hydrate (138 g, 899 mmol) and DMF (1500 ml) were charged to a flask. The mixture was stirred for 15 min to give a clear solution. EDC hydrochloride (172 g, 899 mmol) was charged and mixed for 20 min. The mixture was cooled to 13° C. and (L)-proline benzyl ester hydrochloride (207 g, 856 mmol) charged. Triethylamine (109 g, 1079 mmol) was then charged in 30 min. The resulting suspension was mixed at rt for 1.5 h. The reaction mixture was cooled to 15° C. and 1500 mL of 6.7% $NaHCO_3$ charged in 1.5 h, followed by the addition of 1200 mL of water over 60 min. The mixture was stirred at rt for 30 min, filtered and washed with water/DMF mixture (1:2, 250 mL) and then with water (1500 mL). The wetcake was dried at 55° C. for 24 h to give 282 g of product as a white solid (90%).

The resulting solids (40 g) and 5% Pd/Alumina were charged to a Parr reactor followed by THF (160 mL). The reactor was sealed and purged with nitrogen (6×20 psig) followed by a hydrogen purge (6×30 psig). The reactor was pressurized to 30 psig with hydrogen and agitated at room temperature for approximately 15 hours. The resulting slurry was filtered through a GF/F filter and concentrated to approximately 135 g solution. Heptane was added (120 mL), and the solution was stirred until solids formed. After an addition 2-3 hours additional heptane was added drop-wise (240 mL), the slurry was stirred for approximately 1 hour, then filtered. The solids were dried to afford the title compound.

Example 37C (1R,4R)-1,4-bis(4-nitrophenyl)butane-1,4-diyl dimethanesulfonate

The product from Example 32 (5.01 g, 13.39 mmol) was combined with 2-methyltetrahydrofuran (70 mL) and cooled to −5° C., and N,N-diisopropylethylamine (6.81 g, 52.7 mmol) was added over 30 seconds. Separately, a solution of methanesulfonic anhydride (6.01 g, 34.5 mmol) in 2-methyltetrahydrofuran (30 mL) was prepared and added to the diol slurry over 3 min., maintaining the internal temperature between −15° C. and −25° C. After mixing for 5 min at −15° C., the cooling bath was removed and the reaction was allowed to warm slowly to 23° C. and mixed for 30 minutes. After reaction completion, the crude slurry was carried immediately into the next step.

Example 37D (2S,5S)-1-(4-tert-butylphenyl)-2,5-bis(4-nitrophenyl) pyrrolidine

To the crude product solution from Example 37C (7.35 g, 13.39 mmol) was added 4-tert-butylaniline (13.4 g, 90 mmol) at 23° C. over 1 minute. The reaction was heated to 65° C. for 2 h. After completion, the reaction mixture was cooled to 23° C. and diluted with 2-methyltetrahydrofuran (100 mL) and 1 M HCl (150 mL). After partitioning the phases, the organic phase was treated with 1 M HCl (140 mL), 2-methyltetrahydrofuran (50 mL), and 25 wt % aq. NaCl (100 mL), and the phases were partitioned. The organic phase was washed with 25 wt % aq. NaCl (50 mL), dried over MgSO$_4$, filtered, and concentrated in vacuo to approximately 20 mL. Heptane (30 mL) and additional 2-methyltetrahydrofuran were added in order to induce crystallization. The slurry was concentrated further, and additional heptane (40 mL) was slowly added and the slurry was filtered, washing with 2-methyltetrahydrofuran:heptane (1:4, 20 mL). The solids were suspended in MeOH (46 mL) for 3 h, filtered, and the wet solid was washed with additional MeOH (18 mL). The solid was dried at 45° C. in a vacuum oven for 16 h to provide the title compound (3.08 g, 51% 2-step yield).

Example 37E 4,4'-((2S,5S)-1-(4-tert-butylphenyl)pyrrolidine-2,5-diyl)dianiline

To a 160 ml Parr stirrer hydrogenation vessel was added the product from Example 37D (2 g, 4.49 mmol), followed by 60 ml of THF, and Raney Nickel Grace 2800 (1 g, 50 wt % (dry basis)) under a stream of nitrogen. The reactor was assembled and purged with nitrogen (8×20 psig) followed by purging with hydrogen (8×30 psig). The reactor was then pressurized to 30 psig with hydrogen and agitation (700 rpm) began and continued for a total of 16 h at room temperature. The slurry was filtered by vacuum filtration using a GF/F Whatman glass fiber filter. Evaporation of the filtrate to afford a slurry followed by the addition heptane and filtration gave the crude title compound, which was dried and used directly in the next step.

Example 37F dimethyl (2S,2'S)-1,1'-((2S,2'S)-2,2'-(4,4'-((2S,5S)-1-(4-tert-butylphenyl)pyrrolidine-2,5-diyl)bis(4,1-phenylene)bis(azanediyl)bis(oxomethylene))bis(pyrrolidine-2,1-diyl))bis(3-methyl-1-oxobutane-2,1-diyl)dicarbamate To a solution of the product from Example 37E (1.64 g, 4.25 mmol) in DMF (20 ml), the product from Example 37B (2.89 g, 10.63 mmol), and HATU (4.04 g, 10.63 mmol) in DMF (150 mL) was added triethylamine (1.07 g, 10.63 mmol), and the solution was stirred at room temperature for 90 min. To the reaction mixture was poured 20 mL of water, and the white precipitate obtained was filtered, and the solid was washed with water (3×5 mL). The solid was blow dried for 1 h. The crude material was loaded on a silica gel column and eluted with a gradient starting with ethyl acetate/heptane (3/7), and ending with pure ethyl acetate. The desired fractions were combined and solvent distilled off to give a very light yellow solid, which was dried at 45° C. in a vacuum oven with nitrogen purge for 15 h to give the title compound (2.3 g, 61% yield). $^1$H NMR (400 MHz, DMSO-D6) δ ppm 0.88 (d, J=6.61 Hz, 6H) 0.93 (d, J=6.72 Hz, 6H) 1.11 (s, 9H) 1.63 (d, J=5.42 Hz, 2H) 1.80-2.04 (m, 8H) 2.09-2.19 (m, 2H) 2.44-2.47 (m, 2H) 3.52 (s, 6H) 3.59-3.66 (m, 2H) 3.77-3.84 (m, 2H) 4.02 (t, J=8.40 Hz, 2H) 4.42 (dd, J=7.86, 4.83 Hz, 2H) 5.14 (d, J=6.18 Hz, 2H) 6.17 (d, J=8.67 Hz, 2H) 6.94 (d, J=8.78 Hz, 2H) 7.13 (d, J=8.46 Hz, 4H) 7.31 (d, J=8.35 Hz, 2H) 7.50 (d, J=8.35 Hz, 4H) 9.98 (s, 2H).

Alternately, the product from example 37E (11.7 g, 85 wt %, 25.8 mmol) and the product from example 37B (15.45 g, 56.7 mmol) are suspended in EtOAc (117 mL), diisopropylethylamine (18.67 g, 144 mmol) is added and the solution is cooled to 0° C. In a separate flask, 1-propanephosphonic acid cyclic anhydride (T3P®) (46.0 g, 50 wt % in EtOAc, 72.2 mmol) was dissolved in EtOAc (58.5 mL), and charged to an addition funnel. The T$_3$P solution is added to the reaction mixture drop-wise over 3-4 h and stirred until the reaction is complete. The reaction is warmed to room temperature, and washed with 1M HCl/7.5 wt % NaCl (100 mL), then washed with 5% NaHCO$_3$ (100 mL), then washed with 5% NaCl solution (100 mL). The solution was concentrated to approximately 60 mL, EtOH (300 mL) was added, and the solution was concentrated to 84 g solution.

A portion of the EtOH solution of product (29 g) was heated to 40° C., and added 134 g 40 w % EtOH in H$_2$O. A slurry of seeds in 58 wt/wt % EtOH/H$_2$O was added, allowed to stir at 35-40° C. (e.g, at 35 or 40° C.) for several hours, then cooled to 0° C. The slurry was then filtered, and washed with 58 wt/wt % EtOH/H$_2$O. The product was dried at 40-60° C. (e.g., 40° C.) under vacuum, and then rehydrated by placing a tray of water in the vacuum oven (or in a tray dryer using 40° C. and a humidified atmosphere) to give the title compound in a hydrate crystalline form (Hydrate B).

The seeds described above was a EtOH—H$_2$O solvate of the title compound and was originally made according to the following procedure. A solution was first prepared by slurrying the amorphous, solid title compound in 37 weight % EtOH in heptane at room temperature. The saturated solution (with respect to the amorphous solid) was then filtered over to a new vial to give a clear solution and seeded with partially crystalline solid obtained from the same solvent system. Crystallization took place within a few hours to produce the "Anhydrate A" form of the title compound. Then a solution of 60 w % EtOH in H$_2$O at 5° C. was prepared using the amorphous title compound. To this clear solution was added seeds of mainly Anhydrate A and desolvated EtOH solvate. Conversion to the EtOH—H₂O solvate took place within 2 days to produce the original seeds, which can be used to make additional seeds.

The title compound showed an $EC_{50}$ value of less than about 0.1 nM in HCV 1b-Con1 replicon assays in the presence of 5% FBS.

Example 38

Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate

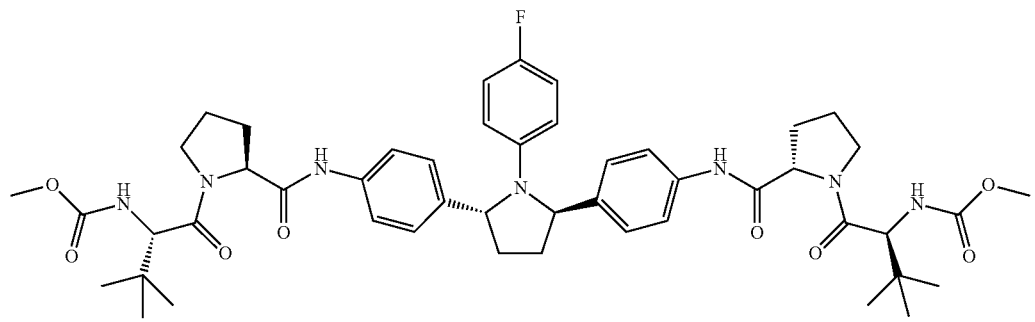

Example 38A (1S,4S)-1,4-bis(4-nitrophenyl)butane-1,4-diyl dimethanesulfonate The title compound was prepared using the methods from Example 37C, substituting the product from Example 33 for the product from Example 32.

Example 38B (2R,5R)-1-(4-fluorophenyl)-2,5-bis(4-nitrophenyl)pyrrolidine

The title compound was prepared using the methods from Example 37D, substituting 4-fluoroaniline for 4-tert-butylaniline.

Example 38C 4,4'-((2R,5R)-1-(4-fluorophenyl)pyrrolidine-2,5-diyl)dianiline

To a solution of the product from Example 38B (2.34 g, 5.74 mmol) in 1:1 ethanol:THF (60 ml) in a 250 mL stainless steel pressure bottle was added $PtO_2$ (0.47 g, 2.06 mmol) and the resulting mixture was placed under $H_2$ pressure (30 psi) and stirred at rt. for 90 min. The mixture was filtered through a nylon membrane and the filtrate was concentrated in vacuo. The crude product was purified by column chromatography on silica gel using a solvent gradient of 0-65% ethyl acetate in hexanes to give the title compound as a solid (0.736 g, 37%).

Example 38D (2S,2'S)-tert-butyl 2,2'-(4,4'-((2R,5R)-1-(4-fluorophenyl)pyrrolidine-2,5-diyl)bis(4,1-phenylene))bis(azanediyl)bis(oxomethylene)dipyrrolidine-1-carboxylate To a solution of the product from Example 38C (3.54 g, 10.19 mmol), (S)-1-(tert-butoxycarbonyl)pyrrolidine-2-carboxylic acid (5.48 g, 25.5 mmol), and HATU (9.69 g, 25.5 mmol) in anhydrous NMP (50 mL) was added N,N-diisopropylethylamine (5.29 ml, 30.6 mmol), and reaction mixture was stirred at room temperature for 30-45 minutes. The reaction mixture diluted with water (500 mL). The precipitated product was filtered and washed with water (3×100 mL), sodium bicarbonate solution (50 mL), and water (50 mL). The product dried at 40° C. for 15 h. This material (8.5 g) was passed through a pad of silica gel and eluted with ethyl acetate to afford the white solid product (7.9 g, 99%).

Example 38E (2S,2'S)—N,N'-(4,4'-((2R,5R)-1-(4-fluorophenyl)pyrrolidine-2,5-diyl)bis(4,1-phenylene))dipyrrolidine-2-carboxamide To a solution of the product from Example 38D (7.9 g, 10.65 mmol) in dichloromethane (50 mL), was added 5M HCl solution in isopropyl alcohol (50 mL) and the reaction mixture was stirred at room temperature for 16 h. The solvent was evaporated by rotavap under vacuum and crude material taken in dichloromethane containing 20% methanol (200 mL). The solution was washed with 5% ammonium hydroxide solution (90 mL), brine (50 mL) and dried over $MgSO_4$. The solution was filtered and concentrated to give 6.5 g of crude product. This material was recrystallized from ethyl acetate/heptane (8/2) to give the title compound (5.0 g, 87% yield).

Example 38F

Dimethyl (2S,2'S)-1,1'-((2S,2'S)-2,2'-(4,4'-((2R,5R)-1-(4-fluorophenyl)pyrrolidine-2,5-diyl)bis(4,1-phenylene))bis(azanediyl)bis(oxomethylene)bis(pyrrolidine-2,1-diyl))bis(3,3-dimethyl-1-oxobutane-2,1-diyl)dicarbamate To a solution of the product from Example 38E (4.14 g, 7.64 mmol), (S)-2-methoxycarbonylamino-3,3-dimethyl-butyric acid (3.62 g, 19.11 mmol), and EDAC (3.66 g, 19.11 mmol) in anhydrous DMF (80 mL) was added N,N-diisopropylethylamine (2.96 g, 22.93 mmol) and the solution was stirred at room temperature for 4 h. The reaction mixture poured into 400 mL of water, and the white precipitate obtained was filtered and washed with water (3×50 mL), sodium bicarbonate (50 mL), water (50 ML), and dried at 45° C. in a vacuum oven with nitrogen purge for 15 h to give 7.0 g of the crude product. The crude material was loaded on silica gel column (150 g silica) and eluted with a gradient starting with ethyl acetate/heptane (7/3), and ending with ethyl acetate. Desired fractions were combined and solvent distilled off to give very light yellow oil, which was triturated MTBE/heptane (1:9) for 1 h. The white solid thus obtained was filtered and dried in a vacuum oven with nitrogen purge to afford 6.1 g of product. The solid 5.5 g was dissolved in 16 mL of methanol and this solution was added into water (220 mL) in a 500 mL flask. The slurry was stirred for 30 minutes, and the solid was collected by filtration, dried at 45° C. with nitrogen purge for 15 h to give the title compound (5.4 g). $^1$H NMR (400 MHz, DMSO-D6) δ ppm 0.96 (s, 18H) 1.64 (d, J=5.53 Hz, 2H) 1.78-1.93 (m, 6H) 1.94-2.06 (m, 2H) 2.09-2.21 (m, 2H) 3.54 (s, 6H) 3.59-3.69 (m, 2H) 3.72-3.83 (m, 2H) 4.20 (d, J=8.89 Hz, 2H) 4.43 (dd, J=7.92, 5.42 Hz, 2H) 5.16 (d, J=6.29 Hz, 2H) 6.20 (dd, J=9.16, 4.39 Hz, 2H) 6.77 (t, J=8.95 Hz, 2H) 7.12 (d, J=8.57 Hz, 4H) 7.50 (d, J=8.57 Hz, 4H) 9.99 (s, 2H). The title compound showed an $EC_{50}$ value of less than about 0.1 nM in HCV 1b-Con1 replicon assays in the presence of 5% FBS.

Example 39

N-(methoxycarbonyl)-L-valyl-N-(4-{(2S,5S)-1-(4-fluorophenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

and

N-(methoxycarbonyl)-L-valyl-N-(4-{(2R,5R)-1-(4-fluorophenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

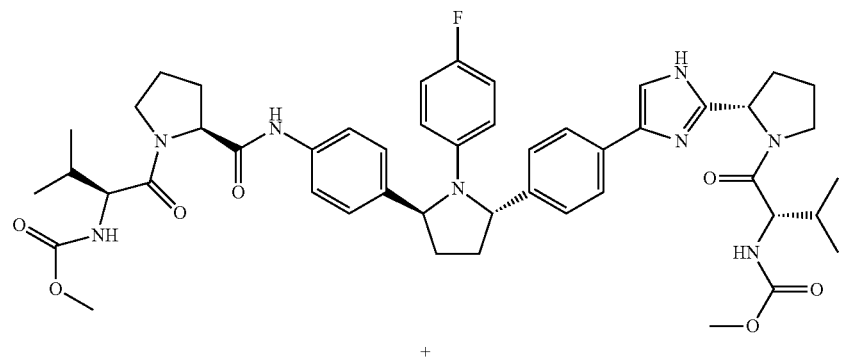

+

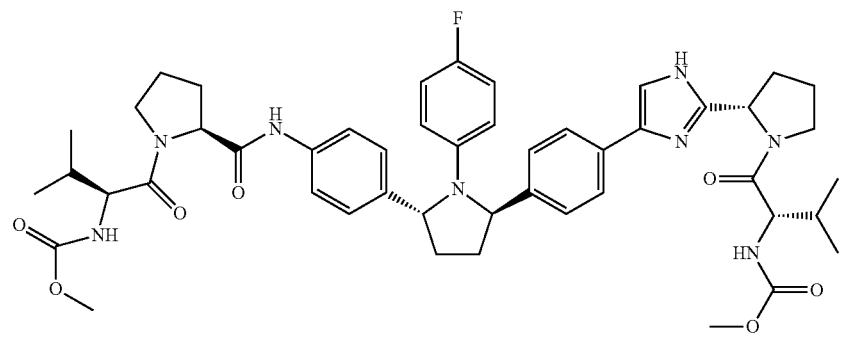

Example 39A 1-(4-bromophenyl)-4-(4-nitrophenyl)butane-1,4-dione

Added benzene (108 mL) to anhydrous zinc(II) chloride (19.62 g, 144 mmol), followed by the addition of diethylamine (11.16 mL, 108 mmol) and 2-methylpropan-2-ol (10.32 mL, 108 mmol) and stirred at room temperature for 2 h. Added 2-bromo-1-(4-bromophenyl)ethanone (20 g, 72.0 mmol) and 1-(4-nitrophenyl)ethanone (17.83 g, 108 mmol) together and stirred mixture for 18 h. Added 5% aq. sulfuric acid (50 mL) and stirred vigorously, then the product was collected by filtration, rinsed with benzene, water, methanol, dichloromethane and dried under vacuum to provide the product (15.0 g, 58% yield, colorless powder).

Example 39B 1-(4-bromophenyl)-4-(4-nitrophenyl)butane-1,4-diol

Dissolved the product from Example 39A (3.64 g, 10.05 mmol) in ethanol (67 mL) and added sodium borohydride (0.837 g, 22.11 mmol) portionwise. After stirring for 1 h at room temperature, the mixture was filtered through celite and washed with methanol and ethyl acetate and the filtrate concentrated to a solid. The solid was dissolved in ethyl acetate (200 mL) and extracted with 1N aq. HCl (200 mL), then brine and the organic layer dried and concentrated to a colorless oil (3.68 g, 100%) that was used directly in the next reaction.

Example 39C 1-(4-bromophenyl)-4-(4-nitrophenyl)butane-1,4-diyl dimethanesulfonate Dissolved the product from Example 39B (3.68 g, 10.05 mmol) in dichloromethane (167 mL) and cooled the solution in an ice bath followed by the addition of triethylamine (4.20 mL, 30.1 mmol) and methanesulfonyl chloride (1.96 mL, 25.1 mmol) dropwise. After stirring for 15 min, the solution was concentrated to a solid (5.25 g, 100%) that was used directly in the next reaction.

Example 39D 2-(4-bromophenyl)-1-(4-fluorophenyl)-5-(4-nitrophenyl)pyrrolidine Dissolved the product from Example 39C (5.25 g, 10.05 mmol) in DMF (31 mL) and then added 4-fluoroaniline (9.65 mL, 101 mmol) and heated solution at 50° C. for 18 h. Solution was cooled to room temperature and 1N aq. HCl added (100 mL) then extracted with ethyl acetate (2×200 mL), then combined organic extracts washed with brine, dried and concentrated to an amber oil to which methanol (10 mL) was added and after 3 h a yellow solid (1.05 g, 24%) resulted as the title compound as a 1/1 mixture of trans pyrrolidine isomers.

Example 39E 1-(4-fluorophenyl)-2-(4-nitrophenyl)-5-(4-(4,4,5,5-tetramethyl-1,3,2-dioxaborolan-2-yl)phenyl)pyrrolidine Dissolved the product from Example 39D (1.05 g, 2.38 mmol), 4,4,4',4',5,5,5',5'-octamethyl-2,2'-bi(1,3,2-dioxaborolane) (0.725 g, 2.86 mmol), [1,1'-bis(diphenylphosphino)ferrocene]dichloropalladium(II) (0.194 g, 0.238 mmol), and potassium acetate (0.35 g, 3.57 mmol) in dioxane (20 mL) and then bubbled nitrogen gas through the solution for 10 min, then heated at 100° C. for 1.5 h. Solution was cooled to room temperature then filtered through celite and washed with ethyl acetate (20 mL). The filtrate was dried, concentrated and the residue purified by column chromatography on silica gel, eluting with a solvent gradient of 10-50% ethyl acetate in hexane to give the title compound (1.09 g, 94%) as a yellow solid and a 1/1 mixture of trans stereoisomers.

Example 39F (2S)-tert-butyl 2-(4-(4-(1-(4-fluorophenyl)-5-(4-nitrophenyl)pyrrolidin-2-yl)phenyl)-1H-imidazol-2-yl)pyrrolidine-1-carboxylate Dissolved the product from Example 39E (1.05 g, 2.15 mmol), the product from Example 26D (0.748 g, 2.365 mmol), [1,1'-bis(diphenylphosphino)ferrocene]dichloropalladium(II) (0.176 g, 0.215 mmol) in a mixture of toluene (10 mL), ethanol (10 mL) and a 1N aq. sodium bicarbonate solution (2.58 mL, 2.58 mmol) and bubbled nitrogen gas through the solution for 10 min, then heated at 90° C. for 3 h. Solution was cooled to room temperature and water (20 mL) added then extracted with dichloromethane (50 mL), then dried, concentrated and the residue purified by column chromatography on silica gel, eluting with a solvent gradient of 0-100% ethyl acetate in hexane to give the title compound (0.28 g, 72%) as a yellow solid and a 1/1 mixture of trans stereoisomers.

Example 39G (2S)-tert-butyl 2-(4-(4-(5-(4-aminophenyl)-1-(4-fluorophenyl)pyrrolidin-2-yl)phenyl)-1H-imidazol-2-yl)pyrrolidine-1-carboxylate Dissolved the product from Example 39F (300 mg, 0.502 mmol) in ethanol (5 mL) and THF (5 mL) then added platinum(IV) oxide (22.8 mg, 0.1 mmol) and a hydrogen balloon and stirred the solution at room temperature for 2.5 h. Solution was filtered through celite and washed with methanol (10 mL), then concentrated to give the title compound (285 mg, 100%) as a colorless semi-solid and a 1/1 mixture of stereoisomers.

Example 39H (2S)-tert-butyl 2-(4-(5-(4-(2-((S)-1-(tert-butoxycarbonyl)pyrrolidin-2-yl)-1H-imidazol-4-yl)phenyl)-1-(4-fluorophenyl)pyrrolidin-2-yl)phenylcarbamoyl)pyrrolidine-1-carboxylate Dissolved the product from Example 39G (285 mg, 0.502 mmol), (S)-1-(tert-butoxycarbonyl)pyrrolidine-2-carboxylic acid (162 mg, 0.753 mmol), HATU (305 mg, 0.803 mmol) and Hunig's base (0.263 mL, 1.506 mmol) in DMSO (5 mL) and stirred at room temperature for 1 h. Dichloromethane (50 mL) was added followed by extraction with water (2×50 mL), the organic extract dried, concentrated and the residue dissolved in methanol (10 mL) followed by the addition of potassium carbonate (400 mg, 2.89 mmol) and stirred the bright yellow solution at room temperature for 30 min. The solution was then filtered and the filtrate concentrated to an oil, which was dissolved in a 95/5 dichloromethane/methanol mixture (50 mL) and extracted with water (20 mL). The organic extract was dried and concentrated to give the title product (350 mg, 91%) as a light yellow solid and a 1/1 mixture of stereoisomers.

Example 39I (2S)—N-(4-(1-(4-fluorophenyl)-5-(4-(2-((S)-pyrrolidin-2-yl)-1H-imidazol-4-yl)phenyl)pyrrolidin-2-yl)phenyl)pyrrolidine-2-carboxamide hydrochloride salt Dissolved the product from Example 39H (350 mg, 0.458 mmol) in 4M hydrochloric acid in dioxane solution (6 mL) and stirred the solution at room temperature for 30 min then concentrated the mixture under high vacuum to a solid (approx. 310 mg) as a hydrochloride salt that was used directly in the next reaction.

Example 39J

N-(methoxycarbonyl)-L-valyl-N-(4-{(2S,5S)-1-(4-fluorophenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

and

N-(methoxycarbonyl)-L-valyl-N-(4-{(2R,5R)-1-(4-fluorophenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

To a mixture of the product from Example 39I (300 mg, 0.45 mmol), (S)-2-(methoxycarbonylamino)-3-methylbutanoic acid (173 mg, 0.99 mmol), and HATU (428 mg, 1.125 mmol) in DMSO (5 ml) was added Hunig's base (0.786 mL, 4.5 mmol), and the reaction was stirred at room temperature for 1 h. Dichloromethane (50 mL) was added followed by extraction with water (2×25 mL), the organic extract dried, concentrated and the residue dissolved in methanol (15 mL) followed by the addition of potassium carbonate (300 mg, 2.17 mmol) and stirred at room temperature for 20 min. The solution was then filtered and the filtrate concentrated to an oil, which was dissolved in a 95/5 dichloromethane/methanol mixture (50 mL) and extracted with water (20 mL). The organic extract was dried and concentrated, and the residue purified by column chromatography on silica gel, eluting with a solvent gradient of 0-25% methanol in dichloromethane to give the title compounds (0.13 g, 33%) as a colorless solid and as a 1/1 mixture of diastereomers. $^1$H NMR (400 MHz, DMSO-D6) δ ppm 11.64 (s, 1H), 9.94 (s, 1H), 7.57 (d, J=8.1 Hz, 2H), 7.47 (m, 3H), 7.33 (d, J=1.7 Hz, 1H), 7.24 (m, 2H), 7.08 (m, 4H), 6.72 (m, 2H), 6.17 (m, 2H), 5.15 (m, 2H), 5.01 (m, 1H), 4.38 (m, 1H), 4.0 (m, 2H), 3.75 (m, 2H), 3.56 (m, 1H), 3.48 (s, 3H), 3.47 (s, 3H), 2.06 (m, 2H), 1.87 (m, 8H), 1.63 (m, 2H), 0.82 (m, 12H). The title compound showed an $EC_{50}$ value of less than about 0.1 nM in HCV 1b-Con1 replicon assays in the presence of 5% FBS.

Example 40

N-(methoxycarbonyl)-L-valyl-N-(4-{(2S,5S)-1-(4-tert-butylphenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

and

N-(methoxycarbonyl)-L-valyl-N-(4-{(2R,5R)-1-(4-tert-butylphenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

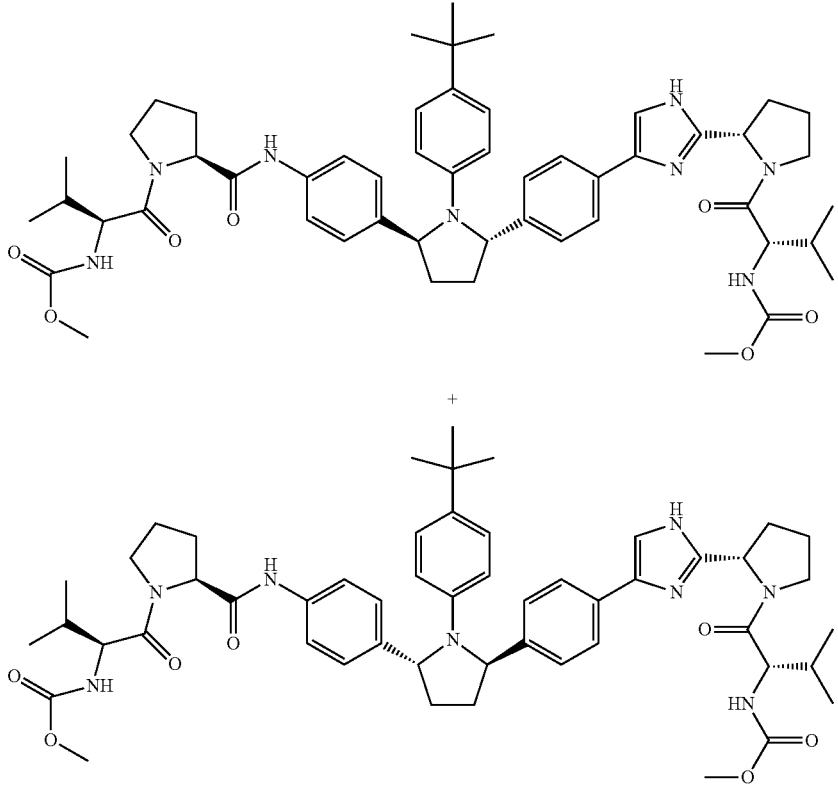

Example 40A 2-(4-bromophenyl)-1-(4-tert-butylphenyl)-5-(4-nitrophenyl)pyrrolidine The product from Example 39C (10.86 g, 20.79 mmol), DMF (65 mL) and 4-tert-butylaniline (26.5 mL, 166 mmol) was reacted according to the procedure in Example 39D to provide the title compound (5.0 g, 50%, yellow solid) as a mixture of cis and trans pyrrolidine stereoisomers.

Example 40B 1-(4-tert-butylphenyl)-2-(4-nitrophenyl)-5-(4-(4,4,5,5-tetramethyl-1,3,2-dioxaborolan-2-yl)phenyl)pyrrolidine The product from Example 40A (2.0 g, 4.17 mmol), 4,4,4',4',5,5,5',5'-octamethyl-2,2'-bi(1,3,2-dioxaborolane) (1.27 g, 5.01 mmol), [1,1'-bis(diphenylphosphino)ferrocene]dichloropalladium(II) (0.681 g, 0.834 mmol), and potassium acetate (0.614 g, 6.26 mmol) in dioxane (35 mL) was reacted according to the procedure in Example 39E to provide the title compound (1.5 g, 68%, yellow solid) as a mixture of stereoisomers.

Example 40C (2S)-tert-butyl 2-(4-(4-(1-(4-tert-butylphenyl)-5-(4-nitrophenyl)pyrrolidin-2-yl)phenyl)-1H-imidazol-2-yl)pyrrolidine-1-carboxylate The product from Example 40B (0.7 g, 1.33 mmol), (S)-tert-butyl 2-(4-bromo-1H-imidazol-2-yl)pyrrolidine-1-carboxylate (0.462 g, 1.463 mmol), [1,1'-bis(diphenylphosphino)ferrocene]dichloropalladium(II) (0.109 g, 0.133 mmol) in a mixture of toluene (6 mL), ethanol (6 mL) and a 1N aq. sodium bicarbonate solution (1.6 mL, 1.6 mmol) was reacted according to the procedure in Example 39F to provide the title compound (0.66 g, 78%, yellow solid) as a mixture of stereoisomers.

Example 40D (2S)-tert-butyl 2-(4-(4-(5-(4-aminophenyl)-1-(4-tert-butylphenyl)pyrrolidin-2-yl)phenyl)-1H-imidazol-2-yl)pyrrolidine-1-carboxylate The product from example 40C (1.37 g, 2.153 mmol), in ethanol (10 mL) and THF (10 mL) then added platinum(IV) oxide (196 mg, 0.862 mmol) and a hydrogen balloon and stirred the solution at room temperature for 48 h. The reaction was then treated according to the procedure in Example 39G to provide the title compound (1.3 g, 100%) as a mixture of stereoisomers.

Example 40E (2R)-tert-butyl 2-(4-(5-(4-(2-((S)-1-(tert-butoxycarbonyl)pyrrolidin-2-yl)-1H-imidazol-4-yl)phenyl)-1-(4-tert-butylphenyl)pyrrolidin-2-yl)phenylcarbamoyl)pyrrolidine-1-carboxylate The product from Example 40D (1.3 g, 2.146 mmol), (S)-1-(tert-butoxycarbonyl)pyrrolidine-2-carboxylic acid (1.386 g, 6.44 mmol), HATU (1.305 g, 3.43 mmol) and Hunig's base (1.124 mL, 6.44 mmol) in DMSO (20 mL) was reacted according to the procedure in Example 39H to provide the title compound (1.01 g, 59%) as a mixture of stereoisomers.

Example 40F (2R)—N-(4-(1-(4-tert-butylphenyl)-5-(4-(2-((S)-pyrrolidin-2-yl)-1H-imidazol-4-yl)phenyl)pyrrolidin-2-yl)phenyl)pyrrolidine-2-carboxamide hydrochloride salt The product from Example 40E (610 mg, 0.76 mmol), in 2M hydrochloric acid in dioxane solution (10 mL) was reacted according to the procedure in Example 39I to provide the title compound (495 mg) as a hydrochloride salt and a mixture of stereoisomers.

Example 40G

N-(methoxycarbonyl)-L-valyl-N-(4-{(2S,5S)-1-(4-tert-butylphenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

and

N-(methoxycarbonyl)-L-valyl-N-(4-{(2R,5R)-1-(4-tert-butylphenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

The product from Example 40F (372 mg, 0.617 mmol), (S)-2-(methoxycarbonylamino)-3-methylbutanoic acid (324 mg, 1.851 mmol), HATU (821 mg, 2.16 mmol) in DMSO (6 ml) and Hunig's base (1.078 ml, 6.17 mmol) was reacted according to the procedure in Example 39J then the reaction was diluted with acetonitrile and water (0.1% TFA) and purified by reversed phase chromatography (C18), eluting with 10-100% acetonitrile in water (0.1% TFA) to give the title compounds (68 mg, 12% yield, white solid) as a 1/1 mixture of diastereomers. $^1$H NMR (free base) (400 MHz, DMSO-D6) δ ppm 0.80-0.96 (m, 12H), 1.10 (s, 9H), 1.65 (d, J=6.07 Hz, 2H), 1.82-2.04 (m, 8H), 2.07-2.20 (m, 3H), 3.52 (s, 3H), 3.53 (s, 3H), 3.58-3.66 (m, 2H), 3.73-3.85 (m, 3H), 3.99-4.08 (m, 2H), 4.43 (dd, J=7.97, 4.93 Hz, 1H), 5.06 (dd, J=6.99, 2.87 Hz, 1H), 5.17 (d, J=6.40 Hz, 2H), 6.20 (d, J=8.89 Hz, 2H), 6.93 (d, J=8.89 Hz, 2H), 7.14 (dd, J=8.51, 2.87 Hz, 4H), 7.30 (t, J=9.11 Hz, 2H), 7.37 (d, J=1.84 Hz, 1H), 7.50 (d, J=8.02 Hz, 2H), 7.61 (d, J=8.13 Hz, 2H), 9.98 (s, 1H), 11.68 (s, 1H). The title compound showed an $EC_{50}$ value of less than about 0.1 nM in HCV 1b-Con1 replicon assays in the presence of 5% FBS.

Example 41

N-(methoxycarbonyl)-L-valyl-N-(4-{(2S,5R)-1-(4-tert-butylphenyl)-5-[4-(2-{(2S)-1-[N-(methoxycarbonyl)-L-valyl]pyrrolidin-2-yl}-1H-imidazol-4-yl)phenyl]pyrrolidin-2-yl}phenyl)-L-prolinamide (ACD v12)

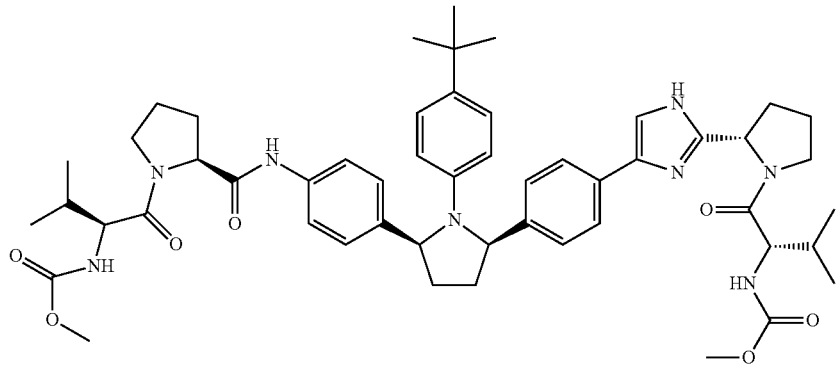 [SMILES: COC(=O)N[C@H](C(=O)N1CCC[C@H]1C(=O)Nc1ccc([C@@H]2CC[C@H](c3ccc(-c4c[nH]c([C@@H]5CCCN5C(=O)[C@@H](NC(=O)OC)C(C)C)n4)cc3)N2c2ccc(C(C)(C)C)cc2)cc1)C(C)C]

To the product from Example 40F (493 mg, 0.818 mmol), (S)-2-(methoxycarbonylamino)-3-methylbutanoic acid (430 mg, 2.454 mmol), HATU (1088 mg, 2.86 mmol) in DMSO (8.2 mL) and Hunig's base (1.5 mL, 8.59 mmol) was reacted according to the procedure in Example 39J then the residue was diluted with acetonitrile and water (0.1% TFA) and purified by reversed phase chromatography (C18), eluting with 10-100% acetonitrile in water (0.1% TFA) to give the title compound (80 mg, 11% yield, white solid). $^1$H NMR (free base) (400 MHz, DMSO-D6) δ ppm 0.89-1.04 (m, 12H), 1.20 (s, 9H), 1.86-2.12 (m, 10H), 2.15-2.27 (m, 3H), 2.43-2.49 (m, 2H), 3.60 (s, 3H), 3.61 (s, 3H), 3.66-3.74 (m, 1H), 3.81-3.93 (m, 2H), 4.06-4.15 (m, 2H), 4.52 (dd, J=7.86, 4.61 Hz, 1H), 4.74 (d, J=5.20 Hz, 2H), 5.14 (dd, J=6.99, 3.31 Hz, 1H), 6.40 (d, J=8.78 Hz, 2H), 7.06-7.11 (m, 2H), 7.32-7.41 (m, 2H), 7.47 (d, J=1.73 Hz, 1H), 7.51 (d, J=7.81 Hz, 4H), 7.65 (d, J=8.46 Hz, 2H), 7.77 (d, J=8.24 Hz, 2H), 10.10 (s, 1H), 11.76 (s, 1H). The title compound showed an EC$_{50}$ value of less than about 0.1 nM in HCV 1b-Con1 replicon assays in the presence of 5% FBS.

Example 42 dimethyl (2S,2'S)-1,1'-((2S,2'S)-2,2'-(4,4'-(4,4'-((2S,5S)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate and dimethyl (2S,2'S)-1,1'-((2S,2'S)-2,2'-(4,4'-(4,4'-((2R,5R)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

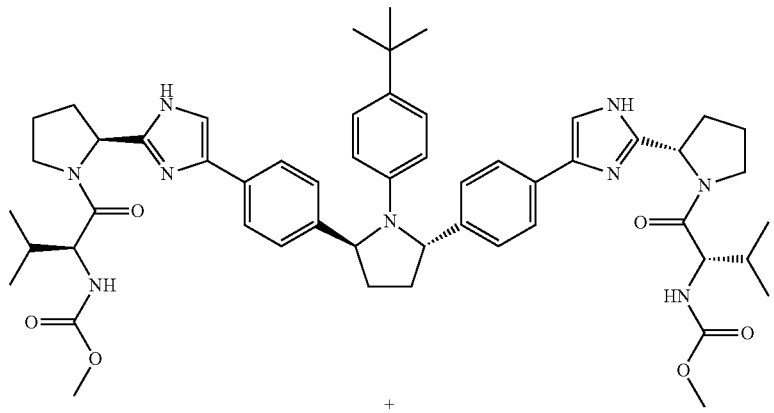

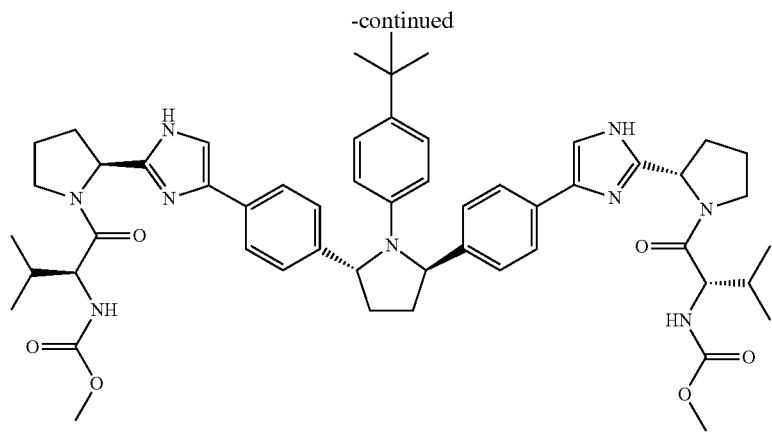

Example 42A

1,4-bis(4-bromophenyl)butane-1,4-diol

The product from Example 26E (3.42 g, 8.63 mmol) was subjected to the conditions described in Example 39B to provide the title product (3.45 g, 100% yield, colorless oil).

Example 42B

1,4-bis(4-bromophenyl)butane-1,4-diyl dimethanesulfonate

The product from Example 42A (3.45 g, 8.63 mmol) was subjected to the conditions described in Example 39C to provide the title product (4.8 g, 100%).

Example 42C

2,5-bis(4-bromophenyl)-1-(4-tert-butylphenyl)pyrrolidine

The product from Example 42B (5.2 g, 9.35 mmol) was subjected to the conditions described in Example 39D, substituting 4-tert-butylaniline (11.91 mL, 74.8 mmol) for 4-fluoroaniline to provide the title product (3.89 g, 81%) as a mixture of isomers.

Example 42D

1-(4-tert-butylphenyl)-2,5-bis(4-(4,4,5,5-tetramethyl-1,3,2-dioxaborolan-2-yl)phenyl)pyrrolidine Dissolved the product from Example 42C (3.88 g, 7.56 mmol), 4,4,4',4',5,5,5',5'-octamethyl-2,2'-bi(1,3,2-dioxaborolane) (6.72 g, 26.5 mmol), [1,1'-bis(diphenylphosphino)ferrocene]dichloropalladium(II) (0.617 g, 0.756 mmol), and potassium acetate (3.34 g, 34.0 mmol) in dimethoxyethane (70 mL) and bubbled nitrogen gas through the solution for 10 min, then heated at 85° C. for 1 h. Solution was cooled to room temperature then filtered through celite and washed with ethyl acetate (20 mL), the filtrate dried, then concentrated and the residue purified by column chromatography on silica gel, eluting with a solvent gradient of 0-10% ethyl acetate in hexane followed by trituration of the resultant solid with diethyl ether to give the title compound (1.14 g, 25%) as a 1/1 mixture of trans stereoisomers.

Example 42E

(2S,2'S)-tert-butyl 2,2'-(4,4'-(4,4'-(1-(4-tert-butylphenyl)pyrrolidine-2,5-diyl)bis(4,1-phenylene))bis(1H-imidazole-4,2-diyl))dipyrrolidine-1-carboxylate Dissolved the products from Example 42D (0.915 g, 1.506 mmol), the product from Example 26D (1.429 g, 4.52 mmol), [1,1'-bis(diphenylphosphino)ferrocene]dichloropalladium (II) (0.123 g, 0.151 mmol) in a mixture of toluene (7 mL), ethanol (7 mL) and a 2N aq. sodium bicarbonate solution (2.64 mL, 5.28 mmol) and bubbled nitrogen gas through the solution for 10 min, then heated at 100° C. for 3 h. Solution was cooled to room temperature and water (20 mL) added then extracted with dichloromethane (50 mL), then dried, concentrated and the residue purified by column chromatography on silica gel, eluting with a solvent gradient of 0-80% ethyl acetate in hexane to give the title compound (0.93 g, 75%) as a 1/1 mixture of trans stereoisomers.

Example 42F

(S)-4,4'-(4,4'-(1-(4-tert-butylphenyl)pyrrolidine-2,5-diyl)bis(4,1-phenylene))bis(2-((S)-pyrrolidin-2-yl)-1H-imidazole) hydrochloride salt To the product from Example 42E (1.11 g, 1.344 mmol), in 4M hydrochloric acid in dioxane solution (5 mL) was reacted according to the procedure in Example 39I to provide the title compound (1.12 g) as a hydrochloride salt and a mixture of stereoisomers.

Example 42G dimethyl (2S,2'S)-1,1'-((2S,2'S)-2,2'-(4,4'-(4,4'-((2S,5S)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate and dimethyl (2S,2'S)-1,1'-((2S,2'S)-2,2'-(4,4'-(4,4'-((2R,5R)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate To a mixture of the products from Example 42F (1.04 g, 1.662 mmol), (S)-2-(methoxycarbonylamino)-3-methylbutanoic acid (0.728 g, 4.15 mmol), and HATU (1.295 g, 3.41 mmol) in DMSO (20 mL) was added Hunig's base (2.322 mL, 13.29 mmol), and the reaction was stirred at room temperature for 1 h. Water (20 mL) was added to form a solid that was dissolved in dichloromethane and purified by column chromatography on silica gel, eluting with a solvent gradient of 0-5% methanol in dichloromethane to give a solid that was diluted with acetonitrile and water (0.1% TFA) and further purified by reversed phase chromatography (C18), eluting with 10-100% acetonitrile in water (0.1% TFA) to give the title compound (92 mg, 6% yield, white solid) as a 1/1 mixture of diastereomers. $^1$H NMR (free base) (400 MHz, DMSO-D6) δ ppm 0.78-0.92 (m, 12H), 1.09 (s, 9H), 1.63-1.74 (m, 2H), 1.85-2.00 (m, 6H), 2.05-2.16 (m, 2H), 3.44-3.50 (m, 4H), 3.52 (s, 6H), 3.70-3.82 (m, 4H), 4.02-4.09 (m, 2H), 5.04 (dd, J=6.67, 3.20 Hz, 2H), 5.19 (t, J=6.18 Hz, 2H), 6.21 (d, J=8.57 Hz, 2H), 6.91 (dd, J=7.16, 1.63 Hz, 2H), 7.14 (dd, J=8.19, 2.22 Hz, 4H), 7.20-7.30 (m, 2H), 7.36 (d, J=1.19 Hz, 2H), 7.61 (d, J=8.13 Hz, 4H), 11.67 (d, J=4.01 Hz, 2H). The title compound showed an $EC_{50}$ value of less than about 0.1 nM in HCV 1b-Con1 replicon assays in the presence of 5% FBS.

Example 43 dimethyl (2S,2'S)-1,1'-((2S,2'S)-2,2'-(4,4'-(4,4'-((2R,5R)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

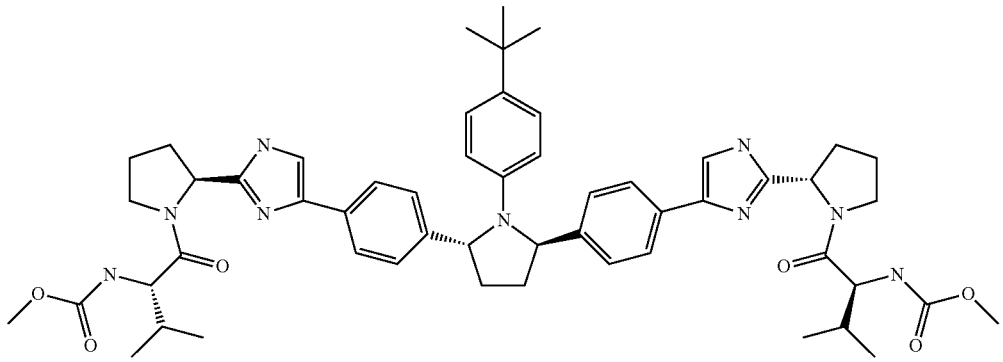

The product from Example 42G was purified by chiral chromatography on a Chirapak IB column eluting with a mixture of hexane/THF/MeOH (80/10/10). The title compound was the first of 2 diastereomers to elute. $^1$H NMR (400 MHz, DMSO-D6) δ ppm 0.78-0.92 (m, 12H), 1.09 (s, 9H), 1.63-1.74 (m, 2H), 1.85-2.00 (m, 6H), 2.05-2.16 (m, 2H), 3.44-3.50 (m, 4H), 3.52 (s, 6H), 3.70-3.82 (m, 4H), 4.02-4.09 (m, 2H), 5.04 (dd, J=6.67, 3.20 Hz, 2H), 5.19 (t, J=6.18 Hz, 2H), 6.21 (d, J=8.57 Hz, 2H), 6.91 (dd, J=7.16, 1.63 Hz, 2H), 7.14 (dd, J=8.19, 2.22 Hz, 4H), 7.20-7.30 (m, 2H), 7.36 (d, J=1.19 Hz, 2H), 7.61 (d, J=8.13 Hz, 4H), 11.67 (d, J=4.01 Hz, 2H). The title compound showed an $EC_{50}$ value of less than about 0.1 nM in HCV 1b-Con1 replicon assays in the presence of 5% FBS.

Example 44 dimethyl (2S,2'S)-1,1'-((2S,2'S)-2,2'-(4,4'-(4,4'-((2S,5S)-1-(4-tert-butylphenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

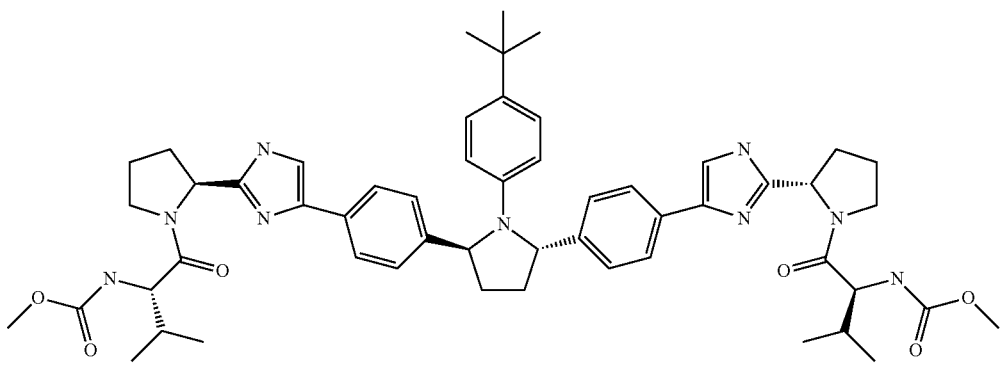

The product from Example 42G was purified by chiral chromatography on a Chirapak IB column eluting with a mixture of hexane/THF/MeOH (80/10/10). The title compound was the second of 2 diastereomers to elute. $^1$H NMR (400 MHz, DMSO-D6) δ ppm 0.78-0.92 (m, 12H), 1.09 (s, 9H), 1.63-1.74 (m, 2H), 1.85-2.00 (m, 6H), 2.05-2.16 (m, 2H), 3.44-3.50 (m, 4H), 3.52 (s, 6H), 3.70-3.82 (m, 4H), 4.02-4.09 (m, 2H), 5.04 (dd, J=6.67, 3.20 Hz, 2H), 5.19 (t, J=6.18 Hz, 2H), 6.21 (d, J=8.57 Hz, 2H), 6.91 (dd, J=7.16, 1.63 Hz, 2H), 7.14 (dd, J=8.19, 2.22 Hz, 4H), 7.20-7.30 (m, 2H), 7.36 (d, J=1.19 Hz, 2H), 7.61 (d, J=8.13 Hz, 4H), 11.67 (d, J=4.01 Hz, 2H). The title compound showed an $EC_{50}$ value of less than about 0.1 nM in HCV 1b-Con1 replicon assays in the presence of 5% FBS.

Example 45 dimethyl (2S,2'S)-1,1'-((2S,2'S)-2,2'-(4,4'-(4,4'-((2S,5S)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate and dimethyl (2S,2'S)-1,1'-((2S,2'S)-2,2'-(4,4'-(4,4'-((2R,5R)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

Example 45A 2,5-bis(4-bromophenyl)-1-(4-fluorophenyl)pyrrolidine

The product from Example 42B (5.2 g, 9.35 mmol) was subjected to the conditions described in Example 39D to provide the title product (6.41 g, 48%) as a mixture of cis and trans isomers.

Example 45B 1-(4-fluorophenyl)-2,5-bis(4-(4,4,5,5-tetramethyl-1,3,2-dioxaborolan-2-yl)phenyl)pyrrolidine The product from Example 45A (2.17 g, 4.57 mmol) was subjected to the conditions described in Example 42D and purified by column chromatography on silica gel, eluting with a solvent gradient of 0-15% ethyl acetate in hexane to give the title compound (1.65 g, 64%) as a mixture of cis and trans stereoisomers.

Example 45C (2S,2'S)-tert-butyl 2,2'-(4,4'-(4,4'-(1-(4-fluorophenyl)pyrrolidine-2,5-diyl)bis(4,1-phenylene))bis(1H-imidazole-4,2-diyl))dipyrrolidine-1-carboxylate The product from Example 45B (1.0 g, 1.756 mmol) was subjected to the conditions described in Example 42E to provide the title product (1.0 g, 72%) as a mixture of cis and trans isomers.

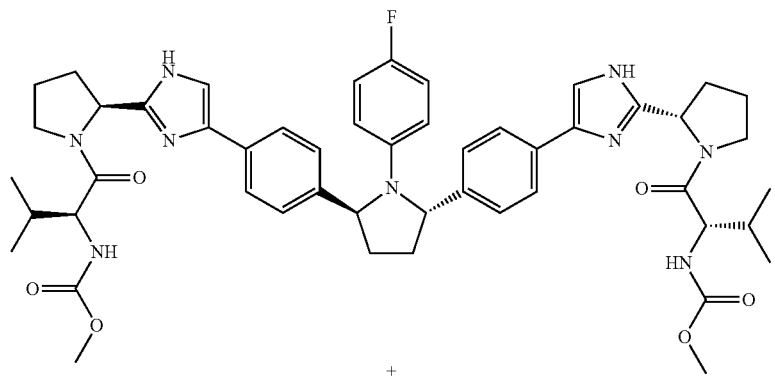

+

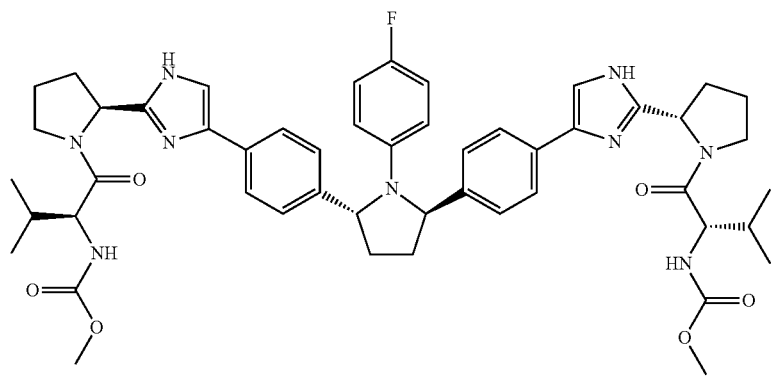

Example 45D (S)-4,4'-(4,4'-(1-(4-fluorophenyl)pyrrolidine-2,5-diyl)bis(4,1-phenylene))bis(2-((S)-pyrrolidin-2-yl)-1H-imidazole)

Dissolved the product from Example 45C (150 mg, 0.19 mmol) in dichloromethane (1 mL) and TFA (1 mL) and stirred the solution at room temperature for 1 h then concentrated the mixture under high vacuum to give a solid that was diluted with acetonitrile and water (0.1% TFA) and purified by reversed phase chromatography (C18), eluting with 10-100% acetonitrile in water (0.1% TFA) to give the title compound (62 mg, 55% yield) as a 1/1 mixture of trans diastereomers that eluted before the cis isomer.

Example 45E dimethyl (2S,2'S)-1,1'-((2S,2'S)-2,2'-(4,4'-(4,4'-((2S,5S)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate and dimethyl (2S,2'S)-1,1'-((2S,2'S)-2,2'-(4,4'-(4,4'-((2R,5R)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate To a mixture of the product from Example 45D (47 mg, 0.08 mmol), (S)-2-(methoxycarbonylamino)-3-methylbutanoic acid (29 mg, 0.168 mmol), and HATU (61 mg, 0.16 mmol) in DMSO (0.8 mL) was added Hunig's base (0.035 mL, 0.2 mmol) was reacted according to the procedure in Example 39J then the residue was diluted with acetonitrile and water (0.1% TFA) and purified by reversed phase chromatography (C18), eluting with 10-100% acetonitrile in water (0.1% TFA) to give the title compound (54 mg, 75% yield, white solid) as a 1/1 mixture of diastereomers. $^1$H NMR (free base) (400 MHz, DMSO-D6) δ ppm 11.62-12.13 (m, 2H), 7.59-7.71 (m, J=8.13 Hz, 3H), 7.46-7.57 (m, J=8.24 Hz, 1H), 7.38 (d, J=1.84 Hz, 2H), 7.10-7.32 (m, 6H), 6.72-6.83 (m, 2H), 6.19-6.31 (m, 2H), 5.17-5.28 (m, 2H), 5.02-5.11 (m, J=6.72 Hz, 2H), 4.05 (t, J=8.40 Hz, 2H), 3.71-3.85 (m, 4H), 3.53 (s, 6H), 2.05-2.21 (m, 4H), 1.94 (s, 6H), 1.64-1.78 (m, 2H), 0.77-0.95 (m, 12H). The title compound showed an $EC_{50}$ value of less than about 0.1 nM in HCV 1b-Con1 replicon assays in the presence of 5% FBS.

Example 46 dimethyl (2S,2'S)-1,1'-((2S,2'S)-2,2'-(4,4'-(4,4'-((2R,5R)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

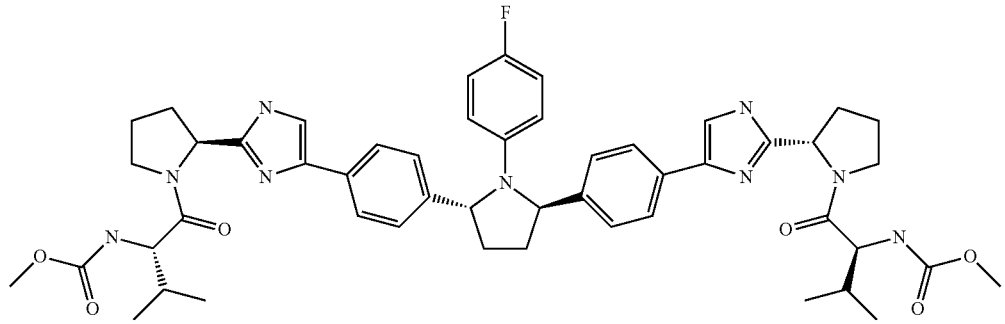

The product from Example 45E was purified by chiral chromatography on a Chirapak IB column eluting with a mixture of hexane/THF/MeOH (85/7.5/7.5). $^1$H NMR (400 MHz, DMSO-D6) δ ppm 11.62-12.13 (m, 2H), 7.59-7.71 (m, J=8.13 Hz, 3H), 7.46-7.57 (m, J=8.24 Hz, 1H), 7.38 (d, J=1.84 Hz, 2H), 7.10-7.32 (m, 6H), 6.72-6.83 (m, 2H), 6.19-6.31 (m, 2H), 5.17-5.28 (m, 2H), 5.02-5.11 (m, J=6.72 Hz, 2H), 4.05 (t, J=8.40 Hz, 2H), 3.71-3.85 (m, 4H), 3.53 (s, 6H), 2.05-2.21 (m, 4H), 1.94 (s, 6H), 1.64-1.78 (m, 2H), 0.77-0.95 (m, 12H). The title compound showed an $EC_{50}$ value of less than about 0.1 nM in HCV 1b-Con1 replicon assays in the presence of 5% FBS.

Example 47 dimethyl (2S,2'S)-1,1'-((2S,2'S)-2,2'-(4,4'-(4,4'-((2S,5S)-1-(4-fluorophenyl)pyrrolidine-2,5-diyl)bis(4,1-phenylene))bis(1H-imidazole-4,2-diyl))bis(pyrrolidine-2,1-diyl))bis(3-methyl-1-oxobutane-2,1-diyl) dicarbamate

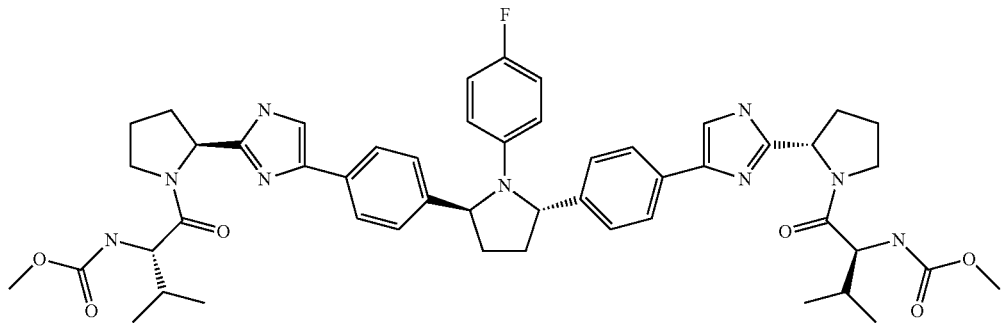

The product from Example 45E was purified by chiral chromatography on a Chirapak IB column eluting with a mixture of hexane/THF/MeOH (85/7.5/7.5). $^1$H NMR (400 MHz, DMSO-D6) δ ppm 11.62-12.13 (m, 2H), 7.59-7.71 (m, J=8.13 Hz, 3H), 7.46-7.57 (m, J=8.24 Hz, 1H), 7.38 (d, J=1.84 Hz, 2H), 7.10-7.32 (m, 6H), 6.72-6.83 (m, 2H), 6.19-6.31 (m, 2H), 5.17-5.28 (m, 2H), 5.02-5.11 (m, J=6.72 Hz, 2H), 4.05 (t, J=8.40 Hz, 2H), 3.71-3.85 (m, 4H), 3.53 (s, 6H), 2.05-2.21 (m, 4H), 1.94 (s, 6H), 1.64-1.78 (m, 2H), 0.77-0.95 (m, 12H). The title compound showed an $EC_{50}$ value of less than about 0.1 nM in HCV 1b-Con1 replicon assays in the presence of 5% FBS.

Example 48 dimethyl (2S,2'S)-1,1'-((2S,2'S)-2,2'-(4,4'-(4,4'-((2S,3R,4R,5S)-1-(4-tert-butylphenyl)-3,4-dimethoxypyrrolidine-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate

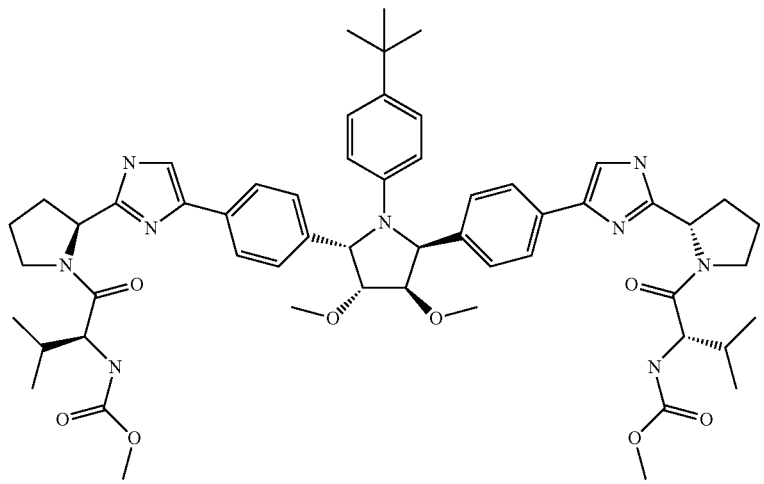 [SMILES: COC(=O)N[C@H](C(=O)N1CCC[C@H]1c1nc(-c2ccc([C@H]3[C@@H](OC)[C@H](OC)[C@H](c4ccc(-c5c[nH]c([C@@H]6CCCN6C(=O)[C@@H](NC(=O)OC)C(C)C)n5)cc4)N3c3ccc(C(C)(C)C)cc3)cc2)c[nH]1)C(C)C]

Example 48A (2S,3R,4R,5S)-2,5-bis(4-(benzyloxy)phenyl)-1-(4-tert-butylphenyl)pyrrolidine-3,4-diol To a solution of (1R,1'R)-1,1'-((4R,5R)-2,2-dimethyl-1,3-dioxolane-4,5-diyl)diethane-1,2-diol (200 mg, 0.90 mmol) in methanol (6 ml) and dichloromethane (3 ml) was added iodobenzene diacetate (696 mg, 2.16 mmol) and the solution was stirred at room temperature for 5 h. Solution was concentrated and to the residue was added 0.1 M $H_2SO_4$ (4 ml) and stirring was continued at room temperature for 18 h. The pH was adjusted to ~6 with solid $NaHCO_3$, and 4-tert-butylaniline (287 µl, 1.80 mmol) was added followed by 4-benzyloxyphenylboronic acid (369 mg, 1.62 mmol) and hexafluoroisopropyl alcohol (4 ml) and stirred at 60° C. for 2 h. Solvent was concentrated and the residue dissolved in ethyl acetate, washed with $H_2O$, 0.33M $K_3PO_4$, brine, dried ($Na_2SO_4$), filtered and concentrated to give crude product which was purified by chromatography on silica gel eluting with 0-20% ethyl acetate/dichloromethane to give title compound (249 mg, 46%).

Example 48B (2S,3R,4R,5S)-2,5-bis(4-(benzyloxy)phenyl)-1-(4-tert-butylphenyl)-3,4-dimethoxypyrrolidine To a solution of the product from Example 48A (200 mg, 0.33 mmol) in THF (2.1 ml) and DMF (0.7 ml) at 0° C. was added, in portions, sodium hydride, 60% in mineral oil (40.0 mg, 1.0 mmol) and stirring continued at 0° C. for 20 min. Iodomethane (0.046 ml, 0.734 mmol) was added and stirring continued at room temperature overnight. Diluted with ethyl acetate, washed with saturated NH₄Cl, H₂O, brine, dried (Na₂SO₄), filtered and concentrated to give crude product which was purified by chromatography on silica gel eluting with 0-20% ethyl acetate/dichloromethane to give title compound (170 mg, 80%).

Example 48C 4,4'-((2S,3R,4R,5S)-1-(4-tert-butylphenyl)-3,4-dimethoxypyrrolidine-2,5-diyl)diphenol To a solution of the product from Example 48B (168 mg, 0.268 mmol) in ethyl acetate (3 ml) was added 10% palladium on carbon (17 mg) and the flask was evacuated and back-filled with H₂ gas. The solution was stirred under a balloon of H₂ gas for 20 h, filtered through Celite, and washed with ethyl acetate and methanol. The filtrate was concentrated and the residue was azeotroped with ether to give title compound (120 mg, 100%) as a white solid.

Example 48D 4,4'-((2S,3R,4R,5S)-1-(4-tert-butylphenyl)-3,4-dimethoxypyrrolidine-2,5-diyl)bis(4,1-phenylene)bis(1,1,2,2,3,3,4,4,4-nonafluorobutane-1-sulfonate)

To a solution of the product from Example 48C (117 mg, 0.261 mmol) in DMF (1.3 ml) was added K₂CO₃ (81 mg, 0.588 mmol) and 1,1,2,2,3,3,4,4,4-nonafluorobutane-1-sulfonyl fluoride (0.101 ml, 0.575 mmol) and the solution was stirred at 100° C. for 1 h. The cooled solution was diluted with ethyl acetate, washed with H₂O, brine, dried (Na₂SO₄), filtered and concentrated to give an oil which was purified by chromatography on silica gel eluting with 0-20% ethyl acetate/hexane to give title compound (195 mg, 73.7% yield).

Example 48E (2S,3R,4R,5S)-1-(4-tert-butylphenyl)-3,4-dimethoxy-2,5-bis(4-(4,4,5,5-tetramethyl-1,3,2-dioxaborolan-2-yl)phenyl)pyrrolidine To a pressure tube was added the product from Example 48D (193 mg, 0.191 mmol), 4,4,4',4',5,5,5',5'-octamethyl-2,2'-bi(1,3,2-dioxaborolane) (102 mg, 0.401 mmol), dicyclohexyl(2',4',6'-triisopropylbiphenyl-2-yl)phosphine (X-Phos) (14.55 mg, 0.031 mmol), potassium acetate (112 mg, 1.145 mmol), and dioxane (1.5 ml) and the solution was degassed with N₂ gas for 30 min. Tris(dibenzylideneacetone)dipalladium(0) (6.99 mg, 7.63 µmol) was added and degassing was continued another 10 min. The tube was sealed and heated with stirring at 100° C. overnight. The cooled solution was diluted with ethyl acetate, washed with H₂O, brine, dried (Na₂SO₄), filtered and the filtrate treated with 3-(mercaptopropyl) silica gel for 1 h. The solution was filtered and solvent removed to give a yellow solid which was purified by chromatography on silica gel eluting with 0-20% ethyl acetate/hexane to give title compound (99 mg, 78% yield) as a white solid.

Example 48F (2S,2'S)-tert-butyl 2,2'-(4,4'-(4,4'-((2S,3R,4R,5S)-1-(4-tert-butylphenyl)-3,4-dimethoxypyrrolidine-2,5-diyl)bis(4,1-phenylene))bis(1H-imidazole-4,2-diyl))dipyrrolidine-1-carboxylate In a sealed tube was combined the product from Example 48E (97 mg, 0.145 mmol), the product from Example 26D (115 mg, 0.363 mmol), 1 M Na₂CO₃ (0.363 ml, 0.363 mmol), EtOH (1.0 ml) and toluene (1.0 ml) and the solution was degassed with N2 gas for 30 min. 1,1'-Bis(diphenylphosphino)ferrocenedichloro palladium(II) dichloromethane complex (10.63 mg, 0.015 mmol) was added and degassing was continued an additional 10 min. The tube was sealed and heated at 100° C. for 3 h. The cooled solution was diluted with ethyl acetate, filtered through Celite and the residue washed with ethyl acetate. The filtrate was concentrated in vacuo and the resulting material was purified chromatography on silica gel using a 12 g silica gel column eluting with 0-2% methanol/dichloromethane to give title compound (85 mg, 66.1% yield).

Example 48G dimethyl (2S,2'S)-1,1'-((2S,2'S)-2,2'-(4,4'-(4,4'-((2S,3R,4R,5S)-1-(4-tert-butylphenyl)-3,4-dimethoxypyrrolidine-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate To a solution of the product from Example 48F (83 mg, 0.094 mmol) in dichloromethane (1.0 ml) was added TFA (1.0 ml, 12.98 mmol) and the solution was stirred at room temperature for 1 h. Solvent was concentrated and the residue was azeotroped 2 times with dichloromethane. The residue was placed under vacuum for 1 h to remove final traces of TFA. To this residue (64.2 mg, 0.094 mmol) was added DMSO (500 µl) followed by (S)-2-(methoxycarbonylamino)-3-methylbutanoic acid (41.1 mg, 0.234 mmol), HATU (89 mg, 0.234 mmol) and hunig's base (82 µl, 0.469 mmol). pH was checked and additional Hunig's base was added to adjust pH to ~9. Stirring was continued at room temperature for 1 h. The solution was diluted with ethyl acetate, washed with H₂O, brine, dried (Na₂SO₄), filtered and concentrated to give crude residue. Purification was run by chromatography on silica gel eluting with 0-4% methanol/dichloromethane over 60 min to give title compound (7.5 mg, 8.01% yield). 1H NMR (400 MHz, CDCl₃) δ ppm 0.86 (s, 12H) 1.13 (s, 9H) 1.86-2.02 (m, 2H) 2.02-2.12 (m, 2H) 2.12-2.25 (m, 2H) 2.25-2.41 (m, 1H) 2.90-3.17 (m, 2H) 3.43 (s, 6H) 3.53-3.65 (m, 2H) 3.70 (s, 6H) 3.74-3.89 (m, 2H) 4.16-4.26 (m, 2H) 4.26-4.37 (m, 1H) 5.18-5.26 (m, 2H) 5.26-5.32 (m, 2H) 5.33-5.41 (m, 2H) 6.28 (d, J=8.78 Hz, 2H) 6.89-6.99 (m, 2H) 7.16 (s, 2H) 7.20 (s, 2H) 7.22 (s, 2H) 7.26 (s, 4H) 7.30-7.48 (br s, 1H) 7.58-7.82 (br s, 2H) 10.08-10.42 (br s, 1H). The title compound showed an EC₅₀ value of less than about 0.1 nM in HCV 1b-Con1 replicon assays in the presence of 5% FBS.

Example 49 dimethyl (2S,2'S)-1,1'-((2S,2'S)-2,2'-(5,5'-((2S,3R, 4R,5S)-1-(4-tert-butylphenyl)-3,4-dimethoxypyrrolidine-2,5-diyl)bis(1H-benzo[d]imidazole-5,2-diyl)) bis(pyrrolidine-2,1-diyl))bis(3-methyl-1-oxobutane-2,1-diyl)dicarbamate

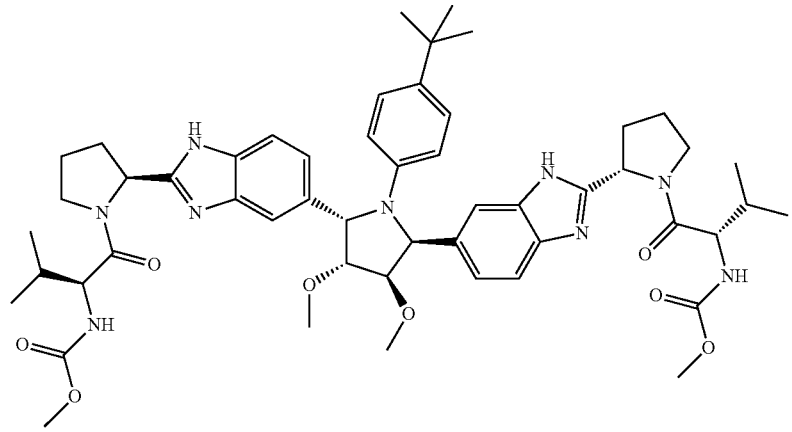 [SMILES: COC(=O)N[C@H](C(=O)N1CCC[C@H]1c1nc2cc([C@H]3[C@@H](OC)[C@H](OC)[C@H](c4ccc5nc([C@@H]6CCCN6C(=O)[C@@H](NC(=O)OC)C(C)C)[nH]c5c4)N3c3ccc(C(C)(C)C)cc3)ccc2[nH]1)C(C)C]

Example 49A (S)-tert-butyl 2-(2-amino-5-bromophenylcarbamoyl) pyrrolidine-1-carboxylate A solution of the 2-amino-4-bromoaniline (6.0 g, 32.1 mmol), Boc-Pro-OH (6.90 g, 32.1 mmol) and HATU (13.42 g, 35.3 mmol) in dry DMSO (160 mL) was treated with diisopropylethylamine (14.0 mL, 10.4 g, 80 mmol) followed by stirring at room temperature for 18 h. The mixture was diluted with ethyl acetate and extracted with water (3×) and saturated sodium chloride solution. Drying (Na$_2$SO$_4$) and concentration in vacuo afforded a brown solid which was used directly in the next step.

Example 49B (S)-tert-butyl 2-(5-bromo-1H-benzo[d]imidazol-2-yl) pyrrolidine-1-carboxylate A solution of the compound of Example 49A in glatial acetic acid (75 mL) was warmed at 60° C. for 3 h. The mixture was cooled and diluted with toluene and concentrated in vacuo. The remainder of the acetic acid was removed by azeotroping with toluene (2×) and the residue was chromatographed over a 360 g silica gel cartridge, eluting with 25-75% ethyl acetate in dichloromethane. These procedures afforded the product (10.0 g, 85%) as a light beige rigid foam.

Example 49C (S)-tert-butyl 2-(6-bromo-1-((2-(trimethylsilyl) ethoxy)methyl)-1H-benzo[d]imidazol-2-yl)pyrrolidine-1-carboxylate A solution of the compound of Example 49B (2.25 g, 6.14 mmol) in dry THF (25 mL) was treated with sodium hydride (295 mg of 60% in oil, 177 mg, 7.37 mmol) followed by stirring at room temperature for 1 h. The solution was then treated with SEM-Chloride (1.20 mL, 1.13 g, 6.76 mmol) followed by stirring at room temperature for 18 h. The mixture was quenched by addition of water and the mixture was diluted with ethyl acetate. The mixture was extracted with water and saturated sodium chloride solution. Drying (Na$_2$SO$_4$) and concentration in vacuo afforded an oil, which was chromatographed over a 100 g silica gel cartridge, eluting with 20-75% ethyl acetate in hexanes. These procedures afforded the product (2.24 g, 73%) as a heavy oil, which solidified after setting for several days. This mixture of both regioisomeric SEM derivatives was not separated for use in the next step.

Example 49D (S)-tert-butyl 2-(6-(4,4,5,5-tetramethyl-1,3,2-dioxaborolan-2-yl)-1-((2-(trimethylsilyl)ethoxy)methyl)-1H-benzo[d]imidazol-2-yl)pyrrolidine-1-carboxylate In a resealable pressure tube, a solution of the compound of Example 49C (2.24 g, 4.51 mmol), bis(pinacolato)diboron (1.26 g, 4.96 mmol), and potassium acetate (1.33 g, 13.53 mmol) in dry dioxane (23 mL) was degassed by nitrogen sparge for 30 min. The solution was treated with 1,1'-bis (diphenylphosphino)ferrocene palladium (II) chloride dichloromethane complex (111 mg, 0.14 mmol) followed by degassing for another 5 min. The pressure tube was sealed and warmed at 90° C. for 4 h. The mixture was cooled and diluted with ethyl acetate, followed by extraction with water and saturated sodium chloride solution. The solution was dried (Na$_2$SO$_4$) and stirred for 1 h with 3-mercaptopropyl) silica gel. After filtration and concentration in vacuo the brown oil was chromatographed over a 100 g silica gel cartridge, eluting with 15-70% ethyl acetate in dichloromethane. These procedures afforded the product (1.99 g, 81%) as a white rigid foam.

Example 49E (S)-tert-butyl 2-(6-((2S,3R,4R,5S)-5-(2-((S)-1-(tert-butoxycarbonyl)pyrrolidin-2-yl)-1-((2-(trimethylsilyl)ethoxy)methyl)-1H-benzo[d]imidazol-5-yl)-1-(4-tert-butylphenyl)-3,4-dihydroxypyrrolidin-2-yl)-1-((2-(trimethylsilyl)ethoxy)methyl)-1H-benzo[d] imidazol-2-yl)pyrrolidine-1-carboxylate A solution of 2,3-O-isopropylidene-D-mannitol (144 mg, 0.65 mmol) and iodobenzenediacetate (501 mg, 1.56 mmol)

in 2:1 methanol-dichloromethane (3 mL) was stirred at room temperature for 5 h. The mixture was concentrated in vacuo to a white paste and then suspended in 0.1 M sulfuric acid solution (1.0 mL) followed by stirring at room temperature for 18 h. The solution was adjusted to pH 6 by addition of solid sodium bicarbonate followed by addition of 4-tert-butylaniline (206 μL, 193 mg, 1.30 mmol) the product from Example 49D (634 mg, 1.17 mmol) and hexafluoroisopropyl alcohol (2.6 mL). The solution was then warmed at 70° C. for 5 h. The solution was cooled and concentrated in vacuo. The residue was dissolved in ethyl acetate and extracted with 0.33 M tribasic potassium phosphate solution and saturated sodium chloride solution. Drying ($Na_2SO_4$) and concentration in vacuo afforded a brown oil, which was chromatographed over a 50 g silica gel cartridge, eluting with 15-85% ethyl acetate in dichloromethane. These procedures afforded the recovered boronate (208 mg) as a viscous brown oil. The column was then re-eluted with 0-20% methanol in dichloromethane to afford the product (159 mg, 23%) as a brown solid.

Example 49F (S)-tert-butyl 2-(6-((2S,3R,4R,5S)-5-(2-((S)-1-(tert-butoxycarbonyl)pyrrolidin-2-yl)-1-((2-(trimethylsilyl)ethoxy)methyl)-1H-benzo[d]imidazol-5-yl)-1-(4-tert-butylphenyl)-3,4-dimethoxypyrrolidin-2-yl)-1-((2-(trimethylsilyl)ethoxy)methyl)-1H-benzo[d]imidazol-2-yl)pyrrolidine-1-carboxylate A solution of the product from Example 49E (154 mg, 0.14 mol) in dry THF was treated with sodium hydride (13 mg of 60% in oil, 8 mg, 0.33 mmol) followed by stirring at room temperature for 30 min. The mixture was treated with methyl iodide (19 μL, 43 mg, 0.30 mmol) followed by stirring at room temperature for 2 h. The mixture was diluted with ethyl acetate and quenched by addition of water. The mixture was extracted with water and saturated sodium chloride solution. Drying ($Na_2SO_4$) and concentration in vacuo afforded a brown oil, which was chromatographed over a 25 g silica gel cartridge, eluting with 0-15% methanol in dichloromethane. These procedures afforded the product (121 mg, 77%) as a beige foam.

Example 49G (S)-5,5'-((2S,3R,4R,5S)-1-(4-tert-butylphenyl)-3,4-dimethoxypyrrolidine-2,5-diyl)bis(2-((S)-pyrrolidin-2-yl)-1H-benzo[d]imidazole)

A solution of the compound of Example 49F (111 mg, 0.10 mmol) in ethanol (1 mL) was treated with 4 N hydrochloric acid solution (2.0 mL) followed by warming at 60° C. for 18 h. The solution was cooled and concentrated in vacuo with ethanol-toluene mixtures (2×) to afford the tetrahydrochloride as a light yellow solid. This material was dissolved in methanol (3 mL) and stirred with Amberlyte IRA 400 (OH-form, 1.4 mequiv/g, 577 mg, 0.81 mequiv) for 1 h. The resin was removed by filtration and the filtrate was concentrated in vacuo to afford the product (29 mg, 45%) as a light amber glass.

Example 49H dimethyl (2S,2'S)-1,1'-((2S,2'S)-2,2'-(5,5'-((2S,3R,4R,5S)-1-(4-tert-butylphenyl)-3,4-dimethoxypyrrolidine-2,5-diyl)bis(1H-benzo[d]imidazole-5,2-diyl))bis(pyrrolidine-2,1-diyl))bis(3-methyl-1-oxobutane-2,1-diyl)dicarbamate A solution of the compound of Example 49G (29 mg, 0.046 mmol), HOBt hydrate (18 mg, 0.114 mmol), EDAC (22 mg, 0.114 mmol) and (S)-2-(methoxycarbonylamino)-3-methylbutanoic acid (20 mg, 0.114 mmol) in dry DMF (0.5 mL) at 0° C. was treated with N-methylmorpholine (15 μL, 14 mg, 0.137 mmol) followed by stirring at 0° C. for 30 min and warming to room temperature for 2 h. The mixture was diluted with ethyl acetate and extracted with water (3×) and saturated sodium chloride solution. Drying ($Na_2SO_4$) and concentration in vacuo afforded an oil which was dissolved in methanol and treated with a small amount of potassium carbonate. After stirring 1 h, the mixture was filtered and concentrated in vacuo to afford a yellow oil, which was chromatographed over a 25 g silica gel cartridge, eluting with 0-15% methanol in dichloromethane to give the product (14 mg, 32%) as a white solid. $^1$H NMR (400 MHz, DMSO-d6) δ 7.39 (m, 4H), 7.30 (m, 4H), 7.07 (t, J=9.1 Hz, 2H), 6.87 (m, 2H), 6.31 (d, J=8.9 Hz, 1H), 5.54 (m, 2H), 5.14 (dd, J=7.6, 4.6 Hz, 2H), 4.14 (m, 2H), 3.77 (m, 4H), 3.51 (m, 6H), 3.28 (m, 6H), 2.15 (m, 4H), 1.04 (s, 9H), 0.86 (m, 12H). The title compound showed an $EC_{50}$ value of from about 0.1 to about 1 nM in HCV 1b-Con1 replicon assays in the presence of 5% FBS.

Example 50 dimethyl (2S,2'S)-1,1'-((2S,2'S)-2,2'-(4,4'-(4,4'-(1-(4-(pentafluorothio)phenyl)-1H-pyrrole-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate

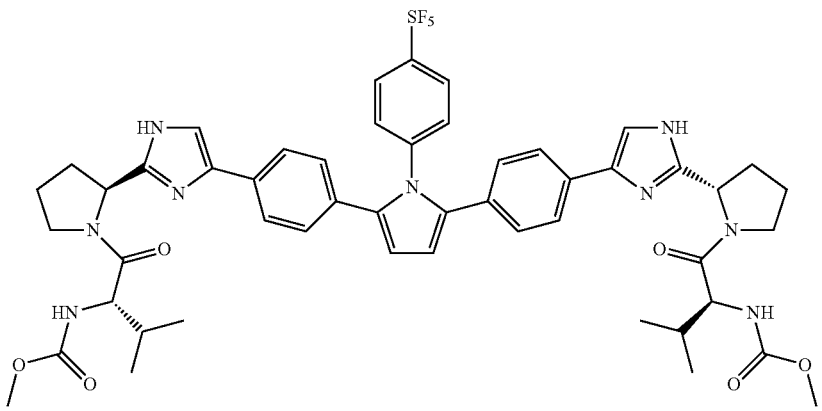

Example 50A

2,5-bis(4-bromophenyl)-1-(4-(pentafluorothio)phenyl)-1H-pyrrole

Title compound was prepared from the product from Example 26E using the methods from Example 26F substituting 4-aminophenylsulfur pentafluoride for 4-tert-butylaniline to provide the desired compound.

Example 50B

1-(4-(pentafluorothio)phenyl)-2,5-bis(4-(4,4,5,5-tetramethyl-1,3,2-dioxaborolan-2-yl)phenyl)-1H-pyrrole Title compound was prepared using the methods from Example 26G substituting the product from Example 50A for the product from Example 26F to provide the desired compound.

Example 50C tert-butyl 2,2'-(4,4'-(4,4'-(1-(4-(pentafluorothio)phenyl)-1H-pyrrole-2,5-diyl)bis(4,1-phenylene))bis(1H-imidazole-4,2-diyl))dipyrrolidine-1-carboxylate Title compound was prepared using the methods from Example 26H substituting the product from Example 50B for the product from Example 26G to provide the desired compound.

Example 50D

4,4'-(4,4'-(1-(4-(pentafluorthio)phenyl)-1H-pyrrole-2,5-diyl)bis(4,1-phenylene))bis(2-(pyrrolidin-2-yl)-1H-imidazole)

Title compound was prepared using the methods from Example 26I substituting the product from Example 50C for the product from Example 26H to provide the desired compound.

Example 50E

Dimethyl (2S,2'S)-1,1'-((2S,2'S)-2,2'-(4,4'-(4,4'-(1-(4-(pentafluorothio)phenyl)-1H-pyrrole-2,5-diyl)bis(4,1-phenylene))bis(1H-imidazole-4,2-diyl))bis(pyrrolidine-2,1-diyl))bis(3-methyl-1-oxobutane-2,1-diyl)dicarbamate Title compound was prepared using the methods from Example 26J substituting the product from Example 50D for the product from Example 26I to provide the desired compound. $^1$HNMR (DMSO-d6; 400 MHz): δ 11.75 (br s, 2H), 7.88 (m, 2H), 7.56 (app d, J=8.35 Hz, 4H), 7.45 (br s, 2H), 7.27 (m, 4H), 6.96 (app d, J=8.35 Hz, 4H), 6.50 (s, 2H), 5.04 (m, 2H), 4.03 (m, 2H), 3.78 (m, 4H), 3.53 (s, 6H), 2.11-1.85 (m, 10H), 0.86 (d, J=6.72 Hz, 6H), 0.82 (d, J=6.72 Hz, 6H). The title compound showed an $EC_{50}$ value of less than about 0.1 nM in HCV 1b-Con1 replicon assays in the presence of 5% FBS.

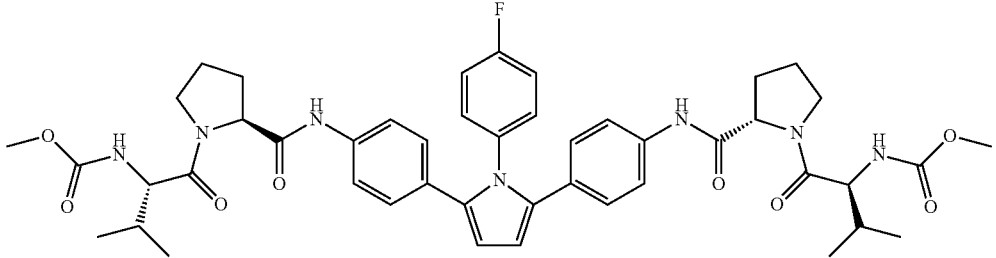

Example 51 dimethyl ([1-(4-fluorophenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})biscarbamate Example 19D (150 mg) and (S)-2-(methoxycarbonylamino)-3-methylbutanoic acid were processed using the method of Example 19E (substituting DMF as solvent) to provide the title compound which was purified using gradient silica gel chromatography (30-70% EtOAc in hexanes) (70 mg). $^1$H NMR (500 MHz, DMSO-D6) δ 9.76 (s, 2H), 7.16 (d, J=8.7, 4H), 7.06 (d, J=8.4, 2H), 6.92 (t, J=8.7, 2H), 6.83 (dd, J=5.0, 8.9, 2H), 6.71 (d, J=8.7, 4H), 6.14 (s, 2H), 4.15 (dd, J=5.1, 7.9, 2H), 3.77 (t, J=8.5, 2H), 3.59-3.50 (m, 2H), 3.40-3.31 (m, 2H), 3.27 (s, 6H), 1.95-1.82 (m, 2H), 1.79-1.52 (m, 8H), 0.67 (d, J=6.8, 6H), 0.62 (d, J=6.7, 6H). MS (ESI; M+H) m/z=853.

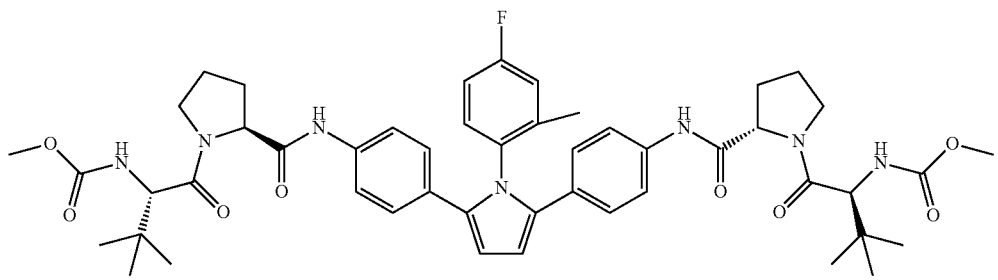

Example 52 dimethyl ([1-(4-fluoro-2-methylphenyl)-1H-pyrrole-2,5-diyl]bis{benzene-4,1-diylcarbamoyl(2S)pyrrolidine-2,1-diyl[(2S)-3,3-dimethyl-1-oxobutane-1,2-diyl]})biscarbamate Example 1A was processed using 4-fluoro-2-methylaniline and the methods from Examples 19A, 19B, 19C, 19D, and 51 ((S)-2-(methoxycarbonylamino)-3,3-dimethylbutanoic acid was used) to provide the title compound. $^1$H NMR (400 MHz, DMSO-D6) δ 9.98 (s, 2H), 7.44-7.36 (m, 5H), 7.09-6.96 (m, 8H), 6.42 (s, 2H), 4.39 (dd, J=5.5, 8.1, 2H), 4.19 (d, J=8.7, 2H), 3.80-3.70 (m, 2H), 3.65-3.56 (m, 2H), 3.52 (s, 6H), 2.20-2.06 (m, 2H), 1.97-1.91 (m, 2H), 1.90-1.76 (m, 4H), 1.63 (s, 3H), 0.94 (s, 18H). MS (ESI; M+H) m/z=895.

carbonylamino)-3-methylbutanoic acid (62.2 mg, 0.355 mmol), HATU (135 mg, 0.355 mmol), and Hunig's Base (0.074 mL, 0.426 mmol), and the resulting mixture was stirred at rt for 90 min and then partitioned between $H_2O$ (1 mL) and EtOAc (2×2 mL). The combined organic layers were dried over $Na_2SO_4$, filtered and concentrated in vacuo. The drying agent was filtered off, and the crude product was purified by column chromatography on silica gel using a solvent gradient of 1-3% MeOH in $CH_2Cl_2$ to give the title compounds as a 1:1 mixture.

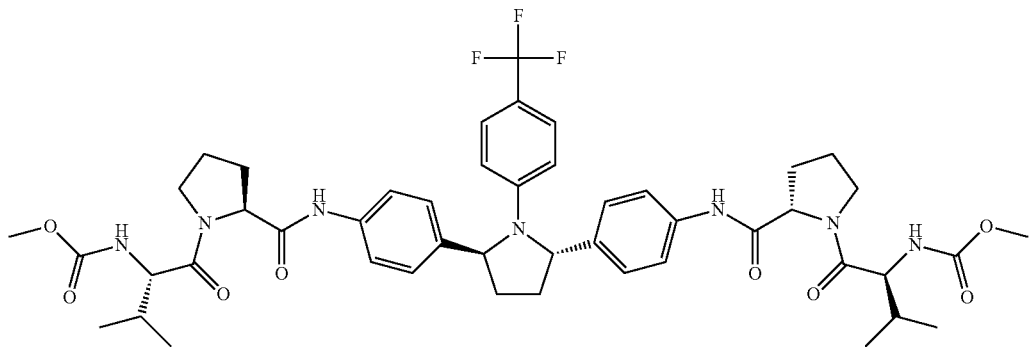

Example 53 dimethyl ({(2S,5S)-1-[4-(trifluoromethyl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate

Example 53A dimethyl ({(2S,5S)-1-[4-(trifluoromethyl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate and dimethyl ({(2R,5R)-1-[4-(trifluoromethyl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate To a solution of the product from Example 23B (84 mg, 0.142 mmol) in DMSO (1.5 mL) was added (S)-2-(methoxy-

Example 53B dimethyl ({(2S,5S)-1-[4-(trifluoromethyl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate The product from Example 53A was separated on a Chiralpak AD-H column using 1:1 hexanes:(1:1 EtOH:2-PrOH). The title compound was the first component to elute. $^1$H NMR (400 MHz, DMSO-D6) δ ppm 0.88 (d, J=6.61 Hz, 6H), 0.93 (d, J=6.61 Hz, 6H), 1.63-1.72 (m, 2H), 1.78-2.06 (m, 8H), 2.06-2.20 (m, 2H), 3.52 (s, 6H), 3.56-3.67 (m, 2H), 3.73-3.86 (m, 2H), 4.03 (t, J=18.51 Hz, 2H), 4.42 (dd, J=17.92, 4.88 Hz, 2H), 5.27 (d, J=6.61 Hz, 2H), 6.36 (d, J=18.67 Hz, 2H), 7.14 (d, J=8.57 Hz, 4H), 7.25 (d, J=8.89 Hz, 2H), 7.31 (d, J=8.35 Hz, 2H), 7.52 (d, J=8.57 Hz, 4H), 10.01 (s, 2H); MS (ESI) m/z 906.3 (M+H)$^+$.

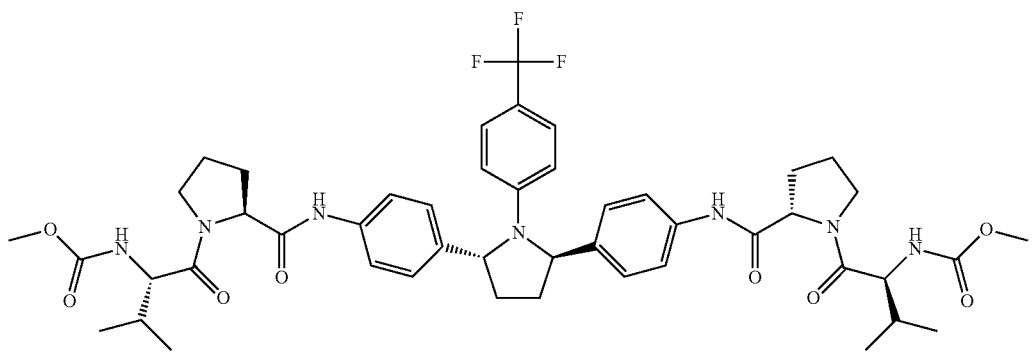

Example 54 dimethyl ({(2R,5R)-1-[4-(trifluoromethyl)phenyl]
pyrrolidine-2,5-diyl}bis{benzene-4,1-diylcarbamoyl
(2S)pyrrolidine-2,1-diyl[(2S)-3-methyl-1-oxobutane-
1,2-diyl]})biscarbamate The product from Example 53A was separated on a Chiralpak AD-H column using 1:1 hexanes:(1:1 EtOH:2-PrOH). The title compound was the second component to elute. $^1$H NMR (400 MHz, DMSO-D6) δ ppm 0.87 (d, J=6.61 Hz, 6H), 0.92 (d, J=6.72 Hz, 6H), 1.64-1.74 (m, 2H), 1.78-2.06 (m, 8H), 2.06-2.22 (m, 2H), 3.52 (s, 6H), 3.56-3.67 (m, 2H), 3.75-3.86 (m, 2H), 3.97-4.08 (m, 2H), 4.37-4.48 (m, 2H), 5.28 (d, J=6.51 Hz, 2H), 6.36 (d, J=8.78 Hz, 2H), 7.14 (d, J=8.57 Hz, 4H), 7.25 (d, J=18.89 Hz, 2H), 7.30 (d, J=18.24 Hz, 2H), 7.52 (d, J=8.57 Hz, 4H), 10.01 (s, 2H); MS (ESI) m/z 906.3 (M+H)$^+$.

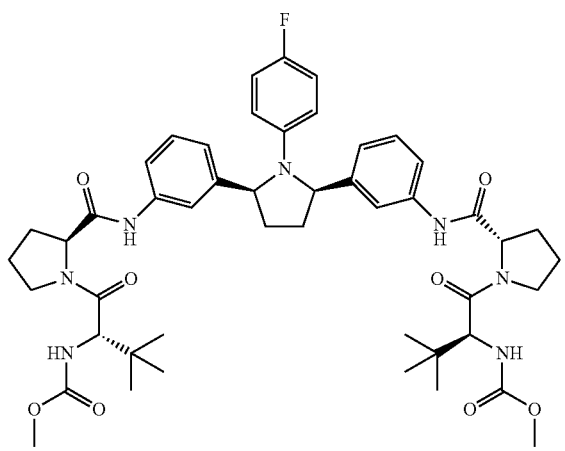 [SMILES: COC(=O)N[C@H](C(=O)N1CCC[C@H]1C(=O)Nc1cccc([C@H]2CC[C@@H](c3cccc(NC(=O)[C@@H]4CCCN4C(=O)[C@@H](NC(=O)OC)C(C)(C)C)c3)N2c2ccc(F)cc2)c1)C(C)(C)C]

Example 55 dimethyl ([(2R,5S)-1-(4-fluorophenyl)pyrrolidine-2,
5-diyl]bis{benzene-3,1-diylcarbamoyl(2S)pyrrolidine-2,1-diyl[(2S)-3,3-dimethyl-1-oxobutane-1,2-
diyl]})biscarbamate

Example 55A 1,4-bis(3-nitrophenyl)butane-1,4-dione

Anhydrous zinc(II) chloride (5.42 g, 39.7 mmol) was stirred in dry benzene (50 mL) under nitrogen while diethylamine (3.10 mL, 29.8 mmol) and t-butanol (2.85 mL, 29.8 mmol) were added. The resulting mixture was stirred at room temperature for 90 min to give a cloudy solution. To this was added 1-(3-nitrophenyl)ethanone (4.97 g, 29.8 mmol) followed by 2-bromo-1-(3-nitrophenyl)ethanone (5.00 g, 19.87 mmol) and the resulting mixture allowed to stir at room temperature overnight. A large portion of the benzene was subsequently removed by decantation. The resulting mixture was then treated with 5% sulfuric acid (25 mL) in a separatory funnel and the aqueous phase drawn off. The organic phase was washed with water (2×25 mL). A third washing resulted in an emulsion. The contents of the funnel were emptied into a large volume of water (750 mL) to which was added sodium chloride and the oil in water mixture rapidly stirred. Methanol was added (75 mL) in portions to try and disperse the oil and promote solidification of the product. After nearly forty eight hours of stirring the product solidified and was collected by vacuum filtration. The filter cake was water washed, dried first in air and then a vacuum oven at 55° C. to provide the title compound (5.85 g, 90% yield) as a pale yellow solid that was used directly in the next step.

Example 55B 1,4-bis(3-nitrophenyl)butane-1,4-diol

Sodium borohydride (0.6173 g, 17.74 mmol) was added to a suspension of Example 55A (2.71 g, 8.26 mmol) in ethanol (150 mL) and stirred at ambient temperature for 3 hours. The reaction was quenched with water (~50 mL) and concentrated to a paste which was taken up in 1:1 MeOH:THF. This suspension was filtered through a celite plug and concentrated. The residue was taken up in toluene and heated with stirring to form a white paste which was then sonicated and scraped until a filterable solid formed. This was filtered, rinsed with toluene and dried under vacuum to afford 2.84 g (100%) of the title compound as an off white solid. MS (DCI) m/z 350 (M+NH$_4$)$^+$.

Example 55C 1,4-bis(3-nitrophenyl)butane-1,4-diyl
dimethanesulfonate

Methanesulfonyl chloride (0.3 mL, 3.87 mmol) was added dropwise to a cold (0° C.) solution of Example 55B (0.5089 g, 1.531 mmol) and triethylamine (0.65 mL, 4.66 mmol) in THF (10 mL). The reaction was removed from the ice bath and stirred at ambient temperature for 30 minutes. Solvent was removed under vacuum to provide the title compound as a solid that was used without purification.

Example 55D 1-(4-fluorophenyl)-2,5-bis(3-nitrophenyl)pyrrolidine

Example 55C (0.733 g, 1.5 mmol) was mixed with 4-fluoroaniline (1.5 mL, 15.63 mmol) and DMF (3 mL). The reaction was stirred at 50° C. for 24 hours. The reaction mixture was partioned between EtOAc and water. The organic portion was washed with water (2×), brine (1×), dried (MgSO$_4$), concentrated. Purification by flash chromatography (silica gel, 0-50% EtOAc/Hexanes). The material was dissolved in EtOAc and washed with 1 M HCl (2×) to remove residual aniline, water (1×), sat aqueous NaHCO$_3$ (1×) and brine (1×) dried (MgSO$_4$) and concentrated to afford the title compound as a mixture of trans and cis isomers (0.45 g, 73%).

Example 55E 3,3'-(1-(4-fluorophenyl)pyrrolidine-2,5-diyl)dianiline

A suspension of Pd/C (0.0527 g, 0.050 mmol) in THF (2 mL) was added to a solution of Example 55D (0.45 g, 1.105 mmol) in THF (7 mL)/EtOH (7 mL) under N$_2$. The flask was flushed with H$_2$ and stirred under 1 atm H$_2$ for 20 hours. The reaction was filtered through a celite plug, rinsed with ~100 mL (1:1 EtOH:THF) and solvent was removed under vacuum. The material was used without purification. MS (DCI) m/z 348 (M+H)$^+$.

Example 55F (2S,2'S)-tert-butyl 2,2'-(3,3'-((2S,5R)-1-(4-fluorophenyl)pyrrolidine-2,5-diyl)bis(3,1-phenylene))bis(azanediyl)bis(oxomethylene)dipyrrolidine-1-carboxylate Diisopropylethylamine (0.8 mL, 4.58 mmol) was added to a mixture of Example 55E (0.382 g, 1.1 mmol), (S)-1-(tert-butoxycarbonyl)pyrrolidine-2-carboxylic acid (0.5950 g, 2.76 mmol) and HATU (0.9196 g, 2.419 mmol) in dichloromethane (12 mL). The reaction was stirred at rt for 1 hr, diluted with dichloromethane, washed with water (2×), brine (1×), dried (MgSO$_4$) and concentrated to give a brown residue. The residue was taken up in ether, sonicated and filtered to afford the title compound as a tan solid. The trans isomers remained in the ether solution and are described further in Example 83. LC/MS Rt 2.27 m/z 742 (M+H)$^+$.

Example 55G (2S,2'S)—N,N'-(3,3'-((2S,5R)-1-(4-fluorophenyl)pyrrolidine-2,5-diyl)bis(3,1-phenylene))dipyrrolidine-2-carboxamide TFA (3 mL, 38.9 mmol) was added to a solution of Example 55F (0.4033 g, 0.544 mmol) in dichloromethane (10 mL). After 90 minutes the reaction was concentrated. The residue was sequentially dissolved in and concentrated in vacuo from the following solvents: dichloromethane (2×), methanol (2×), and ether (1×). This semi-solid was taken up in dichlormethane and washed with sat aq NaHCO$_3$ (2×) water (1×) brine (1×) dried (MgSO$_4$) and filtered to provide the title compound. LC/MS Rt 1.31 m/z 542 (M+H)$^+$.

Example 55H dimethyl ([(2R,5S)-1-(4-fluorophenyl)pyrrolidine-2,5-diyl]bis{benzene-3,1-diylcarbamoyl(2S)pyrrolidine-2,1-diyl[(2S)-3,3-dimethyl-1-oxobutane-1,2-diyl]})biscarbamate Diisopropylethylamine (0.5 mL, 2.86 mmol) was added to a mixture of Example 55G, (S)-2-methoxycarbonylamino-3,3-dimethyl-butyric acid (0.2600 g, 1.374 mmol) and HATU (0.4527 g, 1.191 mmol) in dichloromethane (15 mL). The reaction was stirred at ambient temperature for 18 hours. The reaction was diluted with dichloromethane, washed with water (2×), brine (1×), dried (MgSO$_4$), concentrated and purified by flash chromatography (silica gel, 0-30% EtOAc/dichloromethane) to afford 0.14 g (30%) of the title compound. $^1$H NMR (400 MHz, DMSO-d6) δ 0.96 (s, 9H), 0.98 (s, 9H), 2.06-1.71 (m, 8H), 2.25-2.07 (m, 2H), 2.42 (t, J=7.1, 2H), 3.54 (d, J=3.2, 6H), 3.72-3.59 (m, 2H), 3.86-3.72 (m, 2H), 4.22 (d, J=8.9, 2H), 4.51-4.37 (m, 2H), 4.69 (t, J=11.9, 2H), 6.42-6.28 (m, 2H), 6.96-6.83 (m, 2H), 7.08 (t, J=8.5, 2H), 7.39-7.18 (m, 4H), 7.76-7.54 (m, 4H), 10.03 (d, J=9.8, 2H). MS (ESI) m/z 884 (M+H)$^+$, 882 (M−H)$^+$.

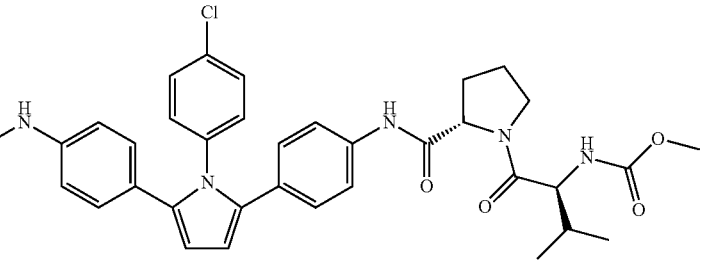

Example 56 dimethyl ([1-(4-chlorophenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})biscarbamate Example 1A was processed using 4-chloroaniline and the methods from Examples 19A, 19B, 19C, 19D, and 51 to provide the title compound (72 mg). $^1$H NMR (400 MHz, DMSO-d6) δ 10.00 (s, 2H), 7.45-7.36 (m, 6H), 7.31 (d, J=8.3, 2H), 7.04 (d, J=8.4, 2H), 6.96 (d, J=8.6, 4H), 6.39 (s, 2H), 4.44-4.37 (m, 2H), 4.06-3.99 (m, 2H), 3.85-3.74 (m, 2H), 3.67-3.56 (m, 2H), 3.52 (s, 6H), 2.20-2.06 (m, 2H), 2.04-1.79 (m, 8H), 0.92 (d, J=6.7, 6H), 0.88 (d, J=6.7, 6H). MS (ESI; M+H) m/z=869.

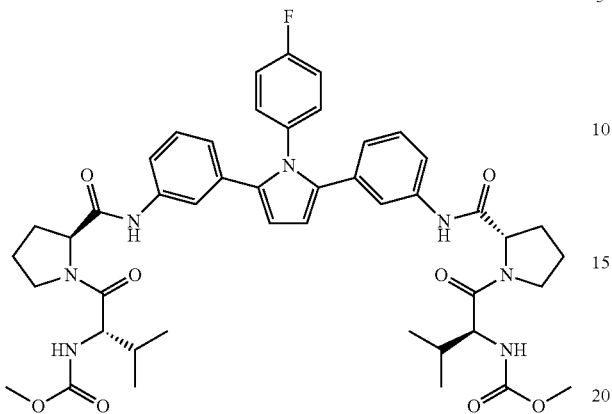

Example 57 dimethyl ([1-(4-fluorophenyl)-1H-pyrrole-2,5-diyl] bis{benzene-3,1-diylcarbamoyl(2S)pyrrolidine-2,1-diyl[(2S)-3-methyl-1-oxobutane-1,2-diyl]})biscarbamate Example 55A was processed using the methods of Example 19A, 19B, 19C, 19D, and 19E to provide the title compound. $^1$H NMR (400 MHz, DMSO-d6) δ 0.99-0.84 (m, 12H), 2.05-1.76 (m, 8H), 2.22-2.05 (m, 2H), 3.53 (s, 6H), 3.70-3.56 (m, 2H), 3.88-3.71 (m, 2H), 4.11-3.93 (m, 2H), 4.42 (dd, J=4.9, 7.9, 2H), 6.40 (s, 2H), 6.54 (d, J=7.9, 2H), 7.18-6.98 (m, 6H), 7.34 (dd, J=8.3, 15.4, 4H), 7.55 (s, 2H), 9.96 (d, J=11.2, 2H). MS (ESI) m/z 852 (M+H)$^+$.

aniline (1.9 mL, 15 mmol). The mixture was heated to 170° C. for 15 minutes under microwave irradiation. The cooled mixture was diluted with water and diethyl ether and stirred vigorously for 15 minutes and then filtered. The crude product was purified by chromatography on silica gel eluting with a solvent gradient of 0-30% ethyl acetate in hexane. Product containing fractions were combined and concentrated under reduced pressure and then triturated with diethyl ether to give the title compound (110 mg, 8% yield).

Example 58B dimethyl ({1-[4-(trifluoromethyl)phenyl]-1H-pyrrole-2,5-diyl}bis{benzene-4,1-diylcarbamoyl(2S) pyrrolidine-2,1-diyl[(2S)-3-methyl-1-oxobutane-1,2-diyl]})biscarbamate Example 58A was processed using the methods of Examples 19B, 19C, 19D, and 51 to provide the title compound (44 mg). $^1$H NMR (400 MHz, DMSO-d6) δ 10.01 (s, 2H), 7.71 (d, J=8.6, 2H), 7.42 (d, J=8.7, 4H), 7.31 (d, J=8.2, 2H), 7.22 (d, J=8.3, 2H), 6.95 (d, J=8.6, 4H), 6.43 (s, 2H), 4.39 (dd, J=5.2, 8.1, 2H), 4.03 (d, J=8.3, 2H), 3.85-3.75 (m, 2H), 3.66-3.56 (m, 2H), 3.52 (s, 6H), 2.18-2.08 (m, 2H), 2.01-1.79 (m, 8H), 0.92 (d, J=6.7, 6H), 0.87 (d, J=6.6, 6H). MS (ESI; M+H) m/z=903.

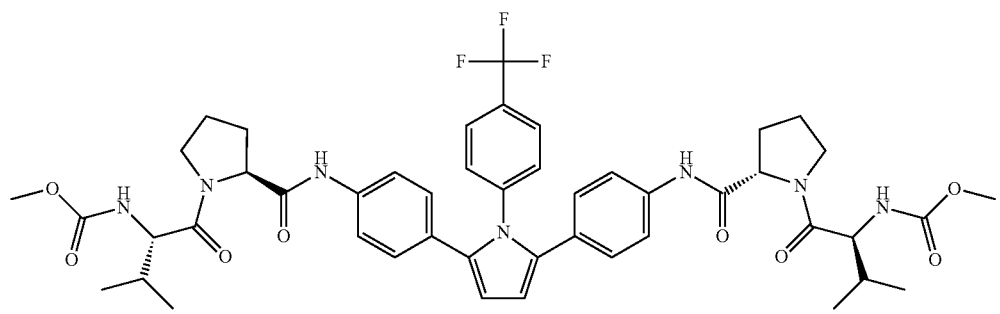

Example 58 dimethyl ({1-[4-(trifluoromethyl)phenyl]-1H-pyrrole-2,5-diyl}bis{benzene-4,1-diylcarbamoyl(2S) pyrrolidine-2,1-diyl[(2S)-3-methyl-1-oxobutane-1,2-diyl]})biscarbamate Example 58A 2,5-bis(4-nitrophenyl)-1-(4-(trifluoromethyl)phenyl)-1H-pyrrole To a slurry of the product from Example 1A (1.00 g, 3.05 mmol) in acetic acid (30 mL) was added 4-(trifluoromethyl)

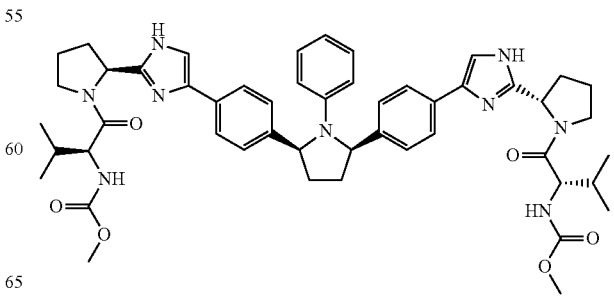

Example 59 methyl {(2S)-1-[(2S)-2-(4-{4-[(2R,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-phenylpyrrolidin-2-yl]phenyl}-1H-imidazol-2-yl)pyrrolidin-1-yl]-3-methyl-1-oxobutan-2-yl}carbamate

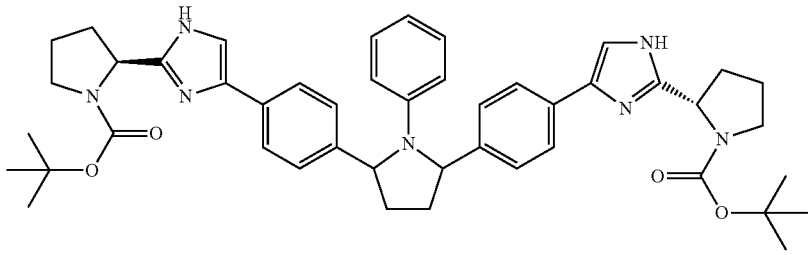 [SMILES: CC(C)(C)OC(=O)N1CCC[C@H]1c1nc(-c2ccc(C3CCC(c4ccc(-c5c[nH]c([C@@H]6CCCN6C(=O)OC(C)(C)C)n5)cc4)N3c3ccccc3)cc2)c[nH]1]

Example 59A (2S,2'S)-tert-butyl 2,2'-(4,4'-(4,4'-(1-phenylpyrrolidine-2,5-diyl)bis(4,1-phenylene))bis(1H-imidazole-4,2-diyl))dipyrrolidine-1-carboxylate Example 42B and aniline were processed using the methods of Examples 39D, 42D, and 42E to provide the title compound as a mixture of stereoisomers. MS (ESI) m/z 770 (M+H)+.

Example 59B 4,4'-{[(2R,5S)-1-phenylpyrrolidine-2,5-diyl]dibenzene-4,1-diyl}bis{2-[(2S)-pyrrolidin-2-yl]-1H-imidazole} (ACD v12)

To the product of Example 59A (30 mg, 0.039 mmol) was added dimethoxyethane (1.5 mL) and a solution of 4N hydrochloric acid in dioxane (3 mL) and the resultant solution stirred at room temperature for 1.5 hr. The solvent was then removed under vacuum and the resultant residue was diluted with acetonitrile and water (0.1% TFA) and purified by reversed phase chromatography (C18), S eluting with 10-100% acetonitrile in water (0.1% TFA) to afford 9.8 mg (44%) of the title compound and 8.5 mg of a mixture of the trans diastereomers (MS (ESI) m/z 570 (M+H)+) that were processed further as described in Example 89. For the title compound: MS (ESI) m/z 570 (M+H)+.

Example 59C methyl {(2S)-1-[(2S)-2-(4-{4-[(2R,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-phenylpyrrolidin-2-yl]phenyl}-1H-imidazol-2-yl)pyrrolidin-1-yl]-3-methyl-1-oxobutan-2-yl}carbamate The product from Example 59B (9.8 mg, 0.012 mmol), (S)-2-(methoxycarbonylamino)-3,3-dimethylbutanoic acid (5.4 mg, 0.031 mmol) and HATU (10.3 mg, 0.027 mmol) in DMSO (1 mL) was added Hunig's base (0.017 mL, 0.098 mmol), and the reaction mixture was stirred at room temperature for 1 hr. The reaction mixture was partitioned between water and ethyl acetate, and the organic layer was dried over MgSO$_4$, filtered and concentrated in vacuo. The crude product was purified by reversed phase chromatography (C18), eluting with 10-100% acetonitrile in water (0.1% TFA) to afford 4.5 mg (41%) of the title compound. 1H NMR (TFA salt) (400 MHz, DMSO-D6) δ ppm 14.50 (bs, 2H), 7.99 (s, 2H), 7.78 (m, 4H), 7.65 (m, 4H), 7.32 (m, 2H), 7.02 (t, J=8.0 Hz, 2H), 6.63 (t, J=7.4 Hz, 1H), 6.40 (d, J=8.2 Hz, 2H), 5.11 (t, J=6.9 Hz, 2H), 4.83 (m, 2H), 4.10 (t, J=7.7 Hz, 2H), 3.82 (m, 6H), 3.48 (s, 6H), 2.40 (m, 2H), 2.08 (m, 2H), 2.00 (m, 6H), 1.85 (m, 2H), 0.85 (m, 2H), 0.80 (m, 12H); MS (ESI) m/z 884 (M+H)+.

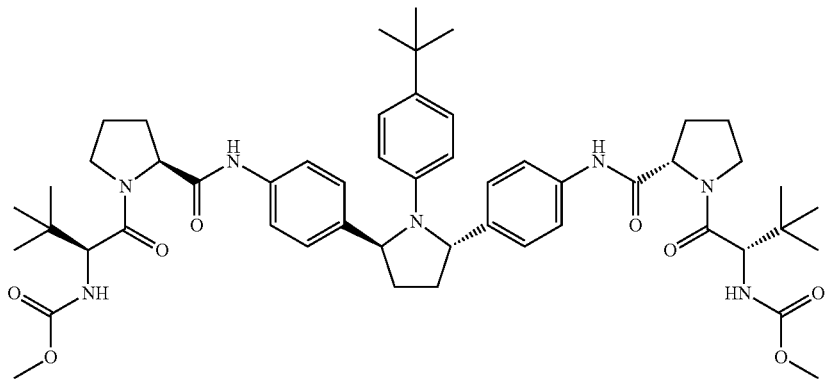 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)(C)C)cc3)N2c2ccc(C(C)(C)C)cc2)cc1)C(C)(C)C]

Example 60 dimethyl ([(2S,5S)-1-(4-tert-butylphenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate

Example 60A dimethyl ([(2S,5S)-1-(4-tert-butylphenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate and dimethyl ([(2R,5R)-1-(4-tert-butylphenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate The product from Example 34D (29.0 mg, 0.05 mmol), (S)-2-(methoxycarbonylamino)-3,3-dimethylbutanoic acid (20.81 mg, 0.110 mmol), EDC (21.09 mg, 0.110 mmol), HOBT (16.85 mg, 0.110 mmol) and N-methylmorpholine (0.027 mL, 0.250 mmol) were combined in DMF (2 mL). The mixture was stirred at room temperature for 3 hours. The reaction mixture was partitioned between ethyl acetate and water. The organic layer was washed with brine twice, dried with sodium sulfate, filtered and evaporated. The residue was purified by chromatography on silica gel eluting with ethyl acetate/hexane (50% to 80%) to give the title compound (32 mg, 69%) as a mixture of trans diastereomers.

Example 60B dimethyl ([(2S,5S)-1-(4-tert-butylphenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate The product from Example 60A was purified by chiral chromatography on a Chiralpak AD-H semi-prep column eluting with a 3:1 mixture of hexane:(2:1 IPA:EtOH). The title compound was the first of the 2 diastereomers to elute. $^1$H NMR (400 MHz, DMSO-D6) δ ppm 0.97 (s, 18H) 1.11 (s, 9H) 1.60-1.65 (m, 2H) 1.79-1.91 (m, 4H) 1.94-2.03 (m, 2H) 2.10-2.18 (m, 2H) 2.44-2.50 (m, 2H) 3.54 (s, 6H) 3.59-3.67 (m, 2H) 3.71-3.82 (m, 2H) 4.21 (d, J=8.89 Hz, 2H) 4.43 (dd, J=7.92, 5.42 Hz, 2H) 5.14 (d, J=6.40 Hz, 2H) 6.18 (d, J=8.89 Hz, 2H) 6.94 (d, J=8.78 Hz, 2H) 7.08 (d, J=8.78 Hz, 2H) 7.13 (d, J=8.57 Hz, 4H) 7.50 (d, J=8.46 Hz, 4H) 9.99 (s, 2H); MS (ESI+) m/z 923 (M+H)+.

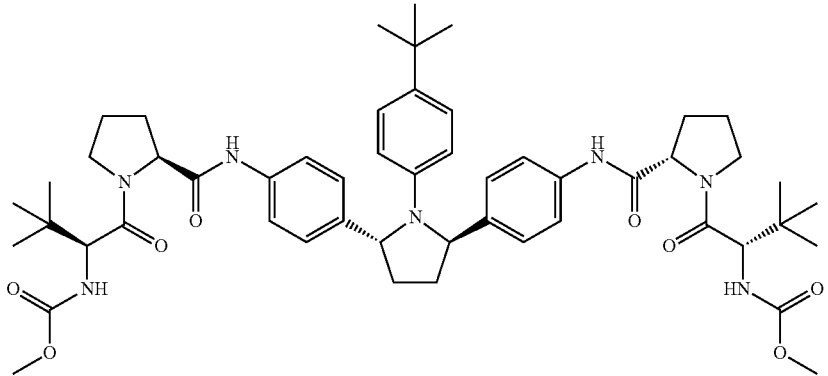 [SMILES: COC(=O)N[C@H](C(=O)N1CCC[C@H]1C(=O)Nc1ccc([C@H]2CC[C@H](c3ccc(NC(=O)[C@@H]4CCCN4C(=O)[C@@H](NC(=O)OC)C(C)(C)C)cc3)N2c2ccc(C(C)(C)C)cc2)cc1)C(C)(C)C]

Example 61 dimethyl ([(2R,5R)-1-(4-tert-butylphenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate The product from Example 60A was purified by chiral chromatography on a Chiralpak AD-H semi-prep column eluting with a 3:1 mixture of hexane:(2:1 IPA:EtOH). The title compound was the second of the 2 diastereomers to elute. $^1$H NMR (400 MHz, DMSO-D6) δ ppm 0.96 (s, 18H) 1.11 (s, 9H) 1.60-1.66 (m, 2H) 1.78-1.92 (m, 4H) 1.94-2.04 (m, 2H) 2.08-2.19 (m, 2H) 2.42-2.50 (m, 2H) 3.54 (s, 6H) 3.59-3.67 (m, 2H) 3.74-3.81 (m, 2H) 4.20 (d, J=8.89 Hz, 2H) 4.43 (dd, J=7.97, 5.37 Hz, 2H) 5.15 (d, J=6.29 Hz, 2H) 6.17 (d, J=8.89 Hz, 2H) 6.94 (d, J=8.89 Hz, 2H) 7.07 (d, J=8.89 Hz, 2H) 7.13 (d, J=8.46 Hz, 4H) 7.50 (d, J=8.57 Hz, 4H) 9.99 (s, 2H); MS (ESI+) m/z 923 (M+H)+.

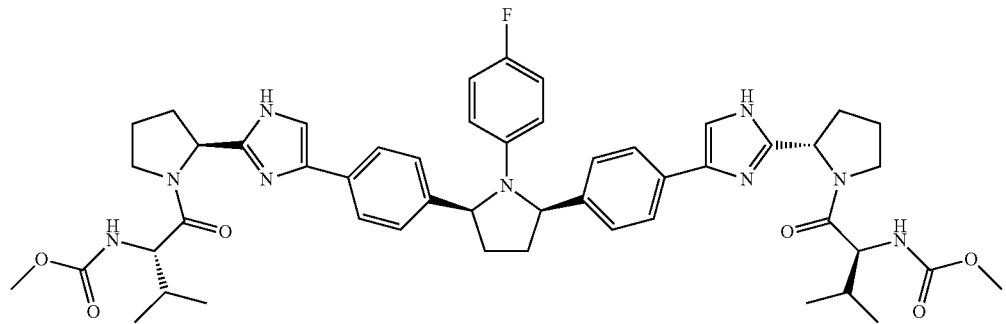

Example 62 methyl {(2S)-1-[(2S)-2-(4-{4-[(2R,5S)-1-(4-fluorophenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

Example 62A 4,4'-{[(2R,5S)-1-(4-fluorophenyl)pyrrolidine-2,5-diyl]dibenzene-4,1-diyl}bis{2-[(2S)-pyrrolidin-2-yl]-1H-imidazole} (ACD v12)

The product from Example 45C (0.15 g, 0.190 mmol) in CH$_2$Cl$_2$ (1 mL) was treated with TFA (1 mL), and the resulting mixture was stirred at rt for 1 h and then concentrated in vacuo. The crude product was purified by column chromatography on C18 silica using a solvent gradient of 10-100% CH$_3$CN in 0.1% aq TFA. The desired cis-pyrrolidine isomer was the second of 2 components to elute. Fractions containing pure cis-isomer were pooled and concentrated in vacuo. The residue was partitioned between saturated aq. NaHCO$_3$ and a 3:1 mixture of CH$_2$Cl$_2$:2-PrOH (3×). The combined organic layers were dried over Na$_2$SO$_4$, filtered and concentrated in vacuo to give the title compound (32 mg, 28%).

Example 62B methyl {(2S)-1-[(2S)-2-(4-{4-[(2R,5S)-1-(4-fluorophenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 62A (32 mg, 54 mmol) was subjected to the method described in Example 5D, substituting (S)-2-(methoxycarbonylamino)-3-methylbutanoic acid for (S)-2-(methoxycarbonyl amino)butanoic acid, to give the title compound (34 mg, 69%). $^1$H NMR (400 MHz, DMSO-D6) δ ppm 0.78-0.93 (m, 12H), 1.78-2.24 (m, 12H), 2.37-2.46 (m, 2H), 3.54 (s, 6H), 3.68-3.87 (m, 4H), 4.66-4.79 (m, 2H), 5.02-5.13 (m, 2H), 6.39 (dd, J=9.16, 4.50 Hz, 2H), 6.81-6.92 (m, 2H), 7.23-7.34 (m, 2H), 7.39-7.80 (m, 12H), 11.67-12.12 (m, 2H); MS (ESI) m/z 902.7 (M+H)$^+$.

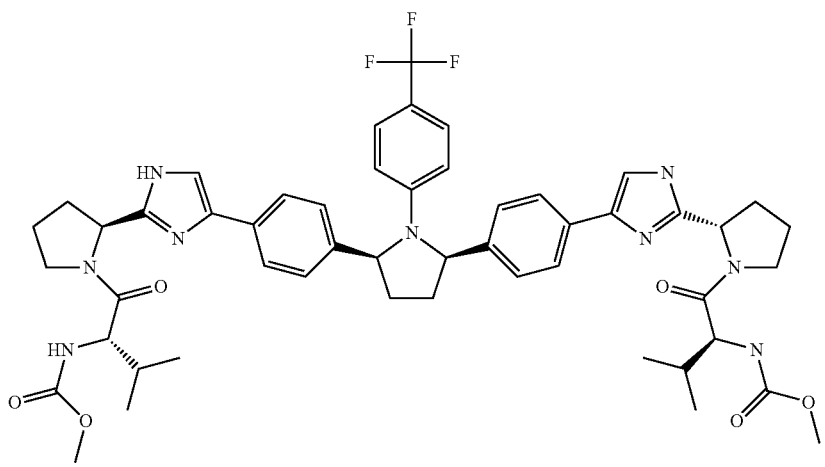 [SMILES: COC(=O)N[C@H](C(=O)N1CCC[C@H]1c1nc(-c2ccc([C@H]3CC[C@@H](c4ccc(-c5c[nH]c([C@@H]6CCCN6C(=O)[C@@H](NC(=O)OC)C(C)C)n5)cc4)N3c3ccc(C(F)(F)F)cc3)cc2)c[nH]1)C(C)C]

Example 63 methyl [(2S)-1-{(2S)-2-[4-(4-{(2R,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate

Example 63A (2R,5S)-2,5-bis(4-bromophenyl)-1-(4-(trifluoromethyl)phenyl)pyrrolidine The product from Example 42B (11.13 g, 20.0 mmol) and 4-(trifluoromethyl)aniline (Aldrich, 32.2 g, 200 mmol) were combined in DMF (50 mL), stirred at 50° C. under nitrogen for 16 hours, cooled and concentrated. The residue was diluted with ethyl acetate, treated with 1M HCl, stirred for 10 minutes and filtered to remove solids. The organic layer of the filtrate was washed with brine, dried ($Na_2SO_4$), filtered and concentrated. The residue was purified by flash chromatography (silica gel, 0 to 1% ethyl acetate/hexane) to give the title compound (1.0 g, 10%) as the second eluting stereoisomer. MS (ESI+) m/z 526 (M+H)$^+$.

Example 63B methyl [(2S)-1-{(2S)-2-[4-(4-{(2R,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate The product from Example 63A (1.0 g, 1.90 mmol) was processed using the methods described in Example 42D, 42E, 42F, and 42G to afford the title compound. $^1$H NMR (free base) (400 MHz, DMSO-$d_6$) δ 0.80-0.95 (m, 12H) 1.83-2.18 (m, 14H) 3.54 (s, 6H) 3.79 (d, J=6.18 Hz, 3H) 3.97-4.15 (m, 3H) 4.87 (d, J=4.88 Hz, 2H) 5.02-5.14 (m, 2H) 6.54 (d, J=8.67 Hz, 2H) 7.15-7.80 (m, 14H) 11.56-12.30 (m, 2H); MS (ESI+) m/z 953 (M+H)$^+$.

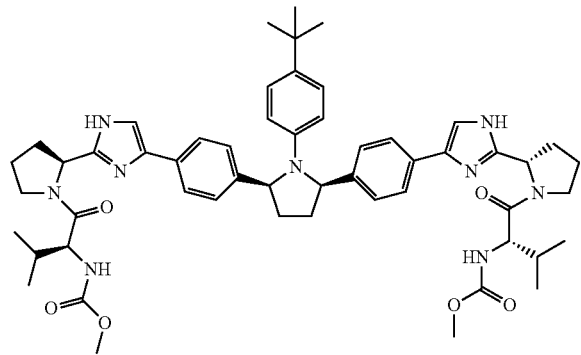 [SMILES: COC(=O)N[C@H](C(=O)N1CCC[C@H]1c1nc(-c2ccc([C@H]3CC[C@@H](c4ccc(-c5c[nH]c([C@@H]6CCCN6C(=O)[C@@H](NC(=O)OC)C(C)C)n5)cc4)N3c3ccc(C(C)(C)C)cc3)cc2)c[nH]1)C(C)C]

Example 64 methyl {(2S)-1-[(2S)-2-(4-{4-[(2R,5S)-1-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

Example 64A (2S,2'R)-2,2'-(4,4'-(4,4'-(1-(4-tert-butylphenyl)pyrrolidine-2,5-diyl)bis(4,1-phenylene))bis(1H-imidazole) bis trifluoroacetate salt Example 42C was processed using the methods of Examples 42D, 42E, and 42F to provide a mixture of cis/trans pyrrolidine isomers. The mixture of stereoisomers was dissolved in 10 ml of 80% (0.1% TFA/water):20% $CH_3CN$ and applied to a 13 g C18 silica column. The column was eluted with a gradient of 0.1% TFA(aq):CH3CN; 80/20 to 50:50 over 25 minutes, giving the cis stereoisomer of the title compound as a light yellow solid trifluoroacetate salt, 88.6 mg, 58%.

Example 64B methyl {(2S)-1-[(2S)-2-(4-{4-[(2R,5S)-1-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 64A was dissolved in 1 ml DMF and added dropwise to a chilled (0-5° C.) solution containing (S)-2-(methoxycarbonylamino)-3-methylbutanoic acid (0.41 g, 0.232 mmole), HOBt (0.036 g, 0.232 mmole), EDAC (0.045 g, 0.232 mmole) and 4-methylmorpholine (0.138 g, 0.150 ml, 1.364 mmole) in 0.5 ml DMF. The pH of the solution was measured and found to be 8. The reaction was stirred a total of 3.5 hr in the ice bath. The reaction mixture was diluted with 50 ml EtOAc and washed with 10% $NaHCO_3$, 10% NaCl, dried over anhydrous $Na_2SO_4$(s), filtered and solvent removed in vacuo leaving a pinkish oil. The oil was dissolved in 5 ml $CH_2Cl_2$ and applied to a 12 g silica gel column. The column was eluted with a gradient of $CH_2Cl_2$/MeOH, 99/1 to 94/6 over 25 minutes giving the title compound as a white solid, 12.5 mg, 11%. 1H NMR (400 MHz, DMSO-D6) d ppm 0.85 (s, 12H) 1.13 (s, 9H) 1.95 (s, 6H) 2.15 (s, 4H) 2.50 (s, 3H) 3.43 (s, 1H) 3.54 (s, 5H) 3.80 (s, 4H) 4.05 (s, 2H) 4.70 (s, 2H) 5.07 (s, 1H) 6.36 (d, J=8.78 Hz, 2H) 7.01 (s, 2H) 7.28 (s, 2H) 7.47 (s, 6H) 7.70 (s, 4H) 11.71 (s, 2H) 12.09 (s, 2H) ESI+:940.8

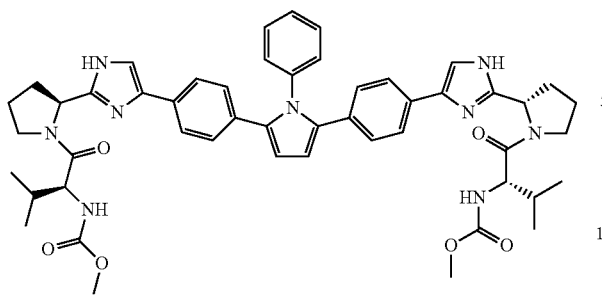

Example 65 methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-phenyl-1H-pyrrol-2-yl]phenyl}-1H-imidazol-2-yl)pyrrolidin-1-yl]-3-methyl-1-oxobutan-2-yl}carbamate

Example 65A (2S,2'R)-tert-butyl 2,2'-(4,4'-(4,4'-(1-phenyl-1H-pyrrole-2,5-diyl)bis(4,1-phenylene))bis(1H-imidazole-4,2-diyl))dipyrrolidine-1-carboxylate Example 26E and aniline were processed using the methods of Examples 19A, 26G, and 26H to provide the title compound (150 mg).

Example 65B (S)-4,4'-(4,4'-(1-phenyl-1H-pyrrole-2,5-diyl)bis(4,1-phenylene))bis(2-((S)-pyrrolidin-2-yl)-1H-imidazole)

To a suspension of the product from Example 65A (186 mg, 0.243 mmol) in dioxane (5 mL) was added HCl/dioxane (5 mL, 20 mmol). The mixture was stirred for 30 minutes and then concentrated under reduced pressure to provide the title compound as a hydrochloride salt.

Example 65C methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-phenyl-1H-pyrrol-2-yl]phenyl}-1H-imidazol-2-yl)pyrrolidin-1-yl]-3-methyl-1-oxobutan-2-yl}carbamate A solution consisting of N1-((ethylimino)methylene)-N3,N3-dimethylpropane-1,3-diamine hydrochloride (90 mg, 0.47 mmol), 1H-benzo[d][1,2,3]triazol-1-ol hydrate (72 mg, 0.47 mmol), (S)-2-(methoxycarbonylamino)-3-methylbutanoic acid (82 mg, 0.47 mmol) and 4-methylmorpholine (0.28 mL, 2.6 mmol) in DMF (1.6 mL) was cooled in an icebath. To this mixture was added dropwise a solution of the product from Example 65B (150 mg, 0.23 mmol) in DMF (0.5 mL). Additional 4-methylmorpholine was added to the mixture until the pH was adjusted to 8. The reaction was stirred for 3.5 hours and then the icebath was removed and the reaction was stirred for an additional 16 hours. Water was then added to the reaction mixture and the resulting precipitate was recovered by filtration. The residue was washed with copious amounts of water followed by diethyl ether. The crude product was purified by chromatography on silica gel eluting with a solvent gradient of 0-5% methanol in $CH_2Cl_2$ to provide the title compound. $^1$H NMR (400 MHz, DMSO-d6) δ 12.12-11.64 (m, 2H), 7.57-7.45 (m, 4H), 7.42-7.36 (m, 2H), 7.36-7.29 (m, 3H), 7.29-7.05 (m, 4H), 7.04-6.91 (m, 4H), 6.54-6.43 (m, 2H), 5.06-4.96 (m, 2H), 4.06-3.96 (m, 2H), 3.84-3.67 (m, 4H), 3.52 (s, 6H), 2.17-1.80 (m, 10H), 0.91-0.76 (m, 12H). MS (ESI; M+H) m/z=881.

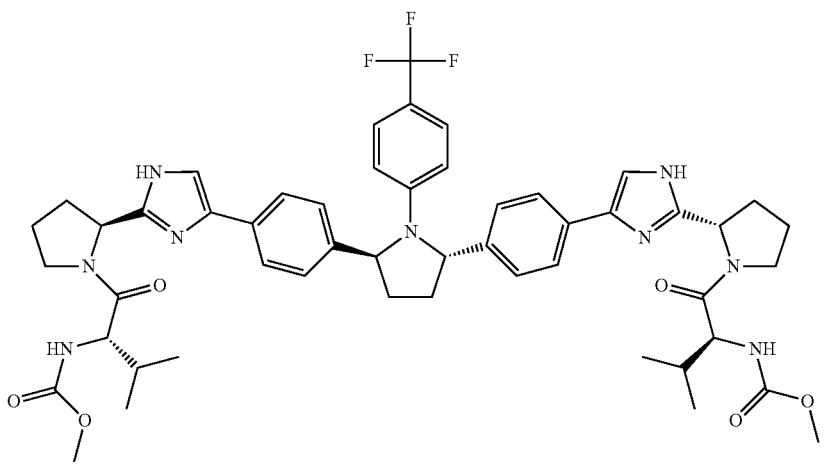 [SMILES: COC(=O)N[C@H](C(=O)N1CCC[C@H]1c1nc(-c2ccc([C@@H]3CC[C@@H](c4ccc(-c5c[nH]c([C@@H]6CCCN6C(=O)[C@@H](NC(=O)OC)C(C)C)n5)cc4)N3c3ccc(C(F)(F)F)cc3)cc2)c[nH]1)C(C)C]

Example 66 methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate

Example 66A (2R,5R)-2,5-bis(4-bromophenyl)-1-(4-(trifluoromethyl)phenyl)pyrrolidine and (2S,5S)-2,5-bis(4-bromophenyl)-1-(4-(trifluoromethyl)phenyl)pyrrolidine The product from Example 42B (11.13 g, 20.0 mmol) and 4-(trifluoromethyl)aniline (32.2 g, 200 mmol) were combined in DMF (50 mL). The mixture was stirred at 50° C. under nitrogen overnight. The reaction mixture was evaporated and the residue was diluted with ethyl acetate, treated with 1M HCl, stirred for 10 minutes, and filtered to remove the solid. The organic layer of filtrate was washed with brine, dried with sodium sulfate, filtered and evaporated. The residue was purified by chromatography on silica gel eluting with ethyl acetate/hexane (0 to 1%). The title compounds (500 mg, 5%) were eluted as the first of 2 stereoisomers and were obtained as a mixture of trans diastereomers.

Example 66B (2R,5R)-2,5-bis(4-(4,4,5,5-tetramethyl-1,3,2-dioxaborolan-2-yl)phenyl)-1-(4-(trifluoromethyl)phenyl)pyrrolidine and (2S,5S)-2,5-bis(4-(4,4,5,5-tetramethyl-1,3,2-dioxaborolan-2-yl)phenyl)-1-(4-(trifluoromethyl)phenyl)pyrrolidine The products from Example 66A (500 mg, 0.952 mmol), bis(pinacolato)diboron (725 mg, 2.86 mmol), potassium acetate (374 mg, 3.81 mmol) and bis(triphenylphosphine)palladium(II) chloride (66.8 mg, 0.095 mmol) were combined in 1,2-dimethoxyethane (10 mL). The mixture was purged with nitrogen for 15 minutes and stirred at 85° C. for 2 hours. The reaction mixture was partitioned between ethyl acetate and 1M HCl. The organic layer was washed with saturated sodium bicarbonate, brine, dried with sodium sulfate, filtered and evaporated. The residue was purified by chromatography on silica gel eluting with hexane to ethyl acetate/hexane (10%) to give a solid which was triturated with dichloromethane/hexane (1:3) to give the title compounds (370 mg, 63%).

Example 66C (2S,2'S)-tert-butyl 2,2'-(4,4'-(4,4'-((2R,5R)-1-(4-(trifluoromethyl)phenyl)pyrrolidine-2,5-diyl)bis(4,1-phenylene))bis(1H-imidazole-4,2-diyl))dipyrrolidine-1-carboxylate and (2S,2'S)-tert-butyl 2,2'-(4,4'-(4,4'-((2S,5S)-1-(4-(trifluoromethyl)phenyl)pyrrolidine-2,5-diyl)bis(4,1-phenylene))bis(1H-imidazole-4,2-diyl))dipyrrolidine-1-carboxylate The products from Example 66B (257 mg, 0.415 mmol), the product from Example 26D (341 mg, 1.079 mmol), potassium phosphate tribasic (352 mg, 1.660 mmol) and 1,1'-bis(di-tert-butylphosphine)ferrocene palladium dichloride (27.0 mg, 0.041 mmol) were combined in THF (4.5 mL)/water (1.5 mL). The mixture was purged with nitrogen for 15 minutes and stirred at 70° C. for 6 hours. The reaction mixture was partitioned between ethyl acetate and saturated sodium bicarbonate. The organic layer was washed with brine, dried with sodium sulfate, filtered and evaporated. The residue was purified by chromatography on silica gel eluting with methanol/dichloromethane (1% to 3%) to give the title compounds (286 mg, 82%) as a solid.

Example 66D (S)-4,4'-(4,4'-((2R,5R)-1-(4-(trifluoromethyl)phenyl)pyrrolidine-2,5-diyl)bis(4,1-phenylene))bis(2-((S)-pyrrolidin-2-yl)-1H-imidazole)

and (S)-4,4'-(4,4'-((2S,5S)-1-(4-(trifluoromethyl)phenyl)pyrrolidine-2,5-diyl)bis(4,1-phenylene))bis(2-((S)-pyrrolidin-2-yl)-1H-imidazole)

To the products from Example 66C (385 mg, 0.459 mmol) in dioxane (6 mL) was added 4M hydrochloric acid in dioxane (10 mL, 40.0 mmol) and the reaction stirred at room temperature for 1 hour. The solvent was evaporated under high vacuum to give the title compounds (approx. 360 mg) as hydrochloride salts.

Example 66E methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate and methyl [(2S)-1-{(2S)-2-[4-(4-{(2R,5R)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate The product from Example 66D (360 mg, 0.459 mmol), (S)-2-(methoxycarbonylamino)-3-methylbutanoic acid (161 mg, 0.919 mmol), 4-methylmorpholine (0.404 mL, 3.68 mmol), N1-((ethylimino)methylene)-N3,N3-dimethylpropane-1,3-diamine hydrochloride (194 mg, 1.011 mmol) and 1H-benzo[d][1,2,3]triazol-1-ol hydrate (155 mg, 1.011 mmol) were combined in DMF (10 mL). The mixture was stirred at room temperature for 20 hours. The reaction mixture was partitioned between ethyl acetate and water. The organic layer was washed with saturated sodium bicarbonate, brine twice, dried with sodium sulfate, filtered and evaporated. The residue was purified by chromatography on silica gel eluting with methanol/dichloromethane (1% to 6%) to give the title compounds (223 mg, 51%) as a solid.

Example 66F methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate The product from Example 66E was purified by chiral chromatography on a Chiralpak IB column eluting with a mixture of hexane/THF/methanol (8/1/1). The title compound was the first of the 2 diastereomers to elute. $^1$H NMR (400 MHz, DMSO-D6) δ ppm 0.78-0.90 (m, 12H) 1.71-1.77 (m, 2H) 1.86-2.02 (m, 6H) 2.09-2.18 (m, 4H) 2.51-2.54 (m, 2H) 3.53 (s, 6H) 3.74-3.84 (m, 4H) 4.04 (t, J=8.35 Hz, 2H) 5.06 (dd, J=6.83, 3.14 Hz, 2H) 5.28-5.41 (m, 2H) 6.41 (d, J=8.67 Hz, 2H) 7.12-7.33 (m, 8H) 7.36-7.72 (m, 6H) 11.62-12.13 (m, 2H); MS (ESI+) m/z 953 (M+H)+.

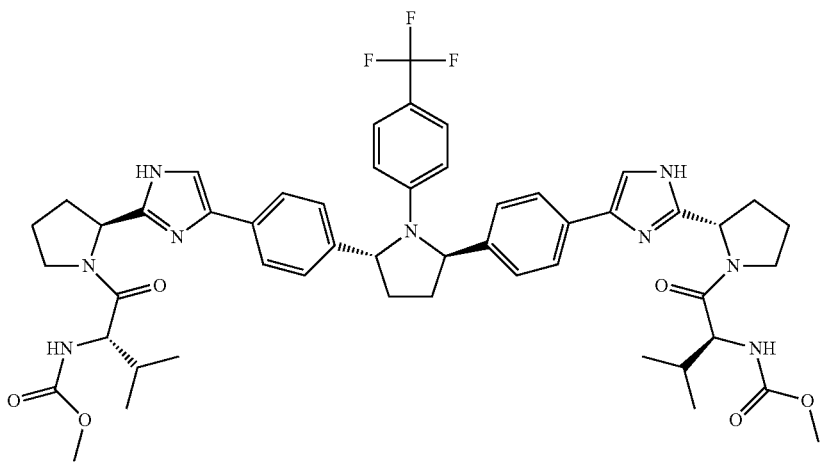 [SMILES: COC(=O)N[C@H](C(=O)N1CCC[C@H]1c1nc(-c2ccc([C@H]3CC[C@H](c4ccc(-c5c[nH]c([C@@H]6CCCN6C(=O)[C@@H](NC(=O)OC)C(C)C)n5)cc4)N3c3ccc(C(F)(F)F)cc3)cc2)c[nH]1)C(C)C]

Example 67 methyl [(2S)-1-{(2S)-2-[4-(4-{(2R,5R)-5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(trifluoromethyl)phenyl]pyrrolidin-2-yl}phenyl)-1H-imidazol-2-yl]pyrrolidin-1-yl}-3-methyl-1-oxobutan-2-yl]carbamate The product from Example 66E was purified by chiral chromatography on a Chiralpak IB S column eluting with a mixture of hexane/THF/methanol (8/1/1). The title compound was the second of the 2 diastereomers to elute. $^1$H NMR (400 MHz, DMSO-D6) δ ppm 0.79-0.91 (m, 12H) 1.71-1.77 (m, 2H) 1.88-2.01 (m, 6H) 2.08-2.17 (m, 4H) 2.51-2.54 (m, 2H) 3.53 (s, 6H) 3.74-3.82 (m, 4H) 4.05 (t, J=8.40 Hz, 2H) 5.00-5.13 (m, 2H) 5.29-5.40 (m, 2H) 6.40 (d, J=8.57 Hz, 2H) 7.12-7.31 (m, 8H) 7.36-7.72 (m, 6H) 11.52-12.15 (m, 2H); MS (ESI+) m/z 953 (M+H)+.

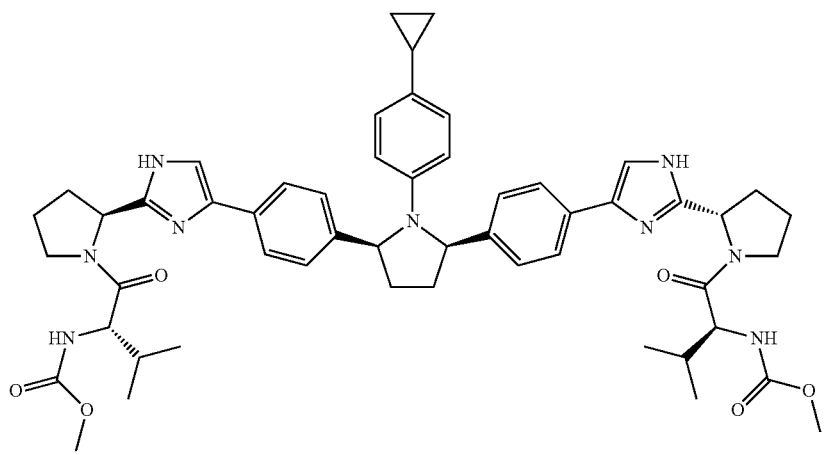 [SMILES: COC(=O)N[C@H](C(=O)N1CCC[C@H]1c1nc(-c2ccc([C@H]3CC[C@@H](c4ccc(-c5c[nH]c([C@@H]6CCCN6C(=O)[C@@H](NC(=O)OC)C(C)C)n5)cc4)N3c3ccc(C4CC4)cc3)cc2)c[nH]1)C(C)C]

Example 68 methyl {(2S)-1-[(2S)-2-(4-{4-[(2R,5S)-1-(4-cyclo-propylphenyl)-5-(4-{2-[(2S)-1-{(2S)-2-[(methoxy-carbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

Example 68A 2,5-bis(4-bromophenyl)-1-(4-cyclopropylphenyl)pyrrolidine

The product from Example 42B (3.14 g, 5.64 mmol) and 4-cyclopropylaniline (6.01 g, 45.2 mmol) were combined in DMF (20 mL). The mixture was stirred at 50° C. under nitrogen for 3 hours. The reaction mixture was partitioned between 1M HCl and ethyl acetate. The organic layer was washed with brine three times, dried with sodium sulfate, filtered and evaporated. The residue was purified by chromatography on silica gel eluting with ethyl acetate/hexane (0.5% to 1%) to give the title compound (2.12 g, 76%) as a mixture of stereoisomers as a sticky solid.

Example 68B 1-(4-cyclopropylphenyl)-2,5-bis(4-(4,4,5,5-tetram-ethyl-1,3,2-dioxaborolan-2-yl)phenyl)pyrrolidine The product from Example 68A (2.12 g, 4.26 mmol), bis(pinacolato)biboron (3.25 g, 12.79 mmol), potassium acetate (1.674 g, 17.05 mmol) and bis(triphenylphosphine)palladium (II) chloride (0.299 g, 0.426 mmol) were combined in 1,2-dimethoxyethane (40 mL). The mixture was purged with nitrogen for 15 minutes and stirred at 85° C. for 2 hours. The reaction mixture was partitioned between ethyl acetate and 1M HCl. The organic layer was washed with saturated sodium bicarbonate, brine, dried with sodium sulfate, filtered and evaporated. The residue was purified by chromatography on silica gel eluting with hexane to ethyl acetate/hexane (10%) to give a solid that was triturated with diethyl ether/hexane (1/3) to give the title compound (1.05, 42%) as a mixture of stereoisomers as a white solid.

Example 68C (2S,2'S)-tert-butyl 2,2'-(4,4'-(4,4'-(1-(4-cyclopropy-lphenyl)pyrrolidine-2,5-diyl)bis(4,1-phenylene))bis(1H-imidazole-4,2-diyl))dipyrrolidine-1-carboxylate The product from Example 68B (1.04 g, 1.759 mmol), the product from Example 26D (1.446 g, 4.57 mmol), PdCl$_2$(dppf) (0.129 g, 0.176 mmol) and 1.0 M sodium carbonate (4.57 mL, 4.57 mmol) were combined in the mixed solvent of ethanol (5 mL)/toluene (5 mL). The mixture was purged with nitrogen for 15 minutes and stirred at 80° C. for 2 hours. The reaction mixture was partitioned between ethyl acetate and saturated sodium bicarbonate, brine, dried with sodium sulfate, filtered and evaporated. The residue was purified by chromatography on silica gel eluting with methanol/dichloromethane (1% to 3%) to give the title compound (1.28 g, 90%) as a mixture of stereoisomers as a solid.

Example 68D (S)-4,4'-(4,4'-((2R,5S)-1-(4-cyclopropylphenyl)pyr-rolidine-2,5-diyl)bis(4,1-phenylene))bis(2-((S)-pyr-rolidin-2-yl)-1H-imidazole)

The product from Example 68C (1.27 g, 1.568 mmol) was dissolved in dichloromethane (12 mL). The mixture was cooled to 0° C. and trifluoroacetic acid (8 mL, 104 mmol) was added slowly. The mixture was warmed to room temperature and stirred for 1 h. The solvent was evaporated and the residue was purified by chromatography on silica gel eluting with methanol/dichloromethane (1% to 10%). The title compound (310 mg, 32%) eluted as the second of 2 stereoisomers.

Example 68E methyl {(2S)-1-[(2S)-2-(4-{4-[(2R,5S)-1-(4-cyclo-propylphenyl)-5-(4-{2-[(2S)-1-{(2S)-2-[(methoxy-carbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product of Example 68D (90 mg, 0.148 mmol), (S)-2-(methoxycarbonylamino)-3-methylbutanoic acid (51.7 mg, 0.295 mmol), 4-methylmorpholine (0.130 mL, 1.181 mmol), N1-((ethylimino)methylene)-N3,N3- dimethylpropane-1,3- diamine hydrochloride (62.2 mg, 0.325 mmol) and 1H-benzo[d][1,2,3]triazol-1-ol hydrate (49.7 mg, 0.325 mmol) were combined in DMF (10 mL). The mixture was stirred at room temperature for 2 hours. The reaction mixture was partitioned between ethyl acetate and water. The organic layer was washed with saturated sodium bicarbonate, brine twice, dried with sodium sulfate, filtered and evaporated. The residue was purified by chromatography on silica gel eluting with methanol/dichloromethane (1% to 4%) to give the title compound (40 mg, 29%) as a solid. $^1$H NMR (400 MHz, DMSO-D6) δ ppm 0.39-0.47 (m, 2H) 0.71-0.78 (m, 2H) 0.82-0.92 (m, 12H) 1.65-1.72 (m, 1H) 1.82-2.03 (m, 8H) 2.09-2.17 (m, 4H) 2.40-2.45 (m, 2H) 3.54 (s, 6H) 3.75-3.83 (m, 4H) 4.02-4.09 (m, 2H) 4.64-4.75 (m, 2H) 5.03-5.11 (m, 2H) 6.32 (d, J=8.67 Hz, 2H) 6.73 (d, J=8.35 Hz, 2H) 7.29 (d, J=8.02 Hz, 2H) 7.37-7.81 (m, 10H) 11.47-12.17 (m, 2H); MS (ESI+) m/z 924.7 (M+H)+.

mately 5 minutes, maintaining the internal temperature <25° C. After the transfer was complete, the slurry was held at 15° C. for 5 min and then the temperature was maintained at 23° C. for 3 h. After reaction completion, the solution was cooled to 5° C., and methanol (31.6 mL, 780 mmol) was added slowly to maintain a temperature <20° C. (note: vigorous evolution of hydrogen). The hazy solution was mixed for an additional 1 h in order to ensure complete quenching. The hazy solution was diluted with EtOAc (500 mL) and 1 M HCl (220 mL). The phases were partitioned, and the organic phase was washed successively with 1 M HCl (2×220 mL), H$_2$O (110 mL), and 25% aq. NaCl (110 mL). The organic layer was concentrated in vacuo, then dissolved in EtOAc, filtered, concentrated and crystallized from EtOAc/hexane to provide the title compound (16.92 g; 100% ee; 47% isolated yield).

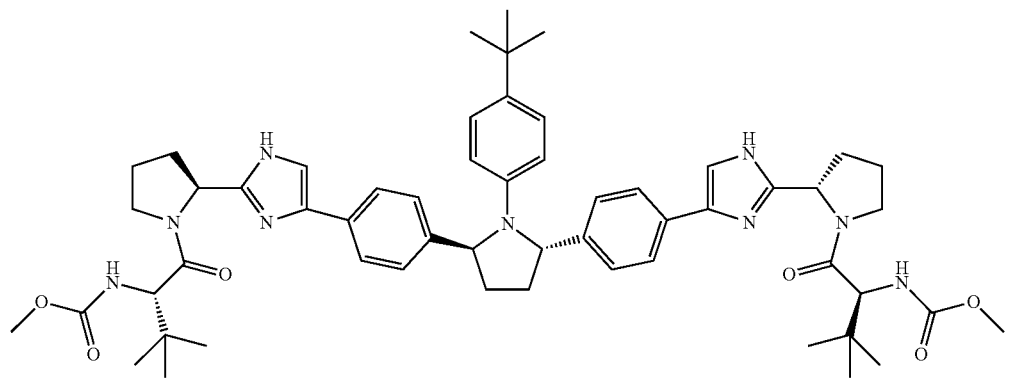

Example 69 methyl {(2S)-1-[(2S)-2-(4-{4-[(2S,5S)-1-(4-tert-butylphenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate

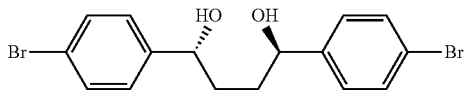 [SMILES: O[C@H](CC[C@@H](O)c1ccc(Br)cc1)c1ccc(Br)cc1]

Example 69A (1R,4R)-1,4-bis(4-bromophenyl)butane-1,4-diol

To (S)-(−)-alpha, alpha-diphenyl-2-pyrrolidinemethanol (3.81 g, 15.04 mmol) was added THF (140 mL) at 23° C. The thin slurry was treated with trimethyl borate (2.189 mL, 19.63 mmol) to form a clear solution. After stirring for 1.5 h, the solution was cooled to 10-15° C., and N,N-diethylaniline borane (33.1 mL, 186 mmol) was added over 5-10 min via a syringe. A slight exotherm and H$_2$ evolution were observed. To a separate vessel was charged Example 26E (35.045 g, 88 mmol), followed by THF (140 mL), to form a slurry. The slurry was cooled to 10° C. The cooled borane solution was transferred via cannula into the dione slurry over approxi-

Example 69B (2S,5S)-2,5-bis(4-bromophenyl)-1-(4-tert-butylphenyl)pyrrolidine To a mixture of the product from Example 69A (0.60 g, 1.500 mmol) in anhydrous CH$_2$Cl$_2$ (15 mL) at 0° C. was added Et$_3$N (0.627 mL, 4.50 mmol), and the resulting mixture was stirred at 0° C. for 10 min until a homogenous solution was obtained. To the cooled solution was added methanesulfonyl chloride (0.292 mL, 3.75 mmol) dropwise, and the resulting mixture was stirred at 0° C. for 1.5 h until the reaction was complete as determined by TLC (1:1 EtOAc:hexanes). Solvent was removed in vacuo to give a solid, which was dried in vacuo. The solid was dissolved in anhydrous DMF (5 mL), and 4-tert-butylaniline (2.39 mL, 15 mmol) was added. The resulting mixture was stirred at 40° C. for 4 h and then was partitioned between 1N aq. HCl (30 mL) and EtOAc (30 mL). The organic layer was washed with H$_2$O and dried over Na$_2$SO$_4$. The drying agent was filtered off, the solvent was removed in vacuo, and the crude product was purified by column chromatography on silica gel using a solvent gradient of 0-20% EtOAc in hexanes. The title compound was obtained as a colorless solid (0.71 g, 92%). $^1$H NMR indicated this material was a 87:13 mixture of trans:cis pyrrolidine isomers.

Example 69C (2S,5S)-1-(4-tert-butylphenyl)-2,5-bis(4-(4,4,5,5-tetramethyl-1,3,2-dioxaborolan-2-yl)phenyl)pyrrolidine The product from Example 69B (0.71 g, 1.38 mmol) was subjected to the conditions described in Example 42D to give the title compound as a colorless solid (0.56 g, 66%).

Example 69D (2S,2'S)-tert-butyl 2,2'-(4,4'-(4,4'-((2S,5S)-1-(4-tert-butylphenyl)pyrrolidine-2,5-diyl)bis(4,1-phenylene))bis(1H-imidazole-4,2-diyl))dipyrrolidine-1-carboxylate The product from Example 69C (0.55 g, 0.91 mmol) was subjected to the conditions described in Example 42E to give the title compound (0.27 g, 36%).

Example 69E (S)-4,4'-(4,4'-((2S,5S)-1-(4-tert-butylphenyl)pyrrolidine-2,5-diyl)bis(4,1-phenylene))bis(2-((S)-pyrrolidin-2-yl)-1H-imidazole)

A solution of the product from Example 69D (0.27 g, 0.33 mmol) in a 1:1 mixture of $CH_2Cl_2$:TFA (4 mL) was stirred at rt for 40 min and then concentrated in vacuo. The residue was partitioned between saturated aq $NaHCO_3$ and a 3:1 mixture of $CH_2Cl_2$:2-PrOH (2×), and the combined organic layers were dried over $Na_2SO_4$. The drying agent was filtered off, and the solvent was removed in vacuo to give the title compound as an amorphous solid (0.18 g, 87%).

Example 69F methyl {(2S)-1-[(2S)-2-(4-{4-[(2S,5S)-1-(4-tert-butylphenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate To a mixture of the product from Example 69E (0.10 g, 0.16 mmol) and (S)-2-(methoxycarbonylamino)-3,3-dimethylbutanoic acid (76 mg, 0.40 mmol) in anhydrous DMSO (1.6 mL) was added HATU (152 mg, 0.40 mmol) and Hunig's base (84 μL, 0.48 mmol). The resulting mixture was stirred at rt for 90 min, and was then partitioned between $H_2O$ (5 mL) and EtOAc (2×5 mL). The combined organic layers were concentrated in vacuo, and the residue was dissolved in MeOH (1 mL). To the solution was added solid $K_2CO_3$ (1-2 mg) and the resulting mixture was stirred at rt for 30 min. The mixture was filter and concentrated in vacuo, and the crude product was purified by column chromatography on silica gel using a solvent gradient of 0-5% MeOH in $CH_2Cl_2$ to give the title compound (0.12 g, 78%). $^1$H NMR (400 MHz, DMSO-D6) δ ppm 0.94 (s, 18H), 1.10 (s, 9H), 1.63-1.77 (m, 2H), 1.84-2.25 (m, 10H), 3.55 (s, 6H), 3.66-3.87 (m, 2H), 4.16-4.28 (m, 2H), 5.03-5.12 (m, 2H), 5.15-5.28 (m, 2H), 6.22 (d, 8.46 Hz, 2H), 6.93 (d, J=8.67 Hz, 2H), 7.07 (d, 2H), 7.15 (d, J=8.13 Hz, 4H), 7.23 (d, 1H), 7.38 (d, J=1.41 Hz, 2H), 7.52 (d, 1H), 7.62 (d, J=8.02 Hz, 4H), 11.66-12.10 (m, 2H). MS (ESI) m/z 969.1 (M+H)$^+$.

Example 70 dimethyl ([(2S,3R,4R,5S)-1-(4-fluorophenyl)-3,4-dimethoxypyrrolidine-2,5-diyl]bis{benzene-4,1-diylcarbamoyl(2S)pyrrolidine-2,1-diyl[(2S)-3-methyl-1-oxobutane-1,2-diyl]}biscarbamate

Example 70A

Tert-butyl 4,4'-((2S,3R,4R,5S)-1-(4-fluorophenyl)-3,4-dihydroxypyrrolidine-2,5-diyl)bis(4,1-phenylene) dicarbamate A solution of 3,4-O-isopropylidene-D-mannitol (444 mg, 2.0 mmol) in 2:1 methanol-dichloromethane (8 mL) was treated with iodobenzene diacetate (1.54 g, 4.79 mmol) followed by stirring at RT for 5 h. The mixture was concentrated in vacuo to remove organic solvents, and the residue was suspended in 0.1 M sulfuric acid solution (4 mL) followed by stirring at RT for 18 h. The mixture was adjusted to pH 6 by addition of solid sodium bicarbonate. The mixture was then sequentially treated with 4-fluoroaniline (383 μL, 444 mg, 4.00 mmol), 4-(tert-butoxycarbonylamino)phenylboronic acid (853 mg, 3.60 mmol) and hexafluoroisopropyl alcohol (8 mL). The solution was warmed at 50° C. for 2 h. The solution was cooled and concentrated in vacuo. The mixture was dissolved in ethyl acetate and extracted with water, 0.33 M tribasic potassium phosphate solution, and saturated sodium chloride solution. Drying ($Na_2SO_4$) and concentration in vacuo afforded a brown solid, which was chromatographed over a 100 g silica gel cartridge, eluting with 5-70% ethyl acetate in dichloromethane. These procedures afforded the title compound (770 mg, 67%) as a nearly white solid. $^1$H NMR (400 MHz, CDCl$_3$) δ 7.35 (d, J=8.3 Hz, 4H), 7.11 (d, J=8.4 Hz, 4H), 6.67 (t, J=8.8 Hz, 2H), 6.51 (s, 2H), 6.22 (dd, J=9.1, 4.3 Hz, 2H), 5.15 (d, J=6.3 Hz, 2H), 4.26 (d, J=5.7 Hz, 2H), 1.51 (s, 18H). MS+ESI m/z (rel abundance) 580 (100, M+H), 602 (15, M+Na), 1159 (18, 2M+H).

Example 70B (2S,3R,4R,5S)-2,5-bis(4-(tert-butoxycarbonylamino)phenyl)-1-(4-fluorophenyl)pyrrolidine-3,4-diyl diacetate A solution of the compound of Example 70A (314 mg, 0.54 mmol), triethylamine (227 μL, 164 mg, 1.65 mmol), and DMAP (13 mg, 0.11 mmol) in 1:1 ethyl acetate-tetrahydrofuran (2.8 mL) was treated with acetic anhydride (128 μL, 138 mg, 1.35 mmol) followed by stirring at RT for 1 h. The mixture was treated with water followed by stirring at RT for 30 min. The mixture was diluted with ethyl acetate and extracted with water, saturated sodium bicarbonate solution

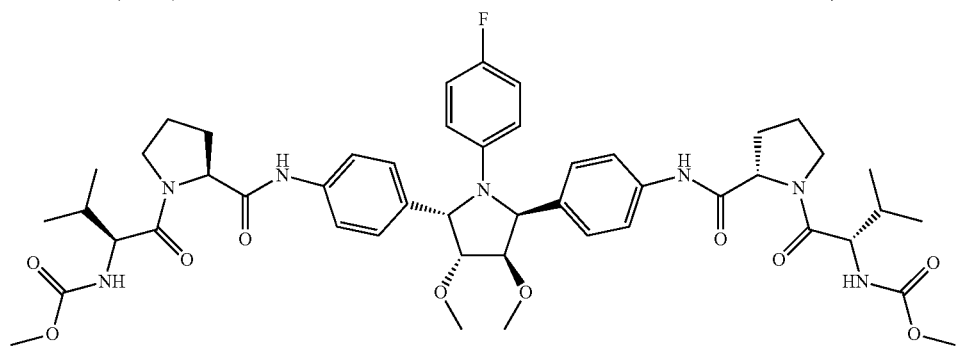

and saturated sodium chloride solution. Drying (Na$_2$SO$_4$) and concentration in vacuo afforded the title compound (330 mg, 92%) as a cream-colored solid, sufficiently pure for further use. $^1$H NMR (400 MHz, CDCl$_3$) δ 7.32 (d, J=8.4 Hz, 4H), 7.07 (d, J=8.5 Hz, 4H), 6.66 (t, J=8.8 Hz, 2H), 6.47 (s, 2H), 6.25 (dd, J=9.2, 4.3 Hz, 2H), 5.53 (dd, J=5.5, 1.9 Hz, 2H), 5.46 (d, J=7.2 Hz, 2H), 1.83 (s, 6H), 1.51 (s, 18H). MS+ESI m/z (rel abundance) 664 (100, M+H).

Example 70C (2S,3R,4R,5S)-2,5-bis(4-aminophenyl)-1-(4-fluorophenyl)pyrrolidine-3,4-diyl diacetate dihydrochloride A solution of 4 N hydrogen chloride in dioxane (8 mL) was treated with the compound of Example 70B (136 mg, 0.21 mmol) followed by stirring at RT for 2 h. (During this time, the mono-deprotection product started precipitating, and ca. 4 mL of dichloromethane was added to speed the reaction by solublizing the mono-hydrochloride) The mixture was added to excess ether and the product collected by filtration and washed with ether. After drying in a vacuum oven at 50° C. for 18 h, these procedures afforded the title compound (92 mg, 84%) as an off-white powder. $^1$H NMR (400 MHz, DMSO-d$_6$) δ 7.28 (m, 8H), 6.81 (t, J=8.9 Hz, 2H), 6.33 (m, 2H), 5.63 (m, 2H), 5.51 (dd, J=5.5, 1.9 Hz, 2H), 1.79 (s, 6H).

Example 70D (2S,3R,4R,5S)-2,5-bis(4-aminophenyl)-1-(4-fluorophenyl)pyrrolidine-3,4-diol In a 25-mL round bottom flask, was dissolved Example 70C (160.5 mg, 0.299 mmol) in MeOH (3 mL), added potassium carbonate (165 mg, 1.197 mmol), and stirred at 25° C. for 1.5 hr. Filtered off the solids, washed with MeOH, and concentrated the filtrate by rotary evaporation to dryness. Purified by flash chromatography (silica gel, Alltech Extract-Clean 10 g column, 8% MeOH/CH$_2$Cl$_2$) to afford the title compound as a yellow solid (85 mg, 75%). $^1$H NMR (400 MHz, DMSO-D6) δ ppm 4.10-4.19 (m, 2H), 4.73 (d, J=2.71 Hz, 2H), 4.80-4.88 (m, 2H), 4.84 (s, 4H), 6.21 (dd, J=9.22, 4.55 Hz, 2H), 6.45 (d, J=8.35 Hz, 4H), 6.72 (t, J=8.95 Hz, 2H), 6.77 (d, J=8.24 Hz, 4H); MS (DCI+) 380 (M+H)$^+$.

Example 70E 4,4'-((2S,3R,4R,5S)-1-(4-fluorophenyl)-3,4-dimethoxypyrrolidine-2,5-diyl)dianiline In an oven-dried 25-mL round bottom flask, dissolved the product of Example 70D (83.6 mg, 0.220 mmol) in anhydrous THF (3 mL) under nitrogen, cooled to 0° C. in an ice water bath, added 60 wt % NaH dispersion in mineral oil (18.51 mg, 0.463 mmol), and stirred at 0° C. for 15 min. Then added iodomethane (0.028 mL, 0.441 mmol) via microsyringe and stirred at 0° C. for 1 hr, then at 25° C. for 3 hr. Removed the solvent by rotary evaporation and dried the residue in vacuo. Purified by flash chromatography (silica gel, Alltech Extract-Clean 10 g column, gradient of 1% to 2% MeOH/CH$_2$Cl$_2$) to afford the title compound as a yellow solid (59 mg, 66%). $^1$H NMR (400 MHz, DMSO-D6) δ ppm 3.25 (s, 6H), 3.92-4.17 (m, 2H), 4.91 (s, 4H), 5.07-5.24 (m, 2H), 6.28 (dd, J=9.16, 4.50 Hz, 2H), 6.47 (d, J=8.46 Hz, 4H), 6.73 (t, J=8.95 Hz, 2H), 6.86 (d, J=8.35 Hz, 4H); MS (DCI+) m/z 408 (M+H)$^+$.

Example 70F (2S,2' S)-tert-butyl 2,2'-(4,4'-((2S,3R,3R,5S)-1-(4-fluorophenyl)-3,4-dimethoxypyrrolidine-2,5-diyl)bis(4,1-phenylene))bis(azanediyl)bis(oxomethylene)dipyrrolidine-1-carboxylate In a 10-mL round bottom flask, dissolved the product of Example 70E (57 mg, 0.140 mmol) in anhydrous DMSO (1.2 mL) under nitrogen, added (S)-1-(tert-butoxycarbonyl)pyrrolidine-2-carboxylic acid (76 mg, 0.350 mmol), HATU (137 mg, 0.350 mmol), and diisopropylethylamine (0.073 mL, 0.420 mmol), and stirred the bright yellow solution at 25° C. for 1 hr. Diluted the reaction with EtOAc (50 mL), washed with H$_2$O (3×25 mL) and brine (15 mL), dried the organic phase over anhydrous MgSO$_4$, filtered, and concentrated by rotary evaporation to a yellow residue. Purified by flash chromatography (silica gel, Alltech Extract-Clean 10 g column, 3% MeOH/CH$_2$Cl$_2$) to afford the title compound as a yellow solid (118 mg). $^1$H NMR (400 MHz, DMSO-D6) δ ppm 1.29 (s, 11H), 1.39 (s, 7H), 1.72-1.95 (m, 6H), 2.08-2.25 (m, 2H), 3.29 (s, 6H), 3.35-3.49 (m, 3H), 4.12 (d, J=0.87 Hz, 2H), 4.15-4.29 (m, 2H), 5.30-5.45 (m, 2H), 6.28 (dd, J=9.22, 4.45 Hz, 2H), 6.75 (t, J=8.89 Hz, 2H), 7.19 (d, J=8.35 Hz, 4H), 7.50 (t, J=8.89 Hz, 4H), 9.70-10.14 (m, 2H); MS (APCI+) m/z 802 (M+H)$^+$.

Example 70G (2S,2' S)—N,N'-(4,4'-((2S,3R,4R,5S)-1-(4-fluorophenyl)-3,4-dimethoxypyrrolidine-2,5-diyl)bis((4,1-phenylene))dipyrrolidine-2-carboxamide Dissolved the product of Example 70F (112 mg, 0.140 mmol) in anhydrous CH$_2$Cl$_2$ (1 mL) under nitrogen, added TFA (1 mL), and stirred at 25° C. for 30 min. Removed the solvent by rotary evaporation, redissolved in 1:5 v/v CH$_2$Cl$_2$/hexanes, and concentrated in vacuo. Took up the residue in EtOAc (50 mL), washed with sat'd aq NaHCO$_3$ (2×15 mL), dried the organic phase over anhydrous MgSO$_4$, filtered, and concentrated by rotary evaporation to afford the title compound as a yellow solid (72 mg, 84%). $^1$H NMR (400 MHz, DMSO-D6) δ ppm 1.57-1.69 (m, 4H), 1.70-1.85 (m, 2H), 1.96-2.10 (m, 2H), 2.82-2.95 (m, 4H), 3.28 (s, 6H), 3.66 (dd, J=8.84, 5.58 Hz, 2H), 4.07-4.17 (m, 2H), 5.30-5.49 (m, 2H), 6.28 (dd, J=9.16, 4.39 Hz, 2H), 6.75 (t, J=8.89 Hz, 2H), 7.18 (d, J=8.57 Hz, 4H), 7.56 (d, J=8.57 Hz, 4H), 9.90 (s, 2H); MS (ESI+) m/z 602 (M+H)$^+$.

Example 70H dimethyl ([(2S,3R,4R,5S)-1-(4-fluorophenyl)-3,4-dimethoxypyrrolidine-2,5-diyl]bis{benzene-4,1-diylcarbamoyl(2S)pyrrolidine-2,1-diyl[(2S)-3-methyl-1-oxobutane-1,2-diyl]})biscarbamate Dissolved the product of Example 70G (69.3 mg, 0.115 mmol) in anhydrous DMF (1.2 mL) under nitrogen, cooled to 0° C., then sequentially added (S)-2-(methoxycarbonylamino)-3-methylbutanoic acid (50.4 mg, 0.288 mmol), HOBT monohydrate (44.1 mg, 0.288 mmol), EDAC (56.3 mg, 0.288 mmol), and N-methylmorpholine (0.038 mL, 0.346 mmol). Removed the cooling bath and stirred at 25° C. for 13 hr. Diluted the reaction with EtOAc (50 mL), washed with sat'd aq NaHCO$_3$ (25 mL), H$_2$O (2×25 mL), and brine (25 mL). Dried the organic phase over anhydrous MgSO$_4$, filtered, and concentrated by rotary evaporation. Purified by flash chromatography (silica gel, 2.5 cm×15 cm, 6% MeOH/CH$_2$Cl$_2$) to afford the title compound as a white solid (48 mg, 85%). $^1$H NMR (400 MHz, DMSO-D6) δ ppm 0.88 (d, J=6.61 Hz, 6H), 0.93 (d, J=6.72 Hz, 6H), 1.80-2.05 (m, 8H), 2.08-2.22 (m, 2H), 3.28 (s, 6H), 3.52 (s, 6H), 3.56-3.69 (m, 2H), 3.77-3.88 (m, 2H), 4.03 (t, J=8.51 Hz, 2H), 4.07-4.16 (m, 2H), 4.43 (dd, J=7.97, 4.83 Hz, 2H), 5.29-5.44 (m, 2H), 6.27 (dd, J=9.22, 4.45 Hz, 2H), 6.75 (t, J=8.89 Hz, 2H), 7.17 (d, J=8.46 Hz, 4H), 7.31 (d, J=8.46 Hz, 2H), 7.49 (d, J=8.57 Hz, 4H), 9.99 (s, 2H); MS (ESI+) m/z 408 (M+H)$^+$.

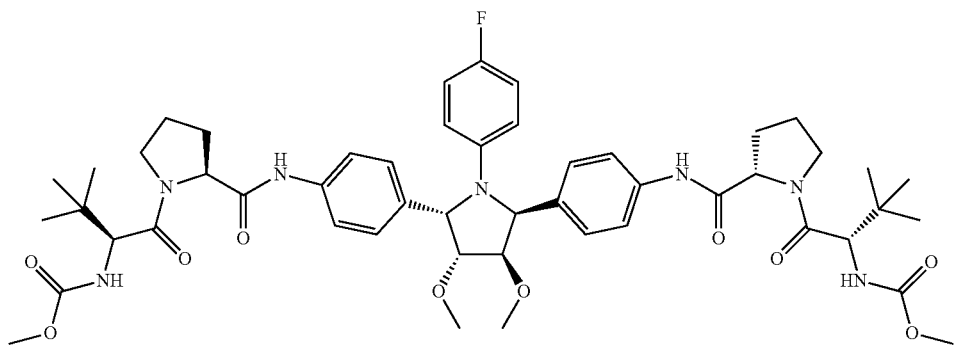

Example 71 dimethyl ([(2S,3R,4R,5S)-1-(4-fluorophenyl)-3,4-dimethoxypyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate Dissolved the product of Example 70D (58.5 mg, 0.097 mmol) in anhydrous DMF (1 mL) under nitrogen, cooled to 0° C., then sequentially added (S)-2-(methoxycarbonylamino)-3,3-dimethylbutanoic acid (46.0 mg, 0.243 mmol), HOBt monohydrate (37.2 mg, 0.243 mmol), EDAC (47.5 mg, 0.243 mmol), and 4-methylmorpholine (0.032 mL, 0.292 mmol). Removed the cooling bath and stirred overnight at 25° C. for 16 hr. Diluted the reaction with EtOAc (50 mL), washed with sat'd aq $NaHCO_3$ (25 mL), $H_2O$ (2×25 mL), and brine (25 mL). Dried the organic phase over anhydrous $MgSO_4$, filtered, and concentrated by rotary evaporation. Purified by flash chromatography (silica gel, 2.5 cm×15 cm, 4% $MeOH/CH_2Cl_2$) to afford the title compound as a cream-colored solid (66 mg, 72%). $^1H$ NMR (400 MHz, DMSO-D6) δ ppm 0.96 (s, 18H), 1.79-1.94 (m, 4H), 1.94-2.06 (m, 2H), 2.10-2.22 (m, 2H), 3.28 (s, 6H), 3.54 (s, 6H), 3.58-3.70 (m, 2H), 3.71-3.86 (m, 2H), 4.06-4.15 (m, 2H), 4.21 (d, J=8.89 Hz, 2H), 4.44 (dd, J=7.92, 5.31 Hz, 2H), 5.31-5.39 (m, 2H), 6.27 (dd, J=9.22, 4.45 Hz, 2H), 6.75 (t, J=8.89 Hz, 2H), 7.08 (d, J=8.78 Hz, 2H), 7.17 (d, J=8.57 Hz, 4H), 7.49 (d, J=8.57 Hz, 4H), 9.99 (s, 2H); MS (ESI+) m/z 945 (M+H)$^+$.

Example 72 dimethyl ([1-(4-tert-butylphenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})biscarbamate

Example 72A 4,4'-(1-(4-tert-butylphenyl)-1H-pyrrole-2,5-diyl) dianiline

Example 1A was processed using the methods described generally in Examples 26F and 19B to provide the title compound. MS (ESI; M+H) m/z=382.

Example 72B (2S,2'S)-tert-butyl 2,2'-(4,4'-(1-(4-tert-butylphenyl)-1H-pyrrole-2,5-diyl)bis(4,1-phenylene)bis(azanediyl)bis(oxomethylene))dipyrrolidine-1-carboxylate To a solution of the product from Example 72A (0.310 g, 0.813 mmol) in DMF (5 mL) was added (S)-1-(tert-butoxycarbonyl)pyrrolidine-2-carboxylic acid (0.385 g, 1.79 mmol) 1-hydroxybenzotriazole hydrate (0.274 g; 1.79 mmol) and N-(3-dimethylaminopropyl)-N'-ethylcarbodiimide hydrochloride (0.343 g, 1.79 mmol) and the mixture stirred overnight. The mixture was poured into water and extracted $CH_2Cl_2$. The organic extract was dried ($Na_2SO_4$), filtered and concentrated to give a crude product that was purified by trituration with ether to give 325 mg (51%) of the title compound. $^1H$ NMR (400 MHz, DMSO-D6) δ 1.25 (s, 24H) 1.83 (s, 6H) 2.15 (s, 2H) 3.45 (m, 4H) 4.18 (s, 2H) 6.40 (s, 2H) 6.98 (s, 6H) 7.37 (s, 6H) 9.98 (s, 2H).

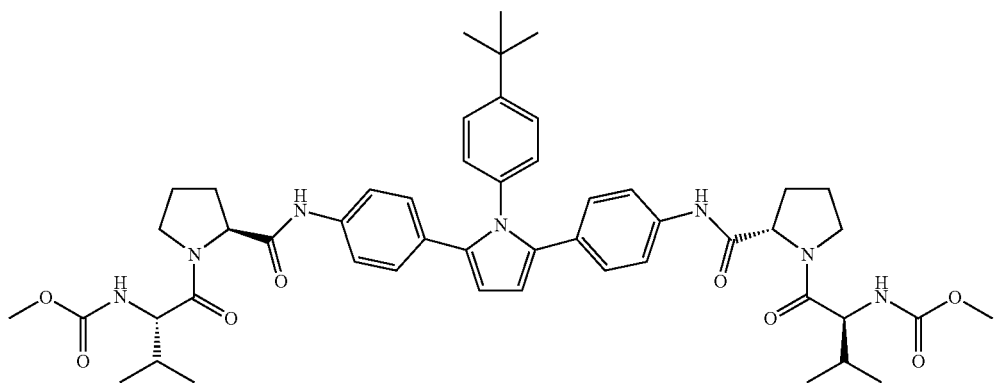

Example 72C (2S,2'S)—N,N'-(4,4'-(1-(4-tert-butylphenyl)-1H-pyrrole-2,5-diyl)bis(4,1-phenylene))dipyrrolidine-2-carboxamide To a solution of the product from Example 72B (0.325 g, 0.419 mmol) in CH$_2$Cl$_2$ (5 mL) at rt was added TFA (1.0 mL) and stirring continued for 5 h. The reaction was concentrated and the residue partitioned between water and 25% isopropyl alcohol-CHCl$_3$. The organic phase was dried (Na$_2$SO$_4$), filtered and concentrated to provide the title compound used directly in the next reaction. MS (DCI; M+H) m/z=576.

Example 72D dimethyl ([1-(4-tert-butylphenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})bis-carbamate The product from Example 72C and the product from (S)-2-(methoxycarbonylamino)-3-methylbutanoic acid were processed using the method described in Example 72B. The crude residue was purified by silica gel chromatography (1% gradient elution from 0% to 4% MeOHCH$_2$Cl$_2$) to provide 129 mg (35%) of the title compound. $^1$H NMR (400 MHz, DMSO-D6) δ 0.89 (s, 12H) 1.25 (s, 9H) 1.89 (s, 6H) 1.98 (s, 2H) 2.13 (s, 2H) 3.52 (s, 6H) 3.61 (s, 2H) 3.80 (s, 2H) 4.00 (s, 2H) 4.39 (s, 2H) 6.38 (s, 2H) 6.95 (s, 6H) 7.34 (s, 8H) 9.96 (s, 2H).

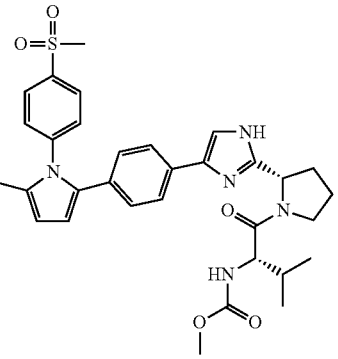

Example 73 methyl [(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[4-(methylsulfonyl)phenyl]-1H-pyrrol-2-yl}phenyl)-1H-imidazol-2-yl]pyrrolidin-1-yl}-3-methyl-1-oxobutan-2-yl]carbamate Example 26E and 4-(methylsulfonyl)aniline were processed using the methods of Examples 26F, 26G, 26H, 65B, and 65C to provide the title compound (78 mg). $^1$H NMR (400 MHz, DMSO-d6) δ 12.17-11.67 (m, 2H), 7.92-7.82 (m, 2H), 7.62-7.49 (m, 4H), 7.48-7.40 (m, 2H), 7.39-7.15 (m, 4H), 7.08-6.92 (m, 4H), 6.59-6.47 (m, 2H), 5.08-4.99 (m, 2H), 4.08-3.98 (m, 2H), 3.84-3.69 (m, 4H), 3.53 (s, 6H), 3.24 (d, J=1.9, 3H), 2.20-1.81 (m, 10H), 0.91-0.77 (m, 12H). MS (ESI; M+H) m/z=959.

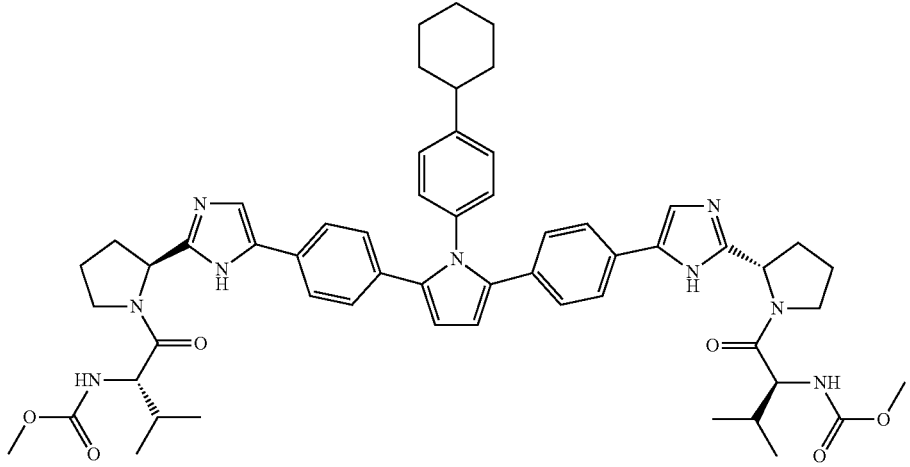

Example 74 methyl {(2S)-1-[(2S)-2-(5-{4-[1-(4-cyclohexylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl]phenyl}-1H-imidazol-2-yl)pyrrolidin-1-yl]-3-methyl-1-oxobutan-2-yl}carbamate

Example 74A 2,5-bis(4-bromophenyl)-1-(4-cyclohexylphenyl)-1H-pyrrole

The product from Example 26E and 4-cyclohexylaniline (Alfa) were processed using the method described in Example 26F to provide 1.23 g (91%) of the title compound. $^1$H NMR (400 MHz, benzene-D6) δ 1.09 (s, 5H) 1.60 (s, 5H) 2.14 (s, 1H) 6.52 (s, 2H) 6.67 (s, 4H) 6.84 (s, 4H) 7.11 (s, 4H).

Example 74B 1-(4-cyclohexylphenyl)-2,5-bis(4-(4,4,5,5-tetramethyl-1,3,2-dioxaborolan-2-yl)phenyl)-1H-pyrrole The product from Example 74A was processed using the method described in Example 26G to provide 1.58 g (60%) of the title compound. MS (ESI; M+H) m/z=630.

Example 74C (2S,2'S)-tert-butyl 2,2'-(5,5'-(4,4'-(1-(4-cyclohexylphenyl)-1H-pyrrole-2,5-diyl)bis(4,1-phenylene))bis(1H-imidazole-5,2-diyl))dipyrrolidine-1-carboxylate A solution of the product from Example 74B (0.400 g, 0.635 mmol) and the product from Example 26D (0.442 g, 1.40 mmol) in toluene (3 mL) and ethanol (3 mL) was treated with 1 M sodium carbonate (2 mL) followed by 1,1'-bis(diphenylphosphino)ferrocene-palladium(II)dichloride dichloromethane complex (0.052 g, 0.064 mmol), the mixture degassed (3×vacuum/purge $N_2$) and then heated to 90° C. for 4 h. The reaction was concentrated and the residue partitioned between 25% isopropyl alcohol-$CHCl_3$. The organic phase was dried ($Na_2SO_4$) concentrated and the residue taken up in ether, sonicated, filtered and dried to provide 499 mg (93%) of the title compound. MS (ESI; M+H) m/z=848.

Example 74D (S)-5,5'-(4,4'-(1-(4-cyclohexylphenyl)-1H-pyrrole-2,5-diyl)bis(4,1-phenylene))bis(2-((S)-pyrrolidin-2-yl)-1H-imidazole)

The product from Example 74C was processed using the method described in Example 19D to provide the title compound. MS (ESI; M+H) m/z=648.

Example 74E methyl {(2S)-1-[(2S)-2-(5-{4-[1-(4-cyclohexylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl]phenyl}-1H-imidazol-2-yl)pyrrolidin-1-yl]-3-methyl-1-oxobutan-2-yl}carbamate To a solution of the product from Example 74D (0.190 g, 0.293 mmol) in DMF (5 mL) was added (S)-2-(methoxycarbonylamino)-3-methylbutanoic acid (0.113 g, 0.645 mmol), 1-hydroxybenzotriazole hydrate (0.099 g; 0.645 mmol) and N-(3-dimethylaminopropyl)-N'-ethylcarbodiimide hydrochloride (0.124 g, 0.645 mmol) and the mixture stirred for 3 h. The mixture was poured into water and extracted $CH_2Cl_2$. The organic layer was concentrated and the residue purified by chromatography (gradient elution from 0% to 4% MeOH—$CH_2Cl_2$) to provide 100 mg (35%) of the title compound. $^1$H NMR (400 MHz, DMSO-D6) δ 0.84 (d, J=6.62 Hz, 6H) 0.87 (d, J=6.72 Hz, 6H) 1.20 (m, 2H) 1.35 (m, 4H) 1.78 (m, 4H) 1.92 (m, 6H) 2.10 (m, 4H) 3.52 (s, 6H) 3.76 (m, 4H) 4.02 (m, 2H) 5.03 (m, 2H) 6.47 (m, 2H) 6.99 (m, 6H) 7.18 (m, 3H) 7.27 (m, 2H) 7.41 (m, 2H) 7.51 (m, 4H) 11.74 (s, 2H).

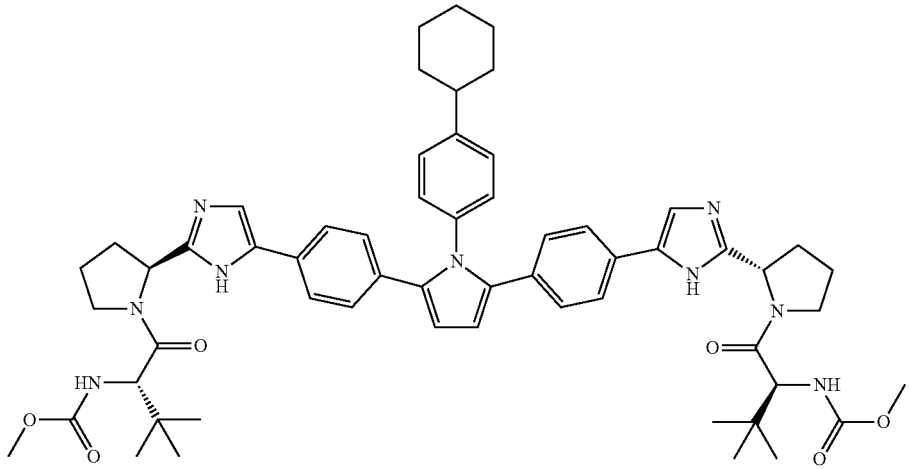

Example 75 methyl {(2S)-1-[(2S)-2-(5-{4-[1-(4-cyclohexylphenyl)-5-(4-{2-[(2S)-1-{(2S)-2-[(methoxycarbonyl)amino]-3,3-dimethylbutanoyl}pyrrolidin-2-yl]-1H-imidazol-5-yl}phenyl)-1H-pyrrol-2-yl]phenyl}-1H-imidazol-2-yl)pyrrolidin-1-yl]-3,3-dimethyl-1-oxobutan-2-yl}carbamate The product from Example 74D and (S)-2-methoxycarbonylamino-3,3-dimethyl-butyric acid (Org. Process Res. Develop. 2008, 12, 69) was processed using the method described in Example 74E to provide 165 mg (57%) of the title compound. $^1$H NMR (400 MHz, DMSO-D6) δ 0.86-0.96 (m, 18H) 1.23 (m, 2H) 1.36 (m, 4H) 1.78 (m, 4H) 1.88-2.00 (m, 4H) 2.10 (m, 4H) 3.54 (s, 6H) 3.77 (m, 4H) 4.21 (m, 2H) 5.05 (m, 2H) 6.46 (s, 2H) 6.96-7.03 (m, 6H) 7.19 (m, 2H) 7.38-7.55 (m, 7H) 7.70 (d, J=8.35 Hz, 1H) 7.97 (d, J=8.46 Hz, 1H) 11.76 (s, 2H).

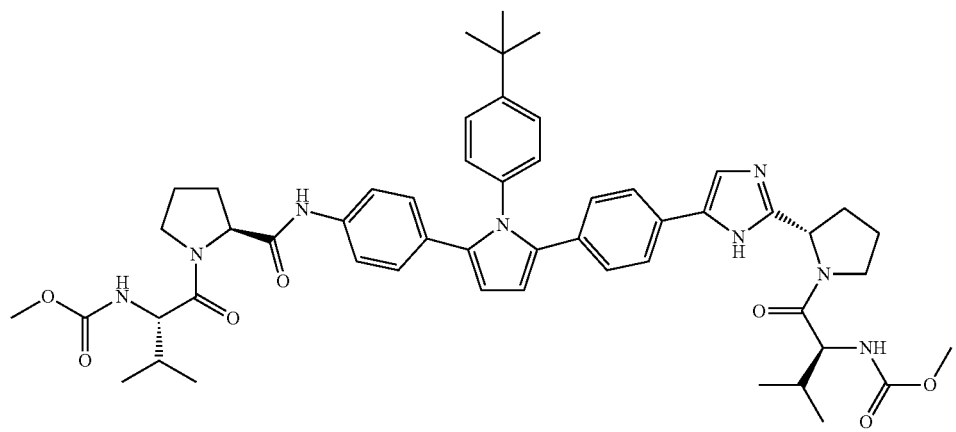

Example 76

N-(methoxycarbonyl)-L-valyl-N-(4-{1-(4-tert-butylphenyl)-5-[4-(2-{(2S)-1-[N-(methoxycarbonyl)-L-valyl]pyrrolidin-2-yl}-1H-imidazol-5-yl)phenyl]-1H-pyrrol-2-yl}phenyl)-L-prolinamide

Example 76A 2-(4-bromophenyl)-1-(4-tert-butylphenyl)-5-(4-nitrophenyl)-1H-pyrrole TFA (0.6 mL, 7.79 mmol) was added to a mixture of the product from Example 39A (1.2335 g, 3.41 mmol) and 4-tert-butylaniline (0.8 mL, 5.07 mmol) in toluene (30 mL) and heated at 110° C. for 17 hours. The cooled reaction mixture was poured into ether/water and stirred until nice solid formed. The mixture was filtered to afford the title compound. $^1$H NMR (400 MHz, BENZENE-D6) δ 1.02 (s, 9H), 6.48 (d, J=3.8, 1H), 6.52 (d, J=3.8, 1H), 6.63 (d, J=8.5, 2H), 6.80 (d, J=8.5, 2H), 6.84 (d, J=8.9, 2H), 6.89 (d, J=8.5, 2H), 7.10 (d, J=8.5, 2H), 7.70 (d, J=8.9, 2H).

Example 76B

N-(methoxycarbonyl)-L-valyl-N-(4-{1-(4-tert-butylphenyl)-5-[4-(2-{(2S)-1-[N-(methoxycarbonyl)-L-valyl]pyrrolidin-2-yl}-1H-imidazol-5-yl)phenyl]-1H-pyrrol-2-yl}phenyl)-L-prolinamide Example 76A was processed using sequentially the methods of Examples 19B, 55F, 39E (reaction temperature=85° C.), 39F, 55G, and 26J (reaction solvent=dichloromethane) to provide the title compound (0.14 g). $^1$H NMR (400 MHz, METHANOL-D4) δ 0.94 (ddd, J=21.1, 19.5, 6.7, 12H), 1.30 (s, 10H), 2.36-1.92 (m, 10H), 3.63 (s, 6H), 3.76-3.67 (m, 1H), 3.89-3.78 (m, 1H), 4.02-3.89 (m, 2H), 4.19 (d, J=7.9, 2H), 4.50 (dd, J=8.1, 5.3, 1H), 5.11 (dd, J=7.6, 5.5, 1H), 6.39 (d, J=3.7, 1H), 6.43 (d, J=3.6, 1H), 7.01 (dt, J=28.2, 8.3, 6H), 7.20 (s, 1H), 7.40 (ddd, J=19.1, 11.9, 5.7, 6H). MS (ESI) m/z 913 (M+H)$^+$.

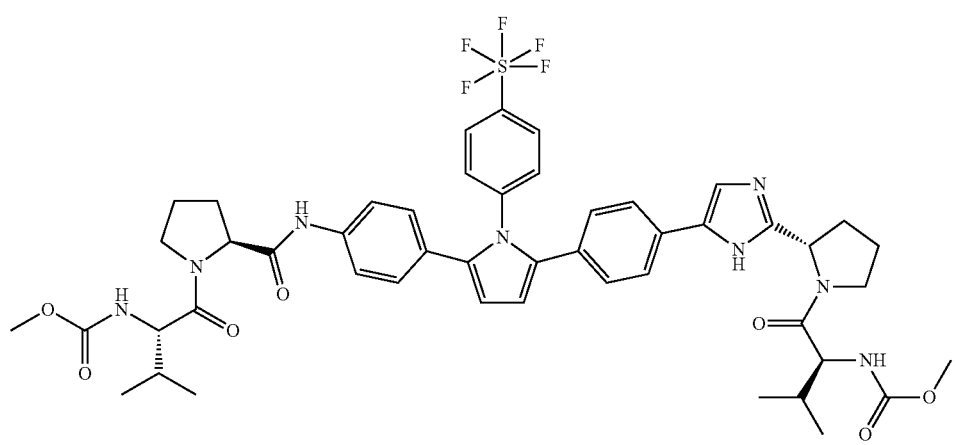

Example 77

N-(methoxycarbonyl)-L-valyl-N-(4-{5-[4-(2-{(2S)-1-[N-(methoxycarbonyl)-L-valyl]pyrrolidin-2-yl}-1H-imidazol-5-yl)phenyl]-1-[4-(pentafluoro-lambda~6~-sulfanyl)phenyl]-1H-pyrrol-2-yl}phenyl)-L-prolinamide Example 39A and 4-aminophenylsulfurpentafluoride were processed using sequentially the methods of Examples 76A, 19B, 55F, 39E (reaction temperature=85° C.), 39F, 55G, and 26J (reaction solvent=DMF) to provide the title compound (0.36 g). ¹H NMR (400 MHz, DMSO-D6) δ 0.86 (ddd, J=6.9, 15.8, 21.6, 12H), 2.04-1.76 (m, 7H), 2.24-2.04 (m, 3H), 3.53 (d, J=3.0, 6H), 3.61 (dd, J=6.7, 16.0, 1H), 3.88-3.67 (m, 3H), 4.03 (dd, J=8.3, 14.1, 2H), 4.40 (dd, J=5.0, 8.0, 1H), 5.12-4.92 (m, 1H), 6.49 (ddd, J=3.6, 14.2, 18.1, 2H), 7.09-6.84 (m, 4H), 7.38-7.12 (m, 4H), 7.50-7.38 (m, 3H), 7.58 (dd, J=8.3, 16.7, 2H), 7.89 (t, J=8.7, 2H), 10.01 (d, J=20.9, 1H), 12.16-11.66 (m, 1H). MS (ESI) m/z 983 (M+H)⁺, 981 (M−H)⁺.

Example 78 methyl {(2S)-1-[(2S)-2-(5-{3-[1-(4-tert-butylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl]phenyl}-1H-imidazol-2-yl)pyrrolidin-1-yl]-3-methyl-1-oxobutan-2-yl}carbamate 2,4'-Dibromoacetophenone and 3'-bromoacetophenone were processed using sequentially the methods of Examples 26E, 26F, 26G, 74C, 19D, and 74E to provide the title compound (232 mg). ¹H NMR (400 MHz, DMSO-D6) δ 0.81-0.91 (m, 12H) 1.25 (s, 9H) 1.93 (m, 4H) 2.11 (m, 4H) 3.53 (s, 6H) 3.78 (m, 4H) 4.04 (m, 2H) 5.03 (m, 2H) 6.49 (m, 2H) 6.90-7.08 (m, 5H) 7.11-7.21 (m, 1H) 7.27-7.55 (m, 9H) 7.71 (d, J=8.35 Hz, 1H) 7.94-8.01 (m, 2H) 11.72 (br s, 2H).

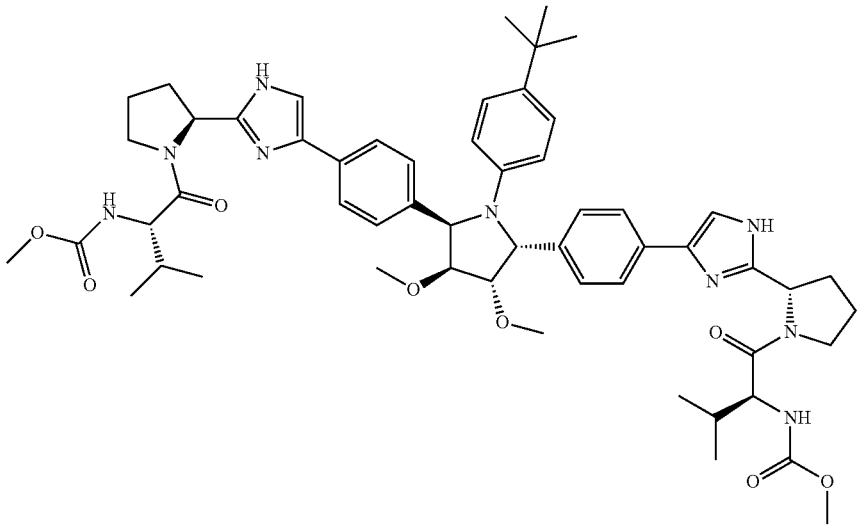

Example 79 methyl {(2S)-1-[(2S)-2-(4-{4-[(2R,3S,4S,5R)-1-(4-tert-butylphenyl)-3,4-dimethoxy-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

Example 79A 1,2:3,4:5,6-Tri-O-isopropylidene-L-mannitol

A solution of L-mannonic acid γ-lactone (9.87 g, 55.4 mmol) in methanol (150 mL) at 0° C. was treated with lithium borohydride (2.1 g, 97 mmol) over 30 min. After addition was complete, the mixture was warmed to RT for 30 min. The mixture was then cautiously treated with a solution of hydrogen chloride in dioxane (4 N, 2 mL). The solution was then concentrated in vacuo, first on the rotary evaporator and then under high vacuum (0.3 mm Hg) while warming with a heat gun to remove the last traces of methanol. The solid obtained was then suspended in acetone (50 mL) and treated with 2,2-dimethoxypropane (41 mL, 34.6 g, 332 mmol) and a solution of hydrogen chloride in dioxane (4 N, 42 mL, 166 mmol) followed by stirring at RT for 18 h. The mixture was concentrated in vacuo to ca. 20% of original volume, and the

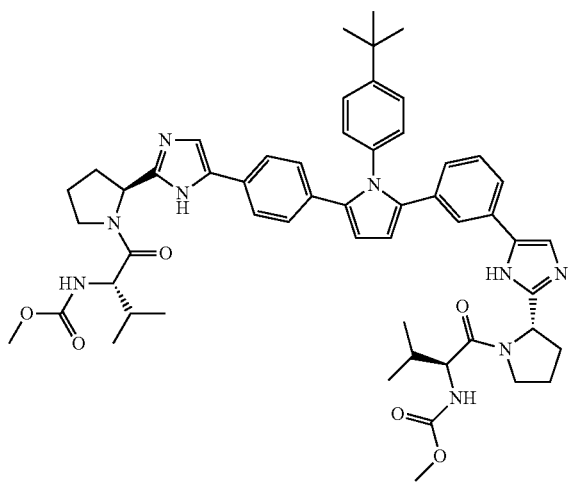 [SMILES: COC(=O)N[C@H](C(=O)N1CCC[C@H]1c1ncc(-c2ccc(-c3ccc(-c4cccc(-c5cnc([C@@H]6CCCN6C(=O)[C@@H](NC(=O)OC)C(C)C)[nH]5)c4)n3-c3ccc(C(C)(C)C)cc3)cc2)[nH]1)C(C)C]

inhomogeneous mixture was added to saturated S sodium bicarbonate solution (200 mL) followed by stirring for 48 h. The precipitate was collected by filtration and washed with water and air dried. The white solid was dissolved in ethanol (200 proof, 175 mL) and filtered through celite to remove particulate matter. The solution was cooled to −78° C. to effect crystallization. The solid was collected by filtration, and the mother liquors concentrated to ca. half volume, and re-cooled to −78° C. The second crop of crystals was collected by filtration and washed with ethanol. After drying in a vacuum oven at 50° C. for 3 h, these procedures afforded the title compound (9.88 g, 59%) as a fluffy white solid. $^1$H NMR (400 MHz, CDCl$_3$) δ 4.19 (dt, J=6.0, 3.0 Hz, 2H), 4.08 (dd, J=8.3, 6.4 Hz, 2H), 3.99 (m, 2H), 3.95 (m, 2H), 1.43 (s, 6H), 1.39 (s, 6H), 1.36 (s, 6H). MS (+ESI) m/z (rel abundance) 303 (100, M+H), 320 (43, M+NH4).

Example 79B 3,4-O-Isopropylidene-L-mannitol

The compound of Example 79A (9.88 g, 32.7 mmol) was suspended in 60% (v/v) acetic acid in water (150 mL) in a 1 L roundbottom and the flask placed on the rotory evaporator and rotated in the heating bath at 45° C. for 1.5 h. The heating bath was reduced in temperature to 40° C. and a line to the vacuum pump was attached to the rotory evaporator. The mixture was concentrated under ca. 1 mm Hg pressure to a wet solid. This material was diluted with dichloromethane (100 mL) and stirred at RT for 10 min. The solution was filtered through celite, and the filtrate concentrated in vacuo. The residue was dissolved in toluene and concentrated in vacuo (2×) to remove residual acetic acid. The white solid was then triturated with ether (60 mL) and collected by filtration. After drying in a vacuum oven for 18 h, these procedures afforded the title compound (2.46 g, 34%) as a white solid. $^1$H NMR (400 MHz, DMSO-d$_6$) δ 5.07 (d, J=4.5 Hz, 2H), 4.45 (t, J=5.7 Hz, 2H), 3.86 (dd, J=4.9, 1.5 Hz, 2H), 3.54 (ddd, J=10.9, 5.5, 3.1 Hz, 2H), 3.48 (d, J=4.6 Hz, 2H), 3.37 (m, 2H), 1.28 (s, 6H).

Example 79C (2R,3S,4S,5R)-1-(4-tert-butylphenyl)-2,5-bis(4-(4-methoxybenzyloxy)phenyl)-pyrrolidine-3,4-diol To a solution of Example 79B (1.0 g, 4.5 mmol) in CH$_3$OH (12.0 mL) and CH$_2$Cl$_2$ (6.0 mL) was added iodobenzene diacetate (3.48 g, 10.8 mmol) and the solution was stirred at room temperature for 5 h. Solvent was removed in vacuo and to the residue was added 0.1 M H$_2$SO$_4$ (4 mL) and the solution was stirred at room temperature for 18 h. The pH was adjusted to ~6 with solid NaHCO$_3$, and 4-tert-butylaniline (1.43 mL, 9.0 mmol) was added followed by 4-(4-methoxybenzyloxy) phenylboronic acid (2.09 g, 8.1 mmol) and hexafluoroisopropyl alcohol (8 mL). The solution was heated at 50° C. for 2 h, cooled and solvent removed in vacuo leaving the aqueous layer which contained quite a bit of solid material. The mixture was diluted with H$_2$O and 0.33 M K$_3$PO$_4$ was added and the mixture was stirred vigorously. The resulting white solid was collected by filtration and dried in a vacuum oven to give title compound (1.49 g, 2.26 mmol, 50%). $^1$H NMR (400 MHz, DMSO-d6) δ ppm 1.10 (s, 9H) 3.75 (s, 6H) 4.21 (s, 2H) 4.95 (s, 2H) 5.02 (d, J=6.9 Hz, 2H) 5.75 (s, 2H) 6.20 (d, J=8.9 Hz, 2H) 6.85-6.97 (m, 10H) 7.05 (d, J=8.6 Hz, 4H) 7.37 (d, J=8.7 Hz, 4H).

Example 79D (2R,3S,4S,5R)-1-(4-tert-butylphenyl)-3,4-dimethoxy-2,5-bis-(4-(4-methoxybenzyloxy)phenyl) pyrrolidine To a solution of Example 79C (1.49 g, 2.26 mmol) in THF (17 mL) and DMF (5.7 mL) at 0° C. was added, in portions, NaH, 60% in mineral oil (0.27 g, 6.77 mmol) and the mixture was stirred at 0° C. for 20 min. Iodomethane (0.31 mL, 4.97 mmol) was added and the reaction mixture was stirred at room temperature for 18 h, diluted with EtOAc, washed with saturated NH$_4$Cl, H$_2$O, and brine, dried (Na$_2$SO$_4$), filtered and solvent removed in vacuo to give an oily product. The oil was diluted with minimal ether and the oil began to solidify and the title compound was isolated as a colorless solid (1.55 g, 2.25 mmol, 100%). $^1$H NMR (400 MHz, CDCl$_3$) δ ppm 1.16 (s, 6H) 3.44 (s, 6H) 3.82 (s, 6H) 4.12-4.17 (m, 2H) 4.94 (s, 4H) 5.22 (dd, J=5.2, 1.63 Hz, 2H) 6.29 (d, J=8.9 Hz, 2H) 6.88-7.00 (m, 10H) 7.12 (d, J=8.6 Hz, 4H) 7.34 (d, J=8.6 Hz, 4H). MS (ESI) m/z 688 (M+H)$^+$.

Example 79E 4,4'-((2R,3S,4S,5R)-1-(4-tert-butylphenyl)-3,4-dimethoxypyrrolidine-2,5-diyl)diphenol To a solution of Example 79D (1.55 g, 2.25 mmol) in CH$_2$Cl$_2$ (9 mL) was added trifluoroacetic acid (9 mL, 117 mmol) and stirring was continued at room temperature for 1 h. Solvent was removed and the crude residue was dissolved in 1:1 EtOAc/saturated NaHCO$_3$. The organic layer was separated, washed with brine, dried (Na$_2$SO$_4$), filtered and solvent removed in vacuo to give title compound (1.0 g, 2.23 mmol, 99%). MS (ESI) m/z 448 (M+H)$^+$.

Example 79F 4,4'-((2R,3S,4S,5R)-1-(4-tert-butylphenyl)-3,4-dimethoxypyrrolidine-2,5-diyl)bis(4,1-phenylene)bis(1,1,2,2,3,3,4,4,4-nonafluorobutane-1-sulfonate)

To a solution of Example 79E (1.0 g, 2.23 mmol) in DMF (12 mL) was added K$_2$CO$_3$ (0.695 g, 5.0 mmol) and 1,1,2,2,3,3,4,4,4-nonafluorobutane-1-sulfonyl fluoride (0.86 mL, 4.9 mmol) and the solution was stirred at 100° C. for 1 h. The cooled solution was diluted with EtOAc, washed with H$_2$O, brine, dried (Na$_2$SO$_4$), filtered and solvent removed in vacuo to give crude product which was purified by flash chromatography on silica gel eluting with 0-20% EtOAc/hexane to give the title compound (1.63 g, 1.61 mmol, 72%). $^1$H NMR (400 MHz, CDCl$_3$) δ ppm 1.17 (s, 9H) 3.42 (s, 6H) 4.10 (dd, J=5.3, 1.90 Hz, 2H) 5.30 (dd, J=5.2, 1.9 Hz, 2H) 6.19 (d, J=8.8 Hz, 2H) 6.99-7.03 (m, 2H) 7.21-7.29 (m, 8H). MS (ESI) m/z 1012 (M+H)$^+$.

Example 79G (2R,3S,4S,5R)-1-(4-tert-butylphenyl)-3,4-dimethoxy-2,5-bis(4-(4,4,5,5-tetramethyl-1,3,2-dioxaborolan-2-yl)phenyl)pyrrolidine To a pressure tube was combined Example 79F (216 mg, 0.21 mmol), 4,4,4',4',5,5,5',5'-octamethyl-2,2'-bi(1,3,2-dioxaborolane) (114 mg, 0.45 mmol), dicyclohexyl(2',4',6'-triisopropylbiphenyl-2-yl)phosphine (16.3 mg, 0.034 mmol), potassium acetate (126 mg, 1.28 mmol) and dioxane (2 mL)

and the mixture was de-gassed with N₂ gas for 30 min. Tris(dibenzylideneacetone)dipalladium(0) (7.8 mg, 8.54 mmol) was added and de-gassing was continued for 10 min. The tube was sealed and heated at 100° C. for 30 min. The cooled solution was diluted with EtOAc, washed with H₂O, brine, dried (Na₂SO₄), filtered and the filtrate treated with 3-mercaptopropyl functionalized silica gel for 1 h, filtered and solvent removed in vacuo to give the title compound (143 mg, 100%).

Example 79H (2S,2'S)-tert-butyl 2,2'-(4,4'-(4,4'-((2R,3S,4S,5R)-1-(4-tert-butylphenyl)-3,4-dimethoxypyrrolidine-2,5-diyl)bis(4,1-phenylene)bis(1H-imidazole-4,2-diyl))dipyrrolidine-1-carboxylate To a pressure tube was combined Example 79G (140 mg, 0.21 mmol), (S)-tert-butyl-2-(4-bromo-1H-imidazol-2-yl)pyrrolidine-1-carboxylate (Example 26D) (166 mg, 0.524 mmol), 1 M Na₂CO₃ (0.524 mL, 0.524 mmol), EtOH (1 mL), and toluene (1 mL) and the mixture was de-gassed with N₂ gas for 30 min. 1,1'-bis(diphenylphosphino)ferrocene-dichloro palladium(II) dichloromethane complex (15.3 mg, 0.021 mmol) was added and de-gassing was continued for 10 min. The tube was sealed and heated at 100° C. for 3 h, then stirred at room temperature for 16 h. The solution was diluted with EtOAc, filtered through Celite and the filtrate washed with brine, dried (Na₂SO₄), filtered and solvent removed in vacuo. Purified by flash chromatography on silica gel eluting with 0-100% EtOAc/hexane to give title compound (119 mg, 0.135 mmol, 64%). ¹H NMR (400 MHz, CDCl₃) δ ppm 1.13 (s, 9H) 1.49 (s, 18H) 1.88-2.02 (m, 2H) 2.06-2.22 (m, 4H) 2.99 (s, 2H) 3.33-3.48 (m, 4H) 3.43 (s, 6H) 4.23 (s, 2H) 4.96 (d, J=5.3 Hz, 2H) 5.29 (d, J=6.9 Hz, 2H) 6.29 (d, J=8.9 Hz, 2H) 6.94 (d, J=8.4 Hz, 2H) 7.13-7.29 (m, 8H). MS (ESI) m/z 886 (M+H)⁺.

Example 79I methyl {(2S)-1-[(2S)-2-(4-{[(2R,3S,4S,5R)-1-(4-tert-butylphenyl)-3,4-dimethoxy-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate To a solution of Example 79H (30 mg, 0.034 mmol) in CH₂Cl₂ (1 mL) was added trifluoroacetic acid (1 mL) and the solution was stirred at room temperature for 1 h. Solvent was removed in vacuo and then dissolved in DMSO (0.5 mL). N,N-diisopropylethylamine was added until pH 9-10, then (S)-2-(methoxycarbonylamino)-3-methylbutanoic acid (14.8 mg, 0.085 mmol) was added followed by HATU (32 mg, 0.085 mmol) and the solution was stirred at room temperature for 1 h. The solution was diluted with EtOAc, washed with H₂O, brine, dried (Na₂SO₄), filtered and solvent removed in vacuo. Dissolved the residue in CH₃OH (2 mL), added solid K₂CO₃ and stirred at room temperature for 30 min. Solid was filtered off and the filtrate was concentrated in vacuo and the residue purified by flash chromatography on silica gel eluting with 0-5% CH₃OH/CH₂Cl₂ to give title compound (21.6 mg, 0.022 mmol, 63%). ¹H NMR (400 MHz, CDCl₃) δ ppm 0.85 (s, 12H) 1.13 (s, 9H) 1.82-2.03 (m, 2H) 2.02-2.24 (m, 4H) 2.32 (br s, 2H) 3.04 (br s, 2H) 3.43 (s, 6H) 3.53-3.65 (m, 2H) 3.70 (s, 6H) 3.75-3.90 (m, 2H) 4.22 (s, 2H) 4.31 (d, J=15.7 Hz, 2H) 5.16-5.33 (m, 4H) 5.37 (d, J=9.1 Hz, 2H) 6.29 (d, J=8.9 Hz, 2H) 6.94 (s, 2H) 7.16 (s, 2H) 7.22 (d, J=8.0 Hz, 4H) 7.31-7.52 (m, 2H) 7.60-7.87 (m, 2H) 10.26 (s, 1H) 10.64 (s, 1H). MS (ESI) m/z 1000 (M+H)⁺.

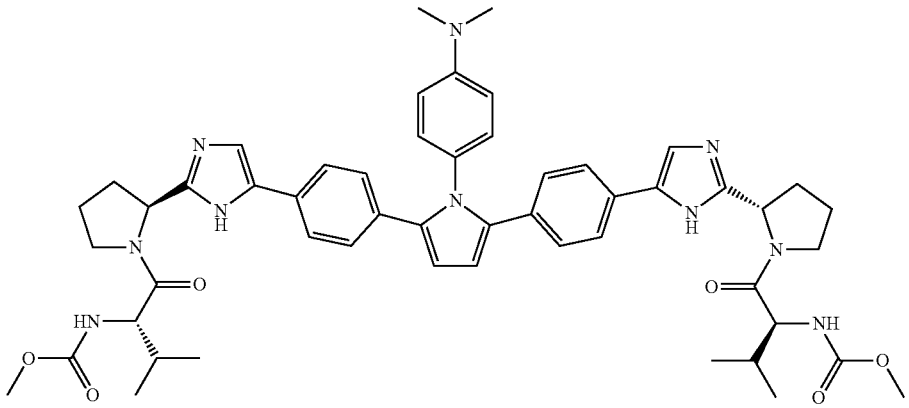

Example 80 methyl [(2S)-1-{(2S)-2-[5-(4-{1-[4-(dimethylamino)phenyl]-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl}phenyl)-1H-imidazol-2-yl]pyrrolidin-1-yl}-3-methyl-1-oxobutan-2-yl]carbamate Example 26E and N,N-dimethyl-p-phenylenediamine were processed using sequentially the methods of Examples 76A, 39E, 39F, 55G (25% isopropylalcohol/chloroform used for extraction), and 26J (reaction solvent=dichloromethane) to provide the title compound (5.6 mg). ¹H NMR (400 MHz, DMSO-d6) δ 0.94-0.75 (m, 12H), 2.04-1.78 (m, 6H), 2.21-2.03 (m, 4H), 2.89 (s, 6H), 3.38 (s, 1H), 3.53 (s, 6H), 3.84-3.68 (m, 3H), 4.10-3.96 (m, 2H), 5.04 (dd, J=2.9, 6.7, 2H), 6.53-6.37 (m, 2H), 6.70-6.54 (m, 2H), 7.12-6.85 (m, 6H), 7.33-7.12 (m, 2H), 7.46-7.34 (m, 2H), 7.60-7.46 (m, 4H), 12.11-11.64 (m, 2H). MS (ESI) m/z 923 (M+H)⁺.

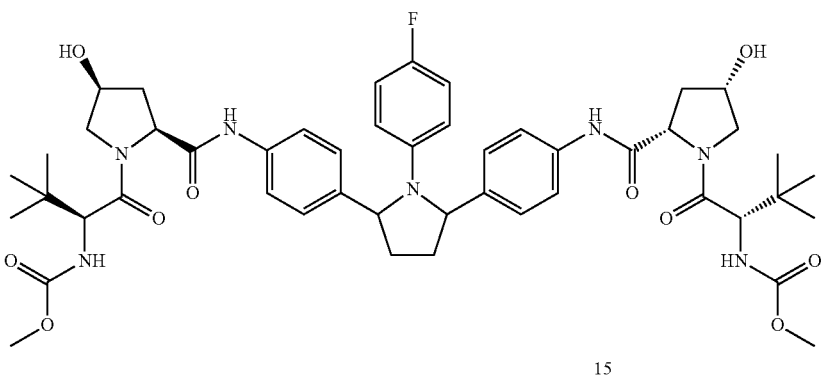

Example 81 dimethyl ([(2S,5S)-1-(4-fluorophenyl)pyrrolidine-2,5-diyl]bis{benzene-4,1-diylcarbamoyl[(2S,4S)-4-hydroxypyrrolidine-2,1-diyl][(2S)-3,3-dimethyl-1-oxobutane-1,2-diyl]})biscarbamate and dimethyl ([(2R,5R)-1-(4-fluorophenyl)pyrrolidine-2,5-diyl]bis{benzene-4,1-diylcarbamoyl[(2S,4S)-4-hydroxypyrrolidine-2,1-diyl][(2S)-3,3-dimethyl-1-oxobutane-1,2-diyl]})biscarbamate

Example 81A (2S,4S)-1-(tert-butoxycarbonyl)-4-hydroxypyrrolidine-2-carboxylic acid To a solution of (2S,4S)-4-hydroxypyrrolidine-2-carboxylic acid (3.9 g, 29.7 mmol) in THF (26.7 mL) and water (13.3 mL) was added di-tert-butyl dicarbonate (7.14 g, 32.7 mmol) and sodium hydroxide (2.0 N, 22.9 mL, 45.8 mmol) and the mixture stirred at room temperature overnight. The mixture then had 10% citric acid (50 mL) added followed by EtOAc and extraction with water and brine. The organic extract was dried, filtered and concentrated to afford 5.31 g (77%) of the title compound. MS (ESI) m/z 232 (M+H)$^+$.

Example 81B (2S,4S)-1-(tert-butoxycarbonyl)-4-(tert-butyldimethylsilyloxy)pyrrolidine-2-carboxylic acid To a solution of Example 81A (5.31, 22.96 mmol) and imidazole (7.82 g, 115 mmol) in dichloromethane (106 mL) and DMF (21.3 mL) was added tert-butyldimethylsilyl chloride (7.61 g, 50.5 mmol) and the mixture stirred at room temperature overnight. The mixture then had water (425 mL) added and the solution was extracted with EtOAc and the organic extract concentrated to a residue that was dissolved in 25% EtOAc and 75% hexanes then extracted with brine and the organic extract concentrated to a solid. The resultant solid was dissolved in methanol (65 mL) and water (85 mL) then lithium hydroxide monohydrate (1.93 g, 46 mmol) added and the solution stirred at room temperature for 2 h. Afterwards water (106 mL) and a solution of 1N aqueous hydrochloric acid was added until a pH of 2 was reached. The mixture was then extracted with a mixture of 25% EtOAc and 75% hexanes, the organic extract dried, filtered and concentrated to a colorless solid. MS (ESI) m/z 346 (M+H)+.

Example 81C (3S,3'S,5S,5'S)-tert-butyl 5,5'-(4,4'-((2S,5S)-1-(4-fluorophenyl)pyrrolidine-2,5-diyl)bis(4,1-phenylene))bis(azanediyl)bis(oxomethylene)bis(3-(tert-butyldimethylsilyloxy)pyrrolidine-1-carboxylate)

and (3S,3'S,5S,5'S)-tert-butyl 5,5'-(4,4'-((2R,5R)-1-(4-fluorophenyl)pyrrolidine-2,5-diyl)bis(4,1-phenylene))bis(azanediyl)bis(oxomethylene)bis(3-(tert-butyldimethylsilyloxy)pyrrolidine-1-carboxylate)

The product of Example 81B (149 mg, 0.432 mmol) and the product from Example 5A (50 mg, 0.144 mmol) were processed using the method described in Example 1F to afford 74 mg (51%) of the title compound as a 1:1 mixture of diastereomers. MS (ESI) m/z 1002 (M+H)+.

Example 81D (2S,2'S,4S,4'S)—N,N'-(4,4'-((2S,5S)-1-(4-fluorophenyl)pyrrolidine-2,5-diyl)bis(4,1-phenylene))bis(4-hydroxypyrrolidine-2-carboxamide)

and (2S,2'S,4S,4'S)—N,N'-(4,4'-((2R,5R)-1-(4-fluorophenyl)pyrrolidine-2,5-diyl)bis(4,1-phenylene))bis(4-hydroxypyrrolidine-2-carboxamide)

The product of Example 81C (74 mg, 0.074 mmol) was dissolved in trifluoroacetic acid (4 mL), water (0.2 mL) and dichloromethane (0.2 mL) and the mixture stirred at room temperature for 3 hours. Afterwards the mixture was concentrated to an oil which was dissolved in 75% CHCl$_3$ and 25% isopropyl alcohol then extracted with a saturated aqueous sodium bicarbonate solution, the organic extract separated, dried, filtered and concentrated to a colorless solid. MS (ESI) m/z 574 (M+H)+.

Example 81E dimethyl ([(2S,5S)-1-(4-fluorophenyl)pyrrolidine-2,5-diyl]bis{benzene-4,1-diylcarbamoyl[(2S,4S)-4-hydroxypyrrolidine-2,1-diyl][(2S)-3,3-dimethyl-1-oxobutane-1,2-diyl]})biscarbamate and dimethyl ([(2R,5R)-1-(4-fluorophenyl)pyrrolidine-2,5-diyl]bis{benzene-4,1-diylcarbamoyl[(2S,4S)-4-hydroxypyrrolidine-2,1-diyl][(2S)-3,3-dimethyl-1-oxobutane-1,2-diyl]})biscarbamate To the product from Example 81D (40 mg, 0.072 mmol), (S)-2-(methoxycarbonylamino)-3,3-dimethylbutanoic acid (34.1 mg, 0.18 mmol) and HATU (60.2 mg, 0.158 mmol) in DMSO (3 mL) was added Hunig's base (0.063 mL, 0.36 mmol), and the reaction mixture was stirred at room temperature for 1 hr. The reaction mixture was partitioned between water and ethyl acetate, and the organic layer was dried over MgSO$_4$, filtered and concentrated in vacuo. The crude product was purified by column chromatography on silica gel using a solvent gradient of 0-10% MeOH in dichloromethane to give the title compound as a 1:1 mixture of stereoisomers (21 mg, 32% yield): $^1$H NMR (400 MHz, DMSO-D6) δ ppm 9.94 (s, 2H), 7.44 (d, J=8.4 Hz, 4H), 7.07 (m, 6H) 6.74 (t, J=8.9 Hz, 2H), 6.15 (dd, J=9.1, 4.4 Hz, 2H), 5.26 (dd, J=6.1, 3.3 Hz, 2H), 5.11 (d, J=5.5 Hz, 2H), 4.33 (t, J=7.8 Hz, 2H), 4.19 (m, 2H), 4.07 (m, 2H), 3.93 (m, 2H), 3.48 (s, 6H), 2.34 (m, 2H), 1.66 (m, 2H), 1.59 (m, 2H), 1.20 (m, 2H), 0.91 (m, 18H).

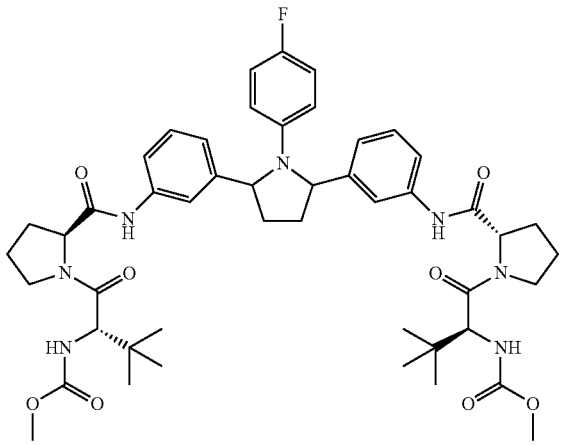

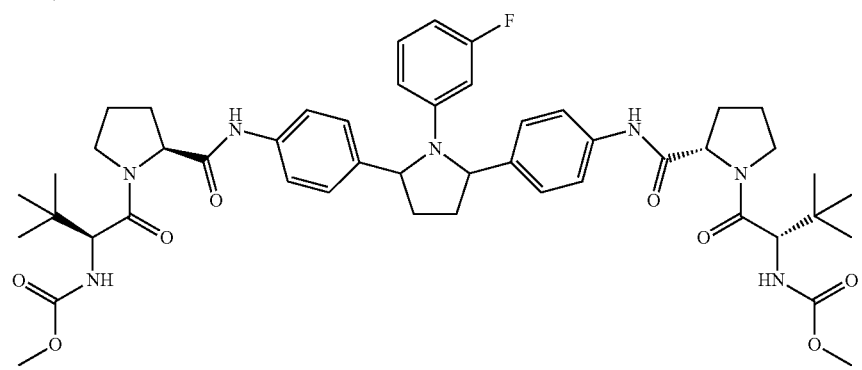 [SMILES: COC(=O)N[C@H](C(=O)N1CCC[C@H]1C(=O)Nc1ccc(C2CCC(c3ccc(NC(=O)[C@@H]4CCCN4C(=O)[C@@H](NC(=O)OC)C(C)(C)C)cc3)N2c2cccc(F)c2)cc1)C(C)(C)C]

Example 82 dimethyl ([(2S,5S)-1-(3-fluorophenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate and dimethyl ([(2R,5R)-1-(3-fluorophenyl)pyrrolidine-2,5-diyl]bis{benzene-4,1-diylcarbamoyl(2S)pyrrolidine-2,1-diyl[(2S)-3,3-dimethyl-1-oxobutane-1,2-diyl]})biscarbamate Example 1C and 3-fluoroaniline were processed using sequentially the methods of Examples 1D, 1E, 1F, 1G, and 1H to provide the title compounds. The trans diastereomers were separated from the cis diastereomer at the stage of 4,4'-(1-(3-fluorophenyl)pyrrolidine-2,5-diyl)dianiline. Data for the title compounds. $^1$H NMR (free base) (400 MHz, DMSO-d$_6$) δ ppm 0.96 (d, J=2.17 Hz, 18H), 1.75-1.92 (m, 7H), 1.93-2.05 (m, 2H), 2.10-2.21 (m, 2H), 2.31-2.44 (m, 2H), 3.43-3.51 (m, 4H), 3.53 (s, 6H), 3.59-3.73 (m, 6H), 3.73-3.82 (m, 2H), 4.21 (d, J=8.89 Hz, 2H), 4.46 (dd, J=7.92, 5.31 Hz, 2H), 4.70 (t, J=4.66 Hz, 2H), 6.07 (d, J=12.90 Hz, 1H), 6.19 (dd, J=8.35, 1.63 Hz, 1H), 6.37 (dt, J=8.35, 2.06 Hz, 1H), 6.97-7.05 (m, 2H), 7.08 (d, J=8.67 Hz, 2H), 7.41 (d, J=7.26 Hz, 4H), 7.60 (d, J=8.57 Hz, 4H), 10.07 (s, 2H). MS (ESI) m/z 885 (M+H)$^+$.

Example 83 dimethyl ([(2S,5S)-1-(4-fluorophenyl)pyrrolidine-2,5-diyl]bis{benzene-3,1-diylcarbamoyl(2S)pyrrolidine-2,1-diyl[(2S)-3,3-dimethyl-1-oxobutane-1,2-diyl]})biscarbamate and dimethyl ([(2R,5R)-1-(4-fluorophenyl)pyrrolidine-2,5-diyl]bis{benzene-3,1-diylcarbamoyl(2S)pyrrolidine-2,1-diyl[(2S)-3,3-dimethyl-1-oxobutane-1,2-diyl]})biscarbamate Example 83A (2S,2'S)-tert-butyl 2,2'-(3,3'-((2S,5S)-1-(4-fluorophenyl)pyrrolidine-2,5-diyl)bis(3,1-phenylene))bis(azanediyl)bis(oxomethylene)dipyrrolidine-1-carboxylate and (2S,2'S)-tert-butyl 2,2'-(3,3'-((2R,5R)-1-(4-fluorophenyl)pyrrolidine-2,5-diyl)bis(3,1-phenylene))bis(azanediyl)bis(oxomethylene)dipyrrolidine-1-carboxylate The ether fraction from the work up of Example 55F was purified using flash chromatography (silica gel, 0-30% EtOAc/dichloromethane) to afford the title compound as a mixture of trans diastereomers. MS (ESI) m/z 742 (M+H)$^+$.

Example 83B dimethyl ([(2S,5S)-1-(4-fluorophenyl)pyrrolidine-2,
5-diyl]bis{benzene-3,1-diylcarbamoyl(2S)pyrroli-
dine-2,1-diyl[(2S)-3,3-dimethyl-1-oxobutane-1,2-
diyl]})biscarbamate and dimethyl ([(2R,5R)-1-(4-fluorophenyl)pyrrolidine-2,
5-diyl]bis{benzene-3,1-diylcarbamoyl(2S)pyrroli-
dine-2,1-diyl[(2S)-3,3-dimethyl-1-oxobutane-1,2-
diyl]})biscarbamate The product from Example 83A was processed using the methods described in Examples 55G and 55H to afford the title compound (0.18 g, 27%). $^1$H NMR (400 MHz, DMSO-D6) δ 0.97 (d, J=4.5, 18H), 1.73-1.60 (m, 2H), 1.92-1.75 (m, 5H), 2.05-1.92 (m, 3H), 2.23-2.05 (m, 2H), 3.54 (d, J=1.5, 6H), 3.71-3.59 (m, 2H), 3.85-3.71 (m, 2H), 4.21 (d, J=8.9, 2H), 4.50-4.37 (m, 2H), 5.14 (d, J=5.7, 2H), 6.30-6.19 (m, 2H), 6.85-6.75 (m, 2H), 6.88 (d, J=7.7, 2H), 7.09 (d, J=8.7, 2H), 7.23 (t, J=7.9, 2H), 7.40-7.30 (m, 2H), 7.58 (d, J=8.1, 2H), 10.07-9.96 (m, 2H). MS (ESI) m/z 884 (M+H)$^+$, 882 (M−H)$^+$.

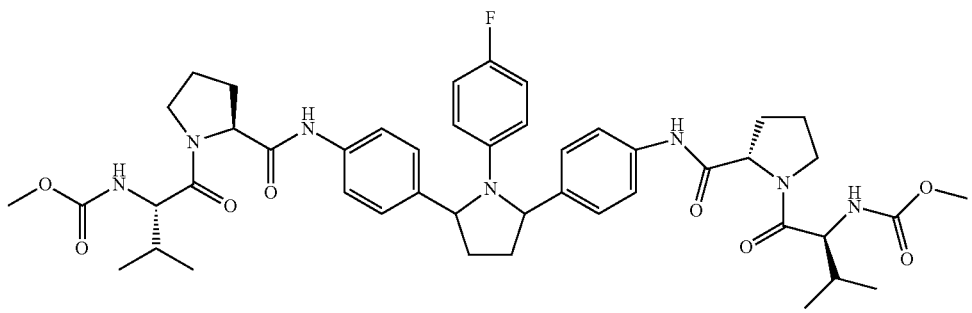

Example 84 dimethyl ([(2S,5S)-1-(4-methylphenyl)pyrrolidine-2,
5-diyl]bis{benzene-4,1-diylcarbamoyl(2S)pyrroli-
dine-2,1-diyl[(2S)-3-methyl-1-oxobutane-1,2-diyl]})
biscarbamate and dimethyl ([(2R,5R)-1-(4-methylphenyl)pyrrolidine-
2,5-diyl]bis{benzene-4,1-diylcarbamoyl(2S)pyrroli-
dine-2,1-diyl[(2S)-3-methyl-1-oxobutane-1,2-diyl]})
biscarbamate The title compound was prepared using the procedures described for the synthesis of Examples 34A, 34B, 34C, 34D, and 34E, substituting 4-methylaniline for 4-tert-butylaniline. 1H NMR (500 MHz, DMSO-D6) δ ppm 0.85-0.90 (m, 6H), 0.90-0.95 (m, 6H), 1.61-1.65 (m, 2H), 1.82-2.01 (m, 8H), 2.03 (s, 3H), 2.09-2.16 (m, 2H), 3.52 (s, 6H), 3.58-3.66 (m, 2H), 3.77-3.84 (m, 2H), 4.02 (t, 2H), 4.40-4.45 (m, 2H), 5.14 (d, J=6.6 Hz, 2H), 6.13-6.18 (m, 2H), 6.72 (d, J=8.4 Hz, 2H), 7.08-7.14 (m, 4H), 7.29-7.34 (m, 2H), 7.46-7.51 (m, 4H), 9.98 (s, 2H); MS m/z 852.3 (M+H)$^+$.

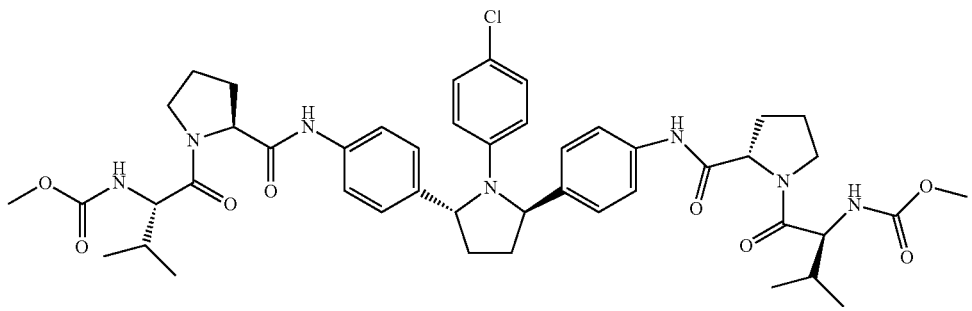

Example 85 dimethyl ([(2S,5S)-1-(4-chlorophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate and dimethyl ([(2R,5R)-1-(4-chlorophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate

Example 85A 1-(4-chlorophenyl)-2,5-bis(4-nitrophenyl)pyrrolidine

The product of Example 1B (0.50 g, 1.51 mmol) was suspended in CH$_2$Cl$_2$ (15 mL). Triethylamine (0.626 mL, 4.51 mmol) was added at 0° C., the resulting mixture was stirred for 30 min, and methanesulfonyl chloride (0.293 mL, 3.76 mmol) was added. The mixture was stirred at rt for 1 hr and then concentrated in vacuo to give a light yellow solid. The solid was dissolved in DMF (6 mL), 4-chloroaniline (1.92 g, 15.05 mmol) was added, and the resulting mixture was stirred at 50° C. overnight. The mixture was partitioned between EtOAc and 1N aq HCl, and the organic layer was dried over Na$_2$SO$_4$, filtered and concentrated in vacuo. The crude product was purified by column chromatography on silica gel using a solvent gradient of 0-12% EtOAc in hexane to give the title compound (0.226 g, 35%).

Example 85B 4,4'-(trans-1-(4-chlorophenyl)pyrrolidine-2,5-diyl)dianiline

To a solution of the product of example 85A (0.214 g, 0.505 mmol) in EtOH (2.52 mL) and THF (2.52 mL) was added platinum(IV) oxide (0.115 g, 0.505 mmol), and the resulting mixture was stirred at rt under 1 atm H$_2$ overnight. The mixture was filtered through celite, and the filtrate was concentrated in vacuo. The crude product was purified by column chromatography on silica gel using a solvent gradient of 0-12% EtOAc in hexane to give a mixture of the title compound and some dechlorinated product (4,4'-(trans-1-phenylpyrrolidine-2,5-diyl)dianiline).

Example 85C dimethyl ([(2S,5S)-1-(4-chlorophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate and dimethyl ([(2R,5R)-1-(4-chlorophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate A mixture of the product from Example 85B was subjected to the procedures described in Examples 34C, 34D, and 34E to give the title compounds free of dechlorinated product. 1H NMR (TFA salt) (400 MHz, DMSO-D6) δ ppm 0.84-0.89 (m, 6H), 0.89-0.94 (m, 6H), 1.61-1.66 (m, 2H), 1.80-2.03 (m, 8H), 2.06-2.18 (m, 2H), 3.51 (s, 6H), 3.56-3.65 (m, 2H), 3.74-3.84 (m, 2H), 4.01 (t, J=8.4 Hz, 2H), 4.36-4.44 (m, 2H), 5.16 (d, J=6.3 Hz, 2H), 6.21 (d, J=8.9 Hz, 2H), 6.93 (d, J=9.0 Hz, 2H), 7.08-7.13 (m, 4H), 7.26-7.31 (m, 2H), 7.46-7.51 (m, 4H), 9.99 (s, 2H). MS m/z 872.3 (M+H)$^+$.

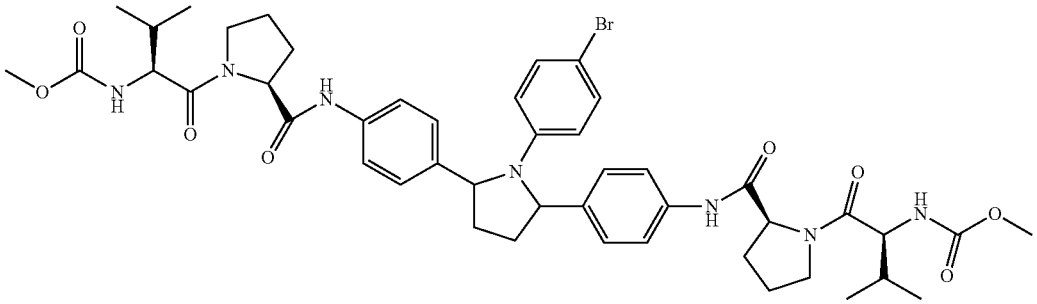

Example 86 dimethyl ([(2S,5S)-1-(4-bromophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate and dimethyl ([(2R,5R)-1-(4-bromophenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate

Example 86A 1-(4-bromophenyl)-2,5-bis(4-nitrophenyl)pyrrolidine

The product from Example 1C (0.7 g, 1.433 mmol) and 4-bromoaniline (2.54 g, 14.33 mmol) were suspended in DMF (6 mL) and stirred at 50° C. overnight. The resulting mixture was partitioned between ethyl acetate (100 mL) and water (50 mL). The organic phase was washed with 1N HCl (2×50 mL) followed by a brine wash then dried over MgSO$_4$ filtered and concentrated. The crude product was purified by chromatography on silica gel using a solvent gradient of 2-50% ethyl acetate in hexane to give the title compound as a mixture of stereoisomers (74.4 mg, 11% yield).

Example 86B (2S,2'S)—N,N'-(4,4'-(1-(4-bromophenyl)pyrrolidine-2,5-diyl)bis(4,1-phenylene))dipyrrolidine-2-carboxamide Example 86A was processed using the methods of Examples 1E, 1F, and 1G to provide the title compound as a mixture of stereoisomers.

Example 86C dimethyl ([1-(4-bromophenyl)pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate The product from Example 86B (78.0 mg, 0.129 mmole) was combined with EDAC (67.0 mg, 0.347 mmol), 1-hydroxybenzotriazole hydrate (49.0 mg, 0.323 mmoles) and (S)-2-(methoxycarbonylamino)-3-methylbutanoic acid (61.0 mg, 0.346 mmole) in dimethylformamide (1.4 mL) at room temperature under a nitrogen atmosphere. To this solution was added diisopropylethylamine (0.113 mL, 0.645 mmol). The mixture was allowed to stir overnight at room temperature followed by partition between ethyl acetate (20 mL) and water (5 mL). The organic phase was washed with water (3×5 mL) then dried over MgSO$_4$, filtered and evaporated to dryness. The crude product was chromatographed by reverse phase (C$_{18}$) HPLC providing the title compound as a 1:1 mixture of (trans) diastereomers (0.045 g, 38% yield) as an off white solid. 1H NMR (free base) (400 MHz, DMSO-D6) δ ppm 0.72-1.03 (m, 12H) 1.65 (s, 2H) 1.79-2.19 (m, 11H) 3.52 (s, 6H) 3.58-3.67 (m, 2H) 3.75-3.86 (m, 2H) 3.95-4.09 (m, 2H) 4.43 (dd, J=7.92, 4.88 Hz, 2H) 5.08-5.25 (m, 2H) 6.19 (d, J=8.89 Hz, 2H) 7.06 (d, J=8.89 Hz, 2H) 7.12 (d, J=7.16 Hz, 4H) 7.31 (dd, J=8.29, 3.96 Hz, 2H) 7.51 (dd, J=8.46, 1.52 Hz, 4H) 10.00 (s, 2H). MS ESI(+) m/z@916.6 (M+H)+.

Example 87 methyl {(2S)-1-[(2S)-2-{5-[(2S,5S)-1-(4-fluorophenyl)-5-{2-[(2S)-1-{(2S)-2-[(methoxycarbonyl)amino]-3,3-dimethylbutanoyl}pyrrolidin-2-yl]-1H-benzimidazol-5-yl}pyrrolidin-2-yl]-1H-benzimidazol-2-yl}pyrrolidin-1-yl]-3,3-dimethyl-1-oxobutan-2-yl}carbamate and methyl {(2S)-1-[(2S)-2-{5-[(2R,5R)-1-(4-fluorophenyl)-5-{2-[(2S)-1-{(2S)-2-[(methoxycarbonyl)amino]-3,3-dimethylbutanoyl}pyrrolidin-2-yl]-1H-benzimidazol-5-yl}pyrrolidin-2-yl]-1H-benzimidazol-2-yl}pyrrolidin-1-yl]-3,3-dimethyl-1-oxobutan-2-yl}carbamate The product from Example 29G (0.045 g, 0.084 mmol), (S)-2-methoxycarbonylamino-3,3-dimethyl-butyric acid (0.037 g, 0.193 mmol), 4-methylmorpholine (0.037 mL, 0.336 mmol), 1H-benzo[d][1,2,3]triazol-1-ol hydrate (0.028 g, 0.185 mmol) and N1-((ethylimino)methylene)-N3,N3-dimethylpropane-1,3-diamine hydrochloride (0.035 g, 0.185 mmol) were combined in 2 mL DMF and stirred for 2 hours. The reaction mixture was partitioned between EtOAc and water. The organic layer was washed 3×20 mL with brine, dried (Na$_2$SO$_4$), filtered and concentrated. The crude material was flash chromatographed on a 4 g Isco Gold silica cartridge eluting with 1.5-8% MeOH in methylene chloride. A second reverse phase C-18 preparative chromatography eluting with 9:1 water/acetonitrile→100% acetonitrile afforded the title compounds (29 mg, 28%; mix of trans diastereomers) as a light tan powder. $^1$H NMR (TFA salt) (400 MHz, DMSO-d$_6$) δ 0.84-0.95 (m, 18H) 1.21-1.46 (m, 4H) 1.75-2.27 (m, 8H) 3.56 (s, 6H) 3.86 (t, J=5.26 Hz, 4H) 4.22 (dd, J=8.57, 4.45 Hz, 2H) 5.15-5.24 (m, 2H) 5.53 (d, J=4.88 Hz, 2H) 6.30 (dd, J=9.11, 4.34 Hz, 2H) 6.75-6.83 (m, 2H) 7.29 (d, J=8.57 Hz, 2H) 7.35 (d, J=8.46 Hz, 2H) 7.48 (d, J=7.92 Hz, 2H) 7.69 (d, J=7.37 Hz, 2H). MS (ESI+) m/z 879 (M+H)$^+$.

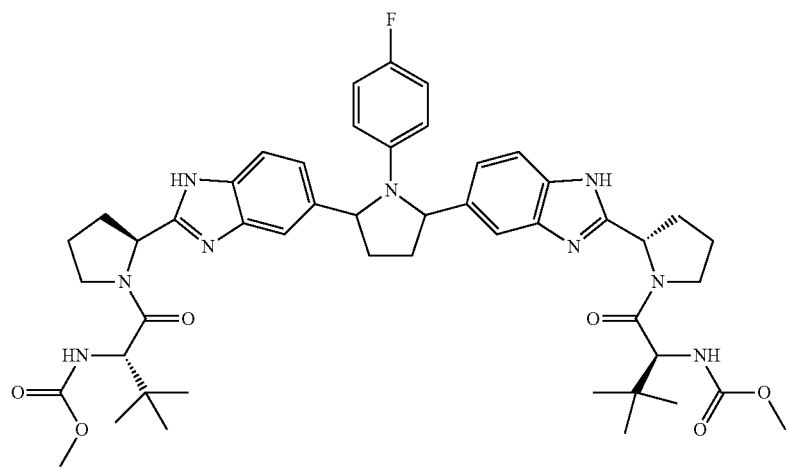 [SMILES: COC(=O)N[C@H](C(=O)N1CCC[C@H]1c1nc2cc(C3CCC(c4ccc5[nH]c([C@@H]6CCCN6C(=O)[C@@H](NC(=O)OC)C(C)(C)C)nc5c4)N3c3ccc(F)cc3)ccc2[nH]1)C(C)(C)C]

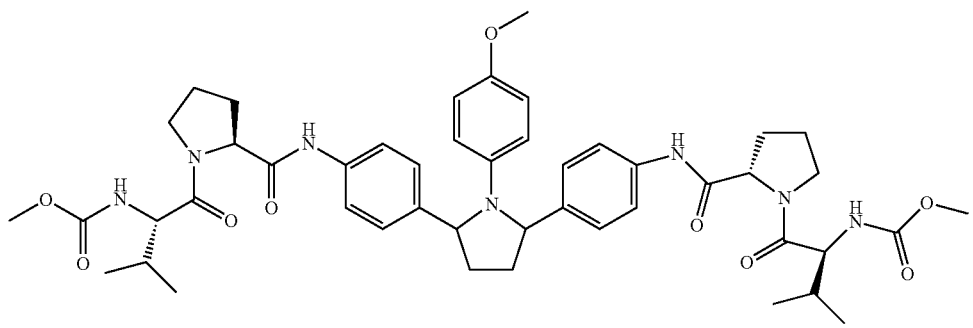

Example 88 dimethyl ([[(2S,5S)-1-(4-methoxyphenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate and dimethyl ([(2R,5R)-1-(4-methoxyphenyl)pyrrolidine-2,5-diyl]bis{benzene-4,1-diylcarbamoyl(2S) pyrrolidine-2,1-diyl[(2S)-3-methyl-1-oxobutane-1,2-diyl]})biscarbamate The title compound was prepared using the procedures described for the synthesis of Examples 34A, 34B, 34C, 34D, and 34E, substituting 4-methoxyaniline for 4-tert-butylaniline. 1H NMR (TFA salt) (400 MHz, DMSO-D6) δ ppm 0.85-0.90 (m, 6H), 0.90-0.95 (m, 6H), 1.60-1.66 (m, 2H), 1.81-2.04 (m, 8H), 2.08-2.19 (m, 2H), 3.52 (s, 9H), 3.57-3.66 (m, 2H), 3.77-3.85 (m, 2H), 4.02 (t, 2H), 4.39-4.46 (m, 2H), 5.12 (d, J=6.3 Hz, 2H), 6.18 (d, J=9.0 Hz, 2H), 6.56 (d, J=9.0 Hz, 2H), 7.09-7.15 (m, 4H), 7.28-7.34 (m, 2H), 7.46-7.52 (m, 4H), 9.97 (s, 2H); MS m/z 868.5 (M+H)+.

Example 89 methyl {(2S)-1-[(2S)-2-(4-{4-[(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-phenylpyrrolidin-2-yl]phenyl}-1H-imidazol-2-yl)pyrrolidin-1-yl]-3-methyl-1-oxobutan-2-yl}carbamate and methyl {(2S)-1-[(2S)-2-(4-{4-[(2R,5R)-5-(4-{2-[(2S)-1-{(2S)-2-[(methoxycarbonyl)amino]-3-methylbutanoyl}pyrrolidin-2-yl]-1H-imidazol-4-yl}phenyl)-1-phenylpyrrolidin-2-yl]phenyl}-1H-imidazol-2-yl)pyrrolidin-1-yl]-3-methyl-1-oxobutan-2-yl}carbamate The trans diastereomers obtained in Example 59B (8.5 mg, 0.0107 mmol), (S)-2-(methoxycarbonylamino)-3-methylbutanoic acid (4.67 mg, 0.027 mmol) and HATU (8.9 mg, 0.023 mmol) in DMSO (1 mL) was added Hunig's base (0.015 mL, 0.085 mmol), and the reaction mixture was stirred at room temperature for 1 hr. The reaction mixture was partitioned between water and ethyl acetate, and the organic layer was dried over MgSO4, filtered and concentrated in vacuo. The crude product was purified by reversed phase chromatography (C18), eluting with 10-100% acetonitrile in water (0.1% TFA) to afford 5.0 mg (53%) of the title compound as a mixture of trans diastereomers. 1H NMR (TFA salt) (400 MHz, DMSO-D6) δ ppm 14.45 (bs, 2H), 7.97 (s, 2H), 7.66 (m, 4H), 7.38 (m, 4H), 7.31 (d, J=7.4 Hz, 2H), 6.92 (t, J=17.6 Hz, 2H), 6.43 (m, 1H), 6.28 (d, J=8.1 Hz, 2H), 5.37 (m, 2H), 5.09 (t, J=6.7 Hz, 2H), 4.09 (t, J=7.7 Hz, 2H), 3.81 (m, 6H), 3.53 (s, 6H), 2.40 (m, 2H), 2.08 (m, 2H), 2.02 (m, 6H), 1.85 (m, 2H), 0.85 (m, 2H), 0.80 (m, 12H); MS (ESI) m/z 884 (M+H)+.

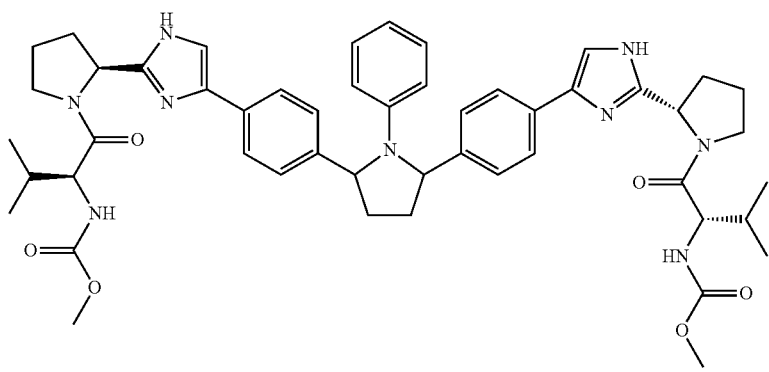 [SMILES: COC(=O)N[C@H](C(=O)N1CCC[C@H]1c1nc(-c2ccc(C3CCC(c4ccc(-c5c[nH]c([C@@H]6CCCN6C(=O)[C@@H](NC(=O)OC)C(C)C)n5)cc4)N3c3ccccc3)cc2)c[nH]1)C(C)C]

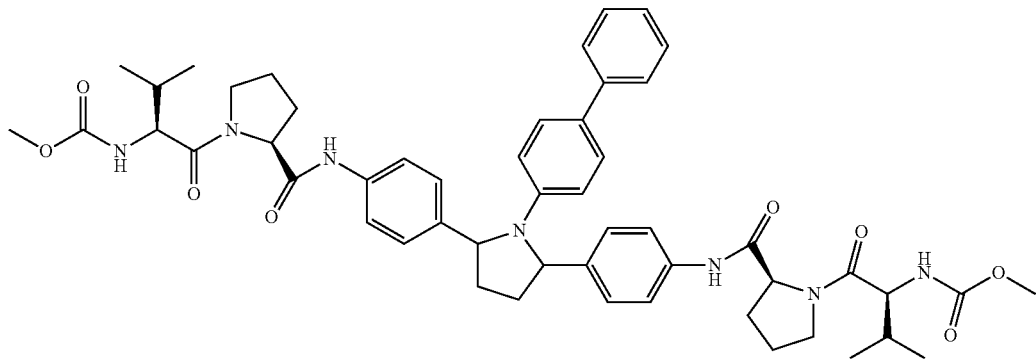

Example 90 dimethyl ([(2S,5S)-1-(biphenyl-4-yl)pyrrolidine-2,5-diyl]bis{benzene-4,1-diylcarbamoyl(2S)pyrrolidine-2,1-diyl[(2S)-3-methyl-1-oxobutane-1,2-diyl]})bis-carbamate and dimethyl ([(2R,5R)-1-(biphenyl-4-yl)pyrrolidine-2,5-diyl]bis{benzene-4,1-diylcarbamoyl(2S)pyrrolidine-2,1-diyl[(2S)-3-methyl-1-oxobutane-1,2-diyl]})bis-carbamate The product from Example 86C (24.9 mg, 0.027 mmole) dissolved in a THF (1 mL) and water (0.3 mL) solution was combined in a microwave tube with phenylboronic acid (6.90 mg, 0.054 mmole), tribasic potassium phosphate (13.37 mg, 0.063 mmole) and 1,1'-bis(di-tert-butylphosphino)ferrocene palladium dichloride (1.42 mg, 2.17 µmole). The tube was sealed and nitrogen bubbled through at room temperature for five minutes. All gas lines were subsequently removed and the reaction vessel immersed in a 50° C. oil bath and heated for two and one half hours. The contents of the tube were partitioned between ethylacetate (5 mL) and brine (1 mL). The organic phase was washed with brine (2×1 mL) then dried over MgSO$_4$, filtered and concentrated. The crude product was purified by silica gel chromatography eluting with 5% EtOAc-hexane and progressing to (75% EtOAc-hexane)+3% methanol to provide as a 1:1 mixture of (trans) diastereomers the title compound (18.6 mg, 75% yield) as a cream colored solid. 1H NMR (400 MHz, DMSO-D6) δ ppm 0.76-0.99 (m, 12H) 1.67 (s, 2H) 1.77-2.19 (m, 11H) 3.52 (s, 6H) 3.58-3.65 (m, 2H) 3.74-3.86 (m, 2H) 3.96-4.08 (m, 2H) 4.44 (d, J=4.99 Hz, 2H) 5.25 (s, 2H) 6.35 (d, J=8.02 Hz, 2H) 7.17 (d, J=7.26 Hz, 5H) 7.24-7.34 (m, 6H) 7.45 (d, J=7.92 Hz, 2H) 7.52 (d, J=7.81 Hz, 4H) 10.00 (s, 2H). MS ESI(+) m/z@915.1 (M+H)+, m/z@972.3 (M+CH$_3$CN+NH$_4$)+.

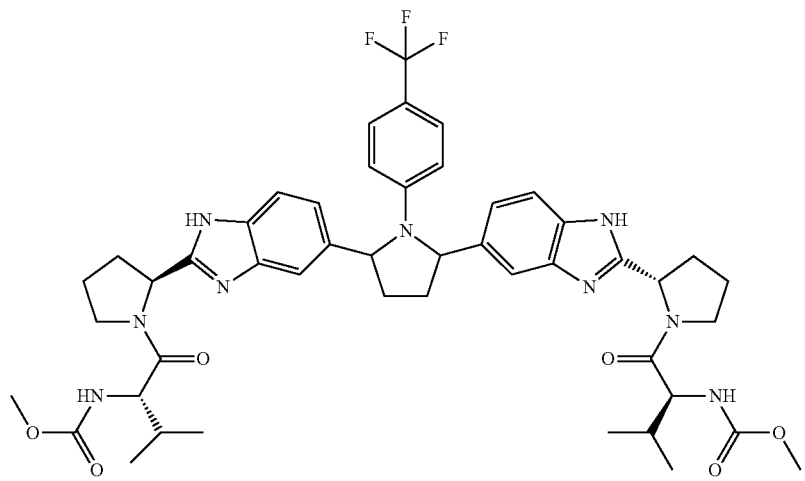

Example 91 methyl {(2S)-1-[(2S)-2-(5-{(2S,5S)-5-{2-[(2S)-1-{(2S)-2-[(methoxycarbonyl)amino]-3-methylbutanoyl}pyrrolidin-2-yl]-1H-benzimidazol-5-yl}-1-[4-(trifluoromethyl)phenyl]pyrrolidin-2-yl}-1H-benzimidazol-2-yl)pyrrolidin-1-yl]-3-methyl-1-oxobutan-2-yl}carbamate and methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(trifluoromethyl)phenyl]pyrrolidin-2-yl}-1H-benzimidazol-2-yl)pyrrolidin-1-yl]-3-methyl-1-oxobutan-2-yl}carbamate

Example 91A (2S,2'S)-2,2'(6,6'-(1-(4-(trifluoromethyl)phenyl)pyrrolidine-2,5-diyl)bis(1H-benzo[d]imidazole-6,2-diyl))dipyrrolidinium chloride Example 28C and 4-trifluoromethylaniline were processed using the methods of Examples 28D-28J to provide the title compound as a mixture of cis and trans stereoisomers.

Example 91B methyl {(2S)-1-[(2S)-2-(5-{(2S,5S)-5-{2-[(2S)-1-{(2S)-2-[(methoxycarbonyl)amino]-3-methylbutanoyl}pyrrolidin-2-yl]-1H-benzimidazol-5-yl}-1-[4-(trifluoromethyl)phenyl]pyrrolidin-2-yl}-1H-benzimidazol-2-yl)pyrrolidin-1-yl]-3-methyl-1-oxobutan-2-yl}carbamate and methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(trifluoromethyl)phenyl]pyrrolidin-2-yl}-1H-benzimidazol-2-yl)pyrrolidin-1-yl]-3-methyl-1-oxobutan-2-yl}carbamate The product from Example 91A (1:1 mixture of cis and trans isomers), 0.018 g, 0.027 mmole), HOBt (0.013 g, 0.082 mmole), EDAC (0.016 g, 0.082 mmole) and (S)-2-(methoxycarbonylamino)-3-methylbutanoic acid (0.014 g, 0.082 mmole) were combined in a 20 ml round bottom flask and dissolved in 1 ml DMF at room temperature, added 4-methylmorpholine (0.015 ml, 0.137 mmole) and the resulting clear slightly brown solution was stirred at room temperature for 2 hr. The reaction mixture was analyzed by LC-MS and determined to be complete. The reaction mixture was diluted with 50 ml EtOAc, washed with 10% NaHCO$_3$ and 10% NaCl, dried over anhydrous Na$_2$SO$_4$(s), filtered and solvent removed in vacuo leaving the title compound as a light brown solid. The material was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The product fractions were collected and evaporated to dryness in vacuo leaving the title compound as a tan solid, (11 mg, 44%) and a mixture of diastereomeric trans isomers. 1H NMR (TFA salt) (400 MHz, DMSO-D6) d ppm 0.67-0.94 (m, 12H) 1.95 (m, 18H) 3.79-3.89 (m, 6H) 4.10 (s, 2H) 5.19 (s, 1H) 5.64 (s, 2H) 6.45 (s, 2H) 7.28 (s, 4H) 7.47 (s, 4H) 7.69 (s, 4H), 12.1 (b, 2H) ESI+(m/z):900.6, ESI−(m/z):898.8.

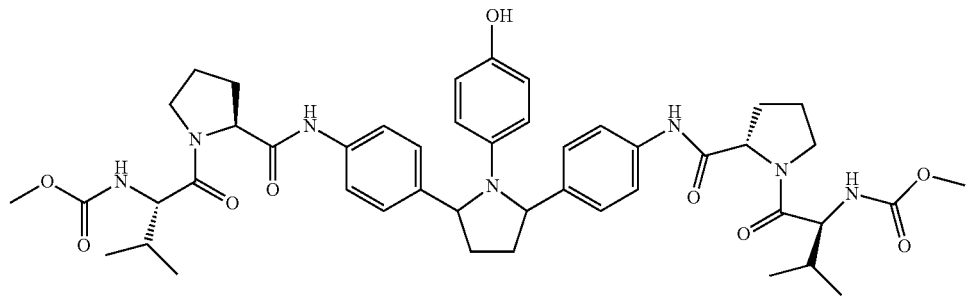

Example 92 dimethyl ([[(2S,5S)-1-(4-hydroxyphenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate and dimethyl ([[(2R,5R)-1-(4-hydroxyphenyl)pyrrolidine-2,5-diyl]bis{benzene-4,1-diylcarbamoyl(2S)pyrrolidine-2,1-diyl[(2S)-3-methyl-1-oxobutane-1,2-diyl]}) biscarbamate To a solution of the product from Example 88 (0.050 g, 0.058 mmol) in CH$_2$Cl$_2$ (1 mL) at −78° C. was added a 1.0 M solution of borontribromide in CH₂Cl₂ (0.29 mL, 0.29 mmol). The resulting dark red color solution was stirred at −78° C. for 4 h, and then warmed to rt and washed with water. The organic layer was dried over sodium sulphate, filtered, and concentrated in vacuo. The crude product was purified by column chromatography on silica gel using a solvent gradient of 0-7.5% MeOH in CH₂Cl₂ to give the title compound (5.5 mg, 12%) as a mixture of trans diastereomers. 1H NMR (400 MHz, DMSO-D6) δ ppm 0.86-0.90 (m, 6H), 0.90-0.95 (m, 6H), 1.58-1.63 (m, 2H), 1.82-2.04 (m, 8H), 2.08-2.19 (m, 2H), 3.52 (s, 6H), 3.58-3.66 (m, 2H), 3.77-3.84 (m, 2H), 4.02 (t, J=8.5 Hz, 2H), 4.40-4.46 (m, 2H), 5.08 (d, J=6.3 Hz, 2H), 6.08 (d, J=8.8 Hz, 2H), 6.38 (d, J=8.8 Hz, 2H), 7.08-7.13 (m, 4H), 7.29-7.34 (m, 2H), 7.45-7.51 (m, 4H), 8.27 (d, J=1.2 Hz, 1H), 9.96 (s, 2H); MS m/z 854.4 (M+H)⁺.

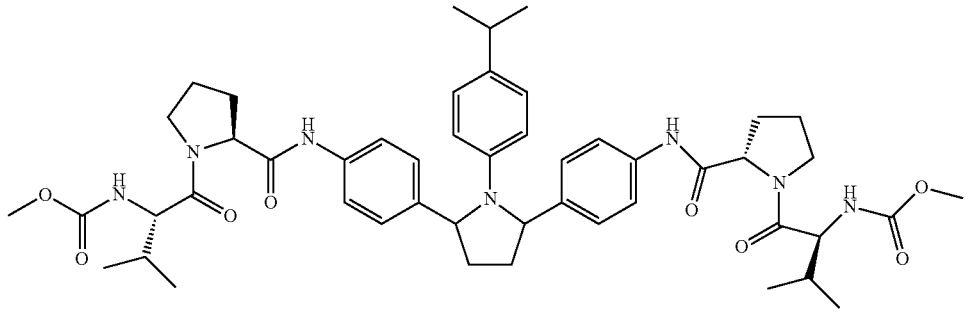

Example 93 dimethyl ({(2S,5S)-1-[4-(propan-2-yl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate and dimethyl ({(2R,5R)-1-[4-(propan-2-yl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate The title compound was prepared as a mixture of trans diastereomers using the procedures described for the synthesis of Examples 34A, 34B, 34C, 34D, and 34E, substituting 4-isopropylaniline for 4-tert-butylaniline. 1H NMR (TFA salt) (400 MHz, DMSO-D6) δ ppm 0.85-0.90 (m, J=5.8, 5.8 Hz, 6H), 0.90-0.96 (m, 6H), 1.02-1.06 (m, 6H), 1.60-1.65 (m, 2H), 1.81-2.04 (m, 8H), 2.08-2.19 (m, 2H), 2.56-2.65 (m, 1H), 3.52 (s, 6H), 3.58-3.66 (m, 2H), 3.76-3.85 (m, 2H), 4.02 (t, J=8.3 Hz, 2H), 4.40-4.45 (m, 2H), 5.14 (d, J=6.5 Hz, 2H), 6.15-6.20 (m, 2H), 6.79 (d, J=8.7 Hz, 2H), 7.09-7.16 (m, 4H), 7.29-7.34 (m, 2H), 7.47-7.52 (m, 4H), 9.97 (s, 2H); MS m/z 880.5 (M+H)⁺.

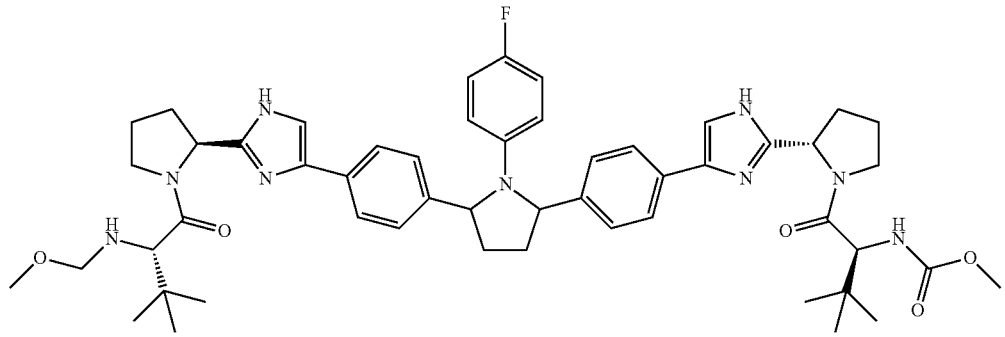

Example 94 methyl {(2S)-1-[(2S)-2-(4-{4-[(2S,5S)-1-(4-fluorophenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate and methyl {(2S)-1-[(2S)-2-(4-{4-[(2R,5R)-1-(4-fluorophenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate The product from Example 45D (28 mg, 0.048 mmol) was subjected to the conditions described in example 45E, substituting (S)-2-(methoxycarbonylamino)-3,3-dimethylbutanoic acid for (S)-2-(methoxycarbonylamino)-3-methylbutanoic acid, to give the title compound (18 mg, 41%) as a mixture of diastereomers. 1H NMR (TFA salt) (400 MHz, DMSO-D6) δ ppm 0.86 (s, 9H), 0.87 (s, 9H), 1.70-1.81 (m, 2H), 1.94-2.25 (m, 6H), 2.34-2.44 (m, 2H), 3.55 (s, 6H), 3.72-3.95 (m, 4H), 4.19 (d, J=8.7 Hz, 2H), 5.09 (t, J=7.2 Hz, 2H), 5.35 (d, J=6.1 Hz, 2H), 6.26 (dd, J=9.1, 4.4 Hz, 2H), 6.81 (t, J=8.9 Hz, 2H), 7.29 (d, J=8.0 Hz, 2H), 7.37 (d, J=7.2 Hz, 4H), 7.68 (dd, J=7.8, 5.4 Hz, 4H), 7.97 (s, 2H), 14.46 (br s, 2H); MS m/z 930.8 (M+H)$^+$.

Example 95 methyl {(2S)-1-[(2S)-2-(4-{4-[(2S,5S)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(4-{4-[(2R,5R)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate

Example 95A (S)-4,4'-(4,4'-((2R,5R)-1-(4-cyclopropylphenyl)pyrrolidine-2,5-diyl)bis(4,1-phenylene))bis(2-((S)-pyrrolidin-2-yl)-1H-imidazole)

and (S)-4,4'-(4,4'-((2S,5S)-1-(4-cyclopropylphenyl)pyrrolidine-2,5-diyl)bis(4,1-phenylene))bis(2-((S)-pyrrolidin-2-yl)-1H-imidazole)

The product from Example 68C (1.27 g, 1.568 mmol) was dissolved in dichloromethane (12 mL). The mixture was cooled to 0° C. and trifluoroacetic acid (8 mL, 104 mmol) was added slowly. The mixture was warmed to room temperature and stirred for 1 h. The solvent was evaporated and the residue was purified by chromatography on silica gel eluting with methanol/dichloromethane (1% to 10%). The title compound was eluted as the first of 2 stereoisomers and was obtained as a mixture of trans diastereomers (510 mg, 53%).

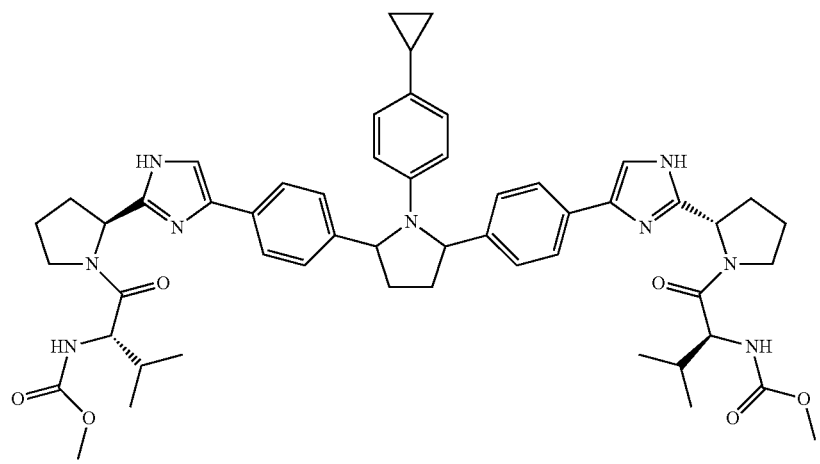 [SMILES: COC(=O)N[C@H](C(=O)N1CCC[C@H]1c1nc(-c2ccc(C3CCC(c4ccc(-c5c[nH]c([C@@H]6CCCN6C(=O)[C@@H](NC(=O)OC)C(C)C)n5)cc4)N3c3ccc(C4CC4)cc3)cc2)c[nH]1)C(C)C]

Example 95B methyl {(2S)-1-[(2S)-2-(4-{4-[(2S,5S)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(4-{4-[(2R,5R)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 95A (150 mg, 0.246 mmol), (S)-2-(methoxycarbonylamino)-3-methylbutanoic acid (86 mg, 0.492 mmol), 4-methylmorpholine (0.216 mL, 1.968 mmol), N1-((ethylimino)methylene)-N3,N3-dimethylpropane-1,3-diamine hydrochloride (104 mg, 0.541 mmol) and 1H-benzo[d][1,2,3]triazol-1-ol hydrate (83 mg, 0.541 mmol) were combined in DMF (10 mL). The mixture was stirred at room temperature for 2 hours. The reaction mixture was partitioned between ethyl acetate and water. The organic layer was washed with saturated sodium bicarbonate, brine twice, dried with sodium sulfate, filtered and evaporated. The residue was purified by chromatography on silica gel eluting with methanol/dichloromethane (1% to 4%) to give the title compound (78 mg, 34%) as a solid. 1H NMR (400 MHz, DMSO-D6) δ ppm 0.35-0.41 (m, 2H) 0.65-0.72 (m, 2H) 0.81-0.92 (m, 12H) 1.58-1.64 (m, 1H) 1.66-1.72 (m, 2H) 1.86-2.03 (m, 6H) 2.07-2.17 (m, 4H) 2.24-2.30 (m, 2H) 3.53 (s, 6H) 3.74-3.82 (m, 4H) 4.04 (t, J=7.86 Hz, 2H) 5.06 (dd, J=6.72, 2.93 Hz, 2H) 5.14-5.26 (m, 2H) 6.19 (d, J=8.67 Hz, 2H) 6.64 (d, J=8.24 Hz, 2H) 7.10-7.30 (m, 6H) 7.34-7.69 (m, 6H) 11.64-12.11 (m, 2H); MS (ESI+) m/z 924.8 (M+H)+.

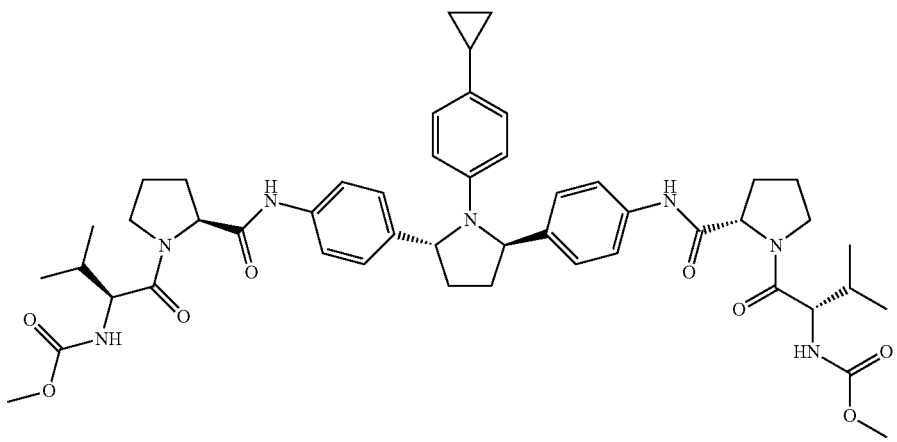

Example 96 dimethyl ([(2R,5R)-1-(4-cyclopropylphenyl)pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate Example 38A and 4-cyclopropylaniline were processed using sequentially the methods of Examples 34A, 34B, 34C, 66D, and 66E to provide the title compound (62 mg). $^1$H NMR (400 MHz, DMSO-$d_6$) δ 0.36-0.46 (m, 2H) 0.63-0.77 (m, 2H) 0.87 (d, J=6.61 Hz, 6H) 0.92 (d, J=6.72 Hz, 6H) 1.52-2.46 (m, 15H) 3.52 (s, 6H) 3.57-3.66 (m, 2H) 3.75-3.85 (m, 2H) 4.02 (t, J=8.46 Hz, 2H) 4.42 (dd, J=8.02, 4.88 Hz, 2H) 5.14 (d, J=6.40 Hz, 2H) 6.14 (d, J=8.78 Hz, 2H) 6.65 (d, J=8.67 Hz, 2H) 7.10 (d, J=8.57 Hz, 4H) 7.30 (d, J=8.35 Hz, 2H) 7.48 (d, J=8.57 Hz, 4H) 9.97 (s, 2H). MS (APCI) m/z 878 (M+H)$^+$.

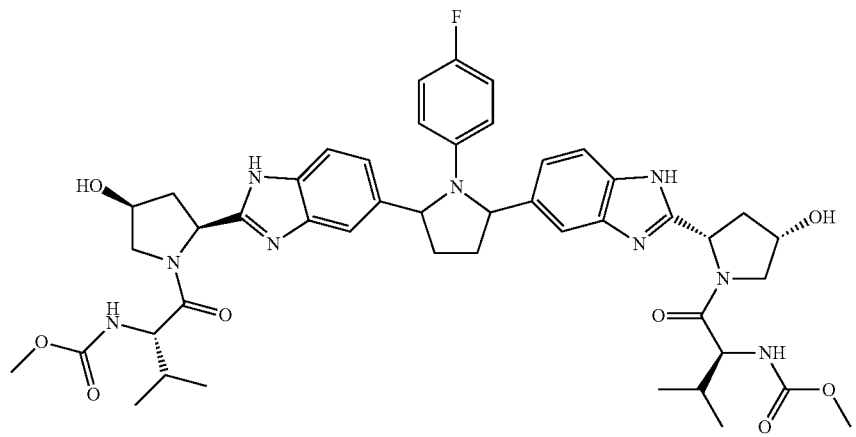

Example 97 methyl {(2S)-1-[(2S,4S)-2-{5-[(2S,5S)-1-(4-fluo-rophenyl)-5-{2-[(2S,4S)-4-hydroxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-hydroxypyrrolidin-1-yl]-3-methyl-1-oxobutan-2-yl}carbamate and methyl {(2S)-1-[(2S,4S)-2-{5-[(2R,5R)-1-(4-fluo-rophenyl)-5-{2-[(2S,4S)-4-hydroxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-hydroxypyrrolidin-1-yl]-3-methyl-1-oxobutan-2-yl}carbamate

Example 97A (2S,4S)-1-(tert-butoxycarbonyl)-4-(tert-butyldimethylsilyloxy)pyrrolidine-2-carboxylic acid (2S,4S)-1-(tert-butoxycarbonyl)-4-hydroxypyrrolidine-2-carboxylic acid (5.31 g, 22.96 mmol) and imidazole (7.82 g, 115 mmol) were combined in dichloromethane (106 mL) and dimethylformamide (22 mL) at ambient temperature and treated with portionwise addition of tert-butylchlorodimethylsilane (7.61 g, 50.5 mmol). The mixture was stirred for 18 hours then diluted with water and extracted into ethyl acetate and concentrated to provide the title compound.

Example 97B

The product from Example 29D (0.906 g, 2.62 mmol) was processed as in Examples 29E, 29F, 29G, and 29H, substituting Example 97A for S-Boc-proline in step 29E to give the title compounds (0.012 g, 13%). 1H NMR (400 MHz, DMSO-D6) δ ppm 0.69-0.85 (m, 12H) 1.27-1.39 (m, 1H) 1.53 (dt, J=21.31, 6.64 Hz, 1H) 1.71 (s, 4H) 1.80-1.90 (m, 2H) 2.02 (d, J=7.70 Hz, 2H) 2.54-2.62 (m, 2H) 3.53 (s, 6H) 3.68 (t, J=10.63 Hz, 2H) 3.93-4.00 (m, 2H) 4.39 (s, 2H) 5.13 (s, 2H) 5.38 (s, 2H) 6.19-6.38 (m, 4H) 6.74 (d, J=2.60 Hz, 2H) 7.08 (s, 2H) 7.21-7.36 (m, 4H) 7.40-7.51 (m, 2H) 12.21-12.38 (m, 2H); MS TFA+ m/z 882.5 (M+H)+.

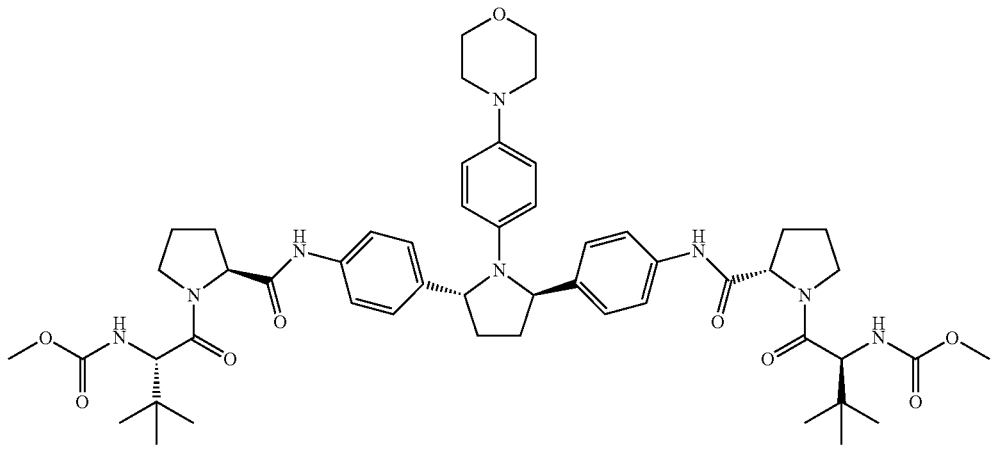

Example 98 dimethyl ({(2R,5R)-1-[4-(morpholin-4-yl)phenyl]pyrrolidine-2,5-diyl}bis{benzene-4,1-diylcarbamoyl(2S)pyrrolidine-2,1-diyl[(2S)-3,3-dimethyl-1-oxobutane-1,2-diyl]})biscarbamate

Example 98A 4-(4-((2R,5R)-2,5-bis(4-nitrophenyl)pyrrolidin-1-yl)phenyl)morpholine The product from Example 38A and 4-morpholinoaniline were processed using the method described in Example 1D using NMP for the solvent to afford the title compound. MS (ESI) m/z 475 (M+H)$^+$.

Example 98B 4,4'-((2R,5R)-1-(4-morpholinophenyl)pyrrolidine-2,5-diyl)dianiline The product from Example 98A in tetrahydrofuran (20 mL) was added to Ra-Ni (water wet, A-7000, 0.8 g, 12.63 mmol) in a 50 mL pressure bottle and stirred for 2 hours at ambient temperature under 30 psi of hydrogen. The mixture was filtered through a nylon membrane and concentrated to afford the title compound (0.31 g, 44%). MS (DCI) m/z 415 (M+H)$^+$.

Example 98C (2S,2'S)-tert-butyl 2,2'-(4,4'-((2R,5R)-1-(4-morpholinophenyl)pyrrolidine-2,5-diyl)bis(4,1-phenylene))bis(azanediyl)bis(oxomethylene)dipyrrolidine-1-carboxylate The product from Example 98B was processed using sequentially the methods of Examples 55F, 55G, and 26J (with (S)-2-(methoxycarbonylamino)-3,3-dimethylbutanoic acid) to afford the title compound (0.13 g). $^1$H NMR (400 MHz, DMSO-D6) δ 0.93 (d, J=20.5, 17H), 1.92-1.79 (m, 4H), 2.05-1.93 (m, 3H), 2.21-2.08 (m, 2H), 2.43 (t, J=6.1, 3H), 2.84-2.75 (m, 4H), 3.54 (s, 6H), 3.68-3.58 (m, 6H), 3.83-3.70 (m, 2H), 4.20 (d, J=8.9, 2H), 4.43 (dd, J=7.9, 5.3, 2H), 5.12 (d, J=6.3, 2H), 6.17 (d, J=9.1, 2H), 6.60 (d, J=9.1, 2H), 7.07 (d, J=8.8, 2H), 7.11 (d, J=8.5, 4H), 7.48 (d, J=8.5, 4H), 9.98 (s, 2H). Impurity $^1$H NMR (400 MHz, DMSO-D6) δ 1.63 (d, J=5.6, 2H), 3.17 (d, J=5.3, 3H), 4.09 (q, J=5.3, 1H). MS (ESI) m/z 952 (M+H$^+$).

Example 99 dimethyl ([(2S,5S)-1-{4-[6-(dimethylamino)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate and dimethyl ([(2R,5R)-1-{4-[6-(dimethylamino)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate

Example 99A 5-(4-(2,5-bis(4-nitrophenyl)pyrrolidin-1-yl)phenyl)-N,N-dimethylpyridin-2-amine The product from Example 86A (25.7 mg, 0.055 mmole) was combined in a microwave tube with 6-(dimethylamino)pyridine-3-ylboronic acid (17.49 mg, 0.105 mmole), tribasic potassium phosphate (24.70 mg, 0.116 mole) and 1,1'-bis(di-tert-butylphosphino)ferrocene palladium dichloride (2.504 mg, 3.84 mole). The tube was sealed and a solvent mixture of THF (2 mL) and water (0.6 mL) added via syringe. The reaction mixture was sparged with nitrogen at room temperature for three minutes during which time the solution turned black in color. Chromatographic analysis indicated that the reaction was complete. The contents of the microwave tube were partitioned between brine (3 mL) and ethyl acetate (3 mL). The water was drawn off and the organic phase dried over MgSO$_4$, filtered and concentrated. The crude product was purified by chromatography on silica gel from 2 up to 20% ethyl acetate in hexane to provide the title compound (26.8 mg, 96% yield) as an orange solid as a mixture of stereoisomers. MS ESI(+) m/z@510.4 (M+H)$^+$.

Example 99B 4,4'-(1-(4-(6-(dimethylamino)pyridin-3-yl)phenyl)pyrrolidine-2,5-diyl)dianiline The product from Example 99A (26.8 mg, 0.053 mmole) was dissolved in THF (526 L) in a round bottom flask to which was subsequently added ethanol (526 L) resulting in a

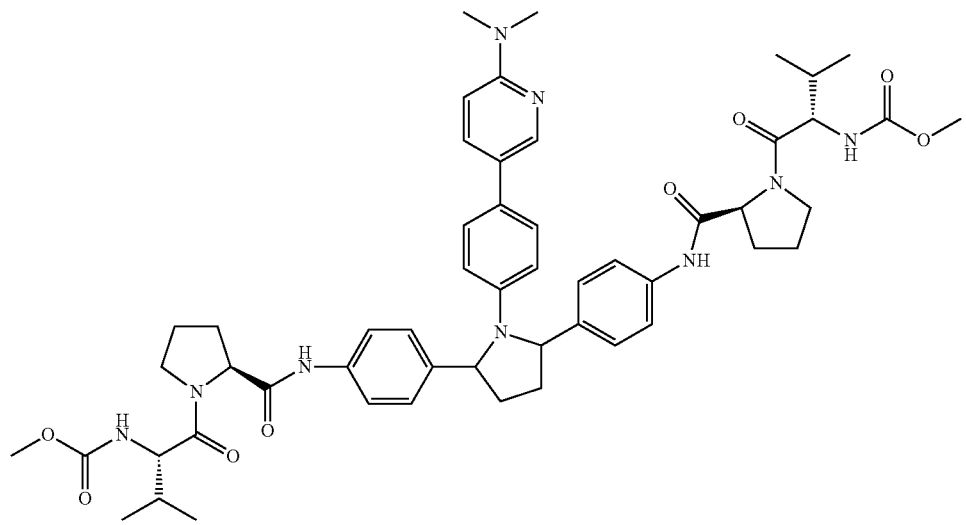

yellow precipitate. To this suspension was added platinum (IV) oxide (3.16 mg, 0.014 mmole). The flask was capped with a septum and the contents vacuum degassed three times. Hydrogen was introduced via a balloon and the mixture allowed to stir at room temperature for two and one half hours. The reaction mixture was vacuum filtered through a sand and celite plug, which was rinsed with THF and methanol until the filtrate was u.v.(−). The filtrate was concentrated in vacuo to provide the title compound in quantitative yield as a white solid as a mixture of stereoisomers. MS ESI(+), m/z@450.7 (M+H)+.

Example 99C (2S,2'S)-tert-butyl 2,2'-(4,4'-(1-(4-(6-(dimethylamino)pyridin-3-yl)phenyl)pyrrolidine-2,5-diyl)bis(4,1-phenylene))bis(azanediyl)bis(oxomethylene)dipyrrolidine-1-carboxylate The product from Example 99B (23.83 mg, 0.053 mmole) was reacted with (S)-1-(tert-butoxycarbonyl)pyrrolidine-2-carboxylic acid (27.8 mg, 0.129 mmole) as described in Example 1F with minor modification. The crude product was recovered by partition of the reaction mixture between ethyl acetate (10 mL) and water (3 mL). The organic phase was washed with water (3×3 mL), dried over MgSO$_4$, filtered and concentrated. Chromatography on silica gel using a solvent gradient of 2-100% ethyl acetate in hexane provided the title compound (32.6 mg, 73% yield) as a cream colored solid as a mixture of stereoisomers.

Example 99D (2S,2'S)—N,N'-(4,4'-(1-(4-(6-(dimethylamino)pyridin-3-yl)phenyl)pyrrolidine-2,5-diyl)bis(4,1-phenylene))dipyrrolidine-2-carboxamide The product from Example 99C (32.6 mg, 0.039 mmole) was reacted with trifluoroacetic acid (0.071 mL, 0.927 mmole) as described in Example 1G to provide the title compound (22.5 mg, 90% yield) as a cream colored solid as a mixture of stereoisomers.

Example 99E dimethyl ([(2S,5S)-1-{4-[6-(dimethylamino)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate and dimethyl ([(2R,5R)-1-{4-[6-(dimethylamino)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate The product from Example 99D (22.5 mg, 0.035 mmole) was reacted with (S)-2-(methoxycarbonylamino)-3-methylbutanoic acid (19.41 mg, 0.111 mmole) as described in Example 86C. Chromatography on silica gel (10% ethyl acetate/90% hexane to 100% ethyl acetate/4% methanol) provided the title compound (14.5 mg, 43.3% yield), an orange yellow solid that darkened somewhat on standing, as a 1:1 mixture of trans diastereomers. 1H NMR (400 MHz, DMSO-D6) δ ppm 0.77-0.99 (m, 12H) 1.67 (s, 2H) 1.76-2.24 (m, 11H) 2.98 (s, 6H) 3.52 (s, 6H) 3.58-3.65 (m, 2H) 3.76-3.90 (m, J=9.54 Hz, 2H) 3.95-4.11 (m, 2H) 4.36-4.47 (m, 2H) 5.19-5.27 (m, 2H) 6.30 (s, 2H) 6.58 (d, J=9.00 Hz, 1H) 7.17 (t, J=8.08 Hz, 4H) 7.30 (d, J==8.02 Hz, 3H) 7.52 (d, J=7.37 Hz, 4H) 7.57-7.63 (m, 1H) 7.63-7.68 (m, 1H) 7.91 (s, 1H) 8.18-8.22 (m, 1H) 10.00 (s, 2H). MS ESI(+) m/z@959.4 (M+H)+.

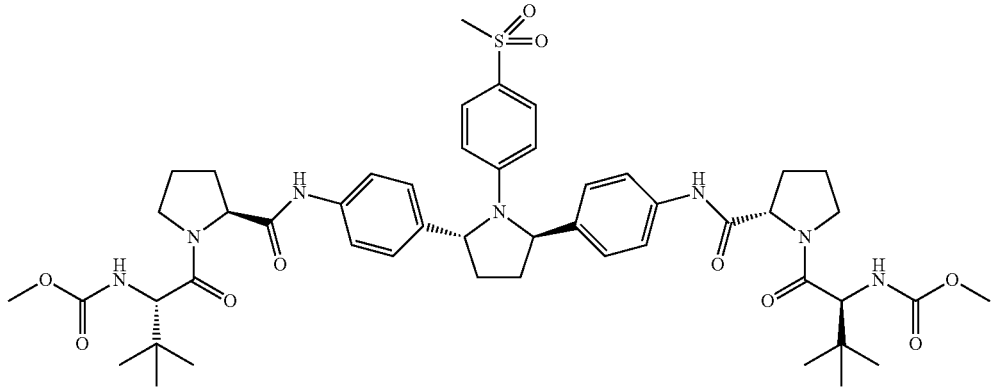

Example 100 dimethyl ({(2R,5R)-1-[4-(methylsulfonyl)phenyl]pyrrolidine-2,5-diyl}bis{benzene-4,1-diylcarbamoyl(2S)pyrrolidine-2,1-diyl[(2S)-3,3-dimethyl-1-oxobutane-1,2-diyl]})biscarbamate Example 38A and 4-(methylsulfonyl)aniline were processed using sequentially the methods of Examples 98A, 98B, 55F, 55G, and 26J (with (S)-2-(methoxycarbonylamino)-3,3-dimethylbutanoic acid; reaction solvent=dichloromethane) to provide the title compound (55 mg). $^1$H NMR (400 MHz, DMSO-D6) δ 0.96 (d, J=5.1, 18H), 1.24 (s, 1H), 1.69 (d, J=5.7, 2H), 2.04-1.74 (m, 7H), 2.22-2.07 (m, 2H), 2.98 (s, 3H), 3.54 (s, 6H), 3.70-3.58 (m, 2H), 3.83-3.70 (m, 2H), 4.20 (d, J=8.9, 2H), 4.43 (dd, J=7.8, 5.4, 2H), 5.32 (d, J=6.1, 2H), 6.39 (d, J=9.0, 2H), 7.08 (d, J=8.8, 2H), 7.15 (d, J=8.6, 4H), 7.43 (d, J=9.0, 2H), 7.53 (d, J=8.6, 4H), 10.03 (s, 2H). MS (ESI) m/z 966 (M+Na)$^+$, 943 (M−H)$^+$.

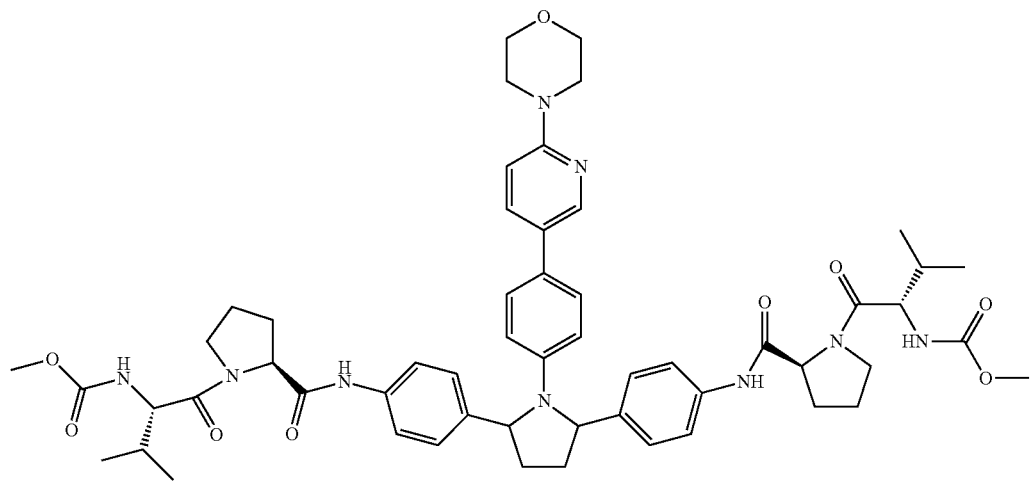

Example 101 dimethyl ([(2S,5S)-1-{4-[6-(morpholin-4-yl)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate and dimethyl ([(2R,5R)-1-{4-[6-(morpholin-4-yl)pyridin-3-yl]phenyl}pyrrolidine-2,5-diyl]bis{benzene-4,1-diylcarbamoyl(2S)pyrrolidine-2,1-diyl[(2S)-3-methyl-1-oxobutane-1,2-diyl]})biscarbamate Example 86A and 4-(5-(4,4,5,5-tetramethyl-1,3,2-dioxaborolan-2-yl)pyridin-2-yl)morpholine were processed using sequentially the methods of Examples 99A, 99B, 1F, 1G, and 86C to provide the title compound as a 1:1 mixture of trans diastereomers. 1H NMR (free base) (400 MHz, DMSO-D6) δ ppm 0.78-1.00 (m, 12H) 1.67 (s, 2H) 1.75-2.20 (m, 11H) 3.36-3.41 (m, 4H) 3.52 (s, 6H) 3.57-3.65 (m, 2H) 3.65-3.72 (m, 4H) 3.79 (s, 2H) 4.02 (s, 2H) 4.36-4.48 (m, 2H) 5.24 (s, 2H) 6.32 (d, J=7.70 Hz, 2H) 6.78 (d, J=9.00 Hz, 1H) 7.12-7.18 (m, 4H) 7.21 (d, J=8.78 Hz, 2H) 7.31 (d, J=8.35 Hz, 2H) 7.52 (d, J=7.48 Hz, 4H) 7.63-7.69 (m, 1H) 8.22-8.27 (m, 1H) 10.00 (s, 2H). MS ESI(+) m/z@1000.6 (M+H)+.

Example 102 dimethyl ({(2S,5S)-1-[4-(pyridin-3-yl)phenyl]pyrrolidine-2,5-diyl}bis {benzene-4,1-diylcarbamoyl(2S) pyrrolidine-2,1-diyl[(2S)-3-methyl-1-oxobutane-1,2-diyl]})biscarbamate and dimethyl ({(2R,5R)-1-[4-(pyridin-3-yl)phenyl]pyrrolidine-2,5-diyl}bis{benzene-4,1-diylcarbamoyl(2S) pyrrolidine-2,1-diyl[(2S)-3-methyl-1-oxobutane-1,2-diyl]})biscarbamate Example 86A and pyridin-3-ylboronic acid were processed using sequentially the methods of Examples 99A, 99B, 1F, 1G, and 86C to provide the title compound as a 1:1 mixture of trans diastereomers (35.8 mg). 1H NMR (free base) (400 MHz, DMSO-D6) δ ppm 0.71-1.05 (m, 11H) 1.68 (s, 2H) 1.87 (s, 8H) 2.06-2.21 (m, 2H) 3.52 (s, 6H) 3.56-3.67 (m, 2H) 3.80 (s, 2H) 4.02 (d, J=1.73 Hz, 2H) 4.43 (dd, J=7.97, 4.93 Hz, 2H) 5.26 (d, J=6.29 Hz, 2H) 6.37 (d, J=7.92 Hz, 2H) 7.17 (dd, J=8.57, 1.95 Hz, 4H) 7.28-7.36 (m, 5H) 7.52 (d, J=7.81 Hz, 4H) 7.82-7.87 (m, 1H) 8.36 (dd, J=4.72, 1.36 Hz, 1H) 8.69 (s, 1H) 10.00 (s, 2H). MS ESI(+) m/z@915.6 (M+H)+

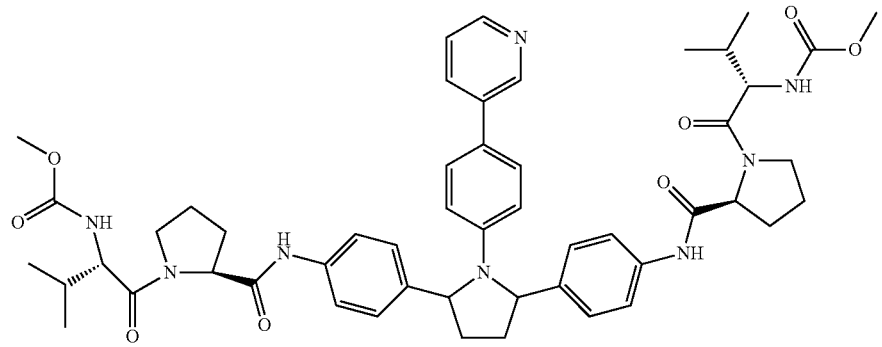 [SMILES: COC(=O)N[C@H](C(=O)N1CCC[C@H]1C(=O)Nc1ccc(C2CCC(c3ccc(NC(=O)[C@@H]4CCCN4C(=O)[C@@H](NC(=O)OC)C(C)C)cc3)N2c2ccc(-c3cccnc3)cc2)cc1)C(C)C]

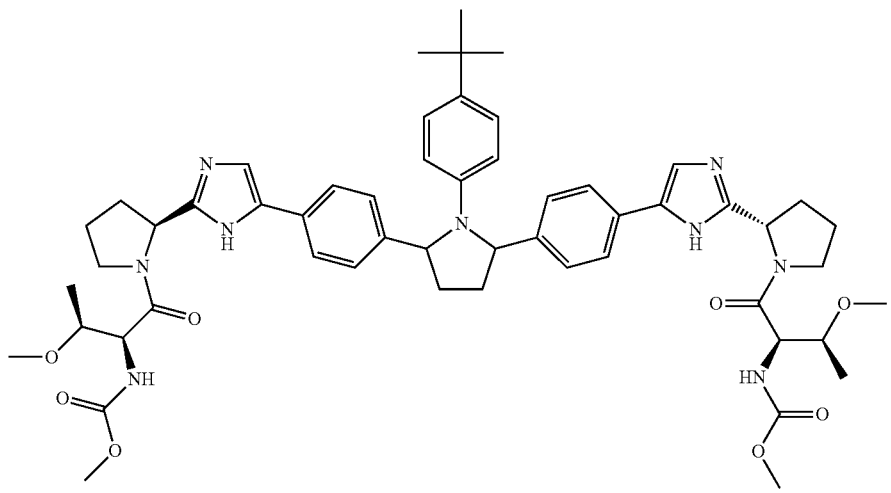

Example 103 methyl [(2S,3S)-1-{(2S)-2-[5-(4-{(2S,5S)-1-(4-tert-butylphenyl)-5-[4-(2-{(2S)-1-[N-(methoxycarbonyl)-O-methyl-D-threonyl]pyrrolidin-2-yl}-1H-imidazol-5-yl)phenyl]pyrrolidin-2-yl}phenyl)-1H-imidazol-2-yl]pyrrolidin-1-yl}-3-methoxy-1-oxobutan-2-yl] carbamate and methyl [(2S,3S)-1-{(2S)-2-[5-(4-{(2R,5R)-1-(4-tert-butylphenyl)-5-[4-(2-{(2S)-1-[N-(methoxycarbonyl)-O-methyl-D-threonyl]pyrrolidin-2-yl}-1H-imidazol-5-yl)phenyl]pyrrolidin-2-yl}phenyl)-1H-imidazol-2-yl]pyrrolidin-1-yl}-3-methoxy-1-oxobutan-2-yl] carbamate The product from Example 201A (0.122 g, 0.639 mmol), and HOBt (0.098 g, 0.639 mmole) were combined and dissolved in 2 ml DMF then cooled in an ice bath between 0-5° C. To this solution was added EDAC (0.123 g, 0.639 mmol) followed by 4-methylmorpholine (0.211 ml, 1.917 mmole) and the mixture was stirred 5 minutes, then added dropwise the mixture of the products from Example 42F (0.2 g, 0.320 mmol), in DMF (2 ml) with a DMF wash (1 ml). The pH of the solution was adjusted with additional 4-methylmorpholine (0.1 ml, 0.96 mmole) and the mixture was stirred a total of 90 minutes in the ice bath. The reaction mixture was analyzed by LC-MS at 90 min and determined the reaction to be complete. The reaction mixture was diluted with 100 ml EtOAc and washed with 25 ml water. The layers were separated and the aqueous layer was extracted with another 100 ml EtOAc. The combined organic extracts were washed with 10% NaHCO$_3$ and 10% NaCl, dried over anhydrous Na$_2$SO$_4$(s), filtered and solvent removed in vacuo leaving a purple oil. The oil was dissolved in 10 ml CH$_2$Cl$_2$ and applied to a 12 g silica gel column. The column was eluted with a gradient of CH$_2$Cl$_2$/MeOH, 99/1 to 95/5 over 25 minutes. The title compounds were isolated as a light yellow solid, 60 mg, 19%. 1H NMR (400 MHz, DMSO-D6) d ppm 0.86 (m, 2H) 1.00-1.18 (m, 15H) 1.27 (m, 2H) 1.70 (m, s H) 1.99 (m, 2H) 2.15 (m, 4H) 3.18 (d, J=10.08 Hz, 6H) 3.54 (s, 6H) 3.81 (m, 4H) 4.27 (m, 2H) 5.06 (m, 2H) 5.21 (d, 2H) 6.21 (d, 2H) 6.94 (d, 2H) 7.17 (d, 2H) 7.29 (d, 2H) 7.38 (d, J=1.73 Hz, 2H) 7.51 (d, 2H) 7.62 (d, J=8.02 Hz, 2H) 11.68 (s, 2H), 12.01 (m, 2H); ESI+:972.6

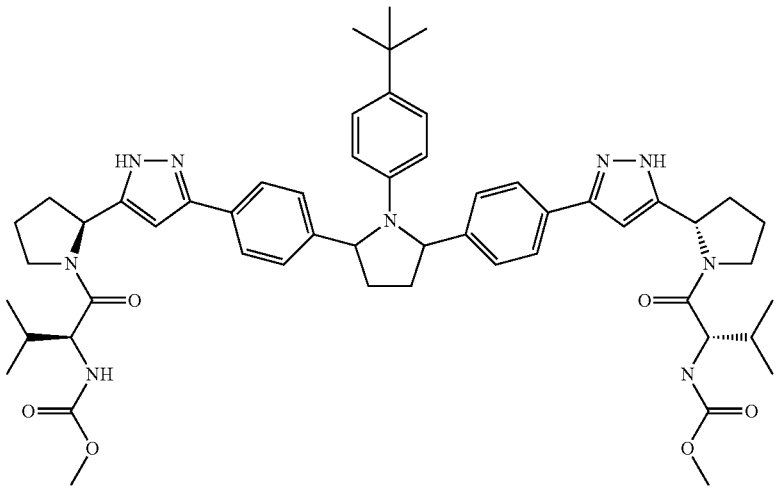 [SMILES: COC(=O)N[C@H](C(=O)N1CCC[C@H]1c1cc(-c2ccc(C3CCC(c4ccc(-c5cc([C@@H]6CCCN6C(=O)[C@@H](NC(=O)OC)C(C)C)[nH]n5)cc4)N3c3ccc(C(C)(C)C)cc3)cc2)n[nH]1)C(C)C]

Example 105 methyl {(2S)-1-[(2S)-2-(3-{4-[(2S,5S)-1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)pyrrolidin-2-yl]phenyl}-1H-pyrazol-5-yl)pyrrolidin-1-yl]-3-methyl-1-oxobutan-2-yl}carbamate and methyl {(2S)-1-[(2S)-2-(3-{4-[(2R,5R)-1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)pyrrolidin-2-yl]phenyl}-1H-pyrazol-5-yl)pyrrolidin-1-yl]-3-methyl-1-oxobutan-2-yl}carbamate

Example 105A 1-(4-tert-butylphenyl)-2,5-bis(4-((trimethylsilyl)ethynyl)phenyl)pyrrolidine To an oven-dried microwave tube (Size M, 5 mL) purged with nitrogen, added the product of Example 42C (340 mg, 0.662 mmol), bis(triphenylphosphine)palladium(II) dichloride (18.60 mg, 0.026 mmol), THF (2 mL), and triethylamine (2 mL). Stirred at room temperature for 5 min, then added copper(I) iodide (2.52 mg, 0.013 mmol), stirred the yellow mixture for 2 min, then nitrogen bubbled through for 15 min. Added trimethylsilylacetylene (0.374 mL, 2.65 mmol), sealed the tube with an aluminum crimp cap, and heated in an oil bath at 70° C. for 20 hr. Cooled the reaction to room temperature, added fresh bis(triphenylphosphine)palladium (II) dichloride (18.60 mg, 0.026 mmol) and copper(I) iodide (2.52 mg, 0.013 mmol), added additional trimethylsilylacetylene (0.374 mL, 2.65 mmol), and continued heating at 80° C. for 24 hr. Cooled the reaction to room temperature, diluted with Et$_2$O (50 mL), washed with H$_2$O (2×25 mL) and brine (25 mL), dried the organic phase over anhydrous MgSO$_4$, filtered, and concentrated by rotary evaporation to a light tan foam (470 mg). Purified by flash chromatography (silica gel, 2.5 cm×10 cm, 2% Et$_2$O/hexanes) to afford the title product as a yellow foam (324 mg, 89%) as a mixture of stereoisomers. MS (ESI+) m/z 548 (M+H)$^+$.

Example 105B 1-(4-tert-butylphenyl)-2,5-bis(4-ethynylphenyl)pyrrolidine

Dissolved the product of Example 105A (322 mg, 0.588 mmol) in anhydrous THF (5 mL) under nitrogen, added 1M TBAF in THF (1.322 mL, 1.322 mmol), and stirred at 25° C. for 30 min. The reaction darkened immediately upon addition and remained a brown color throughout the reaction. Removed solvent by rotary evaporation, dissolved the residue in Et$_2$O (50 mL), washed with H$_2$O (2×25 mL) and brine (25 mL), dried the organic phase over anhydrous MgSO$_4$, filtered, and concentrated by rotary evaporation to a light tan foam (289 mg). Purified by flash chromatography (silica gel, 3.8 cm×14 cm, 20% CH$_2$Cl$_2$/hexanes) to the title compound as a light yellow foam (176 mg, 74%) as a mixture of stereoisomers. MS (ESI+) m/z 404 (M+H)$^+$.

Example 105C (S)-3,3'-(4,4'-(1-(4-tert-butylphenyl)pyrrolidine-2,5-diyl)bis(1-(4,1-phenylene))bis(1-(N-Boc-(S)-pyrrolidin-2-yl)prop-2-yn-1-one In a flame-dried 10-mL round bottom flask, dissolved the product of Example 105B (94.3 mg, 0.234 mmol) in anhydrous THF (2 mL) under nitrogen and cooled to −78° C., added 1.6 M n-BuLi in hexanes (0.365 mL, 0.584 mmol) slowly in a dropwise manner via gas-tight syringe, and stirred the greenish-yellow solution for 1 hr at −78° C. In a separate flame-dried 10-mL round bottom flask purged with nitrogen, was prepared a solution of N-(tert-butoxycarbonyl)-L-proline N'-methoxy-N'-methylamide (166 mg, 0.631 mmol) in anhydrous THF (1 mL), and cooled to −78° C. Added the dianion mixture dropwise via a gas-tight syringe fitted with a 16G needle to the Weinreb amide solution and stirred at −78° C. for 30 min, replaced the dry ice-acetone bath with an ice-water bath, and stirred at 0° C. for 1 hr. Removed the cooling bath and stirred at room temperature for 1 hr, the cloudy yellow mixture became a dark yellow solution. Quenched the reaction with sat'd aq NH$_4$Cl (10 mL), extracted with Et$_2$O (2×25 mL), washed the combined ethereal extracts with H$_2$O (2×25 mL) and brine (25 mL), dried the organic phase over anhydrous MgSO$_4$, filtered, and concentrated by rotary evaporation to a yellow oil (214 mg). Purified by flash chromatography (silica gel, Alltech Extract-Clean 10 g column, gradient of 5% to 7% EtOAc/CH$_2$Cl$_2$) to afford the title compound as a yellow solid (77 mg, 41%) as a mixture of stereoisomers. MS (ESI+) m/z 798 (M+H)$^+$, 1595 (2M+H)$^+$.

Example 105D (2S,2'S)-tert-butyl 2,2'-(3,3'-(4,4'-(1-(4-tert-butylphenyl)pyrrolidine-2,5-diyl)bis(4,1-phenylene))bis(1H-pyrazole-5,3-diyl))dipyrrolidine-1-carboxylate Dissolved the product of Example 105C (75 mg, 0.094 mmol) in anhydrous absolute EtOH (1 mL) under nitrogen, added hydrazine hydrate (0.023 mL, 0.235 mmol), and stirred the yellow solution at room temperature for 1 hr. Removed the solvent by rotary evaporation, azeotroped the yellow oil with toluene (2×5 mL), redissolved in 1:5 v/v CH$_2$C$_2$/hexanes, concentrated, and dried the light yellow solid in vacuo. Purified by flash chromatography (silica gel, 2.5 cm×15 cm, 4% MeOH/CH$_2$Cl$_2$) to afford the title compound as a white solid (59 mg, 76%) as a mixture of stereoisomers. MS (ESI+) m/z 826 (M+H)+, 848 (M+Na)$^+$.

Example 105E (S)-3,3'-(4,4'-(1-(4-tert-butylphenyl)pyrrolidine-2,5-diyl)bis(4,1-phenylene))bis(5-((S)-pyrrolidin-2-yl)-1H-pyrazole Dissolved the product of Example 105D (57.5 mg, 0.070 mmol) in anhydrous CH$_2$Cl$_2$ (2 mL) under nitrogen, added TFA (1 mL, 12.98 mmol), and stirred at 25° C. for 30 min. Removed the solvent by rotary evaporation, took up the residue in 1:5 v/v CH$_2$Cl$_2$/hexanes, concentrated to a yellow residue, and dried in vacuo (83 mg). The TFA salt was dissolved in anhydrous MeOH (7 mL) under nitrogen, treated with pre-washed (H$_2$O and MeOH) and dried Amberlite IRA-400(OH) resin (750 mg, ~15 equivs of OH$^-$ based on ~1.4 mequiv/g dry resin) and stirred at 25° C. for 2 hr. Vacuum filtered in a Büchner funnel and washed the resin thoroughly with MeOH. The filtrate was concentrated by rotary evaporation, the residue taken up in 1:5 v/v CH$_2$Cl$_2$/hexanes, and concentrated in vacuo to give the title compound as a light yellow solid (41 mg, 94%) as a mixture of stereoisomers. MS (ESI+) m/z 626 (M+H)$^+$, 1251 (2M+H)$^+$.

Example 105F methyl {(2S)-1-[(2S)-2-(3-{4-[(2S,5S)-1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)pyrrolidin-2-yl]phenyl}-1H-pyrazol-5-yl)pyrrolidin-1-yl]-3-methyl-1-oxobutan-2-yl}carbamate and methyl {(2S)-1-[(2S)-2-(3-{4-[(2R,5R)-1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)pyrrolidin-2-yl]phenyl}-1H-pyrazol-5-yl)pyrrolidin-1-yl]-3-methyl-1-oxobutan-2-yl}carbamate In an oven-dried 10-mL round bottom flask purged with nitrogen, dissolved the product of Example 105E (39.7 mg, 0.063 mmol) in anhydrous DMF (1 mL) and cooled to 0° C. Added sequentially (S)-2-(methoxycarbonylamino)-3-methylbutanoic acid (23.89 mg, 0.136 mmol), HOBt hydrate (21.37 mg, 0.140 mmol), EDAC (27.3 mg, 0.140 mmol), and N-methylmorpholine (0.021 mL, 0.190 mmol). Removed the cooling bath and stirred the dark yellow solution at 25° C. for 1 hr. Diluted the reaction with EtOAc (50 mL), washed with H$_2$O (3×25 mL) and brine (25 mL), dried the organic phase over anhydrous MgSO$_4$, filtered, and concentrated by rotary evaporation to a light peach solid (63 mg). Dissolved the crude material in CH$_2$Cl$_2$ and purified by flash chromatography (silica gel, 2.5 cm×10 cm, 5% MeOH/CH$_2$Cl$_2$) to afford a 1:1.25 trans:cis product mixture (34 mg, 94% purity). Dissolved the residue in 1:1 v/v DMSO/MeOH (2 mL) and purified by RP-C$_{18}$ HPLC (Waters Prep LC, 40 mm Module with Nova Pak HR C$_{18}$ 6 μm 40×100 mm Prep Pak cartridge) eluting with a 30 min gradient of 90:10 0.1% TFA in H$_2$O/AcCN to 100% AcCN at 20 mL/min. Fractions containing a mixture of the trans diastereomers were concentrated by rotary evaporation, the residue taken up in 1:5 v/v CH$_2$Cl$_2$/hexanes and evaporated (5 times), and dried in vacuo to afford the title compounds as a cream-colored solid (12 mg, 16%). $^1$H NMR (TFA salt) (400 MHz, DMSO-D6) δ ppm 0.76-0.94 (m, 12H), 1.10 (s, 9H), 1.13-1.31 (m, 3H), 1.71 (d, J=5.42 Hz, 2H), 1.82-2.17 (m, 9H), 3.53 (s, 6H), 3.70-3.85 (m, 4H), 4.05 (t, J=8.08 Hz, 2H), 5.09-5.19 (m, 2H), 5.26 (d, J=5.96 Hz, 2H), 6.22 (d, J=8.78 Hz, 2H), 6.39 (d, J=1.30 Hz, 2H), 6.94 (d, J=8.67 Hz, 2H), 7.20-7.31 (m, 6H), 7.62 (d, J=7.92 Hz, 4H); MS (ESI+) m/z 940 (M+H)$^+$.

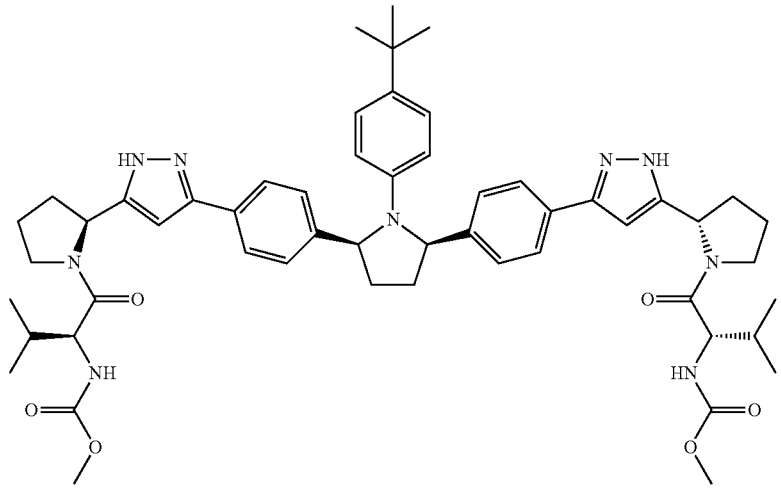 [SMILES: COC(=O)N[C@H](C(=O)N1CCC[C@H]1c1cc(-c2ccc([C@H]3CC[C@@H](c4ccc(-c5cc([C@@H]6CCCN6C(=O)[C@@H](NC(=O)OC)C(C)C)[nH]n5)cc4)N3c3ccc(C(C)(C)C)cc3)cc2)n[nH]1)C(C)C]

Example 106 methyl {(2S)-1-[(2S)-2-(3-{4-[(2R,5S)-1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)pyrrolidin-2-yl]phenyl}-1H-pyrazol-5-yl)pyrrolidin-1-yl]-3-methyl-1-oxobutan-2-yl}carbamate From the preparative HPLC separation of Example 105F was obtained the title compound (cis) as a yellow solid (16 mg, 21%). $^1$H NMR (TFA salt) (400 MHz, DMSO-D6) δ ppm 0.77-0.93 (m, 12H), 1.14 (s, 9H), 1.17-1.31 (m, 2H), 1.80-2.18 (m, 11H), 3.35 (d, J=8.02 Hz, 1H), 3.54 (s, 6H), 3.72-3.85 (m, 4H), 4.06 (t, J=8.29 Hz, 2H), 4.71-4.79 (m, 2H), 5.13-5.20 (m, 2H), 6.35 (d, J=8.78 Hz, 2H), 6.43 (s, 2H), 7.03 (d, J=8.78 Hz, 2H), 7.28 (d, J=8.35 Hz, 2H), 7.55 (d, J=8.24 Hz, 4H), 7.71 (d, J=7.59 Hz, 4H); MS (ESI+) m/z 940 (M+H)$^+$.

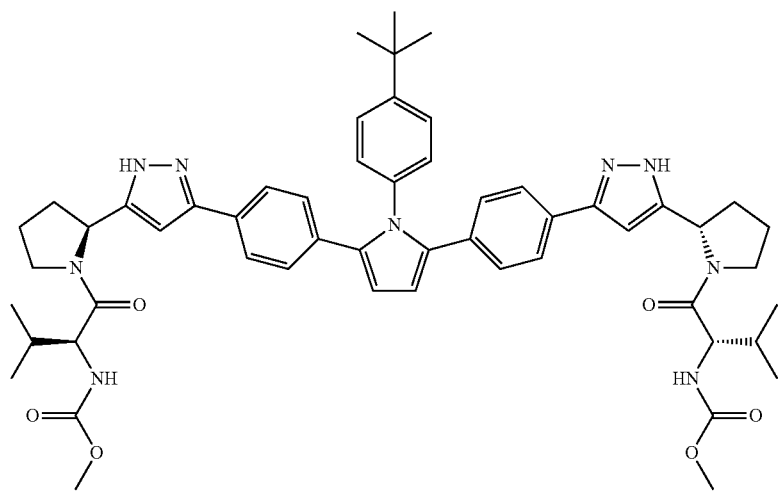 [SMILES: COC(=O)N[C@H](C(=O)N1CCC[C@H]1c1cc(-c2ccc(-c3ccc(-c4ccc(-c5cc([C@@H]6CCCN6C(=O)[C@@H](NC(=O)OC)C(C)C)[nH]n5)cc4)n3-c3ccc(C(C)(C)C)cc3)cc2)n[nH]1)C(C)C]

Example 107 methyl {(2S)-1-[(2S)-2-(3-{4-[1-(4-tert-butylphenyl)-5-(4-{5-[(2S)-1-{(2S)-2-[(methoxycarbonyl)amino]-3-methylbutanoyl}pyrrolidin-2-yl]-1H-pyrazol-3-yl}phenyl)-1H-pyrrol-2-yl]phenyl}-1H-pyrazol-5-yl)pyrrolidin-1-yl]-3-methyl-1-oxobutan-2-yl}carbamate In an oven-dried 5-mL round bottom flask purged with nitrogen, dissolved the product of Example 105E (5.1 mg, 8.15 µmol) in anhydrous DMF (400 µL) and cooled to 0° C. Added sequentially (S)-2-(methoxycarbonylamino)-3-methylbutanoic acid (3.07 mg, 0.018 mmol), HOBt hydrate (2.75 mg, 0.018 mmol), EDAC (3.51 mg, 0.018 mmol), and N-methylmorpholine (2.69 µL, 0.024 mmol). Removed the cooling bath and stirred the dark yellow solution at 25° C. for 18 hr. Diluted the reaction in EtOAc (50 mL), washed with $H_2O$ (2×10 mL) and brine (10 mL), dried the organic over anhydrous $MgSO_4$, filtered, and concentrated by rotary evaporation to a yellow solid (9.6 mg). Dissolved in 1:1 v/v MeOH/DMSO (1.5 mL) and purified by RP-$C_{18}$ HPLC (Waters Prep LC, 40 mm Module with Nova Pak HR $C_{18}$ 6 µm 40×100 mm Prep Pak cartridge) eluting with a 30 min gradient of 90:10 0.1% TFA in $H_2O$/AcCN to 100% AcCN at 20 mL/min. Pure fractions were concentrated by rotary evaporation, azeotroped with toluene (25 mL), the residue was taken up in 1:5 v/v $CH_2Cl_2$/hexanes and evaporated (3 times), then dried in vacuo to afford the title compound as an off-white solid (2.5 mg, 25%). $^1$H NMR (TFA salt) (400 MHz, DMSO-D6) δ ppm 0.76-0.92 (m, 12H), 1.27 (s, 9H), 1.80-2.15 (m, 10H), 3.53 (s, 6H), 3.69-3.84 (m, 4H), 4.05 (t, J=8.24 Hz, 2H), 5.08-5.16 (m, 2H), 6.39 (s, 2H), 6.53 (s, 2H), 7.06 (dd, J=8.29, 2.87 Hz, 6H), 7.26 (d, J=8.35 Hz, 2H), 7.37 (d, J=8.46 Hz, 2H), 7.44-7.55 (m, 4H), 12.92 (s, 2H); MS (ESI+) m/z 936 (M+H)$^+$.

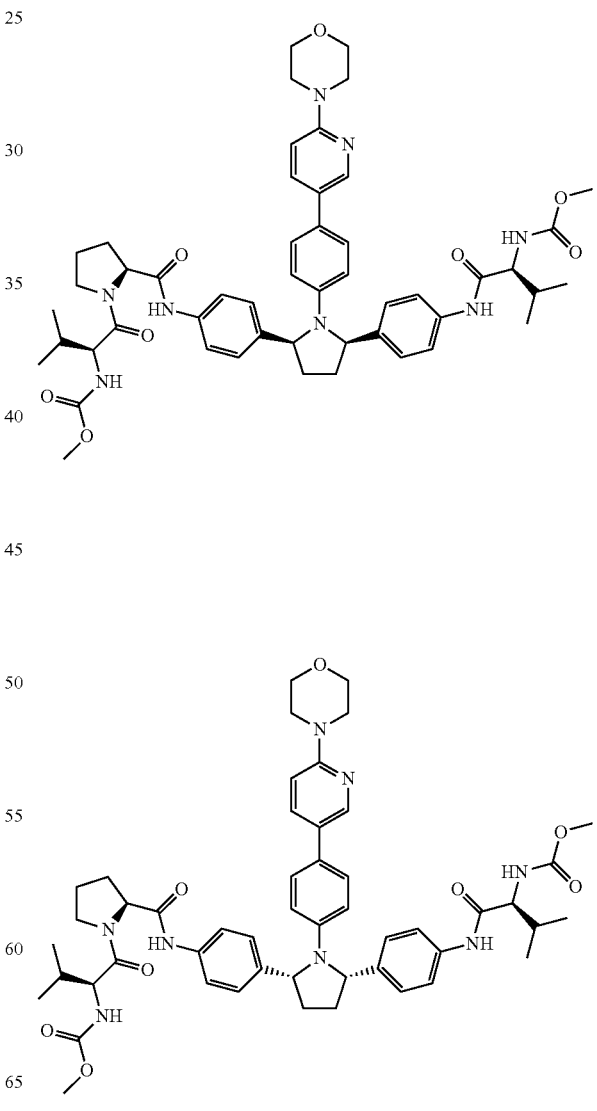

Example 108

N-(methoxycarbonyl)-L-valyl-N-{4-[(2S,5R)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide and N-(methoxycarbonyl)-L-valyl-N-{4-[(2R,5S)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide

Example 108A 4-(5-(4-(2,5-bis(4-nitrophenyl)pyrrolidin-1-yl)phenyl)pyridin-2-yl)morpholine In a microwave tube (size L, 20 mL) purged with nitrogen and sealed with a rubber septum, dissolved the product of Example 86A (160 mg, 0.342 mmol) and 4-[5-(4,4,5,5-tetramethyl-1,3,2-dioxaborolan-2-yl)pyridin-2-yl]morpholine (153 mg, 0.512 mmol) in THF (6 mL), added a solution of potassium phosphate (176 mg, 0.803 mmol) in water (2 mL), and sparged the reaction solution with S nitrogen for 5 min. Added 1,1'-bis(di-tert-butylphosphino)ferrocene palladium dichloride (12.02 mg, 0.018 mmol) and stirred at 25° C. for 15 min. During this process, the reaction darkened quickly to a brown color. Diluted the reaction with EtOAc (50 mL), washed with brine (10 mL), dried the organic phase over anhydrous $MgSO_4$, filtered, and concentrated by rotary evaporation. Dissolved the residue in $CH_2Cl_2$ and purified by flash chromatography (silica gel, Alltech Extract-Clean 10 g column, 20% EtOAc/$CH_2Cl_2$) to afford the title compound as a solid (176 mg, 93%) as a mixture of stereoisomers. $^1$H NMR (400 MHz, DMSO-D6) δ ppm 1.82-1.94 (m, 2H), 2.53-2.62 (m, 2H), 3.37-3.47 (m, 4H), 3.64-3.74 (m, 4H), 5.03 (t, J=5.37 Hz, 2H), 6.40 (d, J=8.89 Hz, 2H), 6.82 (d, J=9.00 Hz, 1H), 7.34 (d, J=8.78 Hz, 2H), 7.69 (dd, J=8.84, 2.55 Hz, 1H), 7.83 (d, J=8.78 Hz, 4H), 8.28 (d, J=8.78 Hz, 4H), 8.29-8.31 (m, 1H); MS (ESI+) m/z 552 (M+H)$^+$.

Example 108B 4,4'-(1-(4-(6-morpholinopyridin-3-yl)phenyl)pyrrolidine-2,5-diyl)dianiline Charged a 100-mL round bottom flask with the product of Example 108A (174.7 mg, 0.317 mmol), partially dissolved in THF (12.50 mL) and absolute EtOH (2.50 mL), evacuated on house vacuum and filled flask with nitrogen, then added platinum (IV) oxide (14.38 mg, 0.063 mmol), evacuated flask on house vacuum and filled with hydrogen from a balloon, repeated evacuation/filling cycle 3 times, and stirred heterogeneous reaction mixture vigorously under hydrogen (1 atm). After 2 hr, charged reaction with additional platinum (IV) oxide (14.38 mg, 0.063 mmol) and continued to vigorously stir under hydrogen at 25° C. After 5 hr, added additional platinum (IV) oxide (14.38 mg, 0.063 mmol). The reaction mixture was then vacuum filtered through a bed of Celite 545 in a Büchner funnel, the filter pad was washed with $CHCl_3$ (100 mL) and hot $CHCl_3$ (2×50 mL), and the filtrate concentrated by rotary evaporation to give the title compound as a yellow solid (101 mg, 65%) as a mixture of stereoisomers. $^1$H NMR (400 MHz, DMSO-D6) δ ppm 1.71-1.87 (m, 2H), 2.24-2.31 (m, 1H), 3.37-3.45 (m, 4H), 3.64-3.74 (m, 4H), 4.57 (t, J=4.99 Hz, 2H), 4.95 (s, 4H), 6.42-6.53 (m, 3H), 6.57 (d, J=8.35 Hz, 4H), 6.76-6.89 (m, 2H), 7.15 (d, J=8.35 Hz, 4H), 7.26 (d, J=8.78 Hz, 2H), 7.68 (dd, J=8.84, 2.44 Hz, 1H), 8.29 (d, J=2.39 Hz, 1H); MS (ESI+) m/z 492 (M+H)$^+$.

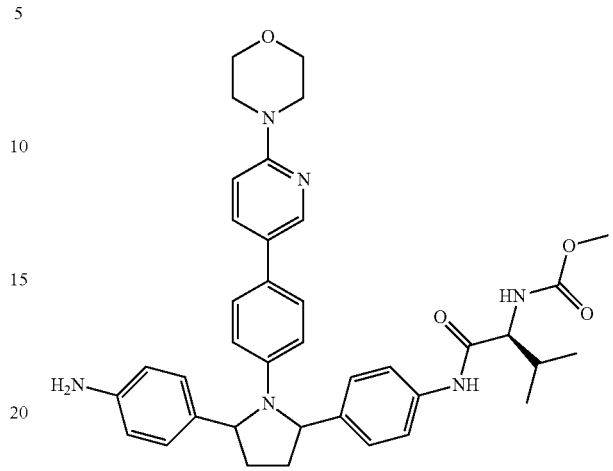

Example 108C methyl (2S)-1-(4-(5-(4-aminophenyl)-1-(4-(6-morpholinopyridin-3-yl)phenyl)pyrrolidin-2-yl)phenylamino)-3-methyl-1-oxobutan-2-ylcarbamate In an oven-dried 5-mL round bottom flask purged with nitrogen, dissolved the product of Example 108B (70 mg, 0.142 mmol) and (S)-2-(methoxycarbonylamino)-3-methylbutanoic acid (26.2 mg, 0.150 mmol) in anhydrous DMSO (1.5 mL), added HATU (58.6 mg, 0.150 mmol) and diisopropylethylamine (0.050 mL, 0.285 mmol), and stirred dark yellow solution at 25° C. for 15 min. Diluted the reaction with MeOH (1.5 mL) and purified by RP-$C_{18}$ HPLC (Waters Prep LC, 40 mm Module with Nova Pak HR $C_{18}$ 6 µm 40×100 mm Prep Pak cartridge) eluting with a 30 min gradient of 95:5 0.1% TFA in $H_2O$/AcCN to 25:75 0.1% TFA in $H_2O$/AcCN, then 10 min to 100% AcCN at 20 mL/min. Pure fractions were concentrated by rotary evaporation (water bath 35°) to a small volume, partitioned between 20% iPrOH/$CHCl_3$ (50 mL), and sat'd aq $NaHCO_3$ (15 mL), separated layers, dried organic extract over anhydrous $MgSO_4$, filtered, and concentrated by rotary evaporation to afford the title compound as a light yellow solid (48 mg, 52%). 1H NMR showed the material to be ~3:1 trans:cis mixture; MS (ESI+) m/z 649 (M+H)$^+$, 1297 (2M+H)$^+$.

Example 108D

N-(methoxycarbonyl)-L-valyl-N-{4-[(2S,5R)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide-ACD v12 and

N-(methoxycarbonyl)-L-valyl-N-{4-[(2R,5S)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide ACD v12

In an oven-dried 5-mL round bottom flask purged with nitrogen, dissolved 3:1 trans/cis mixture of Example 108C (44 mg, 0.068 mmol) and the product of Example 37B (20.31 mg, 0.075 mmol) in anhydrous DMSO (1 mL), added HATU (29.2 mg, 0.075 mmol) and diisopropylethylamine (0.024 mL, 0.136 mmol), and stirred yellow solution at 25° C. for 30 min. Diluted the reaction with MeOH (1 mL) and purified by RP-$C_{18}$ HPLC (Waters Prep LC, 40 mm Module with Nova Pak HR $C_{18}$ 6 µm 40×100 mm Prep Pak cartridge) eluting with a 30 min gradient of 95:5 0.1% TFA in $H_2O$/AcCN to 25:75 0.1% TFA in $H_2O$/AcCN, then 10 min to 100% AcCN at 20 mL/min. The earlier eluting compound (18.8 mg, 31%) was determined by $^1H$ NMR to be the trans diastereomers. The fractions of the later eluting peak were concentrated by rotary evaporation (water bath 35° C.) to small volume, partitioned between 20% iPrOH/$CHCl_3$ (50 mL) and sat'd aq $NaHCO_3$ (15 mL), separated layers, dried the organic phase over anhydrous $MgSO_4$, filtered, and concentrated by rotary evaporation to afford a 2:3 trans:cis mixture as an off-white solid (10 mg). The mixture was dissolved in 1:1 v/v MeOH/DMSO (1.5 mL) and purified by RP-$C_{18}$ HPLC (Phenomenex Luna $C_8$(2) 5 µm 100 Å AXIA column (30 mm×75 mm)) eluting with a gradient of 90:10 10 mM $NH_4OAc$:MeOH to 100% MeOH to afford the title cis compounds as a light beige solid (2 mg, 3%). $^1H$ NMR (400 MHz, DMSO-D6) δ ppm 0.85-0.98 (m, 12H), 1.77-2.06 (m, 7H), 2.09-2.21 (m, 1H), 2.36-2.45 (m, 1H), 3.37-3.42 (m, 4H), 3.51 (s, 3H), 3.53 (s, 3H), 3.59-3.70 (m, 6H), 3.75-3.86 (m, 1H), 3.95 (t, J=8.13 Hz, 1H), 4.02 (t, J=8.57 Hz, 1H), 4.44 (dd, J=8.19, 4.72 Hz, 1H), 4.73 (s, 2H), 6.43 (d, J=8.89 Hz, 2H), 6.80 (d, J=8.89 Hz, 1H), 7.27 (d, J=8.78 Hz, 2H), 7.29-7.38 (m, 2H), 7.44 (dd, J=8.57, 2.71 Hz, 4H), 7.54-7.64 (m, 4H), 7.67 (dd, J=8.89, 2.49 Hz, 1H), 8.27 (d, J=2.49 Hz, 1H), 10.04 (s, 2H); MS (ESI+) m/z 903 (M+H)$^+$, 920 (M+$NH_4$)$^+$, 961 (M+AcCN+$NH_4$)$^+$.

(10.0 g, 50.1 mmol) and THF (100 mL). To this stirring mixture was added portion-wise phenyltrimethylammonium tribromide (19.78 g, 52.6 mmol) over a 15 minutes time period. The resultant mixture was then stirred with monitoring every hour via LCMS. After 3 hr the mixture was then filtered and resulting solids washed with EtOAc. The organic solution was then concentrated, $H_2O$ and 10% aq. $NaHCO_3$ added and washed with EtOAc (2×300 mL). The combined organic layers were then washed with Brine, dried ($MgSO_4$), filtered and concentrated. The residue material was then subjected to purification via crystallization (dissolved material in 100 mL EtOAc and slowly added hexanes until cloudy—let stand for a few hours) to yield 9.81 g (70%) of 2-bromo-1-(4-chloro-3-nitrophenyl)ethanone as an off white colored solid product. 1H NMR (500 MHz, DMSO-D6) δ ppm 5.00 (s, 2H) 7.98 (d, J=8.54 Hz, 1H) 8.24 (dd, J=8.54, 2.14 Hz, 1H) 8.61 (d, J=1.98 Hz, 1H).

Method B:

In a 500 mL round-bottomed flask was added 1-(4-chloro-3-nitrophenyl)ethanone (11.98 g, 60 mmol) in benzene (75 ml) to give a white suspension. Bromine (9.59 g, 60.0 mmol) was added dropwise over 5 minutes to give a deep red solution. Stirred for 1 hour to give a yellow solution that was concentrated in vacuo to a yellow solid. Recrystallized from 9:1 hexane/ethyl acetate to give 2-bromo-1-(4-chloro-3-nitrophenyl)ethanone as yellow needles.

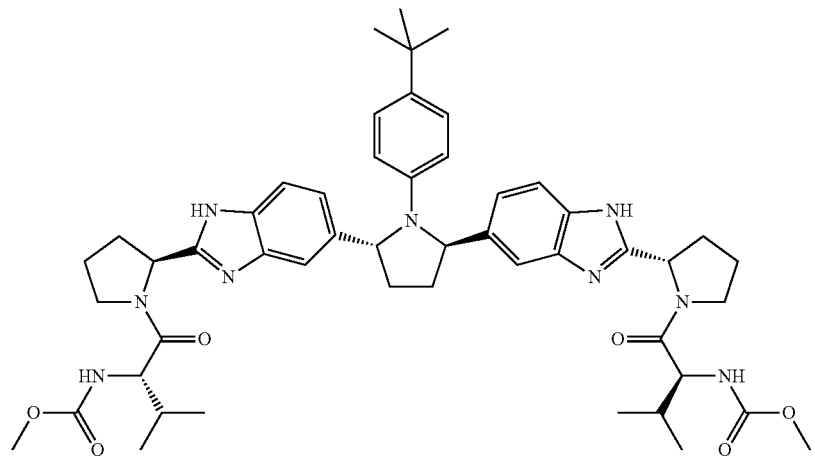

Example 109 methyl {(2S)-1-[(2S)-2-{5-[(2R,5R)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate Example 109A 2-bromo-1-(4-chloro-3-nitrophenyl)ethanone Method A:

To a flask equipped with a magnetic stir bar and under an atmosphere of $N_2$ was added 4'-chloro-3'-nitroacetophenone Example 109B 1,4-bis(4-chloro-3-nitrophenyl)butane-1,4-dione Zinc (II) chloride (14.68 g, 108 mmol) was added to toluene (81 mL), then diethylamine (8.35 mL, 81 mmol) and tert-butanol (7.73 mL, 81 mmol) were added and the resultant heterogenous solution stirred at rt for approx. 2 h. Afterwards Example 109A (15.0 g, 53.9 mmol) and 4'-chloro-3'-nitroacetophenone (16.13 g, 81 mmol) were added to the solution in one portion, and the resultant mixture stirred at rt for 42 h). The reaction was then quenched with 5% aqueous sulfuric acid (500 mL) and stirred vigorously to induce solid formation. The resultant solid was vacuum filtered, then washed with toluene, water, and methanol successively. Then the solid was added to a solution of hot ethyl acetate and resulting heterogeneous solution was stirred for 30 minutes and then the solid was collected and dried overnight in a vacuum oven to provide 16.6 g (78%) of the title compound. ¹H NMR (400 MHz, DMSO-d6) δ 8.61 (d, J=1.9 Hz, 2H), 8.27 (dd, J=8.4, 1.9 Hz, 2H), 7.96 (d, J=8.3 Hz, 2H), 3.48 (s, 4H).

Example 109C (1S,4S)-1,4-bis(4-chloro-3-nitrophenyl)butane-1,4-diol (R)-(+)-alpha,alpha-diphenyl-2-pyrrolidinemethanol (1.08 g, 4.28 mmol) was dissolved in 70 mL of THF at ambient temperature in a dry flask under nitrogen and the timethyl borate (650 uL, 5.54 mmol) was added dropwise. The resulting solution was stirred for 1 hr. The solution was cooled in a cold bath to ~10° C. and the N,N-diethylaniline borane (9.18 mL, 51.6 mmol) was added dropwise with some bubbling. After 15 min, this solution was transferred to an addition funnel and added dropwise to 1,4-bis(4-chloro-3-nitrophenyl)butane-1,4-dione (Example 109B) (10.0 g, 25.2 mmol) suspended in 200 mL of THF and cooled to ~10° C. Bubbling was observed. After the addition, mixture was stirred at ambient temperature for 4 hours. The mixture was cooled in an ice bath and 30 mL MeOH was added dropwise till bubbling stopped, then the mixture was let stir at ambient temperature for 30 min. The mixture was filtered to get rid of a trace of insoluble unreacted SM. The filtrate was concentrated, poured into 1 M HCl and extracted into ethyl acetate, dried over sodium sulfate; concentrated to give the title compound (9.9 g, 99%) as a yellow waxy solid. Chiral HPLC e.e. >99.9% (RR diol was undetectable). ¹H NMR (400 MHz, DMSO-d6) δ 7.94 (d, J=1.9 Hz, 2H), 7.69 (d, J=8.4 Hz, 2H), 7.60 (dd, J=8.4, 1.9 Hz, 2H), 4.65 (m, 2H), 1.62 (m, 4H).

Example 109D

The product of Example 109C was processed as in Example 113A, 113B, 113C, and 113D, substituting 4-t-butylaniline for 4-cyclohexylaniline in the step 113A procedure to give 0.212 g (22%) of the title compound. 1H NMR (400 MHz, DMSO-D6) δ ppm 0.74-0.92 (m, 12H) 1.07 (s, 9H) 1.69 (d, J=4.01 Hz, 2H) 1.86-2.05 (m, 6H) 2.13-2.24 (m, 4H) 2.54 (d, J=2.60 Hz, 2H) 3.51-3.56 (m, 6H) 3.81 (s, 4H) 4.05 (t, J=8.13 Hz, 2H) 5.09-5.18 (m, 2H) 5.35 (d, J=3.47 Hz, 2H) 6.25 (d, J=8.78 Hz, 2H) 6.86-6.96 (m, 2H) 7.07 (t, J=7.81 Hz, 2H) 7.20 (s, 1H) 7.26-7.32 (m, 3H) 7.38 (d, J=8.24 Hz, 1H) 7.46 (d, J=8.24 Hz, 1H) 11.98-12.08 (m, 2H); MS TFA+ m/z 889.

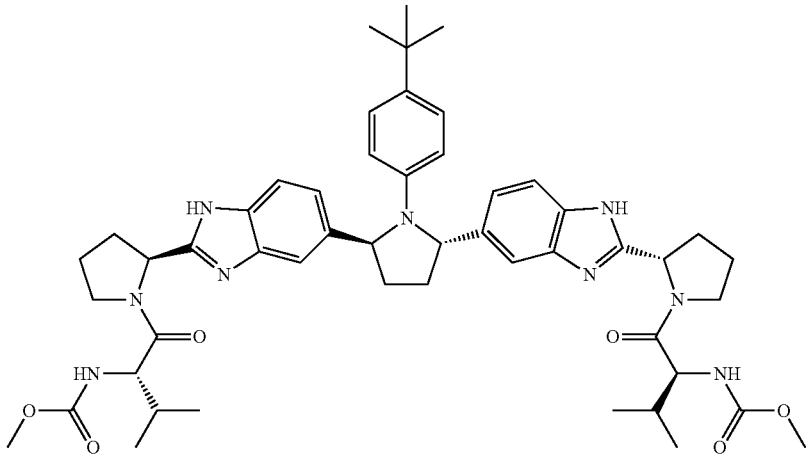

Example 110 methyl {(2S)-1-[(2S)-2-{5-[(2S,5S)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate The product from Example 28K was purified by chiral chromatography on a Chirapak IA column eluting with a mixture of hexane/methanol/tetrahydrofuran (3:1:1) to give the title compound. 1H NMR (400 MHz, DMSO-D6) δ ppm 0.78-0.91 (m, 12H) 1.07 (s, 9H) 1.64-1.73 (m, 2H) 1.89-2.00 (m, 6H) 2.12-2.23 (m, 4H) 3.14-3.24 (m, 2H) 3.52 (s, 6H) 3.76-3.85 (m, 4H) 4.05 (td, J=8.38, 2.33 Hz, 2H) 5.07-5.16 (m, 2H) 5.30-5.39 (m, 2H) 6.23 (d, J=8.78 Hz, 2H) 6.90 (ddd, J=8.95, 4.72, 4.55 Hz, 2H) 7.06 (t, J=9.22 Hz, 2H) 7.17 (s, 1H) 7.23-7.31 (m, 3H) 7.37 (d, J=8.13 Hz, 1H) 7.44 (d, J=8.24 Hz, 1H) 12.02 (d, J=23.42 Hz, 2H); MS ESI+ m/z 888 (M+H)+.

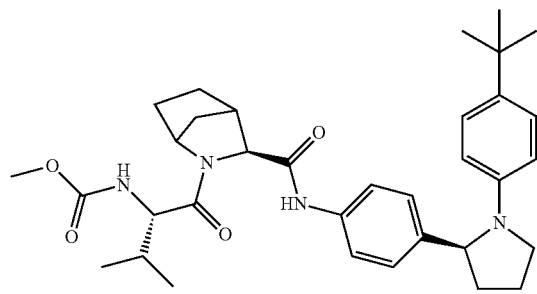

Example 111 dimethyl ([(2S,5S)-1-(4-tert-butylphenyl)pyrrolidine-2,5-diyl]bis{benzene-4,1-diylcarbamoyl(3S)-2-azabicyclo[2.2.1]heptane-3,2-diyl[(2S)-3-methyl-1-oxobutane-1,2-diyl]})biscarbamate

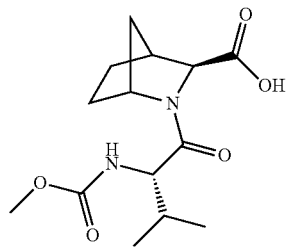 [SMILES: COC(=O)N[C@H](C(=O)N1C2CCC(C2)[C@H]1C(=O)O)C(C)C]

Example 111A (3S)-2-((S)-2-(methoxycarbonylamino)-3-methylbutanoyl)-2-azabicyclo[2.2.1]heptane-3-carboxylic acid (3S)-ethyl 2-azabicyclo[2.2.1]heptane-3-carboxylate (1.25 g, 7.39 mmol), (S)-2-(methoxycarbonylamino)-3-methylbutanoic acid (1.42 g, 8.13 mmol), diisopropylethylamine (6.45 mL, 36.9 mmol), and HATU (2.95 g, 7.76 mmol) were combined in dimethylformamide (40 mL) at ambient temperature and stirred for 2 hours. The solution was diluted with water and the product filtered and dried. The dried ester (1.0 g, 3.06 mmol) was taken up in water (15 mL) and ethanol (15 mL) and treated with sodium hydroxide (0.5 g, 12.5 mmol) at ambient temperature for 17 hours. The solution was washed with ether then the aqueous was neutralized with concentrated HCl to pH 7 and the product extracted into ethyl acetate, dried over sodium sulfate, and concentrated to give the title compound as a waxy solid.

Example 111B dimethyl ([(2S,5S)-1-(4-tert-butylphenyl)pyrrolidine-2,5-diyl]bis{benzene-4,1-diylcarbamoyl(3S)-2-azabicyclo[2.2.1]heptane-3,2-diyl[(2S)-3-methyl-1-oxobutane-1,2-diyl]})biscarbamate The product from Example 37E (0.05 g, 0.13 mmol), the product from example 111A (0.097 g, 0.324 mmol), diisopropylethylamine (0.113 mL, 0.648 mmol), and HATU (0.104 g, 0.272 mmol) were combined in dimethylformamide (2 mL) at ambient temperature and stirred for 3 hours. The solution was poured into brine, extracted into ethyl acetate, concentrated, and purified by combi-flash 12 g silica column, eluting with 0-6% methanol in dichloromethane to give the title compound as a solid. 1H NMR (400 MHz, DMSO-D6) δ ppm 0.91 (d, J=6.72 Hz, 6H) 0.98 (d, J=6.72 Hz, 6H) 1.11 (s, 9H) 1.32 (d, J=8.89 Hz, 2H) 1.36-1.46 (m, 2H) 1.59-1.74 (m, 6H) 1.76-1.84 (m, 2H) 1.90 (td, J=13.88, 6.94 Hz, 2H) 2.01-2.09 (m, 2H) 2.40-2.47 (m, 2H) 2.60 (d, J=1.19 Hz, 2H) 3.52 (s, 6H) 3.94 (s, 2H) 4.04-4.15 (m, 2H) 4.46 (s, 2H) 5.15 (d, J=6.51 Hz, 2H) 6.17 (d, J=8.78 Hz, 2H) 6.94 (d, J=8.78 Hz, 2H) 7.13 (d, J=8.57 Hz, 4H) 7.22 (d, J=8.46 Hz, 2H) 7.49 (d, J=8.57 Hz, 4H) 9.95 (s, 2H)

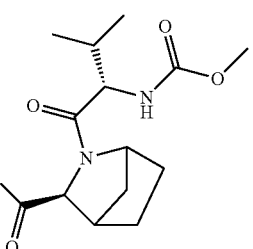
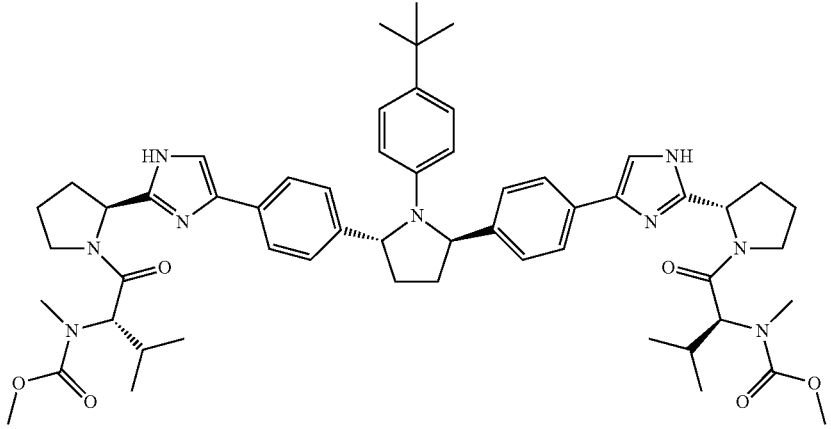

Example 112 methyl {(2S)-1-[(2S)-2-(4-{4-[(2R,5R)-1-(4-tert-butylphenyl)-5-(4-{2-[(2S)-1-{(2S)-2-[(methoxycarbonyl)(methyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}methylcarbamate The product from Example 126H was processed as in Example 42B-42G, substituting (S)-2-(methoxycarbonyl(methyl)amino)-3-methylbutanoic acid for (S)-2-(methoxycarbonylamino)-3-methylbutanoic acid in step 42G, to give 0.07 g (40%) of the title compound as a white solid. 1H NMR (free base) (400 MHz, DMSO-D6) δ ppm 0.76 (d, J=6.61 Hz, 6H) 0.83 (d, J=6.51 Hz, 6H) 1.09 (s, 9H) 1.63-1.75 (m, 2H) 1.86-2.00 (m, 4H) 2.03-2.21 (m, 6H) 2.77 (s, 6H) 3.10-3.22 (m, 4H) 3.63 (s, 6H) 3.74-3.84 (m, 2H) 4.98-5.07 (m, 2H) 5.16-5.23 (m, 2H) 6.21 (d, J=8.78 Hz, 2H) 6.88-6.96 (m, 2H) 7.15 (d, J=8.24 Hz, 4H) 7.22 (d, J=8.35 Hz, 1H) 7.36 (d, J=1.52 Hz, 2H) 7.51 (d, J=8.24 Hz, 1H) 7.61 (d, J=8.13 Hz, 4H) 11.70 (s, 2H); MS ESI+ m/z 968.7 (M+H)+; MS ESI+ m/z 968.7 (M+H)+.

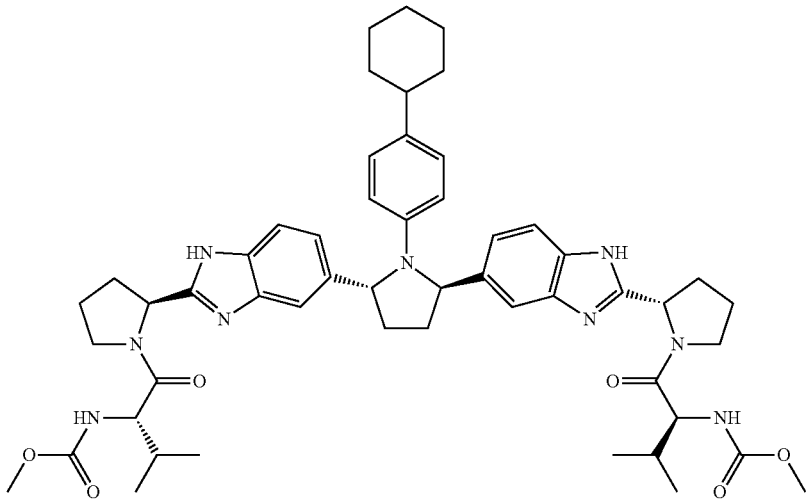

Example 113 methyl {(2S)-1-[(2S)-2-{5-[(2R,5R)-1-(4-cyclohexylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate

Example 113A (2R,5R)-2,5-bis(4-chloro-3-nitrophenyl)-1-(4-cyclohexylphenyl)pyrrolidine The product of Example 109C (2.0 g, 4.99 mmol) and triethylamine (1.51 mL, 14.96 mmol) were dissolved in dichloromethane (50 mL) and cooled in an ice bath. Methanesulfonyl chloride (0.855 mL, 10.97 mmol) in dichloromethane (2 mL) was added dropwise and the resulting mixture was stirred at ambient temperature for 2 hours. The solution was concentrated to dryness and S dissolved in dimethylformamide (8 mL). 4-Cyclohexylaniline (5.24 g, 29.9 mmol) was added and the solution was heated at 65° C. for 2 hours then poured into 1 M HCl and extracted into dichloromethane, concentrated, and purified by combi-flash 80 g silica column, eluting with 0-20% ethyl acetate in hexanes to give 1.38 g (51%) of the title compound.

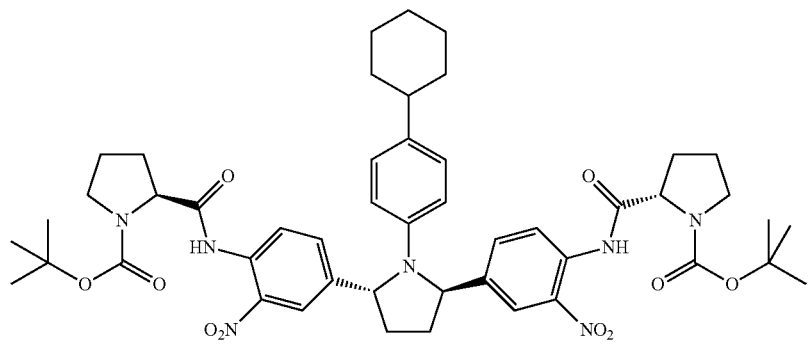 [SMILES: CC(C)(C)OC(=O)N1CCC[C@H]1C(=O)Nc1ccc([C@H]2CC[C@H](c3ccc(NC(=O)[C@@H]4CCCN4C(=O)OC(C)(C)C)c([N+](=O)[O-])c3)N2c2ccc(C3CCCCC3)cc2)cc1[N+](=O)[O-]]

Example 113B (2S,2'S)-tert-butyl 2,2'-(4,4'-((2R,5R)-1-(4-cyclohexylphenyl)pyrrolidine-2,5-diyl)bis(2-nitro-4,1-phenylene))bis(azanediyl)bis(oxomethylene)dipyrrolidine-1-carboxylate The product from Example 113A (1.29 g, 2.39 mmol), (S)-tert-butyl 2-carbamoylpyrrolidine-1-carboxylate (1.53 g, 7.16 mmol), cesium carbonate (2.33 g, 7.16 mmol), 4,5-bis(diphenylphosphino)-9,9-dimethylxanthene (0.33 g, 0.573 mmol), and tris(dibenzylideneacetone)dipalladium(0) (0.328 g, 0.358 mmol) were combined in dioxane (18 mL) and nitrogen was bubbled through the solution for 15 min, then the flask was capped with a reflux condenser and the solution heated at 100° C. for 8 hours. After filtering through celite and concentrating, the residue was purified by combi-flash 80 g silica column, eluting with 0-20% ethyl acetate in dichloromethane to give 1.71 g (80%) of the title compound.

ambient temperature and treated with Platinum (IV) oxide (0.11 g, 0.48 mmol). The flask was evacuated and opened to a hydrogen balloon and stirred for 18 hours then filtered through celite and concentrated to give the title compound.

Example 113D methyl {(2S)-1-[(2S)-2-{5-[(2R,5R)-1-(4-cyclohexylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate Example 113C was processed using the methods of Examples 28I, 28J, and 28K to provide the title compound.

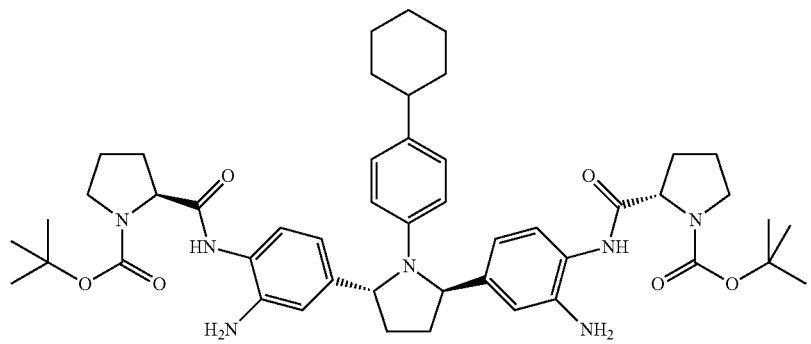 [SMILES: CC(C)(C)OC(=O)N1CCC[C@H]1C(=O)Nc1ccc([C@H]2CC[C@H](c3ccc(NC(=O)[C@@H]4CCCN4C(=O)OC(C)(C)C)c(N)c3)N2c2ccc(C3CCCCC3)cc2)cc1N]

Example 113C (2S,2'S)-tert-butyl 2,2'-(4,4'-((2R,5R)-1-(4-cyclohexylphenyl)pyrrolidine-2,5-diyl)bis(2-amino-4,1-phenylene))bis(azanediyl)bis(oxomethylene)dipyrrolidine-1-carboxylate The product from Example 113B (1.71 g, 1.91 mmol) was dissolved in tetrahydrofuran (10 mL) and ethanol (10 mL) at 1H NMR (400 MHz, DMSO-D6) δ ppm 0.76-0.91 (m, 12H) 1.03-1.29 (m, 6H) 1.55-1.74 (m, 7H) 1.84-2.06 (m, 6H) 2.11-2.25 (m, 6H) 3.53 (s, 6H) 3.81 (s, 4H) 4.02-4.13 (m, 2H) 5.08-5.18 (m, 2H) 5.32-5.38 (m, 2H) 6.24 (d, J=8.57 Hz, 2H) 6.68-6.77 (m, 2H) 7.06 (t, J=7.54 Hz, 2H) 7.19 (s, 1H) 7.26-7.32 (m, 3H) 7.37 (d, J=8.24 Hz, 1H) 7.45 (d, J=8.35 Hz, 1H) 11.98-12.05 (m, 2H); MS ESI+ m/z 914.5.

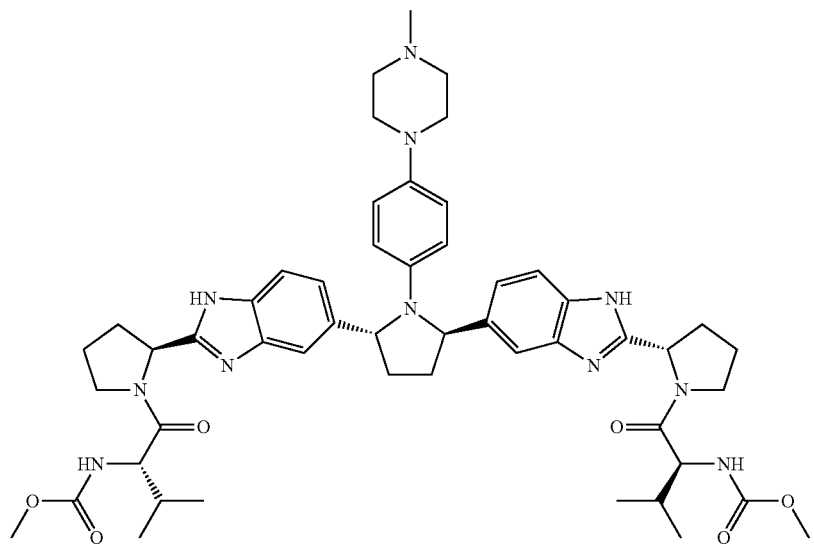

Example 114 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(4-methylpiperazin-1-yl)phenyl]pyrrolidin-2-yl}-1H-benzimidazol-2-yl)pyrrolidin-1-yl]-3-methyl-1-oxobutan-2-yl}carbamate The product of Example 109C (1.0 g, 2.49 mmol) was processed as in Examples 113A-113D, substituting 4-(4-methylpiperazin-1-yl)aniline for 4-cyclohexylaniline in the procedure of Example 113A and substituting Raney Nickel in tetrahydrofuran for platinum(IV) oxide in tetrahydrofuran and ethanol in the procedure of Example 113C to give 0.028 g (50%) of the title compound as a solid. 1H NMR (400 MHz, DMSO-D6) δ ppm 0.77-0.90 (m, 12H) 1.65-1.72 (m, 2H) 1.85-2.04 (m, 8H) 2.13 (s, 3H) 2.15-2.23 (m, 4H) 2.32 (s, 2H) 2.77 (s, 6H) 3.54 (s, 6H) 3.82 (d, J=4.66 Hz, 4H) 4.02-4.08 (m, 2H) 5.09-5.18 (m, 2H) 5.28-5.37 (m, 2H) 6.23 (d, J=8.78 Hz, 2H) 6.54 (ddd, J=9.00, 4.66, 4.55 Hz, 2H) 7.02-7.08 (m, 2H) 7.19 (s, 1H) 7.26-7.31 (m, 3H) 7.36 (d, J=8.13 Hz, 1H) 7.44 (d, J=8.35 Hz, 1H) 12.01 (s, 2H); MS ESI+ m/z 556 (M+H)+.

Example 115 methyl {(2S)-1-[(2S)-2-{6-[(2R,5R)-1-(1,3-benzothiazol-2-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate

Example 115A (2R,5R)-1-allyl-2,5-bis(4-chloro-3-nitrophenyl)pyrrolidine

The product from Example 109C (5.0 g, 12.46 mmol) and allylamine were processed as in Example 113A to give 1.5 g (39%) of the title compound as a thick oil.

Example 115B (2R,5R)-2,5-bis(4-chloro-3-nitrophenyl)pyrrolidine

The product from Example 115A (2.0 g, 4.74 mmol) was dissolved in acetonitrile (40 mL) and water (4 mL) and treated

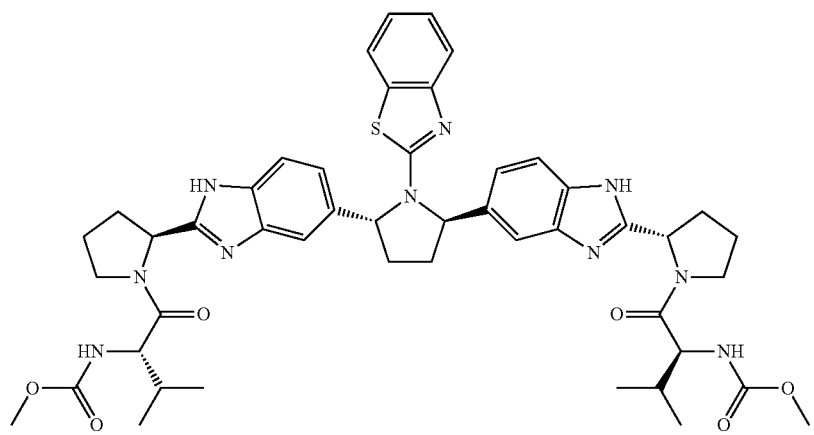

with Tris(triphenylphosphine)rhodium(I) chloride (0.219 g, 0.237 mmol). The mixture was heated at 100° C. and nitrogen was bubbled through the solution for 3 hours. The mixture was partitioned between 5% sodium bicarbonate solution and ethyl acetate, then the organics were concentrated and the product purified by combiflash 80 g silica column eluting with dichloromethane to give 1.33 g (74%) of the title compound.

Example 115C 2-((2R,5R)-2,5-bis(4-chloro-3-nitrophenyl)pyrrolidin-1-yl)benzo[d]thiazole The product from Example 115B (0.335 g, 0.877 mmol), 2-bromobenzo[d]thiazole (0.281 g, 1.32 mmol), tris(dibenzylideneacetone)dipalladium(0) 0.08 g (0.088 mmol), BINAP (0.055 g, 0.088 mmol), and sodium tert-butoxide (0.126 g, 1.32 mmol) were combined in dioxane (8 mL) and nitrogen was bubbled through the solution for 10 minutes. The tube was sealed and heated at 100° C. for 18 hours. The reaction mixture was partitioned between brine and dichloromethane and the organics were concentrated and purified by combi-flash 24 g silica column, eluting with 1:1 hexanes: dichloromethane, followed by 100% dichloromethane to give 0.165 g (37%) of the title compound.

Example 115D methyl {(2S)-1-[(2S)-2-{6-[(2R,5R)-1-(1,3-benzothiazol-2-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate The product from Example 115C was processed as in Examples 113B, 113C, and 113D to give 0.040 g (38%) of the title compound. 1H NMR (400 MHz, DMSO-D6) δ ppm 0.74-0.88 (m, 12H) 1.76-1.84 (m, 2H) 1.85-1.94 (m, 3H) 1.95-2.07 (m, 4H) 2.14-2.26 (m, 4H) 2.61-2.71 (m, 2H) 3.53 (s, 6H) 3.76-3.85 (m, 4H) 4.05 (t, J=8.51 Hz, 2H) 5.10-5.18 (m, 2H) 6.90 (t, J=7.54 Hz, 2H) 7.07-7.16 (m, 3H) 7.22-7.35 (m, 4H) 7.40 (d, J=8.13 Hz, 2H) 7.47 (d, J=8.35 Hz, 1H) 7.52-7.59 (m, 1H) 12.07 (s, 2H); MS ESI+ m/z 889.

Example 116 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-(4,5,6,7-tetrahydro-1,3-benzothiazol-2-yl)pyrrolidin-2-yl]-1H-benzimidazol-2-yl}pyrrolidin-1-yl]-3-methyl-1-oxobutan-2-yl}carbamate Example 116A (S)-pyrrolidine-2-carboxamide hydrochloride salt To (S)-tert-butyl 2-carbamoylpyrrolidine-1-carboxylate (29.8 g, 139 mmol) was added a solution of 4N HCl in dioxane (209 mL, 836 mmol) and the resultant mixture stirred at room temperature for 18 hrs. The mixture was then concentrated and triturated with diethyl ether then vacuum filtered and dried under vacuum to provide 21.6 g (104%) of the title product as a colorless solid.

Example 116B (S)-2-(methoxycarbonylamino)-3-methylbutanoic acid

To (S)-2-amino-3-methylbutanoic acid (57 g, 487 mmol) dissolved in dioxane (277 mL) was added a 2N aqueous sodium hydroxide solution (803 mL, 1606 mmol) followed by the dropwise addition of methyl chloroformate (75 mL, 973 mmol) over 1 hr which caused warming of the solution to occur. After the addition, the mixture was heated at 60° C. for 22 hrs, then cooled and extracted with dichloromethane (400 mL). The resultant aqueous layer was cooled in an ice bath then 12N hydrochloric acid was added dropwise until the pH was 2. The resultant mixture was stirred at 0° C. for 2 hrs then the resultant solid was vacuum filtered and dried in a vacuum oven to provide 80 g (94%) of the title compound as a colorless solid. ¹H NMR (400 MHz, DMSO-d6) δ 12.50 (bs, 1H), 7.34 (d, J=8.6 Hz, 1H), 3.84 (dd, J=8.6, 6.0 Hz, 1H), 3.54 (s, 3H), 2.03 (m, 1H), 0.86 (t, J=7.0 Hz, 6H).

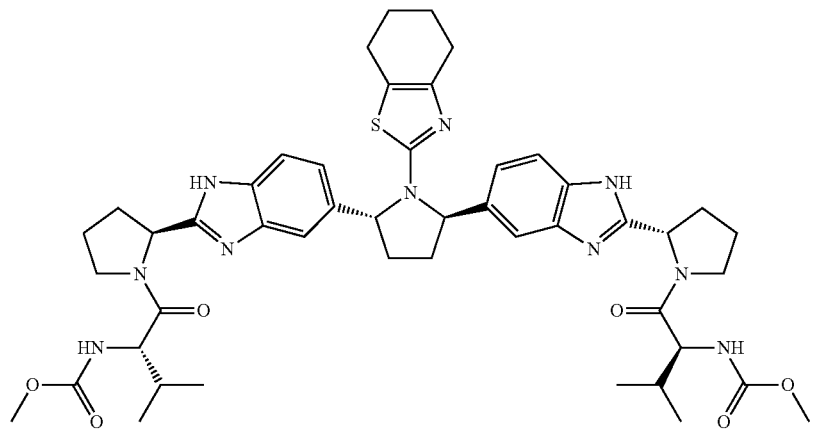

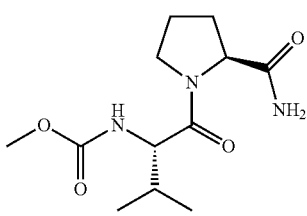 [SMILES: COC(=O)N[C@H](C(=O)N1CCC[C@H]1C(N)=O)C(C)C]

Example 116C methyl (S)-1-((S)-2-carbamoylpyrrolidin-1-yl)-3-methyl-1-oxobutan-2-ylcarbamate To the product of Example 116A (21.6 g, 144 mmol), the product of Example 116B (29.1 g, 166 mmol), 1H-benzo[d][1,2,3]triazol-1-ol hydrate (27.6 g, 180 mmol), N1-((ethylimino)methylene)-N3,N3-dimethylpropane-1,3-diamine hydrochloride (34.6 g, 180 mmol) and 4-methylmorpholine (63.5 mL, 578 mmol) was dissolved in dichloromethane (960 mL) and stirred at room temperature for 18 hrs. The resultant solution was then concentrated to a residue, water was then added and the solution extracted with a 25% isopropanol in chloroform solution (2×2000 mL) the organic layer washed with brine then the organic extract dried over MgSO$_4$, then concentrated to a yellow oil which was purified by column chromatography eluting with a gradient of 0-10% methanol in dichloromethane to provide 25 g (64%) of the title compound as a colorless solid. $^1$H NMR (400 MHz, DMSO-d6) δ 7.28 (m, 2H), 6.81 (s, 1H), 4.24 (dd, J=8.1, 4.4 Hz, 1H), 4.00 (t, J=8.4 Hz, 1H), 3.75 (m, 1H), 3.55 (m, 1H), 3.50 (s, 3H), 2.02 (m, 1H), 1.97 (m, 2H), 1.80 (m, 2H), 0.92 (d, J=6.7 Hz, 3H), 0.86 (d, J=8.6 Hz, 3H).

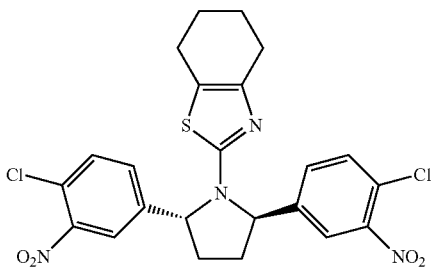 [SMILES: O=[N+]([O-])c1cc([C@H]2CC[C@H](c3ccc(Cl)c([N+](=O)[O-])c3)N2c2nc3c(s2)CCCC3)ccc1Cl]

Example 116D 2-((2R,5R)-2,5-bis(4-chloro-3-nitrophenyl)pyrrolidin-1-yl)-4,5,6,7-tetrahydrobenzo[d]thiazole The product from Example 109C (0.80 g, 1.489 mmol) and 4,5,6,7-tetrahydrobenzo[d]thiazol-2-amine were processed using the method of Example 113A to give 0.375 g (50%) of the title compound

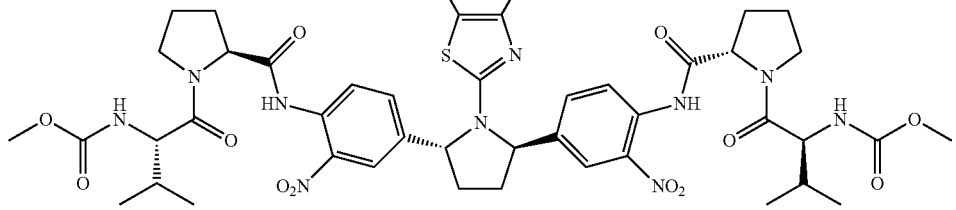

Example 116E dimethyl ([[(2R,5R)-1-(4,5,6,7-tetrahydro-1,3-benzothiazol-2-yl)pyrrolidine-2,5-diyl]bis{(2-nitrobenzene-4,1-diyl)carbamoyl(2S)pyrrolidine-2,1-diyl[(2S)-3-methyl-1-oxobutane-1,2-diyl]})biscarbamate (ACD v12))

The product from Example 116D (0.375 g, 0.722 mmol) was processed as in Example 113B, substituting the product from Example 116C for (S)-tert-butyl 2-carbamoylpyrrolidine-1-carboxylate to give 0.59 g (83%) of the title compound.

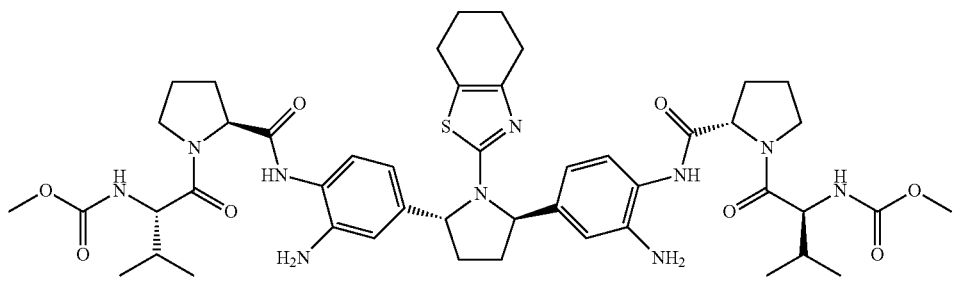

Example 116F dimethyl ([(2R,5R)-1-(4,5,6,7-tetrahydro-1,3-benzothiazol-2-yl)pyrrolidine-2,5-diyl]bis{(2-aminobenzene-4,1-diyl)carbamoyl(2S)pyrrolidine-2,1-diyl[(2S)-3-methyl-1-oxobutane-1,2-diyl]})biscarbamate (ACD v12))

The product from Example 116E (0.59 g, 0.596 mmol) was dissolved in tetrahydrofuran (15 mL) and treated with Raney Nickel slurry in water (0.25 mL). The flask was evacuated and opened to a hydrogen balloon and stirred at ambient temperature for 1 hour. The solution was filtered through a silica plug and concentrated to dryness to give the title compound.

Example 116G methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-(4,5,6,7-tetrahydro-1,3-benzothiazol-2-yl)pyrrolidin-2-yl]-1H-benzimidazol-2-yl}pyrrolidin-1-yl]-3-methyl-1-oxobutan-2-yl}carbamate The product from Example 116F (0.55 g, 0.592 mmol) was dissolved in toluene (6 mL) and treated with acetic acid (0.34 mL, 5.92 mmol) and heated to 65° C. for 4 hours. The solution was concentrated to dryness and purified by combi-flash 12 g silica column, eluting with 0-6% methanol in dichloromethane to give 0.245 g (48%) of the title compound. 1H NMR (400 MHz, DMSO-D6) δ ppm 0.78-0.92 (m, 12H) 1.53-1.61 (m, 4H) 1.67-1.75 (m, 2H) 1.88-2.07 (m, 6H) 2.15-2.27 (m, 6H) 2.41-2.47 (m, 2H) 2.59 (d, J=1.63 Hz, 2H) 3.54 (s, 6H) 3.79-3.87 (m, 4H) 4.07 (t, J=8.57 Hz, 2H) 5.12-5.20 (m, 2H) 5.38-5.46 (m, 2H) 7.05 (dd, J=12.79, 9.00 Hz, 2H) 7.22-7.33 (m, 4H) 7.39 (d, J=8.46 Hz, 1H) 7.46 (d, J=8.46 Hz, 1H) 12.06 (d, J=6.83 Hz, 2H); MS ESI+ m/z 893.5.

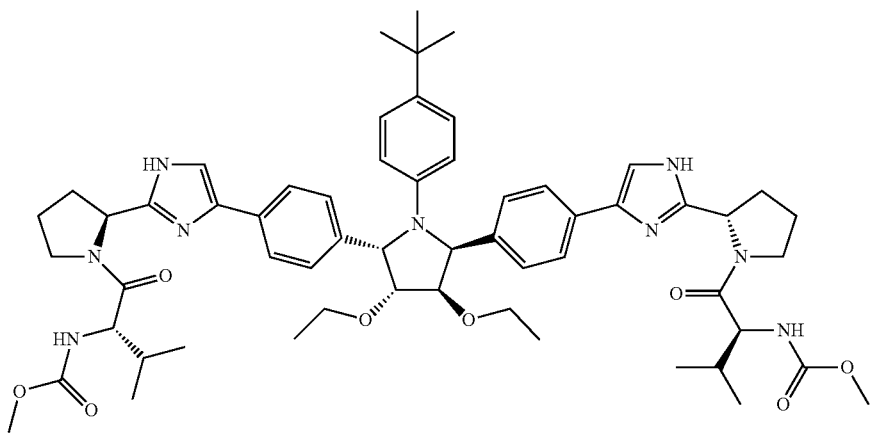

Example 117 methyl {(2S)-1-[(2S)-2-(4-{4-[(2S,3R,4R,5S)-1-(4-tert-butylphenyl)-3,4-diethoxy-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate 3.4-O-isopropylidene-D-mannitol was processed using the methods of Examples 79C, 79D, 79E, 79F, 79G, 79H, and 79I to provide the title compound, wherein iodoethane was used in the O-alkylation step (method of Example 79D) instead of iodomethane. $^1$H NMR (400 MHz, CDCl$_3$) δ ppm 0.86 (t, J=7.4 Hz, 12H) 1.04 (t, J=7.0 Hz, 6H) 1.13 (s, 9H) 1.85-2.03 (m, 4H) 2.03-2.13 (m, 2H) 2.13-2.24 (m, 2H) 2.24-2.40 (m, 2H) 3.03 (m, 2H) 3.54-3.89 (m, 9H) 3.69 (d, J=1.7 Hz, 6H) 4.25 (d, J=5.3 Hz, 2H) 4.31 (br s, 2H) 5.19-5.29 (m, 4H) 5.36 (br s, 2H) 6.28 (d, J=8.8 Hz, 2H) 6.90-6.98 (m, 4H) 7.12-7.23 (m, 6H). MS (ESI) m/z 1029 (M+H)$^+$.

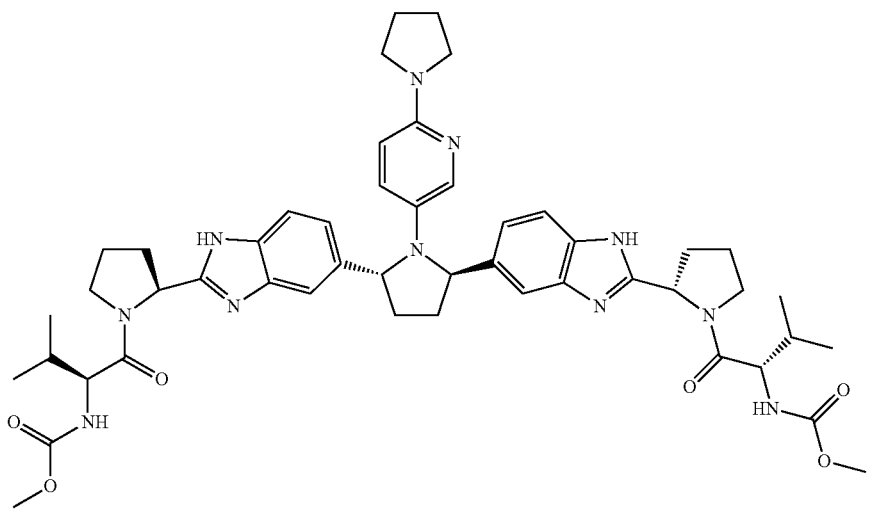 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCCC4)nc3)ccc2[nH]1)C(C)C]

Example 118 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[6-(pyrrolidin-1-yl)pyridin-3-yl]pyrrolidin-2-yl}-1H-benzimidazol-2-yl)pyrrolidin-1-yl]-3-methyl-1-oxobutan-2-yl}carbamate

Example 118A 5-nitro-2-(pyrrolidin-1-yl)pyridine

To a slurry of 2-chloro-5-nitropyridine (10 g, 63.1 mmol) in EtOH (100 mL) at room temperature was added pyrrolidine (15.72 mL, 189 mmol) and the mixture was heated at 70° C. for 18 h. The cooled solution was concentrated in vacuo and the residue partitioned between $CH_2Cl_2$ and 1M NaOH. The organic layer was dried ($Na_2SO_4$), filtered and solvent removed in vacuo to give title compound (9.52 g, 78%). MS (ESI) m/z 194 (M+H)+.

Example 118B 6-(pyrrolidin-1-yl)pyridin-3-amine

Material from Example 118A (9.52 g, 49.3 mmol) was dissolved in THF (50 mL) and DMF (40 mL) and added to a pressure bottle containing Raney Nickel 2800, water slurry (45%) (9.52 g, 162 mmol) stirred for 2 h at 30 psi under $H_2$ gas. The solution was filtered through a nylon membrane, washed with $CH_3OH$ and the filtrate concentrated in vacuo to give the title compound (7.78 g, 97%). 1H NMR (400 MHz, DMSO-d6) δ ppm 1.81-1.91 (m, 4H) 3.17-3.29 (m, 4H) 4.30 (s, 2H) 6.25 (d, J=8.7, 1H), 6.90 (dd, J=2.8, 8.7, 1H), 7.55 (d, J=2.6, 1H). MS (ESI) m/z 164 (M+H)+.

Example 118C (2S,2'S)-tert-butyl 2,2'-(5,5'-((2R,5R)-1-(6-(pyrrolidin-1-yl)pyridine-3-yl)pyrrolidine-2,5-diyl)bis(1H-benzo[d]imidazole-5,2-diyl)dipyrrolidine-1-carboxylate Example 118B and Example 109C were processed using sequentially the methods of Examples 113A, 113B, 116F, and 28I to provide the title compound.

Example 118D methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[6-(pyrrolidin-1-yl)pyridin-3-yl]pyrrolidin-2-yl}-1H-benzimidazol-2-yl)pyrrolidin-1-yl]-3-methyl-1-oxobutan-2-yl}carbamate To a solution of Example 118C (741 mg, 0.94 mmol) in dioxane (4 mL) was added 4 M HCl in dioxane (4.0 mL) and the solution was stirred at room temperature for 30 min. Solvent is removed in vacuo and the residue is dissolved in DMF (9.4 mL). Added N,N-diisopropyethylamine (0.99 mL, 5.65 mmol) followed by (S)-2-(methoxycarbonyl-amino)-3-methylbutanoic acid (379 mg, 2.16 mmol), HOBT (331 mg, 2.16 mmol), and EDC (415 mg, 2.16 mmol) and stirred at room temperature for 18 h. Poured into EtOAc, washed with $H_2O$, brine, dried ($Na_2SO_4$), filtered and removed solvent in vacuo to give crude product which was purified by flash chromatography on silica gel eluting with 0-6% $CH_3OH$/$CH_2Cl_2$ to give the title compound (165 mg, 0.183 mmol, 19%). 1H NMR (400 MHz, DMSO-d6) δ 0.73-0.95 (m, 12H) 1.66-2.27 (m, 12H) 3.09 (br s, 5H) 3.53 (s, 6H) 3.81 (br s, 4H) 4.06 (t, J=8.4 Hz, 2H) 5.13 (br s, 2H) 5.33 (br s, 2H) 6.12 (br s, 1H) 6.64 (br s, 1H) 7.00-7.47 (m, 10H) 12.02 (s, 2H). MS (ESI) m/z 903 (M+H)+.

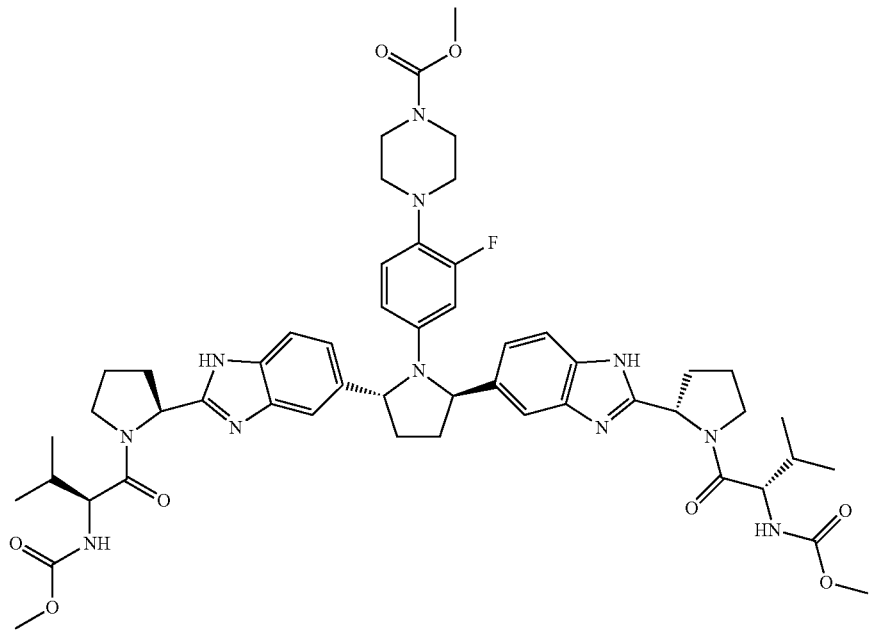 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCN(C(=O)OC)CC4)c(F)c3)ccc2[nH]1)C(C)C]

Example 119 methyl 4-{4-[(2R,5R)-2,5-bis(2-{(2S)-1-[N-(methoxycarbonyl)-L-valyl]pyrrolidin-2-yl}-1H-benzimidazol-5-yl)pyrrolidin-1-yl]-2-fluorophenyl}piperazine-1-carboxylate

Example 119A 1-(2-fluoro-4-nitrophenyl)piperazine

To a warm solution of piperazine (7.78 g, 90 mmol) in DMSO (40 mL) was added dropwise 1,2-difluoro-4-nitrobenzene (2.0 mL, 18.07 mmol). The solution was stirred at 70° C. for 2 h, cooled 10 to room temperature, diluted with EtOAc, washed with $H_2O$, brine, dried ($Na_2SO_4$), filtered and solvent removed in vacuo to give the title compound (4.05 g, 17.98 mmol, 100%). $^1$H NMR (400 MHz, $CDCl_3$) δ ppm 3.03-3.09 (m, 4H) 3.26-3.29 (m, 4H) 6.91 (t, J=8.8 Hz, 1H) 7.91 (dd, J=13.1, 2.6 Hz, 1H) 7.96-8.01 (m, 1H). MS (ESI) m/z 226 (M+H)$^+$.

Example 119B

Methyl 4-(2-fluoro-4-nitrophenyl)piperazine-1-carboxylate

To a solution of Example 119A (4.0 g, 17.76 mmol) in dioxane (40 mL) at 0° C. was added 2 M NaOH (29.3 mL, 58.6 mmol) followed by dropwise addition of methyl chloroformate (2.75 mL, 35.5 mmol). The solution was warmed to room temperature and stirred for 2 h. Diluted with EtOAc and added 1 N HCl until all solid had dissolved, separated the phases and washed the organic phase with 1 N HCl, $H_2O$, brine, dried ($Na_2SO_4$), filtered and removed solvent in vacuo to give the title compound (4.69 g, 16.56 mmol, 93%). $^1$H NMR (400 MHz, $CDCl_3$) δ ppm 3.20-3.31 (m, 4H) 3.62-3.71 (m, 4H) 3.75 (s, 3H) 6.92 (t, J=8.8 Hz, 1H) 7.93 (dd, J=12.9, 2.6 Hz, 1H) 7.98-8.02 (m, 1H). MS (ESI) m/z 284 (M+H)$^+$.

Example 119C

Methyl 4-(4-amino-2-fluorophenyl)piperazine-1-carboxylate

To a solution of Example 119B (3.0 g, 10.59 mmol) in EtOAc (40 mL) was added 10% palladium on carbon (300 mg) and the solution was stirred under a balloon of $H_2$ gas for 1.5 h. The solution was filtered through Celite, the catalyst washed with EtOAc, and the filtrate concentrated in vacuo to give the title compound (2.68 g, 10.59 mmol, 100%).

Example 119D methyl 4-{4-[(2R,5R)-2,5-bis(2-{(2S)-1-[N-(methoxycarbonyl)-L-valyl]pyrrolidin-2-yl}-1H-benzimidazol-5-yl)pyrrolidin-1-yl]-2-fluorophenyl}piperazine-1-carboxylate Example 119C and Example 109C were processed using sequentially the methods of Examples 113A-113C, 261, and 118D to provide the title compound. $^1$H NMR (400 MHz, DMSO-d6) δ ppm 0.75-0.93 (m, 12H) 1.69 (br s, 2H) 1.82-2.07 (m, 7H) 2.10-2.28 (m, 4H) 2.61-2.73 (m, 5H) 3.54 (s, 6H) 3.56 (s, 3H) 3.82 (br s, 4H) 3.99-4.11 (m, 2H) 5.09-5.19 (m, 2H) 5.29-5.41 (m, 2H) 6.01-6.13 (m, 2H) 6.61-6.72 (m, 1H) 7.06 (s, 2H) 7.20 (s, 1H) 7.29 (d, J=9.1 Hz, 3H) 7.38 (d, J=8.1 Hz, 1H) 7.46 (d, 1H) 12.04 (s, 2H). MS (ESI) m/z 993 (M+H)$^+$.

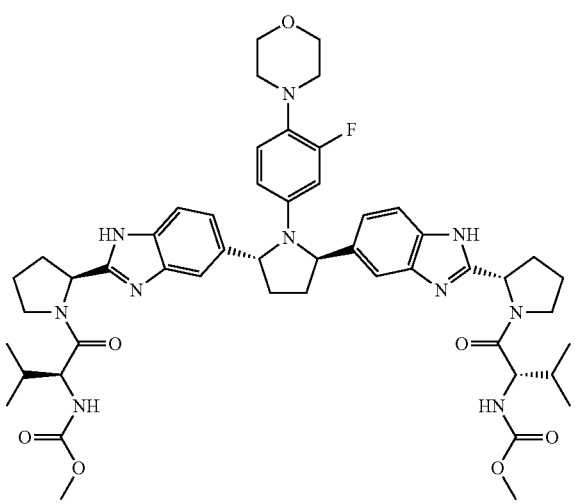 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCOCC4)c(F)c3)ccc2[nH]1)C(C)C]

Example 120 methyl {(2S)-1-[(2S)-2-{5-[(2R,5R)-1-[3-fluoro-4-(morpholin-4-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate

Example 120A 4-(2-Fluoro-4-nitrophenyl)morpholine

A suspension of morpholine (4.72 mL, 4.72 g, 54.2 mmol) and dibasic potassium phosphate (9.44 g, 54.2 mmol) in DMSO (27 mL) was treated with 3,4-difluoronitrobenzene (3.0 mL, 4.31 g, 27.1 mmol) was warmed at 60° C. for 18 h. The solution was cooled and diluted with ethyl acetate and extracted with water (3×) and saturated sodium chloride solution. Drying (Na$_2$SO$_4$) and concentration in vacuo afforded the title compound (6.32 g, ca. 100%) as a yellow solid. $^1$H NMR (400 MHz, CDCl$_3$) δ 8.00 (ddd, J=9.0, 2.6, 0.9 Hz, 1H), 7.92 (dd, J=13.1, 2.6 Hz, 1H), 6.92 (t, J=8.8 Hz, 1H), 3.88 (m, 4H), 3.29 (dd, J=5.5, 4.0 Hz, 4H). MS+DCI m/z (rel abundance) 227 (10, M+H), 244 (100, M+NH4).

Example 120B

3-Fluoro-4-morpholinoaniline

A solution of the compound of Example 120A (2.26 g, 10.00 mmol) in ethyl acetate (35 mL) was treated with 10% palladium on carbon (300 mg) followed by hydrogenation under one atmosphere pressure for 6 h. The mixture was filtered through celite and concentrated in vacuo to afford the title compound as a white solid.

Example 120C 4-(4-((2R,5R)-2,5-bis(4-chloro-3-nitrophenyl)pyrrolidin-1-yl)-2-fluorophenyl)morpholine A solution of the compound of Example 109C (2.00 g, 4.99 mmol) and triethylamine (4.17 mL, 3.03 g, 29.9 mmol) in dry dichloromethane (25 mL) at 0° C. was treated with methanesulfonyl chloride (1.17 mL, 1.71 g, 14.96 mmol) followed by stirring at 0° C. for 30 min. The solution was warmed to RT and then concentrated in vacuo. The residue was combined with the compound of Example 120B and N,N-dimethylaniline (1.26 mL, 1.21 g, 9.98 mmol) and dissolved in dry DMF (14 mL) followed by warming at 50° C. for 2 h. The solution was cooled and diluted with ethyl acetate, followed by extraction with water (3×) and 1 N hydrochloric acid solution (2×) and saturated sodium chloride solution. Drying (Na$_2$SO$_4$) and concentration in vacuo afforded an orange oil, which was chromatographed over a 340 g silica gel cartridge, eluting with 10-80% ethyl acetate in hexanes. These procedures afforded the title compound (1.39 g, 50%) as an orange rigid foam. $^1$H NMR (400 MHz, CDCl$_3$) δ 7.92 (m, 2H), 7.58 (m, 9H), 7.31 (dd, J=8.3, 2.1 Hz, 2H), 6.69 (s, 1H), 5.99 (m, 2H), 5.20 (d, J=7.1 Hz, 2H), 3.79 (m, 4H), 2.92 (m, 6H), 2.54 (m, 2H), 1.88 (m, 2H).

Example 120D

Dimethyl (2R,2'R)-1,1'-((2S,2'S)-2,2'-(4,4'-((2R,5R)-1-(3-fluoro-4-morpholinophenyl)pyrrolidin-2,5-diyl)bis(2-nitro-4,1-phenylene))bis(azanediyl)bis(oxomethylene)bis(pyrrolidine-2,1-diyl))bis(3-methyl-1-oxobutane-2,1-diyl)dicarbamate In a microwave tube, a suspension of the Example 120C (1.39 g, 2.48 mmoL), the compound of Example 116C (2.02 g, 7.43 mmol), XantPhos (129 mg, 0.22 mmol) and cesium carbonate (2.42 g, 7.43 mmoL) in dioxane (14 mL) was degassed by nitrogen sparge for 30 min. The mixture was treated with tris(dibenzylideneacetone)dipalladium (0) (68 mg, 0.074 mmol) followed by degassing for another 5 min. The microwave tube was sealed and the mixture was warmed at 100° C. for 2 h. The mixture was cooled and diluted with ethyl acetate and extracted with water (3×) and saturated sodium chloride solution. The solution was dried (Na$_2$SO$_4$) and stirred overnight with 3-(mercaptopropyl) silica gel. Filtration and concentration in vacuo afforded a solid, which was chromatographed over a 340 g silica gel cartridge, eluting with 0-10% methanol in dichloromethane. These procedures afforded the title compound as an orange solid. $^1$H NMR (400 MHz, DMSO-d6) δ ppm 0.80-0.90 (m, 12H) 1.74 (br s, 2H) 1.82-2.03 (m, 10H) 2.08-2.20 (m, 2H) 2.71-2.81 (m, 4H) 3.52 (s, 6H) 3.62 (m, 4H) 3.76 (s, 2H) 4.02 (m, 2H) 4.50 (d, J=4.4 Hz, 2H) 5.39 (s, 2H) 6.04-6.19 (m, 2H) 6.72-6.81 (m, 1H) 7.32 (d, J=8.4 Hz, 2H) 7.47-7.60 (m, 4H) 7.80 (d, J=1.5 Hz, 2H) 10.41 (s, 2H). MS (ESI) m/z 1031 (M+H)$^+$.

Example 120E

Dimethyl (2S,2'S)-1,1'-((2S,2'S)-2,2'-(4,4'-((2R,5R)-1-(3-fluoro-4-morpholinophenyl)pyrrolidine-2,5-diyl)bis(2-amino-4,1-phenylene)bis(azanediyl)bis(oxomethylene)bis(pyrrolidine-2,1diyl)bis(3-methyl-1-oxobutane-2,1-diyl)dicarbamate To a solution of Example 120D (640 mg, 0.621 mmol) in EtOH (4 mL) and THF (4 mL) was added PtO$_2$ (35 mg) and the solution was stirred under a balloon of H$_2$ gas for 16 h. The solution was filtered through Celite and washed with EtOAc.

The filtrate was concentrated in vacuo to give the title compound (322 mg, 0.332 mmol, 53%).

Example 120F methyl {(2S)-1-[(2S)-2-{5-[(2R,5R)-1-[3-fluoro-4-(morpholin-4-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate To a solution of Example 120E (320 mg, 0.33 mmol) in toluene (1.5 mL) was added glacial acetic acid (0.057 mL, 0.99 mmol) and the solution was stirred at 50° C. for 3 h. The cooled solution was concentrated in vacuo and azeotroped 2 times with toluene. The crude product was purified by flash chromatography on silica gel eluting with 0-4% $CH_3OH/CH_2Cl_2$ to give the title compound (100 mg, 0.107 mmol, 32%). $^1H$ NMR (400 MHz, DMSO-d6) δ ppm 0.72-0.92 (m, 12H) 1.69 (br s, 2H) 1.81-2.10 (m, 8H) 2.11-2.28 (m, 4H) 2.64-2.78 (m, 4H) 3.54 (s, 6H) 3.59 (s, 4H) 3.73-3.92 (m, 4H) 4.06 (s, 2H) 5.02-5.21 (m, 2H) 5.36 (s, 2H) 6.03-6.14 (m, 2H) 6.60-6.73 (m, 1H) 7.00-7.15 (m, 2H) 7.15-7.37 (m, 4H) 7.36-7.61 (m, 2H) 12.06 (br s, 2H). MS (ESI) m/z 935 (M+H)$^+$.

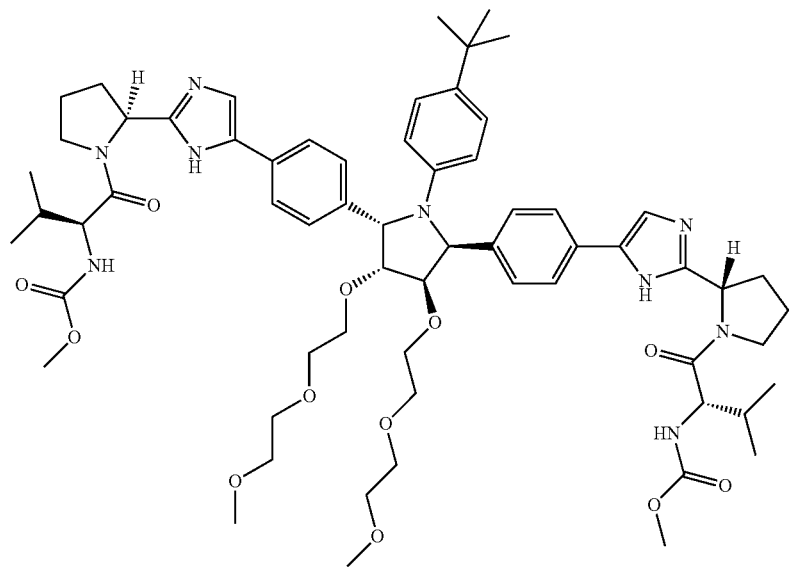 [SMILES: COCCOCCO[C@H]1[C@H](OCCOCCOC)[C@H](c2ccc(-c3cnc([C@@H]4CCCN4C(=O)[C@@H](NC(=O)OC)C(C)C)[nH]3)cc2)N(c2ccc(C(C)(C)C)cc2)[C@H]1c1ccc(-c2cnc([C@@H]3CCCN3C(=O)[C@@H](NC(=O)OC)C(C)C)[nH]2)cc1]

Example 121 methyl [(2S)-1-{(2S)-2-[5-(4-{(2S,3R,4R,5S)-1-(4-tert-butylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-3,4-bis[2-(2-methoxyethoxy)ethoxy]pyrrolidin-2-yl}phenyl)-1H-imidazol-2-yl]pyrrolidin-1-yl}-3-methyl-1-oxobutan-2-yl]carbamate 3,4-O-isopropylidene-D-mannitol was processed using sequentially the methods of Examples 79C, 79D (1-bromo-2-(2-methoxyethoxy)ethane as the alkylating agent with added sodium iodide), 79E-79G, 79H (18 hour reaction time), 66D, and 66E to provide the title compound (46 mg) as a light yellow solid. $^1H$ NMR (400 MHz, DMSO-d$_6$) δ 7.60 (d, J=7.9 Hz, 4H), 7.50 (d, J=8.4 Hz, 2H), 7.38 (s, 2H), 7.29 (d, J=8.6 Hz, 2H), 7.19 (s, 4H), 6.90 (m, 2H), 6.27 (d, J=8.6 Hz, 2H), 5.37 (s, 2H), 5.07 (d, J=3.6 Hz, 2H), 4.32 (s, 2H), 4.06 (m, 2H), 3.78 (d, J=6.0 Hz, 2H), 3.66 (d, J=4.2 Hz, 4H), 3.53 (s, 6H), 3.17 (s, 6H), 2.10 (m, 4H), 1.93 (m, 4H), 1.07 (s, 9H), 0.86 (m, 12H). MS (+ESI) m/z (rel abundance) 1177 (100, M+H), 1199 (5, M+Na).

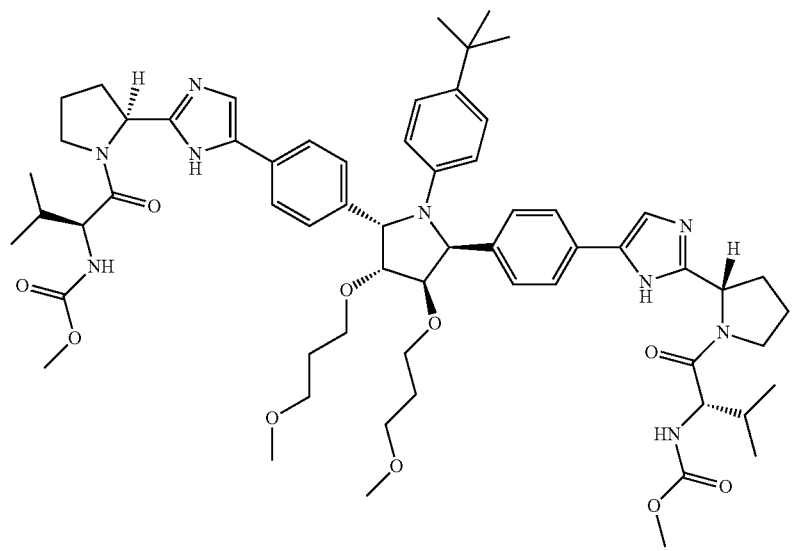 [SMILES: COCCCO[C@H]1[C@H](OCCCOC)[C@H](c2ccc(-c3cnc([C@@H]4CCCN4C(=O)[C@@H](NC(=O)OC)C(C)C)[nH]3)cc2)N(c2ccc(C(C)(C)C)cc2)[C@H]1c1ccc(-c2cnc([C@@H]3CCCN3C(=O)[C@@H](NC(=O)OC)C(C)C)[nH]2)cc1]

Example 122 methyl {(2S)-1-[(2S)-2-(5-{4-[(2S,3R,4R,5S)-1-(4-tert-butylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-3,4-bis(3-methoxypropoxy)pyrrolidin-2-yl]phenyl}-1H-imidazol-2-yl)pyrrolidin-1-yl]-3-methyl-1-oxobutan-2-yl}carbamate 3.4-O-isopropylidene-D-mannitol was processed using sequentially the methods of Examples 79C, 79D (1-bromo-3-methoxypropane as the alkylating agent with added sodium iodide), 79E-79H, 66D, and 66E to provide the title compound. $^1$H NMR (400 MHz, DMSO-$d_6$) δ 7.60 (s, 4H), 7.52 (m, 2H), 7.37 (m, 2H), 7.30 (m, 4H), 7.18 (d, J=7.1 Hz, 4H), 6.91 (m, 2H), 6.24 (m, 2H), 5.40 (m, 2H), 5.06 (m, 2H), 4.31 (m, 2H), 4.11 (m, 2H), 3.78 (s, 4H), 3.66 (m, 4H), 3.56 (m, 10H), 3.14 (m, 14H), 2.14 (m, 6H), 1.94 (d, J=3.5 Hz, 8H), 1.43 (m, 6H), 1.07 (s, 10H), 0.89 (d, J=6.1 Hz, 6H), 0.84 (d, J=5.9 Hz, 6H).

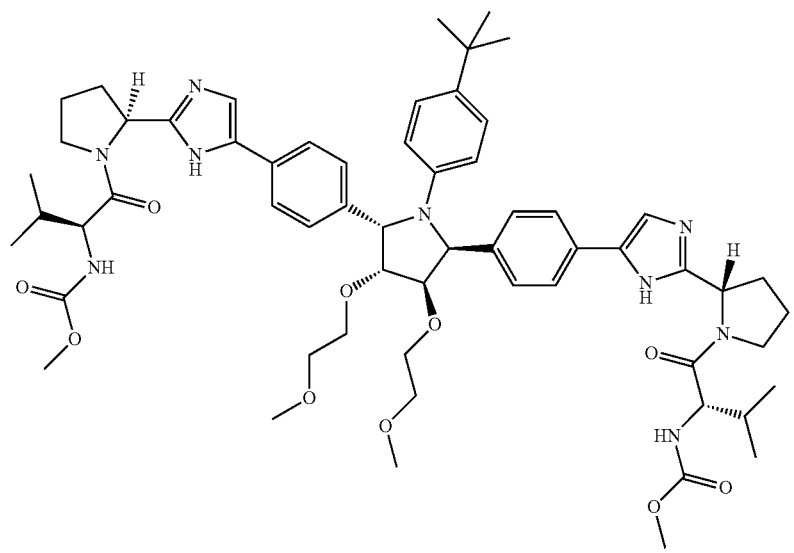 [SMILES: COCCO[C@H]1[C@H](OCCOC)[C@H](c2ccc(-c3cnc([C@@H]4CCCN4C(=O)[C@@H](NC(=O)OC)C(C)C)[nH]3)cc2)N(c2ccc(C(C)(C)C)cc2)[C@H]1c1ccc(-c2cnc([C@@H]3CCCN3C(=O)[C@@H](NC(=O)OC)C(C)C)[nH]2)cc1]

Example 123 methyl {(2S)-1-[(2S)-2-(5-{4-[(2S,3R,4R,5S)-1-(4-tert-butylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)-3,4-bis(2-methoxyethoxy)pyrrolidin-2-yl]phenyl}-1H-imidazol-2-yl)pyrrolidin-1-yl]-3-methyl-1-oxobutan-2-yl}carbamate 3.4-O-isopropylidene-D-mannitol was processed using sequentially the methods of Examples 79C, 79D (1-bromo-2-methoxyethane as the alkylating agent with added sodium iodide), 79E, 79F, 79G, and 79H, wherein Example 126G replaced (S)-tert-butyl-2-(4-bromo-1H-imidazol-2-yl)pyrrolidine-1-carboxylate in applying the method of Example 79H, to provide the title compound (43 mg) as a light beige solid. $^1$H NMR (400 MHz, DMSO-d$_6$) δ 7.60 (d, J=8.0 Hz, 4H), 7.47 (m, 2H), 7.37 (m, 2H), 7.27 (m, 4H), 7.19 (s, 4H), 6.90 (d, J=8.6 Hz, 2H), 6.26 (d, J=8.7 Hz, 2H), 5.37 (s, 2H), 5.06 (d, J=3.7 Hz, 2H), 4.30 (s, 2H), 4.03 (m, 2H), 3.79 (s, 4H), 3.66 (m, 6H), 3.53 (s, 6H), 3.25 (m, 6H), 3.12 (s, 6H), 2.13 (m, 4H), 1.94 (m, 6H), 1.07 (s, 9H), 0.89 (d, J=6.6 Hz, 6H), 0.84 (d, J=6.6 Hz, 6H). MS+ESI m/z (rel abundance) 1088 (100, M+H).

Example 124 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-6-yl}-1-[6-(morpholin-4-yl)pyridin-3-yl]pyrrolidin-2-yl}-1-1H-benzimidazol-2-yl)pyrrolidin-1-yl]-3-methyl-1-oxobutan-2-yl}carbamate Example 109C and Example 154B were processed using the methods of Examples 113A, 113B, 116F, 28I (reaction conducted at 50° C. for 4 h), 66D, and 66E to provide the title compound (120 mg) as a light beige solid. $^1$H NMR (400 MHz, DMSO-d$_6$) δ 12.03 (s, 1H), 7.46 (d, J=8.2 Hz, 1H), 7.45 (s, 1H), 7.31 (d, J=6.4 Hz, 3H), 7.21 (s, 1H), 7.06 (t, J=8.0 Hz, 2H), 6.64 (m, 1H), 6.49 (m, 1H), 5.36 (d, J=6.2 Hz, 2H), 5.13 (s, 2H), 4.04 (m, 2H), 3.77 (m, 3H), 3.55 (m, 9H), 3.04 (s, 4H), 2.19 (s, 3H), 1.95 (m, 5H), 1.73 (s, 3H), 0.82 (m, 12H). MS+ESI m/z (rel S abundance) 918 (100, M+H).

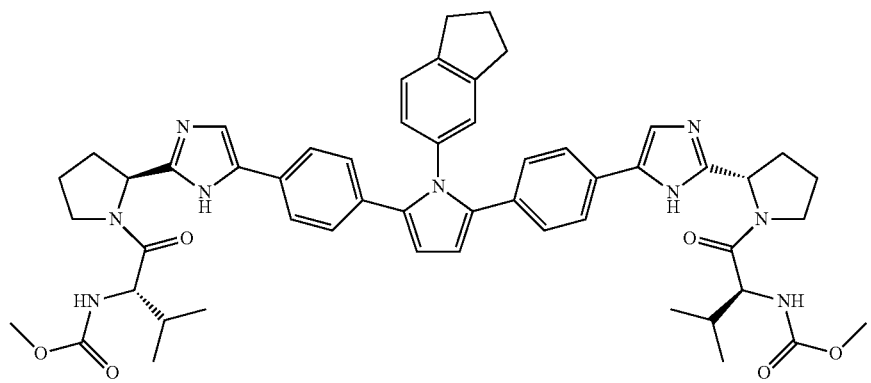

Example 125 methyl {(2S)-1-[(2S)-2-(5-{4-[1-(2,3-dihydro-1H-inden-5-yl)-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl]phenyl}-1H-imidazol-2-yl)pyrrolidin-1-yl]-3-methyl-1-oxobutan-2-yl}carbamate Example 26E and 5-aminoindan were processed using the methods of Examples 76A, 39E, 39F, 55G, and 26J (reaction solvent=dichloromethane) to provide the title compound (0.1446 g). $^1$H NMR (400 MHz, DMSO-D6) δ 0.91-0.79 (m, 12H), 2.18-1.87 (m, 12H), 2.74 (t, J=6.7, 2H), 2.86 (t, J=6.8, 2H), 3.53 (s, 6H), 3.84-3.68 (m, 4H), 4.10-3.98 (m, 2H), 5.03 (dd, J=6.8, 2.9, 2H), 6.54-6.40 (m, 2H), 7.10-6.86 (m, 5H), 7.22-7.13 (m, 2H), 7.33-7.22 (m, 2H), 7.45-7.35 (m, 2H), 7.53 (dd, J=13.7, 8.5, 4H), 11.70 (s, 1H), 12.07-11.96 (m, 1H). MS (ESI) m/z 920 (M+H)$^+$, 918 (M−H)$^+$.

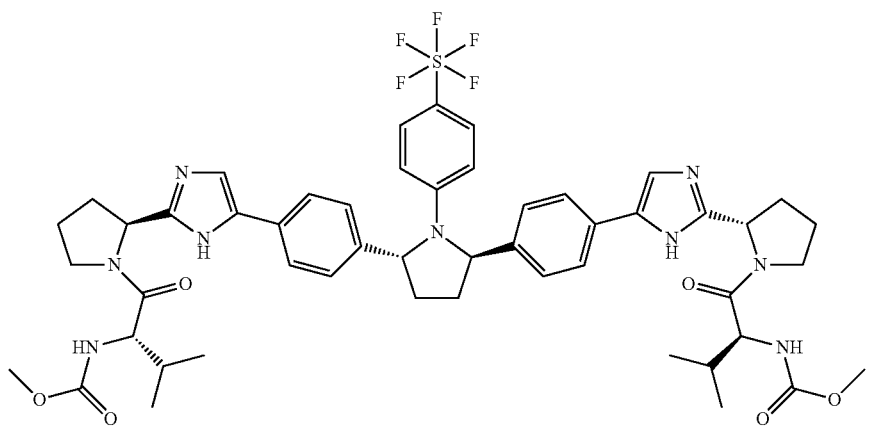

Example 126 methyl [(2S)-1-{(2S)-2-[5-(4-{(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-[4-(pentafluoro-lambda~6~-sulfanyl)phenyl]pyrrolidin-2-yl}phenyl)-1H-imidazol-2-yl]pyrrolidin-1-yl}-3-methyl-1-oxobutan-2-yl] carbamate

Example 126A (S)-2-(methoxycarbonylamino)-3-methylbutanoic acid

A mixture of (S)-2-amino-3-methylbutanoic acid (10.0 g, 85.0 mmol), NaOH (3.41 g, 85.0 mmol) and NaHCO$_3$ (4.7 g, 44.4 mmol) in H$_2$O (85 mL) was cooled to 0° C. A mixture of methyl chloroformate (7.3 mL, 94.0 mmol) dissolved in Et$_2$O (40 mL) was slowly added to the aqueous S mixture and stirred for 20 hours coming to ambient temperature. Mixture was adjusted to pH 2.0 with HCl (conc). The mixture was extracted with CH$_2$Cl$_2$ (3×100 mL) and then dried (MgSO$_4$), filtered and concentrated to afford 7.5 g (50%) of the title compound. MS (ESI) m/z 176 (M+H)$^+$.

Example 126B (S)-tert-butyl 2-formylpyrrolidine-1-carboxylate

A mixture of oxalyl chloride (14.1 mL, 161 mmol) in CH$_2$Cl$_2$ (331 mL) was cooled to −75° C. Dimethylsulfoxide (19.4 mL, 273 mmol) in CH$_2$Cl$_2$ (70 mL) was slowly added over 30 minutes followed by stirring at −75° C. for an additional 15 minutes. At −75° C. (S)-tert-butyl 2-(hydroxymethyl)pyrrolidine-1-carboxylate (25.0 g, 124 mmol) in CH$_2$Cl$_2$ (132 mL) was added slowly over one hour, followed by a further 15 minutes of stirring. Then, still at −75° C., Et$_3$N (87 mL, 621 mmol) was added over 30 minutes followed by another 15 minutes of stirring. Mixture was then allowed to stir at 0° C. for 90 minutes. Mixture was quenched with 10% aqueous Citric acid at 0° C. The mixture was diluted with 10%/aqueous Citric acid and partitioned. Organic was washed with H$_2$O (5×150 mL) and Brine. The organic was then dried (MgSO$_4$), filtered and concentrated to afford 24.7 g (100%) of the title compound. MS (ESI) m/z 200 (M+H)$^+$.

Example 126C (S)-tert-butyl 2-(1H-imidazol-2-yl)pyrrolidine-1-carboxylate

A mixture of Example 126B (24.7 g, 124.0 mmol) and NH$_4$OH (62.0 mL, 497 mmol) in methanol (62 mL) was stirred at 0° C. followed by slow addition of glyoxal hydrate (29.9 mL, 262 mmol) over 10 minutes. Mixture was stirred for 16 hours at ambient temperature. The mixture was concentrated, diluted with H$_2$O and extracted with EtOAc (3×200 mL). The organic was then dried (MgSO$_4$), filtered and concentrated. Purification by trituration with tBuOMe afforded 15.5 g (53%) of the title compound. MS (ESI) m/z 238 (M+H)$^+$.

Example 126D (S)-tert-butyl 2-(4,5-dibromo-1H-imidazol-2-yl)pyrrolidine-1-carboxylate A mixture of Example 126C (15.5 g, 65.4 mmol) in CH$_2$Cl$_2$ (260 mL) was stirred at 0° C. followed by portionwise addition of 1-bromopyrrolidine-2,5-dione (24.5, 137.0 mmol) over 10 minutes. Mixture was stirred 0° C. for 90 minutes. Mixture was concentrated, diluted with EtOAc (600 mL) and washed with H$_2$O (3×200 mL) and brine. The organic was then dried (MgSO$_4$), filtered and concentrated. Purification by trituration with Et$_2$O afforded 24.9 g (96%) of the title compound. MS (ESI) m/z 396 (M+H)$^+$.

Example 126E (S)-tert-butyl 2-(5-bromo-1H-imidazol-2-yl)pyrrolidine-1-carboxylate A mixture of Example 126D (12.5 g, 31.5 mmol) in dioxane (400 mL) and H$_2$O (400 mL) had a solution of Na$_2$SO$_3$ (43.7 g, 347 mmol) in H$_2$O (400 mL) added and was heated to reflux for 21 hours. The mixture was concentrated to half volume and extracted with CH$_2$Cl$_2$ (3×200 mL). The organic was then washed with brine, dried (MgSO$_4$), filtered and concentrated. Purification by trituration (CH$_2$Cl$_2$, tBuOMe, and Hexanes) afforded 5.2 g (52%) of the title compound. MS (ESI) m/z 317 (M+H)$^+$.

Example 126F (S)-5-bromo-2-(pyrrolidin-2-yl)-1H-imidazole hydrochloride

A mixture of Example 126E (5.0 g, 15.8 mmol) in 4M HCl/Dioxane (40 mL) was allowed to stir for one hour. The mixture was concentrated to afford 3.99 g (100%) of the title compound. MS (ESI) m/z 217 (M+H)$^+$.

Example 126G methyl (S)-1-((S)-2-(5-bromo-1H-imidazol-2-yl)pyrrolidin-1-yl)-3-methyl-1-oxobutan-2-ylcarbamate A mixture of Example 126F (3.99 g, 15.8 mmol), Example 126A (2.77 g, 15.8 mmol), N-(3-dimethylaminopropyl)-N'-ethylcarbodiimide hydrochloride (3.63 g, 19.0 mmol), 1-Hydroxy-benzotriazole hydrate (2.90 g, 19.0 mmol) and N-methylmorpholine (12.2 mL, 111.0 mmol) in DMF (150 mL) were allowed to stir overnight. Mixture was diluted with $H_2O$ and extracted with EtOAc (3×300 mL). The organic was washed with $H_2O$ and Brine. The organic was then dried ($MgSO_4$), filtered and concentrated. Purification by chromatography (silica gel, 75% EtOAc in Hexanes) afforded 5.2 g (88%) of the title compound. $^1$H NMR (400 MHz, DMSO-$d_6$) δ ppm 0.79 (dd, J=6.67, 3.63 Hz, 6H), 1.84-1.96 (m, 3H), 2.02-2.14 (m, 2H), 3.51 (s, 3H), 3.66-3.80 (m, 2H), 3.96-4.03 (m, 1H), 4.91-4.99 (m, 1H), 7.06 (d, J=1.52 Hz, 1H), 7.26 (d, J=8.46 Hz, 1H), 12.01 (s, 1H). MS (ESI) m/z 373 (M+H)$^+$.

Example 126H (1S,4S)-1,4-bis(4-bromophenyl)butane-1,4-diol (1S,4S)-1,4-bis(4-bromophenyl)butane-1,4-diol was prepared using the method of Example 69A and (R)-alpha,alpha-diphenyl-2-pyrrolidinemethanol).

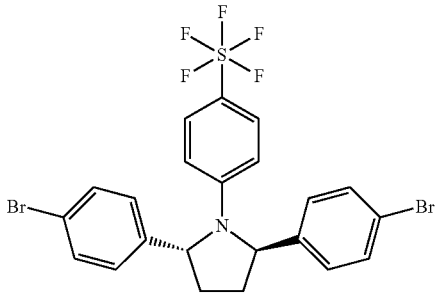 [SMILES: FS(F)(F)(F)(F)c1ccc(N2[C@@H](c3ccc(Br)cc3)CC[C@@H]2c2ccc(Br)cc2)cc1]

Example 126I (2R,5R)-2,5-bis(4-bromophenyl)-1-(4-sulfur pentafluoride phenyl)pyrrolidine A solution of methanesulfonic anhydride (2.95 mL, 23.02 mmol) in 2-Me THF (15 mL) was cooled in ice/salt bath to ~0° C. To this cold solution a solution of Example 126H (4.0524 g, 10.13 mmol) and N,N-diisopropylethylamine (5.5 mL, 31.8 mmol) in 2-Me THF (40 mL) was added dropwise over 40 minutes. The reaction was slowly warmed to 20° C. At this time 4-aminophenylsulfur pentafluoride (7.1238 g, 32.5 mmol) was added and the mixture was warmed to 38° C. for 17 hours. The reaction was cooled and partioned between EtOAc and water. The organic fraction was washed with water (2×) brine (1×) and concentrated. Purification by flash chromatography (silica gel, EtOAc/hexane) afforded the title compound (1.95 g, 33%). LC/MS Rt 2.38 m/z 584 (M+H)$^+$.

Example 126J (2R,5R)-1-(4-sulfur pentafluoride phenyl)-2,5-bis(4-(4,4,5,5-tetramethyl-1,3,2-dioxaborolan-2-yl)phenyl)pyrrolidine The product from Example 126I was processed using the method described in Example 39E to afford the title compound (1.67 g, 74%). MS (ESI) m/z 678 (M+H)$^+$.

Example 126K methyl [(2S)-1-{(2S)-2-[5-(4-{(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-[4-(pentafluoro-lambda~6~-sulfanyl)phenyl]pyrrolidin-2-yl}phenyl)-1H-imidazol-2-yl]pyrrolidin-1-yl}-3-methyl-1-oxobutan-2-yl] carbamate The product from Example 126J and Example 126G were processed using the method described in Example 39F to afford the title compound (0.75 g, 30%). $^1$H NMR (400 MHz, DMSO-d6) δ 0.85 (dd, J=6.7, 15.8, 12H), 2.26-1.66 (m, 14H), 3.53 (s, 6H), 3.87-3.63 (m, 4H), 4.14-3.91 (m, 2H), 5.06 (dd, J=3.0, 6.7, 2H), 5.34 (s, 2H), 6.34 (d, J=9.1, 2H), 7.17 (d, J=8.2, 4H), 7.26 (dd, J=8.4, 17.3, 2H), 7.75-7.34 (m, 8H), 12.22-11.46 (m, 2H). MS (ESI) m/z 1010 (M+H)$^+$, 1008 (M−H)$^+$.

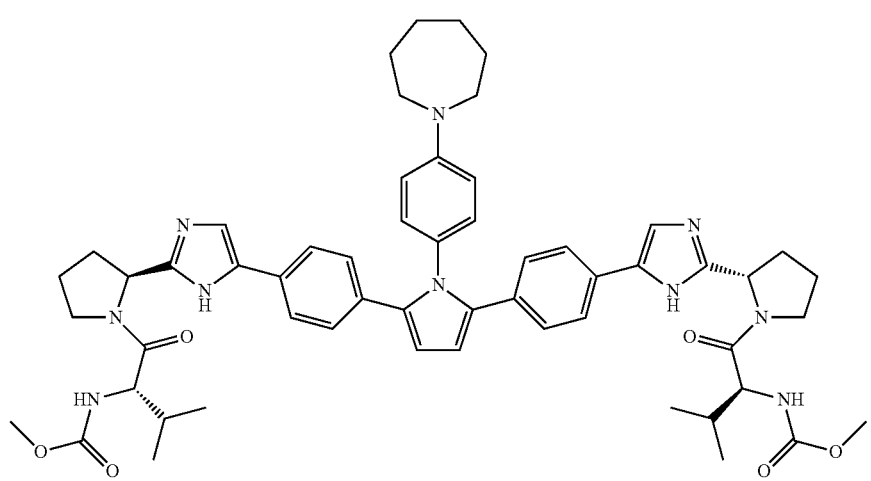

Example 127 methyl [(2S)-1-{(2S)-2-[5-(4-{1-[4-(azepan-1-yl)phenyl]-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl}phenyl)-1H-imidazol-2-yl]pyrrolidin-1-yl}-3-methyl-1-oxobutan-2-yl]carbamate Example 26E and 4-(1-azepanyl)aniline were processed using the methods of Examples 76A, 39E, 39F, 55G, and 26J (reaction solvent=dichloromethane) to provide the title compound (6.1 mg). MS (ESI) m/z 977 (M+H)$^+$.

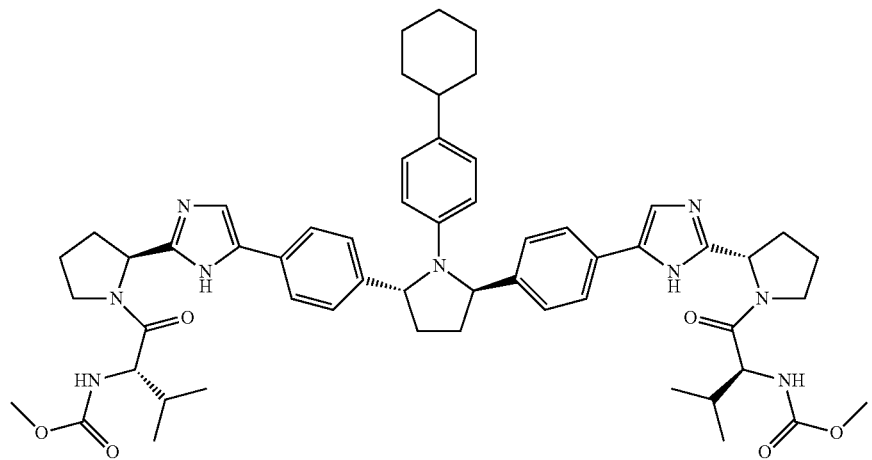

Example 128 methyl {(2S)-1-[(2S)-2-(5-{4-[(2R,5R)-1-(4-cyclohexylphenyl)-5-(4-{2-[(2S)-1-{(2S)-2-[(methoxycarbonyl)amino]-3-methylbutanoyl}pyrrolidin-2-yl]-1H-imidazol-5-yl}phenyl)pyrrolidin-2-yl]phenyl}-1H-imidazol-2-yl)pyrrolidin-1-yl]-3-methyl-1-oxobutan-2-yl}carbamate Example 126H and 4-cyclohexylaniline were processed using the methods of Examples 126I, 126J, and 126K to provide the title compound (0.14 g). $^1$H NMR (400 MHz, DMSO-D6) δ 0.85 (dd, J=16.6, 6.9, 12H), 1.32-1.06 (m, 8H), 1.65 (dd, J=19.1, 6.2, 7H), 2.27-1.82 (m, 13H), 3.53 (s, 6H), 3.78 (d, J=6.8, 2H), 4.10-3.95 (m, 2H), 5.06 (dd, J=6.9, 3.1, 2H), 5.19 (t, J=6.7, 2H), 6.21 (d, J=8.7, 2H), 6.76 (dd, J=8.6, 3.7, 2H), 7.19-7.08 (m, 4H), 7.34-7.19 (m, 2H), 7.37 (d, J=1.8, 1H), 7.50 (t, J=11.3, 1H), 7.65-7.57 (m, 3H), 11.68 (s, 1H), 12.10-11.93 (m, 1H). MS (ESI) m/z 966 (M+H)$^+$.

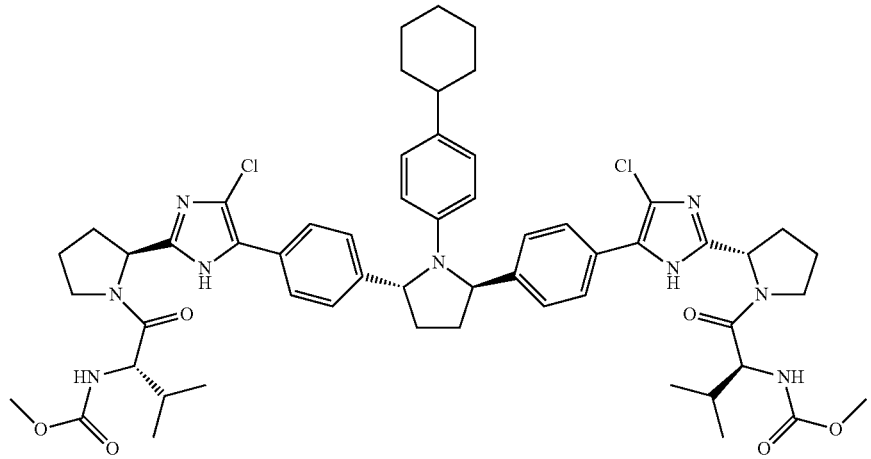

Example 129 methyl {(2S)-1-[(2S)-2-(4-chloro-5-{4-[(2R,5R)-5-(4-{4-chloro-2-[(2S)-1-{(2S)-2-[(methoxycarbonyl)amino]-3-methylbutanoyl}pyrrolidin-2-yl]-1H-imidazol-5-yl}phenyl)-1-(4-cyclohexylphenyl)pyrrolidin-2-yl]phenyl}-1H-imidazol-2-yl)pyrrolidin-1-yl]-3-methyl-1-oxobutan-2-yl}carbamate N-Chlorosuccinimide (0.046 g, 0.342 mmol) was added to a solution of the product from Example 128 (0.1435 g, 0.149 mmol) in dichloromethane (7 mL) and stirred at ambient temperature for 17 hours. The reaction was diluted with dichloromethane and washed with sat aq NaHCO₃ (2×) and concentrated. The residue was purified by flash chromatography (silica gel, MeOH/dichloromethane) then by prep HPLC to afford the title compound (20.4 mg, 13%). ¹H NMR (free base) (400 MHz, DMSO-D6) δ 0.94-0.73 (m, 12H), 1.39-0.99 (m, 8H), 1.75-1.41 (m, 6H), 2.27-1.77 (m, 12H), 3.53 (s, 6H), 3.86-3.66 (m, 3H), 4.08-3.96 (m, 2H), 5.11-4.89 (m, 2H), 5.30-5.12 (m, 1H), 5.55-5.33 (m, 1H), 6.21 (d, J=8.7, 1H), 6.88-6.67 (m, 2H), 6.94 (dd, J=4.3, 8.4, 1H), 7.42-7.02 (m, 6H), 7.56-7.42 (m, 3H), 7.61 (t, J=8.5, 1H), 11.68 (d, J=10.7, 1H), 12.49-12.26 (m, 1H). MS (ESI) m/z 1034 (M+H)⁺.

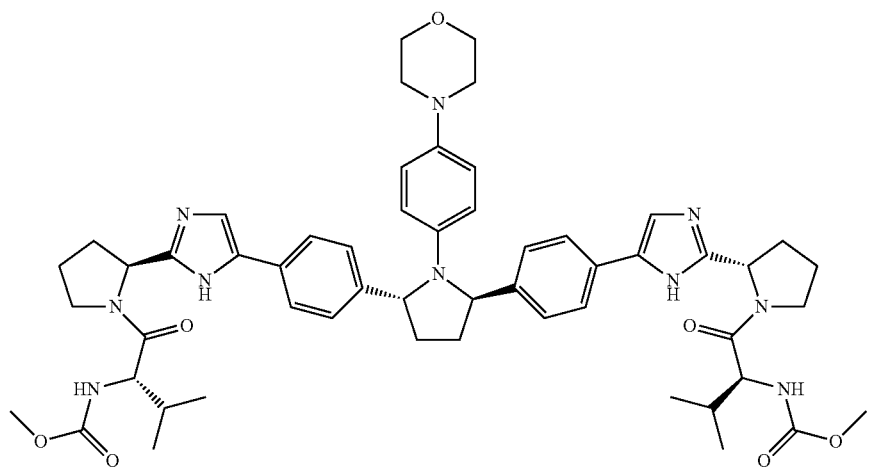

Example 130 methyl [(2S)-1-{(2S)-2-[5-(4-{(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-[4-(morpholin-4-yl)phenyl]pyrrolidin-2-yl}phenyl)-1H-imidazol-2-yl]pyrrolidin-1-yl}-3-methyl-1-oxobutan-2-yl]carbamate Example 126H and 4-morpholinoaniline were processed using sequentially the methods of Examples 126I, 39E, 39F, 39I, and 26J (reaction solvent=dichloromethane) to provide the title compound (0.16 g). ¹H NMR (300 MHz, DMSO-D6) δ 0.86 (dd, J=12.2, 6.6, 12H), 1.77-1.55 (m, 2H), 2.03-1.77 (m, 6H), 2.21-2.03 (m, 4H), 2.45-2.39 (m, 1H), 2.58-2.54 (m, 1H), 2.82-2.74 (m, 4H), 3.53 (s, 6H), 3.67-3.57 (m, 4H), 3.77 (d, J=6.1, 3H), 4.04 (t, J=8.3, 2H), 5.06 (dd, J=6.7, 3.0, 2H), 5.18 (t, J=5.0, 2H), 6.22 (d, J=9.0, 2H), 6.58 (dd, J=9.0, 1.9, 2H), 7.14 (d, J=8.4, 4H), 7.32-7.17 (m, 3H), 7.37 (d, J=1.8, 2H), 7.55-7.41 (m, 1H), 7.63 (t, J=10.0, 4H), 11.68 (s, 1H), 12.15-11.90 (m, 1H). MS (ESI) m/z 969 (M+H)⁺.

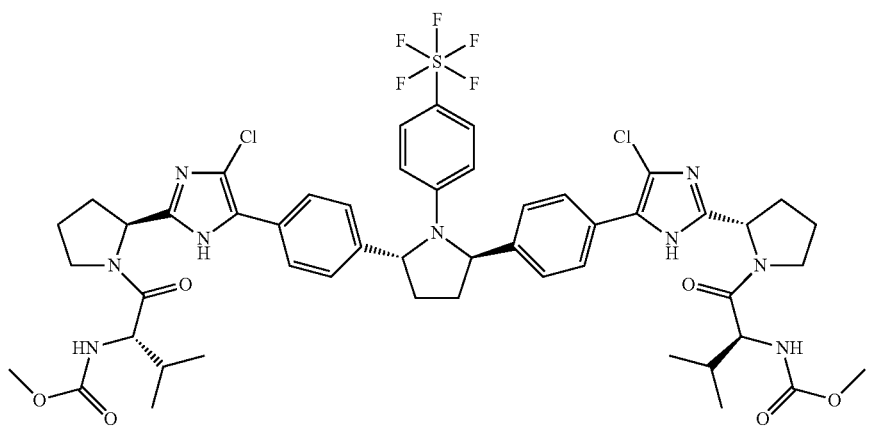

Example 131 methyl [(2S)-1-{(2S)-2-[4-chloro-5-(4-{(2R,5R)-5-(4-{4-chloro-2-[(2S)-1-{(2S)-2-[(methoxycarbonyl)amino]-3-methylbutanoyl}pyrrolidin-2-yl]-1H-imidazol-5-yl}phenyl)-1-[4-(pentafluoro-lambda~6~-sulfanyl)phenyl]pyrrolidin-2-yl}phenyl)-1H-imidazol-2-yl]pyrrolidin-1-yl}-3-methyl-1-oxobutan-2-yl]carbamate The product from Example 126K was processed using the method described in Example 129. The mixture of mono and dichlorinated products was purified via reverse phase HPLC to afford the title compound (90.9 mg, 19%). $^1$H NMR (free base) (500 MHz, DMSO-D6) δ 0.84 (dd, J=6.8, 16.1, 12H), 2.23-1.70 (m, 13H), 3.53 (s, 6H), 3.85-3.66 (m, 4H), 4.02 (ddd, J=4.8, 10.8, 16.1, 3H), 5.05-4.91 (m, 2H), 5.43 (d, J=5.8, 2H), 6.36 (d, J=9.1, 2H), 7.28 (d, J=8.4, 2H), 7.34 (d, J=8.3, 4H), 7.46 (d, J=9.4, 2H), 7.72-7.58 (m, 4H), 12.43 (s, 2H). MS (ESI) m/z 1078 (M+H)$^+$.

Example 132 methyl [(2S)-1-{(2S)-2-[4-chloro-5-(4-{(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-[4-(pentafluoro-lambda~6~-sulfanyl)phenyl]pyrrolidin-2-yl}phenyl)-1H-imidazol-2-yl]pyrrolidin-1-yl}-3-methyl-1-oxobutan-2-yl]carbamate The product from Example 126K was processed using the method described in Example 129. The mixture of mono and dichlorinated products was purified via reverse phase HPLC to afford the title compound (33.3 mg, 7%). $^1$H NMR (free base) (500 MHz, DMSO-D6) δ 0.94-0.76 (m, 12H), 2.24-1.63 (m, 13H), 3.53 (d, J=1.2, 6H), 3.86-3.68 (m, 4H), 4.10-3.98 (m, 2H), 5.02-4.93 (m, 1H), 5.06 (dd, J=3.2, 7.1, 1H), 5.48-5.30 (m, 2H), 6.35 (d, J=9.1, 2H), 7.21-7.10 (m, 2H), 7.36-7.21 (m, 4H), 7.58-7.38 (m, 4H), 7.73-7.59 (m, 4H), 12.50-11.65 (m, 2H). MS (ESI) m/z 1044 (M+H)$^+$, 1042 (M−H)$^+$.

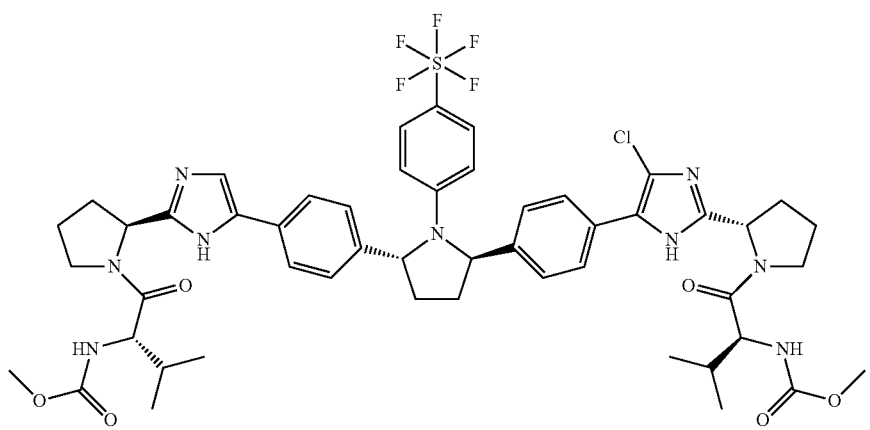

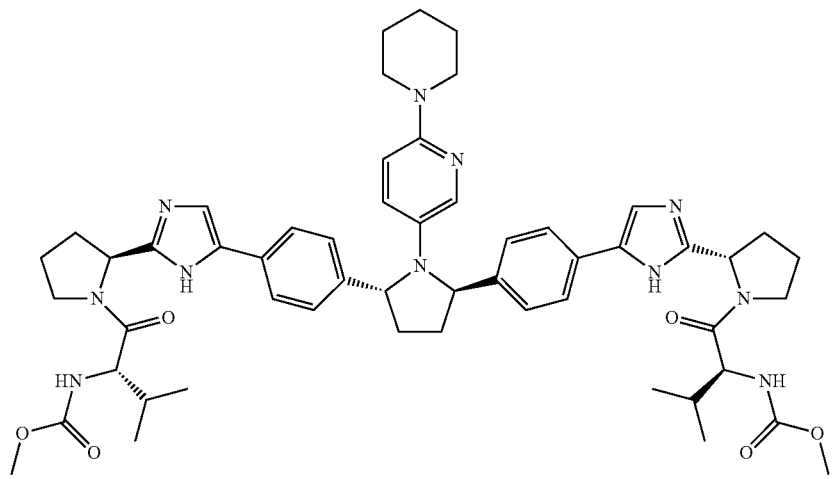

Example 133 methyl [(2S)-1-{(2S)-2-[5-(4-{(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-[6-(piperidin-1-yl)pyridin-3-yl]pyrrolidin-2-yl}phenyl)-1H-imidazol-2-yl]pyrrolidin-1-yl}-3-methyl-1-oxobutan-2-yl]carbamate Example 126H and 6-(piperidin-1-yl)pyridine-3-amine were processed using sequentially the methods of Examples 126I, 39E, 39F, 39I, and 26J (reaction solvent=dichloromethane) to provide the title compound (91.4 mg). $^1$H NMR (400 MHz, DMSO-D6) δ 0.85 (dt, J=7.1, 14.3, 12H), 1.24 (s, 2H), 1.44 (s, 6H), 1.70 (d, J=5.2, 2H), 2.04-1.82 (m, 6H), 2.23-2.04 (m, 4H), 3.21-3.03 (m, 4H), 3.53 (s, 6H), 3.87-3.67 (m, 4H), 4.12-3.96 (m, 2H), 5.06 (dd, J=3.2, 7.0, 2H), 5.20 (t, J=6.8, 2H), 6.49 (dd, J=3.1, 9.1, 1H), 6.60 (dd, J=2.9, 9.2, 1H), 7.20-7.10 (m, 4H), 7.33-7.20 (m, 3H), 7.38 (d, J=1.8, 2H), 7.51 (t, J=10.4, 1H), 7.64 (dd, J=8.1, 15.7, 3H), 11.69 (s, 1.4H), 12.06 (t, J=32.1, 0.6H).

Example 134 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-6-yl}-1-[6-(piperidin-1-yl)pyridin-3-yl]pyrrolidin-2-yl}-1H-benzimidazol-2-yl)pyrrolidin-1-yl]-3-methyl-1-oxobutan-2-yl}carbamate Example 109C and 6-(piperidin-1-yl)pyridine-3-amine were processed using sequentially the methods of Examples 113A, 113B, 116F (Ra-Ni reduction conducted in an SS pressure bottle for 120 min at 30 psi at room temperature), 28I (reaction conducted at 50° C. for 4 hours), 39I, and 26J (reaction solvent=dichloromethane) to provide the title compound (71 mg). $^1$H NMR (400 MHz, METHANOL-D4) δ 0.89 (ddd, J=6.5, 20.7, 26.0, 12H), 1.62-1.43 (m, 6H), 2.48-1.80 (m, 13H), 2.72-2.60 (m, 2H), 3.10-2.97 (m, 4H), 3.64 (s, 6H), 3.93-3.78 (m, 2H), 4.09-3.94 (m, 2H), 4.22 (d, J=7.3, 2H), 5.21 (dd, J=5.2, 7.6, 1H), 5.44-5.30 (m, 2H), 6.50 (d, J=9.1, 1H), 6.83-6.71 (m, 1H), 7.59-7.15 (m, 7H). MS (ESI) m/z 916 (M+H)$^+$, 914 (M−H)$^+$.

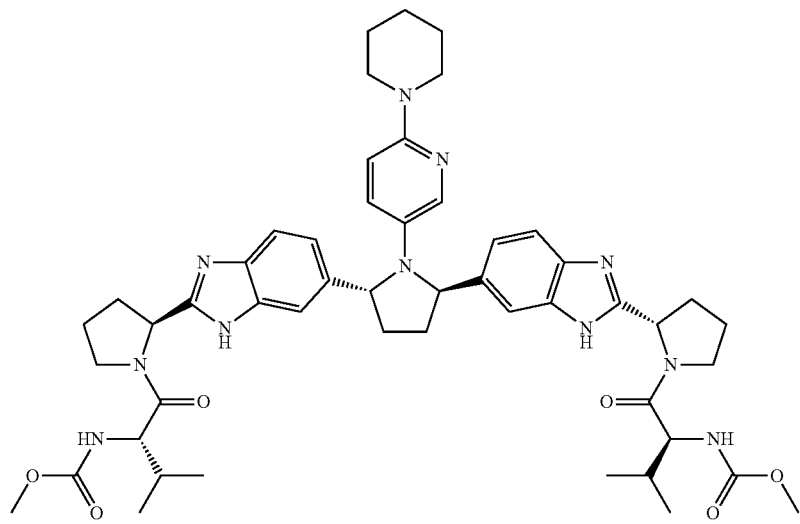

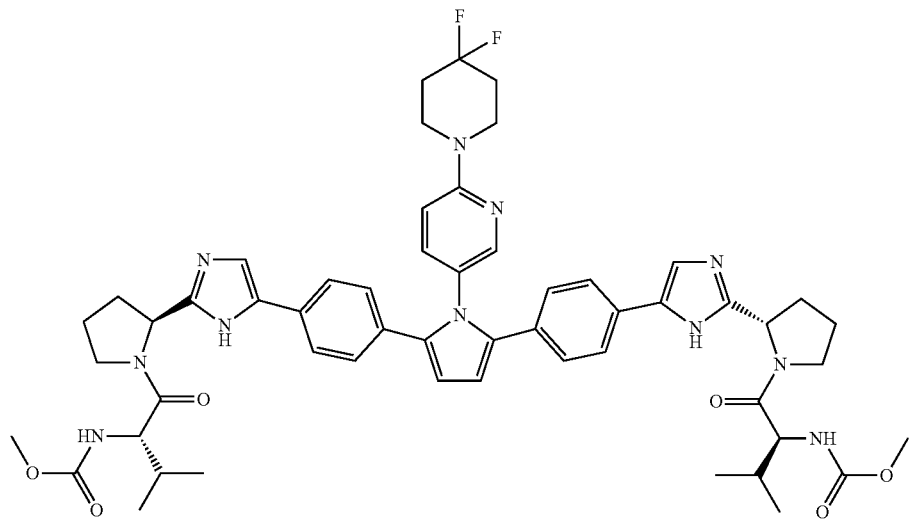

Example 135 methyl [(2S)-1-{(2S)-2-[5-(4-{1-[6-(4,4-difluoropiperidin-1-yl)pyridin-3-yl]-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl}phenyl)-1H-imidazol-2-yl]pyrrolidin-1-yl}-3-methyl-1-oxobutan-2-yl] carbamate

Example 135A 2-(4,4-difluoropiperidin-1-yl)-5-nitropyridine

To a slurry of 2-chloro-5-nitropyridine (5 g, 31.5 mmol) and 4,4-difluoropiperidine hydrochloride (4.97 g) in ethanol (40 mL) at ambient temperature was added N,N-diisopropylethylamine (12.00 mL, 69.4 mmol) and the mixture heated to 70° C. for 18 hours. The reaction was concentrated, partitioned between $CH_2Cl_2$ and 1M NaOH. The organic phase concentrated and purified by chromatography (elution with 2% MeOH—CH2Cl2 then 3% MeOH—CH2Cl2) to provide the title compound as a yellow oil. MS (DCI) m/z 261 $(M+NH_4)^+$.

Example 135B 6-(4,4-difluoropiperidin-1-yl)pyridin-3-amine

The product from Example 135A (4.56 g, 18.75 mmol) and solvent THF (20 mL)/DMF were added to Ra-Ni 2800, water slurry (4.56 g, 78 mmol) in a 250 mL SS pressure bottle and stirred for 2 hr at 30 psi and ambient temperature. The mixture was filtered through a nylon membrane and washed with MeOH. The filtrate was concentrated and dried under vacuum to afford the title compound (3.40 g, 85%). $^1H$ NMR (400 MHz, DMSO-D6) δ 2.03-1.88 (m, 4H), 3.49-3.38 (m, 4H), 4.61 (s, 2H), 6.73 (d, J=8.8, 1H), 6.93 (dd, J=2.9, 8.8, 1H), 7.61 (d, J=2.6, 1H). MS (ESI) m/z 214 $(M+H^+)$.

Example 135C 5-(2,5-bis(4-(2-((S)-pyrrolidin-2-yl)-1H-imidazol-5-yl)phenyl)-1H-pyrrol-1-yl)-2-(4,4-difluoropiperidin-1-yl)pyridine TFA (0.046 mL, 0.596 mmol) was added to a mixture of the product from Example 138B (0.2114 g, 0.298 mmol) and the product from Example 135B (0.095 g, 0.447 mmol) in toluene (2.98 mL). The mixture was heated at 110° C. for 18 hours. The reaction was cooled and additional TFA (0.023 mL, 0.298 mmol) was added and stirred for another hour. The solvent was removed under reduced pressure and azatroped with toluene to afford the title compound.

Example 135D methyl [(2S)-1-{(2S)-2-[5-(4-{1-[6-(4,4-difluoropiperidin-1-yl)pyridin-3-yl]-5-(4-{2-[(2S)-1-{(2S)-2-[(methoxycarbonyl)amino]-3-methylbutanoyl}pyrrolidin-2-yl]-1H-imidazol-5-yl}phenyl)-1H-pyrrol-2-yl}phenyl)-1H-imidazol-2-yl]pyrrolidin-1-yl}-3-methyl-1-oxobutan-2-yl] carbamate The product from Example 135C was processed using the method described in Example 26J to afford the title compound. $^1H$ NMR (400 MHz, DMSO-D6) δ 0.94-0.73 (m, 12H), 2.03-1.82 (m, 10H), 2.20-2.04 (m, 4H), 3.53 (s, 6H), 3.64 (s, 4H), 3.86-3.69 (m, 4H), 4.04 (dd, 2H), 5.04 (dd, J=3.0, 7.0, 2H), 6.53-6.39 (m, 2H), 6.93-6.79 (m, 1H), 7.06 (d, J=8.4, 3H), 7.13 (dd, J=10.9, 19.3, 1H), 7.30-7.21 (m, 2H), 7.39-7.30 (m, 1H), 7.42 (d, J=1.7, 1H), 7.48-7.43 (m, 1H), 7.66-7.49 (m, 4H), 7.85 (dd, J=2.7, 9.7, 1H), 12.16-11.64 (m, 2H). MS (ESI) m/z 1000 $(M+H)^+$, 998 $(M-H)^+$.

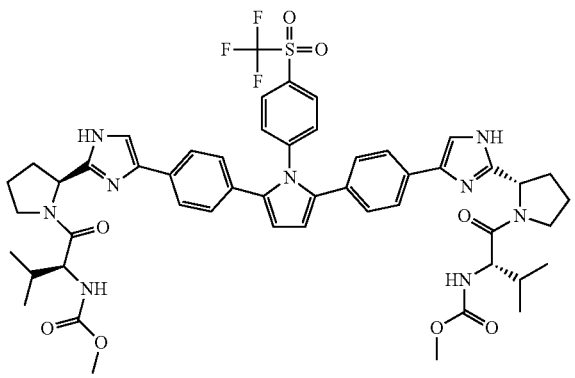 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)C(C)C)n5)cc4)n3-c3ccc(S(=O)(=O)C(F)(F)F)cc3)cc2)c[nH]1)C(C)C]

Example 136 methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-{4-[(trifluoromethyl)sulfonyl]phenyl}-1H-pyrrol-2-yl]phenyl}-1H-imidazol-2-yl)pyrrolidin-1-yl]-3-methyl-1-oxobutan-2-yl}carbamate

Example 136A 2,5-bis(4-bromophenyl)-1-(4-(trifluoromethylsulfonyl)phenyl)-1H-pyrrole To a slurry of the product from Example 26E (0.60 g, 1.52 mmol) and 4-(trifluoromethylsulfonyl)aniline (0.51 g, 2.27 mmol) in toluene (12 mL) was added a 1N solution of titanium(IV) chloride (1.6 mL, 1.6 mmol) in toluene. The mixture was stirred overnight at room temperature and then heated to reflux for 3 hours. The cooled mixture was filtered and the solid residue was suspended in a mixture of water and diethyl ether. The solid was diluted with water and ether and stirred vigorously for 15 minutes. The mixture was filtered and then washed thoroughly with diethyl ether to give the title compound as a crude mixture that was used in subsequent reactions without further purification (0.60 g, 68% yield crude).

Example 136B methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-{4-[(trifluoromethyl)sulfonyl]phenyl}-1H-pyrrol-2-yl]phenyl}-1H-imidazol-2-yl)pyrrolidin-1-yl]-3-methyl-1-oxobutan-2-yl}carbamate Example 136A was processed using sequentially the methods of Examples 26G, 26H, 65B, and 65C to provide the title compound (90 mg). $^1$H NMR (400 MHz, DMSO-D6) δ 12.20-11.68 (m, 2H), 8.17-8.04 (m, 2H), 7.63-7.42 (m, 8H), 7.31-7.15 (m, 2H), 7.02-6.90 (m, 4H), 6.64-6.53 (m, 2H), 5.08-4.97 (m, 2H), 4.05-3.97 (m, 2H), 3.83-3.69 (m, 4H), 3.53 (s, 6H), 2.18-1.79 (m, 10H), 0.90-0.78 (m, 12H). MS (ESI; M+H) m/z=1013.

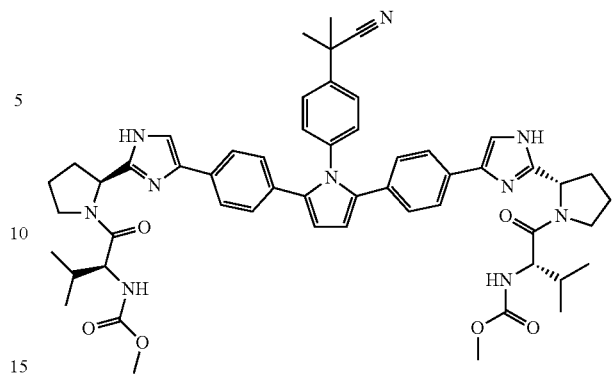

Example 137 methyl [(2S)-1-{(2S)-2-[4-(4-{1-[4-(2-cyanopropan-2-yl)phenyl]-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl}phenyl)-1H-imidazol-2-yl]pyrrolidin-1-yl}-3-methyl-1-oxobutan-2-yl]carbamate Example 26E and 2-(4-aminophenyl)-2-methylpropanenitrile were processed using sequentially the methods of Examples 26F, 26G, 26H, 65B, and 65C to provide the title compound (100 mg). $^1$H NMR (400 MHz, DMSO-D6) δ 12.15-11.68 (m, OH), 7.58-7.44 (m, OH), 7.44-7.36 (m, OH), 7.30-7.12 (m, OH), 7.07-6.91 (m, OH), 6.55-6.42 (m, OH), 5.06-4.96 (m, OH), 4.02 (t, J=8.3, OH), 3.81-3.67 (m, OH), 3.52 (s, OH), 2.15-1.82 (m, OH), 1.65 (s, OH), 0.90-0.74 (m, 1H). MS (ESI; M+H) m/z=948.

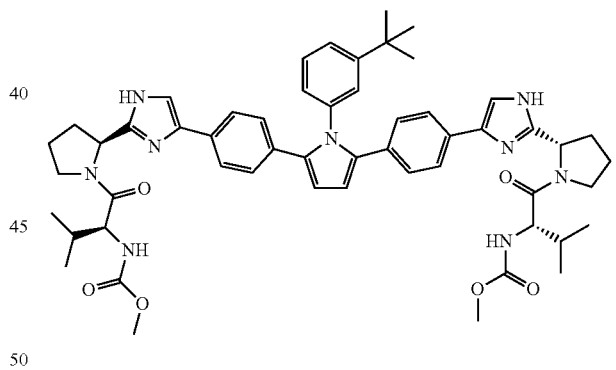

Example 138 methyl {(2S)-1-[(2S)-2-(4-{4-[1-(3-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate

Example 138A 1,4-bis(4-(4,4,5,5-tetramethyl-1,3,2-dioxaborolan-2-yl)phenyl)butane-1,4-dione To a solution of the product from Example 26E (2.00 g, 5.05 mmol), bis(pinacolato)diborane (3.85 g, 15.15 mmol), potassium acetate (1.982 g, 20.20 mmol) in dimethoxyethane (50 mL) at room temperature was added PdCl$_2$(dppf)-CH$_2$Cl$_2$ adduct (0.412 g, 0.505 mmol) and the mixture degassed (purge with N$_2$). The mixture was heated to reflux for 1 hour. The cooled mixture was filtered through celite and washed with ethyl acetate. The filtrate was washed with water, brine and dried (Na$_2$SO$_4$). After filtration and removal of solvent, the residue was purified by chromatography (80 g column; gradient elution from 0% to 40% ethyl acetate-hexanes) to provide the title compound (2.22 g; 90%) as a white solid. $^1$HNMR (CDCl$_3$; 400 MHz): δ 8.02 (AA'XX', J=8.24 Hz, 4H), 7.91 (AA'XX', J=8.13 Hz, 4H), 3.47 (s, 4H), 1.36 (s, 24H).

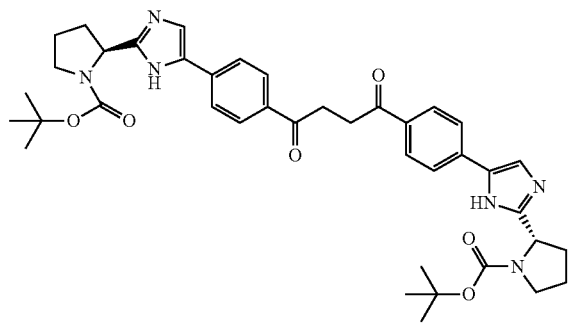 [SMILES: CC(C)(C)OC(=O)N1CCC[C@H]1c1ncc(-c2ccc(C(=O)CCC(=O)c3ccc(-c4cnc([C@@H]5CCCN5C(=O)OC(C)(C)C)[nH]4)cc3)cc2)[nH]1]

Example 138B di-tert-butyl (2S,2'S)-2,2'-[(1,4-dioxobutane-1,4-diyl)bis(benzene-4,1-diyl-1H-imidazole-5,2-diyl)]dipyrrolidine-1-carboxylate A solution of the product from Example 138A (2.22 g, 4.53 mmol), PdCl$_2$(dppf)-CH$_2$Cl$_2$ adduct (0.37 g, 0.45 mmol), 1 M sodium carbonate (18 mL, 18 mmol) and the product from Example 26D (4.30 g, 13.6 mmol) in ethanol (23 mL)/toluene (23 mL) was degassed (purge N$_2$) and heated in oil bath at 90° C. overnight. The cooled mixture was concentrated and the residue partitioned between water and ethyl acetate. The organic phase was concentrated and the residue was purified by chromatography (gradient elution from 30% to 100% ethyl acetate-hexane) to provide the title compound (1.90 g, 59%) as a light tan solid. $^1$HNMR (DMSO-d$_6$; 400 MHz): δ 12.06 (m, 2H), 8.04-7.96 (m, 4H), 7.89-7.78 (m, 4H), 7.69 (m, 2H), 4.85-4.75 (m, 2H), 3.53 (m, 2H), 3.35 (m, 4H), 2.24-1.87 (m, 10H), 1.39 (br s, 8H), 1.14 (br s, 10H). MS (ESI; M+H) m/z=709.

Example 138C (S)-4,4'-(4,4'-(1-(3-tert-butylphenyl)-1H-pyrrole-2,5-diyl)bis(4,1-phenylene))bis(2-((S)-pyrrolidin-2-yl)-1H-imidazole)

To a solution of the product from Example 138B (180 mg, 0.25 mmol) and 3-tert-butylaniline (57 mg, 0.38 mmol) in toluene (2.0 mL) was added trifluoroacetic acid (39 μL 0.50 mmol). The mixture was heated to 110° C. overnight. To the cooled mixture was added trifluoroacetic acid (0.4 mL) and the mixture was stirred for 1 hour at room temperature. The mixture was concentrated under reduced pressure. The residue was partitioned between 25% isopropyl alcohol in CHCl$_3$ and saturated sodium bicarbonate solution. The organic layer was separated and dried over Na$_2$SO$_4$, filtered and concentrated under reduced pressure to provide the title compound.

Example 138D methyl {(2S)-1-[(2S)-2-(4-{4-[1-(3-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate A solution consisting of N1-((ethylimino)methylene)-N3,N3-dimethylpropane-1,3-diamine hydrochloride (109 mg, 0.57 mmol), 1H-benzo[d][1,2,3]triazol-1-ol hydrate (87 mg, 0.57 mmol), (S)-2-(methoxycarbonylamino)-3-methylbutanoic acid (100 mg, 0.57 mmol) and 4-methylmorpholine (0.14 mL, 1.0 mmol) in DMF (2.6 mL) was cooled in an icebath. To this mixture was added the product from Example 138C (161 mg, 0.26 mmol). Additional 4-methylmorpholine was added to the mixture until the pH was adjusted to 8. The reaction was stirred for 3.5 hours and then the icebath was removed and the reaction was stirred for an additional 16 hours. Water was then added to the reaction mixture and the resulting precipitate was recovered by filtration. The residue was washed with copious amounts of water followed by diethyl ether. The crude product was purified by chromatography on silica gel eluted with a solvent gradient of 0-5% methanol in CH$_2$Cl$_2$ to provide the title compound (15 mg, 6% yield). $^1$H NMR (400 MHz, DMSO-D6) δ 12.04-11.65 (m, 2H), 7.57-7.45 (m, 4H), 7.43-7.35 (m, 2H), 7.33-7.08 (m, 5H), 7.05-6.91 (m, 4H), 6.79 (t, J=7.5, 1H), 6.53-6.40 (m, 2H), 5.05-4.99 (m, 2H), 4.02 (t, J=8.3, 2H), 3.82-3.68 (m, 4H), 3.56-3.47 (m, 6H), 2.18-1.79 (m, 10H), 1.09 (s, 9H), 0.89-0.75 (m, 12H). MS (ESI; M+H) m/z=937.

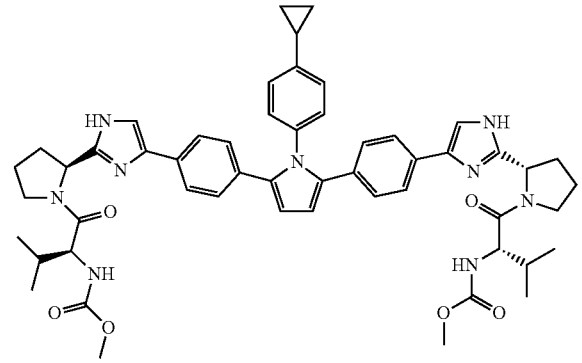 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)C(C)C)n5)cc4)n3-c3ccc(C4CC4)cc3)cc2)c[nH]1)C(C)C]

Example 139 methyl {(2S)-1-[(2S)-2-(4-{4-[1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate Example 139A (S)-4,4'-(4,4'-(1-(4-cyclopropylphenyl)-1H-pyrrole-2,5-diyl)bis(4,1-phenylene))bis(2-((S)-pyrrolidin-2-yl)-1H-imidazole)tetrakis(2,2,2-trifluoroacetate)

To a solution of the product from Example 138B (0.30 g 0.43 mmol) and 4-cyclopropylaniline (85 mg, 0.64 mmol) in toluene (3.4 mL) was added trifluoroacetic acid (65 μL 0.85 mmol). The mixture was heated to 110° C. overnight. To the cooled mixture was added trifluoroacetic acid (1.0 mL) and the mixture was stirred for 1 hour at room temperature. The mixture was concentrated under reduced pressure and then triturated with diethyl ether to provide the title compound (0.42 g, 28% yield).

Example 139B methyl {(2S)-1-[(2S)-2-(4-{4-[1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate The title compound was prepared using the methods from Example 138D substituting the product from Example 139A for the product from Example 138C to provide the title compound (150 mg, 40% yield). $^1$H NMR (400 MHz, DMSO-D6) δ 12.09-11.63 (m, 2H), 7.56-7.46 (m, 4H), 7.44-7.35 (m, 2H), 7.30-7.11 (m, 2H), 7.07-6.88 (m, 8H), 6.54-6.39 (m, 2H), 5.07-4.97 (m, 2H), 4.03 (t, J=8.3, 2H), 3.83-3.66 (m, 4H), 3.52 (s, 6H), 2.18-1.79 (m, 10H), 1.26-1.19 (m, 1H), 0.98-0.90 (m, 2H), 0.90-0.74 (m, 12H), 0.69-0.60 (m, 2H). MS (ESI; M+H) m/z=921.

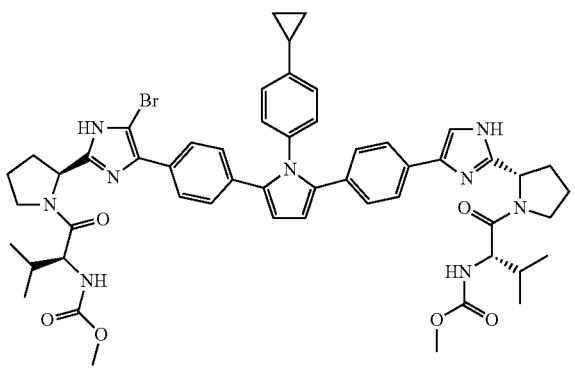 [SMILES: COC(=O)N[C@H](C(=O)N1CCC[C@H]1c1nc(-c2ccc(-c3ccc(-c4ccc(-c5nc([C@@H]6CCCN6C(=O)[C@@H](NC(=O)OC)C(C)C)[nH]c5Br)cc4)n3-c3ccc(C4CC4)cc3)cc2)c[nH]1)C(C)C]

Example 140 methyl [(2S)-1-{(2S)-2-[5-bromo-4-(4-{1-(4-cyclopropylphenyl)-5-[4-(2-{(2S)-1-[N-(methoxycarbonyl)-L-valyl]pyrrolidin-2-yl}-1H-imidazol-4-yl)phenyl]-1H-pyrrol-2-yl}phenyl)-1H-imidazol-2-yl]pyrrolidin-1-yl}-3-methyl-1-oxobutan-2-yl]carbamate To a suspension of the product from Example 139 (47 mg, 0.051 mmol) in CH$_2$Cl$_2$ (0.5 mL) was added a mixture of 1-bromopyrrolidine-2,5-dione (9.1 mg, 0.051 mmol) in CH$_2$Cl$_2$ (0.5 mL). The mixture was stirred overnight at room temperature then concentrated under reduced pressure and triturated with diethyl ether to provide a mixture of brominated compounds that was subjected to reverse phase HPLC purification eluted with a gradient of 10-100% CH$_3$CN in 0.1% aqueous trifluoroacetic acid to afford the title compound (8 mg, 13% yield). $^1$H NMR (TFA salt) (400 MHz, DMSO-D6) δ 14.32 (s, 1H), 12.44 (s, 1H), 7.97 (s, 1H), 7.62-7.48 (m, 4H), 7.31 (d, J=8.4, 1H), 7.24 (d, J=8.5, 1H), 7.18-7.08 (m, 4H), 7.09-7.00 (m, 4H), 6.61 (d, J=3.7, 1H), 6.57 (d, J=3.7, 1H), 5.07 (t, J=7.0, 1H), 4.98-4.91 (m, 1H), 4.08 (t, J=7.9, 1H), 4.02 (t, J=8.3, 1H), 3.90-3.67 (m, 4H), 3.52 (s, 3H), 3.51 (s, 3H), 2.18-1.83 (m, 10H), 1.22 (s, 1H), 1.01-0.93 (m, 2H), 0.89-0.72 (m, 12H), 0.70-0.62 (m, 2H). MS (ESI; M+H) m/z=1000.

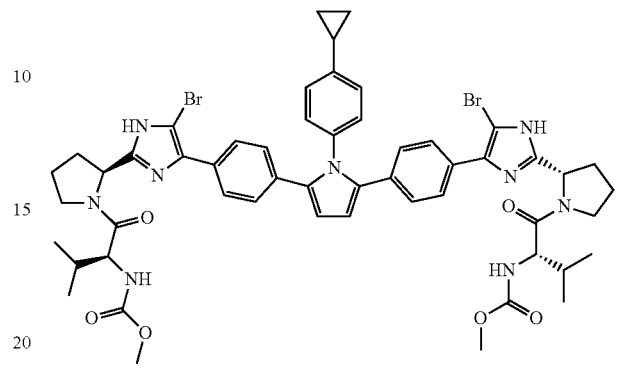

Example 141 methyl {(2S)-1-[(2S)-2-(5-bromo-4-{4-[5-(4-{5-bromo-2-[(2S)-1-{(2S)-2-[(methoxycarbonyl)amino]-3-methylbutanoyl}pyrrolidin-2-yl]-1H-imidazol-4-yl}phenyl)-1-(4-cyclopropylphenyl)-1H-pyrrol-2-yl]phenyl}-1H-imidazol-2-yl)pyrrolidin-1-yl]-3-methyl-1-oxobutan-2-yl}carbamate The title compound was formed as an additional product in Example 140. The mixture of products was subjected to reverse phase HPLC purification eluted with a gradient of 10-100% CH$_3$CN in 0.1% aqueous trifluoroacetic acid to afford the title compound (15 mg, 23% yield). $^1$H NMR (TFA salt) (400 MHz, DMSO-D6) δ 12.43 (s, 2H), 7.54 (dd, 4H), 7.25 (d, J=8.4, 2H), 7.15-7.08 (m, 4H), 7.08-7.00 (m, 4H), 6.55 (s, 2H), 4.99-4.89 (m, 2H), 4.02 (t, J=8.3, 2H), 3.82-3.68 (m, 4H), 3.51 (s, 6H), 2.22-2.03 (m, 4H), 2.00-1.81 (m, 6H), 1.27-1.19 (m, 1H), 1.02-0.92 (m, 2H), 0.90-0.77 (m, 12H), 0.70-0.61 (m, 2H). MS (ESI; M+H) m/z=1078.

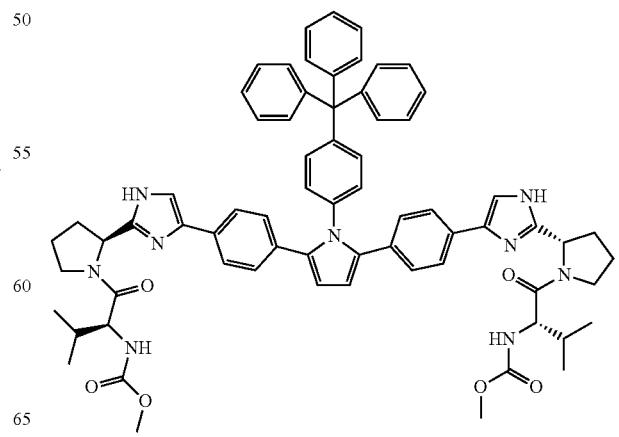

Example 142 methyl {(2S)-1-[(2S)-2-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-(4-tritylphenyl)-1H-pyrrol-2-yl]phenyl}-1H-imidazol-2-yl)pyrrolidin-1-yl]-3-methyl-1-oxobutan-2-yl}carbamate

Example 142A (S)-4,4'-(4,4'-(1-(4-tritylphenyl)-1H-pyrrole-2,5-diyl)bis(4,1-phenylene))bis(2-((S)-pyrrolidin-2-yl)-1H-imidazole)tetrakis(2,2,2-trifluoroacetate)

The title compound was prepared using the methods from Example 139A substituting 4-tritylaniline for 4-cyclopropylaniline to provide the title compound.

Example 142B methyl {(2S)-1-[(2S)-2-(5-bromo-4-{4-[5-(4-{5-bromo-2-[(2S)-1-{(2S)-2-[(methoxycarbonyl)amino]-3-methylbutanoyl}pyrrolidin-2-yl]-1H-imidazol-4-yl}phenyl)-1-(4-cyclopropylphenyl)-1H-pyrrol-2-yl]phenyl}-1H-imidazol-2-yl)pyrrolidin-1-yl]-3-methyl-1-oxobutan-2-yl}carbamate The title compound was prepared using the methods from Example 138D substituting the product from Example 142A for the product from Example 138C to provide the title compound (71 mg, 43% yield). ¹H NMR (400 MHz, DMSO-D6) δ 12.15-11.69 (m, 2H), 7.61-7.48 (m, 4H), 7.46-7.37 (m, 2H), 7.35-7.15 (m, 11H), 7.10-6.91 (m, 14H), 6.55-6.44 (m, 2H), 5.11-5.00 (m, 2H), 4.03 (t, J=8.5, 2H), 3.86-3.70 (m, 4H), 3.52 (s, 6H), 2.21-1.83 (m, 10H), 0.92-0.76 (m, 12H). MS (ESI; M+H) m/z=1123.

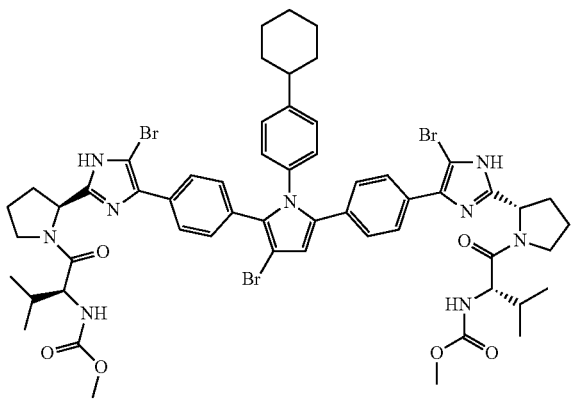 [SMILES: COC(=O)N[C@H](C(=O)N1CCC[C@H]1c1nc(-c2ccc(-c3cc(Br)c(-c4ccc(-c5nc([C@@H]6CCCN6C(=O)[C@@H](NC(=O)OC)C(C)C)[nH]c5Br)cc4)n3-c3ccc(C4CCCCC4)cc3)cc2)c(Br)[nH]1)C(C)C]

Example 143 methyl {(2S)-1-[(2S)-2-(5-bromo-4-{4-[4-bromo-5-(4-{5-bromo-2-[(2S)-1-{(2S)-2-[(methoxycarbonyl)amino]-3-methylbutanoyl}pyrrolidin-2-yl]-1H-imidazol-4-yl}phenyl)-1-(4-cyclohexylphenyl)-1H-pyrrol-2-yl]phenyl}-1H-imidazol-2-yl)pyrrolidin-1-yl]-3-methyl-1-oxobutan-2-yl}carbamate To a suspension of the product from Example 74 (100 mg, 0.10 mmol) in CH₂Cl₂ (1.0 mL) at −78° C. was added a mixture of 1-bromopyrrolidine-2,5-dione (59 mg, 0.33 mmol) in CH₂Cl₂ (1.0 mL). The mixture was stirred for 3 hours, warming to room temperature then concentrated under reduced pressure and triturated with diethyl ether to provide the title compound (103 mg, 83% yield). ¹H NMR (400 MHz, DMSO-D6) δ 12.47 (s, 1H), 11.02 (s, 1H), 7.54 (d, J=26.1, 4H), 7.29-6.98 (m, 10H), 6.71 (s, 1H), 5.01-4.90 (m, 2H), 4.02 (t, J=8.1, 2H), 3.86-3.67 (m, 4H), 3.52 (s, 6H), 2.18-1.58 (m, 16H), 1.35-1.20 (m, 5H), 0.90-0.76 (m, 12H). MS (ESI; M+H) m/z=1200.

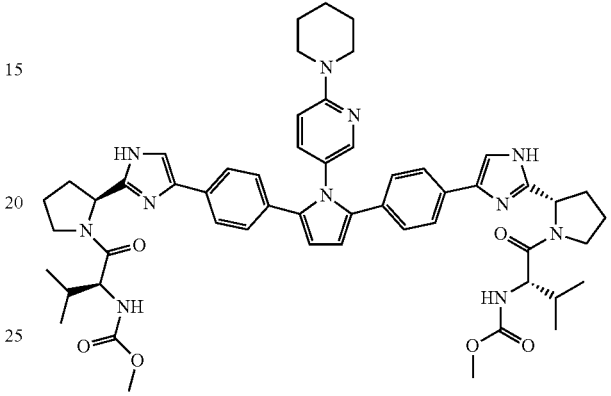

Example 144 methyl [(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]-1H-pyrrol-2-yl}phenyl)-1H-imidazol-2-yl]pyrrolidin-1-yl}-3-methyl-1-oxobutan-2-yl]carbamate

Example 144A 5-nitro-2-(piperidin-1-yl)pyridine

To a slurry of 2-chloro-5-nitropyridine (100 g, 632 mmol) in ethanol (2000 mL) at room temperature was added piperidine (206 mL, 2.08 mol) and the mixture heated to 60° C. for 30 minutes. The cooled mixture was concentrated and the residue taken up in CH₂Cl₂ then washed with saturated NaHCO₃ and brine. The mixture was dried (Na₂SO₄), filtered, and concentrated to provide the title compound as a yellow solid (130.4 g, 99% yield). ¹H NMR (400 MHz, DMSO-D6) δ 8.94 (d, J=2.9, 1H), 8.17 (dd, J=9.6, 2.9, 1H), 6.93 (d, J=9.6, 1H), 3.79-3.73 (m, 4H), 1.69-1.64 (m, 2H), 1.61-1.51 (m, 4H).

Example 144B tert-butyl 6-(piperidin-1-yl)pyridin-3-ylcarbamate

To a solution of the product from Example 144A (130.4 g, 629 mmol) and di-tert-butyl dicarbonate (165 g, 755 mmol) in ethanol (750 mL) was added PtO₂ (5.4 g, 24 mmol). The mixture was pressurized at 40 psi with H₂ and stirred overnight at room temperature. To ensure complete reaction additional PtO₂ (3.2 g, 14 mmol) was added and the pressurized mixture was heated to 50° C. for 1 hour. The mixture was then filtered, concentrated under reduced pressure and absorbed onto silica gel and placed on top of a 4 to 5" plug of silica in a 3000 mL sintered glass funnel. Material was eluted with 15% diethyl ether in CH₂Cl₂ and the filtrate was concentrated under reduced pressure and the residue triturated with boiling hexanes. Additional product was recovered upon concentration of the filtrate, which was then chromatographed on silica gel eluted with 10% diethyl ether in CH₂Cl₂. The appropriate fractions were collected and concentrated then triturated with boiling hexanes. The two lots of lavender solids were combined to provide the title compound (100 g, 57% yield). ¹H NMR (400 MHz, DMSO) δ 9.02 (bs, 1H), 8.11 (s, 1H), 7.63-7.54 (m, 1H), 6.74 (d, J=9.1, 1H), 3.42-3.37 (m, 4H), 1.57-1.49 (m, 6H), 1.45 (9, 1H).

Example 144C 6-(piperidin-1-yl)pyridin-3-amine dihydrochloride

The product from Example 144B (1.00 g, 3.62 mmol) was added slowly to 4 M hydrochloric acid (10 mL, 40 mmol) and stirred at room temperature. After stirring overnight, ether was added and the solid filtered. Dried in vacuum oven to a white solid (0.817 g; 84%). ¹H NMR (400 MHz, methanol-d4) δ 1.77 (s, 6H), 3.65 (s, 4H), 7.41 (d, J=9.8 Hz, 1H), 7.70 (d, J=2.6 Hz, 1H), 7.79 (dd, J=2.7, 9.8 Hz, 1H).

Example 144D 5-(2,5-bis(4-(2-((S)-pyrrolidin-2-yl)-1H-imidazol-4-yl)phenyl)-1H-pyrrol-1-yl)-2-(piperidin-1-yl)pyridine To a solution of the product from Example 138B (0.20 g, 0.28 mmol) and the product from Example 144C (0.11 g, 0.42 mmol) in toluene (2.8 mL) was added TFA (22 μL, 0.28 mmol). The mixture was stirred at 110° C. for 3 hours. To the cooled mixture was added TFA (0.5 mL) and the mixture was stirred for 1 h at rt. The solvent was then removed under reduced pressure and triturated with diethylether and dried to provide 0.31 g of the desired compound as a TFA salt. ¹HNMR (DMSO-d₆; 400 MHz): δ 9.78 (br s, 2H), 7.84 (d, J=2.71 Hz, 1H), 7.75 (s, 2H), 7.67 (AA'XX', J=8.34 Hz, 4H), 7.35 (dd, J=9.11, 2.71 Hz, 1H), 7.18 (AA'XX', J=8.46 Hz, 4H), 6.79 (d, J=9.11 Hz, 1H), 6.53 (s, 2H), 4.79 (app t, J=7.81 Hz, 2H), 3.4-3.2 (m, 4H), 2.44-2.36 (m, 2H), 2.25-1.98 (m, 6H), 1.65-1.45 (m, 6H).

Example 144E methyl [(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]-1H-pyrrol-2-yl]phenyl)-1H-imidazol-2-yl]pyrrolidin-1-yl}-3-methyl-1-oxobutan-2-yl]carbamate To a solution of N1-((ethylimino)methylene)-N3,N3-dimethylpropane-1,3-diamine hydrochloride (0.17 g, 0.89 mmol), 1H-benzo[d][1,2,3]triazol-1-ol hydrate (0.14 g, 0.89 mmol), (S)-2-(methoxycarbonylamino)-3-methylbutanoic acid (0.16 g, 0.89 mmol) in DMF (1.0 mL) was added 4-methylmorpholine (0.3 mL, 2.7 mmol). This mixture was stirred at room temperature for 15 minutes and then added to a solution of the product from Example 144D (0.31 g, 0.25 mmol) and 4-methylmorpholine (0.2 mL, 1.8 mmol) in DMF (0.7 mL). After stirring 4 h, water was added to this mixture and the solid collected by filtration then washed with water and diethylether. The residue was purified on silica gel eluted with 60% THF/Hexanes to provide 100 mg of the title compound. ¹H NMR (400 MHz, DMSO) δ 12.17-11.70 (m, 2H), 7.84-7.76 (m, 1H), 7.64-7.50 (m, 4H), 7.49-7.40 (m, 2H), 7.31-7.02 (m, 7H), 6.76-6.69 (m, 1H), 6.52-6.41 (m, 2H), 5.09-5.01 (m, 2H), 4.04 (t, J=8.3, 2H), 3.83-3.71 (m, 4H), 3.53 (s, 6H), 3.50-3.44 (m, 4H), 2.18-2.04 (m, 4H), 2.03-1.86 (m, 6H), 1.61-1.46 (m, 6H), 0.90-0.79 (m, 12H). MS (ESI; M+H) m/z=965.

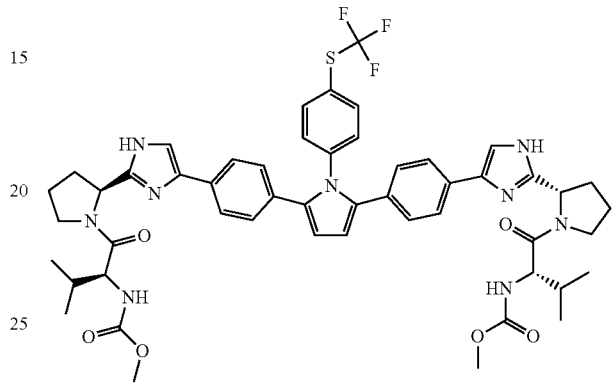

Example 145 methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-{4-[(trifluoromethyl)sulfanyl]phenyl}-1H-pyrrol-2-yl]phenyl}-1H-imidazol-2-yl)pyrrolidin-1-yl]-3-methyl-1-oxobutan-2-yl}carbamate Example 138B and 4-(trifluoromethylthio)aniline were processed using the methods of Examples 139A and 138D to provide the title compound (19 mg). ¹H NMR (400 MHz, DMSO-D6) δ 12.18-11.65 (m, 2H), 7.73-7.63 (m, 2H), 7.60-7.48 (m, 4H), 7.45-7.39 (m, 2H), 7.31-7.15 (m, 4H), 7.06-6.92 (m, 4H), 6.58-6.46 (m, 2H), 5.08-5.00 (m, 2H), 4.03 (t, J=8.4, 2H), 3.85-3.69 (m, 4H), 3.53 (s, 6H), 2.23-1.79 (m, 10H), 0.93-0.77 (m, 12H). MS (ESI; M+H) m/z=981.

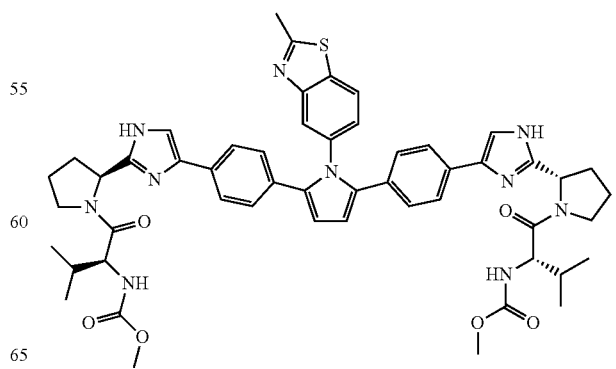

Example 146 methyl {(2S)-1-[(2S)-2-(4-{4-[5-(4-{2-[(2S)-1-{(2S)-2-[(methoxycarbonyl)amino]-3-methylbutanoyl}pyrrolidin-2-yl]-1H-imidazol-4-yl}phenyl)-1-(2-methyl-1,3-benzothiazol-5-yl)-1H-pyrrol-2-yl]phenyl}-1H-imidazol-2-yl)pyrrolidin-1-yl]-3-methyl-1-oxobutan-2-yl}carbamate Example 138B and 2-methylbenzo[d]thiazol-5-amine dihydrochloride were processed using the methods of Examples 139A and 138D to provide the title compound (19 mg). $^1$H NMR (400 MHz, DMSO-D6) δ 12.04-11.63 (m, 2H), 8.02-6.85 (m, 15H), 6.58-6.45 (m, 2H), 5.07-4.96 (m, 2H), 4.02 (t, J=8.4, 2H), 3.86-3.67 (m, 4H), 3.53 (s, 6H), 2.75 (s, 3H), 2.21-1.78 (m, 10H), 0.93-0.76 (m, 12H). MS (ESI; M+H) m/z=952.

Example 148 methyl {(2S)-1-[(2S)-2-(4-{4-[1-(1H-indazol-6-yl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate Example 138B and 1H-indazol-6-amine were processed using the methods of Examples 139A and 138D to provide the title compound (24 mg). $^1$H NMR (400 MHz, DMSO-D6) δ 13.08-12.99 (m, 1H), 12.05-11.62 (m, 2H), 8.13-8.04 (m, 1H), 7.74-7.66 (m, 1H), 7.54-7.42 (m, 4H), 7.41-7.34 (m, 2H), 7.31-7.09 (m, 3H), 7.05-6.77 (m, 5H), 6.58-6.47 (m, 2H), 5.06-4.97 (m, 2H), 4.02 (t, J=8.4, 2H), 3.83-3.66 (m, 4H), 3.53 (s, 6H), 2.20-1.78 (m, 10H), 0.89-0.76 (m, 12H). MS (ESI; M+H) m/z=921.

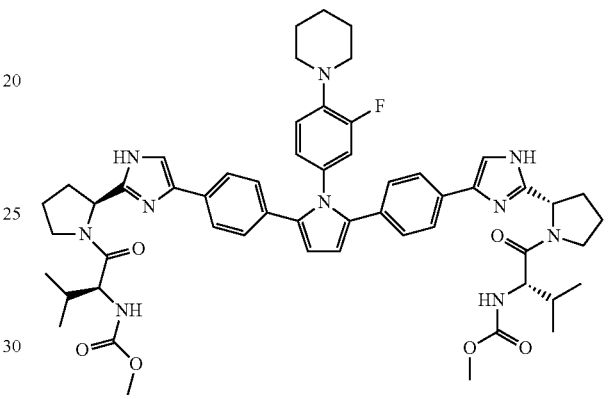

Example 149 methyl [(2S)-1-{(2S)-2-[4-(4-{1-[3-fluoro-4-(piperidin-1-yl)phenyl]-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl}phenyl)-1H-imidazol-2-yl]pyrrolidin-1-yl}-3-methyl-1-oxobutan-2-yl]carbamate Example 138B and 3-fluoro-4-(piperidin-1-yl)aniline were processed using the methods of Examples 139A and 138D to provide the title compound. $^1$H NMR (400 MHz, DMSO-D6) δ 12.15-11.69 (m, 2H), 7.62-7.49 (m, 4H), 7.48-7.39 (m, 2H), 7.32-7.15 (m, 2H), 7.12-6.77 (m, 7H), 6.52-6.42 (m, 2H), 5.08-4.99 (m, 2H), 4.04 (t, J=8.4, 2H), 3.84-3.70 (m, 4H), 3.53 (s, 6H), 3.01-2.89 (m, 4H), 2.19-1.82 (m, 10H), 1.68-1.43 (m, 6H), 0.92-0.75 (m, 12H). MS (ESI; M+H) m/z=982.

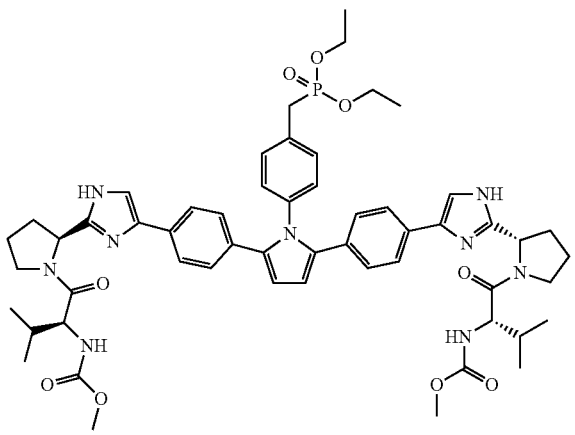 [SMILES: CCOP(=O)(Cc1ccc(-n2c(-c3ccc(-c4c[nH]c([C@@H]5CCCN5C(=O)[C@@H](NC(=O)OC)C(C)C)n4)cc3)ccc2-c2ccc(-c3c[nH]c([C@@H]4CCCN4C(=O)[C@@H](NC(=O)OC)C(C)C)n3)cc2)cc1)OCC]

Example 147 diethyl (4-{2,5-bis[4-(2-{(2S)-1-[N-(methoxycarbonyl)-L-valyl]pyrrolidin-2-yl}-1H-imidazol-4-yl)phenyl]-1H-pyrrol-1-yl}benzyl)phosphonate Example 138B and diethyl 4-aminobenzylphosphonate were processed using the methods of Examples 139A and 138D to provide the title compound. $^1$H NMR (400 MHz, DMSO-D6) δ 12.19-11.63 (m, 2H), 7.56-7.44 (m, 4H), 7.42-7.34 (m, 2H), 7.32-7.10 (m, 4H), 7.10-6.91 (m, 6H), 6.53-6.40 (m, 2H), 5.10-4.98 (m, 2H), 4.03 (t, J=8.4, 2H), 3.91-3.67 (m, 8H), 3.53 (s, 6H), 3.23 (d, J=21.8, 2H), 2.22-1.80 (m, 10H), 1.15-1.04 (m, 6H), 0.92-0.77 (m, 12H). MS (ESI; M+H) m/z=1031.

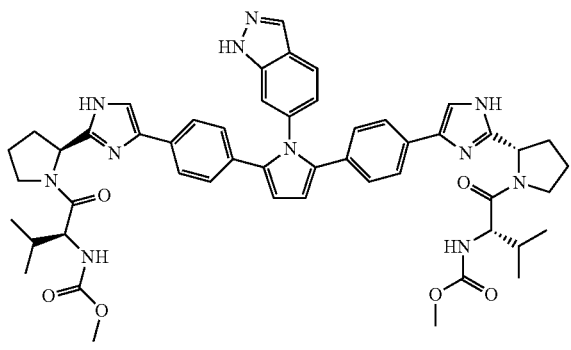 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)C(C)C)n5)cc4)n3-c3ccc4cn[nH]c4c3)cc2)c[nH]1)C(C)C]

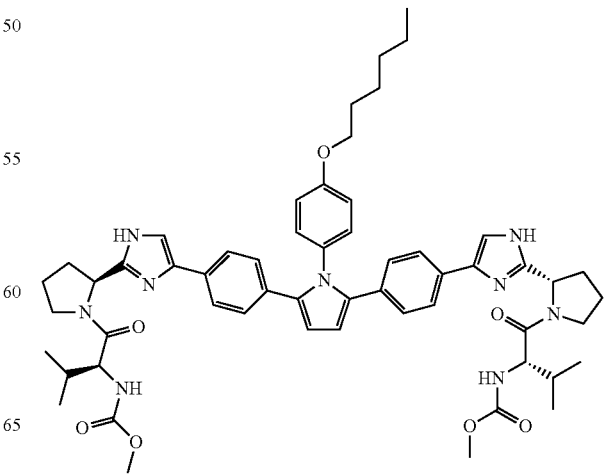

Example 150 methyl [(2S)-1-{(2S)-2-[4-(4-{1-[4-(hexyloxy)phe-
nyl]-5-(4-{2-[(2S)-1-{(2S)-2-[(methoxycarbonyl)
amino]-3-methylbutanoyl}pyrrolidin-2-yl]-1H-imi-
dazol-4-yl}phenyl)-1H-pyrrol-2-yl}phenyl)-1H-
imidazol-2-yl]pyrrolidin-1-yl}-3-methyl-1-oxobutan-
2-yl]carbamate Example 138B and 4-(hexyloxy)aniline were processed using the methods of Examples 139A and 138D to provide the title compound (15 mg). $^1$H NMR (400 MHz, DMSO-D6) δ 12.12-11.67 (m, 2H), 7.59-7.48 (m, 4H), 7.45-7.39 (m, 2H), 7.30-7.13 (m, 2H), 7.08-6.96 (m, 6H), 6.90-6.83 (m, 2H), 6.52-6.42 (m, 2H), 5.07-5.01 (m, 2H), 4.04 (t, J=8.5, 2H), 3.92 (t, J=6.4, 2H), 3.83-3.70 (m, 4H), 3.53 (s, 6H), 2.19-1.83 (m, 10H), 1.73-1.63 (m, 2H), 1.45-1.21 (m, 6H), 0.92-0.77 (m, 15H). MS (ESI; M+H) m/z=981.

Example 151

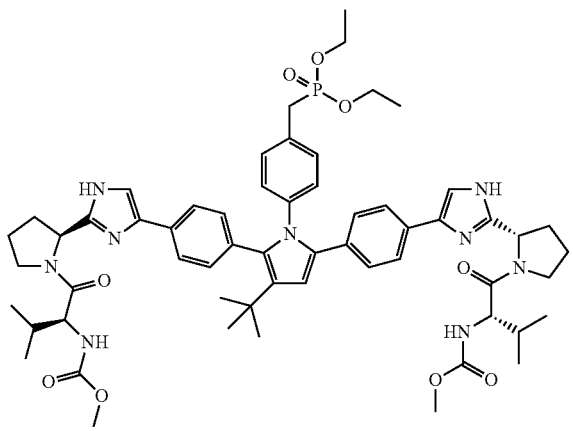 [SMILES: CCOP(=O)(Cc1ccc(-n2c(-c3ccc(-c4c[nH]c([C@@H]5CCCN5C(=O)[C@@H](NC(=O)OC)C(C)C)n4)cc3)cc(C(C)(C)C)c2-c2ccc(-c3c[nH]c([C@@H]4CCCN4C(=O)[C@@H](NC(=O)OC)C(C)C)n3)cc2)cc1)OCC]

diethyl (4-{3-tert-butyl-2,5-bis[4-(2-{(2S)-1-[N-
(methoxycarbonyl)-L-valyl]pyrrolidin-2-yl}-1H-
imidazol-4-yl)phenyl]-1H-pyrrol-1-yl}benzyl)phos-
phonate The title compound was formed as an additional product from Example 147. The mixture of products was purified by chromatography on silica gel eluted with a solvent gradient of 0-5% methanol in $CH_2Cl_2$ to provide the title compound. $^1$H NMR (400 MHz, DMSO-D6) δ 11.68 (d, J=13.5, 2H), 7.55-7.39 (m, 5H), 7.37-7.23 (m, 3H), 7.21-6.90 (m, 8H), 6.43 (s, 1H), 5.07-4.99 (m, 2H), 4.06-3.97 (m, 2H), 3.83-3.58 (m, 8H), 3.53 (s, 6H), 3.07 (d, J=21.5, 2H), 2.20-1.81 (m, 10H), 1.15 (s, 9H), 0.98 (t, J=7.0, 6H), 0.90-0.78 (m, 12H). MS (ESI; M+H) m/z=1087.

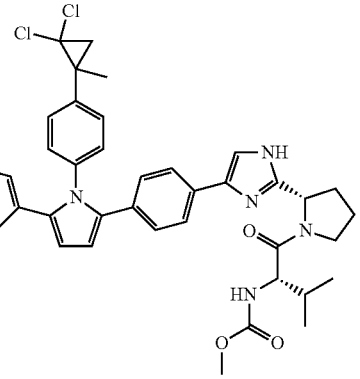

Example 152 methyl [(2S)-1-{(2S)-2-[4-(4-{1-[4-(2,2-dichloro-1-
methylcyclopropyl)phenyl]-5-(4-{2-[(2S)-1-{(2S)-2-
[(methoxycarbonyl)amino]-3-methylbutanoyl})pyr-
rolidin-2-yl]-1H-imidazol-4-yl}phenyl)-1H-pyrrol-2-
yl}phenyl)-1H-imidazol-2-yl]pyrrolidin-1-yl}-3-
methyl-1-oxobutan-2-yl]carbamate Example 138B and 4-(2,2-dichloro-1-methylcyclopropyl) aniline were processed using the methods of Examples 139A and 138D to provide the title compound (36 mg). $^1$H NMR (400 MHz, DMSO-D6) δ 12.18-11.68 (m, 2H), 7.55-7.42 (m, 4H), 7.41-7.22 (m, 6H), 7.17-6.90 (m, 6H), 6.57-6.44 (m, 2H), 5.08-5.00 (m, 2H), 4.03 (t, J=8.3, 2H), 3.86-3.69 (m, 4H), 3.53 (s, 6H), 2.22 (t, J=8.5, 1H), 2.18-1.81 (m, 10H), 1.79-1.72 (m, 1H), 1.65 (s, 3H), 0.92-0.77 (m, 12H). MS (ESI; M+H) m/z=1003.

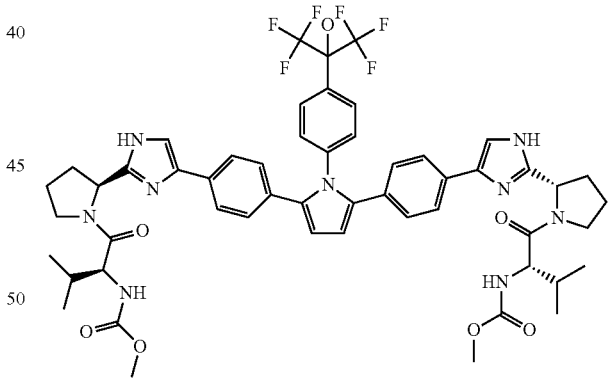

Example 153 methyl [(2S)-1-{(2S)-2-[4-(4-{1-[4-(1,1,1,3,3,3-
hexafluoro-2-hydroxypropan-2-yl)phenyl]-5-(4-{2-
[(2S)-1-{(2S)-2-[(methoxycarbonyl)amino]-3-
methylbutanoyl}pyrrolidin-2-yl]-1H-imidazol-4-
yl}phenyl)-1H-pyrrol-2-yl}phenyl)-1H-imidazol-2-
yl]pyrrolidin-1-yl}-3-methyl-1-oxobutan-2-yl]
carbamate Example 138B and 2-(4-aminophenyl)-1,1,1,3,3,3-hexafluoropropan-2-ol were processed using the methods of Examples 139A and 138D to provide the title compound (45 mg). ¹H NMR (400 MHz, DMSO-D6) δ 12.08-11.71 (m, 2H), 8.80 (s, 1H), 8.01-7.37 (m, 8H), 7.33-7.13 (m, 4H), 7.06-6.89 (m, 4H), 6.57-6.47 (m, 2H), 5.03 (d, J=6.8, 2H), 4.03 (t, J=8.4, 2H), 3.77 (d, J=6.2, 4H), 3.53 (s, 6H), 2.21-1.80 (m, 10H), 0.92-0.76 (m, 12H). MS (ESI; M+H) m/z=1047.

2H), 5.10-5.00 (m, 2H), 4.04 (t, J=8.7, 2H), 3.85-3.72 (m, 4H), 3.69-3.59 (m, 4H), 3.53 (s, 6H), 3.45-3.37 (m, 4H), 2.20-1.82 (m, 10H), 0.94-0.77 (m, 12H). MS (ESI; M+H) m/z=967.

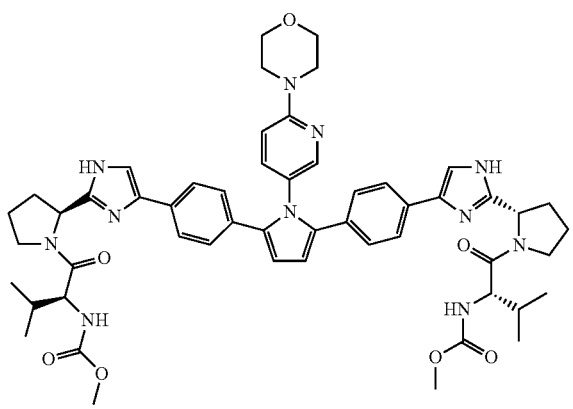 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)C(C)C)n5)cc4)n3-c3ccc(N4CCOCC4)nc3)cc2)c[nH]1)C(C)C]

Example 154 methyl [(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(morpholin-4-yl)pyridin-3-yl]-1H-pyrrol-2-yl}phenyl)-1H-imidazol-2-yl]pyrrolidin-1-yl}-3-methyl-1-oxobutan-2-yl]carbamate Example 154A 4-(5-nitropyridin-2-yl)morpholine The title compound was prepared using the methods from Example 144A substituting morpholine for piperidine to provide the title compound.

Example 154B 6-morpholinopyridin-3-amine

To a solution of the product from Example 154A (12.5, 59.5 mmol) in THF (150 mL) was added to Ra-Ni 2800, water slurry (12.5 g, 212 mmol) in a 500 mL SS pressure bottle. The mixture was pressurized (H₂, 30 psi) and stirred for 2 hours at room temperature. The mixture was filtered and then concentrated under reduced pressure to provide the title compound.

Example 154C methyl [(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(morpholin-4-yl)pyridin-3-yl]-1H-pyrrol-2-yl}phenyl)-1H-imidazol-2-yl]pyrrolidin-1-yl}-3-methyl-1-oxobutan-2-yl]carbamate Example 138B and Example 154B were processed using the methods of Examples 139A and 138D to provide the title compound. ¹H NMR (400 MHz, DMSO-D6) δ 12.16-11.69 (m, 2H), 7.89-7.80 (m, 1H), 7.63-7.50 (m, 4H), 7.50-7.40 (m, 2H), 7.39-7.02 (m, 7H), 6.80-6.71 (m, 1H), 6.52-6.41 (m,

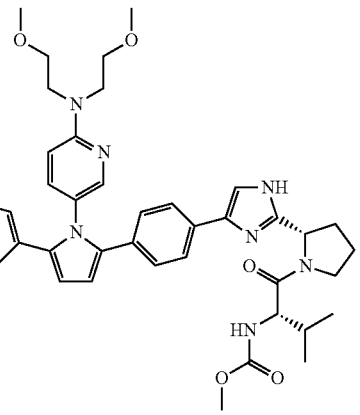

Example 155 methyl {(2S)-1-[(2S)-2-(4-{4-[1-{6-[bis(2-methoxyethyl)amino]pyridin-3-yl}-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate Example 155A N,N-bis(2-methoxyethyl)-5-nitropyridin-2-amine The title compound was prepared using the methods from Example 144A substituting bis(2-methoxyethyl)amine for piperidine to provide the title compound.

Example 155B

N2,N2-bis(2-methoxyethyl)pyridine-2,5-diamine

Example 155A was processed using the methods of Example 154B to provide the title compound.

Example 155C methyl {(2S)-1-[(2S)-2-(4-{4-[1-{6-[bis(2-methoxyethyl)amino]pyridin-3-yl}-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate Example 138B and Example 155B were processed using the methods of Examples 139A and 138D to provide the title compound. ¹H NMR (400 MHz, DMSO-D6) δ 12.17-11.67 (m, 2H), 7.86-7.77 (m, 1H), 7.63-7.49 (m, 4H), 7.49-7.38 (m, 2H), 7.34-7.20 (m, 3H), 7.20-7.03 (m, 4H), 6.64-6.56 (m, 1H), 6.52-6.40 (m, 2H), 5.09-5.00 (m, 2H), 4.04 (t, J=8.2, 2H), 3.84-3.69 (m, 4H), 3.65-3.57 (m, 4H), 3.53 (s, 6H), 3.47-3.40 (m, 4H), 3.21 (s, 6H), 2.20-1.84 (m, 10H), 0.84 (m, 12H). MS (ESI; M+H) m/z=1013.

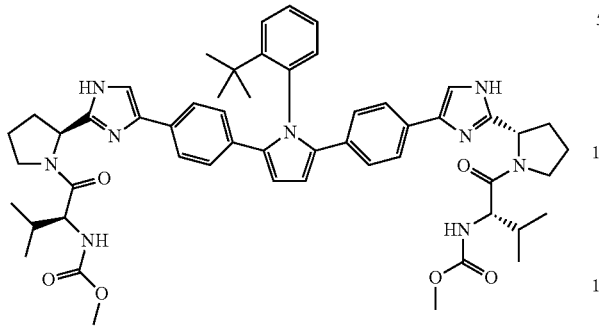

Example 156 methyl {(2S)-1-[(2S)-2-(4-{4-[1-(2-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl]phenyl}-1H-imidazol-2-yl)pyrrolidin-1-yl]-3-methyl-1-oxobutan-2-yl}carbamate Example 138B and 2-tert-butylaniline were processed using the methods of Examples 139A and 138D to provide the title compound (10 mg). ¹H NMR (400 MHz, DMSO-D6) δ 12.07-11.64 (m, 2H), 7.61-7.11 (m, 12H), 7.06-6.93 (m, 4H), 6.65-6.49 (m, 2H), 5.08-4.97 (m, 2H), 4.04 (t, J=7.2, 2H), 3.82-3.69 (m, 4H), 3.53 (s, 6H), 2.17-1.83 (m, 10H), 0.92-0.77 (m, 21H). MS (ESI; M+H) m/z=937.

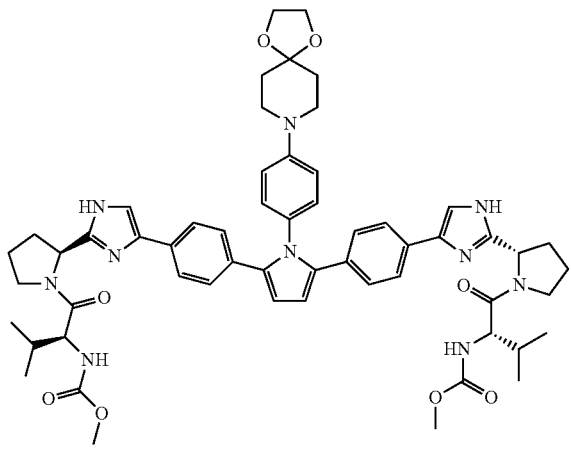 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)C(C)C)n5)cc4)n3-c3ccc(N4CCC5(CC4)OCCO5)cc3)cc2)c[nH]1)C(C)C]

Example 157 methyl [(2S)-1-{(2S)-2-[4-(4-{1-[4-(1,4-dioxa-8-azaspiro[4.5]dec-8-yl)phenyl]-5-(4-{2-[(2S)-1-{(2S)-2-[(methoxycarbonyl)amino]-3-methylbutanoyl}pyrrolidin-2-yl]-1H-imidazol-4-yl}phenyl)-1H-pyrrol-2-yl}phenyl)-1H-imidazol-2-yl]pyrrolidin-1-yl}-3-methyl-1-oxobutan-2-yl]carbamate Example 138B and 4-(1,4-dioxa-8-azaspiro[4.5]decan-8-yl)aniline were processed using the methods of Examples 139A and 138D to provide the title compound (156 mg). ¹H NMR (400 MHz, DMSO-D6) δ 12.06-11.65 (m, 2H), 7.59-7.46 (m, 4H), 7.44-7.36 (m, 2H), 7.30-7.13 (m, 2H), 7.09-6.96 (m, 4H), 6.90 (p, 4H), 6.53-6.39 (m, 2H), 5.08-4.98 (m, 2H), 4.04 (t, J=8.4, 2H), 3.90 (s, 4H), 3.86-3.71 (m, 4H), 3.53 (s, 6H), 3.29-3.20 (m, 4H), 2.19-1.83 (m, 10H), 1.73-1.64 (m, 4H), 0.93-0.77 (m, 12H). MS (ESI; M+H) m/z=1022.

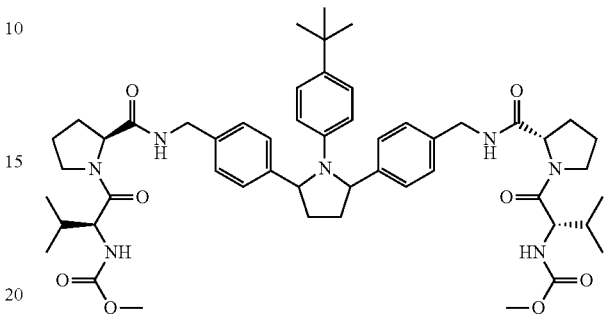

Example 158 dimethyl ([1-(4-tert-butylphenyl)pyrrolidine-2,5-diyl]bis{benzene-4,1-diylmethanediylcarbamoyl(2S)pyrrolidine-2,1-diyl[(2S)-3-methyl-1-oxobutane-1,2-diyl]})biscarbamate Example 158A 4,4'-(1-(4-tert-butylphenyl)pyrrolidine-2,5-diyl)dibenzonitrile A solution of Example 42C (2.0 g, 3.9 mmol) and copper(I) cyanide (1.047 g, 11.69 mmol) in DMF (19 mL) was heated in a microwave for 7 hours at 160° C. Afterwards the mixture was poured in water (700 mL) and then concentrated ammonium hydroxide (40 mL) was added and the solution extracted with EtOAc. The organic extract was dried, filtered, concentrated and the residue purified by flash chromatography (silica gel, EtOAc/hexanes) to afford 1.23 g (78%) of the title compound. MS (ESI) m/z 406 (M+H)⁺.

Example 158B 4,4'-(1-(4-tert-butylphenyl)pyrrolidine-2,5-diyl)bis(4,1-phenylene)dimethanamine To a solution of Example 158A (0.63 g, 1.554 mmol) in THF (21 mL) was added lithium aluminum hydride (0.236 g, 6.21 mmol) then stirred at room temperature for 20 minutes and at 70° C. for 1 hour. The mixture was then cooled in an ice bath and a solution of saturated aqueous ammonium chloride was added followed by extraction with EtOAc and the organic layer extracted with Rochelle's solution. The organic solution was then dried, filtered and concentrated to give the title compound. MS (ESI) m/z 414 (M+H)⁺.

Example 158C dimethyl ([1-(4-tert-butylphenyl)pyrrolidine-2,5-diyl]bis{benzene-4,1-diylmethanediylcarbamoyl(2S)pyrrolidine-2,1-diyl[(2S)-3-methyl-1-oxobutane-1,2-diyl]})biscarbamate The product from Example 158B (45 mg, 0.109 mmol), the product from Example 37B (62.2 mg, 0.228 mmol) and HATU (91 mg, 0.239 mmol) in DMSO (3 mL) was added Hunig's base (0.095 mL, 0.544 mmol), and the reaction mixture was stirred at room temperature for 1 hr. The reaction mixture was partitioned between water and dichloromethane, and the organic layer was dried over MgSO₄, filtered and concentrated. Purification by flash chromatography (silica gel, 0-10% methanol/dichloromethane) afforded 55 mg (55%) of the title compound as a mixture of stereoisomers. 1H NMR (400 MHz, DMSO-D6) δ ppm 8.11 (m, 2H), 7.08 (s, 2H), 6.95 (m, 8H), 6.74 (d, J=8.8 Hz, 2H), 5.97 (d, J=8.7 Hz, 2H), 5.01 (m, 2H), 4.15 (m, 4H), 4.05 (m, 4H), 3.80 (m, 2H), 3.31 (s, 6H), 2.40 (m, 2H), 1.90 (m, 2H), 1.85 (m, 4H), 1.80 (m, 4H), 0.95 (s, 9H), 0.70 (m, 2H), 0.65 (m, 12H); MS (ESI) m/z 923 (M+H)+.

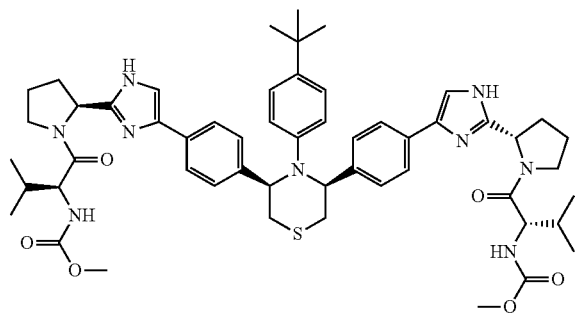 [SMILES: COC(=O)N[C@H](C(=O)N1CCC[C@H]1c1nc(-c2ccc([C@H]3CSC[C@@H](c4ccc(-c5c[nH]c([C@@H]6CCCN6C(=O)[C@@H](NC(=O)OC)C(C)C)n5)cc4)N3c3ccc(C(C)(C)C)cc3)cc2)c[nH]1)C(C)C]

Example 159 methyl {(2S)-1-[(2S)-2-(4-{4-[(3S,5R)-4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)thiomorpholin-3-yl]phenyl}-1H-imidazol-2-yl)pyrrolidin-1-yl]-3-methyl-1-oxobutan-2-yl}carbamate Example 159A 2,2'-thiobis(1-(4-bromophenyl)ethanone)

A solution of 2-bromo-1-(4-bromophenyl)ethanone (27.8 g, 100 mmol) was dissolved in acetone, the solution was cooled in an ice bath then sodium sulfide nonahydrate (12.01 g, 50 mmol) dissolved in water (100 mL) was added dropwise over 45 minutes time. The resultant solution was stirred an additional 2 hours at room temperature, the solid formed in the reaction was collected and then washed with water then ethanol and dried in a vacuum oven to provide 18.5 g (43%) of the title compound.

Example 159B 2,2'-thiobis(1-(4-bromophenyl)ethanol)

To a solution of Example 159A (5.0 g, 11.68 mmol) in ethanol (78 mL) was added sodium borohydride (0.972 g, 25.7 mmol) portionwise and the mixture was stirred at room temperature for 20 minutes. Afterwards the solution was concentrated, then a solution of 1N aqueous hydrochloric acid (100 mL) was added and extracted with EtOAc. The organic extract was dried, filtered and concentrated to 5.05 g (100%) of a colorless solid as the title compound.

Example 159C

N,N'-(2,2'-thiobis(1-(4-bromophenyl)ethane-2,1-diyl))bis(4-tert-butylaniline)

To a solution of Example 159B (5.05 g, 11.68 mmol) in THF (145 mL) and dichloromethane (145 mL) was added triethylamine (4.86 mL, 35.1 mmol) and the mixture cooled in an ice bath. To this solution was added methanesulfonyl chloride (2.276 mL, 29.2 mmol) dropwise followed by stirring at 0° C. for an additional 30 minutes followed by concentration at room temperature to a residue. The resultant residue was dissolved in DMF (39 mL) followed by the addition of 4-tert-butylaniline (18.62 mL, 117 mmol) and the mixture heated at 50° C. for 5 hours. Afterwards 1N aqueous hydrochloric acid was added followed by extraction with EtOAc. The organic extract was dried, filtered and concentrated. Purification by flash chromatography (silica gel, 0-30% EtOAc/hexanes) afforded 2.67 g (42%) of the title compound.

Example 159D 3,5-bis(4-bromophenyl)-4-(4-tert-butylphenyl)thiomorpholine

To a solution of Example 159C (350 mg, 0.504 mmol) in toluene (5 mL) was added silica gel (1.0 g) that had been dehydrated by heating at 180° C. in a vacuum oven for 3 hours, and trifluoromethanesulfonic acid (0.045 mL, 0.504 mmol) and heated at 100° C. for 3 hours. After cooling to ambient temperature, dichloromethane was added and the silica gel was removed by filtration and the solution extracted with half-saturated aqueous sodium bicarbonate solution. The organic extract was dried, filtered and concentrated to afford 220 mg (80%) of the title compound as a mixture of isomers. MS (ESI) m/z 546 (M+H)+.

Example 159E 4-(4-tert-butylphenyl)-3,5-bis(4-(4,4,5,5-tetramethyl-1,3,2-dioxaborolan-2-yl)phenyl)thiomorpholine The product of Example 159D (200 mg, 0.367 mmol) was processed using the method described in Example 42D to provide 105 mg (45%) of the title compound as a mixture of isomers. MS (ESI) m/z 640 (M+H)+.

Example 159F (2S,2'S)-tert-butyl 2,2'-(4,4'-(4,4'-(4-(4-tert-butylphenyl)thiomorpholine-3,5-diyl)bis(4,1-phenylene))bis(1H-imidazole-4,2-diyl))dipyrrolidine-1-carboxylate The product of Example 159E (190 mg, 0.297 mmol) and the product from Example 26D (282 mg, 0.891 mmol) were processed using the method described in Example 42E to provide 110 mg (43%) of the title compound as a mixture of isomers. MS (ESI) m/z 859 (M+H)+.

Example 159G 4-(4-tert-butylphenyl)-3,5-bis(4-(2-((S)-pyrrolidin-2-yl)-1H-imidazol-4-yl)phenyl)thiomorpholine To the product of Example 159F (110 mg, 0.128 mmol) was added dimethoxyethane (5 mL) and a solution of 4N hydrochloric acid in dioxane (5 mL) and the resultant solution stirred at room temperature for 1 hr. The solvent was then removed under vacuum and the resultant residue was diluted with acetonitrile and water (0.1% TFA) and purified by reversed phase chromatography (C18), eluting with 10-100% acetonitrile in water (0.1% TFA) to afford 12 mg (14%) of the title compound as a mixture of stereoisomers. MS (ESI) m/z 658 (M+H)+.

Example 159H methyl {(2S)-1-[(2S)-2-(4-{4-[(3S,5R)-4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)thiomorpholin-3-yl]phenyl}-1H-imidazol-2-yl)pyrrolidin-1-yl]-3-methyl-1-oxobutan-2-yl}carbamate The product from Example 159G (10 mg, 0.015 mmol), (S)-2-(methoxycarbonylamino)-3-methylbutanoic acid (5.86 mg, 0.033 mmol) and HATU (12.71 mg, 0.033 mmol) in DMSO (0.5 mL) was added Hunig's base (0.013 mL, 0.076 mmol), and the reaction mixture was stirred at room temperature for 1.5 hr. The reaction mixture was partitioned between water and dichloromethane, and the organic layer was dried over MgSO$_4$, filtered and concentrated in vacuo. The crude product was redissolved in methanol (5 mL) then added potassium carbonate (50 mg) then stirred at room temperature for 20 minutes, the solids removed by filtration, the filtrate concentrated and purified by chromatography (silica gel, 0-10% methanol/dichloromethane) to afford 7 mg (47%) of the title compound. 1H NMR (400 MHz, DMSO-D6) δ ppm 11.65 (m, 2H), 7.47 (m, 2H), 7.32 (m, 4H), 7.23 (m, 4H), 6.85 (m, 4H), 5.02 (m, 2H), 4.38 (m, 2H), 4.02 (m, 2H), 3.75 (m, 4H), 3.52 (s, 6H), 3.10 (m, 2H), 2.66 (m, 2H), 2.08 (m, 4H), 1.91 (m, 4H), 0.97 (s, 9H), 0.82 (m, 12H); MS (ESI) m/z 973 (M+H)+.

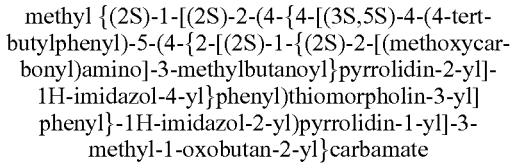

Example 160 methyl {(2S)-1-[(2S)-2-(4-{4-[(3S,5S)-4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)thiomorpholin-3-yl]phenyl}-1H-imidazol-2-yl)pyrrolidin-1-yl]-3-methyl-1-oxobutan-2-yl}carbamate and methyl {(2S)-1-[(2S)-2-(4-{4-[(3R,5R)-4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)thiomorpholin-3-yl]phenyl}-1H-imidazol-2-yl)pyrrolidin-1-yl]-3-methyl-1-oxobutan-2-yl}carbamate The product from Example 159E (100 mg, 0.156 mmol), the product from Example 126G (146 mg, 0.391 mmol), and [1,1'-bis(diphenylphosphino)ferrocene]dichloropalladium(II) dichloromethane adduct (25.5 mg, 0.031 mmol) in a mixture of toluene (3 mL), ethanol (3 mL) and a 1N aq. sodium bicarbonate solution (0.469 mL, 4.69 mmol) and bubbled nitrogen gas through the solution for 10 min, then heated at 80° C. for 18 h. Solution was cooled to room temperature and water (20 mL) added then extracted with dichloromethane (50 mL), then dried, concentrated and the residue purified by reversed phase chromatography (C18), eluting with 10-100% acetonitrile in water (0.1% TFA) to afford 8.5 mg (6%) of the title compound as a mixture of stereoisomers. 1H NMR (free base) (400 MHz, DMSO-D6) δ ppm 11.70 (bs, 2H), 7.64 (m, 4H), 7.45 (m, 2H), 7.37 (m, 4H), 7.28 (m, 2H), 7.01 (m, 2H), 6.46 (d, J=8.7 Hz, 2H), 5.38 (m, 2H), 5.07 (m, 2H), 4.03 (m, 2H), 3.52 (s, 6H), 3.10 (m, 2H), 2.12 (m, 4H), 1.91 (m, 4H), 1.12 (s, 9H), 0.86 (m, 12H); MS (ESI) m/z 973 (M+H)+.

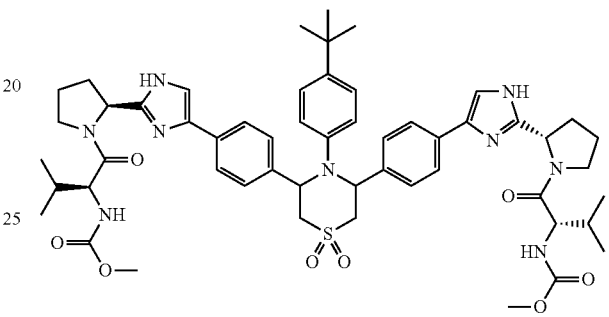

Example 161 methyl {(2S)-1-[(2S)-2-(4-{4-[4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1,1-dioxidothiomorpholin-3-yl]phenyl}-1H-imidazol-2-yl)pyrrolidin-1-yl]-3-methyl-1-oxobutan-2-yl}carbamate

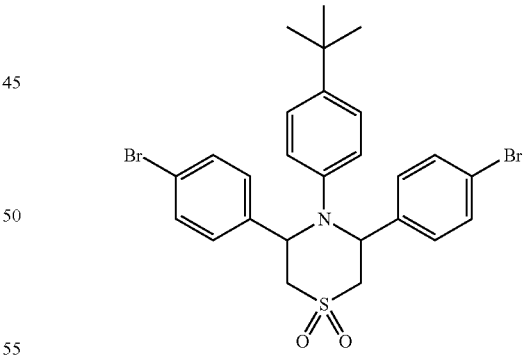

Example 161A 3,5-bis(4-bromophenyl)-4-(4-tert-butylphenyl)thiomorpholine 1,1-dioxide (ACD v12)

A solution of Example 159D (850 mg, 1.56 mmol) in mixture of acetone (15 mL), water (5 mL) and THF (5 mL) was added a solution of osmium tetroxide (2.5% in tert-butanol, 0.587 mL, 0.047 mmol) and the mixture was stirred at room temperature for 1.5 hr. The solution was then diluted with water and extracted with EtOAc, the organic extract dried, filtered and concentrated to afford 900 mg (100%) of the title compound. MS (ESI) m/z 578 (M+H)+.

Example 161B methyl {(2S)-1-[(2S)-2-(4-{4-[4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-1,1-dioxidothiomorpholin-3-yl]phenyl}-1H-imidazol-2-yl)pyrrolidin-1-yl]-3-methyl-1-oxobutan-2-yl}carbamate Example 161A was processed using sequentially the methods of Examples 42D, 42E, 159G, and 159H to provide the title compound as a mixture of trans stereoisomers. 1H NMR (400 MHz, DMSO-D6) δ ppm 11.73 (bs, 2H), 7.64 (m, 4H), 7.55 (m, 2H), 7.44 (m, 4H), 7.24 (m, 2H), 7.04 (m, 2H), 6.60 (m, 2H), 5.48 (m, 2H), 5.06 (m, 2H), 4.04 (m, 2H), 3.78 (m, 6H), 3.52 (s, 6H), 2.11 (m, 4H), 1.92 (m, 6H), 1.13 (s, 9H), 0.92 (m, 12H); MS (ESI) m/z 1005 (M+H)+.

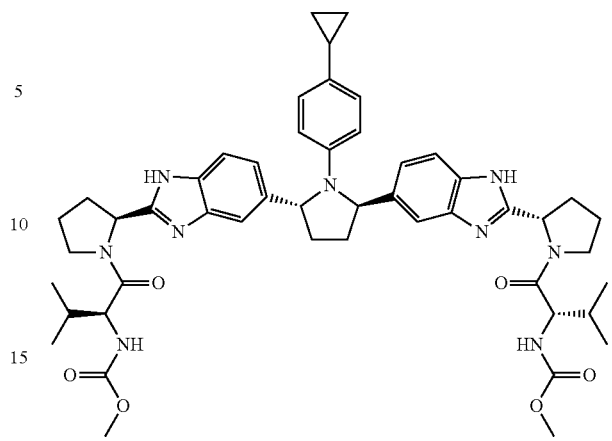

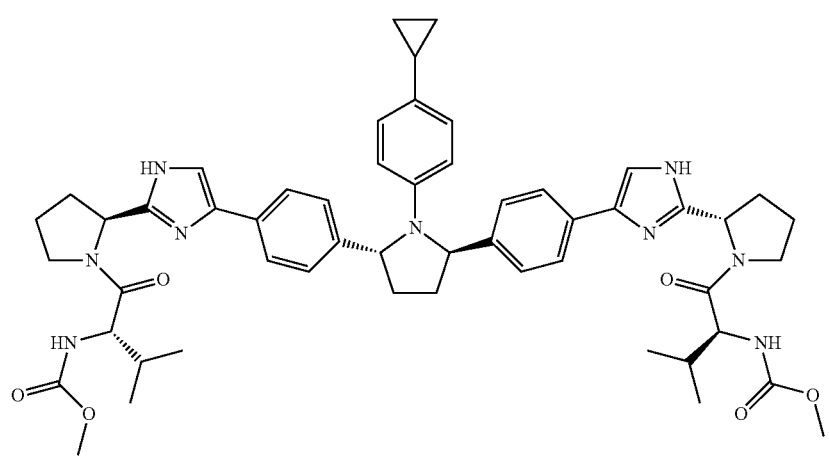 [SMILES: COC(=O)N[C@H](C(=O)N1CCC[C@H]1c1nc(-c2ccc([C@H]3CC[C@H](c4ccc(-c5c[nH]c([C@@H]6CCCN6C(=O)[C@@H](NC(=O)OC)C(C)C)n5)cc4)N3c3ccc(C4CC4)cc3)cc2)c[nH]1)C(C)C]

Example 162 methyl {(2S)-1-[(2S)-2-(4-{4-[(2R,5R)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 95B was purified by chiral chromatography on a Chiralpak IB column eluting with a mixture of hexane/THF/methanol (85/10/5). The title compound was the first of the 2 diastereomers to elute. 1H NMR (400 MHz, DMSO-D6) δ ppm 0.33-0.43 (m, 2H) 0.65-0.72 (m, 2H) 0.79-0.91 (m, 12H) 1.56-1.64 (m, 1H) 1.66-1.72 (m, 2H) 1.84-2.03 (m, 6H) 2.06-2.19 (m, 4H) 3.53 (s, 6H) 3.73-3.84 (m, 4H) 4.04 (t, J=8.35 Hz, 2H) 5.06 (dd, J=6.89, 3.09 Hz, 2H) 5.14-5.23 (m, 2H) 6.19 (d, J=8.67 Hz, 2H) 6.60-6.67 (m, 2H) 7.09-7.31 (m, 6H) 7.34-7.68 (m, 6H) 11.62-12.11 (m, 2H); MS (ESI+) m/z 924.6 (M+H).

Example 163 methyl {(2S)-1-[(2S)-2-{5-[(2R,5R)-1-(4-cyclopropylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate Example 109C and 4-cyclopropylaniline were processed using sequentially the methods of Examples 113A (cyclization reaction conducted at room temperature overnight), 113B, 113C, 28I (reaction conducted at 50° C. for 3 hours), 28J, and 66E to provide the title compound (122 mg) as a solid. 1H NMR (400 MHz, DMSO-D6) δ ppm 0.32-0.39 (m, 2H) 0.63-0.69 (m, 2H) 0.77-0.90 (m, 12H) 1.53-1.61 (m, 1H) 1.66-1.74 (m, 2H) 1.86-2.04 (m, 8H) 2.14-2.23 (m, 4H) 3.54 (s, 6H) 3.78-3.87 (m, 4H) 4.00-4.07 (m, 2H) 5.10-5.18 (m, 2H) 5.31-5.39 (m, 2H) 6.22 (d, J=8.67 Hz, 2H) 6.57-6.65 (m, 2H) 7.00-7.07 (m, 2H) 7.16-7.32 (m, 4H) 7.36 (d, J=8.13 Hz, 1H) 7.44 (d, J=8.24 Hz, 1H) 11.97-12.27 (m, 2H); MS (ESI+) m/z 872.5 (M+H)+.

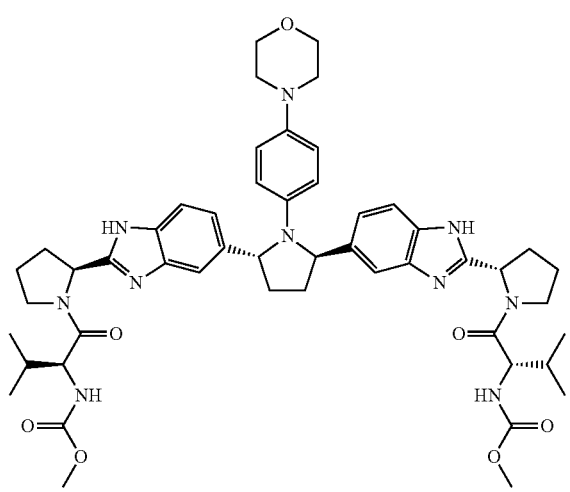 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCOCC4)cc3)ccc2[nH]1)C(C)C]

Example 164 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(morpholin-4-yl)phenyl]pyrrolidin-2-yl}-1H-benzimidazol-2-yl)pyrrolidin-1-yl]-3-methyl-1-oxobutan-2-yl}carbamate Example 109C and 4-morpholinoaniline were processed using sequentially the methods of Examples 113A (cyclization reaction conducted at room temperature overnight), 113B, 113C, 28I (reaction conducted at 50° C. for 2 hours), 28J, and 28K to provide the title compound (100 mg) as a solid. 1H NMR (400 MHz, DMSO-D6) δ ppm 0.76-0.91 (m, 12H) 1.66-1.72 (m, 2H) 1.87-2.03 (m, 8H) 2.15-2.22 (m, 4H) 2.72-2.78 (m, 4H) 3.53 (s, 6H) 3.57-3.62 (m, 4H) 3.78-3.86 (m, 4H) 4.00-4.12 (m, 2H) 5.09-5.18 (m, 2H) 5.30-5.37 (m, 2H) 6.25 (d, J=8.78 Hz, 2H) 6.52-6.59 (m, 2H) 7.05 (t, J=7.54 Hz, 2H) 7.18-7.32 (m, 4H) 7.36 (d, J=8.13 Hz, 1H) 7.44 (d, J=8.24 Hz, 1H) 11.91-12.28 (m, 2H); MS (ESI+) m/z 917.5 (M+H)+.

Example 165 dimethyl ([(2R,5R)-1-{4-[6-(morpholin-4-yl)pyridin-3-yl]phenyl})pyrrolidine-2,5-diyl]bis {(2-aminobenzene-4,1-diyl)carbamoyl(2S)pyrrolidine-2,1-diyl[(2S)-3-methyl-1-oxobutane-1,2-diyl]}) biscarbamate

Example 165A (2R,5R)-2,5-bis(4-chloro-3-nitrophenyl)-1-(4-iodophenyl)pyrrolidine Example 109C (3.34 g, 6.0 mmol) and 4-iodoaniline (7.88 g, 36.0 mmol) were processed using the method of Example 113A with the reaction allowed to proceed for 4 days at room temperature to provide the title compound (2.01 g, 57%) as a yellow solid.

Example 165B 4-(5-(4-((2R,5R)-2,5-bis(4-chloro-3-nitrophenyl)pyrrolidin-1-yl)phenyl)pyridin-2-yl)morpholine The product from 165A (1.869 g, 3.2 mmol), 4-(5-(4,4,5,5-tetramethyl-1,3,2-dioxaborolan-2-yl)pyridin-2-yl)morpholine (0.929 g, 3.20 mmol), potassium phosphate (1.359 g, 6.40 mmol), tris(dibenzylideneacetone)dipalladium(0) (0.029 g, 0.032 mmol) and 1,3,5,7-tetramethyl-6-phenyl-2,4,8-trioxa-6-phosphaadamante (0.028 g, 0.096 mmol) were combined in THF (18 mL)/water (6 mL). The mixture was purged with nitrogen for 15 minutes and stirred at room temperature for 24 hours. The reaction mixture was partitioned between ethyl acetate and saturated sodium bicarbonate. The organic layer was washed with brine, dried with sodium sulfate, filtered and evaporated. The residue was purified by chromatography on silica gel eluting with ethyl acetate/hexane (20% to 40%) to give the title compound (1.01 g, 51%) as a solid.

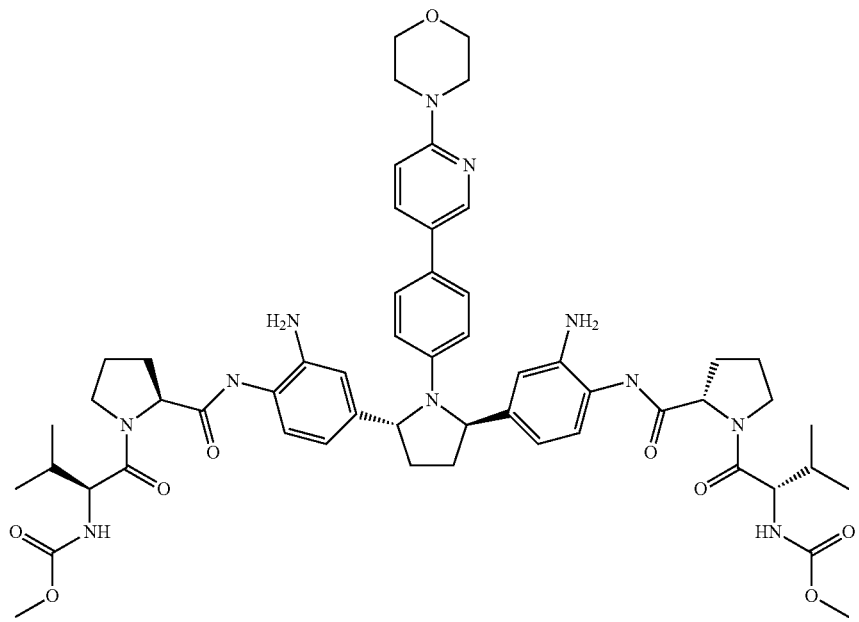 [SMILES: COC(=O)N[C@H](C(=O)N1CCC[C@H]1C(=O)Nc1ccc([C@H]2CC[C@H](c3ccc(NC(=O)[C@@H]4CCCN4C(=O)[C@@H](NC(=O)OC)C(C)C)c(N)c3)N2c2ccc(-c3ccc(N4CCOCC4)nc3)cc2)cc1N)C(C)C]

Example 165C dimethyl (2S,2'S)-1,1'-((2S,2'S)-2,2'-(4,4'-((2R,5R)-1-(4-(6-morpholinopyridin-3-yl)phenyl)pyrrolidine-2,5-diyl)bis(2-nitro-4,1-phenylene))bis(azanediyl)bis(oxomethylene)bis(pyrrolidine-2,1-diyl))bis(3-methyl-1-oxobutane-2,1-diyl)dicarbamate The product from Example 165B (683 mg, 1.10 mmol), the product from Example 116C (895 mg, 3.30 mmol), cesium carbonate (1004 mg, 3.08 mmol), tris(dibenzylideneacetone)dipalladium(0) (60.4 mg, 0.066 mmol) and (9,9-dimethyl-9H-xanthene-4,5-diyl)bis(diphenylphosphine) (115 mg, 0.198 mmol) were combined in dioxane (15 mL). The mixture was purged with nitrogen for 15 minutes and stirred at 100° C. for 3 hours. The mixture was partitioned between ethyl acetate and saturated sodium bicarbonate. The organic layer was washed with brine, dried with sodium sulfate, filtered and evaporated. The residue was purified by chromatography on silica gel eluting with methanol/dichloromethane (1% to 3%) to give the title compound (631 mg, 53%) as a solid.

Example 165D dimethyl ([(2R,5R)-1-{4-[6-(morpholin-4-yl)pyridin-3-yl]phenyl}pyrrolidine-2,5-diyl]bis {(2-aminobenzene-4,1-diyl)carbamoyl(2S)pyrrolidine-2,1-diyl[(2S)-3-methyl-1-oxobutane-1,2-diyl]}) biscarbamate The product from Example 165C (628 mg, 0.576 mmol) and Ra-Ni 2800 (628 mg) were combined in THF (40 mL). The mixture was hydrogenated at 30 psi for 4 hours. The mixture was filtered and the filtrate was evaporated. The residue was purified by chromatography on silica gel eluting with methanol/dichloromethane (2% to 5%) to give the title compound (590 g, 99%) as a solid. 1H NMR (400 MHz, DMSO-D6) δ ppm 0.88 (d, J=6.61 Hz, 6H) 0.91 (d, J=6.72 Hz, 6H) 1.62-1.69 (m, 2H) 1.82-2.04 (m, 8H) 2.10-2.20 (m, 2H) 2.52-2.56 (m, 2H) 3.37-3.41 (m, 4H) 3.52 (s, 6H) 3.56-3.62 (m, 2H) 3.65-3.70 (m, 4H) 3.78-3.85 (m, 2H) 3.98-4.07 (m, 2H) 4.36-4.44 (m, 2H) 4.87 (s, 4H) 5.06 (d, J=6.32 Hz, 2H) 6.36 (d, J=8.78 Hz, 2H) 6.42 (d, J=8.02 Hz, 2H) 6.57 (d, J=1.19 Hz, 2H) 6.78 (d, J=8.89 Hz, 1H) 6.96 (d, J=8.02 Hz, 2H) 7.23 (d, J=8.78 Hz, 2H) 7.36 (d, J=8.24 Hz, 2H) 7.68 (dd, J=8.78, 2.49 Hz, 1H) 8.27 (d, J=2.49 Hz, 1H) 9.24 (s, 2H); MS (ESI+) m/z 1030.6 (M+H)+.

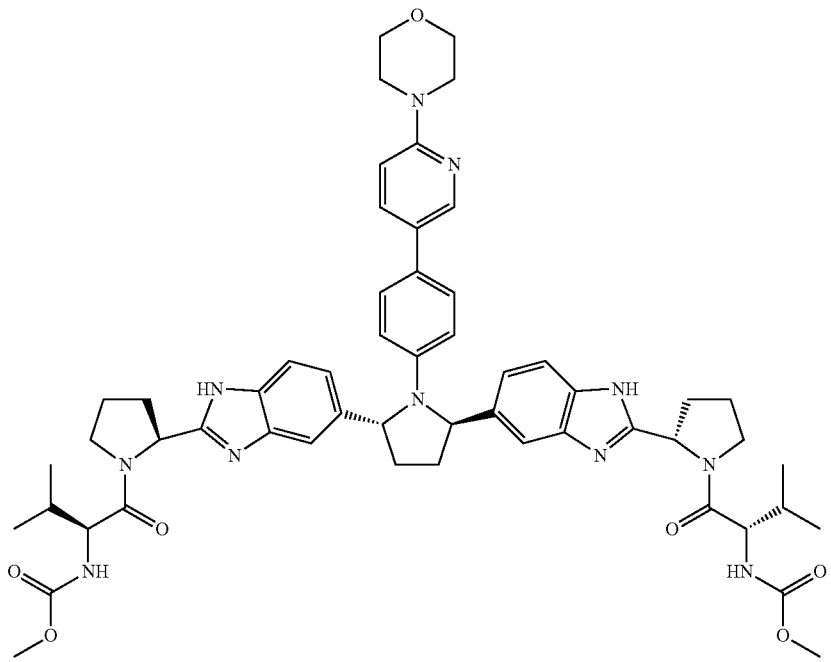 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(-c4ccc(N5CCOCC5)nc4)cc3)ccc2[nH]1)C(C)C]

Example 166 methyl {(2S)-1-[(2S)-2-{5-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-{4-[6-(morpholin-4-yl)pyridin-3-yl]phenyl}pyrrolidin-2-yl]-1H-benzimidazol-2-yl}pyrrolidin-1-yl]-3-methyl-1-oxobutan-2-yl}carbamate The product from Example 165D (520 g, 0.505 mmol) and acetic acid (0.087 mL, 1.514 mmol) were combined in toluene (10 mL). The mixture was stirred at 50° C. for 4 hours. The solvent was evaporated and the residue was purified by chromatography on silica gel eluting with methanol/dichloromethane (2% to 5%) to give the title compound (309 mg, 62%) as a solid. 1H NMR (400 MHz, DMSO-D6) δ ppm 0.73-0.90 (m, 12H) 1.70-1.76 (m, 2H) 1.84-2.05 (m, 8H) 2.14-2.21 (m, 2H) 2.55-2.60 (m, 2H) 3.34-3.39 (m, 4H) 3.53 (s, 6H) 3.62-3.69 (m, 4H) 3.75-3.87 (m, 4H) 4.02-4.08 (m, 2H) 5.06-5.17 (m, 2H) 5.40-5.47 (m, 2H) 6.40 (d, J=8.67 Hz, 2H) 6.75 (d, J=8.89 Hz, 1H) 7.02-7.20 (m, 4H) 7.25 (s, 1H) 7.28 (d, J=8.46 Hz, 2H) 7.34 (s, 1H) 7.39 (d, J=8.13 Hz, 1H) 7.47 (d, J=8.24 Hz, 1H) 7.60 (d, J=8.60 Hz, 1H) 8.21 (s, 1H) 11.96-12.11 (m, 2H); MS (ESI+) m/z 994.5 (M+H)+.

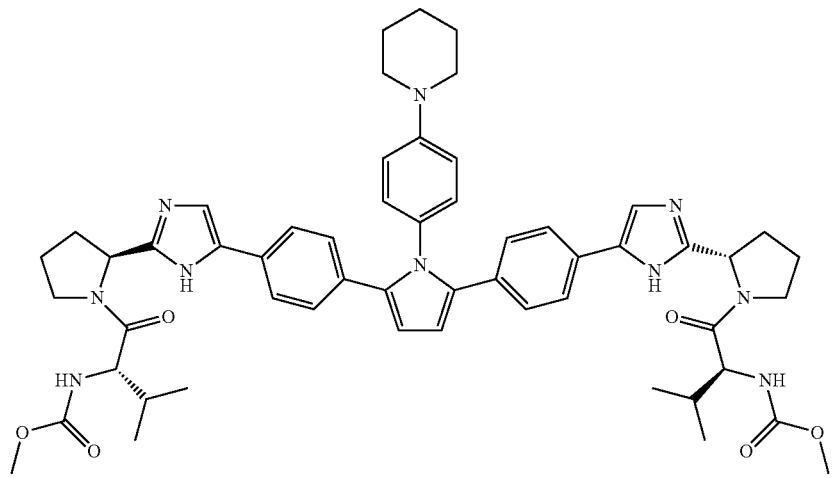

Example 167 methyl [(2S)-1-{(2S)-2-[5-(4-{5-(4-{2-[(2S)-1-
{(2S)-2-[(methoxycarbonyl)amino]-3-
methylbutanoyl}pyrrolidin-2-yl]-1H-imidazol-5-
yl}phenyl)-1-[4-(piperidin-1-yl)phenyl]-1H-pyrrol-
2-yl}phenyl)-1H-imidazol-2-yl]pyrrolidin-1-yl}-3-
methyl-1-oxobutan-2-yl]carbamate Example 26E and 4-piperidinoaniline (Maybridge) were processed using sequentially the methods of Examples 26F, 26G, 74C, 19D, and 74E to provide the title compound (106 mg). $^1$H NMR (400 MHz, DMSO-D6) δ 0.83 (d, J=6.73 Hz, 6H) 0.87 (d, J=6.73 Hz, 6H) 1.50-1.62 (m, 6H) 1.90-2.15 (m, 10H) 3.13 (m, 4H) 3.53 (s, 6H) 3.77 (m, 4H) 4.04 (m, 2H) 5.04 (m, 2H) 6.47 (m, 2H) 6.80-7.35 (m, 10H) 7.42 (m, 2H) 7.53 (m, 4H) 11.73 (s, 2H).

Example 168 methyl [(2S)-1-{(2S)-2-[5-(4-{5-(4-{2-[(2S)-1-
{(2S)-2-[(methoxycarbonyl)amino]-3-
methylbutanoyl}pyrrolidin-2-yl]-1H-imidazol-5-
yl}phenyl)-1-[4-(tricyclo[3.3.1.1~3,7~]dec-1-yl)
phenyl]-1H-pyrrol-2-yl}phenyl)-1H-imidazol-2-yl]
pyrrolidin-1-yl}-3-methyl-1-oxobutan-2-yl]
carbamate Example 26E and 4-(1-adamantanyl)aniline hydrochloride (Enamine) were processed using sequentially the methods of Examples 26F, 26G, 74C, 19D, and 74E to provide the title compound (320 mg). $^1$H NMR (400 MHz, methanol-D4) δ 0.91 (m, 12H) 1.75-2.35 (m, 25H) 3.64 (s, 6H) 3.84 (m, 2H) 4.00 (m, 2H) 4.20 (m, 2H) 5.12 (m, 2H) 6.48 (s, 2H) 7.02 (m, 6H) 7.31 (m, 4H) 7.46 (m, 6H) 7.72 (d, J=8.13 Hz, 1H) 7.82 (d, J=8.24 Hz, 1H).

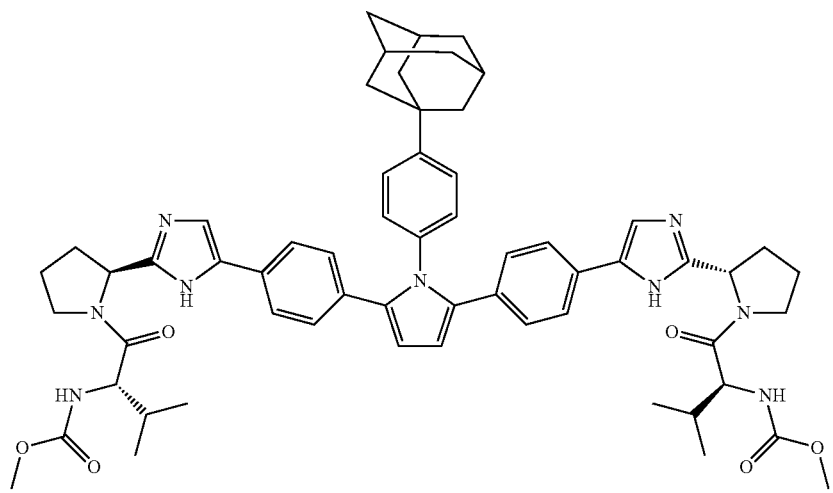

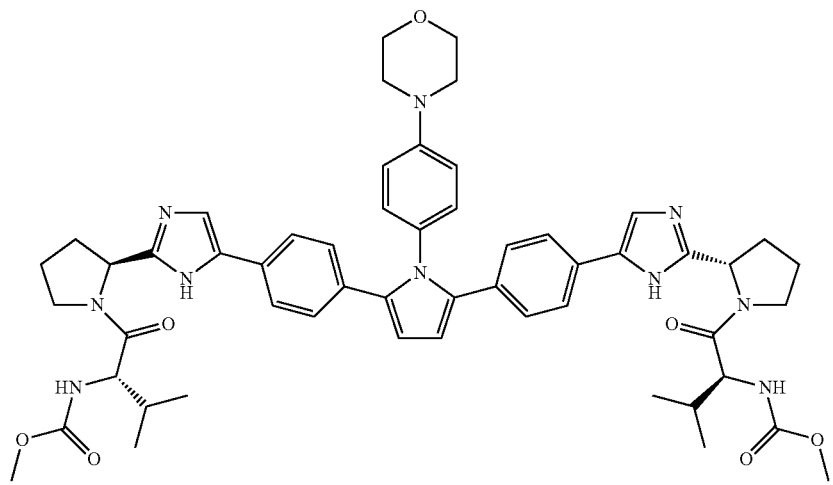

Example 169 methyl [(2S)-1-{(2S)-2-[5-(4-{5-(4-{2-[(2S)-1-{(2S)-2-[(methoxycarbonyl)amino]-3-methylbutanoyl}pyrrolidin-2-yl]-1H-imidazol-5-yl}phenyl)-1-[4-(morpholin-4-yl)phenyl]-1H-pyrrol-2-yl}phenyl)-1H-imidazol-2-yl]pyrrolidin-1-yl}-3-methyl-1-oxobutan-2-yl]carbamate Example 26E and 4-morpholinoaniline (Aldrich) were processed using sequentially the methods of Examples 26F, 26G, 74C, 19D, and 74E to provide the title compound (133 mg). $^1$H NMR (400 MHz, DMSO-D6) δ 0.83 (d, J=6.83 Hz, 6H) 0.87 (d, J=6.61 Hz, 6H) 1.88-2.17 (m, 10H) 3.11 (m, 4H) 3.53 (s, 6H) 3.70-3.80 (m, 8H) 3.97-4.08 (m, 2H) 5.04 (m, 2H) 6.41-6.51 (m, 2H) 6.84-7.35 (m, 10H) 6.93-7.02 (m, 6H) 11.71-12.03 (m, 2H).

Example 170 methyl {(2S)-1-[(2S)-2-(5-bromo-4-{4-[(2S,5S)-5-(4-{5-bromo-2-[(2S)-1-{(2S)-2-[(methoxycarbonyl)amino]-3-methylbutanoyl}pyrrolidin-2-yl]-1H-imidazol-4-yl}phenyl)-1-(4-tert-butylphenyl)pyrrolidin-2-yl]phenyl}-1H-imidazol-2-yl)pyrrolidin-1-yl]-3-methyl-1-oxobutan-2-yl}carbamate To a solution of Example 44 (0.100 g, 0.106 mmol) in CH$_2$Cl$_2$ (5 mL) at rt was added N-bromosuccinimide (0.019 mL, 0.223 mmol). After 15 min, the reaction was washed with saturated NaHCO$_3$ and concentrated. Residue purified by chromatography (1% gradient elution from 0% to 4% MeOH—CH$_2$Cl$_2$; 12 g column) to provide 60 mg (51%) of the title compound as a light yellow solid. $^1$H NMR (400 MHz, DMSO-D6) δ 0.8 (d, J=6.61 Hz, 6H) 0.87 (d, J=6.56 Hz, 6H) 1.11 (s, 9H) 1.72-1.75 (m, 2H) 1.87-1.98 (m, 7H)

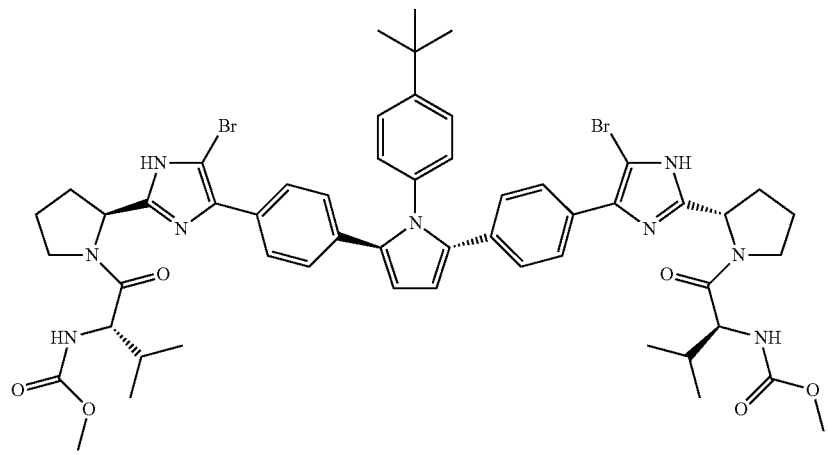

2.10-2.15 (m, 5H) 3.53 (s, 6H) 3.70-3.75 (m, 4H) 4.00=4.06 (m, 2H) 4.96-5.00 (m, 2H) 5.27-5.35 (m, 2H) 6.24 (d, J=8.78 Hz, 2H) 6.97 (d, J=8.78 Hz, 2H) 7.24-7.35 (m, 6H) 7.60-7.65 (m, 4H) 12.41 (m, 2H).

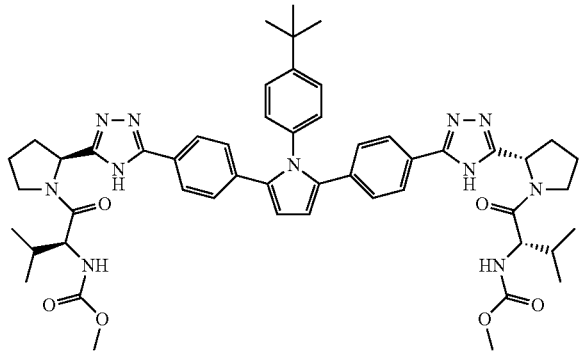 [SMILES: COC(=O)N[C@H](C(=O)N1CCC[C@H]1c1nnc(-c2ccc(-c3ccc(-c4ccc(-c5nnc([C@@H]6CCCN6C(=O)[C@@H](NC(=O)OC)C(C)C)[nH]5)cc4)n3-c3ccc(C(C)(C)C)cc3)cc2)[nH]1)C(C)C]

Example 171 methyl {(2S)-1-[(2S)-2-(5-{4-[(2S,5S)-1-(4-tert-butylphenyl)-5-(4-{5-[(2S)-1-{(2S)-2-[(methoxycarbonyl)amino]-3-methylbutanoyl}pyrrolidin-2-yl]-4H-1,2,4-triazol-3-yl}phenyl)pyrrolidin-2-yl]phenyl}-4H-1,2,4-triazol-3-yl)pyrrolidin-1-yl]-3-methyl-1-oxobutan-2-yl}carbamate and methyl {(2S)-1-[(2S)-2-(5-{4-[(2R,5R)-1-(4-tert-butylphenyl)-5-(4-{5-[(2S)-1-{(2S)-2-[(methoxycarbonyl)amino]-3-methylbutanoyl}pyrrolidin-2-yl]-4H-1,2,4-triazol-3-yl}phenyl)pyrrolidin-2-yl]phenyl}-4H-1,2,4-triazol-3-yl)pyrrolidin-1-yl]-3-methyl-1-oxobutan-2-yl}carbamate Example 171A Dimethyl 4,4'-(1-(4-tert-butylphenyl)pyrrolidine-2,5-diyl)dibenzoate A mixture of Example 42C (0.5 g, 0.974 mmol), Et$_3$N (0.407 mL, 2.92 mmol) and [1,1'-Bis(diphenylphosphino)ferrocene]dichloropalladium(II) (71.3 mg, 0.097 mmol) in methanol (20 mL) was subjected to an atmosphere of carbon monoxide gas (60 psi) for 24 hours at 100° C. The mixture was filtered through celite and concentrated. Purification by chromatography (silica gel, 25% EtOAc in hexanes) afforded 396 mg (86%) of the title compound. MS (ESI) m/z 472 (M+H)$^+$.

Example 171B 4,4'-(1-(4-tert-butylphenyl)pyrrolidine-2,5-diyl)dibenzohydrazide

A mixture of Example 171A (350 mg, 0.742 mmol) and Hydrazine (0.140 µL, 4.45 mmol) in methanol (10 mL) was refluxed for 72 hours. The mixture was concentrated to afford 350 mg of the title compound as a mixture of stereoisomers. MS (ESI) m/z 472 (M+H)$^+$.

Example 171C (2S,2'S)-tert-butyl 2,2'-(5,5'-(4,4'-(1-(4-tert-butylphenyl)pyrrolidine-2,5-diyl)bis(4,1-phenylene))bis(4H-1,2,4-triazole-5,3-diyl))dipyrrolidine-1-carboxylate A mixture of Example 171B (105 mg, 0.223 mmol), (S)-1-N-Boc-2-cyano-pyrrolidine (175 mg, 0.891 mmol), and K$_2$CO$_3$ (9.23 mg, 0.067 mmol) in n-butanol (0.5 mL) was heated to 150° C. for 90 minutes in a microwave. The mixture was diluted with EtOAc and then washed with H$_2$O and Brine. The organic was then dried (MgSO$_4$), filtered and concentrated. Purification by chromatography (silica gel, 90% EtOAc in Hexanes) afforded 59 mg (32%) of the title compound as a mixture of stereoisomers. MS (ESI) m/z 829 (M+H)$^+$.

Example 171D (S)-5,5'-(4,4'-(1-(4-tert-butylphenyl)pyrrolidine-2,5-diyl)bis(4,1-phenylene))bis(3-((S)-pyrrolidin-2-yl)-4H-1,2,4-triazole)pentahydrochloride A mixture of Example 171C (59 mg, 0.071 mmol) in 4M HCl/Dioxane (2 mL) was allowed to stir for one hour. The mixture was concentrated to afford 58 mg (100%) of the title compound as a mixture of stereoisomers. MS (ESI) m/z 628 (M+H)$^+$.

Example 171E methyl {(2S)-1-[(2S)-2-(5-{4-[(2S,5S)-1-(4-tert-butylphenyl)-5-(4-{5-[(2S)-1-{(2S)-2-[(methoxycarbonyl)amino]-3-methylbutanoyl}pyrrolidin-2-yl]-4H-1,2,4-triazol-3-yl}phenyl)pyrrolidin-2-yl]phenyl}-4H-1,2,4-triazol-3-yl)pyrrolidin-1-yl]-3-methyl-1-oxobutan-2-yl}carbamate and methyl {(2S)-1-[(2S)-2-(5-{4-[(2R,5R)-1-(4-tert-butylphenyl)-5-(4-{5-[(2S)-1-{(2S)-2-[(methoxycarbonyl)amino]-3-methylbutanoyl}pyrrolidin-2-yl]-4H-1,2,4-triazol-3-yl}phenyl)pyrrolidin-2-yl]phenyl}-4H-1,2,4-triazol-3-yl)pyrrolidin-1-yl]-3-methyl-1-oxobutan-2-yl}carbamate A mixture of Example 171D (58 mg, 0.071 mmol), (S)-2-(methoxycarbonylamino)-3-methylbutanoic acid (25 mg, 0.142 mmol), N-(3-dimethylaminopropyl)-N'-ethylcarbodiimide hydrochloride (30 mg, 0.157 mmol), 1-Hydroxy-benzotriazole hydrate (24 mg, 0.157 mmol) and N-methylmorpholine (78 µL, 0.712 mmol) in DMF (1 mL) were allowed to stir overnight. Mixture was diluted with EtOAc. The organic was then washed with H$_2$O and Brine. The organic was then dried (MgSO$_4$), filtered and concentrated. Compound subjected to HPLC purification on a semi-prep C18 reverse-phased column using a gradient of 10-100% acetonitrile in 0.1% aq. TFA to afford both the title compounds of Example 171 (24 mg, 70%) which eluted first (trans isomers) and title compound of Example 172 which eluted second (Cis isomer). $^1$H NMR (free base) (400 MHz, DMSO-d$_6$) δ ppm 0.27 (d, J=6.72 Hz, 2H), 0.71 (dd, J=6.61, 2.49 Hz, 2H), 0.78-0.95 (m, 9H), 1.03 (d, J=6.07 Hz, 12H), 1.09 (s, 9H), 1.22 (s, 2H), 1.65-1.77 (m, 3H), 1.82-2.30 (m, 10H), 3.52 (s, 6H), 3.57-3.66 (m, 1H), 3.71-3.92 (m, 3H), 4.00-4.16 (m, 2H), 5.07-5.15 (m, 1H), 5.25-5.34 (m, 2H), 5.65 (d, J=4.88 Hz, 1H), 6.21 (dd, J=8.73, 3.20 Hz, 2H), 6.94 (dd, J=8.78, 2.82 Hz, 2H), 7.16-7.46 (m, 6H), 7.83-7.92 (m, 4H), 14.01 (s, 1H); MS (ESI) m/z 943 (M+H)+.

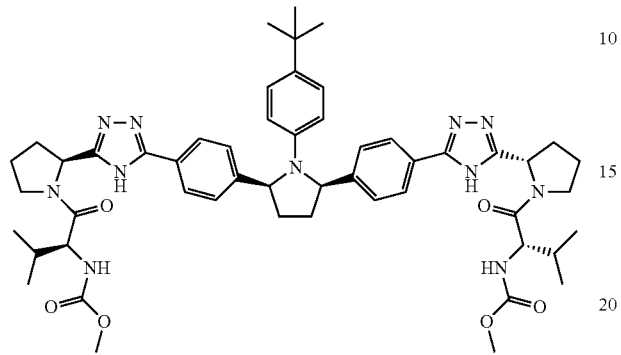

Example 172 methyl {(2S)-1-[(2S)-2-(5-{4-[(2R,5S)-1-(4-tert-butylphenyl)-5-(4-{5-[(2S)-1-{(2S)-2-[(methoxycarbonyl)amino]-3-methylbutanoyl}pyrrolidin-2-yl]-4H-1,2,4-triazol-3-yl}phenyl)pyrrolidin-2-yl]phenyl}-4H-1,2,4-triazol-3-yl)pyrrolidin-1-yl]-3-methyl-1-oxobutan-2-yl}carbamate The title compound, Example 172, was the second eluting compound described in the procedures for Example 171E. The procedure afforded 21 mg (61%) of the title compound (Cis isomer). $^1$H NMR (free base) (400 MHz, DMSO-$d_6$) δ ppm 0.27 (d, J=6.29 Hz, 2H), 0.71 (d, J=6.61 Hz, 2H), 0.81-0.96 (m, 9H), 1.03 (d, J=6.07 Hz, 12H), 1.12 (s, 9H), 1.22 (s, 2H), 1.82-2.30 (m, 12H), 3.52 (s, 6H), 3.72-3.91 (m, 4H), 4.03-4.17 (m, 2H), 4.33 (d, J=4.23 Hz, 1H), 4.73-4.83 (m, 2H), 5.09-5.18 (m, 2H), 6.33 (d, J=8.78 Hz, 2H), 7.03 (dd, J=8.78, 3.04 Hz, 2H), 7.29 (d, J=7.70 Hz, 1H), 7.57-7.69 (m, 4H), 7.92-8.01 (m, 4H), 13.84 (s, 2H); MS (ESI) m/z 943 (M+H)+.


Example 173 methyl {(2S)-1-[(2S)-2-(2-{4-[(2S,5S)-1-(4-tert-butylphenyl)-5-(4-{4-[(2S)-1-{(2S)-2-[(methoxycarbonyl)amino]-3-methylbutanoyl}pyrrolidin-2-yl]-1H-imidazol-2-yl}phenyl)pyrrolidin-2-yl]phenyl}-1H-imidazol-4-yl)pyrrolidin-1-yl]-3-methyl-1-oxobutan-2-yl}carbamate and methyl {(2S)-1-[(2S)-2-(2-{4-[(2R,5R)-1-(4-tert-butylphenyl)-5-(4-{4-[(2S)-1-{(2S)-2-[(methoxycarbonyl)amino]-3-methylbutanoyl}pyrrolidin-2-yl]-1H-imidazol-2-yl}phenyl)pyrrolidin-2-yl]phenyl}-1H-imidazol-4-yl)pyrrolidin-1-yl]-3-methyl-1-oxobutan-2-yl}carbamate

Example 173A 4,4'-(1-(4-tert-butylphenyl)pyrrolidine-2,5-diyl)dibenzonitrile A mixture of Example 42C (1.0 g, 1.948 mmol) and CuCN (523 mg, 5.84 mmol) in Dimethylformamide (9.5 mL) was heated to 160° C. for 4.5 hours in a microwave. Mixture was poured into a dimethylamine/H$_2$O mixture (1/10) and extracted with EtOAc (3×150 mL). The combined organics were washed with H$_2$O and Brine. The organic was then dried (MgSO$_4$), filtered and concentrated. Purification by chromatography (silica gel, 20% EtOAc in Hexanes) afforded 395 mg (50%) of the title compound. MS (ESI) m/z 406 (M+H)+.

Example 173B dimethyl 4,4'-(1-(4-tert-butylphenyl)pyrrolidine-2,5-diyl)dibenzimidate A mixture of Example 173A (0.5 g, 1.233 mmol) in anhydrous MeOH (12 mL) at 0° C. was bubbled an excess amount of HCl (g) for 45 minutes. Mixture was then stirred at ambient temperature for 24 hours and then concentrated to afford the title compound.

Example 173C 4,4'-(1-(4-tert-butylphenyl)pyrrolidine-2,5-diyl)dibenzimidamide A mixture of Example 173B (0.579 g, 1.233 mmol) in anhydrous MeOH (12 mL) at 0° C. was bubbled an excess amount of NH$_3$ (g) for 45 minutes. Mixture was then stirred at ambient temperature for 24 hours and then concentrated and subjected to purification via chromatography (C18 reverse-phased column using a gradient of 10-100% acetonitrile in 0.1% aq. TFA) to afford the title compound as a mixture of trans isomers; Cis isomer was discarded. MS (ESI) m/z 440 (M+H)+.

Example 173D methyl (S)-1-((S)-2-(2-diazoacetyl)pyrrolidin-1-yl)-3-methyl-1-oxobutan-2-ylcarbamate A mixture of Example 37B (100 mg, 0.367 mmol) and Et$_3$N (154 μL, 1.102 mmol) in tetrahydrofuran (4 mL) at 0° C. was added Isobutyl chloroformate (50 μL, 0.386 mmol). Mixture was then stirred at 0° C. for 30 minutes followed by addition of excess diazomethane in Et₂O. Mixture was allowed to slowly come to ambient temperature over 3 hours. Mixture was then concentrated and diluted with EtOAc. Organic was then washed with saturated aqueous NaHCO₃ and brine. Organic was dried (MgSO₄), filtered and concentrated. Purification by chromatography (silica gel, 100% EtOAc) afforded 82 mg (75%) of the title compound. MS (ESI) m/z 297 (M+H)⁺.

Example 173E methyl (S)-1-((S)-2-(2-bromoacetyl)pyrrolidin-1-yl)-3-methyl-1-oxobutan-2-ylcarbamate A mixture of Example 173D (70 mg, 0.236 mmol) in HOAc (0.6 mL) at ambient temperature was added 48% HBr (80 μL, 0.709 mmol). Mixture was stirred at ambient temperature for 1 hour. Mixture was poured into ice/H₂O and extracted with CH₂Cl₂ (3×75 mL). Organic was dried (Na₂SO₄), filtered and concentrated afford 63 mg (76%) of the title compound. MS (ESI) m/z 350 (M+H)⁺.

Example 173F methyl {(2S)-1-[(2S)-2-(2-{4-[(2S,5S)-1-(4-tert-butylphenyl)-5-(4-{4-[(2S)-1-{(2S)-2-[(methoxycarbonyl)amino]-3-methylbutanoyl}pyrrolidin-2-yl]-1H-imidazol-2-yl}phenyl)pyrrolidin-2-yl]phenyl}-1H-imidazol-4-yl)pyrrolidin-1-yl]-3-methyl-1-oxobutan-2-yl}carbamate and methyl {(2S)-1-[(2S)-2-(2-{4-[(2R,5R)-1-(4-tert-butylphenyl)-5-(4-{4-[(2S)-1-{(2S)-2-[(methoxycarbonyl)amino]-3-methylbutanoyl}pyrrolidin-2-yl]-1H-imidazol-2-yl}phenyl)pyrrolidin-2-yl]phenyl}-1H-imidazol-4-yl)pyrrolidin-1-yl]-3-methyl-1-oxobutan-2-yl}carbamate A mixture of Example 173E (59.6 mg, 0.171 mmol), Example 173C (25 mg, 0.057 mmol) and K₂CO₃ (65 mg, 0.470 mmol) in tetrahydrofuran (1 mL) was refluxed for 4 hours. Mixture was diluted with CH₂Cl₂ and washed with H₂O and Brine. The organic was then dried (MgSO₄), filtered and concentrated. Compound subjected to HPLC purification on a semi-prep C18 reverse-phased column using a gradient of 10-100% acetonitrile in 0.1% aq. TFA to afford 4.5 mg (6.7%) the title compound Example 173 (Trans isomers). ¹H NMR (free base) (400 MHz, DMSO-d₆) δ ppm 0.78-0.89 (m, 12H), 1.09 (s, 9H), 1.68-1.74 (m, 4H), 1.88-2.04 (m, 8H), 3.52 (s, 6H), 3.70-3.78 (m, 4H), 4.04 (t, J=8.19 Hz, 2H), 5.07 (t, J=4.61 Hz, 2H), 5.26 (s, 2H), 6.21 (d, J=8.46 Hz, 2H), 6.82 (s, 2H), 6.93 (d, J=8.67 Hz, 2H), 7.22 (d, J=8.89 Hz, 2H), 7.26 (d, J=8.13 Hz, 4H), 7.78 (d, J=8.13 Hz, 4H), 7.82 (d, J=7.70 Hz, 2H), 12.11-12.20 (m, 2H). MS (ESI) m/z 941 (M+H)⁺.

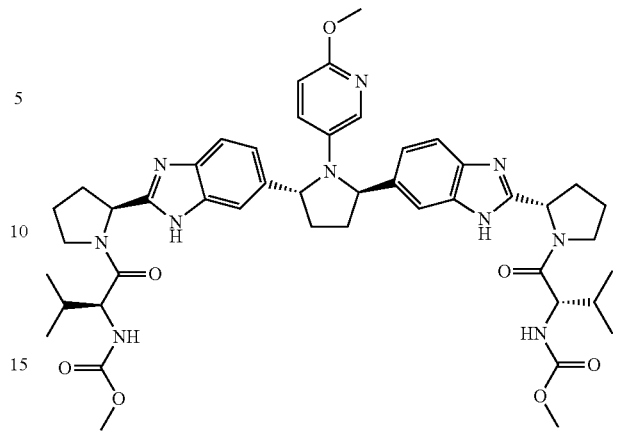

Example 174 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-6-yl}-1-(6-methoxypyridin-3-yl)pyrrolidin-2-yl]-1H-benzimidazol-2-yl}pyrrolidin-1-yl]-3-methyl-1-oxobutan-2-yl}carbamate Example 109C and 6-methoxypyridin-3-amine were processed using sequentially the methods of Examples 113A (dichloromethane used as solvent and cyclization conducted at room temperature overnight), 165C, 113C, and 166 to provide the title compound which was purified by HPLC on a semi-prep C18 reverse-phased column using a gradient of 10-100% acetonitrile in 0.1% aq. TFA to afford 27 mg of the title compound. ¹H NMR (free base) (400 MHz, DMSO-d₆) δ ppm 0.76-0.86 (m, 12H), 1.69-1.76 (m, 2H), 1.84-2.04 (m, 4H), 2.13-2.22 (m, 4H), 2.52-2.60 (m, 2H), 3.52 (s, 6H), 3.55 (s, 3H), 3.76-3.85 (m, 4H), 4.05 (t, J=8.40 Hz, 2H), 5.08-5.16 (m, 2H), 5.31-5.41 (m, 2H), 6.36-6.45 (m, 2H), 6.74 (dd, J=9.00, 3.04 Hz, 2H), 7.05 (t, J=8.57 Hz, 2H), 7.15-7.24 (m, J=17.02 Hz, 3H), 7.28 (d, J=8.46 Hz, 2H), 7.31 (s, 1H), 7.37 (d, J=8.13 Hz, 1H), 7.45 (d, J=8.13 Hz, 1H), 12.03 (s, 2H); MS (ESI) m/z 864 (M+H)⁺.

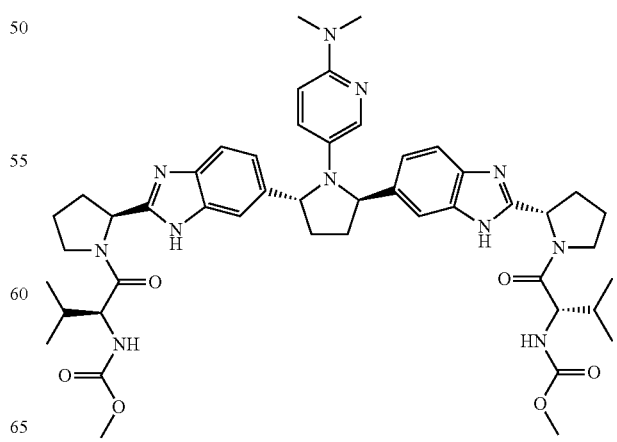

Example 175 methyl {(2S)-1-[(2S)-2-{6-[(2R,5R)-1-[6-(dimethylamino)pyridin-3-yl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate

Example 175A

N,N-dimethyl-5-nitropyridin-2-amine

A mixture of 2-chloro-5-nitropyridine (5.0 g, 31.5 mmol) and 40% solution of Dimethylamine (10.66 g, 95 mmol) in ethanol (40 mL) was heated to 75° C. for 1 hour. The mixture was cooled to ambient temperature, diluted with $CH_2Cl_2$ and washed with saturated aqueous $NaHCO_3$ (3×100 mL) and brine. The organic was dried ($MgSO_4$), filtered and concentrated to afford 5.27 g (100%) of the title compound. MS (ESI) m/z 168 (M+H)$^+$.

Example 175B $N^2,N^2$-dimethylpyridine-2,5-diamine

A mixture of Example 175A (5.27 g, 31.5 mmol) and Raney Nickel (5.27 g, 90 mmol) in tetrahydrofuran (60 mL) was subjected to an atmosphere (30 psi) of hydrogen gas for 2 hours at ambient temperature. Mixture was filtered and concentrated to afford 4.3 g (100%) of the title compound. MS (ESI) m/z 138 (M+H)$^+$.

Example 175C methyl {(2S)-1-[(2S)-2-{6-[(2R,5R)-1-[6-(dimethylamino)pyridin-3-yl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate Example 175B was processed using the methods referred to or described in Example 174 to provide the title compound (8.5 mg). $^1$H NMR (free base) (400 MHz, DMSO-$d_6$) δ ppm 0.75-0.86 (m, 12H), 1.71 (d, J=4.99 Hz, 2H), 1.86-2.05 (m, 6H), 2.12-2.23 (m, 3H), 2.55 (s, 2H), 2.70 (s, 6H), 3.16 (s, 2H), 3.52 (s, 6H), 3.81 (s, 3H), 4.05 (t, J=8.35 Hz, 2H), 5.09-5.18 (m, 2H), 5.33 (d, J=5.53 Hz, 2H), 6.33 (d, J=9.00 Hz, 1H), 6.63 (dd, J=9.05, 2.98 Hz, 1H), 7.04 (d, J=7.70 Hz, 2H), 7.19-7.31 (m, 4H), 7.34-7.48 (m, 2H), 12.02 (s, 2H); MS (ESI) m/z 877 (M+H)$^+$.

Example 176 methyl {(2S)-1-[(2S)-2-{6-[(2R,5R)-1-(6-tert-butylpyridin-3-yl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate 6-tert-Butylpyridin-3-amine was processed using the methods referred to or described in Example 174 to provide the title compound (62.5 mg) of the title compound. $^1$H NMR (free base) (400 MHz, DMSO-$d_6$) δ ppm 0.74-0.88 (m, 12H), 1.08 (s, 9H), 1.68-1.77 (m, 2H), 1.83-2.04 (m, 7H), 2.12-2.23 (m, 4H), 2.53-2.61 (m, 2H), 3.16 (d, J=5.20 Hz, 2H), 3.52 (s, 6H), 3.76-3.85 (m, 4H), 4.00-4.11 (m, 3H), 5.08-5.16 (m, 2H), 5.37-5.46 (m, 2H), 6.54-6.61 (m, 1H), 6.88-6.96 (m, 2H), 7.08 (t, J=9.00 Hz, 2H), 7.20 (s, 1H), 7.25-7.31 (m, 3H), 7.39 (d, J=8.13 Hz, 1H), 7.47 (d, J=8.24 Hz, 1H), 7.60 (d, J=3.25 Hz, 1H), 12.04 (d, J=27.76 Hz, 2H); MS (ESI) m/z 890 (M+H)$^+$.

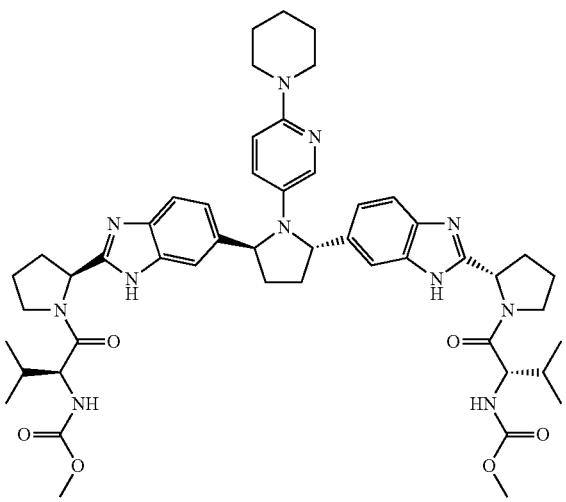 [SMILES: COC(=O)N[C@H](C(=O)N1CCC[C@H]1c1nc2ccc([C@@H]3CC[C@@H](c4ccc5nc([C@@H]6CCCN6C(=O)[C@@H](NC(=O)OC)C(C)C)[nH]c5c4)N3c3ccc(N4CCCCC4)nc3)cc2[nH]1)C(C)C]

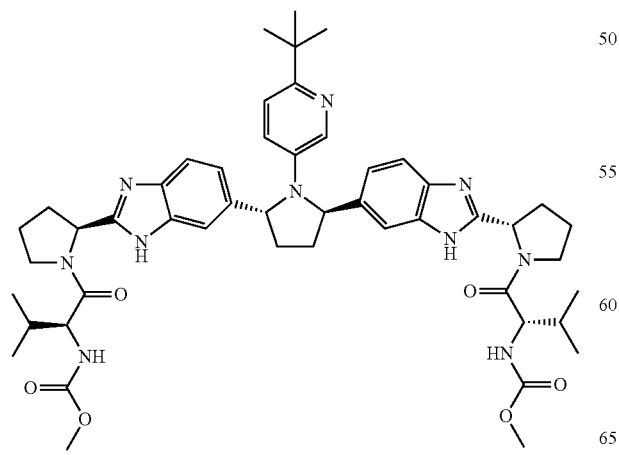

Example 177 methyl {(2S)-1-[(2S)-2-(6-{(2S,5S)-5-{2-[(2S)-1-{(2S)-2-[(methoxycarbonyl)amino]-3-methylbutanoyl}pyrrolidin-2-yl]-1H-benzimidazol-6-yl}-1-[6-(piperidin-1-yl)pyridin-3-yl]pyrrolidin-2-yl}-1H-benzimidazol-2-yl)pyrrolidin-1-yl]-3-methyl-1-oxobutan-2-yl}carbamate

Example 177A 5-((2S,5S)-2,5-bis(4-chloro-3-nitrophenyl)pyrrolidin-1-yl)-2-(piperidin-1-yl)pyridine (1R,4R)-1,4-bis(4-chloro-3-nitrophenyl)butane-1,4-diol (prepared using (S)-(+)-alpha,alpha-diphenyl-2-pyrrolidinemethanol and the method of Example 109C) (0.60 g, 1.5 mmol) was processed using the method described in Example 182A to give the title compound (0.41 g, 50%).

Example 177B dimethyl (2S,2'S)-1,1'-((2S,2'S)-2,2'-(4,4'-((2S,5S)-
1-(6-(piperidin-1-yl)pyridin-3-yl)pyrrolidine-2,5-
diyl)bis(2-nitro-4,1-phenylene))bis(azanediyl)bis
(oxomethylene)bis(pyrrolidine-2,1-diyl))bis(3-
methyl-1-oxobutane-2,1-diyl)dicarbamate The product from Example 177A (0.20 g, 0.369 mmol) was combined with the product from Example 116C (0.30 g, 1.11 mmol), cesium carbonate (0.336 g, 1.03 mmol), Xantphos (38 mg, 0.066 mmol) and tris(dibenzylideneacetone)dipalladium (20.3 mg, 0.022 mmol). Anhydrous 1,4-dioxane (3.7 mL) was added, and the mixture was bubbled with $N_2$ gas for 15 min. The resulting mixture was stirred in a sealed tube at 100° C. for 2 h. The mixture was cooled to ambient temperature, diluted with water and extracted with ethyl acetate. The organic extract was washed with brine, dried ($NaSO_4$), filtered and concentrated. Purification by flash chromatography twice (silica gel, 0-10% MeOH/$CH_2Cl_2$) afforded the title compound (235 mg, 60%).

Example 177C dimethyl (2S,2'S)-1,1'-((2S,2'S)-2,2'-(4,4'-((2S,5S)-
1-(6-(piperidin-1-yl)pyridin-3-yl)pyrrolidine-2,5-
diyl)bis(2-amino-4,1-phenylene))bis(azanediyl)bis
(oxomethylene)bis(pyrrolidine-2,1-diyl))bis(3-
methyl-1-oxobutane-2,1-diyl)dicarbamate To a solution of the product from Example 177B (237 mg, 0.234 mmol) in ethanol (1.2 mL) and tetrahydrofuran (1.2 mL) was added platinum(IV) oxide (13.29 mg, 0.059 mmol). The mixture was placed under a hydrogen atmosphere for about 1 hour. The mixture was filtered over celite, washing with methanol and concentrated. Purification by flash chromatography (silica gel, 0-10% MeOH/$CH_2Cl_2$) afforded the title compound (186 mg, 84%).

Example 177D methyl {(2S)-1-[(2S)-2-(6-{(2S,5S)-5-{2-[(2S)-1-
{(2S)-2-[(methoxycarbonyl)amino]-3-
methylbutanoyl}pyrrolidin-2-yl]-1H-benzimidazol-
6-yl}-1-[6-(piperidin-1-yl)pyridin-3-yl]pyrrolidin-2-
yl}-1H-benzimidazol-2-yl)pyrrolidin-1-yl]-3-
methyl-1-oxobutan-2-yl}carbamate To a solution of the product from Example 177C (113 mg, 0.119 mmol) in toluene (1.2 mL) was added acetic acid (34 µL, 0.593 mmol) and 3 A molecular sieves. The mixture was heated to 60° C. for 2 hours. The reaction was cooled to ambient temperature and diluted with ethyl acetate. The organic phase was washed with saturated aqueous $NaHCO_3$, dried ($Na_2SO_4$), filtered and concentrated. The crude product was purified by reverse-phase HPLC (C18) using a solvent gradient of 10-90% $CH_3CN$ in water (0.1% TFA). Fractions containing the desired product were pooled and concentrated in vacuo, and the residue was partitioned between saturated aq. $NaHCO_3$, and $CH_2Cl_2$. The organic layer was dried ($Na_2SO_4$), filtered and concentrated to afford the title compound (9 mg, 8%). 1H NMR (400 MHz, DMSO-D6) δ ppm 0.78-0.85 (m, 7H), 0.87 (dd, J=6.7, 3.0 Hz, 6H), 1.23 (s, 1H), 1.43 (s, 6H), 1.72 (s, 2H), 1.97 (s, 5H), 2.18 (s, 3H), 3.09 (s, 4H), 3.30 (s, 2H), 3.53 (d, J=11.5 Hz, 6H), 3.81 (s, 4H), 4.07 (s, 2H), 5.13 (s, 2H), 5.33 (s, 2H), 6.48 (d, J=4.4 Hz, 1H), 6.59-6.64 (m, 1H), 7.05 (s, 2H), 7.22 (s, 1H), 7.25-7.34 (m, 4H), 7.37 (s, 1H), 7.44 (s, 1H), 12.06 (s, 2H); MS (ESI) m/z 916 (M+H)+.

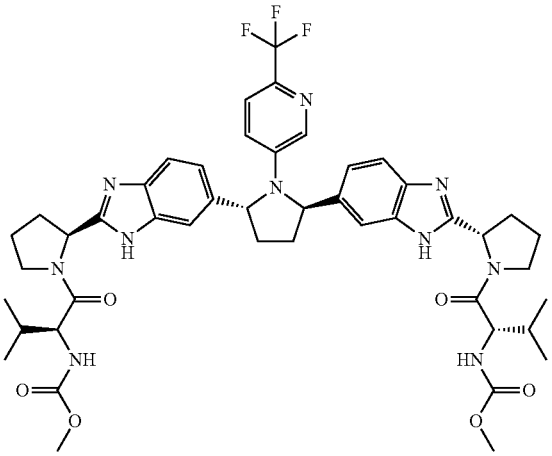 [SMILES: COC(=O)N[C@H](C(=O)N1CCC[C@H]1c1nc2ccc([C@H]3CC[C@H](c4ccc5nc([C@@H]6CCCN6C(=O)[C@@H](NC(=O)OC)C(C)C)[nH]c5c4)N3c3ccc(C(F)(F)F)nc3)cc2[nH]1)C(C)C]

Example 178 methyl {(2S)-1-[(2S)-2-(6-{(2R,5R)-5-{2-[(2S)-1-
{(2S)-2-[(methoxycarbonyl)amino]-3-
methylbutanoyl}pyrrolidin-2-yl]-1H-benzimidazol-
6-yl}-1-[6-(trifluoromethyl)pyridin-3-yl]pyrrolidin-
2-yl}-1H-benzimidazol-2-yl)pyrrolidin-1-yl]-3-
methyl-1-oxobutan-2-yl}carbamate Example 109C and 5-amino-2-(trifluoromethyl)pyridine were processed using sequentially the methods of Examples 182A, 177B, 177C, and 177D to provide the title compound. 1H NMR (400 MHz, DMSO-D6) δ ppm 0.79-0.89 (m, 15H), 1.61 (s, 4H), 1.97 (s, 6H), 2.19 (s, 5H), 3.50-3.58 (m, 7H), 3.82 (s, 4H), 3.99-4.10 (m, 2H), 5.15 (s, 2H), 6.89-6.98 (m, 2H), 7.19 (s, 1H), 7.26-7.34 (m, 4H), 7.36 (d, J=8.2 Hz, 1H), 11.94 (d, J=12.9 Hz, 2H). MS m/z 901 (M+H)+.

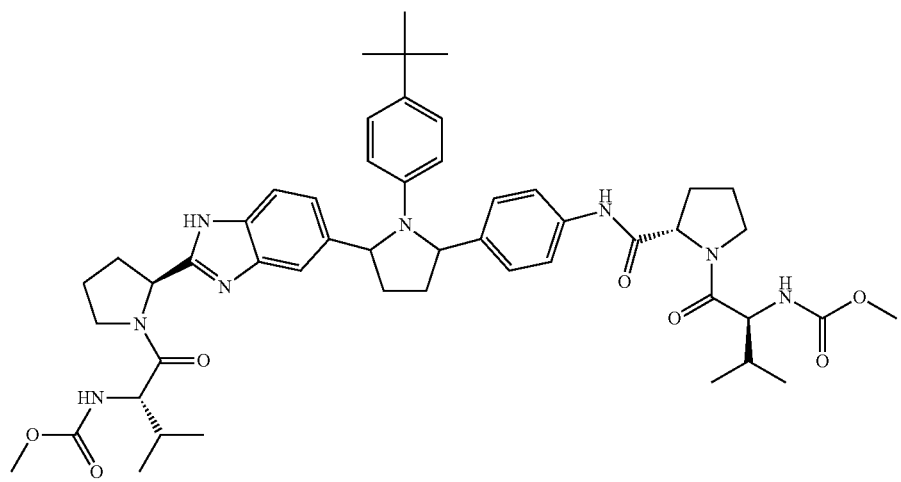

Example 179

N-(methoxycarbonyl)-L-valyl-N-{4-[(2S,5S)1-(4-tert-butylphenyl)-5-(2-{(2S)-1-[N-(methoxycarbonyl)-L-valyl]pyrrolidin-2-yl}-1H-benzimidazol-5-yl)pyrrolidin-2-yl]phenyl}-L-prolinamide and N-(methoxycarbonyl)-L-valyl-N-{4-[(2R,5R)-1-(4-tert-butylphenyl)-5-(2-{(2S)-1-[N-(methoxycarbonyl)-L-valyl]pyrrolidin-2-yl}-1H-benzimidazol-5-yl)pyrrolidin-2-yl]phenyl}-L-prolinamide

Example 179A 1-(4-chloro-3-nitrophenyl)-4-(4-nitrophenyl)butane-1,4-dione

To a mixture of zinc chloride (39.1 g, 287 mmol) in benzene (215 mL) was added diethylamine (22.24 mL, 215 mmol) and 2-methylpropan-2-ol (20.57 mL, 215 mmol). The resulting mixture was stirred at rt for 2 h, and 2-bromo-1-(4-nitrophenyl)ethanone (35.0 g, 143 mmol) and 1-(4-chloro-3-nitrophenyl)ethanone (42.9 g, 215 mmol) were added in one portion. The resulting mixture was stirred at rt overnight. Added 5% aq. $H_2SO_4$ (50 mL) and stirred vigorously to induce precipitation. The resulting solid was collected by filtration and washed successively with benzene, water, methanol, and $CH_2Cl_2$. The solid was dried in vacuo to give the title compound.

Example 179B 1-(4-chloro-3-nitrophenyl)-4-(4-nitrophenyl)butane-1,4-diol

To a solution of the product from Example 179A (10.0 g, 27.6 mmol) in EtOH (220 mL) was added sodium borohydride (2.190 g, 57.9 mmol) in several portions over 1 h. The resulting mixture was stirred at rt for 1 h, filtered through celite, and concentrated in vacuo. The residue was dissolved in EtOAc and washed by 1N aq. HCl. The organic layer was dried over $Na_2SO_4$, filtered and concentrated in vacuo to give the title compound (9.29 g, 92%)

Example 179C 1-(4-tert-butylphenyl)-2-(4-chloro-3-nitrophenyl)-5-(4-nitrophenyl)pyrrolidine To a solution of product from Example 179B (9.29 g, 25.3 mmol) in anhydrous $CH_2Cl_2$ (200 mL) at 0° C. was added triethylamine (10.53 mL, 76 mmol), followed by dropwise addition of methanesulfonyl chloride (4.93 mL, 63.3 mmol). The resulting mixture was stirred at 0° C. for 2 h, and then concentrated in vacuo. The resulting solid was dissolved in anhydrous DMF (70 mL), 4-tert-butylaniline (40.4 mL, 253 mmol) was added, and the resulting mixture was stirred at 50° C. for 1 h. The resulting mixture was cooled to rt and poured into ice cold 1N aq. HCl (500 mL) to give a yellow precipitate. The precipitate was collected by filtration and dried to give the title compound (13.2 g).

Example 179D 4-(1-(4-tert-butylphenyl)-5-(4-nitrophenyl)pyrrolidin-2-yl)-N-(4-methoxybenzyl)-2-nitroaniline The product from Example 179C (13.2 g, 27.5 mmol) and 4-methoxybenzylamine (18 mL, 139 mmol) were combined and stirred at 145° C. for 1.5 h. The mixture was cooled to rt, and $CH_2Cl_2$ was added. The resulting precipitate was filtered off, and the filtrate was washed successively with 1N aq. HCl and saturated aq. $NaHCO_3$. The organic layer was dried over $Na_2SO_4$, filtered and concentrated in vacuo. The crude product was purified by column chromatography on silica gel using a solvent gradient of 0-25% EtOAc in hexane to give the title compound (5.0 g, 31%).

Example 179E 4-(5-(4-aminophenyl)-1-(4-tert-butylphenyl)pyrrolidin-2-yl)-N1-(4-methoxybenzyl)benzene-1,2-diamine To a solution of the product from Example 179D (2.74 g, 4.72 mmol) in EtOH (25 mL) and THF (25 mL) was added platinum(IV) oxide (0.5 g, 2.2 mmol). The resulting mixture was stirred at rt under 1 atm H₂ overnight. The mixture was filtered through celite, washed with methanol, and the filtrate was concentrated in vacuo. The crude product was purified by column chromatography on silica gel using a solvent gradient of 0-45% EtOAc in hexane to give the title compound (1.74 g, 71%).

Example 179F (2S)-tert-butyl 2-(4-(5-(3-((S)-1-(tert-butoxycarbonyl)pyrrolidine-2-carboxamido)-4-(4-methoxybenzylamino)phenyl)-1-(4-tert-butylphenyl)pyrrolidin-2-yl)phenylcarbamoyl)pyrrolidine-1-carboxylate To a mixture of the product from Example 179E (1.74 g, 3.33 mmol), (S)-1-(tert-butoxycarbonyl)pyrrolidine-2-carboxylic acid (1.793 g, 8.33 mmol) and HATU (3.17 g, 8.33 mmol) in DMSO (33 mL) was added Hunig's base (1.746 mL, 10.00 mmol). The resulting mixture was stirred at rt for 1 h and was partitioned between H₂O and CH₂Cl₂. The organic layer was dried over Na₂SO₄, filtered and concentrated in vacuo. The crude product was purified by column chromatography on silica gel using a solvent gradient of 0-25% EtOAc in hexane to give the title compound (2.1 g, 69%).

Example 179G (2S)-tert-butyl 2-(4-(5-(4-amino-3-((S)-1-(tert-butoxycarbonyl)pyrrolidine-2-carboxamido)phenyl)-1-(4-tert-butylphenyl)pyrrolidin-2-yl)phenylcarbamoyl)pyrrolidine-1-carboxylate To a solution of the product from Example 179F (1.06 g, 1.16 mmol) in CH₂Cl₂ (40 mL) and H₂O (2 mL) was added 2,3-dichloro-5,6-dicyano-1,4-benzoquinone (DDQ) (0.316 g, 1.393 mmol) in several portions. The mixture was stirred at rt for 20 min and was washed with saturated. aq. NaHCO₃. The organic layer was dried over Na₂SO₄, filtered and concentrated in vacuo. The crude product was purified by column chromatography on silica gel using a solvent gradient of 0-25% EtOAc in hexane to give the title compound (0.53 g, 57%).

Example 179H (2S)-tert-butyl 2-(4-(5-(2-((S)-1-(tert-butoxycarbonyl)pyrrolidin-2-yl)-1H-benzo[d]imidazol-5-yl)-1-(4-tert-butylphenyl)pyrrolidin-2-yl)phenylcarbamoyl)pyrrolidine-1-carboxylate A solution of product from Example 179G (0.526 g, 0.662 mmol) in acetic acid (4.73 mL, 83 mmol) was stirred at 65° C. for 1 h. The resulting mixture was partitioned between CH₂Cl₂ and saturated aq. NaHCO₃. The organic layer was dried over Na₂SO₄, filtered and concentrated in vacuo. The crude product was purified by column chromatography on silica gel using a solvent gradient of 0-2.5% MeOH in CH₂Cl₂ to give the title compound (0.23 g, 45%).

Example 179I (S)—N-(4-((2S,5S)-1-(4-tert-butylphenyl)-5-(2-((S)-pyrrolidin-2-yl)-1H-benzo[d]imidazol-5-yl)pyrrolidin-2-yl)phenyl)pyrrolidine-2-carboxamide and (S)—N-(4-((2R,5R)-1-(4-tert-butylphenyl)-5-(2-((S)-pyrrolidin-2-yl)-1H-benzo[d]imidazol-5-yl)pyrrolidin-2-yl)phenyl)pyrrolidine-2-carboxamide To a solution of the product from Example 179H (0.302 g, 0.389 mmol) in CH₂Cl₂ (3 mL) was added TFA (2.5 mL), and the resulting mixture was stirred at rt for 1.5 h. The mixture was concentrated in vacuo, and the crude product was purified by reversed-phase HPLC (C18) using a solvent gradient of 10-100% acetonitrile in H₂O (0.1% TFA). The trans-pyrrolidine isomer eluted before the cis-pyrrolidine isomer. Fractions containing the trans-isomer were concentrated in vacuo, and the residue was partitioned between CH₂Cl₂ and saturated aq. NaHCO₃. The organic layer was dried over Na₂SO₄, filtered and concentrated in vacuo to give the title compound (83 mg, 37%).

Example 179J

N-(methoxycarbonyl)-L-valyl-N-{4-[(2S,5S)1-(4-tert-butylphenyl)-5-(2-{(2S)-1-[N-(methoxycarbonyl)-L-valyl]pyrrolidin-2-yl}-1H-benzimidazol-5-yl)pyrrolidin-2-yl]phenyl}-L-prolinamide and N-(methoxycarbonyl)-L-valyl-N-{4-[(2R,5R)-1-(4-tert-butylphenyl)-5-(2-{(2S)-1-[N-(methoxycarbonyl)-L-valyl]pyrrolidin-2-yl}-1H-benzimidazol-5-yl)pyrrolidin-2-yl]phenyl}-L-prolinamide To a mixture of the product from Example 179I (83 mg, 0.144 mmol), (S)-2-(methoxycarbonylamino)-3-methylbutanoic acid (63 mg, 0.361 mmol), and HATU (0.137 g, 0.361 mmol) in DMSO (1.5 mL) was added Hunig's base (0.101 mL, 0.578 mmol), and the resulting mixture was stirred at rt for 1 h. The mixture was partitioned between CH₂Cl₂ and H₂O. The organic layer was dried over Na₂SO₄, filtered and concentrated in vacuo. The crude product was purified by column chromatography on silica gel using a solvent gradient of 0-3.5% MeOH in CH₂Cl₂ to give the title compounds (80 mg, 60%). 1H NMR (400 MHz, DMSO-D6) δ ppm 0.74-0.99 (m, 12H), 1.09 (s, 9H), 1.59-1.73 (m, 2H), 1.81-2.05 (m, 6H), 2.07-2.24 (m, 2H), 3.50-3.56 (m, 6H), 3.58-3.67 (m, 1H), 3.76-3.85 (m, 2H), 3.99-4.10 (m, 2H), 4.43 (dd, J=8.0, 4.9 Hz, 1H), 5.08-5.16 (m, 1H), 5.16-5.25 (m, 1H), 5.26-5.37 (m, 1H), 6.21 (d, J=8.8 Hz, 2H), 6.88-6.97 (m, 2.5H), 7.00-7.08 (m, 1H), 7.11-7.20 (m, J=5.7 Hz, 2.5H), 7.21-7.34 (m, 2H), 7.37 (dd, -8.2, 2.0 Hz, 0.5H), 7.45 (d, J=8.3 Hz, 0.5H), 7.50 (d, J=8.3 Hz, 2H), 9.98 (s, 1H), 12.01 (m, 1H); MS m/z 891.6 (M+H)⁺.

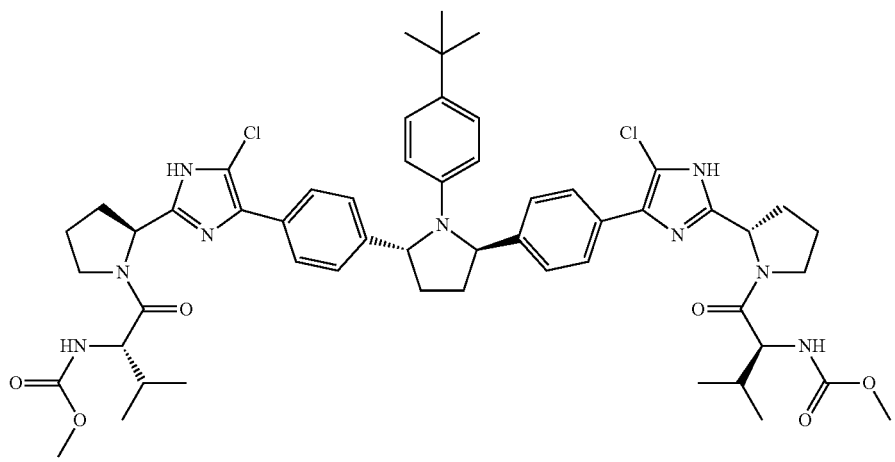 [SMILES: COC(=O)N[C@H](C(=O)N1CCC[C@H]1c1nc(-c2ccc([C@H]3CC[C@H](c4ccc(-c5nc([C@@H]6CCCN6C(=O)[C@@H](NC(=O)OC)C(C)C)[nH]c5Cl)cc4)N3c3ccc(C(C)(C)C)cc3)cc2)c(Cl)[nH]1)C(C)C]

Example 180 methyl {(2S)-1-[(2S)-2-(4-{4-[(2R,5R)-1-(4-tert-butylphenyl)-5-(4-{5-chloro-2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-5-chloro-1H-imidazol-2-yl)pyrrolidin-1-yl]-3-methyl-1-oxobutan-2-yl}carbamate To a solution of the product from Example 43 (114 mg, 0.121 mmol) in $CH_2Cl_2$ (1.2 mL) was added N-chlorosuccinimide (54 mg, 0.41 mmol), and the resulting mixture was stirred at rt for 9 h. The mixture was diluted by $CH_2Cl_2$ and washed with saturated aq $NaHCO_3$. The organic layer was dried over $Na_2SO_4$, filtered, and concentrated in vacuo. The crude product was subjected to reversed-phase HPLC (C18) using a solvent gradient of 40%-100% acetonitrile in water (0.1% TFA). Fractions containing the desired product were pooled and concentrated in vacuo. The residue was purified on a preparative TLC plate, eluting with 3% MeOH in $CH_2Cl_2$ to give the title compound (3.5 mg, 3%). 1H NMR (400 MHz, DMSO-D6) δ ppm 0.80-0.92 (m, 12H), 1.11 (s, 9H), 1.72 (d, J=5.0 Hz, 2H), 1.87-2.04 (m, 6H), 2.05-2.23 (m, 2H), 3.53 (s, 6H), 3.72-3.82 (m, 2H), 4.04 (t, J=8.4 Hz, 2H), 4.98 (dd, J=6.8, 3.5 Hz, 2H), 5.29 (dd, J=3.5, 2.5 Hz, 2H), 6.23 (d, J=8.8 Hz, 2H), 6.96 (d, J=8.8 Hz, 2H), 7.27 (d, J=8.6 Hz, 2H), 7.32 (d, J=8.2 Hz, 4H), 7.61 (d, J=8.1 Hz, 4H), 12.41 (s, 2H); MS m/z 1009.1 (M+H)+.

Example 181 methyl {(2S)-1-[(2S)-2-(4-{4-[(2R,5R)-1-(4-tert-butyl-2-chlorophenyl)-5-(4-{5-chloro-2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-5-chloro-1H-imidazol-2-yl)pyrrolidin-1-yl]-3-methyl-1-oxobutan-2-yl}carbamate The product from Example 43 (114 mg, 0.121 mmol) was subjected to the procedure described in Example 180 to give the title compound (4.7 mg, 4%). 1H NMR (TFA salt) (400 MHz, DMSO-D6) δ ppm 0.78-0.89 (m, 12H), 1.05 (s, 9H), 1.85-1.97 (m, 10H), 2.04-2.18 (m, 4H), 3.52 (s, 6H), 3.69-3.81 (m, 4H), 4.03 (t, J=8.3 Hz, 2H), 4.95 (dd, J=7.0, 4.0 Hz, 2H), 5.53 (d, J=7.5 Hz, 2H), 6.91-6.95 (m, 1H), 6.96-7.02 (m, 2H), 7.26 (d, J=8.5 Hz, 2H), 7.30-7.41 (m, 4H), 7.49 (d, J=7.6 Hz, 4H), 12.34 (s, 2H); MS m/z 1045.1 (M+H)+.

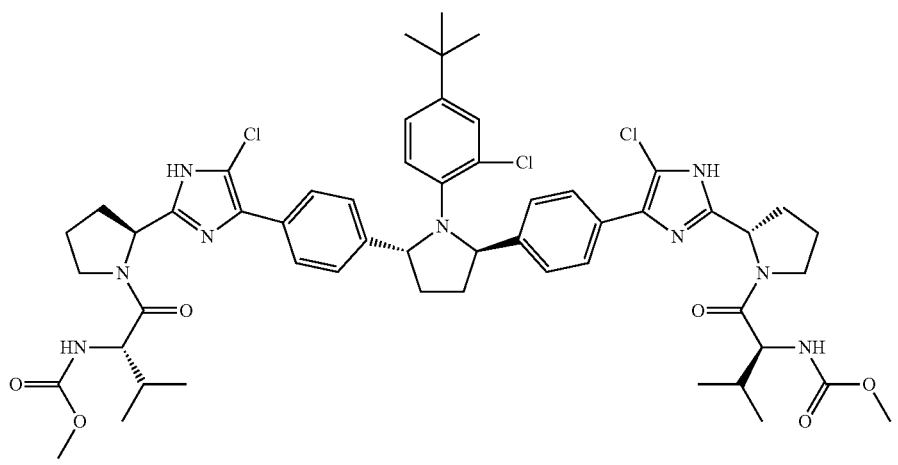 [SMILES: COC(=O)N[C@H](C(=O)N1CCC[C@H]1c1nc(-c2ccc([C@H]3CC[C@H](c4ccc(-c5nc([C@@H]6CCCN6C(=O)[C@@H](NC(=O)OC)C(C)C)[nH]c5Cl)cc4)N3c3ccc(C(C)(C)C)cc3Cl)cc2)c(Cl)[nH]1)C(C)C]

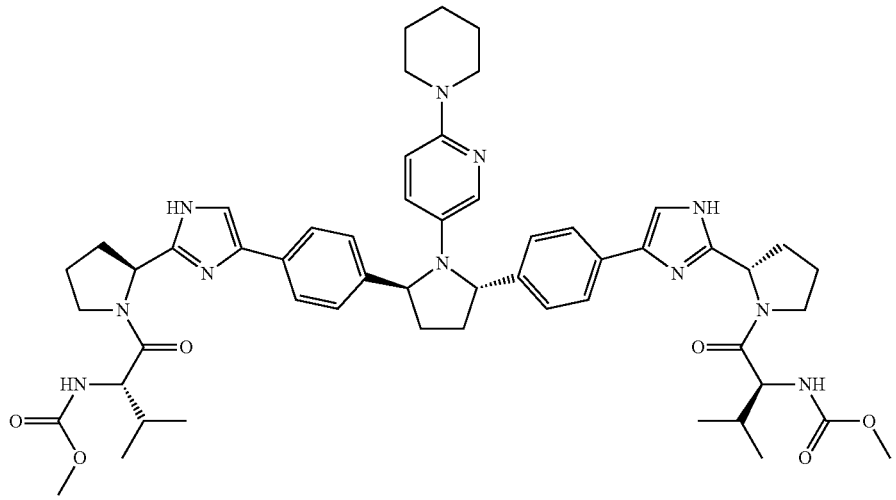 [SMILES: COC(=O)N[C@H](C(=O)N1CCC[C@H]1c1nc(-c2ccc([C@@H]3CC[C@@H](c4ccc(-c5c[nH]c([C@@H]6CCCN6C(=O)[C@@H](NC(=O)OC)C(C)C)n5)cc4)N3c3ccc(N4CCCCC4)nc3)cc2)c[nH]1)C(C)C]

Example 182 methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]pyrrolidin-2-yl}phenyl)-1H-imidazol-2-yl]pyrrolidin-1-yl}-3-methyl-1-oxobutan-2-yl]carbamate

Example 182A 5-((2S,5S)-2,5-bis(4-bromophenyl)pyrrolidin-1-yl)-2-(piperidin-yl)pyridine To a suspension of the product of Example 69A (0.50 g, 1.25 mmol) in anhydrous $CH_2Cl_2$ (12 mL) at 0° C. was added $Et_3N$ (0.52 mL, 3.75 mmol), followed by methanesulfonyl chloride (0.243 mL, 3.12 mmol). The resulting mixture was stirred and 0° C. for 90 min and then evaporated to dryness. The solid was dissolved in anhydrous DMF (10 mL), and Example 144C (1108 mg, 6.25 mmol) was added. The resulting mixture was stirred at 40° C. overnight, and was partitioned between 0.2 N aq HCl and EtOAc. The organic layer was dried over $Na_2SO_4$, filtered and concentrated in vacuo. The crude product was purified by column chromatography on silica gel using a solvent gradient of EtOAc and hexane to give the title compound (107 mg, 16%).

Example 182B methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]pyrrolidin-2-yl}phenyl)-1H-imidazol-2-yl]pyrrolidin-1-yl}-3-methyl-1-oxobutan-2-yl]carbamate The product from Example 182A was subjected to the procedures described in Examples 42D, 42E, 42F, and 42G to give the title compound. 1H NMR (free base) (400 MHz, DMSO-D6) δ ppm 0.80-0.94 (m, 12H), 1.24 (s, 4H), 1.44 (s, 6H), 1.89-2.04 (m, 6H), 2.07-2.20 (m, 4H), 3.12 (s, 4H), 3.53 (s, 6H), 3.77 (d, J=6.7 Hz, 2H), 4.05 (t, -8.4 Hz, 2H), 5.06 (dd, J=6.7, 3.0 Hz, 2H), 5.19 (d, J=6.4 Hz, 2H), 6.45-6.53 (m, 1H), 6.56-6.63 (m, 1H), 7.15 (d, J=8.2 Hz, 4H), 7.21-7.32 (m, 4H), 7.38 (d, J=1.8 Hz, 2H), 7.62 (d, J=8.0 Hz, 4H), 11.69 (s, 2H); MS m/z=968.8 (M+H)+.

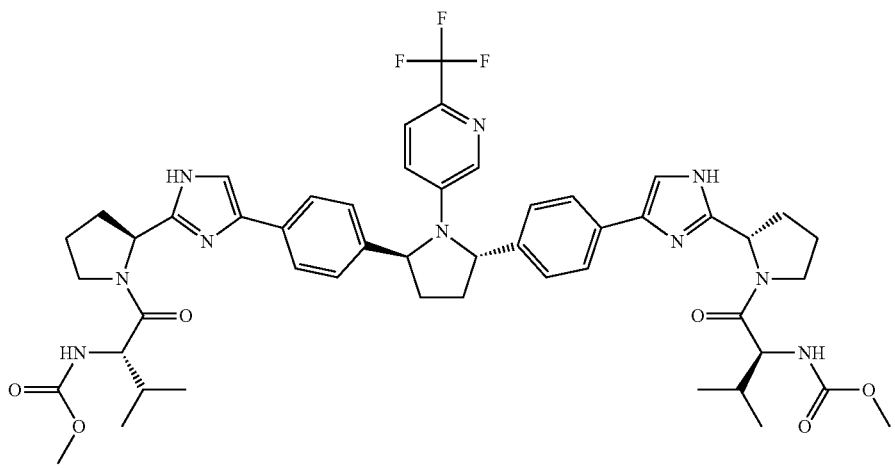 [SMILES: COC(=O)N[C@H](C(=O)N1CCC[C@H]1c1nc(-c2ccc([C@@H]3CC[C@@H](c4ccc(-c5c[nH]c([C@@H]6CCCN6C(=O)[C@@H](NC(=O)OC)C(C)C)n5)cc4)N3c3ccc(C(F)(F)F)nc3)cc2)c[nH]1)C(C)C]

Example 183 methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(trifluoromethyl)pyridin-3-yl]pyrrolidin-2-yl}phenyl)-1H-imidazol-2-yl]pyrrolidin-1-yl}-3-methyl-1-oxobutan-2-yl]carbamate

Example 183A 5-((2S,5S)-2,5-bis(4-bromophenyl)pyrrolidin-1-yl)-2-(trifluoromethyl)pyridine The product from Example 69A (1.0 g, 2.5 mmol) was subjected to the procedure described in Example 182A, substituting 6-(trifluoromethyl)pyridin-3-amine for Example 144C, to give the title compound (0.13 g, 10%).

Example 183B methyl [(2S)-1-{(2S)-2-[4-(4-{(2S,5S)-5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(trifluoromethyl)pyridin-3-yl]pyrrolidin-2-yl}phenyl)-1H-imidazol-2-yl]pyrrolidin-1-yl}-3-methyl-1-oxobutan-2-yl]carbamate The product from Example 183A was subjected to the procedures described in Examples 42D, 42E, 42F, and 42G to give the title compound. 1H NMR (TFA salt) (400 MHz, DMSO-D6) δ ppm 0.75-0.91 (m, 12H), 1.84 (d, J=5.6 Hz, 2H), 1.96-2.10 (m, 6H), 2.11-2.20 (m, J=10.8, 5.5 Hz, 2H), 3.54 (s, 6H), 3.76-3.91 (m, 4H), 4.10 (t, J=7.9 Hz, 2H), 5.11 (t, J=6.8 Hz, 2H), 5.56 (d, J=5.1 Hz, 2H), 6.74 (dd, J=8.8, 2.5 Hz, 1H), 7.32 (d, J=8.5 Hz, 2H), 7.41 (d, J=7.8 Hz, 4H), 7.44-7.48 (m, J=8.8 Hz, 1H), 7.71 (d, J=8.2 Hz, 4H), 7.76 (d, J=2.5 Hz, 1H), 7.97 (s, 2H), 14.50 (s, 2H); MS m/z 953.6 (M+H)$^+$.

Example 184 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-6-yl}-1-[2-(piperidin-1-yl)pyrimidin-5-yl]pyrrolidin-2-yl}-1H-benzimdazol-2-yl)pyrrolidin-1-yl]-3-methyl-1-oxobutan-2-yl}carbamate

Example 184A 2-(piperidin-1-yl)pyrimidin-5-amine

To a suspension of 2-chloro-5-nitropyrimidine (1.5 g, 9.40 mmol) in EtOH (15 mL) was added piperidine (2.79 mL, 28.2 mmol), and the resulting mixture was refluxed for 2 h. The cooled mixture was concentrated in vacuo, and the residue was partitioned between $CH_2Cl_2$ and saturated aq. $NaHCO_3$. The organic layer was dried over $Na_2SO_4$, filtered and concentrated in vacuo to give a solid (1.65 g, 84%). The solid was placed in a 250 mL stainless steel pressure bottle and dissolved in THF (20 mL). Raney-Ni 2800 in water slurry (1.650 g, 28.1 mmol) was added, and the mixture was stirred at rt for 2 h under $H_2$ gas at a pressure of 30 psi. The mixture was filtered through a nylon membrane and concentrated in vacuo to give the title compound (1.4 g, 99%).

Example 184B 5-((2R,5R)-2,5-bis(4-chloro-3-nitrophenyl)pyrrolidin-1-yl)-2-(piperidin-1-yl)pyrimidine The product from Example 109C (1.09 g, 2.72 mmol) was subjected to the conditions described in Example 182A, substituting Example 184A for Example 144C, to give the title compound (0.59 g, 40%).

Example 184C methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-6-yl}-1-[2-(piperidin-1-yl)pyrimidin-5-yl]pyrrolidin-2-yl}-1H-benzimdazol-2-yl)pyrrolidin-1-yl]-3-methyl-1-oxobutan-2-yl}carbamate The product from Example 184B was subjected to the procedures described in Examples 177B, 177C, and 177D to

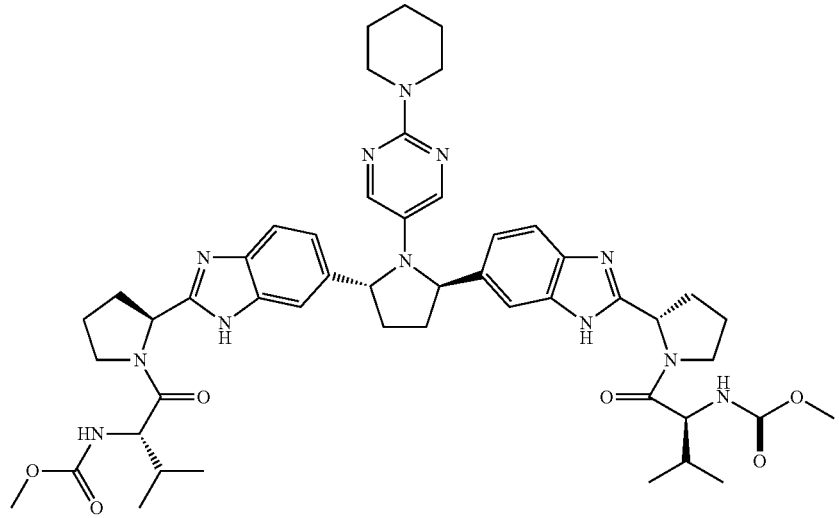

give the title compound. 1H NMR (TFA salt) (400 MHz, DMSO-D6) δ ppm 0.71-0.91 (m, 12H), 1.24 (s, 2H), 1.32-1.41 (m, 4H), 1.44-1.52 (m, 2H), 1.82 (d, J=5.1 Hz, 2H), 1.92-2.26 (m, 12H), 3.86 (s, 6H), 4.12 (t, 8.0 Hz, 2H), 5.20 (dd, J=8.0, 5.2 Hz, 2H), 5.54 (d, J=6.2 Hz, 2H), 7.33 (d, J=8.3 Hz, 2H), 7.40 (d, J=7.8 Hz, 2H), 7.51 (s, 2H), 7.57-7.61 (m, 2H), 7.72 (d, J=8.3 Hz, 2H); MS m/z 917.5 (M+H)$^+$.

Example 185B 4-(5-(4-(2,5-bis(4-bromophenyl)pyrrolidin-1-yl)phenyl)pyridin-2-yl)morpholine The product from Example 185A (0.1 g, 0.171 mmol), 4-(5-(4,4,5,5-tetramethyl-1,3,2-dioxaborolan-2-yl)pyridin-2-yl)morpholine (0.050 g, 0.171 mmol), potassium phosphate (0.028 mL, 0.343 mmol), tris(dibenzylideneacetone)

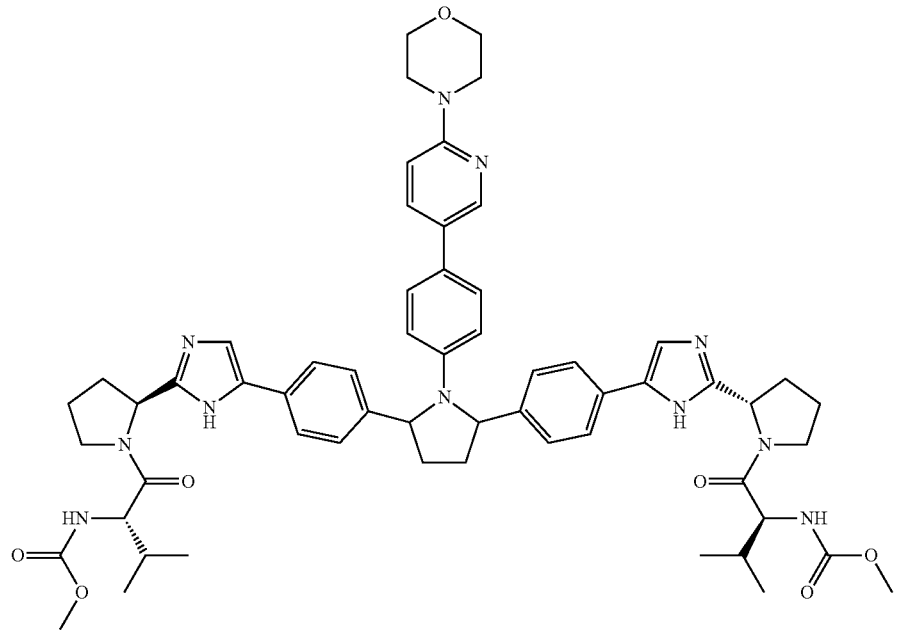 [SMILES: COC(=O)N[C@H](C(=O)N1CCC[C@H]1c1ncc(-c2ccc(C3CCC(c4ccc(-c5cnc([C@@H]6CCCN6C(=O)[C@@H](NC(=O)OC)C(C)C)[nH]5)cc4)N3c3ccc(-c4ccc(N5CCOCC5)nc4)cc3)cc2)[nH]1)C(C)C]

Example 185 methyl {(2S)-1-[(2S)-2-(5-{4-[(2S,5S)-5-(4-{2-[(2S)-1-{(2S)-2-[(methoxycarbonyl)amino]-3-methylbutanoyl}pyrrolidin-2-yl]-1H-imidazol-5-yl}phenyl)-1-{4-[6-(morpholin-4-yl)pyridin-3-yl]phenyl}pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(5-{4-[(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-{4-[6-(morpholin-4-yl)pyridin-3-yl]phenyl}pyrrolidin-2-yl]phenyl}-1H-imidazol-2-yl)pyrrolidin-1-yl]-3-methyl-1-oxobutan-2-yl}carbamate

Example 185A 2,5-bis(4-bromophenyl)-1-(4-iodophenyl)pyrrolidine

The product from Example 42B (1.39 g, 2.499 mmol) in DMF (6.25 mL) was treated with 4-iodoaniline (Aldrich, 4.38 g, 19.99 mmol), heated at 40-50° C. for two hours, cooled and diluted into EtOAc. The EtOAc layer was washed 3×50 mL with 1 M HCl, with water, brine, dried (Na$_2$SO$_4$), filtered and concentrated. Purification by flash chromatography on an ISCO 40 g silica cartridge eluting with 0-20% EtOAc in hexane afforded the title compound as a tan foam as a mixture of stereoisomers (0.96 g, 66%). MS (ESI) m/z 584 (M+H)$^+$.

dipalladium(0) (1.570 mg, 1.715 µmol) and 1,3,5,7-tetramethyl-6-phenyl-2,4,8-trioxa-6-phosphaadamante (1.504 mg, 5.14 µmol) were combined in THF (1.2 mL)/water (0.4 mL). The mixture was sparged with nitrogen for 15 minutes diluted into EtOAc, washed with 1M sodium bicarbonate, brine, dried (Na$_2$SO$_4$), filtered and concentrated. Purification by flash chromatography on an Isco 12 g silica cartridge eluting with 20-70% EtOAc in hexane gave the title compound as a cream colored powder (91 mg, 86%). %). MS (ESI) m/z 620 (M+H)$^+$.

Example 185C methyl {(2S)-1-[(2S)-2-(5-{4-[(2S,5S)-5-(4-{2-[(2S)-1-{(2S)-2-[(methoxycarbonyl)amino]-3-methylbutanoyl}pyrrolidin-2-yl]-1H-imidazol-5-yl}phenyl)-1-{4-[6-(morpholin-4-yl)pyridin-3-yl]phenyl}pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(5-{4-[(2R,5R)-5-(4-{2-[(2S)-1-{(2S)-2-[(methoxycarbonyl)amino]-3-methylbutanoyl}pyrrolidin-2-yl]-1H-imidazol-5-yl}phenyl)-1-{4-[6-(morpholin-4-yl)pyridin-3-yl]phenyl}pyrrolidin-2-yl]phenyl}-1H-imidazol-2-yl)pyrrolidin-1-yl]-3-methyl-1-oxobutan-2-yl}carbamate The product from Example 185B was processed as described in Example 42D, 42E, 42F, and 42G to afford the title compounds. $^1$H NMR (free base) (400 MHz, DMSO-d$_6$) δ 0.77-0.94 (m, 12H) 1.71-2.47 (m, 16H) 3.36-3.42 (m, 4H) 3.53 (s, 6H) 3.63-3.71 (m, 4H) 3.74-3.84 (m, 3H) 4.00-4.08 (m, 1H) 4.79 (d, J=4.23 Hz, 1H) 5.02-5.11 (m, 2H) 5.24-5.32 (m, 1H) 6.37 (d, J=8.89 Hz, 1H) 6.49 (d, J=8.78 Hz, 1H) 6.79 (dd, J=14.91, 8.95 Hz, 1H) 7.12-7.78 (m, 15H) 8.23-8.31 (m, 1H) 11.64-12.11 (m, 2H). MS (ESI) m/z 1046 (M+H)$^+$.

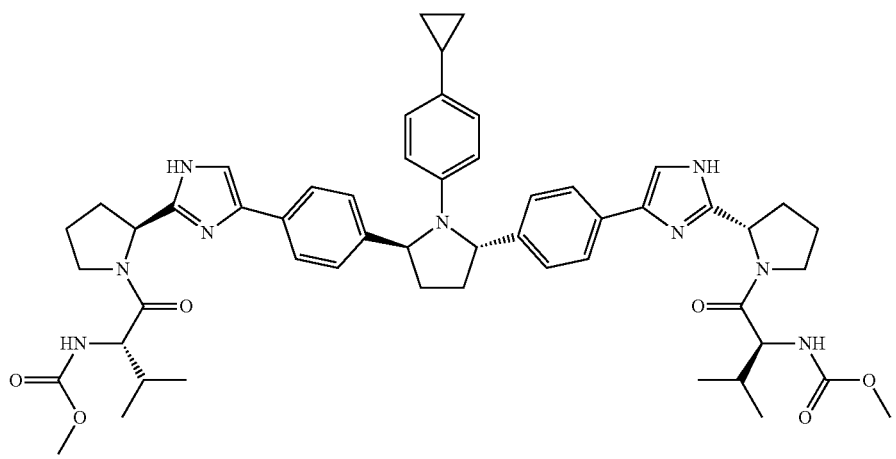 [SMILES: COC(=O)N[C@H](C(=O)N1CCC[C@H]1c1nc(-c2ccc([C@@H]3CC[C@@H](c4ccc(-c5c[nH]c([C@@H]6CCCN6C(=O)[C@@H](NC(=O)OC)C(C)C)n5)cc4)N3c3ccc(C4CC4)cc3)cc2)c[nH]1)C(C)C]

Example 186 methyl {(2S)-1-[(2S)-2-(4-{4-[(2S,5S)-1-(4-cyclopropylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)pyrrolidin-2-yl]phenyl}-1H-imidazol-2-yl)pyrrolidin-1-yl]-3-methyl-1-oxobutan-2-yl}carbamate The product from Example 95B was purified by chiral chromatography on a Chiralpak IB column eluting with a mixture of hexane/THF/methanol (85/10/5). The title compound was the second of the 2 diastereomers to elute. 1H NMR (400 MHz, DMSO-D6) δ ppm 0.35-0.42 (m, 2H) 0.65-0.73 (m, 2H) 0.80-0.92 (m, 12H) 1.58-1.65 (m, 1H) 1.67-1.71 (m, 2H) 1.87-2.02 (m, 6H) 2.07-2.17 (m, 4H) 3.53 (s, 6H) 3.70-3.85 (m, 4H) 4.05 (t, J=8.35 Hz, 2H) 5.06 (dd, J=6.72, 2.82 Hz, 2H) 5.16-5.25 (m, 2H) 6.19 (d, J=8.67 Hz, 2H) 6.64 (d, J=8.57 Hz, 2H) 7.09-7.32 (m, 6H) 7.36-7.69 (m, 6H) 11.60-12.09 (m, 2H); MS (ESI+) m/z 924.6 (M+H).

Example 187 dimethyl ([(2R,5R)-1-{3-[6-(morpholin-4-yl)pyridin-3-yl]phenyl}pyrrolidine-2,5-diyl]bis {(2-aminobenzene-4,1-diyl)carbamoyl(2S)pyrrolidine-2,1-diyl[(2S)-3-methyl-1-oxobutane-1,2-diyl]}) biscarbamate

Example 187A (2R,5R)-2,5-bis(4-chloro-3-nitrophenyl)-1-(3-iodophenyl)pyrrolidine The mesylate of Example 109C (4.17 g, 7.48 mmol) in DMF (15 ml) was treated with 3-iodoaniline (Aldrich, 7.2 mL, 59.8 mmol), stirred at ambient temperature for 48 hours and diluted into EtOAc. The EtOAc layer was washed 3×50 mL with 1 M HCl, with water, brine, dried (Na₂SO₄), filtered and concentrated. Purification by flash chromatography on an Isco 300 g silica cartridge eluting with 10-30% EtOAc in hexane afforded the title compound as a bright yellow foam (2.6 g, 60%). MS (ESI) m/z 584 (M+H)⁺.

Example 187B 4-(5-(3-((2R,5R)-2,5-bis(4-chloro-3-nitrophenyl)pyrrolidin-1-yl)phenyl)pyridin-2-yl)morpholine The product from Example 187A (1.4 g, 2.396 mmol), 4-(5-(4,4,5,5-tetramethyl-1,3,2-dioxaborolan-2-yl)pyridin-2-yl)morpholine (0.695 g, 2.396 mmol), potassium phosphate (1.017 g, 4.79 mmol), tris(dibenzylideneacetone)dipalladium(0) (0.022 g, 0.024 mmol) and 1,3,5,7-tetramethyl-6-phenyl-2,4,8-trioxa-6-phosphaadamantane (0.021 g, 0.072 mmol) were combined in THF (18 mL)/water (6 mL). The mixture was sparged with nitrogen for 15 minutes, stirred for 6 hours diluted into EtOAc, washed with 1M sodium bicarbonate, brine, dried ($Na_2SO_4$), filtered and concentrated. Purification by flash chromatography on an Isco 120 g silica cartridge eluting with 20-60% EtOAc in hexane gave the title compound as a yellow glass (1.1 g, 74%). MS (ESI) m/z 620 $(M+H)^+$.

Example 187C dimethyl ([(2R,5R)-1-{3-[6-(morpholin-4-yl)pyridin-3-yl]phenyl}pyrrolidine-2,5-diyl]bis{(2-aminobenzene-4,1-diyl)carbamoyl(2S)pyrrolidine-2,1-diyl[(2S)-3-methyl-1-oxobutane-1,2-diyl]}) biscarbamate The product from Example 187B (0.5 g, 0.806 mmol), was processed using the methods in Examples 165C and 165D to afford the title compound (400 mg, 45% two steps). $^1$H NMR (400 MHz, DMSO-$d_6$) δ 0.89 (dd, J=11.82, 6.61 Hz, 12H) 1.35-2.22 (m, 14H) 3.36-3.46 (m, 8H) 3.52 (s, 6H) 3.56-3.86 (m, 4H) 3.97-4.43 (m, 4H) 4.85 (s, 4H) 5.09 (s, 2H) 6.25 (d, J=7.26 Hz, 1H) 6.42-6.51 (m, 3H) 6.58 (s, 2H) 6.66 (d, J=7.59 Hz, 1H) 6.81 (d, J=8.78 Hz, 1H) 6.95-7.02 (m, 3H) 7.36 (d, J=8.35 Hz, 2H) 7.51 (dd, J=8.73, 2.33 Hz, 1H) 8.12 (d, J=2.06 Hz, 1H) 9.23 (s, 2H). MS (ESI) m/z 1031 $(M+H)^+$.

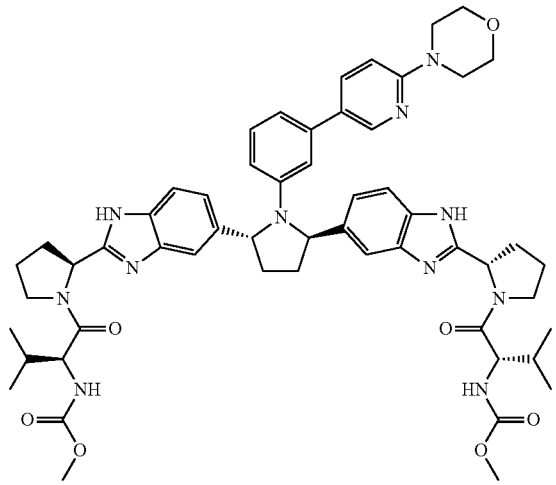 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cccc(-c4ccc(N5CCOCC5)nc4)c3)ccc2[nH]1)C(C)C]

Example 188 methyl {(2S)-1-[(2S)-2-{5-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-{3-[6-(morpholin-4-yl)pyridin-3-yl]phenyl}pyrrolidin-2-yl]-1H-benzimidazol-2-yl}pyrrolidin-1-yl]-3-methyl-1-oxobutan-2-yl}carbamate The product from Example 187C (0.4 g, 0.388 mmol) was treated with acetic acid (0.089 ml, 1.553 mmol) in toluene (7.77 ml) at 50° C. for 4 hours, cooled and concentrated. The residue was dissolved in EtOAc, washed with 10% sodium bicarbonate, brine, dried ($Na_2SO_4$), filtered and concentrated. Purification by flash chromatography on an Isco Gold 12 g silica cartridge eluting with 1-6% MeOH in dichloromethane afforded the title compound (183 mg, 45%). $^1$H NMR (400 MHz, DMSO-$d_6$) δ 0.71-0.90 (m, 12H) 1.62-2.28 (m, 14H) 3.37-3.43 (m, 4H) 3.53 (s, 6H) 3.64-3.68 (m, 4H) 3.80 (s, 4H) 4.05 (t, J=8.35 Hz, 2H) 5.08-5.19 (m, 2H) 5.48 (s, 2H) 6.29 (d, J=8.02 Hz, 1H) 6.54-6.64 (m, 2H) 6.76 (d, J=8.89 Hz, 1H) 6.93 (d, J=4.66 Hz, 1H) 7.11 (d, J=8.13 Hz, 2H) 7.23-7.30 (m, 3H) 7.34-7.40 (m, 2H) 7.46 (s, 2H) 8.05 (s, 1H) 12.01 (s, 2H). MS (ESI) m/z 995 $(M+H)^+$.

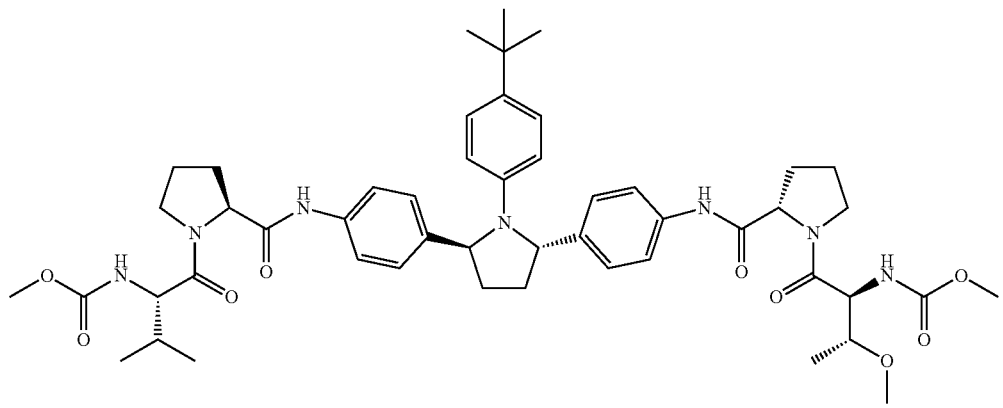

Example 189 methyl [(2S,3R)-1-{(2S)-2-[(4-{(2S,5S)-1-(4-tert-butylphenyl)-5-[4-({[(2S)-1-{(2S)-2-[(methoxycarbonyl)amino]-3-methylbutanoyl}pyrrolidin-2-yl]carbonyl}amino)phenyl]pyrrolidin-2-yl}phenyl)carbamoyl]pyrrolidin-1-yl}-3-methoxy-1-oxobutan-2-yl]carbamate

Example 189A (S)-tert-butyl 2-(4-((2S,5S)-1-(4-tert-butylphenyl)-5-(4-((S)-1-((S)-2-(methoxycarbonylamino)-3-methylbutanoyl)pyrrolidine-2-carboxamido)phenyl)pyrrolidin-2-yl)phenylcarbamoyl)pyrrolidine-1-carboxylate To a solution of the product from Example 213 (33 mg, 0.052 mmol) in anhydrous DMSO (0.5 mL) was added (S)-1-(tert-butoxycarbonyl)pyrrolidine-2-carboxylic acid (13.3 mg, 0.062 mmol), HATU (23.5 mg, 0.062 mmol) and Hunig's base (18 μL, 0.10 mmol). The resulting mixture was stirred at rt for 90 min and then partitioned between H₂O and EtOAc. The organic layer was dried over Na₂SO₄, filtered, and concentrated in vacuo. The crude product was purified by column chromatography on silica gel using a solvent gradient of 0-10% MeOH in CH₂Cl₂ to give the title compound (33 mg, 76%).

Example 189B methyl [(2S,3R)-1-{(2S)-2-[(4-{(2S,5S)-1-(4-tert-butylphenyl)-5-[4-({[(2S)-1-{(2S)-2-[(methoxycarbonyl)amino]-3-methylbutanoyl}pyrrolidin-2-yl]carbonyl}amino)phenyl]pyrrolidin-2-yl}phenyl)carbamoyl]pyrrolidin-1-yl}-3-methoxy-1-oxobutan-2-yl]carbamate A solution of the product from Example 189A (30 mg, 0.036 mmol) in a 1:1 mixture of CH₂Cl₂:TFA (0.4 mL) was stirred at rt for 45 min. The mixture was concentrated in vacuo, and the residue was partitioned between saturated aq. NaHCO₃ and EtOAc (2×). The combined organic layers were dried over Na₂SO₄, filtered and concentrated in vacuo to give a solid. The solid was subjected to the procedure described in Example 189A (27 mg), substituting (2S,3R)-3-methoxy-2-(methoxycarbonylamino)butanoic acid for (S)-1-(tert-butoxycarbonyl)pyrrolidine-2-carboxylic acid, to give the title compound (17 mg, 52%). 1H NMR (400 MHz, DMSO-D6) δ ppm 0.85-0.97 (m, 6H), 1.08-1.19 (m, 12H), 1.60-1.66 (m, 2H), 1.80-2.05 (m, 8H), 2.08-2.20 (m, 2H), 3.25 (s, 3H), 3.42-3.50 (m, 2H), 3.52 (s, 3H), 3.53 (s, 3H), 3.58-3.72 (m, 2H), 3.76-3.87 (m, 2H), 3.98-4.06 (m, 1H), 4.26 (t, J=7.81 Hz, 1H), 4.38-4.46 (m, 2H), 5.15 (d, J=6.40 Hz, 2H), 6.17 (d, J=8.78 Hz, 2H), 6.94 (d, J=8.89 Hz, 2H), 7.13 (d, J=8.24 Hz, 4H), 7.32 (t, J=8.84 Hz, 2H), 7.49 (dd, J=8.57, 2.06 Hz, 4H), 9.96 (d, J=15.51 Hz, 2H). MS (ESI) m/z 910.6 (M+H)⁺.

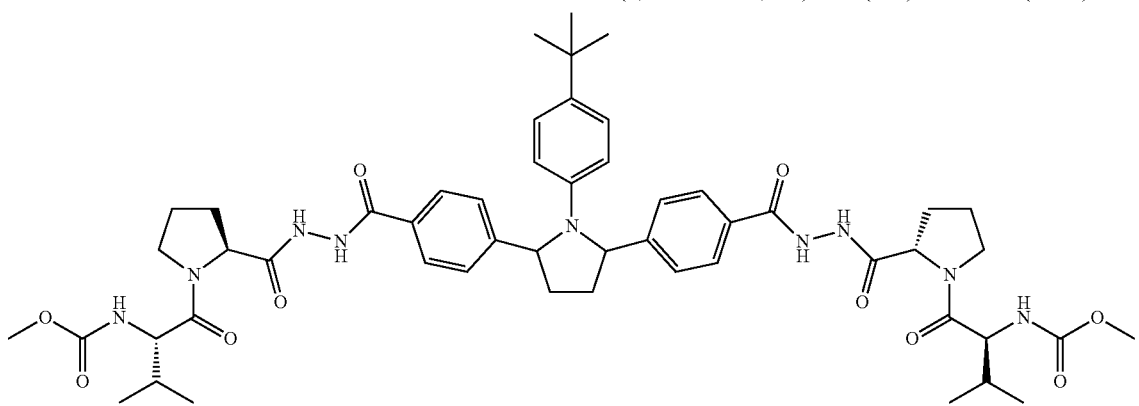

Example 190 dimethyl ([1-(4-tert-butylphenyl)pyrrolidine-2,5-diyl]bis{benzene-4,1-diylcarbonylhydrazine-2,1-diylcarbonyl(2S)pyrrolidine-2,1-diyl[(2S)-3-methyl-1-oxobutane-1,2-diyl]}biscarbamate)

To a solution of the product from Example 171B (50 mg, 0.106 mmol) and the product from Example 37B (72 mg, 0.27 mmol) in anhydrous DMSO (1 mL) was added HATU (100 mg, 0.27 mmol) and Hunig's base (56 μL, 0.32 mmol). The resulting mixture was stirred at rt for 90 min, and then partitioned between H₂O and EtOAc (2×). The combined organic layers were dried over Na₂SO₄, filtered, and concentrated in vacuo. The crude product was purified by column chromatography on silica gel using a solvent gradient of 0-10% MeOH in CH₂Cl₂ to give the title compound (68 mg, 65%) as a mixture of cis and trans stereoisomers. 1H NMR (400 MHz, DMSO-D6) δ ppm 0.81-0.98 (m, 12H), 1.08-1.17 (m, 9H), 1.64-1.77 (m, 2H), 1.78-2.06 (m, 8H), 2.07-2.22 (m, 2H), 3.50-3.55 (m, 6H), 3.58-3.69 (m, 2H), 3.70-3.83 (m, 2H), 3.96-4.08 (m, 2H), 4.38-4.49 (m, J=8.13 Hz, 2H), 4.76-4.87 (m, 0.7H), 5.28-5.40 (m, 1.3H), 6.14-6.33 (m, 2H), 6.92-7.08 (m, 2H), 7.27-7.38 (m, J=8.02 Hz, 5H), 7.62 (d, J=8.35 Hz, 1H), 7.79-7.96 (m, 4H), 9.87-9.98 (m, 2H), 10.31-10.44 (m, 2H); MS (ESI) m/z 981.1 (M+H)⁺.

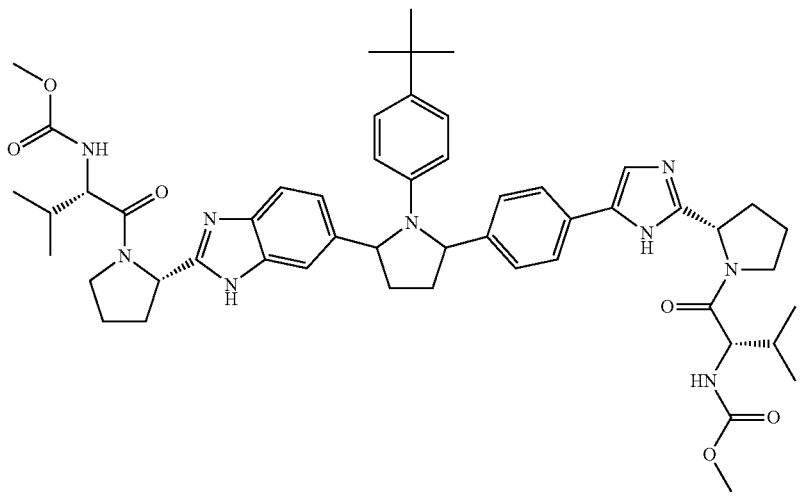 [SMILES: COC(=O)N[C@H](C(=O)N1CCC[C@H]1c1ncc(-c2ccc(C3CCC(c4ccc5nc([C@@H]6CCCN6C(=O)[C@@H](NC(=O)OC)C(C)C)[nH]c5c4)N3c3ccc(C(C)(C)C)cc3)cc2)[nH]1)C(C)C]

Example 191 methyl {(2S)-1-[(2S)-2-(5-{4-[(2S,5S)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(5-{4-[(2R,5R)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate

Example 191A 1-(4-bromophenyl)-4-(4-chloro-3-nitrophenyl)butane-1,4-dione

Zinc chloride (2.73 g, 20 mmole) was treated with anhydrous benzene (10 mL) followed by diethylamine (1.55 mL, 15 mmole) and tert-butanol (1.4 mL, 15 mmole) and the resulting slurry was stirred at room temperature for 1.75 hr until all solids had dissolved. To the cloudy suspension was added 4'-chloro-3'-nitroacetophenone followed by 2,4'-dibromoacetophenone and the resulting light yellow slurry was stirred at room temperature for 68 hours. The resulting thick white slurry was treated with 25 mL 5% aqueous sulfuric acid with stirring and the resulting slurry was filtered. The solid was washed with water (50 mL), MeOH (50 mL) and CH$_2$Cl$_2$ (50 mL), then dried in vacuo at room temperature for 1 hr and at 55° C. for 5 hr. giving the title compound as a white solid, 3.4 g, 86%.

Example 191B 1-(4-bromophenyl)-4-(4-chloro-3-nitrophenyl)butane-1,4-diol

The product from Example 191A (4.62 g, 11.65 mmole) was mixed with EtOH (100 mL) and the resulting slurry was treated in portions over a five minute period with solid NaBH$_4$ (0.97 g, 25.6 mmole). The resulting foaming slurry was stirred and heated at reflux for 1 hr. The reaction was deemed complete by LC-MS. The reaction mixture was cooled to room temperature and concentrated in vacuo to an oily residue. The residue was dissolved in CH$_2$Cl$_2$ and applied to an 80 g silica gel column. The column was eluted with a gradient of hexane/acetone, 90/10 to 20/80 over 32 minutes. The fractions containing product were pooled and concentrated in vacuo giving the title compound as a white solid, 3.14 g, 67%.

Example 191C 1-(4-bromophenyl)-4-(4-chloro-3-nitrophenyl)butane-1,4-diyl dimethanesulfonate The product from Example 191B (3.14 g, 7.84 mmole) was dissolved in 70 mL CH$_2$Cl$_2$ and cooled in an ice-acetone bath to −10° C. Triethylamine (3.82 mL, 27.4 mmole) was added dropwise to the cold solution, followed by dropwise addition of methanesulfonyl chloride (1.53 mL, 19.59 mmole) in 20 mL CH$_2$Cl$_2$ over 10 minutes. The resulting clear solution was stirred in the cold for 90 min. The reaction was deemed complete by LC-MS analysis and the solvent was removed in vacuo leaving a light yellow solid as the title compound, (4.36 g, 100%), that was used directly in the next reaction.

Example 191D 2-(4-bromophenyl)-1-(4-tert-butylphenyl)-5-(4-chloro-3-nitrophenyl)pyrrolidine The light yellow solid, obtained in Example 191C (4.36 g, 7.84 mmole) was treated with DMF (15 mL) followed by dropwise addition of 4-tert-butylaniline (12.47 mL, 78 mmole), then placed in an oil bath at 52° C. and stirred for a total of 12 hr. The reaction mixture was concentrated in vacuo to an oily residue. The mixture was diluted with 100 mL EtOAc and washed with 50 mL 0.5 M HCl. The aqueous layer was back extracted with 100 mL EtOAc. The combined organic extracts were washed with 10% NaHCO$_3$, 10% NaCl, dried over anhydrous Na$_2$SO$_4$(s), filtered and solvent removed in vacuo leaving a reddish oil. The oil was dissolved in CH$_2$Cl$_2$ (10 mL) and applied to an 80 g silica gel column. The column was eluted with a gradient of hexane/Acetone, 90/10 to 30/70 over 32 minutes. The title compound was isolated as a 1:1 mixture of cis and trans-pyrrolidine isomers, 3.13 g, 75%.

Example 191E 4-(5-(4-bromophenyl)-1-(4-tert-butylphenyl)pyrrolidin-2-yl)-N-(2,4-dimethoxybenzyl)-2-nitroaniline The product from Example 191D (1.1 g, 2.14 mmole) was treated with 2,4-dimethoxybenzylamine (3.22 mL, 21.41 mmole) and the resulting slurry was heated at 140° C. (oil bath) for 1 hr. The resulting homogeneous red reaction mixture was concentrated in vacuo leaving a red oil. The oil was diluted with 30 mL $CH_2Cl_2$, filtered solid and applied the filtrate to a 120 g silica gel column. The column was eluted with $CH_2Cl_2$ over a 25 min period. The fractions were pooled and concentrated in vacuo giving the title compound as an orange foamy solid as a mixture of stereoisomers (1.18 g).

Example 191F 4-(5-(4-bromophenyl)-1-(4-tert-butylphenyl)pyrrolidin-2-yl)-N1-(2,4-dimethoxybenzyl)benzene-1,2-diamine The product from example 191E (1.18 g, 1.831 mmole) was dissolved in a mixture of THF (10 mL):EtOH (10 mL):EtOAc (10 mL), treated with $PtO_2$ (42 mg) and evacuated 10 minutes, followed by introduction of $H_2$ (g) via balloon. The reaction mixture was stirred overnight at room temperature. The next day, the reaction mixture was filtered and the solvent removed in vacuo leaving a dark green foamy solid. The solid was dissolved in 10 mL $CH_2Cl_2$ applied to a 40 g silica gel column and eluted with a gradient of hexane/EtOAc; 90/10 to 30/70 over 20 minutes. The title compound was isolated as a white foamy solid as a mixture of isomers 0.54 g, 48%.

Example 191G methyl (2S)-1-((2S)-2-(5-(5-(4-bromophenyl)-1-(4-tert-butylphenyl)pyrrolidin-2-yl)-2-(2,4-dimethoxybenzylamino)phenylcarbamoyl)pyrrolidin-1-yl)-3-methyl-1-oxobutan-2-ylcarbamate (S)-1-((S)-2-(methoxycarbonylamino)-3-methylbutanoyl)pyrrolidine-2-carboxylic acid (0.339 g, 1.245 mmole) and HOBt (0.191 g, 1.245 mmole) were dissolved in DMF (4 mL) cooled in an ice bath and treated with EDAC (0.245 g, 1.245 mmole) and N-Methylmorpholine (NMM) (0.55 mL, 4.98 mmole). The resulting solution was stirred 5 minutes in the ice bath, treated dropwise with the product from Example 191F in DMF (4 mL) and the resulting dark mixture was stirred in the ice bath for 1 hr then at room temperature for 18 hr. The next day, the reaction mixture was diluted with EtOAc (50 mL) and the organic layer was washed with 10% $NaHCO_3$ and 10% NaCl, dried over anhydrous $Na_2SO_4$(s), filtered and the solvent was removed in vacuo leaving an oily residue as the title compound as a mixture of isomers (0.65 g). ESI+(m/z): 868.2.

Example 191H methyl (2S)-1-((2S)-2-(2-amino-5-(5-(4-bromophenyl)-1-(4-tert-butylphenyl)pyrrolidin-2-yl)phenylcarbamoyl)pyrrolidin-1-yl)-3-methyl-1-oxobutan-2-ylcarbamate The product from example 191G (0.65 g, 0.748 mmole) was dissolved in $CH_2Cl_2$ (10 mL) then added concentrated trifluoroacetic acid (2 mL, 26 mmole)) and the reaction mixture was stirred 10 minutes. The solvent was removed in vacuo and the residue was re-evaporated twice from $CH_2Cl_2$ and once from toluene. The residue was dissolved in EtOAc (100 mL) washed with 10% $NaHCO_3$, dried over anhydrous $Na_2SO_4$(s), filtered and solvent removed in vacuo leaving a brown foamy material as the title compound as a mixture of isomers (0.5 g).

Example 191I methyl (2S)-1-((2S)-2-(6-(5-(4-bromophenyl)-1-(4-tert-butylphenyl)pyrrolidin-2-yl)-1H-benzo[d]imidazol-2-yl)pyrrolidin-1-yl)-3-methyl-1-oxobutan-2-ylcarbamate The product from Example 191H (0.5 g, 0.696 mmole) was treated with acetic acid (5 mL, 87 mmole) and heated in an oil bath at 75° C. for 70 min. The reaction mixture was cooled to room temperature and concentrated in vacuo leaving an oily residue. The residue was dissolved in EtOAc (100 mL) washed with 10%0/$NaHCO_3$ (20 mL) and 10% NaCl (20 mL), dried over anhydrous $Na_2SO_4$(s), filtered and solvent removed in vacuo leaving a brown foamy solid. The residue was dissolved in 10 mL $CH_2Cl_2$ and applied to a 12 g silica gel column. The column was eluted with a gradient of $CH_2Cl_2$/MeOH, 99/1 to 95/5 over 15 minutes and the product was isolated as a tan solid as a mixture of isomers (0.31 g). ESI (m/z)+: 702.3.

Example 191J methyl (2S)-1-((2S)-2-(6-(1-(4-tert-butylphenyl)-5-(4-(4,4,5,5-tetramethyl-1,3,2-dioxaborolan-2-yl)phenyl)pyrrolidin-2-yl)-1H-benzo[d]imidazol-2-yl)pyrrolidin-1-yl)-3-methyl-1-oxobutan-2-ylcarbamate The product from Example 191I (0.31 g, 0.442 mmole), bis(pinacolato)diboron (0.34 g, 1.327 mmole) and potassium acetate (0.17 g, 1.77 mmole) were combined and dissolved in toluene (5 mL), added 1,1'-bis(diphenylphosphino)ferrocenedichloro palladium(II) dichloromethane complex (32 mg, 0.044 mmole) and the reaction mixture was bubbled with $N_2$ for 5 minutes, sealed and placed in an oil bath at 95° C. for 2 hr. The mixture was cooled to room temperature and diluted with EtOAc (100 mL) washed with water (20 mL) and 10% NaCl (20 mL), dried over anhydrous $Na_2SO_4$(s), filtered and solvent removed in vacuo leaving a brown oil. The oil was dissolved in $CH_2Cl_2$ (10 mL), applied to a 12 g silica gel column and the column was eluted with a gradient of hexane:EtOAc, 50:50 to 0:100 over 18 minutes. The title compound was isolated as a white solid as a mixture of isomers (0.23 g).

Example 191K (2S)-tert-butyl 2-(5-(4-(1-(4-tert-butylphenyl)-5-(2-((S)-1-((S)-2-(methoxycarbonylamino)-3-methylbutanoyl)pyrrolidin-2-yl)-1H-benzo[d]imidazol-6-yl)pyrrolidin-2-yl)phenyl)-1H-imidazol-2-yl)pyrrolidine-1-carboxylate The product from example 191J (0.23 g, 0.308 mmole) and the product from Example 26D (0.195 g, 0.615 mmole) were combined in a 20 mL microwave tube and dissolved in toluene (1.5 mL)/ethanol (1.5 mL). To this solution was added 1M aqueous sodium carbonate 0.92 mL, 0.92 mmole) followed by 1,1'-bis(diphenylphosphino)ferrocenedichloro palladium (II) dichloromethane complex (23 mg, 0.036 mmole) and the resulting mixture was bubbled with $N_2$ for 10 minutes, sealed and heated at 100° C. for 2 hr. The reaction mixture was cooled to room temperature and diluted with EtOAc (50 mL). The aqueous carbonate layer was separated and the organic layer was washed with water (20 mL) and 10% NaCl (20 mL), dried over anhydrous $Na_2SO_4$(s), filtered and solvent removed in vacuo leaving a foamy solid. The solid was dissolved in 10 mL $CH_2Cl_2$ and applied to a 12 g silica gel column. The column was eluted with a gradient of $CH_2Cl_2$/MeOH, 99/1 to 95/5 over 20 minutes. The title compound was obtained as a tan solid as a mixture of isomers (0.11 g).

Example 191L (2S)-2-(5-(4-(1-(4-tert-butylphenyl)-5-(2-((S)-1-((S)-2-(methoxycarbonylamino)-3-methylbutanoyl)pyrrolidin-2-yl)-1H-benzo[d]imidazol-6-yl)pyrrolidin-2-yl)phenyl)-1H-imidazol-2-yl)pyrrolidinium chloride The product from example 191K (0.11 g, 0.28 mmole) was dissolved in dioxane (2 mL), then added 4N HCl/dioxane (1 mL). The resulting solid mass is stirred 30 minutes at room temperature. The solvent is removed in vacuo leaving a tan solid as the title compound as a mixture of isomers (0.092 g) which stored under vacuum overnight.

(0.020 g, 0.116 mmole) and HOBt (000.018 g, 0.116 mmole) were combined in a 25 mL RB flask and dissolved in DMF (1 mL). The reaction mixture was placed in an ice bath and treated with EDAC (0.022 g, 0.116 mmole) and N-methylmorpholine (0.12 mL, 1.091 mmole. The light yellow reaction mixture was stirred in the ice bath for 1 hr, then stirred at room temperature for 9 hr. The reaction mixture was diluted with EtOAc (100 mL) washed with water (20 mL) and 10% NaCl (20 mL), dried over anhydrous $Na_2SO_4$(s), filtered and solvent removed in vacuo leaving an oily residue. The residue was dissolved in 5 mL $CH_2Cl_2$ and applied to a 12 g silica gel column. The column was eluted with a gradient of $CH_2Cl_2$/MeOH, 99/1 to 95/5 over 22 minutes. The title compound was isolated from the first fraction eluted from the column as a white solid consisting of a mixture of trans-pyrrolidine isomers, 21 mg, 19%. $^1$H NMR (400 MHz, DMSO-$d_6$) δ ppm 0.71-0.95 (m, 12H) 1.11 (s, 9H) 1.99 (m, 6H) 2.13 (m, 4H) 3.53 (s, 6H) 3.81 (m, 4H) 4.04 (m, 4H) 5.06 (m, 2H) 5.11-5.15 (m, 1H) 5.18-5.26 (m, 1H) 5.32 (m, 1H) 6.25 (m, 2H) 6.86-6.96 (m, 1H) 7.05 (m, 2H) 7.33 (m, 6H) 7.61 (m, 2H) 11.53 (s, 1H) 11.68 (s, 1H) 12.00 (m, 2H); ESI+: 914.5.

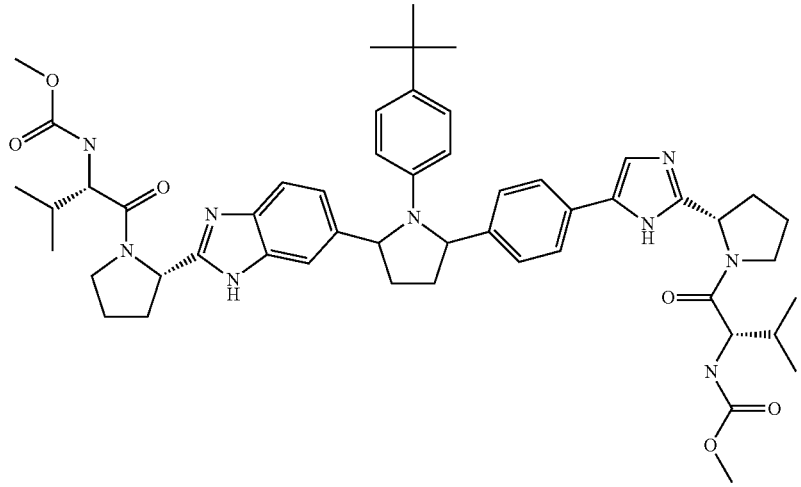 [SMILES: COC(=O)N[C@H](C(=O)N1CCC[C@H]1c1ncc(-c2ccc(C3CCC(c4ccc5nc([C@@H]6CCCN6C(=O)[C@@H](NC(=O)OC)C(C)C)[nH]c5c4)N3c3ccc(C(C)(C)C)cc3)cc2)[nH]1)C(C)C]

Example 191M methyl {(2S)-1-[(2S)-2-(5-{4-[(2S,5S)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(5-{4-[(2R,5R)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate The product from example 191L (0.092 g, 0.116 mmole), (S)-2-(methoxycarbonylamino)-3-methylbutanoic acid Example 192 methyl {(2S)-1-[(2S)-2-(5-{4-[(2R,5S)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate and methyl {(2S)-1-[(2S)-2-(5-{4-[(2S,5R)-1-(4-tert-butylphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]phenyl}-1H-imidazol-2-yl)pyrrolidin-1-yl]-3-methyl-1-oxobutan-2-yl}carbamate The title compound was isolated from the late fraction eluted from the column described in Example 191M as a white solid as a mixture of cis pyrrolidine isomers, 18 mg, 17%. ¹H NMR (free base) (400 MHz, DMSO-$d_6$) δ ppm 0.71-0.95 (m, 12H) 1.11 (s, 9H) 1.99 (m, 6H) 2.13 (m, 4H) 3.53 (s, 6H) 3.81 (m, 4H) 4.04 (m, 4H) 4.72 (m, 1H), 4.83 (m, 1H) 5.11-5.15 (m, 1H) 5.18-5.26 (m, 1H) 5.32 (m, 1H) 6.25 (m, 2H) 6.86-6.96 (m, 1H) 7.05 (m, 2H) 7.33 (m, 6H) 7.61 (m, 2H) 11.53 (s, 1H) 11.68 (s, 1H) 12.00 (m, 2H); ESI+: 914.5.

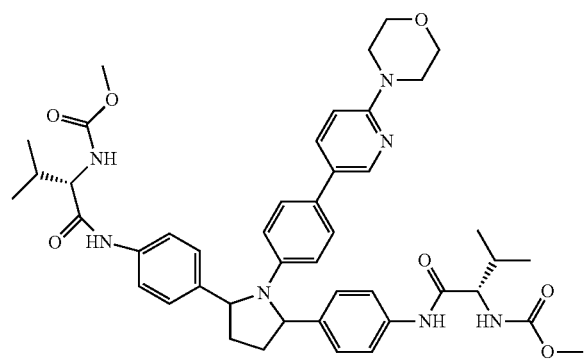 [SMILES: COC(=O)N[C@H](C(=O)Nc1ccc(C2CCC(c3ccc(NC(=O)[C@@H](NC(=O)OC)C(C)C)cc3)N2c2ccc(-c3ccc(N4CCOCC4)nc3)cc2)cc1)C(C)C]

Example 193 dimethyl ([(2S,5S)-1-{4-[6-(morpholin-4-yl)pyridin-3-yl]phenyl}pyrrolidine-2,5-diyl]bis{benzene-4,1-diylimino[(2S)-3-methyl-1-oxobutane-1,2-diyl]}) biscarbamate and dimethyl ([(2R,5R)-1-{4-[6-(morpholin-4-yl)pyridin-3-yl]phenyl}pyrrolidine-2,5-diyl]bis{benzene-4,1-diylimino[(2S)-3-methyl-1-oxobutane-1,2-diyl]}) biscarbamate Example 86A and 4-(5-(4,4,5,5-tetramethyl-1,3,2-dioxaborolan-2-yl)pyridin-2-yl)morpholine were processed using sequentially the methods of Examples 99A, 99B, and 1F (substituting (S)-2-(methoxycarbonylamino)-3-methylbutanoic acid (38.2 mg, 0.218 mmole) for (S)-1-(tert-butoxycarbonyl)pyrrolidine-2-carboxylic acid). Reverse phase (C18) HPLC provided the title compound, a white solid, as a 1:1 mixture of trans diastereomers (40.4 mg, 50.6% yield). 1H NMR (free base) (400 MHz, DMSO-D6) δ ppm 0.89 (d, J=6.72 Hz, 12H) 1.67 (d, J=5.64 Hz, 2H) 1.92-2.04 (m, 2H) 3.37-3.41 (m, 4H) 3.53 (d, J=2.06 Hz, 6H) 3.67 (d, J=5.10 Hz, 4H) 3.94 (t, J=8.08 Hz, 2H) 5.25 (s, 2H) 6.33 (d, J=8.67 Hz, 2H) 6.78 (d, J=8.89 Hz, 1H) 7.14-7.23 (m, 6H) 7.32 (d, J=8.67 Hz, 2H) 7.54 (d, J=7.92 Hz, 4H) 7.66 (dd, J=8.84, 2.55 Hz, 1H) 8.26 (d, J=2.49 Hz, 1H) 10.01 (s, 2H). MS ESI(+) m/z 806.5 (M+H)+.

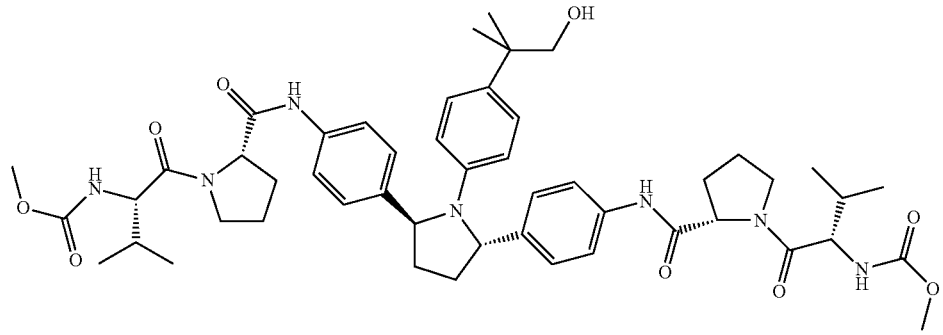 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)CO)cc2)cc1)C(C)C]

Example 194 dimethyl ({(2S,5S)-1-[4-(1-hydroxy-2-methylpropan-2-yl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate)

Example 194A ethyl 2-methyl-2-(4-nitrophenyl)propanoate

Into a 500 mL Morton flask equipped for mechanical stirring was added at room temperature under nitrogen ethyl 2-(4-nitrophenyl)acetate (10.0 g, 55.2 mmole), anhydrous dimethylformamide (200 mL) 18-crown-6 (2.189 g, 8.28 mmole) and methyl iodide (23.13 mL, 370 mmole). The flask was cooled in an ice bath and sodium hydride as a 60% mineral oil dispersion (7.73 g, 193 mmole) was added in portions so as to maintain the internal temperature at or below +10° C. The addition required fifty three minutes. On completion of the addition the reaction mixture was allowed to slowly warm to room temperature and stirred overnight. Subsequent cooling in an ice bath was followed by the drop wise addition of water (200 mL) with vigorous stirring. The mixture was partitioned between water (1200 mL) and ethyl ether (200 mL). The aqueous phase was extracted with ethyl ether (3×200 mL each) and the combined organics water washed (3×150 mL), dried over MgSO₄, filtered and concentrated to provide the title compound in nearly quantitative yield sufficiently pure for use as isolated.

Example 194B 2-methyl-2-(4-nitrophenyl)propan-1-ol

To a solution of the product from Example 194A (12.32 g, 55.2 mmole) in anhydrous THF (300 mL) at room temperature under nitrogen was added dropwise via cannulae 1M BH₃ in THF (200 mL) over ten and one half minutes. On completion of the addition the flask was equipped with a condenser and the mixture heated under nitrogen to reflux in an oil bath for ten hours before cooling to room temperature. The reaction was quenched by the cautious drop wise addition of methanol (60 mL). The resulting mixture was concentrated to an oil which was then dissolved in ethyl acetate (150 mL) and treated with 1N HCl and allowed to stir at room temperature for one hour. The resulting organic phase was washed with brine (4×50 mL), dried over MgSO$_4$, filtered and concentrated. The residue was taken up in toluene (25 mL) and re-concentrated. The oily solid was suspended in hexane (50 mL) and collected by vacuum filtration. The cake was washed with hexane (50 mL) then dried under vacuum to provide the title compound (9.55 g, 89% yield) as a light orange solid. MS (DCI+) m/z@213.1 (M+NH$_4$)+.

Example 194C 2-(4-aminophenyl)-2-methylpropan-1-ol

The product from Example 194B (0.321 g, 1.644 mmole) was dissolved in a mixture of THF (10 mL) and ethanol (2 mL). To this was added platinum(IV)oxide (0.030 g, 0.131 mmole). The flask was capped with a septum and the contents vacuum degassed three times. Hydrogen was introduced via a balloon and the mixture stirred at room temperature. An additional 38.2 mg (0.167 mmole) of catalyst was added in two aliquots before chromatographic analysis indicated that the starting material was consumed. After stirring overnight under hydrogen the mixture was filtered through a sand/celite plug followed by an ethyl acetate rinse. The filtrate was concentrated to dryness and the residue purified by chromatography on amine modified silica gel eluting with ethyl acetate-hexane beginning at 8% and advancing to 66% ethyl acetate to provide the title compound (0.3645 g, 68% yield) as a clear oil. MS (DCI+) m/z@183.1 (M+NH$_4$)+.

Example 194D 2-(4-((2S,5S)-2,5-bis(4-nitrophenyl)pyrrolidin-1-yl)phenyl)-2-methylpropan-1-ol The product from Example 194C (0.595 g, 3.60 mmole) was combined in DMF (3 mL) with (1R,4R)-1,4-bis(4-nitrophenyl)butane-1,4-diyl dimethanesulfonate (0.259 g, 0.530 mmole), prepared as described in Example 37C, then heated overnight under nitrogen in an oil bath at 50° C. The reaction mixture was partitioned between ethyl acetate (50 mL) and water (50 mL). The organic phase was water washed (3×25 mL), dried over MgSO$_4$, filtered and concentrated to an oil. Chromatography on silica gel eluting with ethyl acetate-hexane provided the title compound (0.0835 g, 34.1% yield) as an orange semi-solid.

Example 194E 2-(4-((2S,5S)-2,5-bis(4-aminophenyl)pyrrolidin-1-yl)phenyl)-2-methylpropan-1-ol The product from Example 194D (83.5 mg, 0.181 mmole) was reacted as described in Example 99B to provide the title compound in quantitative yield as a light yellow solid. MS (DCI+) m/z@402.3 (M+H)+.

Example 194F dimethyl ({(2S,5S)-1-[4-(1-hydroxy-2-methylpropan-2-yl)phenyl]pyrrolidine-2,5-diyl}bis{benzene-4,1-diylcarbamoyl(2S)pyrrolidine-2,1-diyl[(2S)-3-methyl-1-oxobutane-1,2-diyl]})biscarbamate)

The product from Example 194E (73.0 mg, 0.181 mmole) was reacted with the product from Example 37B (104.0 mg, 0.380 mmole) as described in Example 37F. The title compound was isolated after purification by reverse phase (C18) HPLC as an off white solid (97.4 mg, 59% yield). 1H NMR (free base) (400 MHz, DMSO-D6) δ ppm 0.79-0.96 (m, 12H) 1.03 (s, 6H) 1.61 (s, 2H) 1.76-2.04 (m, 8H) 2.04-2.17 (m, 2H) 3.20 (dd, J=5.42, 1.84 Hz, 2H) 3.51 (s, 6H) 3.60 (dd, 2H) 3.78 (s, 2H) 4.01 (t, 8.46 Hz, 2H) 4.35-4.49 (m, 3H) 5.14 (s, 2H) 6.16 (d, J=8.78 Hz, 2H) 6.89 (d, J=8.78 Hz, 2H) 7.12 (d, J=8.57 Hz, 4H) 7.29 (d, J=8.35 Hz, 2H) 7.48 (d, J=8.46 Hz, 4H) 9.97 (s, 2H). MS ESI(+), m/z 910.7 (M+H)+.

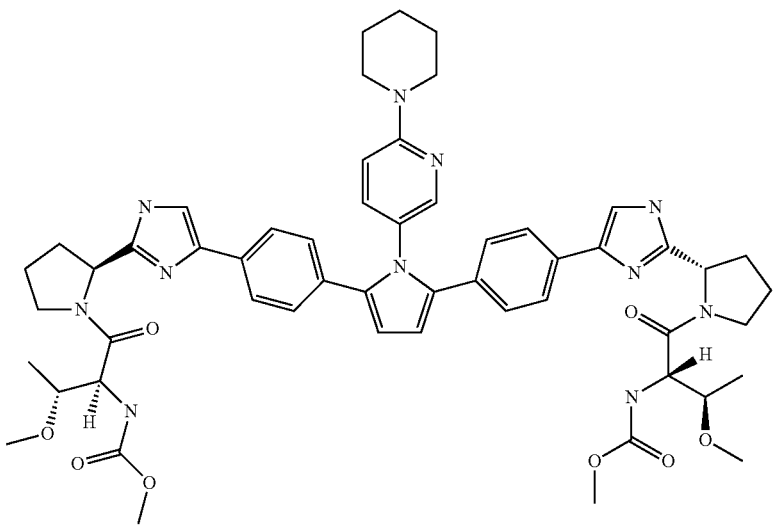 [SMILES: COC(=O)N[C@H](C(=O)N1CCC[C@H]1c1nc(-c2ccc(-c3ccc(-c4ccc(-c5c[nH]c([C@@H]6CCCN6C(=O)[C@@H](NC(=O)OC)[C@@H](C)OC)n5)cc4)n3-c3ccc(N4CCCCC4)nc3)cc2)c[nH]1)[C@@H](C)OC]

Example 195 methyl [(1S,2R)-2-methoxy-1-({(2S)-2-[4-(4-{5-[4-(2-{(2S)-1-[N-(methoxycarbonyl)-O-methyl-L-threonyl]pyrrolidin-2-yl}-1H-imidazol-4-yl)phenyl]-1-(6-piperidin-1-ylpyridin-3-yl)-1H-pyrrol-2-yl}phenyl)-1H-imidazol-2-yl]pyrrolidin-1-yl}carbonyl)propyl]carbamate The title compound was prepared using the methods from Example 144E substituting (2S,3S)-3-methoxy-2-(methoxycarbonylamino)butanoic acid for (S)-2-(methoxycarbonylamino)-3-methylbutanoic acid to provide the title compound (280 mg, 37% yield). $^1$H NMR (400 MHz, DMSO-D6) δ 12.12-11.70 (m, 2H), 7.85-7.76 (m, 1H), 7.63-7.49 (m, 4H), 7.49-7.39 (m, 2H), 7.34-7.03 (m, 7H), 6.77-6.69 (m, 1H), 6.54-6.41 (m, 2H), 5.08-4.99 (m, 2H), 4.27 (t, J=7.6, 2H), 3.86-3.75 (m, 4H), 3.54 (s, 6H), 3.50-3.43 (m, 4H), 3.17 (s, 6H), 2.19-1.88 (m, 10H), 1.61-1.44 (m, 6H), 1.12-0.99 (m, 6H). MS (ESI; M+H) m/z=997.

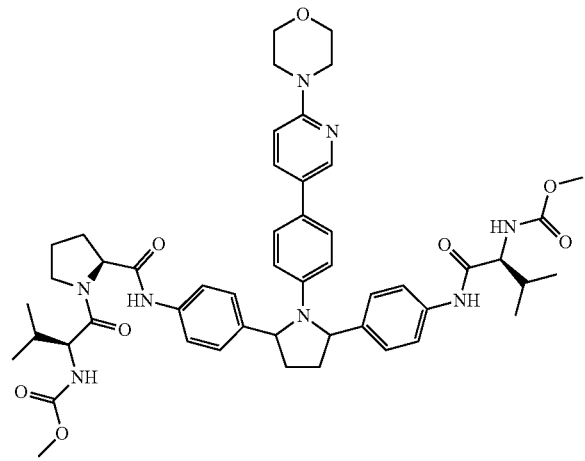 [SMILES: COC(=O)N[C@H](C(=O)Nc1ccc(C2CCC(c3ccc(NC(=O)[C@@H]4CCCN4C(=O)[C@@H](NC(=O)OC)C(C)C)cc3)N2c2ccc(-c3ccc(N4CCOCC4)nc3)cc2)cc1)C(C)C]

Example 196

N-(methoxycarbonyl)-L-valyl-N-{4-[(2S,5S)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide and N-(methoxycarbonyl)-L-valyl-N-{4-[(2R,5R)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide

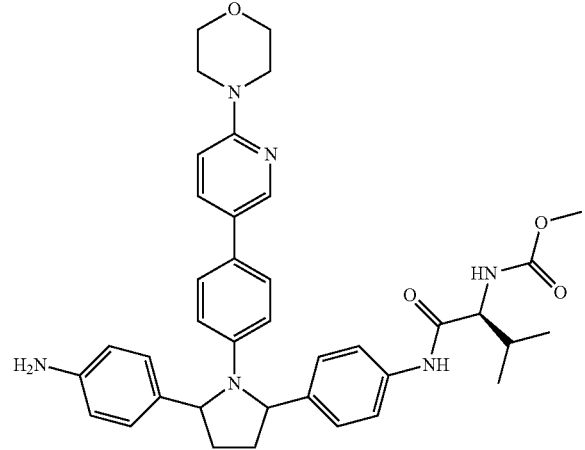 [SMILES: COC(=O)N[C@H](C(=O)Nc1ccc(C2CCC(c3ccc(N)cc3)N2c2ccc(-c3ccc(N4CCOCC4)nc3)cc2)cc1)C(C)C]

Example 196A methyl (2S)-1-(4-(5-(4-aminophenyl)-1-(4-(6-morpholinopyridin-3-yl)phenyl)pyrrolidin-2-yl)phenylamino)-3-methyl-1-oxobutan-2-ylcarbamate In an oven-dried 5-mL round bottom flask purged with nitrogen, dissolved 4,4'-(1-(4-(6-morpholinopyridin-3-yl)phenyl)pyrrolidine-2,5-diyl)dianiline (30 mg, 0.061 mmol; prepared from Example 86A and 4-(5-(4,4,5,5-tetramethyl-1,3,2-dioxaborolan-2-yl)pyridin-2-yl)morpholine using the methods of Examples 99A and 99B), and (S)-2-(methoxycarbonylamino)-3-methylbutanoic acid (11.22 mg, 0.064 mmol) in anhydrous DMSO (1 mL), added HATU (26.3 mg, 0.067 mmol) and diisopropylethylamine (0.021 mL, 0.122 mmol), and stirred yellow solution at 25° C. for 30 min. Diluted the reaction with MeOH (1 mL) and purified by RP-$C_{18}$ HPLC (Waters Prep LC, 40 mm Module with Nova Pak HR $C_{18}$ 6 μm 40×100 mm Prep Pak cartridge) eluting with a 30 min gradient of 95:5 0.1% TFA in $H_2O$/AcCN to 25:75 0.1% TFA in $H_2O$/AcCN, then 10 min to 100% AcCN at 20 mL/min. Pure fractions were concentrated by rotary evaporation (water bath 35°) to a small volume, partitioned between 20% iPrOH/CHCl$_3$ (50 mL) and sat'd aq NaHCO$_3$ (15 mL), separated layers, dried the organic extract over anhydrous MgSO$_4$, filtered, and concentrated by rotary evaporation to afford the title compound as an off-white solid (14.6 mg, 37%) as a mixture of stereoisomers. MS (ESI+) m/z 649 (M+H)$^+$, 707 (M+AcCN+NH$_4$)$^+$, 1297 (2M+H)$^+$.

Example 196B

N-(methoxycarbonyl)-L-valyl-N-{4-[(2S,5S)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide and N-(methoxycarbonyl)-L-valyl-N-{4-[(2R,5R)-5-(4-{[N-(methoxycarbonyl)-L-valyl]amino}phenyl)-1-{4-[6-(morpholin-4-yl)pyridin-3-yl]phenyl}pyrrolidin-2-yl]phenyl}-L-prolinamide In a nitrogen-purged 5-mL round bottom flask, dissolved the product of Example 196A (14 mg, 0.022 mmol) in anhydrous DMSO (1 mL), added the product of Example 37B (6.46 mg, 0.024 mmol), HATU (9.30 mg, 0.024 mmol), and diisopropylethylamine (7.54 μL, 0.043 mmol). Stirred at 25° C. for 1 hr, diluted the reaction with MeOH (1 mL) and purified by RP-$C_{18}$ HPLC (Waters Prep LC, 40 mm Module with Nova Pak HR $C_{18}$ 6 μm 40×100 mm Prep Pak cartridge) eluting with a 30 min gradient of 95:5 0.1% TFA in $H_2O$/AcCN to 25:75 0.1% TFA in $H_2O$/AcCN, then 10 min to 100% AcCN at 20 mL/min. Pure fractions were concentrated by rotary evaporation (water bath 35° C.) to near-dryness, the residue taken up in 1:5 v/v CH$_2$Cl$_2$/hexanes and evaporated (3 times), and the residue dried in vacuo to give a yellow solid (11 mg). The TFA salt was dissolved in 20% iPrOH/CHCl$_3$ (30 mL), washed thoroughly with sat'd aq NaHCO$_3$ (5 mL), extracted the aqueous phase with 20% iPrOH/CHCl$_3$ (20 mL), dried the combined organic extracts over anhydrous MgSO4, filtered, and concentrated by rotary evaporation to afford the title compounds as a white solid (7 mg, 35%). $^1$H NMR (400 MHz, DMSO-D6) δ ppm 0.83-0.96 (m, 12H), 1.60-1.71 (m, 2H), 1.81-2.21 (m, 7H), 3.36-3.43 (m, 4H), 3.49-3.56 (m, 6H), 3.58-3.65 (m, 1H), 3.65-3.70 (m, 4H), 3.75-3.85 (m, 1H), 3.94 (t, J=8.08 Hz, 1H), 4.02 (t, J=8.19 Hz, 1H), 4.42 (dd, J=7.86, 4.93 Hz, 1H), 5.24 (d, J=5.31 Hz, 2H), 6.32 (d, J=8.35 Hz, 2H), 6.78 (d, J=9.00 Hz, 1H), 7.13-7.19 (m, 4H), 7.21 (d, J=8.78 Hz, 2H), 7.26-7.35 (m, 2H), 7.48-7.56 (m, 4H), 7.66 (dd, J=7.86, 1.14 Hz, 1H), 8.25 (d, J=2.17 Hz, 1H), 10.00 (d, J=3.47 Hz, 2H); MS (ESI+) m/z 903 (M+H)$^+$.

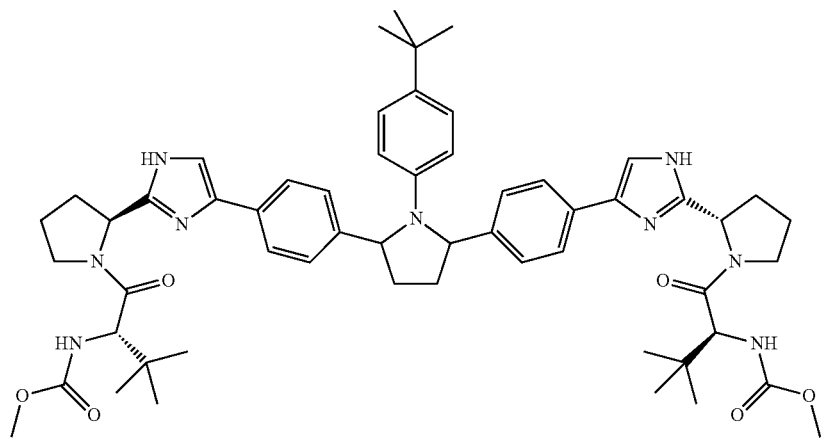

Example 197 methyl {(2S)-1-[(2S)-2-(4-{4-[(2S,5S)-1-(4-tert-butylphenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate and methyl {(2S)-1-[(2S)-2-(4-{4-[(2R,5R)-1-(4-tert-butylphenyl)-5-(4-{2-[(2S)-1-{(2S)-2-[(methoxycarbonyl)amino]-3,3-dimethylbutanoyl}pyrrolidin-2-yl]-1H-imidazol-4-yl}phenyl)pyrrolidin-2-yl]phenyl}-1H-imidazol-2-yl)pyrrolidin-1-yl]-3,3-dimethyl-1-oxobutan-2-yl}carbamate The product from Example 42F (0.228 g, 0.364 mmol) was processed as in Example 1H to give 0.035 g (10%) of the title compound as a solid as a mixture of trans isomers. 1H NMR (free base) (400 MHz, DMSO-D6) δ ppm 0.91 (d, J=7.59 Hz, 18H) 1.08 (s, 9H) 1.63-1.73 (m, 2H) 1.83-2.24 (m, 12H) 3.54 (s, 6H) 3.70-3.80 (m, 2H) 4.21 (d, J=7.92 Hz, 2H) 5.06 (dd, J=6.99, 3.52 Hz, 2H) 5.15-5.25 (m, 2H) 6.21 (d, J=8.67 Hz, 2H) 6.92 (dd, J=8.73, 2.44 Hz, 2H) 7.05 (d, J=8.78 Hz, 2H) 7.14 (dd, J=8.24, 3.47 Hz, 4H) 7.37 (s, 2H) 7.61 (d, J=8.02 Hz, 4H) 11.69 (s, 2H); MS ESI+m/z 968.8 (M+H)+.

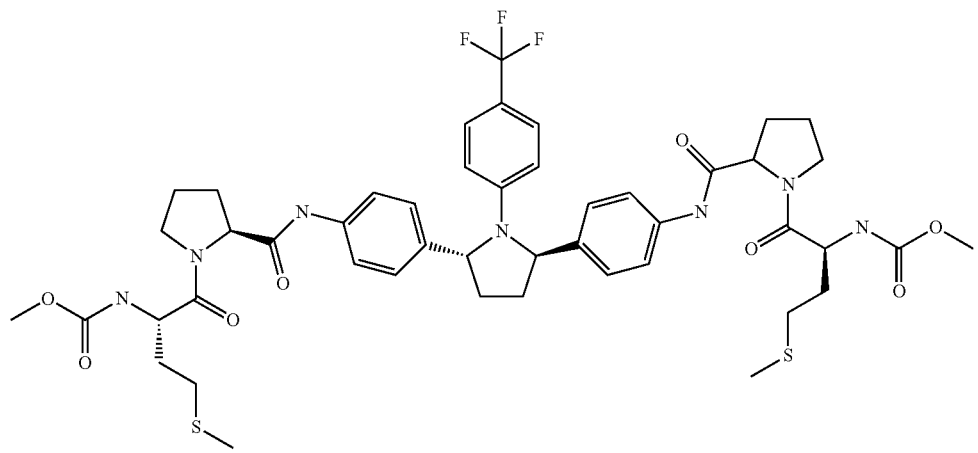

Example 198 methyl [(2S)-1-{(2S)-2-[(4-{(2R,5R)-5-{4-[({1-[(2S)-2-[(methoxycarbonyl)amino]-4-(methylsulfanyl)butanoyl]pyrrolidin-2-yl}carbonyl)amino]phenyl}-1-[4-(trifluoromethyl)phenyl]pyrrolidin-2-yl}phenyl)carbamoyl]pyrrolidin-1-yl}-4-(methylsulfanyl)-1-oxobutan-2-yl]carbamate

Example 198A (S)-2-(methoxycarbonylamino)-4-(methylthio)butanoic acid

To a solution of (S)-2-amino-4-(methylthio)butanoic acid (1.0 g, 6.7 mmol) in dioxane at 0° C. was added NaOH (11.06 g, 22.12 mmol) followed by dropwise addition of methyl chloroformate (1.04 mL, 13.4 mmol) and the solution was warmed to room temperature with stirring over 2 h. The solution was diluted with EtOAc, washed with 1 N HCl, brine, dried ($Na_2SO_4$), filtered and solvent removed in vacuo to give the title compound (1.3 g, 6.27 mmol, 94%). $^1$H NMR (400 MHz, $CDCl_3$) δ ppm 1.95-2.07 (m, 1H) 2.07-2.13 (m, 3H) 2.14-2.28 (m, 1H) 2.59 (t, J=7.4 Hz, 2H) 3.71 (s, 3H) 4.52 (br s, 1H) 5.33 (br s, 1H).

Example 198B (2S,2'S)—N,N'-(4,4'-((2R,5R)-1-(4-(trifluoromethyl)phenyl)pyrrolidine-2,5-diyl)bis(4,1-phenylene)dipyrrolidine-2-carboxamide Example 38A and 4-trifluoromethylaniline were processed using the methods of Examples 34A, 34B, 34C, and 34D to provide the title compound.

Example 198C methyl [(2S)-1-{(2S)-2-[(4-{(2R,5R)-5-{4-[({1-[(2S)-2-[(methoxycarbonyl)amino]-4-(methylsulfanyl)butanoyl]pyrrolidin-2-yl}carbonyl)amino]phenyl}-1-[4-(trifluoromethyl)phenyl]pyrrolidin-2-yl}phenyl)carbamoyl]pyrrolidin-1-yl}-4-(methylsulfanyl)-1-oxobutan-2-yl]carbamate Example 198B and Example 198A were processed using the method of Example 1H to provide the title compound which was purified by flash chromatography on silica gel eluting with 10-80% EtOAc/$CH_2Cl_2$ (29 mg). $^1$H NMR (400 MHz, $CDCl_3$) δ ppm 1.78 (d, J=6.1 Hz, 2H) 1.83-2.00 (m, 6H) 2.02 (s, 6H) 2.04-2.26 (m, 4H) 2.43-2.61 (m, 8H) 3.47-3.83 (m, 4H) 3.69 (s, 6H) 4.75 (dd, J=8.0, 2.0 Hz, 4H) 5.15 (d, J=6.7 Hz, 2H) 5.43 (d, 2H) 6.32 (d, J=8.7 Hz, 2H) 7.09 (d, J=8.5 Hz, 4H) 7.18 (d, J=8.8 Hz, 2H) 7.42 (d, J=8.6 Hz, 4H) 9.05 (s, 2H). MS (ESI) m/z 971 (M+H)$^+$.

Example 199 methyl [(2S,3S)-1-{(2S)-2-[(4-{(2R,5R)-5-(4-{[(1-{(2S,3S)-2-[(methoxycarbonyl)amino]-3-methylpentanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-3-methyl-1-oxopentan-2-yl]carbamate

Example 199A (2S,3S)-2-(methoxycarbonylamino)-3-methylpentanoic acid

To a solution of (2S,3S)-2-amino-3-methylpentanoic acid (1.0 g, 7.62 mmol) in dioxane (10 mL) at 0° C. was added NaOH (12.58 g, 25.2 mmol) followed by dropwise addition of methyl chloroformate (1.18 mL, 15.25 mmol). The solution was warmed to room temperature with stirring over 2 h, diluted with EtOAc, washed with 1 N HCl, brine, dried ($Na_2SO_4$), filtered and solvent removed in vacuo to give the title compound (1.4 g, 7.4 mmol, 97%). $^1$H NMR (400 MHz, $CDCl_3$) δ ppm 1.27-1.39 (m, 1H) 1.38-1.53 (m, 2H) 1.58-1.72 (m, 3H) 1.82-1.94 (m, 2H) 2.04 (d, J=3.8 Hz, 2H) 3.70 (s, 3H) 4.94 (br s, 1H).

Example 199B methyl [(2S,3S)-1-{(2S)-2-[(4-{(2R,5R)-5-(4-{[(1-{(2S,3S)-2-[(methoxycarbonyl)amino]-3-methylpentanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-3-methyl-1-oxopentan-2-yl]carbamate To a solution of Example 198B (60 mg, 0.101 mmol) in DMSO (0.5 mL) was added Example 199A (48 mg, 0.254 mmol), followed by HATU (96 mg, 0.254 mmol) and N,N-diisopropylethylamine (0.089 mL, 0.507 mmol) and the solution was stirred at room temperature for 1 h. Diluted with EtOAc, washed with $H_2O$, brine, dried ($Na_2SO_4$), filtered and removed solvent in vacuo to give crude product which was purified by flash chromatography on silica gel eluting with 10-80% EtOAc/$CH_2Cl_2$ to give the title compound (11 mg, 0.012 mmol, 12%). $^1$H NMR (400 Hz, $CDCl_3$) δ ppm 0.78-1.00 (m, 12H) 1.69-1.81 (m, 4H) 1.81-1.94 (m, 2H) 1.99-2.10 (m, 2H) 2.09-2.24 (m, 2H) 2.50 (br s, 2H) 2.53-2.61 (m, 2H) 3.63 (br s, 2H) 3.68 (s, 6H) 3.75-3.87 (m, 2H) 4.34 (t, J=8.5 Hz, 2H) 4.79 (d, J=6.3 Hz, 2H) 5.14 (d, J=6.6 Hz, 2H) 5.28 (d, J=9.3 Hz, 2H) 6.32 (d, J=8.7 Hz, 2H) 7.08 (d, J=8.4 Hz, 4H) 7.18 (d, J=8.8 Hz, 2H) 7.41 (d, J=8.5 Hz, 4H) 9.23 (s, 2H). MS (ESI) m/z 935 (M+H)$^+$.

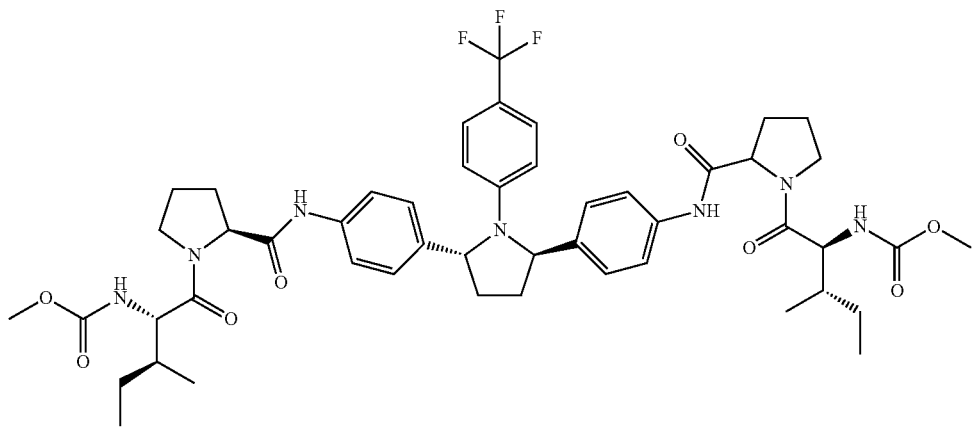

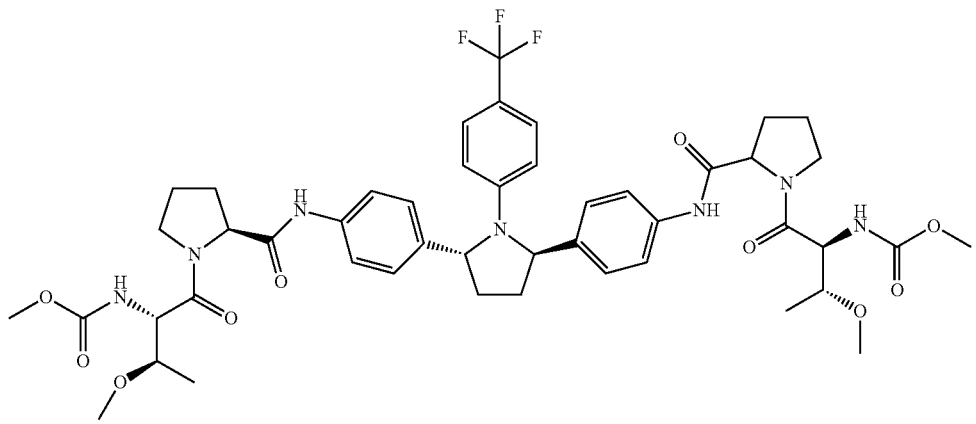

Example 200 methyl [(2S,3R)-3-methoxy-1-{(2S)-2-[(4-{(2R,5R)-5-(4-{[(1-{(2S,3R)-3-methoxy-2-[(methoxycarbonyl)amino]butanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-1-oxobutan-2-yl]carbamate

Example 200A (2S,3R)-3-Methoxy-2-(methoxycarbonylamino)butanoic acid

A solution of O-methyl-L-threonine (1.01 g, 7.59 mmol) in saturated bicarbonate solution (93 mL) was treated dropwise with methyl chloroformate (900 μL, 1.10 g, 11.61 mmol), followed by stirring at RT for 24 h. The mixture was extracted methyl t-butyl ether and cooled to 0° C. The mixture was adjusted to pH 1-2 by addition of concentrated hydrochloric acid solution. The mixture was extracted with ethyl acetate (3×) and the combined extracts were extracted with saturated sodium chloride solution and dried (Na$_2$SO$_4$). The solution was concentrated in vacuo to afford the title compound (1.31 g, 90%) as a white solid. $^1$H NMR (400 MHz, CDCl$_3$) δ 5.44 (d, J=8.7 Hz, 1H), 4.39 (dd, J=8.7, 2.3 Hz, 1H), 4.00 (dd, J=6.2, 2.4 Hz, 1H), 3.71 (s, 3H), 3.36 (s, 3H), 1.21 (t, J=7.2 Hz, 3H). MS (+ESI) m/z (rel abundance) 192 (60, M+H), 209 (100, M+NH4).

Example 200B methyl [(2S,3R)-3-methoxy-1-{(2S)-2-[(4-{(2R,5R)-5-(4-{[(1-{(2S,3R)-3-methoxy-2-[(methoxycarbonyl)amino]butanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-1-oxobutan-2-yl]carbamate Example 198B (60 mg, 0.101 mmol) and Example 200A (48.5 mg, 0.254 mmol) were processed in the same manner as Example 199B to give the title compound (10.5 mg, 0.011 mmol, 11%). $^1$H NMR (400 MHz, CDCl$_3$) δ ppm 1.19 (s, 3H) 1.21 (s, 3H) 1.78 (d, J=6.1 Hz, 2H) 1.94-2.16 (m, 6H) 2.40-2.57 (m, 4H) 3.36 (s, 6H) 3.66-3.84 (m, 6H) 3.69 (s, 6H) 4.64-4.72 (m, 2H) 4.81 (d, J=8.1 Hz, 2H) 5.14 (d, J=6.7 Hz, 2H) 5.64 (d, J=7.9 Hz, 2H) 6.31 (d, J=8.8 Hz, 2H) 7.08 (d, J=8.6 Hz, 4H) 7.18 (d, J=8.8 Hz, 2H) 7.43 (d, J=8.6 Hz, 4H) 8.85 (s, 2H). MS (ESI) m/z 939 (M+H)$^+$.

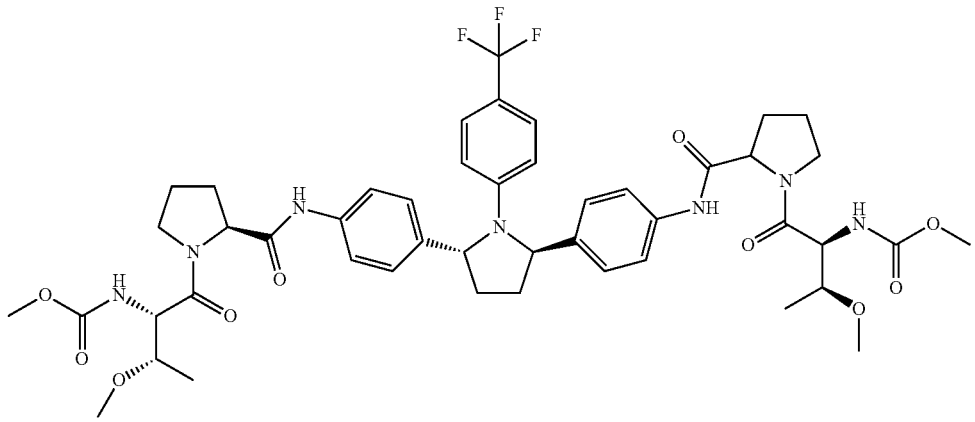

Example 201 methyl [(2S,3S)-3-methoxy-1-{(2S)-2-[(4-{(2R,5R)-5-(4-{[(1-{(2S,3S)-3-methoxy-2-[(methoxycarbonyl)amino]butanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-1-oxobutan-2-yl]carbamate

Example 201A (2S,3S)-3-Methoxy-2-(methoxycarbonylamino)butanoic acid

A solution of allo-O-methyl-L-threonine (519 mg, 3.90 mmol) in saturated sodium bicarbonate solution (47.6 mL) was treated dropwise with methyl chloroformate (453 µL, 553 mg, 5.85 mmol) followed by stirring at RT for 18 h. The mixture was extracted with ether and the aqueous phase was cooled to 0° C. and acidified to pH 2-3 by addition of concentrated hydrochloric acid solution. The mixture was extracted with ethyl acetate (3×). The combined organic layers were extracted with saturated sodium chloride solution and dried ($Na_2SO_4$). Concentration in vacuo afforded the title compound (640 mg, 86%) as a colorless oil. $^1$H NMR (400 MHz, $CDCl_3$) δ 5.48 (d, J=7.8 Hz, 1H), 4.52 (d, J=4.7 Hz, 1H), 3.71 (s, 3H), 3.39 (s, 3H), 1.25 (t, J=7.6 Hz, 3H).

Example 201B methyl [(2S,3S)-3-methoxy-1-{(2S)-2-[(4-{(2R,5R)-5-(4-{[(1-{(2S,3S)-3-methoxy-2-[(methoxycarbonyl)amino]butanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-1-oxobutan-2-yl]carbamate Example 198B (40 mg, 0.068 mmol) and Example 201A (32.3 mg, 0.169 mmol) were processed in the same manner as Example 199B to give the title compound (22 mg, 0.023 mmol, 35%). $^1$H NMR (400 MHz, $CDCl_3$) δ ppm 1.24 (s, 3H) 1.25 (s, 3H) 1.78 (d, J=6.2 Hz, 2H) 1.87-1.99 (m, 2H) 1.99-2.16 (m, 4H) 2.45-2.58 (m, 4H) 3.20 (s, 6H) 3.46-3.56 (m, 2H) 3.65-3.83 (m, 6H) 3.69 (s, 6H) 4.51-4.59 (m, 2H) 4.78 (d, J=6.7 Hz, 2H) 5.14 (d, J=6.7 Hz, 2H) 5.39 (d, J=9.3 Hz, 2H) 6.30 (d, J=8.7 Hz, 2H) 7.08 (d, J=8.5 Hz, 4H) 7.16 (d, J=8.8 Hz, 2H) 7.40 (d, J=8.5 Hz, 4H) 8.94 (s, 2H). MS (ESI) m/z 939 (M+H)$^+$.

Example 202 methyl [(1S)-2-{(2S)-2-[(4-{(2R,5R)-5-(4-{[(1-{(2S)-2-[(methoxycarbonyl)amino]-2-phenylacetyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-2-oxo-1-phenylethyl]carbamate

Example 202A (S)-2-(methoxycarbonylamino)-2-phenylacetic acid

To a solution of (S)-2-amino-2-phenylacetic acid (0.5 g, 3.31 mmol) in dioxane at 0° C. was added NaOH (5.46 g, 10.92 mmol) followed by dropwise addition of methyl chloroformate (0.51 mL, 6.62 mmol) and the solution was warmed to room temperature with stirring over 1 h. Diluted with EtOAc, washed with 1 N HCl, brine, dried ($Na_2SO_4$), filtered and removed solvent in vacuo to give the title compound (0.35 g, 1.673 mmol, 51%).

Example 202B methyl [(1S)-2-{(2S)-2-[(4-{(2R,5R)-5-(4-{[(1-{(2S)-2-[(1-[methoxycarbonyl)amino]-2-phenylacetyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-2-oxo-1-phenylethyl]carbamate Example 198B (40 mg, 0.068 mmol) and Example 202A (35 mg, 0.169 mmol) were processed in the same manner as Example 199B to give the title compound (7.5 mg, 7.7 µmol, 11%). $^1$H NMR (400 MHz, $CDCl_3$) δ ppm 1.76-2.05 (m, 8H) 2.43-2.58 (m, 4H) 3.18-3.29 (m, 2H) 3.57-3.65 (m, 2H) 3.67 (s, 6H) 4.82-4.86 (m, 2H) 5.18 (d, J=6.9 Hz, 2H) 5.48 (d, J=7.7 Hz, 2H) 5.99 (d, J=7.7 Hz, 2H) 6.35 (d, J=8.8 Hz, 2H) 7.11 (d, J=8.5 Hz, 4H) 7.21 (d, J=8.7 Hz, 2H) 7.27-7.32 (m, 4H) 7.32-7.43 (m, 10H) 8.92 (s, 2H). MS (ESI) m/z 975 (M+H)$^+$.

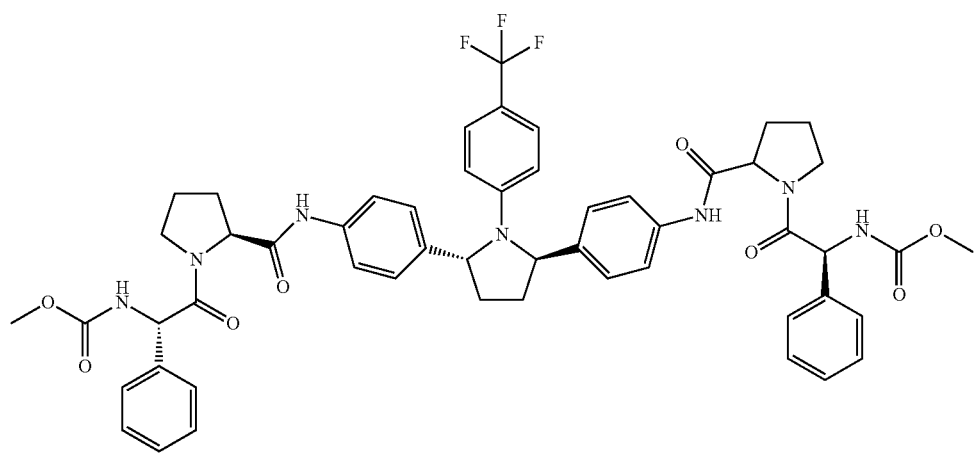

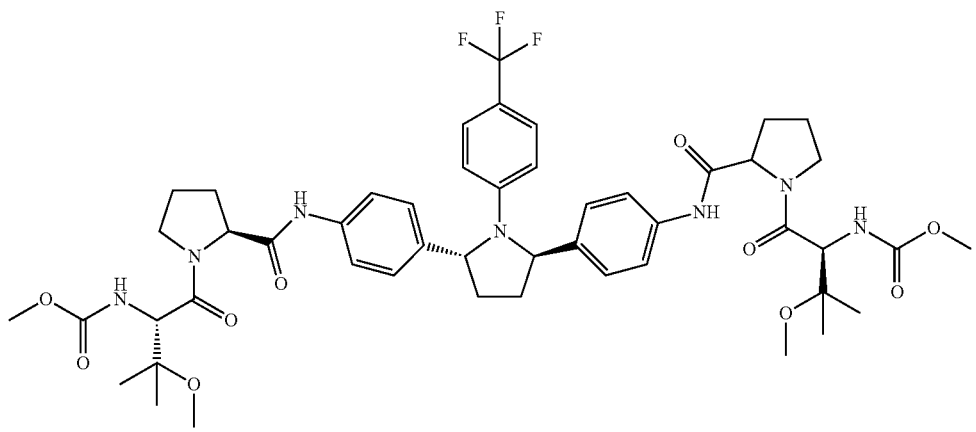

Example 203 methyl [(2S)-3-methoxy-1-{(2S)-2-[(4-{(2R,5R)-5-(4-{[(1-{(2S)-3-methoxy-2-[(methoxycarbonyl)amino]-3-methylbutanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-3-methyl-1-oxobutan-2-yl]carbamate

Example 203A (S)-(tert-butoxycarbonylamino)-3-hydroxy-3-methylbutanoic acid

A solution of the (S)-2-amino-3-hydroxy-3-methylbutanoic acid (252 mg, 1.89 mmol) in saturated sodium bicarbonate solution (6.3 mL) and tetrahydrofuran (6.3 mL) was treated with di-tert-butyl-dicarbonate (764 mg, 3.50 mmol) followed by stirring at RT for 24 h. The mixture was concentrated in vacuo to remove tetrahydrofuran and the mixture was extracted with hexanes. The aqueous phase was cooled to 0° C. and was acidified to pH 3 by addition of 1 M citric acid solution. The mixture was extracted with ethyl acetate and the combined organic layers were dried (Na$_2$SO$_4$). Concentration in vacuo afforded a gummy solid, containing other impurities in addition to the desired product. This material was dissolved in ethyl acetate and the mixture filtered through a millipore filter to remove undissolved material. The filtrate was concentrated in vacuo and after setting at RT for a week, eventually solidified to give the title compound as a white solid. $^1$H NMR (400 MHz, Methanol-d$_4$) δ 4.08 (s, 1H), 1.45 (s, 9H), 1.29 (s, 3H), 1.25 (s, 3H). MS (−ESI) m/z (rel abundance) 232 (100, M−H).

Example 203B (S)-2-(tert-butoxycarbonylamino)-3-methoxy-3-methylbutanoic acid To a solution of Example 203A (363 mg, 1.56 mmol) in THF (7 mL) at 0° C. was added NaH (373 mg, 9.34 mmol) and stirring was continued for 15 min. Iodomethane (0.78 mL, 12.45 mmol) was added and the solution was allowed to warm to room temperature and stirred for 18 h. Solution was quenched with H$_2$O, diluted with EtOAc, washed with H$_2$O, brine, dried (Na$_2$SO$_4$), filtered and solvent removed to give the title compound (165 mg, 0.67 mmol, 43%). MS (ESI) m/z 248 (M+H)$^+$.

Example 203C (S)-3-methoxy-2-(methoxycarbonylamino)-3-methylbutanoic acid

To a solution of Example 203B (163 mg, 0.66 mmol) in CH$_2$Cl$_2$ (2 mL) was added trifluoroacetic acid (2 mL) and the solution was stirred at room temperature for 1 h. Solvent was removed in vacuo and the residue was suspended in saturated NaHCO$_3$, extracted with EtOAc, the organic extracts combined, washed with brine, dried (Na$_2$SO$_4$), filtered and solvent removed in vacuo. The residue was dissolved in dioxane (1 mL) and 1 M NaOH (1.1 mL, 2.175 mmol) was added followed by the dropwise addition of methyl chloroformate (0.102 mL, 1.3 mmol). The solution was stirred at room temperature for 16 h, diluted with EtOAc, washed with 1 N HCl, brine, dried (Na$_2$SO$_4$), filtered and solvent removed in vacuo to give the title compound (96 mg, 0.468 mmol, 71%).

Example 203D methyl [(2S)-3-methoxy-1-{(2S)-2-[(4-{(2R,5R)-5-(4-{[(1-{(2S)-3-methoxy-2-[(methoxycarbonyl)amino]-3-methylbutanoyl}pyrrolidin-2-yl)carbonyl]amino}phenyl)-1-[4-(trifluoromethyl)phenyl]pyrrolidin-2-yl}phenyl)carbamoyl]pyrrolidin-1-yl}-3-methyl-1-oxobutan-2-yl]carbamate Example 198B (80.7 mg, 0.136 mmol) and Example 203C (70 mg, 0.341 mmol) were processed in the same manner as Example 199B to give the title compound (62 mg, 0.064 mmol, 47%). $^1$H NMR (400 MHz, CDCl$_3$) δ ppm 1.25 (s, 3H) 1.33 (s, 3H) 1.39 (s, 2H) 1.74-1.82 (m, 2H) 1.89 (s, 2H) 1.93-2.16 (m, 5H) 2.38-2.59 (m, 4H) 3.16-3.27 (m, 2H) 3.24 (s, 3H) 3.43-3.56 (m, 2H) 3.69 (s, 3H) 3.71-3.78 (m, 2H) 3.80 (s, 3H) 3.84-3.94 (m, 1H) 4.61 (s, 1H) 4.70-4.81 (m, 2H) 5.15 (d, J=6.3 Hz, 2H) 5.58 (s, 1H) 6.32 (d, J=8.7 Hz, 2H) 7.05-7.13 (m, 4H) 7.19 (d, J=8.7 Hz, 2H) 7.33-7.50 (m, 4H) 8.71 (s, 1H) 8.92 (s, 1H). MS (ESI) m/z 967 (M+H)$^+$.

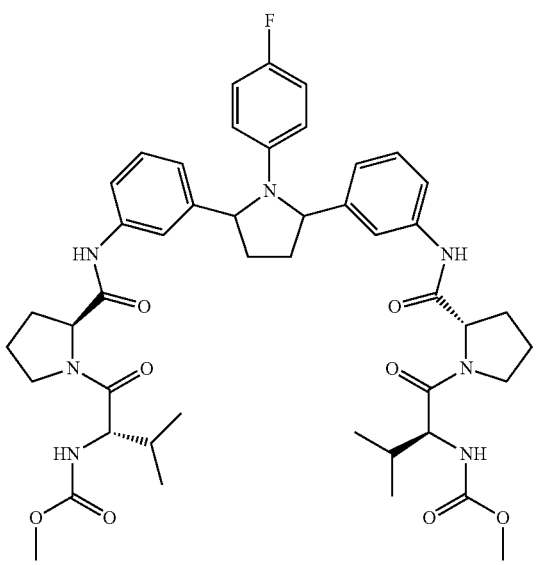 [SMILES: COC(=O)N[C@H](C(=O)N1CCC[C@H]1C(=O)Nc1cccc(C2CCC(c3cccc(NC(=O)[C@@H]4CCCN4C(=O)[C@@H](NC(=O)OC)C(C)C)c3)N2c2ccc(F)cc2)c1)C(C)C]

Example 204 dimethyl ([(2S,5S)-1-(4-fluorophenyl)pyrrolidine-2,
5-diyl]bis{benzene-3,1-diylcarbamoyl(2S)pyrroli-
dine-2,1-diyl[(2S)-3-methyl-1-oxobutane-1,2-diyl]})
biscarbamate and dimethyl ([(2R,5R)-1-(4-fluorophenyl)pyrrolidine-2,
5-diyl]bis{benzene-3,1-diylcarbamoyl(2S)pyrroli-
dine-2,1-diyl[(2S)-3-methyl-1-oxobutane-1,2-diyl]})
biscarbamate Example 204A (2S,2'S)-tert-butyl 2,2'-(3,3'-((2S,5S)-1-(4-fluorophe-
nyl)pyrrolidine-2,5-diyl)bis(3,1-phenylene))bis
(azanediyl)bis(oxomethylene)dipyrrolidine-1-car-
boxylate and (2S,2'S)-tert-butyl 2,2'-(3,3'-((2R,5R)-1-(4-fluo-
rophenyl)pyrrolidine-2,5-diyl)bis(3,1-phenylene))bis
(azanediyl)bis(oxomethylene)dipyrrolidine-1-car-
boxylate The ether fraction from the work up of Example 55F was concentrated and purified by flash chromatography (silica gel, dichloromethane/EtOAc) to afford the title compound as a mixture of trans diastereomers (0.20 g, 10%). MS (ESI) m/z 742 (M+H)$^+$.

Example 204B dimethyl ([(2S,5S)-1-(4-fluorophenyl)pyrrolidine-2,
5-diyl]bis{benzene-3,1-diylcarbamoyl(2S)pyrroli-
dine-2,1-diyl[(2S)-3-methyl-1-oxobutane-1,2-diyl]})
biscarbamate and dimethyl ([(2R,5R)-1-(4-fluorophenyl)pyrrolidine-2,
5-diyl]bis{benzene-3,1-diylcarbamoyl(2S)pyrroli-
dine-2,1-diyl[(2S)-3-methyl-1-oxobutane-1,2-diyl]})
biscarbamate The product from Example 204A was processed using the method described in Examples 19D and 19E (used (S)-2-(methoxycarbonylamino)-3-methylbutanoic acid) to afford the title compounds (60.5 mg, 22%). 1H NMR (free base) (400 MHz, DMSO-D6) δ 0.99-0.81 (m, 12H), 1.67 (dd, J=3.4, 5.0, 3H), 2.06-1.79 (m, 8H), 2.20-2.06 (m, 5H), 3.52 (d, J=2.3, 6H), 3.63 (q, J=7.1, 1H), 3.88-3.75 (m, 1H), 4.08-3.96 (m, 2H), 4.41 (dt, J=12.8, 25.2, 2H), 5.11 (d, J=28.1, 2H), 6.24 (dd, J=6.0, 10.9, 2H), 6.80 (td, J=4.2, 8.9, 2H), 6.88 (dd, J=5.5, 6.4, 2H), 7.22 (ddd, J=5.3, 10.4, 20.8, 2H), 7.32 (d, J=8.3, 2H), 7.43-7.34 (m, 2H), 7.57 (d, J=7.8, 2H), 10.00 (d, J=7.8, 2H). MS (ESI) m/z 856 (M+H)$^+$.

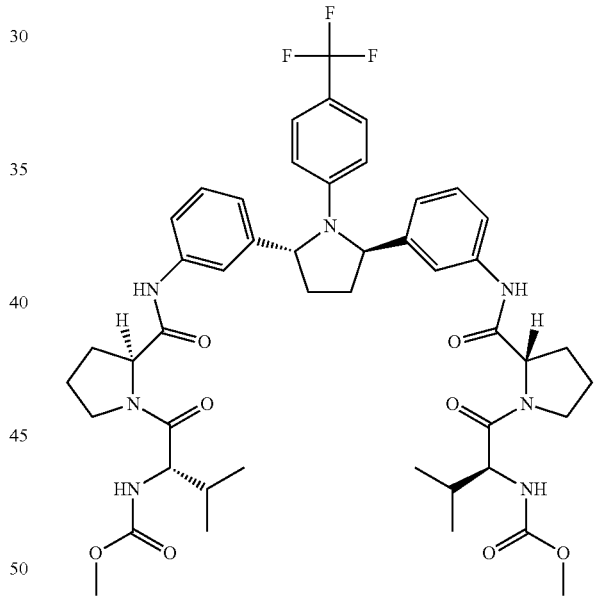

Example 205 dimethyl ({(2R,5R)-1-[4-(trifluoromethyl)phenyl]
pyrrolidine-2,5-diyl}bis{benzene-3,1-diylcarbamoyl
(2S)pyrrolidine-2,1-diyl[(2S)-3-methyl-1-oxobutane-
1,2-diyl]})biscarbamate Example 205A (1S,4S)-1,4-bis(3-nitrophenyl)butane-1,4-diol The product from Example 55A was processed using the method described in Example 33 to afford the title compound (1.74 g, 84%). MS (DCI) m/z 350 (M+NH$_4$)$^+$.

Example 205B (2R,5R)-2,5-bis(3-nitrophenyl)-1-(4-(trifluoromethyl)phenyl)pyrrolidine The product from Example 205A and 4-aminobenzotrifluoride were processed using the method described in Examples 55C and 55D to afford the title compound (0.27 g, 19%). MS (ESI) m/z 858 (M+H)+.

Example 205C 3,3'-((2R,5R)-1-(4-(trifluoromethyl)phenyl)pyrrolidine-2,5-diyl)dianiline The product from Example 205B was processed using the method described in Example 55E. The title compound was isolated by flash chromatography (silica gel, methanol/dichloromethane). MS (ESI) m/z 398 (M+H)+, 396 (M−H)+.

Example 205D (2S,2'S)-tert-butyl 2,2'-(3,3'-((2R,5R)-1-(4-(trifluoromethyl)phenyl)pyrrolidine-2,5-diyl)bis(3,1-phenylene))bis(azanediyl)bis(oxomethylene)dipyrrolidine-1-carboxylate The product from Example 205C was processed using the method described in Example 19C replacing DMF with dichloromethane to afford the title compound (0.36 g, 77%). MS (ESI) m/z 792 (M+H+).

Example 205E dimethyl ({(2R,5R)-1-[4-(trifluoromethyl)phenyl]pyrrolidine-2,5-diyl}bis{benzene-3,1-diylcarbamoyl(2S)pyrrolidine-2,1-diyl[(2S)-3-methyl-1-oxobutane-1,2-diyl]})biscarbamate The product from Example 205D was processed using the method described in Examples 19D and 19E (used (S)-2-(methoxycarbonylamino)-3-methylbutanoic acid and replacing HATU with HOBt and EDC) to afford the title compound (13.5 mg, 3%). $^1$H NMR (TFA salt) (400 MHz, METHANOL-D4) δ 1.08-0.89 (m, 12H), 1.88-1.73 (m, 2H), 2.32-1.93 (m, 10H), 2.62 (t, J=6.9, 2H), 3.64 (s, 6H), 3.77-3.67 (m, 2H), 4.00-3.90 (m, 2H), 4.20 (d, J=8.0, 2H), 4.56-4.45 (m, 2H), 5.26 (d, J=6.5, 2H), 6.42 (d, J=8.8, 2H), 6.98 (d, J=7.6, 2H), 7.17 (d, J=7.4, 2H), 7.27 (t, J=7.8, 2H), 7.52-7.37 (m, 4H). MS (ESI) m/z 906 (M+H)+, 904 (M−H)+.

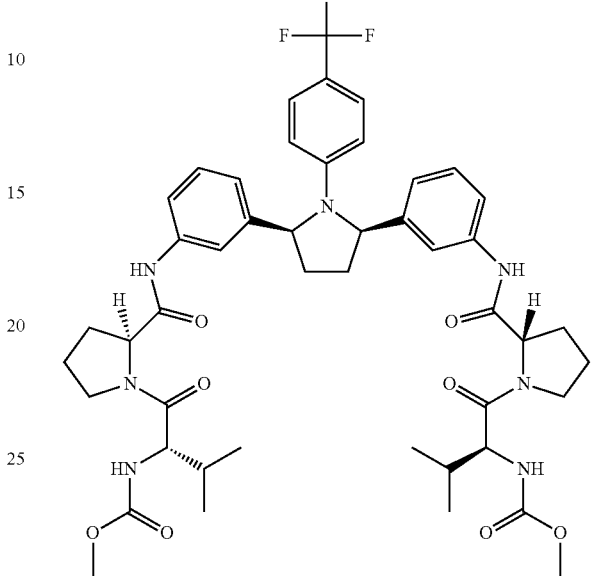

Example 206 dimethyl ({(2R,5S)-1-[4-(trifluoromethyl)phenyl]pyrrolidine-2,5-diyl}bis{benzene-3,1-diylcarbamoyl(2S)pyrrolidine-2,1-diyl[(2S)-3-methyl-1-oxobutane-1,2-diyl]})biscarbamate The product for Example 206 was isolated from the purification of Example 205E (12.5 mg, 3%). $^1$H NMR (TFA salt) (400 MHz, DMSO-D6) δ 0.90 (dt, J=6.2, 10.3, 12H), 2.23-1.73 (m, 12H), 2.47-2.39 (m, 6H), 3.52 (d, J=3.3, 4H), 3.89-3.73 (m, 2H), 4.03 (t, J=8.4, 2H), 4.44 (dd, J=4.9, 7.8, 2H), 4.83 (t, J=5.5, 2H), 6.50 (d, J=8.7, 2H), 7.36-7.15 (m, 6H), 7.39 (d, J=8.7, 2H), 7.73-7.57 (m, 4H), 10.04 (d, J=10.0, 2H). MS (ESI) m/z 906 (M+H)+, 904 (M−H)+.

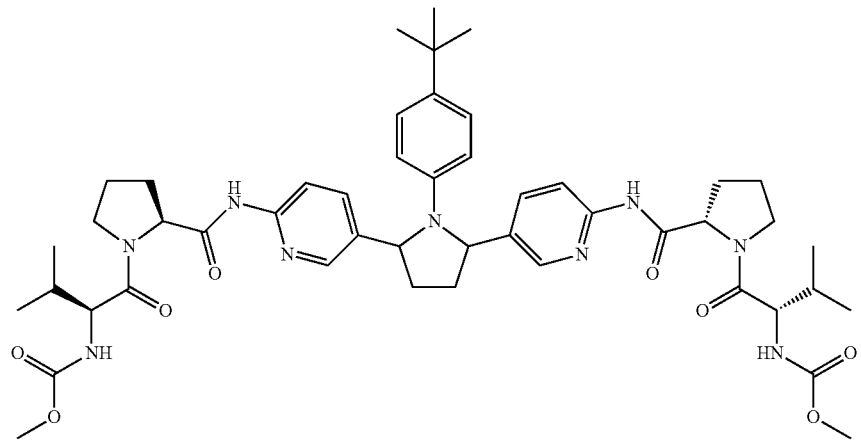 [SMILES: COC(=O)N[C@H](C(=O)N1CCC[C@H]1C(=O)Nc1ccc(C2CCC(c3ccc(NC(=O)[C@@H]4CCCN4C(=O)[C@@H](NC(=O)OC)C(C)C)nc3)N2c2ccc(C(C)(C)C)cc2)cn1)C(C)C]

Example 207 dimethyl ([(2S,5S)-1-(4-tert-butylphenyl)pyrrolidine-2,5-diyl]bis{pyridine-5,2-diylcarbamoyl(2S)pyrrolidine-2,1-diyl[(2S)-3-methyl-1-oxobutane-1,2-diyl]}) biscarbamate and dimethyl ([(2R,5R)-1-(4-tert-butylphenyl)pyrrolidine-2,5-diyl]bis{pyridine-5,2-diylcarbamoyl(2S)pyrrolidine-2,1-diyl[(2S)-3-methyl-1-oxobutane-1,2-diyl]})biscarbamate

Example 207A 1,4-bis(6-chloropyridin-3-yl)butane-1,4-dione

The zinc chloride (3.04 g, 22.82 mmol), tert-butyl alcohol (1.576 mL, 16.71 mmol) and diethylamine (1.731 mL, 16.71 mmol) were combined in benzene (12 mL). The resulting slurry was stirred at room temperature for 2 hours until all solid dissolved. To this slurry was added 1-(6-chloropyridin-3-yl)ethanone (2.60 g, 16.71 mmol; reference: *Bioorganic & Medicinal Chemistry Letters*, 1998, 8, 3087-3092), followed by 2-bromo-1-(6-chloropyridin-3-yl)ethanone (2.61 g, 11.14 mmol; reference: *Bioorganic & Medicinal Chemistry Letters*, 1998, 8, 3087-3092). The resulting clear yellow solution was stirred at room temperature for 88 hours. The thick reaction mixture was treated with 5% $H_2SO_4$ (10 mL), stirred for 30 minutes, filtered and dried to give the title compound (2.91 g, 85%) as a solid.

Example 207B 1,4-bis(6-chloropyridin-3-yl)butane-1,4-diol

The product from Example 207A (2.90 g, 9.38 mmol) and sodium borohydride (0.745 g, 19.70 mmol) were combined in ethanol (94 mL) at 0° C. The mixture was warmed to room temperature and stirred for 6 hours. The solvent was evaporated and the residue was partitioned between ethyl acetate and 1M HCl. The organic layer was washed with water, brine, dried with sodium sulfate, filtered and evaporated to give the title compound (2.62 g, 89%).

Example 207C 1,4-bis(6-chloropyridin-3-yl)butane-1,4-diyl dimethanesulfonate The product from Example 207B (2.23 g, 7.12 mmol) and triethylamine (2.98 mL, 21.36 mmol) were combined in dichloromethane (50 mL). The mixture was cooled to −20° C. and methanesulfonyl chloride (1.383 mL, 17.80 mmol) was added. The mixture was stirred at room temperature for 1 hour. The solvent was evaporated to give the title product (approx 3.34 g) which was directly used for the next reaction.

Example 207D 5,5'-(1-(4-tert-butylphenyl)pyrrolidine-2,5-diyl)bis(2-chloropyridine)

The product from Example 207C (3.34 g, 7.12 mmol) and 4-tert-butylaniline (6.38 g, 42.7 mmol) were combined in DMF (20 mL). The mixture was stirred at room temperature for 24 hours. The reaction mixture was partitioned between ethyl acetate and 1M HCl. The organic layer was washed with brine twice, dried with sodium sulfate, filtered and evaporated. The residue was purified by chromatography on silica gel eluting with ethyl acetate/hexane (5% to 30%) to give the title compound (2.95 g, 97%) as a yellow solid as a mixture of stereoisomers.

Example 207E dimethyl ([(2S,5S)-1-(4-tert-butylphenyl)pyrrolidine-2,5-diyl]bis{pyridine-5,2-diylcarbamoyl(2S)pyrrolidine-2,1-diyl[(2S)-3-methyl-1-oxobutane-1,2-diyl]}) biscarbamate and dimethyl ([(2R,5R)-1-(4-tert-butylphenyl)pyrrolidine-2,5-diyl]bis{pyridine-5,2-diylcarbamoyl(2S)pyrrolidine-2,1-diyl[(2S)-3-methyl-1-oxobutane-1,2-diyl]})biscarbamate The product from Example 207D (0.171 g, 0.40 mmol), the product from Example 116C (0.326 g, 1.200 mmol), cesium carbonate (0.365 g, 1.120 mmol), tris(dibenzylideneacetone)dipalladium(0) (0.022 g, 0.024 mmol) and (9,9-dimethyl-9H-xanthene-4,5-diyl)bis(diphenylphosphine) (0.042 g, 0.072 mmol) were combined in dioxane (4 mL). The mixture was purged with nitrogen for 15 minutes and stirred at 100° C. for 3 hours. The reaction mixture was partitioned between ethyl acetate and saturated sodium bicarbonate. The organic layer was washed with brine, dried with sodium sulfate, filtered and evaporated. The residue was purified by chromatography on silica gel eluting with methanol/dichloromethane (1% to 4%) to give the title compound (5 mg, 1%) as a mixture of trans diastereomers. 1H NMR (500 MHz, DMSO-D6) δ ppm 0.88 (t, J=6.41 Hz, 6H) 0.92 (t, J=7.32 Hz, 6H) 1.12 (s, 9H) 1.68-1.75 (m, 2H) 1.81-1.99 (m, 8H) 2.07-2.18 (m, 2H) 2.50-2.53 (m, 2H) 3.52 (s, 6H) 3.57-3.64 (m, 2H) 3.78-3.86 (m, 2H) 3.98-4.03 (m, 2H) 4.55-4.63 (m, 2H) 5.27 (d, J=6.26 Hz, 2H) 6.18-6.27 (m, 2H) 6.99 (dd, J=8.77, 1.60 Hz, 2H) 7.28-7.37 (m, 2H) 7.59 (dd, J=8.62, 2.06 Hz, 2H) 7.96 (d, J=8.39 Hz, 2H) 8.12-8.20 (m, 2H) 10.53 (s, 2H); MS (ESI+) m/z 896.6 (M+H)+.

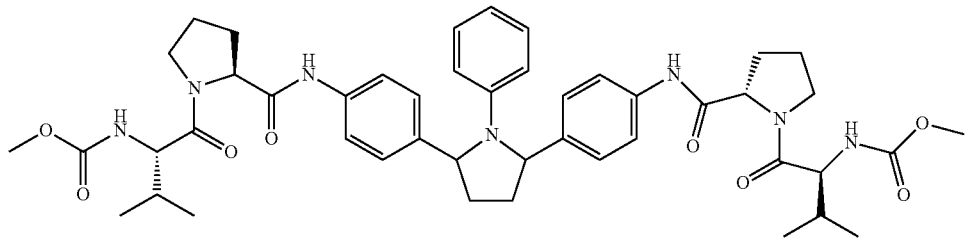

Example 208 dimethyl ([(2S,5S)-1-phenylpyrrolidine-2,5-diyl]bis{benzene-4,1-diylcarbamoyl(2S)pyrrolidine-2,1-diyl[(2S)-3-methyl-1-oxobutane-1,2-diyl]})biscarbamate and dimethyl ([(2R,5R)-1-phenylpyrrolidine-2,5-diyl]bis{benzene-4,1-diylcarbamoyl(2S)pyrrolidine-2,1-diyl[(2S)-3-methyl-1-oxobutane-1,2-diyl]})biscarbamate The title compound was isolated from Example 85C as an additional product. 1H NMR (TFA salt) (400 MHz, DMSO-D6) δ ppm 0.83-0.88 (m, 6H), 0.88-0.94 (m, 6H), 1.60-1.65 (m, 2H), 1.79-2.02 (m, 8H), 2.06-2.18 (m, 2H), 3.51 (s, 6H), 3.55-3.64 (m, 2H), 3.75-3.83 (m, 2H), 4.01 (t, J=8.3 Hz, 2H), 4.38-4.43 (m, 2H), 5.16 (d, J=6.4 Hz, 2H), 6.23 (d, J=8.3 Hz, 2H), 6.39 (t, J=7.3 Hz, 1H), 6.90 (t, J=7.9 Hz, 2H), 7.09-7.14 (m, 4H), 7.25-7.31 (m, 2H), 7.45-7.50 (m, 4H), 9.97 (s, 2H); MS m/z 838.4 (M+H)$^+$.

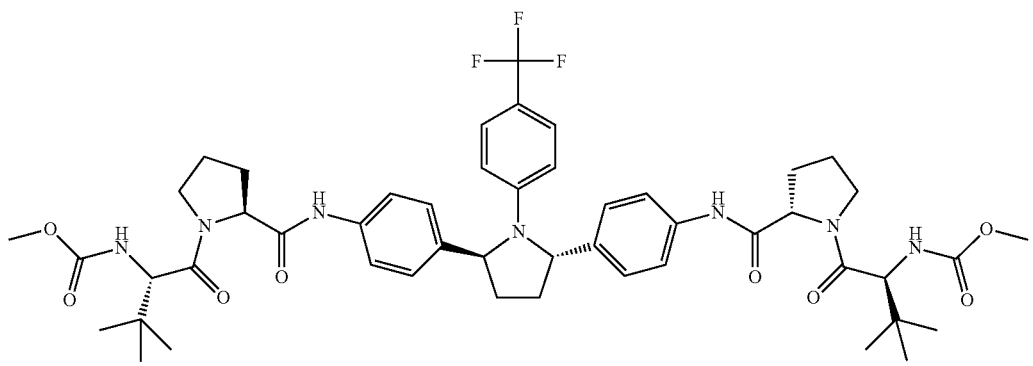

Example 209 dimethyl ({(2S,5S)-1-[4-(trifluoromethyl)phenyl]pyrrolidine-2,5-diyl}bis{benzene-4,1-diylcarbamoyl(2S)pyrrolidine-2,1-diyl[(2S)-3,3-dimethyl-1-oxobutane-1,2-diyl]})biscarbamate The product from Example 23C was separated by chiral chromatography on a Chiralpak AD-H semi-prep column eluting with 40% 2-PrOH:EtOH (1:1)/60% hexanes. The title compound was the first of 2 components to elute. 1H NMR (400 MHz, DMSO-D6) δ ppm 0.97 (s, 18H), 1.61-1.73 (m, 2H), 1.75-1.93 (m, 4H), 1.94-2.06 (m, 2H), 2.08-2.21 (m, 2H), 3.54 (s, 6H), 3.57-3.70 (m, 2H), 3.70-3.83 (m, 2H), 4.21 (d, J=8.89 Hz, 2H), 4.38-4.48 (m, 2H), 5.27 (d, J=6.51 Hz, 2H), 6.37 (d, J=8.78 Hz, 2H), 7.08 (d, J=8.89 Hz, 2H), 7.15 (d, J=8.57 Hz, 4H), 7.25 (d, J=8.89 Hz, 2H), 7.52 (d, J=8.57 Hz, 4H), 10.02 (s, 2H); MS (ESI) m/z 951.6 (M+H)$^+$.

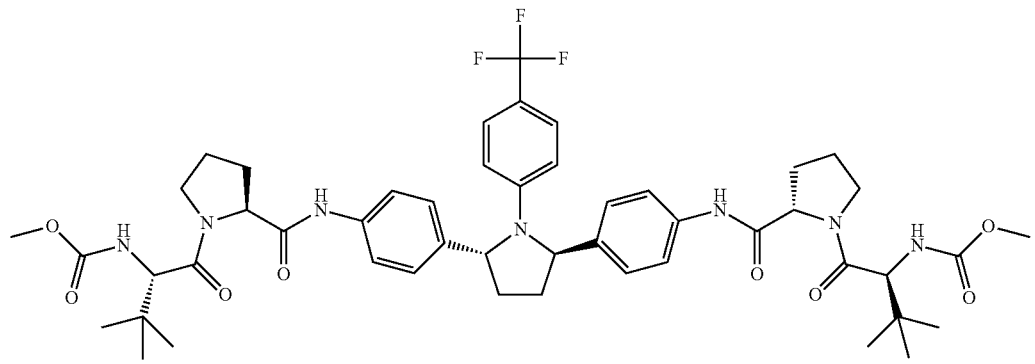

Example 210 dimethyl ({(2R,5R)-1-[4-(trifluoromethyl)phenyl]pyrrolidine-2,5-diyl}bis{benzene-4,1-diylcarbamoyl(2S)pyrrolidine-2,1-diyl[(2S)-3,3-dimethyl-1-oxobutane-1,2-diyl]})biscarbamate The product from Example 23C was separated by chiral chromatography on a Chiralpak AD-H semi-prep column eluting with 40% 2-PrOH:EtOH (1:1)/60% hexanes. The title compound was the second of 2 components to elute. 1H NMR (400 MHz, DMSO-D6) δ ppm 0.96 (s, 18H), 1.64-1.75 (m, 2H), 1.76-1.93 (m, 4H), 1.94-2.06 (m, 2H), 2.07-2.21 (m, 2H), 3.54 (s, 6H), 3.58-3.70 (m, 2H), 3.70-3.86 (m, 2H), 4.20 (d, J=8.89 Hz, 2H), 4.38-4.47 (m, 2H), 5.28 (d, J=6.18 Hz, 2H), 6.36 (d, J=8.89 Hz, 2H), 7.07 (d, J=8.89 Hz, 2H), 7.14 (d, J=8.57 Hz, 4H), 7.25 (d, J=8.78 Hz, 2H), 7.52 (d, J=8.57 Hz, 4H), 10.03 (s, 2H); MS (ESI) m/z 951.4 (M+H)+.

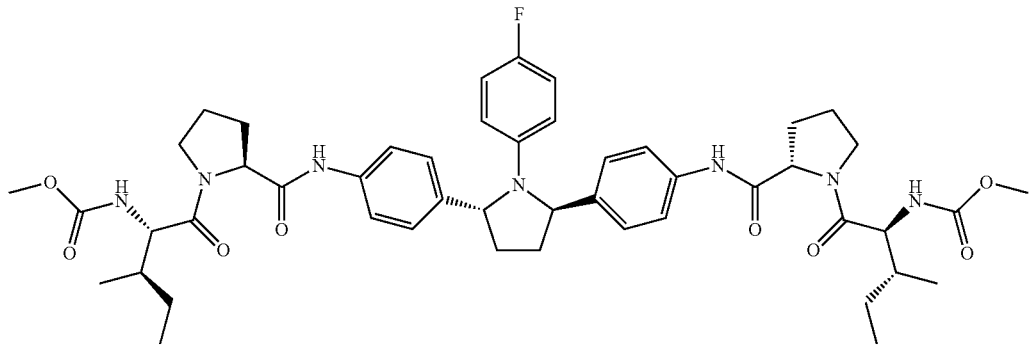

Example 211 dimethyl ([(2R,5R)-1-(4-fluorophenyl)pyrrolidine-2,5-diyl]bis{benzene-4,1-diylcarbamoyl(2S)pyrrolidine-2,1-diyl[(2S,3R)-3-methyl-1-oxopentane-1,2-diyl]})biscarbamate The product from Example 25 was separated by chiral chromatography on a Chiralpak AD-H semi-prep column eluting with 50% 2-PrOH:EtOH (1:1)/50% hexanes. The title compound was the second of 2 components to elute. 1H NMR (400 MHz, DMSO-D6) δ ppm 0.76-0.92 (m, 12H), 1.05-1.19 (m, 2H), 1.37-1.54 (m, 2H), 1.57-1.70 (m, 2H), 1.69-1.96 (m, 6H), 1.94-2.07 (m, 2H), 2.07-2.22 (m, 2H), 3.53 (s, 6H), 3.55-3.64 (m, 2H), 3.69-3.83 (m, 2H), 4.17-4.28 (m, 2H), 4.42 (dd, J=7.81, 5.20 Hz, 2H), 5.16 (d, J=6.29 Hz, 2H), 6.20 (dd, J=9.22, 4.45 Hz, 2H), 6.77 (t, J=8.95 Hz, 2H), 7.13 (d, J=8.46 Hz, 4H), 7.49 (d, J=8.46 Hz, 2H), 9.97 (s, 2H); MS (ESI) m/z 884.4 (M+H)+.

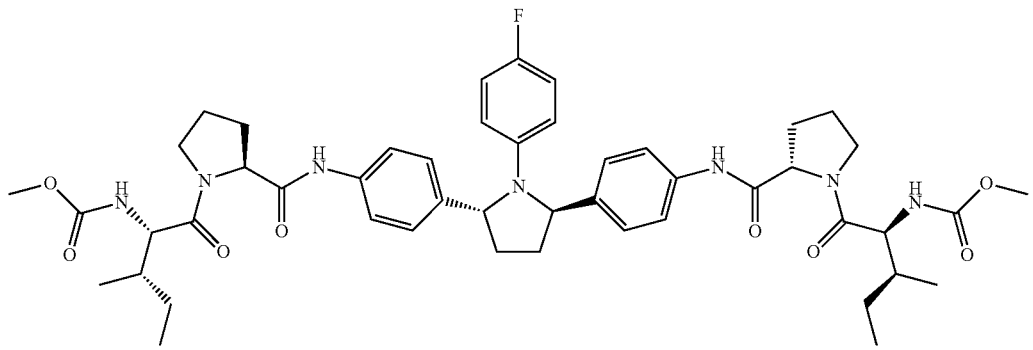

Example 212 dimethyl ([(2R,5R)-1-(4-fluorophenyl)pyrrolidine-2,5-diyl]bis{benzene-4,1-diylcarbamoyl(2S)pyrrolidine-2,1-diyl[(2S,3S)-3-methyl-1-oxopentane-1,2-diyl]})biscarbamate The product from Example 24 was separated by chiral chromatography on a Chiralpak AD-H semi-prep column eluting with 50% 2-PrOH:EtOH (1:1)/50% hexanes. The title compound was the second of 2 components to elute. 1H NMR (400 MHz, DMSO-D6) δ ppm 0.80 (t, J=7.37 Hz, 6H), 0.88 (d, J=6.72 Hz, 6H), 1.02-1.18 (m, 2H), 1.41-1.59 (m, 2H), 1.59-1.75 (m, 4H), 1.80-1.95 (m, 4H), 1.95-2.06 (m, 2H), 2.08-2.23 (m, 2H), 3.52 (s, 6H), 3.56-3.67 (m, 2H), 3.74-3.89 (m, 2H), 4.07 (t, J=8.95 Hz, 2H), 4.39-4.47 (m, 2H), 5.16 (d, J=6.18 Hz, 2H), 6.20 (dd, J=9.22, 4.45 Hz, 2H), 6.78 (t, J=8.95 Hz, 2H), 7.13 (d, J=8.46 Hz, 4H), 7.35 (d, J=8.46 Hz, 2H), 7.50 (d, J=8.57 Hz, 4H), 9.99 (s, 2H); MS (ESI) m/z 884.4 (M+H)$^+$.

Example 213

N-(methoxycarbonyl)-L-valyl-N-{4-[(2S,5S)-5-(4-aminophenyl)-1-(4-tert-butylphenyl)pyrrolidin-2-yl]phenyl}-L-prolinamide To a solution of the product from Example 37B (17.7 mg, 0.065 mmol) and the product from Example 37E (50 mg, 0.130 mmol) in anhydrous DMSO (1.3 mL) was added HATU (27.1 mg, 0.071 mmol) and Hunig's Base (0.015 mL, 0.084 mmol). The resulting mixture was stirred at rt for 30 min, and was then partitioned between H$_2$O (5 mL) and EtOAc (3×5 mL). The combined organic layers were dried over Na$_2$SO$_4$. The drying agent was filtered off, and solvent was removed in vacuo. The crude product was purified by column chromatography on silica gel using a solvent gradient of 0-5% MeOH in CH$_2$Cl$_2$ to give the title compound (20 mg, 24%). 1H NMR (400 MHz, DMSO-D6) δ ppm 0.88 (d, J=6.72 Hz, 3H), 0.93 (d, J=6.72 Hz, 3H), 1.11 (s, 9H), 1.52-1.66 (m, 2H), 1.79-2.06 (m, 4H), 2.06-2.20 (m, 1H), 2.34-2.47 (m, 2H), 3.52 (s, 3H), 3.56-3.67 (m, 1H), 3.74-3.87 (m, 1H), 4.02 (t, J=8.51 Hz, 1H), 4.42 (dd, J=8.08, 4.83 Hz, 1H), 4.83-4.94 (m, 2H), 5.02 (d, J=7.16 Hz, 0.5H), 5.08 (d, 7.59 Hz, 0.5H), 6.18 (d, 8.78 Hz, 2H), 6.48 (d, J=8.35 Hz, 2H), 6.84 (d, J=8.35 Hz, 2H), 6.93 (d, J=8.89 Hz, 2H), 7.11 (d, J=8.57 Hz, 2H), 7.31 (d, J=8.35 Hz, 1H), 7.48 (d, J=8.57 Hz, 2H), 9.97 (s, 1H); MS (ESI) m/z 640.3 (M+H)$^+$.

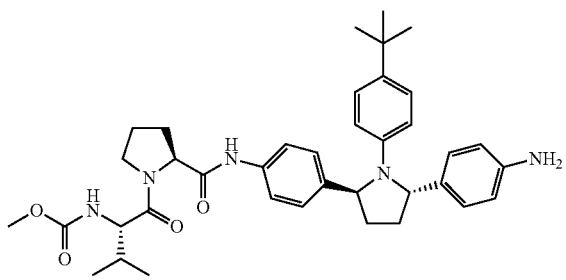 [SMILES: COC(=O)N[C@H](C(=O)N1CCC[C@H]1C(=O)Nc1ccc([C@@H]2CC[C@@H](c3ccc(N)cc3)N2c2ccc(C(C)(C)C)cc2)cc1)C(C)C]

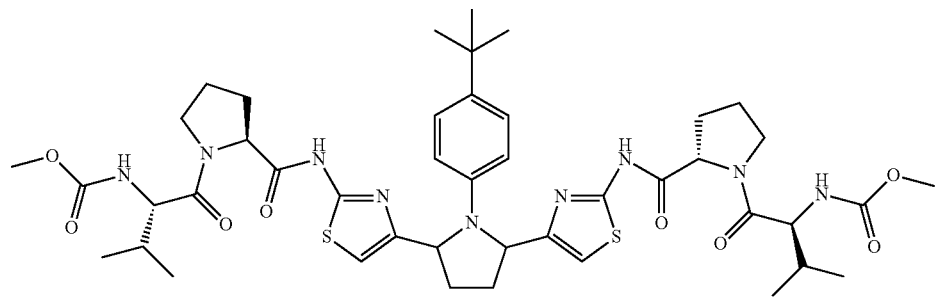

Example 214 dimethyl (2S,2'S)-1,1'-((2S,2'S)-2,2'-(4,4'-((2R,5R)-1-(4-tert-butylphenyl)pyrrolidine-2,5-diyl)bis(thiazole-4,2-diyl)bis(azanediyl)bis(oxomethylene))bis(pyrrolidine-2,1-diyl))bis(3-methyl-1-oxobutane-2,1-diyl)dicarbamate and dimethyl (2S,2'S)-1,1'-((2S,2'S)-2,2'-(4,4'-((2S,5S)-1-(4-tert-butylphenyl)pyrrolidine-2,5-diyl)bis(thiazole-4,2-diyl)bis(azanediyl)bis(oxomethylene))bis(pyrrolidine-2,1-diyl))bis(3-methyl-1-oxobutane-2,1-diyl)dicarbamate

Example 214A diethyl 1-(4-tert-butylphenyl)pyrrolidine-2,5-dicarboxylate

A solution of diethyl meso-2,5-dibromoadipate (2.0 g, 5.55 mmol) and 4-tert-butylaniline (3.32 g, 22.22 mmol) in dimethoxyethane (12 mL) was stirred at reflux for 10 h. The cooled mixture was partitioned between EtOAc (100 mL) and 1N aq HCl (2×100 mL), and the organic layer was dried over $Na_2SO_4$. The drying agent was filtered off, and the solvent was removed in vacuo. The crude product was purified by column chromatography on silica gel using a solvent gradient of 0-20% EtOAc in hexanes to give the title compound as an oil (1.95 g, quant.). 1H NMR indicated a 3:2 mixture of cis:trans pyrrolidine isomers.

Example 214B 1-(4-tert-butylphenyl)pyrrolidine-2,5-dicarboxylic acid

To a solution of the product from Example 214A (1.95 g, 5.61 mmol) in MeOH (50 mL) was added a solution of NaOH (0.95 g, 23.8 mmol) in $H_2O$ (10 mL). The resulting mixture was stirred at rt overnight. The mixture was concentrated in vacuo to ca. 10 mL and was poured into 1N HCl (50 mL). The mixture was extracted with $CH_2Cl_2$ (3×50 mL), and the combined organic layers were dried over $Na_2SO_4$. The drying agent was filtered off, and the solvent was removed in vacuo to give the title compound as a light orange solid (1.42 g, 87%) as a mixture of stereoisomers.

Example 214C trans-1-(4-tert-butylphenyl)pyrrolidine-2,5-dicarboxylic acid

The product from Example 214B was subjected to column chromatography on C18 silica gel using a solvent gradient of 10-60% acetonitrile in $H_2O$ (0.1% TFA). The title compound was the first of 2 major components to elute.

Example 214D 1,1'-(trans-1-(4-tert-butylphenyl)pyrrolidine-2,5-diyl)bis(2-diazoethanone)

To a solution of the product from Example 214C (0.963 g, 3.31 mmol) in dry $CH_2Cl_2$ (20 mL) at 0° C. was added oxalyl chloride (1.157 mL, 13.22 mmol), followed by 2-3 drops of DMF, and the resulting mixture was stirred at rt for 30 min until no further bubbling was observed. The cooled mixture was conc by evaporation with dry $N_2$, and the residue was dissolved in dry $CH_2Cl_2$ (10 mL). To the 0° C. solution was added a solution of diazomethane in $Et_2O$ (~0.6 M, 20 mL) and the resulting mixture was stirred at 0° C. for 1 h. The mixture was concentrated in vacuo, and the crude product was purified by column chromatography on silica gel using a solvent gradient of 0-100% EtOAc in hexanes to give the title compound (0.54 g, 48%).

Example 214E 4,4'-(trans-1-(4-tert-butylphenyl)pyrrolidine-2,5-diyl)dithiazol-2-amine A solution of the product from Example 214D (0.50 g, 1.47 mmol) in $Et_2O$ (10 mL) was treated dropwise with 48% aq. hydrogen bromide (0.500 mL, 4.42 mmol). The resulting mixture was stirred at rt for 30 min. Water (1 mL) was added, and the mixture was extracted with $Et_2O$ (3×10 mL). The combined organic layers were dried over $Na_2SO_4$, filtered, and concentrated in vacuo. The residue was dissolved in EtOH (15 mL). To the resulting solution was added thiourea (0.45 g, 5.89 mmol), and the resulting mixture was stirred at rt for 1 h and then concentrated to ca. 1 mL. Water (10 mL) was added, and the pH was neutralized using saturated aq. $NaHCO_3$. The resulting solid was collected by filtration and dried in vacuo to give the title compound (0.455 g, 77%).

Example 214F (2S,2'S)-tert-butyl 2,2'-(4,4'-(trans-1-(4-tert-butylphenyl)pyrrolidine-2,5-diyl)bis(thiazole-4,2-diyl)bis(azanediyl)bis(oxomethylene))dipyrrolidine-1-carboxylate A mixture of the product from Example 214E (0.2 g, 0.501 mmol), (S)-1-(tert-butoxycarbonyl)pyrrolidine-2-carboxylic acid (0.431 g, 2.002 mmol), and N1-((ethylimino)methylene)-N3,N3-dimethylpropane-1,3-diamine hydrochloride (1.151 g, 6.01 mmol) in DMF (4 mL) and pyridine (4 mL) was stirred at rt overnight. The mixture was partitioned between 1N aq. HCl and EtOAc (3×), and the combined organic layers were dried over $Na_2SO_4$. The drying agent was filtered off, and the solvent was removed in vacuo. The crude product was purified by column chromatography on silica gel using a solvent gradient of 0-100% EtOAc in hexanes to give the title compound (0.28 g, 71%) as a mixture of trans diastereomers.

Example 214G dimethyl (2S,2'S)-1,1'-((2S,2'S)-2,2'-(4,4'-((2R,5R)-1-(4-tert-butylphenyl)pyrrolidine-2,5-diyl)bis(thiazole-4,2-diyl)bis(azanediyl)bis(oxomethylene))bis(pyrrolidine-2,1-diyl))bis(3-methyl-1-oxobutane-2,1-diyl)dicarbamate and dimethyl (2S,2'S)-1,1'-((2S,2'S)-2,2'-(4,4'-((2S,5S)-1-(4-tert-butylphenyl)pyrrolidine-2,5-diyl)bis(thiazole-4,2-diyl)bis(azanediyl)bis(oxomethylene))bis(pyrrolidine-2,1-diyl))bis(3-methyl-1-oxobutane-2,1-diyl)dicarbamate A solution of the product from Example 214F was stirred in 2N HCl in dioxane (0.4 mL) for 1 h and then concentrated in vacuo. The residue was subjected to the procedure described in Example 10 to give the title compound as mixture of trans diastereomers. 1H NMR (free base) (400 MHz, DMSO-D6) δ ppm 0.80-0.97 (m, 14H), 1.12-1.16 (m, 9H), 1.69-2.06 (m, 8H), 2.08-2.22 (m, 2H), 3.51-3.57 (m, 6H), 3.57-3.68 (m, 2H), 3.77-3.91 (m, 2H), 3.95-4.06 (m, 2H), 4.47-4.59 (m, J=7.16 Hz, 1H), 5.08-5.17 (m, 2H), 6.31 (t, J=8.24 Hz, 2H), 6.70 (d, J=21.04 Hz, 2H), 7.02 (dd, J=8.67, 6.40 Hz, 2H), 7.35 (d, J=8.35 Hz, 2H), 12.24 (s, 2H).

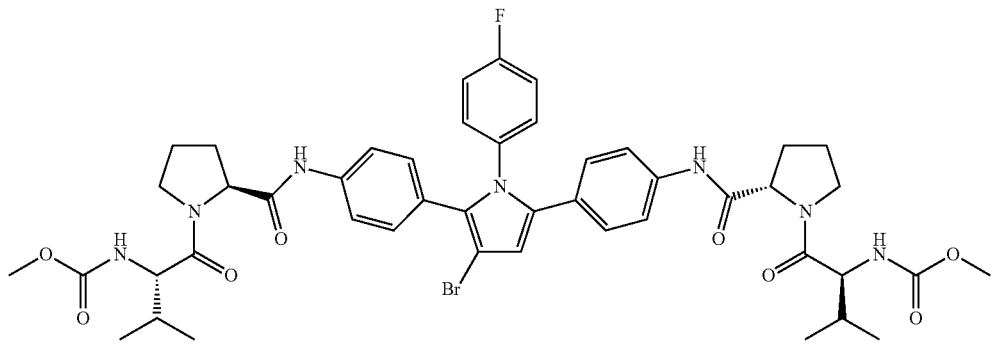

Example 215 dimethyl ([3-bromo-1-(4-fluorophenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})biscarbamate To a suspension of the product from Example 51 (455 mg, 0.534 mmol) in $CH_2Cl_2$ (2.7 mL) was added a mixture of 1-bromopyrrolidine-2,5-dione (95 mg, 0.534 mmol) in $CH_2Cl_2$ (2.7 mL). The mixture was stirred overnight at room temperature then concentrated under reduced pressure and triturated with diethyl ether to provide a mixture of compounds that was subjected to reverse phase HPLC purification eluted with a gradient of 60-100% MeOH in 10 mM ammonium acetate to afford the title compound (84 mg, 17% yield). $^1$H NMR (free base) (400 MHz, DMSO-D6) δ 10.06 (s, 1H), 10.02 (s, 1H), 7.46 (d, J=8.7, 2H), 7.41 (d, J=8.7, 2H), 7.30 (d, J=7.7, 2H), 7.15-7.03 (m, 6H), 6.98 (d, J=8.7, 2H), 6.53 (s, 1H), 4.45-4.33 (m, 2H), 4.01 (t, J=7.7, 2H), 3.85-3.73 (m, 2H), 3.66-3.54 (m, 2H), 3.51 (s, 6H), 2.20-2.05 (m, 2H), 2.03-1.77 (m, 8H), 0.97-0.79 (m, 12H). MS (ESI; M+H) m/z=933.

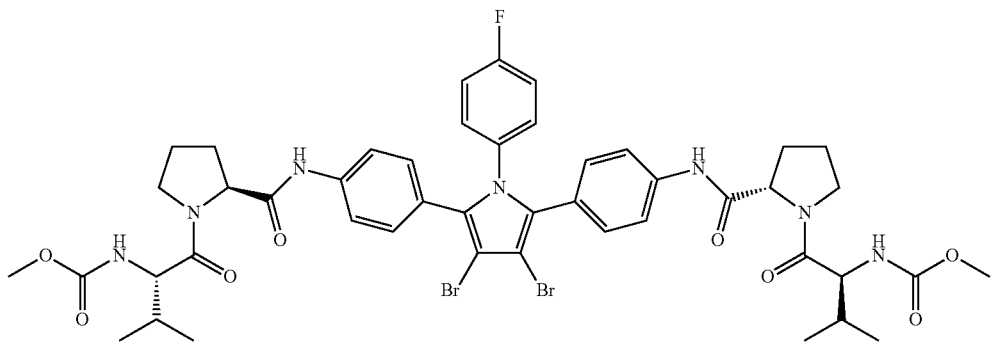

Example 216 dimethyl ([3,4-dibromo-1-(4-fluorophenyl)-1H-pyrrole-2,5-diyl]bis{benzene-4,1-diylcarbamoyl(2S)pyrrolidine-2,1-diyl[(2S)-3-methyl-1-oxobutane-1,2-diyl]})biscarbamate The title compound was formed as an additional product in Example 215. The mixture of products was subjected to reverse phase HPLC purification eluted with a gradient of 60-100% MeOH 10 in 10 mM ammonium acetate to afford the title compound (125 mg, 23% yield). $^1$H NMR (free base) (400 MHz, DMSO-D6) δ 10.08 (bs, 2H), 7.47 (d, J=8.7, 4H), 7.33-7.27 (m, 2H), 7.13-7.01 (m, 8H), 4.43-4.35 (m, 2H), 4.01 (t, J=8.4, 2H), 3.84-3.74 (m, 2H), 3.65-3.55 (m, 2H), 3.51 (s, 6H), 2.21-2.05 (m, 2H), 2.05-1.78 (m, 8H), 0.91 (d, J=6.7, 6H), 0.86 (d, J=6.6, 6H). MS (ESI; M+H) m/z=1011.

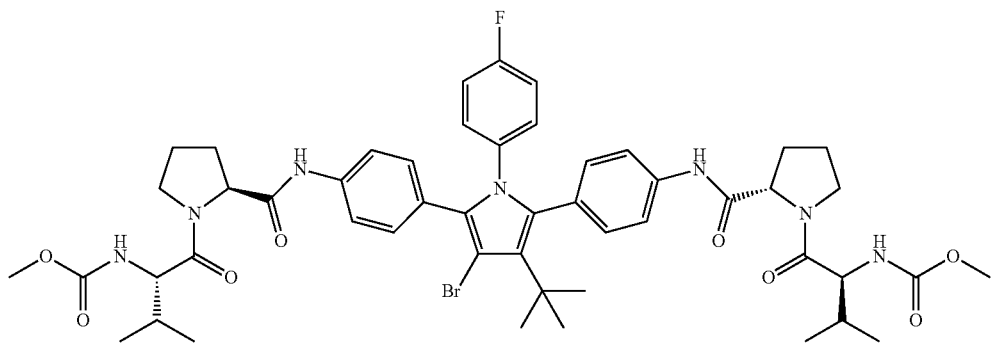

Example 217

The title compound was formed as a by-product in Example 215. The mixture of products was subjected to reverse phase HPLC purification eluted with a gradient of 60-100% MeOH in 10 mM ammonium acetate to afford the title compound (61 mg, 12% yield). $^1$H NMR (free base) (400 MHz, DMSO-D6) δ 10.00 (s, 2H), 7.41 (d, J=8.7, 2H), 7.38 (d, J=8.9, 2H), 7.29 (d, J=6.6, 2H), 7.14 (d, J=7.3, 1H), 7.11-7.05 (m, 3H), 7.01-6.93 (m, 2H), 6.89 (t, J=8.7, 2H), 4.37 (dd, J=4.9, 7.4, 2H), 4.00 (t, J=8.4, 2H), 3.84-3.74 (m, 2H), 3.64-3.55 (m, 2H), 3.51 (s, 6H), 2.19-2.05 (m, 2H), 2.03-1.78 (m, 8H), 1.23 (s, 9H), 0.91 (dd, J=2.1, 6.6, 6H), 0.86 (d, J=6.4, 6H). MS (ESI; M+H) m/z=989.

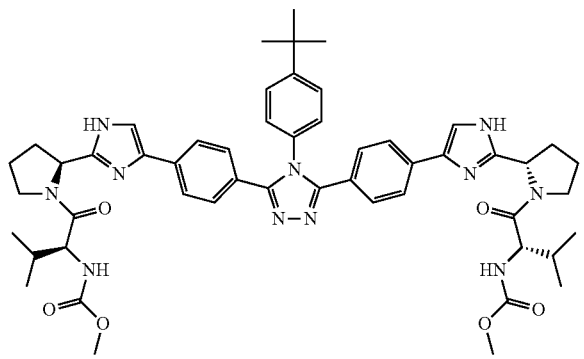 [SMILES: COC(=O)N[C@H](C(=O)N1CCC[C@H]1c1nc(-c2ccc(-c3nnc(-c4ccc(-c5c[nH]c([C@@H]6CCCN6C(=O)[C@@H](NC(=O)OC)C(C)C)n5)cc4)n3-c3ccc(C(C)(C)C)cc3)cc2)c[nH]1)C(C)C]

Example 218 methyl {(2S)-1-[(2S)-2-(4-{4-[4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-4H-1,2,4-triazol-3-yl]phenyl}-1H-imidazol-2-yl)pyrrolidin-1-yl]-3-methyl-1-oxobutan-2-yl}carbamate

Example 218A 4-bromo-N'-(4-bromobenzoyl)benzoylhydrazide

Dissolved equimolar amounts of 4-bromobenzohydrazide (1.097 g, 5 mmol) and 4-bromobenzoyl chloride (1.120 g, 5 mmol) in anhydrous pyridine (25 mL) under nitrogen and heated at reflux (oil bath 135° C.) for 6 hr. Cooled reaction to room temperature, poured the mixture into absolute EtOH (100 mL), and cooled in a freezer overnight to give white crystals. Collected solids by vacuum filtration, washed solids with absolute EtOH (2×5 mL), and dried in vacuo to afford the title compound as a white solid (953 mg, 48%). $^1$H NMR (400 MHz, DMSO-D6) δ ppm 7.75 (d, J=8.57 Hz, 4H), 7.86 (d, J=8.46 Hz, 4H), 10.63 (s, 2H); MS (ESI−) m/z 395/397/399 (M−H)⁻ with two bromines.

Example 218B 3,5-bis(4-bromophenyl)-4-(4-tert-butylphenyl)-4H-1,2,4-triazole In an oven-dried 10-mL round bottom flask, equipped with a septum and purged with nitrogen, 4-tert-butylaniline (450 mg, 3.01 mmol) was dissolved in anhydrous 1,2-dichlorobenzene (1.5 mL) and the solution cooled to 0° C. A solution of phosphorus oxychloride (0.047 mL, 0.502 mmol) in anhydrous 1,2-dichlorobenzene (0.5 mL) was added slowly in dropwise manner from a gas-tight syringe. Upon completion of addition, removed the cooling bath and stirred at room temperature for 1 hr to form the phosphoryl triamide in situ (reaction became progressively cloudy). Then added the product of Example 218A (200 mg, 0.502 mmol), replaced septum with a reflux condenser, and heated reaction in an oil bath at 200° C. for 4 hr. Cooled light brown colored solution to room temperature, then placed in a freezer for 3 days and collected an off-white solid (20 mg, 4-bromo-N-(4-tert-butylphenyl)benzamide by-product) by vacuum filtration. The filtrate was treated with hexanes (~50 mL) and the cloudy solution cooled in a freezer for 30 min. Collected an off-white solid (73 mg) by vacuum filtration and concentrated the filtrate by rotary evaporation to a solution of product in 1,2-dichlorobenzene. The latter was purified by flash chromatography (silica gel, 3.8 cm×15 cm bed, gradient of CH₂Cl₂, 20% EtOAc/CH₂Cl₂, and 30% EtOAc/CH₂Cl₂) to afford the title compound as a fluffy white solid (154 mg, 60%). $^1$H NMR (400 MHz, CDCl₃) δ ppm 1.36 (s, 9H), 7.06 (d, J=8.46 Hz, 2H), 7.29 (d, J=8.57 Hz, 4H), 7.43 (d, J=8.57 Hz, 4H), 7.46 (d, J=8.57 Hz, 2H); MS (ESI+) m/z 510/512/514 (M+H)⁺ with two bromines.

Example 218C 4-(4-tert-butylphenyl)-3,5-bis((4(4,4,5,5-tetramethyl-1,3,2-dioxaborolan-2-yl)phenyl)-4H-1,2,4-triazole Charged an oven-dried 25-mL round bottom flask, purged with nitrogen, with the product of Example 218B (144.2 mg, 0.282 mmol), bis(pinacalato)diboron (215 mg, 0.846 mmol), potassium acetate (90 mg, 0.917 mmol), and anhydrous dioxane (1.5 mL). Sparged the mixture with nitrogen for 30 min, added 1,1'-bis(diphenylphosphino)ferrocene-palladium(II) dichloride dichloromethane complex (23.03 mg, 0.028 mmol), re-sparged with nitrogen for 5 min, replaced rubber septum with a glass stopper, and heated in an oil bath (85° C.) for 2 hr. Cooled reaction to room temperature, vacuum filtered through a small bed of Celite 545, washed catalyst thoroughly with $CH_2Cl_2$, and concentrated the filtrate by rotary evaporation to a dark brown oil. Purified by flash chromatography (silica gel, Alltech Extract-Clean 10 g column, 1:1 EtOAc/$CH_2Cl_2$) to afford a dark beige solid (230 mg). Repurified by flash chromatography (silica gel, Alltech Extract-Clean 10 g column, 3% MeOH/$CH_2Cl_2$) eluting with to afford the title compound as a beige solid (171 mg, 100%). $^1$H NMR (400 MHz, CDCl$_3$) δ ppm 1.27 (s, 9H), 1.33 (s, 24H), 7.06 (d, J=8.46 Hz, 2H), 7.38-7.47 (m, 6H), 7.71 (d, J=7.92 Hz, 4H); MS (ESI+) m/z 606 (M+H)$^+$, 1211 (2M+H)$^+$.

Example 218D (2S,2'S)-tert-butyl 2,2'-(4,4'-(4,4'-(4-(4-tert-butylphenyl)-4H-1,2,4-triazole-3,5-diyl)bis(4,1-phenylene))bis(1H-imidazole-4,2-diyl))dipyrrolidine-1-carboxylate Charged a nitrogen-purged microwave tube (size M, 5 mL) with the product of Example 218C (171 mg, 0.282 mmol), the product of Example 26D (223 mg, 0.706 mmol), and a mixture of absolute EtOH (1.5 mL) and toluene (1.5 mL), then added 1M aq sodium carbonate (0.706 mL, 0.706 mmol) and sparged the mixture with nitrogen for 20 min. Added 1,1'-bis(diphenylphosphino)ferrocene-palladium(II)dichloride dichloromethane complex (23.07 mg, 0.028 mmol), sparged again with nitrogen for 5 min, sealed the tube with an aluminum crimp cap, and heated in a microwave reactor (Personal Chemistry Emrys Creator) with stirring at 100° C. for 1 hr. Cooled the reaction to room temperature, diluted reaction in EtOAc (75 mL), washed with $H_2O$ (2×25 mL) and brine (25 mL), dried organic phase over anhydrous MgSO$_4$, filtered, and concentrated by rotary evaporation to a yellow solid (330 mg). Purified by flash chromatography (silica gel, 3.8 cm×15 cm, gradient of 4%, 6%, 8%, and 10% MeOH/$CH_2Cl_2$) to afford the title compound as a light yellow solid (135 mg, 58%). MS (ESI+) m/z 824 (M+H)$^+$.

Example 218E 4-(4-tert-butylphenyl)-3,5-bis(4-(2-((S)-pyrrolidin-2-yl)-1H-imidazol-4-yl)phenyl)-4H-1,2,4-triazole Dissolved the product of Example 218D (131.5 mg, 0.160 mmol) in anhydrous $CH_2Cl_2$ (2 mL) under nitrogen, added trifluoroacetic acid (1 mL, 12.85 mmol), and stirred at 25° C. for 30 min. Removed the solvent by rotary evaporation, took up the residue in 20% iPrOH/CHCl$_3$ (50 mL), washed with sat'd aq NaHCO$_3$ (10 mL), extracted the aqueous phase with 20% iPrOH/CHCl$_3$ (2×25 mL), dried the combined organic extracts over anhydrous MgSO$_4$, filtered, and concentrated by rotary evaporation. Took up residue in 1:5 v/v $CH_2Cl_2$/hexanes and concentrated in vacuo to afford the title compound as a light tan solid (114 mg). $^1$H NMR (400 MHz, DMSO-D6) δ ppm 1.30 (s, 9H), 1.66-1.94 (m, 6H), 1.98-2.12 (m, 2H), 2.80-3.07 (m, 4H), 3.70-3.86 (m, 1H), 4.12-4.22 (m, 2H), 4.34 (d, J=4.01 Hz, 1H), 7.34 (t, J=8.08 Hz, 6H), 7.47-7.57 (m, 4H), 7.68 (d, J=8.35 Hz, 4H), 11.90 (s, 2H); MS (ESI+) 624 (M+H)$^+$; (ESI−) m/z 622 (M−H)$^-$.

Example 218F (methyl {(2S)-1-[(2S)-2-(4-{4-[4-(4-tert-butylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-4H-1,2,4-triazol-3-yl]phenyl}-1H-imidazol-2-yl)pyrrolidin-1-yl]-3-methyl-1-oxobutan-2-yl}carbamate In an oven-dried 5-mL round bottom flask purged with nitrogen, dissolved the product of Example 218E (50 mg, 0.080 mmol) in anhydrous DMF (1 mL), and cooled to 0° C. Added sequentially (S)-2-(methoxycarbonylamino)-3-methylbutanoic acid (29.5 mg, 0.168 mmol), HOBt hydrate (27.6 mg, 0.180 mmol), EDAC (35.3 mg, 0.180 mmol), and N-methylmorpholine (0.035 mL, 0.321 mmol). Stirred the solution at 25° C. for 15 hr. Diluted the reaction in EtOAc (50 mL), washed with sat'd aq NaHCO$_3$ (25 mL), $H_2O$ (3×25 mL), and brine (25 mL), dried the organic phase over anhydrous MgSO$_4$, filtered, and concentrated by rotary evaporation to an off-white solid (72 mg). Purified by flash chromatography (silica gel, Alltech Extract-Clean 10 g column, gradient of 6% to 8% MeOH/$CH_2Cl_2$) to afford the title compound as an off-white solid (49 mg, 65%). $^1$H NMR (400 MHz, DMSO-D6) δ ppm 0.82 (d, J=6.72 Hz, 6H), 0.86 (d, J=6.72 Hz, 6H), 1.29 (s, 9H), 1.79-2.01 (m, 5H), 2.03-2.22 (m, 4H), 3.53 (s, 6H), 3.70-3.86 (m, 4H), 4.04 (t, J=8.35 Hz, 2H), 5.04 (dd, J=6.67, 3.20 Hz, 2H), 7.23-7.43 (m, 8H), 7.48-7.60 (m, 4H), 7.61-7.73 (m, 4H), 11.77-12.21 (m, 2H); MS (ESI+) m/z 939 (M+H)$^+$.

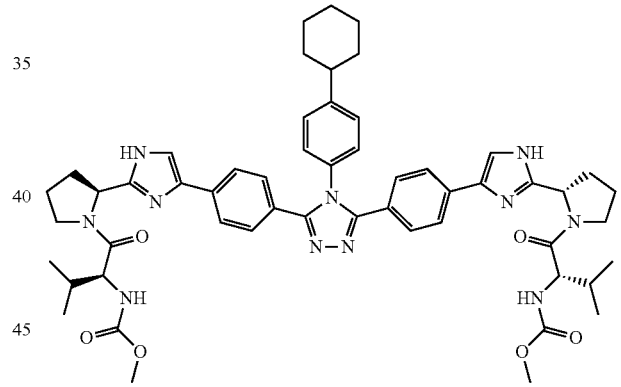

Example 219 methyl {(2S)-1-[(2S)-2-(4-{4-[4-(4-cyclohexylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-4H-1,2,4-triazol-3-yl]phenyl}-1H-imidazol-2-yl)pyrrolidin-1-yl]-3-methyl-1-oxobutan-2-yl}carbamate Example 219A 3,5-bis(4-bromophenyl)-4-(4-cyclohexylphenyl)-4H-1,2,4-triazole In an oven-dried 10-mL round bottom flask, equipped with a septum and purged with nitrogen, 4-cyclohexylaniline (545 mg, 3.01 mmol) was dissolved in anhydrous 1,2-dichlorobenzene (1.5 mL) and the solution cooled to 0° C. A solution of phosphorus oxychloride (78 mg, 0.502 mmol) in anhydrous 1,2-dichlorobenzene (0.5 mL) was added slowly in a dropwise manner from a gas-tight syringe. The reaction became an unstirrable solid gel; removed the cooling bath, added additional 1,2-dichlorobenzene (0.5 mL), sonicated the mixture, and stirred the thick suspension at room temperature for 1 hr to form the phosphoryl triamide in situ. Added the product of Example 218A (200 mg, 0.502 mmol), replaced the septum with a reflux condenser, and heated the reaction in an oil bath at 200° C. for 4 hr under nitrogen. The reaction quickly became a homogeneous gold colored solution upon refluxing. Cooled the solution to room temperature and purified by flash chromatography (silica gel, 3.8 cm×15 cm, gradient of $CH_2Cl_2$ to 20% $EtOAc/CH_2Cl_2$ to 40% $EtOAc/CH_2Cl_2$) to afford the title compound as a fluffy white solid (201 mg, 74%). $^1$H NMR (400 MHz, $CDCl_3$) δ ppm 1.19-1.33 (m, 1H) 1.35-1.50 (m, 4H) 1.78 (d, J=14.42 Hz, 1H) 1.84-1.98 (m, 4H) 2.51-2.65 (m, 1H) 7.04 (d, J=8.35 Hz, 2H) 7.28 (d, J=8.57 Hz, 6H) 7.43 (d, J=8.57 Hz, 4H); MS (ESI+) m/z 536/538540 (M+H)$^+$, 1072/1074/1076 (2M+H)$^+$ with two bromines.

Example 219B 4-(4-cyclohexylphenyl)-3,5-bis(4(4,4,5,5-tetramethyl-1,3,2-dioxaboralan-2-yl)phenyl)-4H-1,2,4-triazole Charged an oven-dried 10-mL round bottom flask, purged with nitrogen, with the product of Example 219A (100 mg, 0.186 mmol), bis(pinacalato)diboron (142 mg, 0.558 mmol), potassium acetate (59.4 mg, 0.605 mmol), and anhydrous dioxane (3 mL). Sparged the thick white mixture with nitrogen for 30 min, added 1,1'-bis(diphenylphosphino)ferrocene-palladium(II)dichloride dichloromethane complex (15.20 mg, 0.019 mmol), re-sparged with nitrogen for 5 min, replaced rubber septum with a glass stopper, and heated in an oil bath (85° C.). Reaction became homogeneous upon heating and darkened with time to a reddish-brown color. TLC (SiO2, 50% $EtOAc/CH_2Cl_2$). After 2 hr, cooled reaction to room temperature, added additional bis(pinacalato)diboron (71 mg, ~1.5 equiv) and potassium acetate (30 mg, ~1.75 equiv), and heated for 1 hr at 85° C. Cooled the brown colored reaction to room temperature, vacuum filtered through a small bed of Celite 545, washed the collected solids thoroughly with $CH_2Cl_2$, and concentrated the filtrate by rotary evaporation to a brown foam. Purified by silica gel flash chromatography (Alltech Extract-Clean column, 10 g bed) eluting with 30% $EtOAc/CH_2Cl_2$ to afford the product as a light brown oil (190 mg). Repurified by silica gel flash chromatography (Alltech Extract-Clean column, 10 g bed) eluting with 3% $MeOH/CH_2Cl_2$ to afford the title compound as a light beige foam (122 mg, 100%). MS (ESI+) m/z 632 (M+H)$^+$, 1263 (2M+H)$^+$.

Example 219C methyl {(2S)-1-[(2S)-2-(4-{4-[4-(4-cyclohexylphenyl)-5-(4-{2-[(2S)-1-{(2S)-2-[(methoxycarbonyl)amino]-3-methylbutanoyl}pyrrolidin-2-yl]-1H-imidazol-4-yl}phenyl)-4H-1,2,4-triazol-3-yl]phenyl}-1H-imidazol-2-yl)pyrrolidin-1-yl]-3-methyl-1-oxobutan-2-yl}carbamate Charged a nitrogen-purged microwave tube (size M, 5 mL) with the product of Example 219B (118 mg, 0.187 mmol), the product of Example 126G (174 mg, 0.467 mmol), and a mixture of absolute EtOH (1 mL) and toluene (1 mL), then added 1 M aq sodium carbonate (0.467 mL, 0.467 mmol) and sparged the mixture with nitrogen for 20 min. Added 1,1'-bis(diphenylphosphino)ferrocene-palladium(II)dichloride dichloromethane complex (15.26 mg, 0.019 mmol), sparged again with nitrogen for 5 min, sealed the tube with an aluminum crimp cap, and heated in a microwave reactor (Personal Chemistry Emrys Creator) with stirring at 100° C. for 1 hr. Cooled reaction to room temperature, diluted reaction in EtOAc (50 mL), washed with $H_2O$ (2×25 mL) and brine (25 mL), dried the organic phase over anhydrous $MgSO_4$, filtered, and concentrated by rotary evaporation to a solid. Purified by flash chromatography (silica gel, step gradient 5% to 8% to 100% $MeOH/CH_2Cl_2$) to afford the product as a tan solid (72 mg) which was ~85% pure (2 main impurities). Dissolved impure product in 1.5 mL 1:1 v/v MeOH/DMSO and purified by RP-C18 HPLC (Waters Prep LC, 40 mm Module with Nova Pak HR $C_{18}$ 6 μm 40×100 mm Prep Pak cartridge) eluting with a 30 min gradient of 95:5 0.1% TFA in $H_2O$/AcCN to 25:75 0.1% TFA in $H_2O$/AcCN, then 10 min to 100% AcCN at 20 mL/min. Pure fractions were concentrated by rotary evaporation (water bath 35° C.) to a small volume, partitioned between 20% $iPrOH/CHCl_3$ (50 mL) and sat'd aq $NaHCO_3$ (15 mL), separated layers, dried the organic extract over anhydrous $MgSO_4$, filtered, and concentrated by rotary evaporation to afford the title compound as a white solid (34.5 mg, 19%). $^1$H NMR (400 MHz, DMSO-D6) δ ppm 0.83 (d, J=6.72 Hz, 6H) 0.86 (d, J=6.72 Hz, 6H) 1.29-1.47 (m, 5H) 1.65-2.01 (m, 12H) 2.04-2.21 (m, 4H) 3.53 (s, 6H) 3.72-3.84 (m, 4H) 4.04 (t, 8.40 Hz, 2H) 5.04 (dd, J=6.89, 3.20 Hz, 2H) 7.23-7.40 (m, 10H) 7.51-7.72 (m, 6H) 11.84 (s, 2H); MS (ESI+) m/z 965 (M+H)$^+$.

Examples 220-308 were prepared in analogous fashion according to the methods and conditions illustrated in the foregoing schemes and examples.

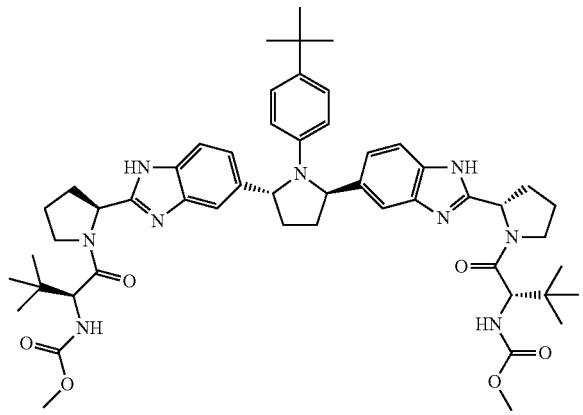 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)(C)C)nc5c4)N3c3ccc(C(C)(C)C)cc3)ccc2[nH]1)C(C)(C)C]

Example 220 methyl {(2S)-1-[(2S)-2-{5-[(2R,5R)-1-(4-tert-butylphenyl)-5-{2-[(2S)-1-{(2S)-2-[(methoxycarbonyl)amino]-3,3-dimethylbutanoyl}pyrrolidin-2-yl]-1H-benzimidazol-5-yl}pyrrolidin-2-yl]-1H-benzimidazol-2-yl}pyrrolidin-1-yl]-3,3-dimethyl-1-oxobutan-2-yl}carbamate $^1$H NMR (400 MHz, DMSO-d6) δ ppm 0.88 (d, J=13.55 Hz, 18H), 1.07 (s, 9H), 1.62-1.78 (m, 2H), 1.91-2.09 (m, 4H), 2.10-2.26 (m, 4H), 2.54-2.62 (m, 2H), 3.55 (s, 6H), 3.74-3.90 (m, 4H), 4.23 (dd, J=8.78, 4.55 Hz, 2H), 5.09-5.23 (m, 2H), 5.31-5.43 (m, 2H), 6.26 (d, J=8.89 Hz, 2H), 6.84-6.97 (m, 2H), 7.06 (dd, J=8.29, 2.55 Hz, 2H), 7.12 (t, J=9.43 Hz, 2H), 7.20 (s, 1H), 7.30 (s, 1H), 7.38 (d, J=8.24 Hz, 1H) 7.45 (d, J=8.24 Hz, 1H), 12.02 (s, 2H); MS (ESI+) m/z 916 (M+H)$^+$.

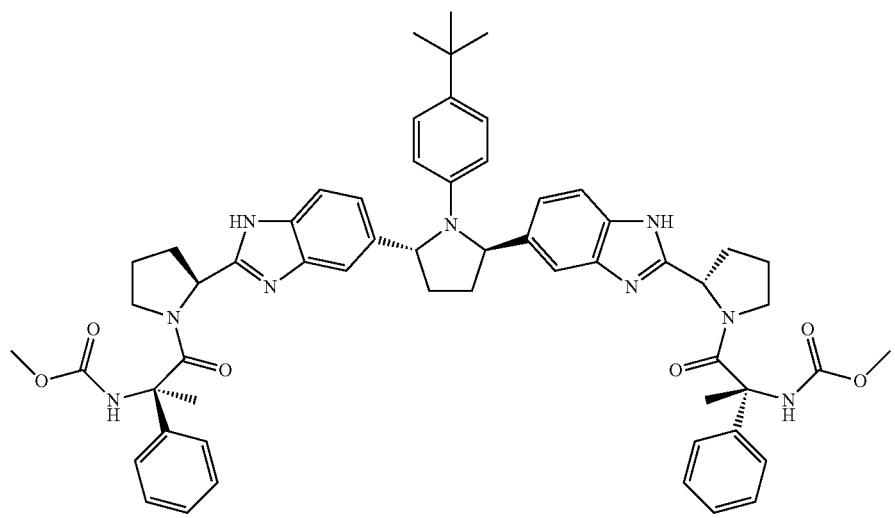

Example 221 dimethyl ([(2R,5R)-1-(4-tert-butylphenyl)pyrrolidine-2,5-diyl]bis{1H-benzimidazole-5,2-diyl(2S)pyrrolidine-2,1-diyl[(2R)-1-oxo-2-phenylpropane-1,2-diyl]})biscarbamate $^1$H NMR (400 MHz, DMSO-d6) δ ppm 1.03-1.10 (m, 9H), 1.49-1.58 (m, 2H), 1.67 (d, J=16.70 Hz, 6H), 1.70-1.95 (m, 4H), 2.04 (s, 3H), 2.35-2.43 (m, 1H), 2.97-3.11 (m, 2H), 3.22-3.29 (m, 1H), 3.50 (s, 6H), 3.61-3.91 (m, 1H), 5.08-5.22 (m, 2H), 5.29-5.49 (m, 2H), 6.21-6.39 (m, 2H), 6.84-6.99 (m, 2H), 7.07-7.50 (m, 17H), 7.53 (d, J=8.24 Hz, 1H), 7.61 (s, 2H), 12.10 (two s, 2H); MS (ESI+) m/z 984 (M+H)$^+$.

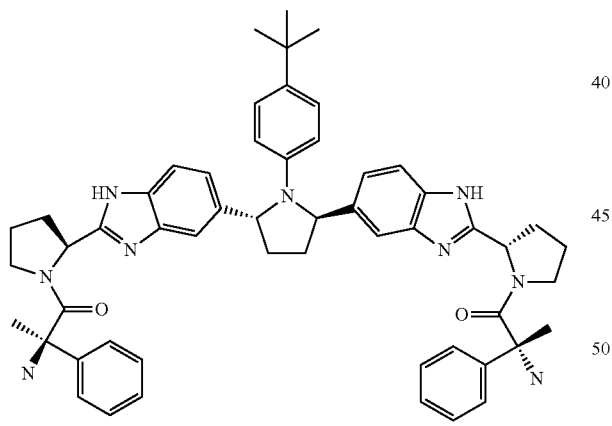

Example 222

(2R,2'R)-1,1'-{[(2R,5R)-1-(4-tert-butylphenyl)pyrrolidine-2,5-diyl]bis[1H-benzimidazole-5,2-diyl(2S)pyrrolidine-2,1-diyl]}bis(2-amino-2-phenylpropan-1-one)

$^1$H NMR (400 MHz, DMSO-d6) δ ppm 1.10 (s, 9H), 1.55-1.66 (m, 3H), 1.68-1.82 (m, 4H), 1.83-2.02 (m, 5H), 1.93 (s, 6H), 2.12-2.31 (m, 3H), 2.57 (d, J=3.90 Hz, 2H), 5.26-5.36 (m, 2H), 5.41-5.57 (m, 2H), 6.30 (d, J=8.78 Hz, 2H), 6.93 (d, J=8.78 Hz, 2H), 7.17-7.31 (m, 2H), 7.38 (s, 2H), 7.47-7.66 (m, 13H), 8.43 (s, 6H); MS (ESI+) m/z 868 (M+H)$^+$.

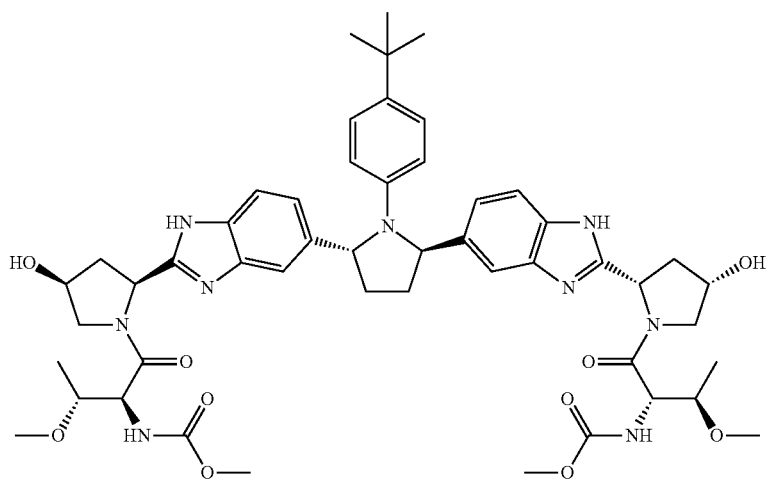

Example 223 methyl {(2S,3R)-1-[(2S,4S)-2-{5-[(2R,5R)-1-(4-tert-butylphenyl)-5-(2-{(2S,4S)-4-hydroxy-1-[N-(methoxycarbonyl)-O-methyl-L-threonyl]pyrrolidin-2-yl}-1H-benzimidazol-5-yl)pyrrolidin-2-yl]-1H-benzimidazol-2-yl}-4-hydroxypyrrolidin-1-yl]-3-methoxy-1-oxobutan-2-yl}carbamate ¹H NMR (400 MHz, DMSO-d6) δ ppm 0.96 (d, J=5.96 Hz, 6H), 1.09 (s, 9H), 1.74 (d, J=5.64 Hz, 2H), 2.06-2.15 (m, 3H), 2.96-3.03 (m, 1H), 3.10 (s, 6H), 3.55 (s, 6H), 3.72 (dd, J=9.65, 2.39 Hz, 3H), 3.94 (dd, J=10.25, 4.72 Hz, 2H), 4.23-4.33 (m, 2H), 4.38 (t, J=7.10 Hz, 1H), 4.44-4.53 (m, 2H), 5.26 (dd, J=8.46, 4.23 Hz, 2H), 5.49 (d, J=5.53 Hz, 2H), 6.25 (d, J=8.78 Hz, 2H), 6.94 (d, J=8.78 Hz, 2H), 7.22 (d, J=8.46 Hz, 2H), 7.37 (d, J=7.59 Hz, 2H), 7.46 (s, 2H), 7.69 (d, J=7.92 Hz, 2H); MS (ESI+) m/z 952 (M+H)⁺.

Example 224 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(1-methoxy-2-methylpropan-2-yl)phenyl]pyrrolidin-2-yl}-1H-benzimidazol-2-yl)pyrrolidin-1-yl]-3-methyl-1-oxobutan-2-yl}carbamate 1H NMR (400 MHz, DMSO-D6) δ ppm 0.74-0.93 (m, 12H) 1.04 (s, 6H) 1.69 (d, J=4.34 Hz, 2H) 1.85-1.94 (m, 2H) 1.95-2.03 (m, 6H) 2.13-2.25 (m, 2H) 2.53-2.63 (m, 4H) 3.11 (s, 3H) 3.53 (s, 6H) 3.81 (s, 4H) 4.05-4.15 (m, 2H) 5.09-5.19 (m, 2H) 5.32-5.41 (m, 2H) 6.25 (d, J=8.78 Hz, 2H) 6.87 (ddd, J=8.89, 4.77, 4.55 Hz, 2H) 7.07 (t, J=7.37 Hz, 2H) 7.20 (s, 1H) 7.25-7.33 (m, 3H) 7.38 (d, J=8.24 Hz, 1H) 7.46 (d, J=8.46 Hz, 1H) 12.00-12.09 (m, 2H); MS ESI+ 918.

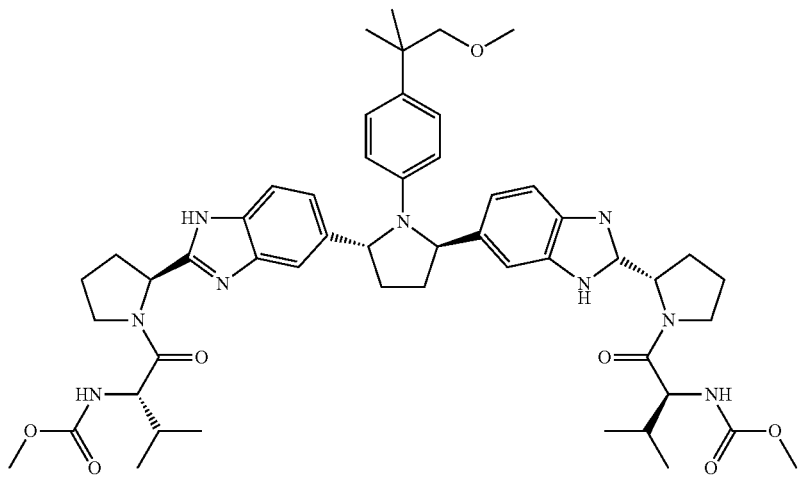

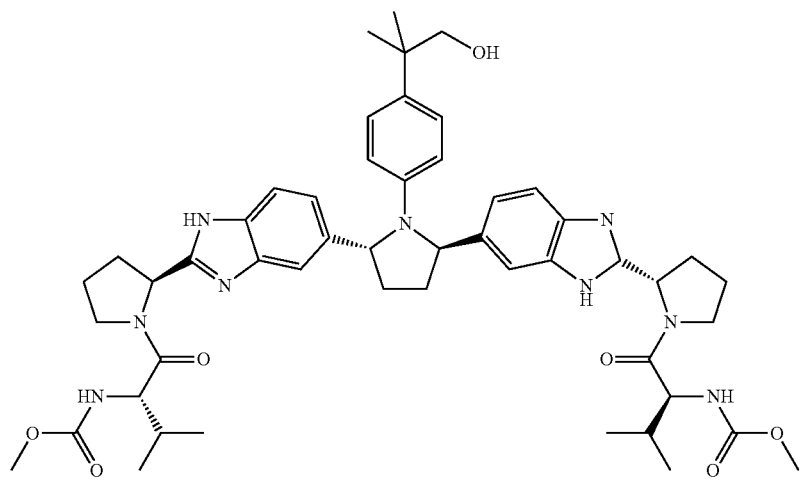

Example 225 methyl {(2S)-1-[(2S)-2-{6-[(2R,5R)-1-[4-(1-hydroxy-2-methylpropan-2-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.76-0.91 (m, 12H) 1.01 (d, J=2.60 Hz, 6H) 1.64-1.72 (m, 2H) 1.91 (dd, J=14.42, 6.83 Hz, 2H) 1.95-2.05 (m, 4H) 2.14-2.23 (m, 4H) 2.54-2.60 (m, 2H) 3.53 (s, 6H) 3.76-3.87 (m, 4H) 4.11 (q, J=4.77 Hz, 4H) 4.42 (s, 1H) 5.09-5.17 (m, 2H) 5.31-5.40 (m, 2H) 6.25 (d, J=8.78 Hz, 2H) 6.83-6.92 (m, 2H) 7.07 (t, J=7.21 Hz, 2H) 7.20 (s, 1H) 7.26-7.32 (m, 3H) 7.38 (d, J=8.13 Hz, 1H) 7.46 (d, J=8.35 Hz, 1H) 11.99-12.06 (m, 2H); MS ESI+ m/z 904.5 (M+H)+.

Example 226 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-{2-[4-(trifluoromethyl)phenyl]-1,3-thiazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.73-0.91 (m, 12H) 1.79-1.95 (m, 4H) 1.96-2.06 (m, 4H) 2.15-2.27 (m, 2H) 2.69-2.76 (m, 2H) 3.43-3.50 (m, 2H) 3.53 (s, 6H) 3.78-3.88 (m, 4H) 4.01-4.10 (m, 2H) 5.11-5.18 (m, 2H) 5.32-5.41 (m, 2H) 6.43 (s, 1H) 7.09-7.18 (m, 2H) 7.27 (dd, J=8.24, 2.39 Hz, 2H) 7.35 (s, 1H) 7.41-7.46 (m, 2H) 7.51 (d, J=8.35 Hz, 1H) 7.57-7.62 (m, 2H) 7.64-7.70 (m, 2H) 12.12 (s, 2H); MS ESI+ m/z 983.4 (M+H)+.

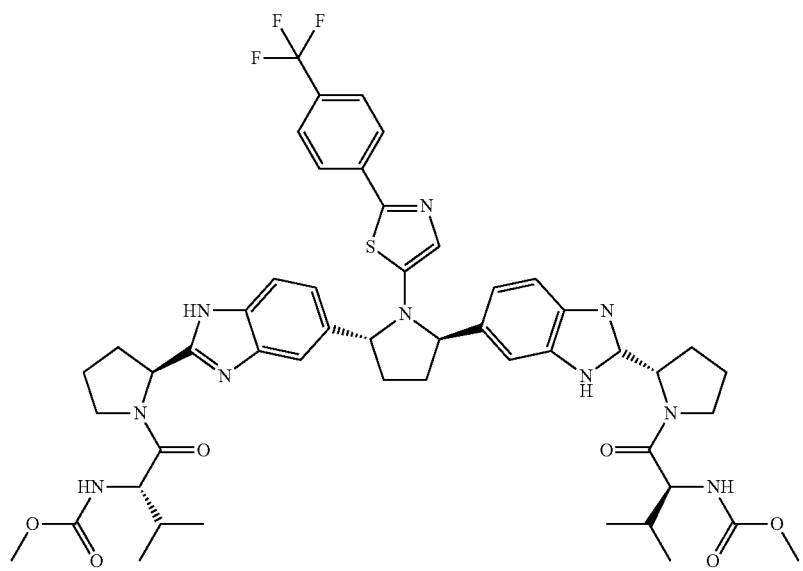

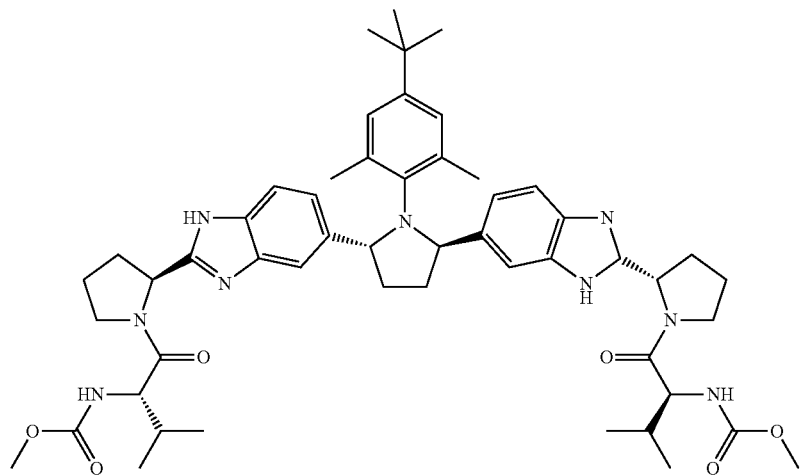

Example 227 methyl {(2S)-1-[(2S)-2-{6-[(2R,5R)-1-(4-tert-butyl-2,6-dimethylphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.77-0.89 (m, 12H) 1.02 (s, 9H) 1.84-2.05 (m, 10H) 2.13-2.19 (m, 4H) 2.24-2.30 (m, 6H) 3.53 (s, 6H) 3.80 (s, 4H) 4.04 (t, J=8.08 Hz, 2H) 5.07-5.14 (m, 2H) 5.25 (s, 2H) 6.61 (dd, J=5.10, 2.71 Hz, 2H) 7.06 (dd, J=11.87, 8.51 Hz, 2H) 7.20-7.37 (m, 6H) 11.89 (s, 1H) 11.99 (s, 1H); MS ESI+ m/z 916.6 (M+H)+.

Example 228 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-(4-phenylcyclohexyl)pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.78-0.93 (m, 12H) 1.15-1.44 (m, 4H) 1.46-1.59 (m, 2H) 1.67-1.78 (m, 2H) 1.84-1.96 (m, 4H) 1.98-2.10 (m, 4H) 2.14-2.27 (m, 4H) 2.67-2.75 (m, 2H) 3.07-3.21 (m, 1H) 3.45-3.52 (m, 1H) 3.54 (s, 6H) 3.78-3.91 (m, 4H) 4.03-4.13 (m, 2H) 4.64-4.73 (m, 2H) 5.17 (d, J=4.88 Hz, 2H) 7.00-7.06 (m, 2H) 7.09 (t, J=7.32 Hz, 2H) 7.14-7.24 (m, 3H) 7.30 (d, J=8.46 Hz, 2H) 7.38 (d, J=8.02 Hz, 1H) 7.43-7.50 (m, 3H) 12.00 (s, 2H); MS ESLD+ m/z 914.

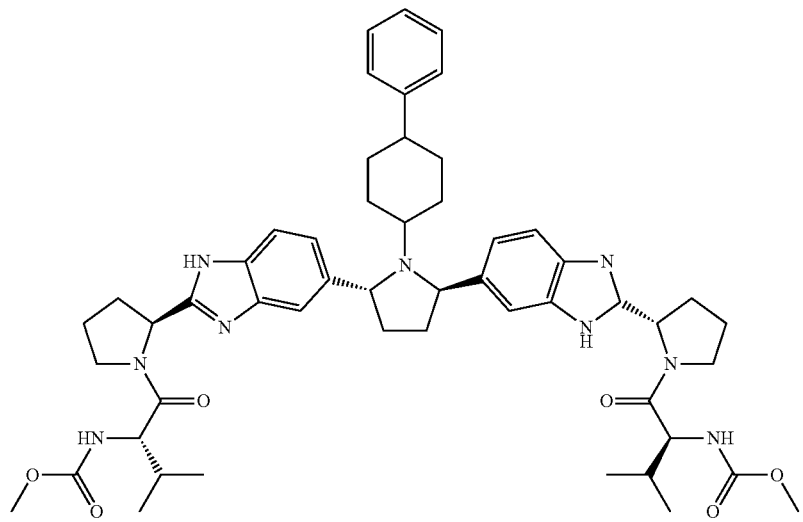

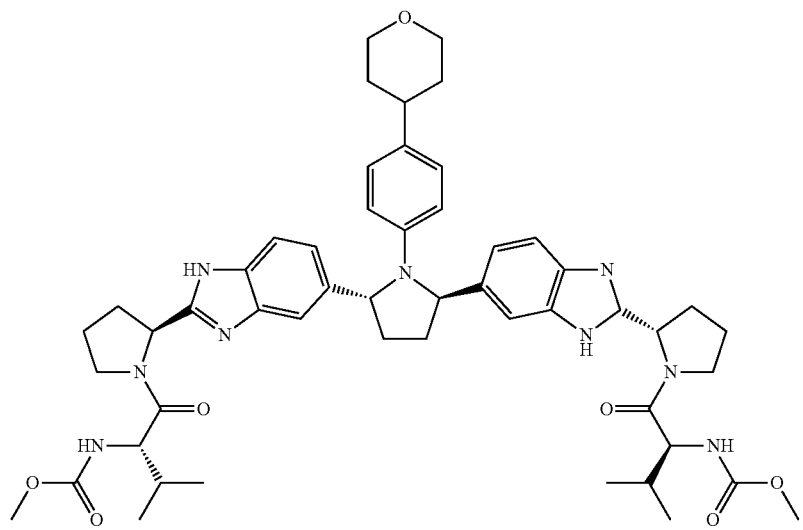

Example 229 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(tetrahydro-2H-pyran-4-yl)phenyl]pyrrolidin-2-yl}-1H-benzimidazol-2-yl)pyrrolidin-1-yl]-3-methyl-1-oxobutan-2-yl}carbamate 1H NMR (400 MHz, DMSO-D6) d ppm 0.73-0.94 (m, 12H) 1.41-1.60 (m, 6H) 1.65-1.75 (m, 2H) 1.86-1.94 (m, 2H) 1.95-2.05 (m, 4H) 2.14-2.24 (m, 4H) 2.37-2.46 (m, 2H) 3.53 (s, 6H) 3.77-3.86 (m, 7H) 4.02-4.10 (m, 2H) 5.09-5.17 (m, 2H) 5.32-5.39 (m, 2H) 6.26 (d, J=8.67 Hz, 2H) 6.72-6.81 (m, 2H) 7.06 (t, J=7.64 Hz, 2H) 7.20 (s, 1H) 7.26-7.31 (m, 3H) 7.37 (d, J=8.13 Hz, 1H) 7.45 (d, J=8.13 Hz, 1H) 12.00-12.05 (m, 2H); MS ESLD+ m/z 917 (M+H)+.

Example 230 methyl {(2S)-1-[(2S,4S)-2-{6-[(2R,5R)-1-(4-tert-butylphenyl)-5-{2-[(2S,4S)-4-hydroxy-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}-4-hydroxypyrrolidin-1-yl]-3-methyl-1-oxobutan-2-yl}carbamate 1H NMR (500 MHz, DMSO-D6) d ppm 0.67-0.91 (m, 12H) 1.07 (s, 9H) 1.69 (d, J=3.97 Hz, 2H) 1.78-1.89 (m, 2H) 2.01 (d, J=13.12 Hz, 2H) 2.37-2.44 (m, 2H) 3.53 (s, 6H) 3.67 (d, J=10.07 Hz, 2H) 3.95-4.07 (m, 4H) 4.38 (s, 2H) 5.12 (s, 2H) 5.37 (s, 2H) 6.25 (d, J=8.54 Hz, 2H) 6.34 (s, 2H) 6.86-6.94 (m, 2H) 7.09 (d, J=7.93 Hz, 2H) 7.22-7.33 (m, 4H) 7.39-7.51 (m, 2H) 12.27 (d, J=21.05 Hz, 2H); MS ESLD+ m/z 920.

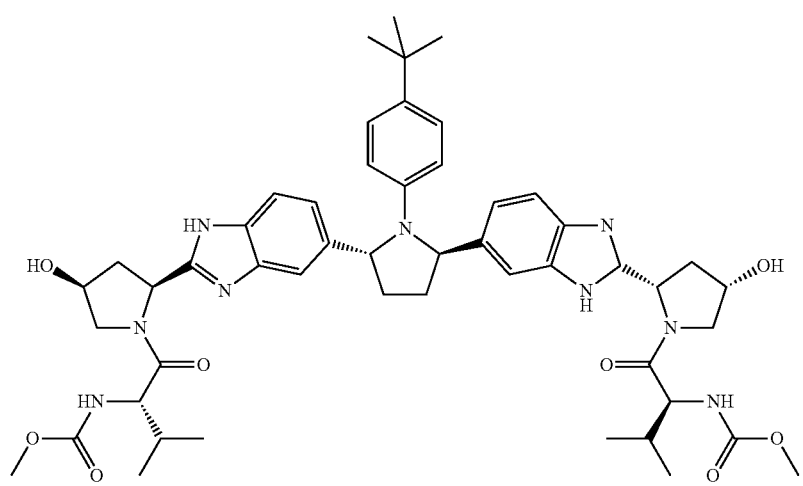

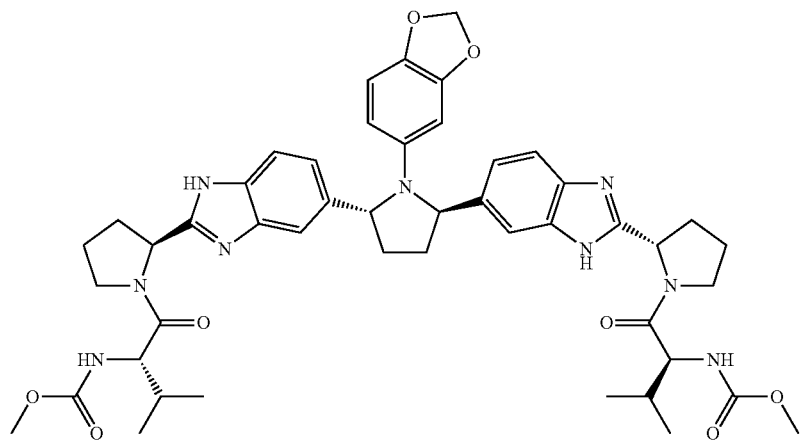

Example 231 methyl {(2S)-1-[(2S)-2-{6-[(2R,5R)-1-(1,3-benzo-dioxol-5-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.78-0.91 (m, 12H) 1.64-1.72 (m, 2H) 1.86-2.04 (m, 6H) 2.14-2.24 (m, 4H) 3.29 (s, 2H) 3.54 (s, 6H) 3.82 (s, 4H) 4.05-4.11 (m, 2H) 5.10-5.18 (m, 2H) 5.29-5.36 (m, 2H) 5.66 (d, J=2.93 Hz, 1H) 5.70-5.75 (m, 2H) 5.99 (d, J=2.28 Hz, 1H) 6.45-6.51 (m, 1H) 7.02-7.09 (m, 2H) 7.21 (s, 1H) 7.28 (s, 1H) 7.31 (d, J=6.40 Hz, 2H) 7.37 (d, J=8.13 Hz, 1H) 7.45 (d, J=8.24 Hz, 1H) 12.03 (s, 2H); MS TFA+ m/z 876.8 (M+H)+.

Example 232 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-5-yl}-1-(4-{[(4S)-2-oxo-1,3-oxazolidin-4-yl]methyl}phenyl)pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.77-0.92 (m, 12H) 1.63-1.74 (m, 2H) 1.86-2.04 (m, 6H) 2.13-2.26 (m, 4H) 2.55-2.65 (m, 2H) 3.25-3.33 (m, 2H) 3.54 (s, 6H) 3.75-3.87 (m, 6H) 4.05-4.17 (m, 3H) 5.09-5.19 (m, 2H) 5.36 (d, J=5.10 Hz, 2H) 6.27 (d, J=8.57 Hz, 2H) 6.71-6.79 (m, 2H) 7.05 (t, J=9.60 Hz, 2H) 7.20 (s, 1H) 7.27-7.33 (m, 3H) 7.37 (d, J=8.24 Hz, 1H) 7.45 (d, J=8.13 Hz, 1H) 7.63 (s, 1H) 12.03 (s, 2H); MS ESI+ m/z 931.5 (M+H)+.

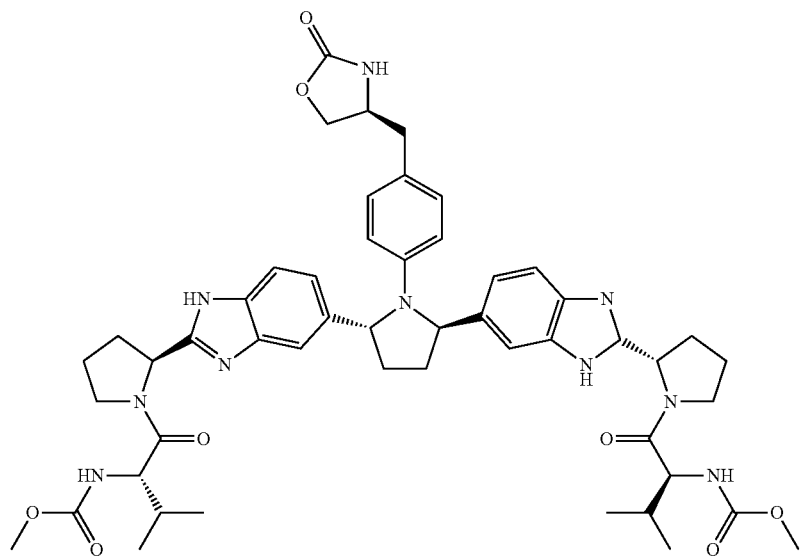

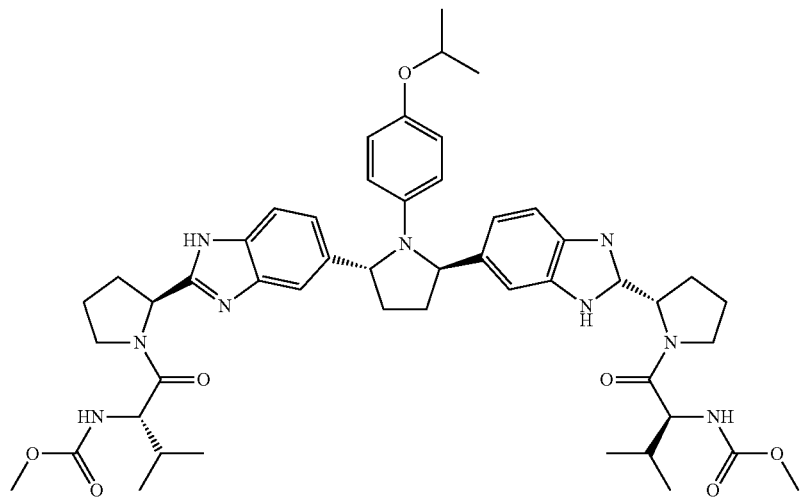

Example 233 methyl {(2S)-1-[(2S)-2-(6-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(propan-2-yloxy)phenyl]pyrrolidin-2-yl}-1H-benzimidazol-2-yl)pyrrolidin-1-yl]-3-methyl-1-oxobutan-2-yl}carbamate 1H NMR (400 MHz, DMSO-D6) d ppm 0.76-0.89 (m, 12H) 1.07 (t, J=5.42 Hz, 6H) 1.68 (d, J=3.47 Hz, 2H) 1.85-2.05 (m, 6H) 2.14-2.25 (m, 4H) 2.58 (d, J=4.77 Hz, 2H) 3.53 (s, 6H) 3.81 (s, 4H) 4.05 (t, J=8.40 Hz, 2H) 4.13-4.25 (m, 1H) 5.08-5.20 (m, 2H) 5.32 (d, J=5.31 Hz, 2H) 6.23 (d, J=9.00 Hz, 2H) 6.45-6.55 (m, 2H) 7.05 (t, J=8.19 Hz, 2H) 7.20 (s, 1H) 7.26-7.33 (m, 3H) 7.37 (d, J=8.24 Hz, 1H) 7.44 (d, J=8.35 Hz, 1H) 12.02 (d, J=4.55 Hz, 2H); MS ESI+ m/z 890.4 (M+H)+.

Example 234 methyl {(2S)-1-[(2S)-2-{5-[(2R,5R)-1-[2-(4-fluorophenyl)-1,3-thiazol-5-yl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.75-0.85 (m, 12H) 1.77-1.83 (m, 2H) 1.87-1.93 (m, 2H) 1.95-2.06 (m, 4H) 2.14-2.25 (m, 6H) 3.53 (s, 6H) 3.77-3.86 (m, 4H) 4.03-4.10 (m, 2H) 5.12-5.18 (m, 2H) 5.28-5.35 (m, 2H) 7.06-7.16 (m, 5H) 7.28 (dd, J=8.29, 2.01 Hz, 2H) 7.33 (s, 1H) 7.40-7.45 (m, 2H) 7.47-7.55 (m, 3H) 12.10 (s, 2H); MS ESI+ m/z 933.4 (M+H)+.

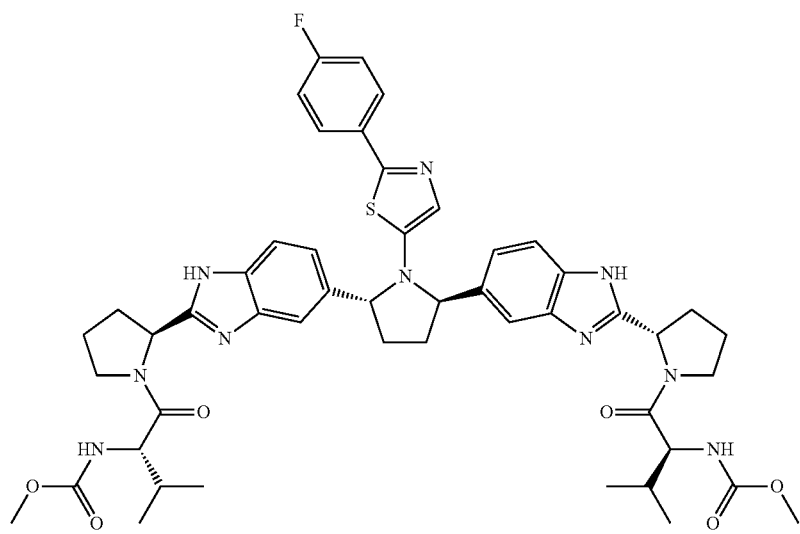

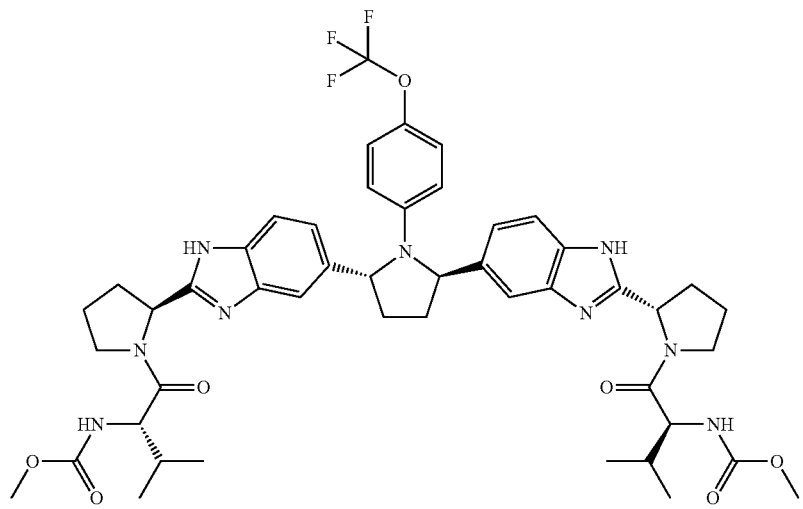

Example 235 methyl {(2S)-1-[(2S)-2-(5-{(2R,5R)-5-{2-[(2S)-1-
{(2S)-2-[(methoxycarbonyl)amino]-3-
methylbutanoyl}pyrrolidin-2-yl]-1H-benzimidazol-
5-yl}-1-[4-(trifluoromethoxy)phenyl]pyrrolidin-2-
yl}-1H-benzimidazol-2-yl)pyrrolidin-1-yl]-3-
methyl-1-oxobutan-2-yl}carbamate 1H NMR (400 MHz, DMSO-D6) d ppm 0.74-0.87 (m, 12H) 1.67-1.76 (m, 2H) 1.86-1.92 (m, 2H) 1.96-2.06 (m, 4H) 2.15-2.23 (m, 6H) 3.53 (s, 6H) 3.77-3.88 (m, 4H) 4.05 (t, J=8.84 Hz, 2H) 5.12 (t, J=7.05 Hz, 2H) 5.37-5.46 (m, 2H) 6.34 (d, J=9.11 Hz, 2H) 6.89 (q, J=7.30 Hz, 2H) 7.02-7.11 (m, 2H) 7.21 (s, 1H) 7.26-7.33 (m, 3H) 7.39 (d, J=8.35 Hz, 1H) 7.47 (d, J=8.13 Hz, 1H) 12.06 (d, J=17.02 Hz, 2H); MS ESI+ m/z 916.4 (M+H)+.

Example 236 methyl {(2S)-1-[(2S,4S)-2-{5-[(2R,5R)-1-(4-tert-
butylphenyl)-5-{2-[(2S,4S)-4-methoxy-1-{(2S)-2-
[(methoxycarbonyl)amino]-3-
methylbutanoyl}pyrrolidin-2-yl]-1H-benzimidazol-
5-yl}pyrrolidin-2-yl]-1H-benzimidazol-2-yl}-4-
methoxypyrrolidin-1-yl]-3-methyl-1-oxobutan-2-
yl}carbamate 1H NMR (400 MHz, DMSO-D6) d ppm 0.75-0.88 (m, 12H) 1.07 (s, 9H) 1.67-1.76 (m, 2H) 1.88-2.00 (m, 4H) 2.06-2.16 (m, 2H) 3.12-3.21 (m, 2H) 3.25 (d, J=4.23 Hz, 6H) 3.54 (s, 6H) 3.59-3.69 (m, 2H) 4.02-4.13 (m, 4H) 4.16-4.28 (m, 2H) 5.11 (td, J=9.38, 6.51 Hz, 2H) 5.35 (t, J=5.37 Hz, 2H) 6.23-6.28 (m, 2H) 6.90 (d, J=8.89 Hz, 2H) 7.06 (d, J=10.19 Hz, 2H) 7.22 (d, J=3.25 Hz, 1H) 7.25-7.32 (m, 3H) 7.38 (d, J=8.35 Hz, 1H) 7.45 (d, J=8.24 Hz, 1H) 11.79 (d, J=18.32 Hz, 2H); MS ESI+ m/z 948.5 (M+H)+.

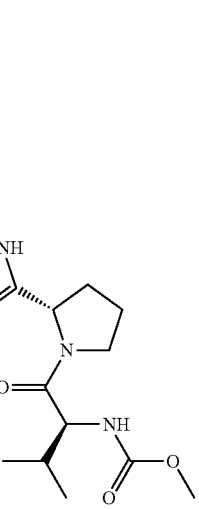

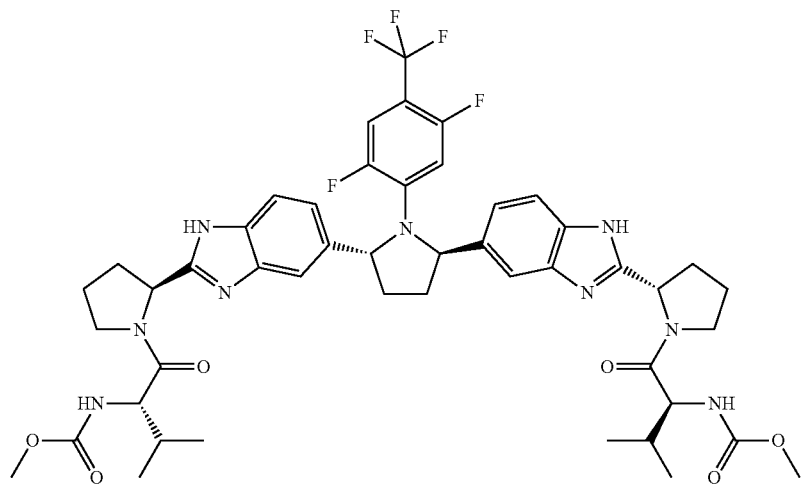

Example 237 methyl {(2S)-1-[(2S)-2-{5-[(2R,5R)-1-[2,5-difluoro-4-(trifluoromethyl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.74-0.90 (m, 12H) 1.74-1.83 (m, 2H) 1.86-1.93 (m, 2H) 1.94-2.05 (m, 4H) 2.13-2.25 (m, 4H) 3.44-3.48 (m, 2H) 3.53 (s, 6H) 3.77-3.88 (m, 4H) 4.06 (t, J=4.23 Hz, 2H) 5.10-5.16 (m, 2H) 5.63-5.74 (m, 2H) 6.60-6.73 (m, 1H) 7.04-7.20 (m, 4H) 7.24-7.31 (m, 3H) 7.38 (d, J=8.46 Hz, 1H) 7.46 (d, J=8.13 Hz, 1H) 12.08 (d, J=27.11 Hz, 2H); MS ESI+ m/z 936.4 (M+H)+.

Example 238 methyl {(2S)-1-[(2S)-2-{6-[(2R,5R)-1-[3-fluoro-4-(trifluoromethyl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.75-0.90 (m, 12H) 1.71-1.79 (m, 2H) 1.87-1.95 (m, 2H) 1.97-2.04 (m, 4H) 2.13-2.25 (m, 6H) 3.53 (s, 6H) 3.77-3.86 (m, 4H) 4.04-4.11 (m, 2H) 5.11-5.18 (m, 2H) 5.46-5.56 (m, 2H) 6.24 (dd, J=8.24, 2.39 Hz, 2H) 7.04-7.11 (m, 2H) 7.19-7.25 (m, 2H) 7.28 (dd, J=8.46, 3.69 Hz, 2H) 7.32 (s, 1H) 7.41 (d, J=8.13 Hz, 1H) 7.49 (d, J=8.24 Hz, 1H) 12.09 (dd, J=15.72, 2.17 Hz, 2H); MS ESI+ m/z 918.4 (M+H)+.

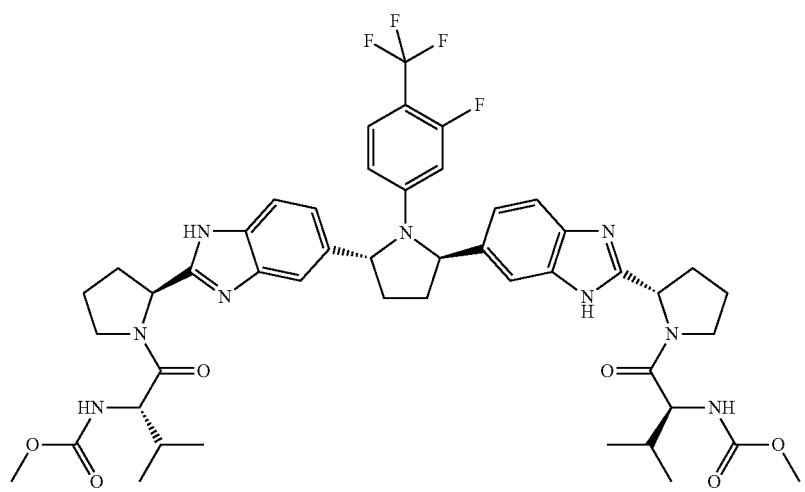

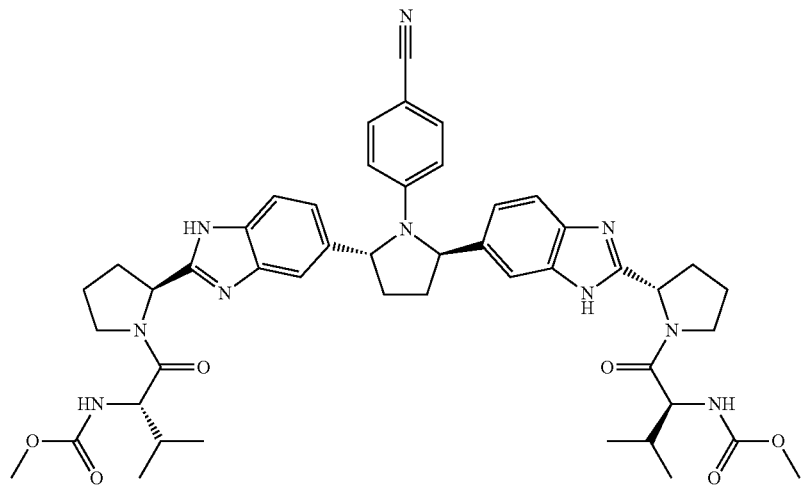

Example 239 methyl {(2S)-1-[(2S)-2-{6-[(2R,5R)-1-(4-cyanophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.76-0.90 (m, 12H) 1.70-1.79 (m, 2H) 1.90 (dd, J=12.25, 6.40 Hz, 2H) 1.95-2.02 (m, 4H) 2.15-2.24 (m, 6H) 3.54 (s, 6H) 3.78-3.85 (m, 4H) 4.06 (t, J=8.29 Hz, 2H) 5.10-5.16 (m, 2H) 5.46-5.55 (m, 2H) 6.42 (d, J=8.67 Hz, 2H) 7.05 (dd, J=12.90, 8.57 Hz, 2H) 7.22 (s, 1H) 7.25-7.34 (m, 5H) 7.40 (d, J=8.24 Hz, 1H) 7.47 (d, J=8.24 Hz, 1H) 12.09 (s, 2H); MS ESI+ m/z 857.4 (M+H)+.

Example 240 methyl {(2S)-1-[(2S)-2-{6-[(2R,5R)-1-[4-(2-cyanopropan-2-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.75-0.91 (m, 12H) 1.47 (s, 6H) 1.67-1.76 (m, 2H) 1.85-1.95 (m, 2H) 1.96-2.03 (m, 4H) 2.15-2.24 (m, 6H) 3.53 (s, 6H) 3.77-3.85 (m, 4H) 4.05 (t, J=8.46 Hz, 2H) 5.10-5.17 (m, 2H) 5.37-5.45 (m, 2H) 6.34 (d, J=8.89 Hz, 2H) 6.97-7.04 (m, 2H) 7.07 (t, J=8.35 Hz, 2H) 7.21 (s, 1H) 7.28 (d, J=10.52 Hz, 3H) 7.39 (d, J=8.13 Hz, 1H) 7.47 (d, J=8.24 Hz, 1H) 12.05 (d, J=13.01 Hz, 2H); MS ESI+ m/z 899.4 (M+H)+.

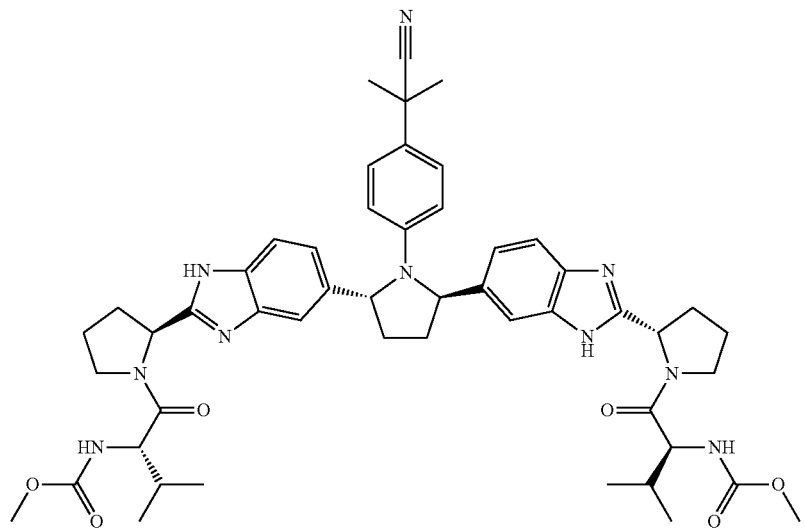

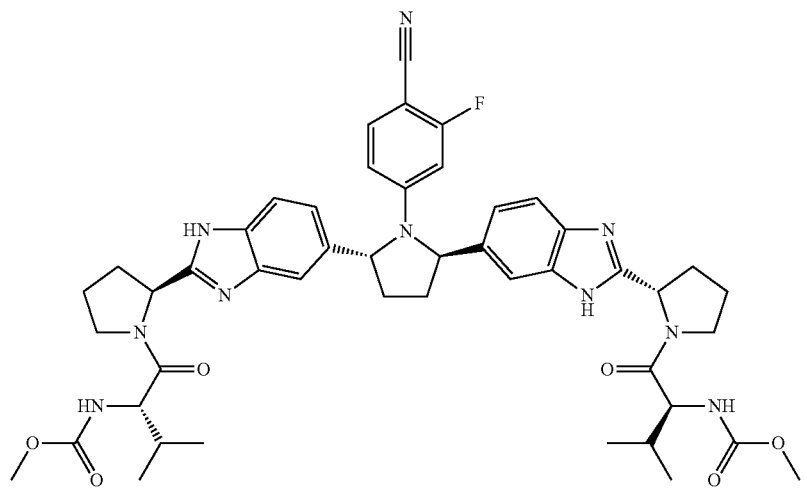

Example 241 methyl {(2S)-1-[(2S)-2-{6-[(2R,5R)-1-(4-cyano-3-fluorophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.74-0.92 (m, 12H) 1.74 (t, J=9.00 Hz, 2H) 1.87-1.94 (m, 2H) 1.96-2.06 (m, 4H) 2.15-2.25 (m, 4H) 2.55-2.63 (m, 2H) 3.54 (s, 6H) 3.82 (s, 4H) 4.06 (t, J=8.40 Hz, 2H) 5.14 (d, J=2.28 Hz, 2H) 5.55 (dd, J=16.26, 6.07 Hz, 2H) 6.18-6.33 (m, 2H) 7.01-7.15 (m, 2H) 7.23 (s, 1H) 7.25-7.35 (m, 4H) 7.42 (d, J=7.70 Hz, 1H) 7.49 (d, J=8.46 Hz, 1H) 12.10 (s, 2H); MS ESI+ m/z 875.4 (M+H)+.

Example 242 methyl {(2S)-1-[(2S)-2-{6-[(2R,5R)-1-(2,2-difluoro-1,3-benzodioxol-5-yl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.75-0.91 (m, 12H) 1.69-1.77 (m, 2H) 1.91 (dd, J=14.26, 6.67 Hz, 2H) 1.96-2.07 (m, 4H) 2.14-2.24 (m, 4H) 2.54-2.60 (m, 2H) 3.53 (s, 6H) 3.78-3.86 (m, 4H) 4.06 (t, J=8.40 Hz, 2H) 5.10-5.17 (m, 2H) 5.36-5.44 (m, 2H) 6.05 (dd, J=9.11, 2.17 Hz, 1H) 6.29 (d, J=2.60 Hz, 1H) 6.89-6.95 (m, 1H) 7.06 (t, J=8.51 Hz, 2H) 7.22 (s, 1H) 7.26-7.33 (m, 3H) 7.39 (d, J=8.35 Hz, 1H) 7.47 (d, J=7.59 Hz, 1H) 12.03-12.09 (m, 2H); MS ESI+ m/z 912.8 (M+H)+.

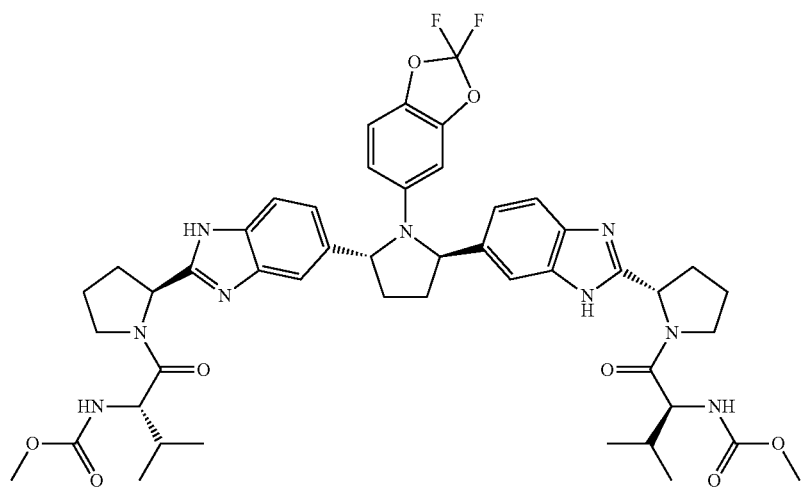

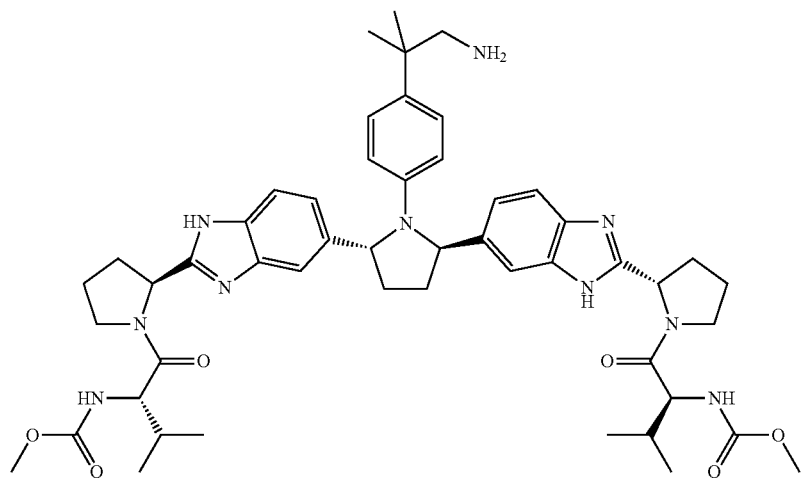

Example 243 methyl {(2S)-1-[(2S)-2-{6-[(2R,5R)-1-[4-(1-amino-2-methylpropan-2-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) d ppm 0.74-0.92 (m, 12H) 1.01 (d, J=5.20 Hz, 6H) 1.65-1.76 (m, 2H) 1.86-1.93 (m, 2H) 1.98 (d, J=4.01 Hz, 4H) 2.13-2.25 (m, 4H) 2.41 (s, 2H) 2.53-2.61 (m, 2H) 3.53 (s, 6H) 3.81 (s, 4H) 4.05 (t, J=8.35 Hz, 2H) 5.08-5.17 (m, 2H) 5.32-5.41 (m, 2H) 6.27 (d, J=8.89 Hz, 2H) 6.81-6.92 (m, 2H) 7.07 (t, J=7.97 Hz, 2H) 7.20 (s, 1H) 7.25-7.32 (m, 3H) 7.38 (d, J=8.13 Hz, 1H) 7.46 (d, J=8.13 Hz, 1H) 12.02 (d, J=19.63 Hz, 2H); MS ESI+ m/z 903.4 (M+H)+.

Example 244 methyl (2-{4-[(2R,5R)-2-{2-[(2S)-1-{(2S)-2-[(methoxycarbonyl)amino]-3-methylbutanoyl}pyrrolidin-2-yl]-1H-benzimidazol-5-yl}-5-{2-[(2S)-1-{(2S)-2-[(methoxycarbonyl)amino]-3-methylbutanoyl}pyrrolidin-2-yl]-1H-benzimidazol-6-yl}pyrrolidin-1-yl]phenyl}-2-methylpropyl)carbamate 1H NMR (400 MHz, DMSO-D6) d ppm 0.75-0.91 (m, 12H) 1.00 (d, J=6.07 Hz, 6H) 1.64-1.75 (m, 2H) 1.83-1.94 (m, 2H) 1.96-2.05 (m, 4H) 2.14-2.23 (m, 4H) 2.89-3.00 (m, 2H) 3.17 (d, J=5.20 Hz, 2H) 3.42 (s, 3H) 3.53 (s, 6H) 3.77-3.87 (m, 4H) 3.99-4.07 (m, 2H) 5.08-5.20 (m, 2H) 5.32-5.42 (m, 2H) 6.27 (d, J=8.46 Hz, 2H) 6.72-6.80 (m, 1H) 6.83-6.93 (m, 2H) 7.07 (t, J=8.62 Hz, 2H) 7.20 (s, 1H) 7.26-7.33 (m, 3H) 7.38 (d, J=8.13 Hz, 1H) 7.45 (d, J=8.57 Hz, 1H) 12.03 (d, J=12.36 Hz, 2H)

MS ESI+ m/z 961.4 (M+H)+

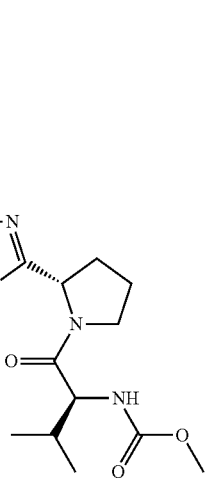

485

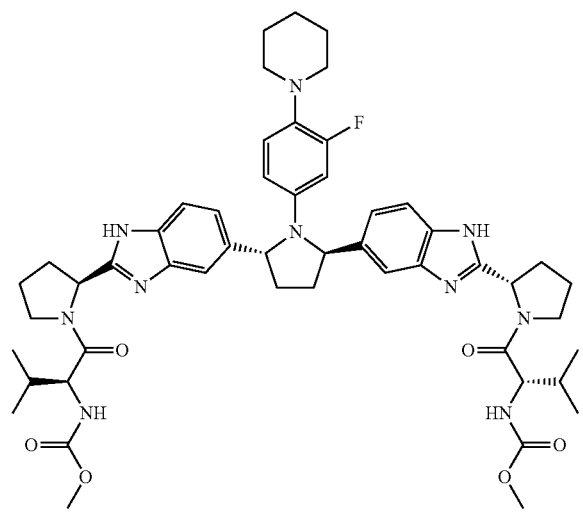 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCCCC4)c(F)c3)ccc2[nH]1)C(C)C]

Example 245 methyl {(2S)-1-[(2S)-2-{5-[(2R,5R)-1-[3-fluoro-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate MS (ESI) m/z 934 (M+H)$^+$

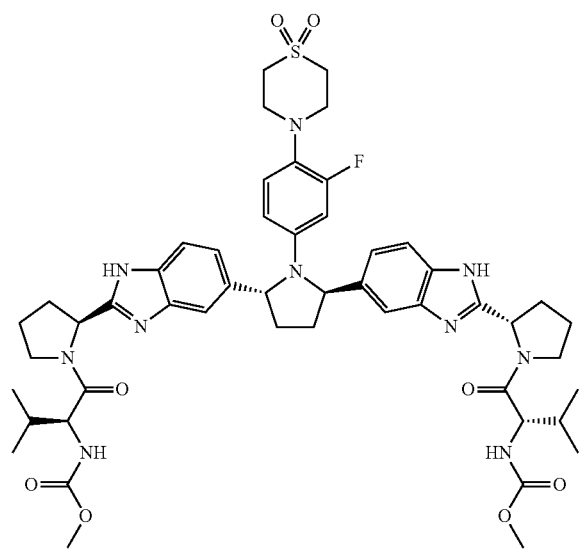 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCS(=O)(=O)CC4)c(F)c3)ccc2[nH]1)C(C)C]

Example 246 methyl {(2S)-1-[(2S)-2-{5-[(2R,5R)-1-[4-(1,1-dioxidothiomorpholin-4-yl)-3-fluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate MS (ESI) m/z 984 (M+H)$^+$

486

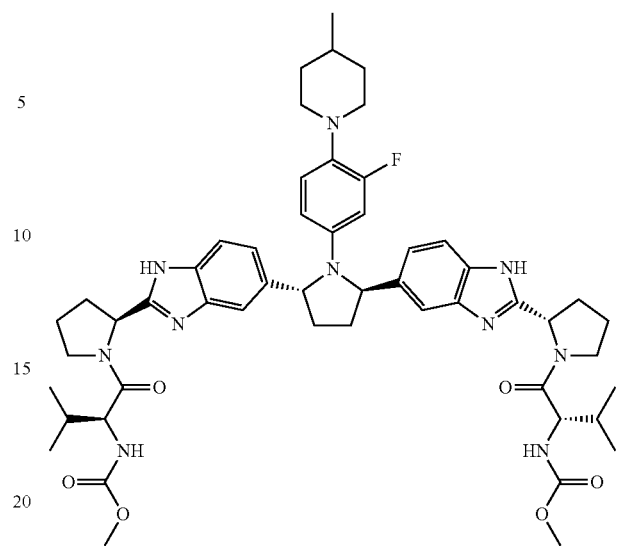

Example 247 methyl {(2S)-1-[(2S)-2-{5-[(2R,5R)-1-[3-fluoro-4-(4-methylpiperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbmate MS (ESI) m/z 948 (M+H)$^+$

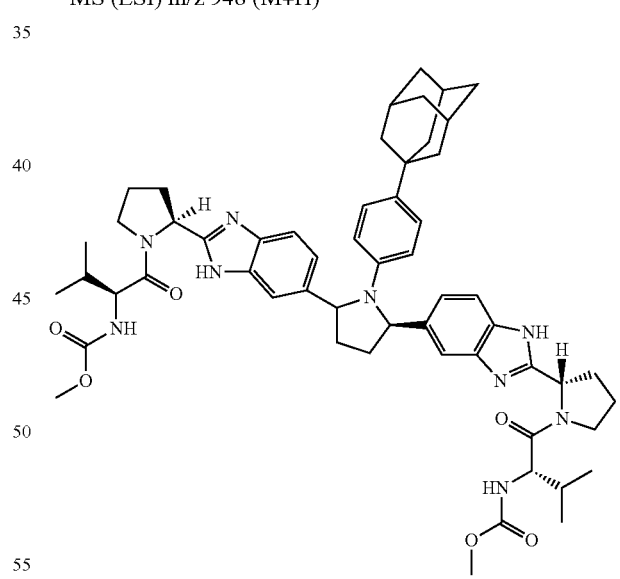

Example 248 methyl {(2S)-1-[(2S)-2-(6-{(5R)-5-{2-[(2S)-1-{(2S)-2-[(methoxycarbonyl)amino]-3-methylbutanoyl}pyrrolidin-2-yl]-1H-benzimidazol-5-yl}-1-[4-(tricyclo[3.3.1.1~3,7~]dec-1-yl)phenyl]pyrrolidin-2-yl]-1H-benzimidazol-2-yl)pyrrolidin-1-yl]-3-methyl-1-oxobutan-2-yl}carbamate +ESI m/z (rel abundance) 967 (100, M+H)

487 488

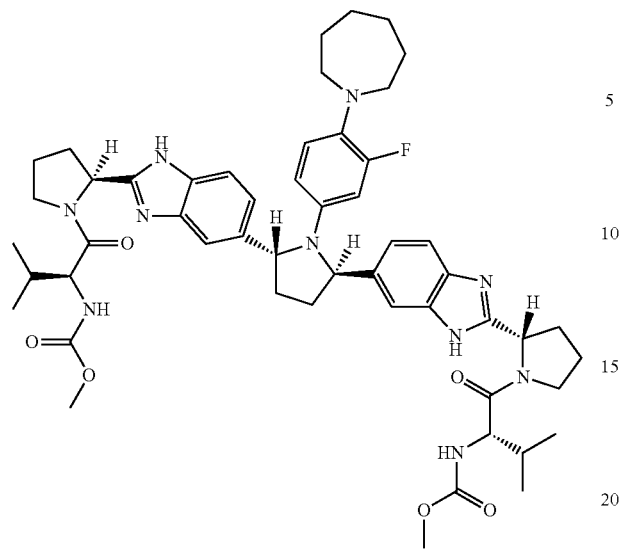

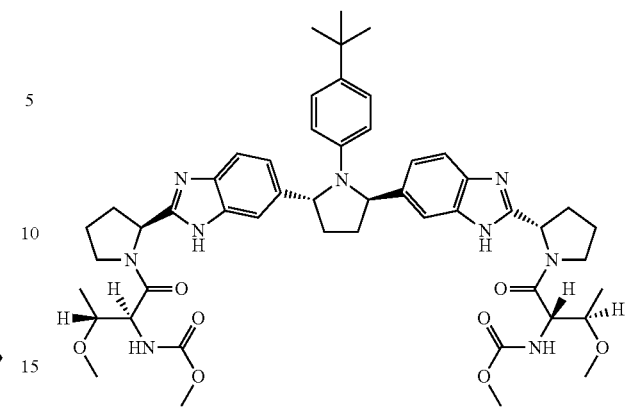

Example 249 methyl {(2S)-1-[(2S)-2-{6-[(2R,5R)-1-[4-(azepan-1-yl)-3-fluorophenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate +ESI m/z (rel abundance) 948 (100, M+H)

Example 250 methyl {(2S,3R)-1-[(2S)-2-{6-[(2R,5R)-1-(4-tert-butylphenyl)-5-(2-{(2S)-1-[N-(methoxycarbonyl)-O-methyl-L-threonyl]pyrrolidin-2-yl}-1H-benzimidazol-6-yl)pyrrolidin-2-yl]-1H-benzimidazol-2-yl}pyrrolidin-1-yl]-3-methoxy-1-oxobutan-2-yl}carbmate MS (ESI) m/z 920 (M+H)+.

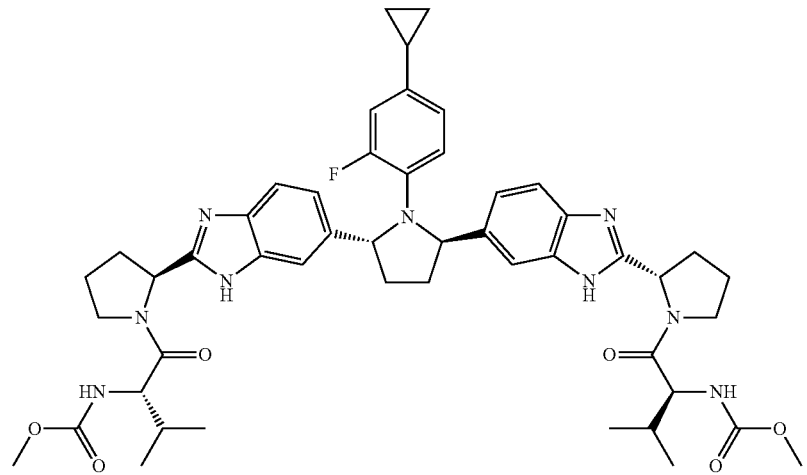

Example 251 methyl {(2S)-1-[(2S)-2-{6-[(2R,5R)-1-(4-cyclopropyl-2-fluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate MS (ESI) m/z 890 (M+H)+.

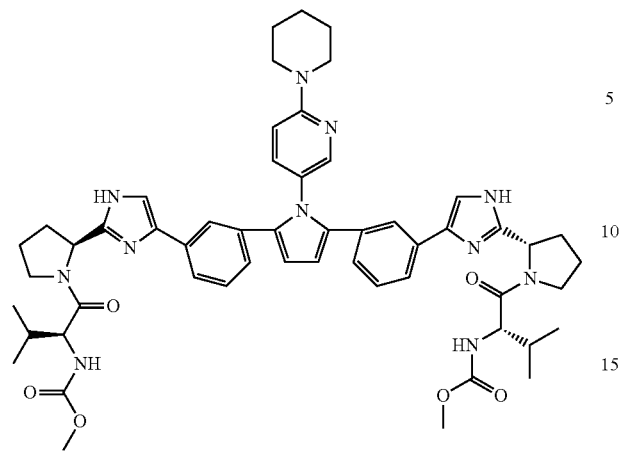

Example 252 methyl [(2S)-1-{(2S)-2-[4-(3-{5-(3-{2-[(2S)-1-
{(2S)-2-[(methoxycarbonyl)amino]-3-
methylbutanoyl}pyrrolidin-2-yl]-1H-imidazol-4-
yl}phenyl)-1-[6-(piperidin-1-yl)pyridin-3-yl]-1H-
pyrrol-2-yl}phenyl)-1H-imidazol-2-yl]pyrrolidin-1-
yl}-3-methyl-1-oxobutan-2-yl]carbamate MS (ESI; M+H) m/z=964.5.

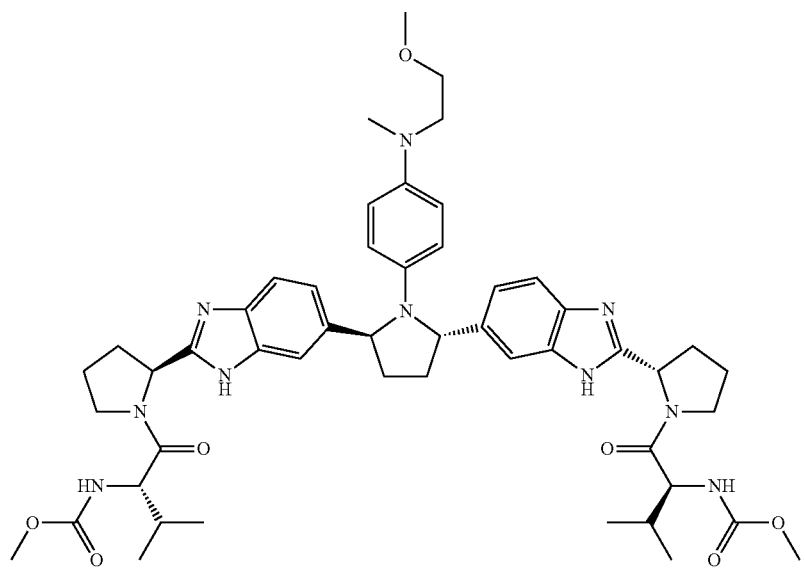

Example 253 methyl {(2S)-1-[(2S)-2-{6-[(2S,5S)-5-{2-[(2S)-1-
{(2S)-2-[(methoxycarbonyl)amino]-3-
methylbutanoyl}pyrrolidin-2-yl]-1H-benzimidazol-
6-yl}-1-{4-[(2-methoxyethyl)(methyl)amino]
phenyl}pyrrolidin-2-yl]-1H-benzimidazol-2-
yl]pyrrolidin-1-yl]-3-methyl-1-oxobutan-2-
yl}carbamate MS (ESI; M+H) m/z=919.4

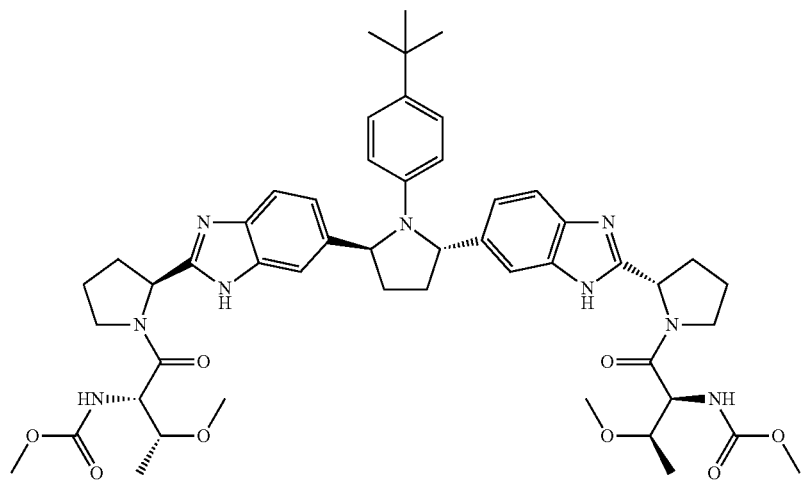

Example 254 methyl {(2S,3R)-1-[(2S)-2-{6-[(2S,5S)-1-(4-tert-butylphenyl)-5-(2-{(2S)-1-[N-(methoxycarbonyl)-O-methyl-L-threonyl]pyrrolidin-2-yl}-1H-benzimidazol-6-yl)pyrrolidin-2-yl]-1H-benzimidazol-2-yl}pyrrolidin-1-yl]-3-methoxy-1-oxobutan-2-yl}carbmate MS (ESI; M+H) m/z=920.5

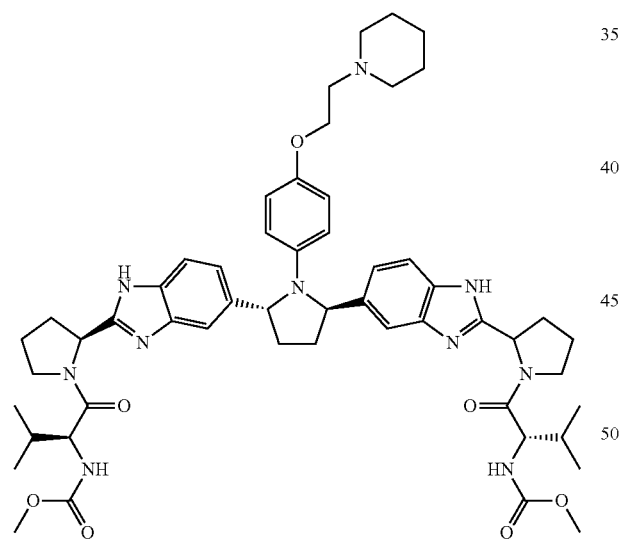

Example 255 methyl [(2S)-1-(2-{5-[(2R,5R)-5-[2-(1-{(2S)-2-[(methoxycarbonyl)amino]-3-methylbutanoyl}pyrrolidin-2-yl)-1H-benzimidazol-5-yl]-1-{4-[2-(piperidin-1-yl)ethoxy]phenyl}pyrrolidin-2-yl}-1H-benzimidazol-2-yl}pyrrolidin-1-yl)-3-methyl-1-oxobutan-2-yl] carbmate MS (ESI; M+H) m/z=959.6

Example 256 methyl {(2S)-1-[(2S)-2-{5-[(2R,5R)-1-[3-chloro-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (ESI+) m/z 949.5 (M+H)+

493    494

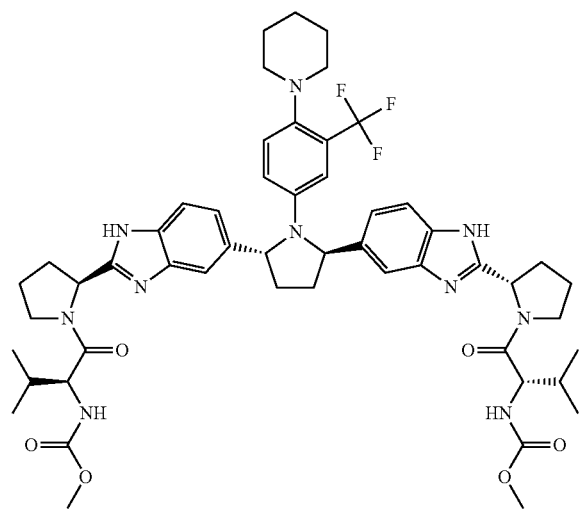 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCCCC4)c(C(F)(F)F)c3)ccc2[nH]1)C(C)C]

Example 257 methyl {(2S)-1-[(2S)-2-(5-{(2R,5R)-5-{2-[(2S)-1-{(2S)-2-[(methoxycarbonyl)amino]-3-methylbutanoyl}pyrrolidin-2-yl]-1H-benzimidazol-5-yl}-1-[4-(piperidin-1-yl)-3-(trifluoromethyl)phenyl]pyrrolidin-2-yl}-1H-benzimidazol-2-yl)pyrrolidin-1-yl]-3-methyl-1-oxobutan-2-yl}carbamate (ESI+) m/z 983.5 (M+H)+

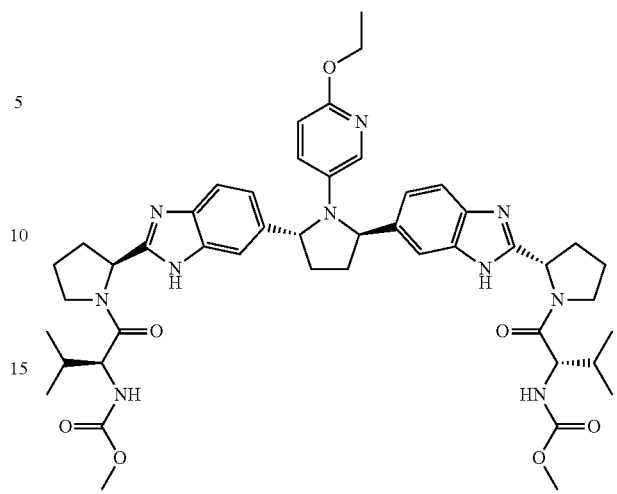

Example 259 methyl {(2S)-1-[(2S)-2-{6-[(2R,5R)-1-(6-ethoxypyridin-3-yl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+ m/z 878 (M+H)+

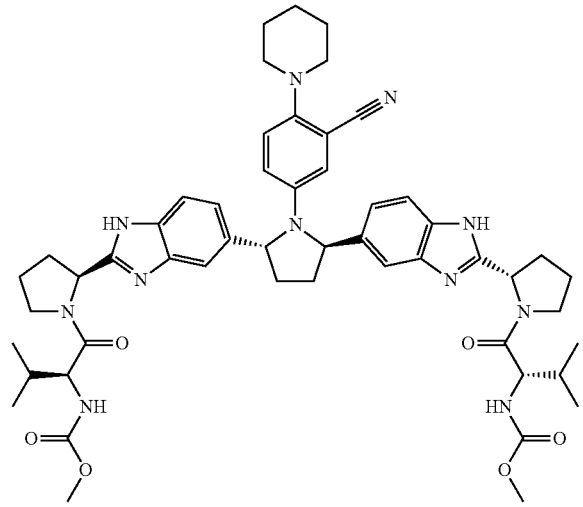 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCCCC4)c(C#N)c3)ccc2[nH]1)C(C)C]

Example 258 methyl {(2S)-1-[(2S)-2-{5-[(2R,5R)-1-[3-cyano-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ESI+) m/z 940.4 (M+H)+

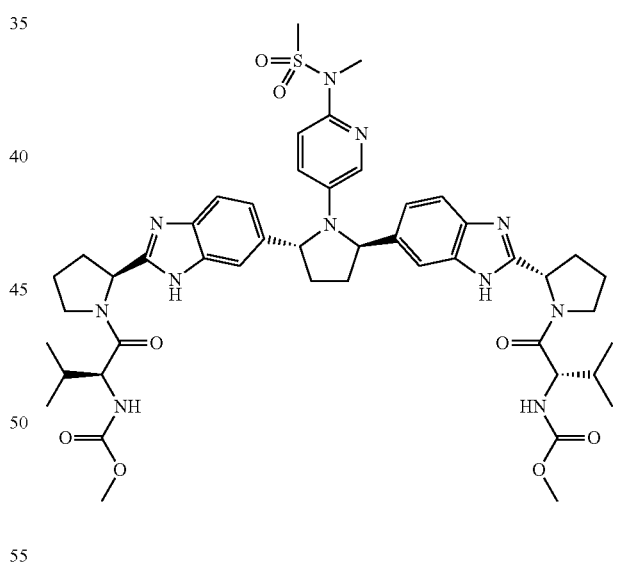

Example 260 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-6-yl}-1-{6-[methyl(methylsulfonyl)amino]pyridin-3-yl}pyrrolidin-2-yl]-1H-benzimidazol-2-yl}pyrrolidin-1-yl]-3-methyl-1-oxobutan-2-yl}carbamate ESI+ m/z 940 (M+H)+

495

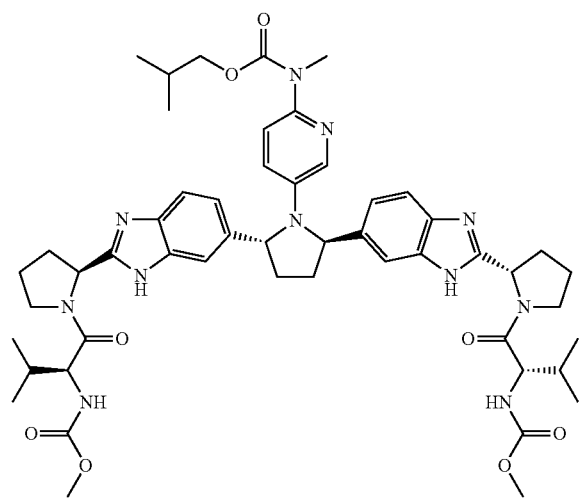 [SMILES: COC(=O)N[C@H](C(=O)N1CCC[C@H]1c1nc2ccc([C@H]3CC[C@H](c4ccc5nc([C@@H]6CCCN6C(=O)[C@@H](NC(=O)OC)C(C)C)[nH]c5c4)N3c3ccc(N(C)C(=O)OCC(C)C)nc3)cc2[nH]1)C(C)C]

Example 261

2-methylpropyl {5-[(2R,5R)-2,5-bis(2-{(2S)-1-[N-(methoxycarbonyl)-L-valyl]pyrrolidin-2-yl}-1H-benzimidazol-6-yl)pyrrolidin-1-yl]pyridin-2-yl}methylcarbamate ESI+ m/z 963 (M+H)+

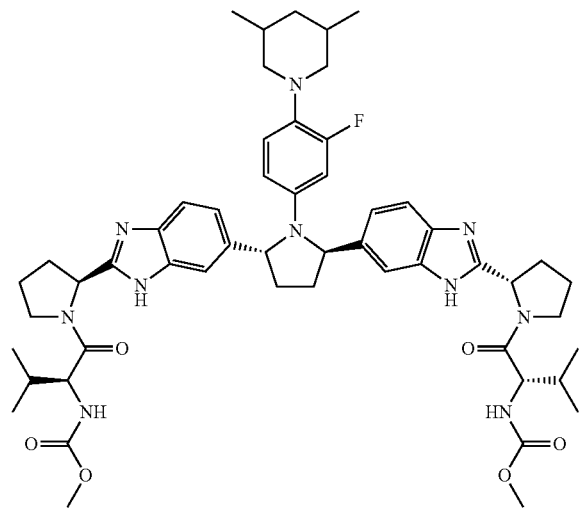 [SMILES: COC(=O)N[C@H](C(=O)N1CCC[C@H]1c1nc2ccc([C@H]3CC[C@H](c4ccc5nc([C@@H]6CCCN6C(=O)[C@@H](NC(=O)OC)C(C)C)[nH]c5c4)N3c3ccc(N4CC(C)CC(C)C4)c(F)c3)cc2[nH]1)C(C)C]

Example 262 methyl {(2S)-1-[(2S)-2-{6-[(2R,5R)-1-[4-(3,5-dimethylpiperidin-1-yl)-3-fluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+ m/z 962 (M+H)+

496

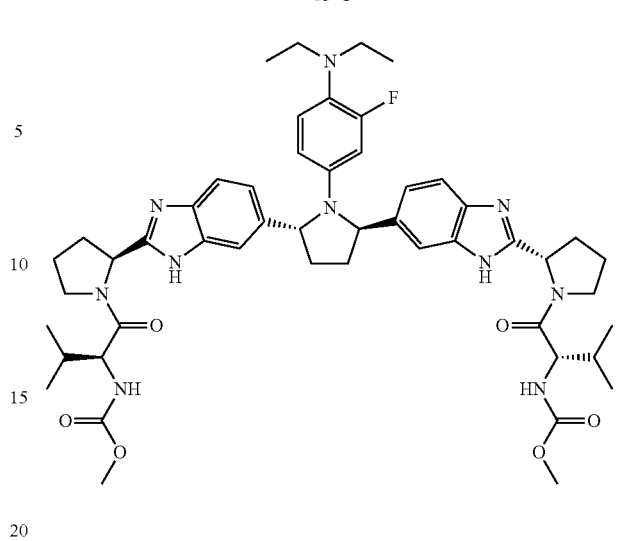

Example 263 methyl {(2S)-1-[(2S)-2-{6-[(2R,5R)-1-[4-(diethylamino)-3-fluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+m/z 922 (M+H)+

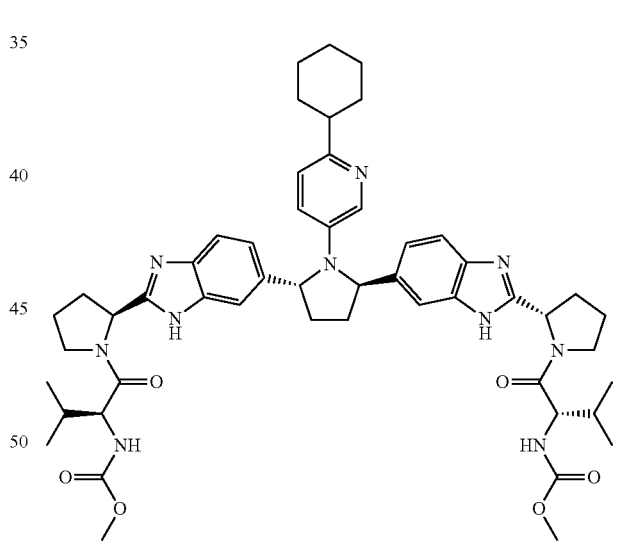

Example 264 methyl {(2S)-1-[(2S)-2-{6-[(2R,5R)-1-(6-cyclohexylpyridin-3-yl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate LC/MS: m/z 916.4 TFA method

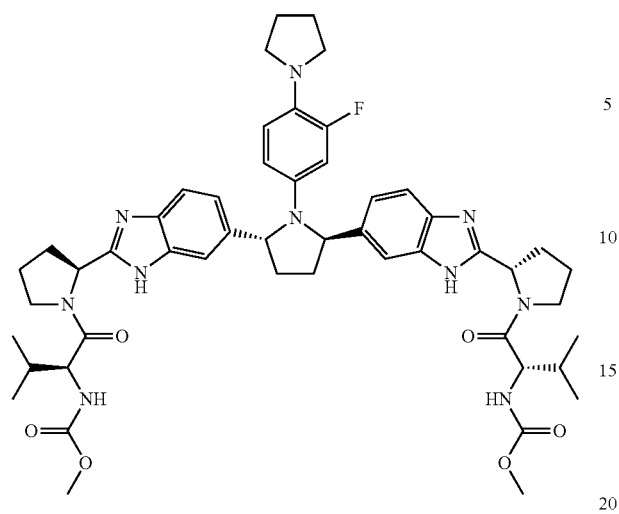

Example 265 methyl {(2S)-1-[(2S)-2-{6-[(2R,5R)-1-[3-fluoro-4-(pyrrolidin-1-yl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+ (m/z): 919.4 (m+H)

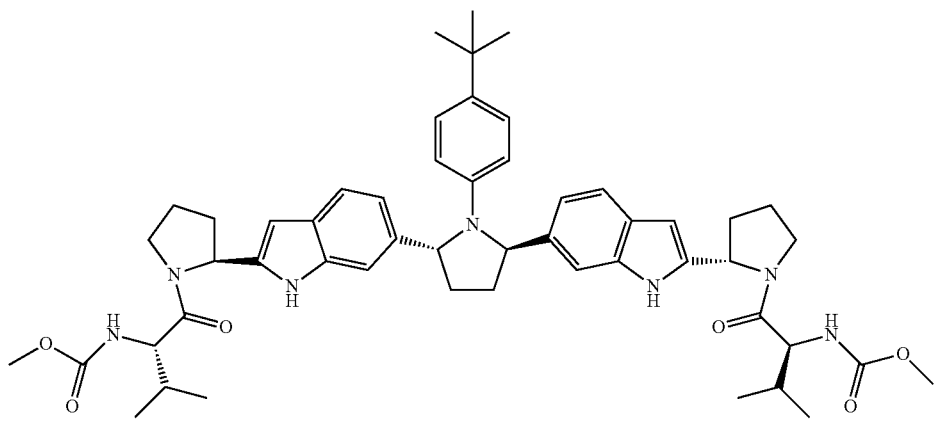

Example 266 methyl {(2S)-1-[(2S)-2-{6-[(2R,5R)-1-(4-tert-butylphenyl)-5-{2-[(2S)-1-{(2S)-2-[(methoxycarbonyl)amino]-3-methylbutanoyl}pyrrolidin-2-yl]-1H-indol-6-yl}pyrrolidin-2-yl]-1H-indol-2-yl}pyrrolidin-1-yl]-3-methyl-1-oxobutan-2-yl}carbamate m/z=886.5 (LC/MS)

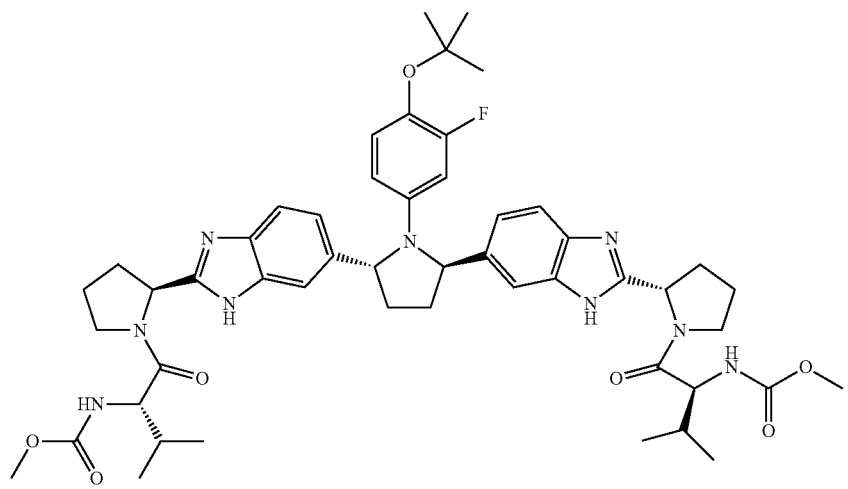

Example 267 methyl {(2S)-1-[(2S)-2-{6-[(2R,5R)-1-(4-tert-bu-
toxy-3-fluorophenyl)-5-{2-[(2S)-1-{(2S)-2-[(meth-
oxycarbonyl)amino]-3-methylbutanoyl}pyrrolidin-2-
yl]-1H-benzimidazol-6-yl}pyrrolidin-2-yl]-1H-
benzimidazol-2-yl}pyrrolidin-1-yl]-3-methyl-1-
oxobutan-2-yl}carbamate (ESI; M+H) m/z=922.4

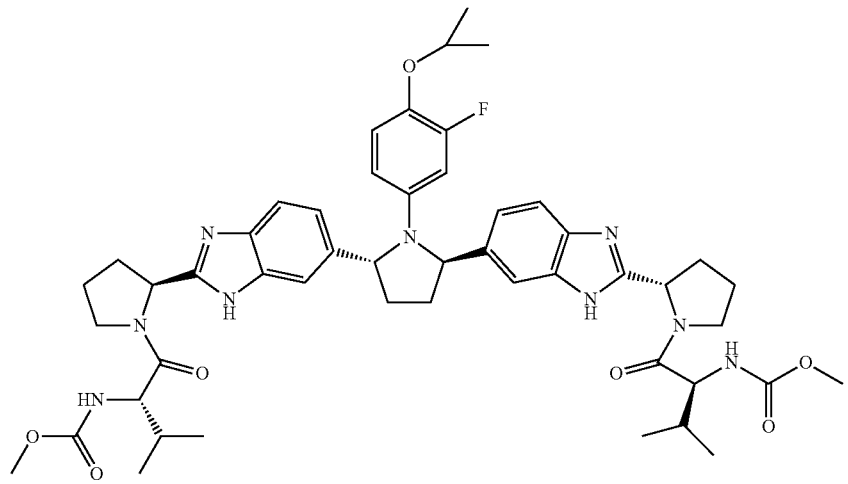

Example 268 methyl {(2S)-1-[(2S)-2-{6-[(2R,5R)-1-[3-fluoro-4-
(propan-2-yloxy)phenyl]-5-{2-[(2S)-1{(2S)-2-
[(methoxycarbonyl)amino]-3-
methylbutanoyl}pyrrolidin-2-yl]-1H-benzimidazol-
6-yl}pyrrolidin-2-yl]-1H-benzimidazol-2-
yl}pyrrolidin-1-yl]-3-methyl-1-oxobutan-2-
yl}carbamate (ESI; M+H) m/z=908.5

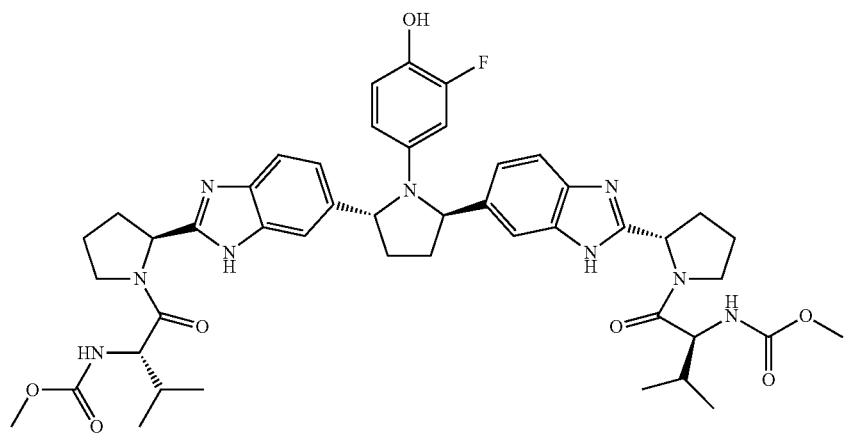

Example 269 methyl {(2S)-1-[(2S)-2-{6-[(2R,5R)-1-(3-fluoro-4-hydroxyphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate (ESI; M+H) m/z=866.3

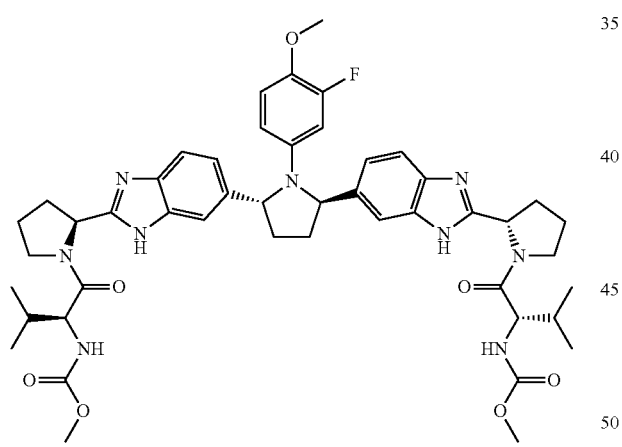

Example 270 methyl {(2S)-1-[(2S)-2-{6-[(2R,5R)-1-(3-fluoro-4-methoxyphenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate (ESI; M+H) m/z=880

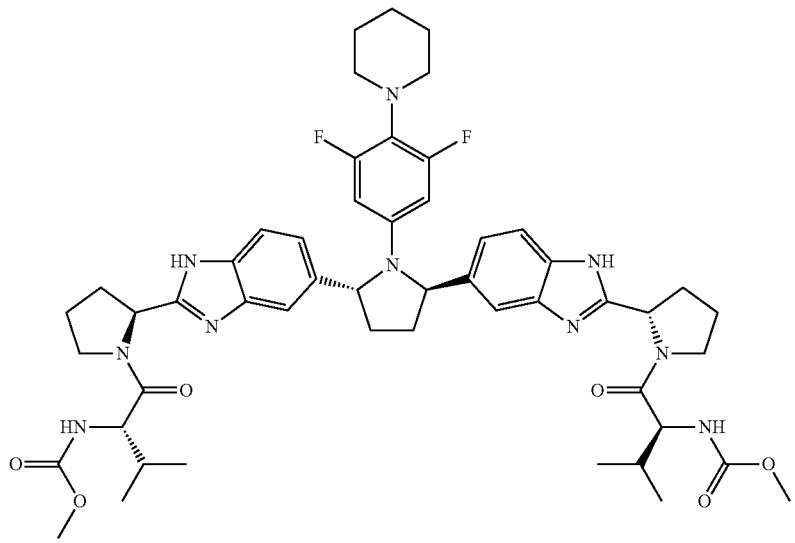 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(N4CCCCC4)c(F)c3)ccc2[nH]1)C(C)C]

Example 271 methyl {(2S)-1-[(2S)-2-{5-[(2R,5R)-1-[3,5-difluoro-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate 1HNMR (400 MHz, DMSO-D6) δ ppm 0.73-0.90 (m, 12H) 1.32-2.28 (m, 20H) 2.76 (s, 4H) 3.54 (s, 6H) 3.82 (s, 4H) 3.99-4.12 (m, 2H) 5.10-5.20 (m, 2H) 5.36 (d, J=7.59 Hz, 2H) 5.83-5.95 (m, 2H) 7.01-7.14 (m, 2H) 7.20 (s, 1H) 7.26-7.33 (m, 3H) 7.41 (d, J=8.24 Hz, 1H) 7.49 (d, J=8.24 Hz, 1H) 12.01-12.31 (m, 2H); MS (ESI; M+H) m/z=951.5.

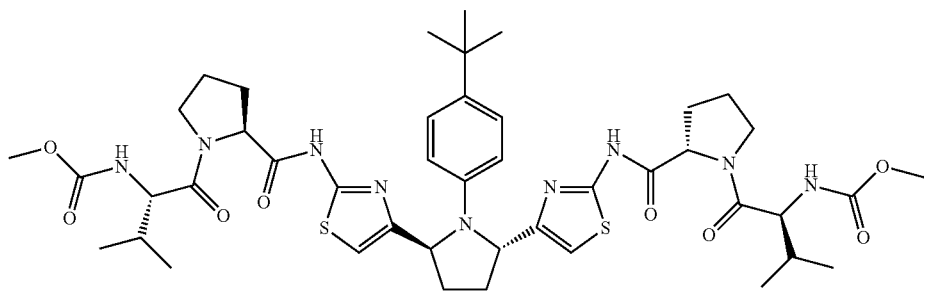

Example 272 dimethyl ([(2S,5S)-1-(4-tert-butylphenyl)pyrrolidine-2,5-diyl]bis{1,3-thiazole-4,2-diylcarbamoyl(2S)pyrrolidine-2,1-diyl[(2S)-3-methyl-1-oxobutane-1,2-diyl]})biscarbamate ESI m/z 908.4 (M+H)

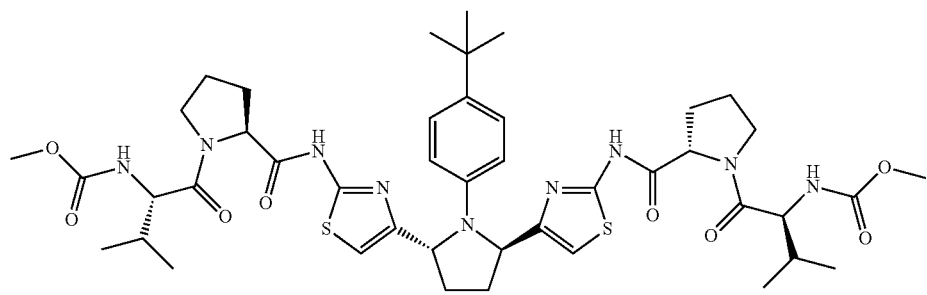

Example 273 dimethyl ([(2R,5R)-1-(4-tert-butylphenyl)pyrrolidine-2,5-diyl]bis{1,3-thiazole-4,2-diylcarbamoyl(2S)pyrrolidine-2,1-diyl[(2S)-3-methyl-1-oxobutane-1,2-diyl]})biscarbamate ESI m/z 908.4 (M+H)

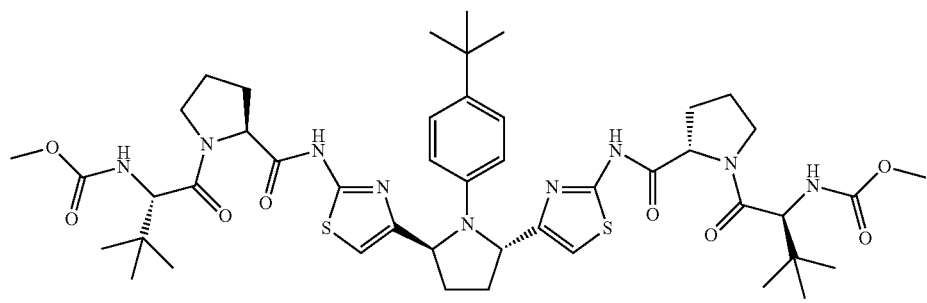

Example 274 dimethyl ([(2S,5S)-1-(4-tert-butylphenyl)pyrrolidine-2,5-diyl]bis{1,3-thiazole-4,2-diylcarbamoyl(2S)pyrrolidine-2,1-diyl[(2S)-3,3-dimethyl-1-oxobutane-1,2-diyl]})biscarbamate ESI m/z 936.5 (M+H)

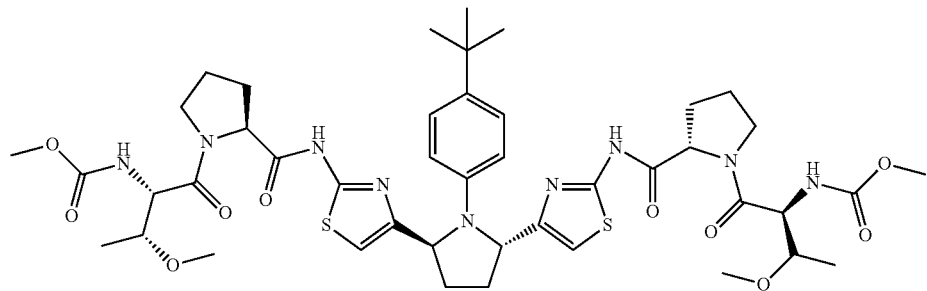

Example 275 dimethyl ([(2S,5S)-1-(4-tert-butylphenyl)pyrrolidine-2,5-diyl]bis{1,3-thiazole-4,2-diylcarbamoyl(2S)pyrrolidine-2,1-diyl[(2S,3R)-3-methoxy-1-oxobutane-1,2-diyl]})biscarbamate ESI m/z 940.5 (M+H)

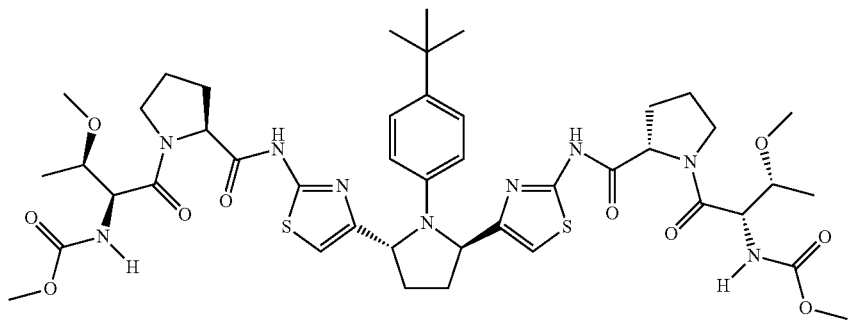
Example 276
dimethyl ([(2R,5R)-1-(4-tert-butylphenyl)pyrrolidine-2,5-diyl]bis{1,3-thiazole-4,2-diylcarbamoyl(2S)pyrrolidine-2,1-diyl[(2S,3R)-3-methoxy-1-oxobutane-1,2-diyl]})biscarbamate
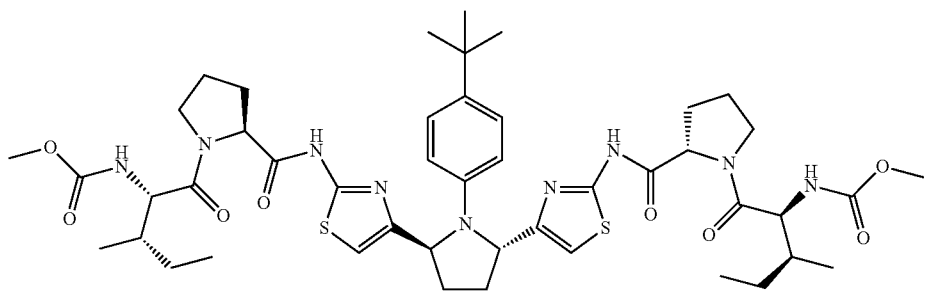
Example 277
dimethyl ([(2S,5S)-1-(4-tert-butylphenyl)pyrrolidine-2,5-diyl]bis{1,3-thiazole-4,2-diylcarbamoyl(2S)pyrrolidine-2,1-diyl[(2S,3S)-3-methyl-1-oxopentane-1,2-diyl]})biscarbamate
ESI m/z 936.5 (M+H)
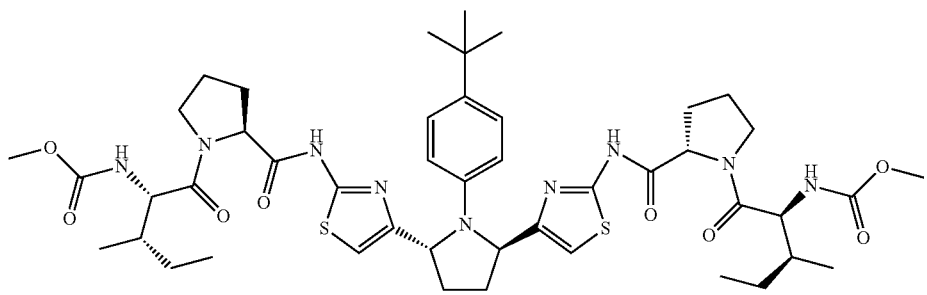

Example 278 dimethyl ([(2R,5R)-1-(4-tert-butylphenyl)pyrrolidine-2,5-diyl]bis{1,3-thiazole-4,2-diylcarbamoyl(2S)pyrrolidine-2,1-diyl[(2S,3S)-3-methyl-1-oxopentane-1,2-diyl]})biscarbamate

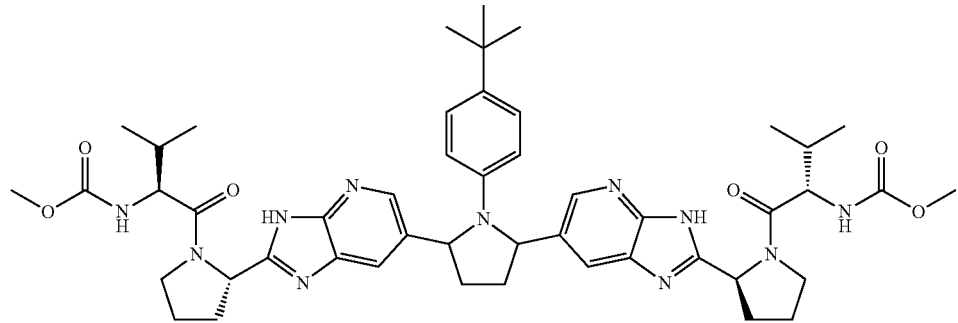

Example 279 methyl {(2S)-1-[(2S)-2-{6-[1-(4-tert-butylphenyl)-5-{2-[(2S)-1-{(2S)-2-[(methoxycarbonyl)amino]-3-methylbutanoyl}pyrrolidin-2-yl]-3H-imidazo[4,5-b]pyridin-6-yl}pyrrolidin-2-yl]-3H-imidazo[4,5-b]pyridin-2-yl}pyrrolidin-1-yl]-3-methyl-1-oxobutan-2-yl}carbamate LCMS m/z 890 (M+H)

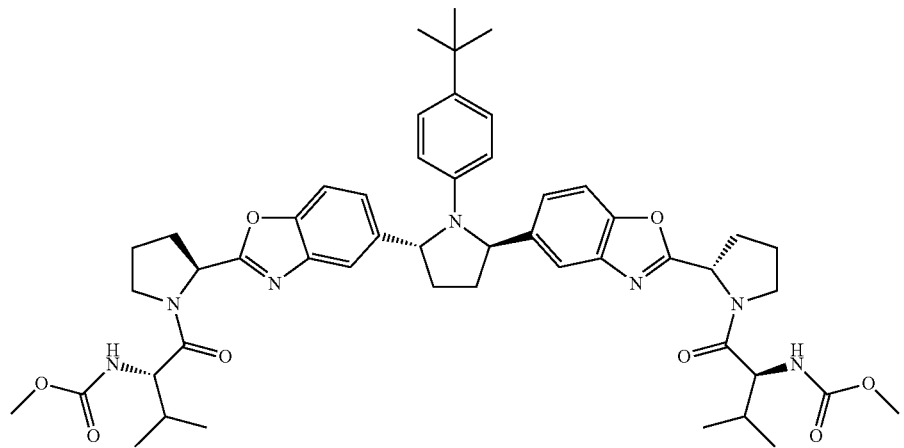

Example 280 methyl {(2S)-1-[(2S)-2-{6-[(2R,5R)-1-(4-tert-butylphenyl)-5-{2-[(2S)-1-{(2S)-2-[(methoxycarbonyl)amino]-3-methylbutanoyl}pyrrolidin-2-yl]-1,3-benzoxazol-6-yl}pyrrolidin-2-yl]-1,3-benzoxazol-2-yl}pyrrolidin-1-yl]-3-methyl-1-oxobutan-2-yl}carbamate

ESI+: (M+H): 890.5

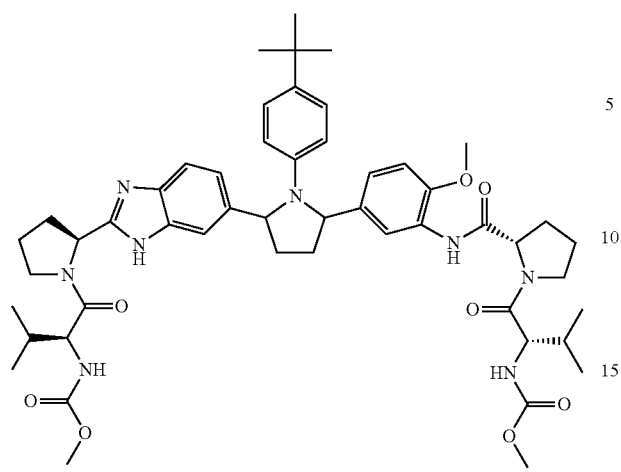

Example 281

N-(methoxycarbonyl)-L-valyl-N-{5-[1-(4-tert-butylphenyl)-5-(2-{(2S)-1-[N-(methoxycarbonyl)-L-valyl]pyrrolidin-2-yl}-1H-benzimidazol-6-yl)pyrrolidin-2-yl]-2-methoxyphenyl}-L-prolinamide

ESI+: (M+H): 921.5

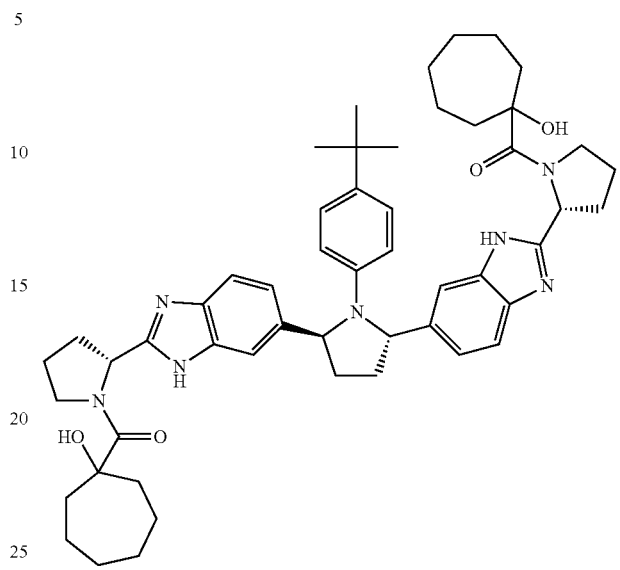

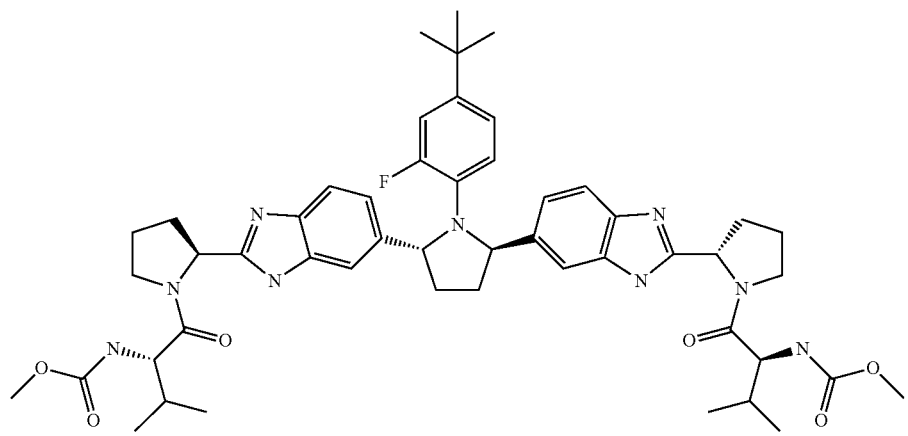

Example 282 methyl {(2S)-1-[(2S)-2-{6-[(2R,5R)-1-(4-tert-butyl-2-fluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate

ESI+: (M+H): 906.4

Example 283

{[(2R,5R)-1-(4-tert-butylphenyl)pyrrolidine-2,5-diyl]bis[1H-benzimidazole-6,2-diyl(2S)pyrrolidine-2,1-diyl]}bis[(1-hydroxycycloheptyl)methanone]

MS (ESI) positive ion 854 (M+H)+.

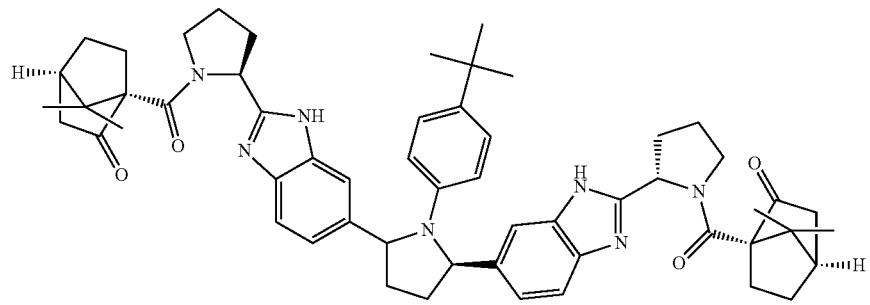 [SMILES: CC(C)(C)c1ccc(N2C(c3ccc4nc([C@@H]5CCCN5C(=O)[C@]56CC[C@H](CC5=O)C6(C)C)[nH]c4c3)CC[C@@H]2c2ccc3nc([C@@H]4CCCN4C(=O)[C@]45CC[C@H](CC4=O)C5(C)C)[nH]c3c2)cc1]
Example 284
(1S,4R,1'S,4'R)-1,1'-{[(2R)-1-(4-tert-butylphenyl)
pyrrolidine-2,5-diyl]bis[1H-benzimidazole-6,2-diyl
(2S)pyrrolidine-2,1-diylcarbonyl]}bis(7,7-dimethyl-
bicyclo[2.2.1]heptan-2-one)
MS (ESI) positive ion 902 (M+H)+.
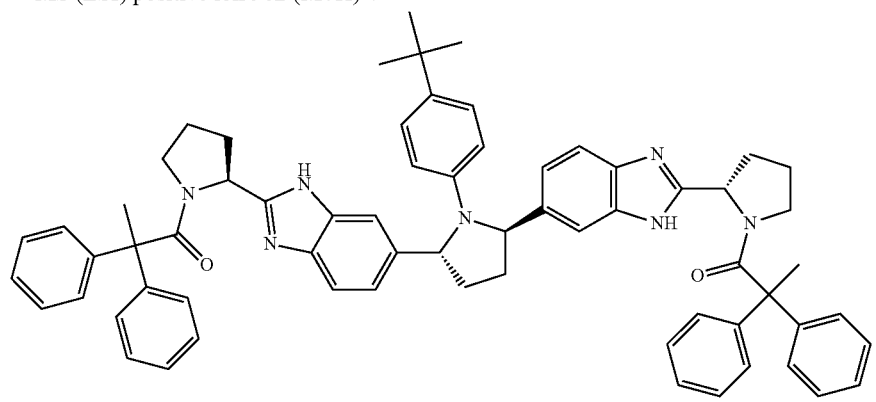
Example 285
1,1'-{[(2R,5R)-1-(4-tert-butylphenyl)pyrrolidine-2,5-
diyl]bis[1H-benzimidazole-6,2-diyl(2S)pyrrolidine-
2,1-diyl]}bis(2,2-diphenylpropan-1-one)
MS (ESI) positive ion (M+H)+. Is not observed but
MS (APCI) positive ion 990 (M+H)+ observed
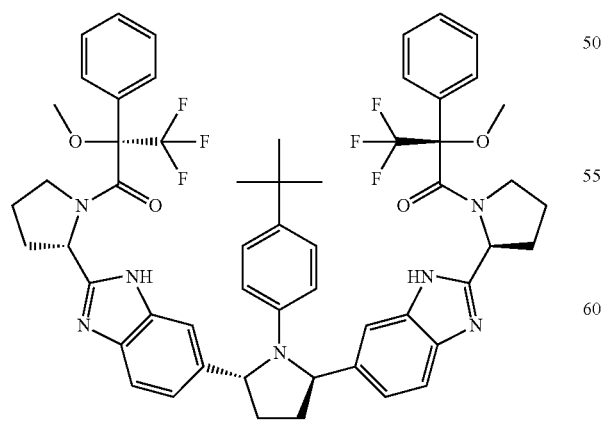

Example 286

(2S,2'S)-1,1'-{[(2R,5R)-1-(4-tert-butylphenyl)pyrrolidine-2,5-diyl]bis[1H-benzimidazole-6,2-diyl(2S)pyrrolidine-2,1-diyl]}bis(3,3,3-trifluoro-2-methoxy-2-phenylpropan-1-one)

MS (ESI) positive ion 1006 (M+H)$^+$.

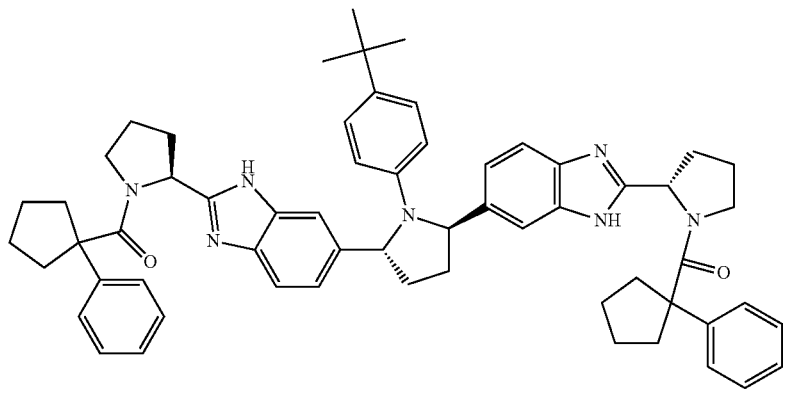 [SMILES: CC(C)(C)c1ccc(N2[C@@H](c3ccc4nc([C@@H]5CCCN5C(=O)C5(c6ccccc6)CCCC5)[nH]c4c3)CC[C@@H]2c2ccc3nc([C@@H]4CCCN4C(=O)C4(c5ccccc5)CCCC4)[nH]c3c2)cc1]

Example 287

{[(2R,5R)-1-(4-tert-butylphenyl)pyrrolidine-2,5-diyl]bis[1H-benzimidazole-6,2-diyl(2S)pyrrolidine-2,1-diyl]}bis[(1-phenylcyclopentyl)methanone]

MS (ESI) positive ion 918.6 (M+H)$^+$.

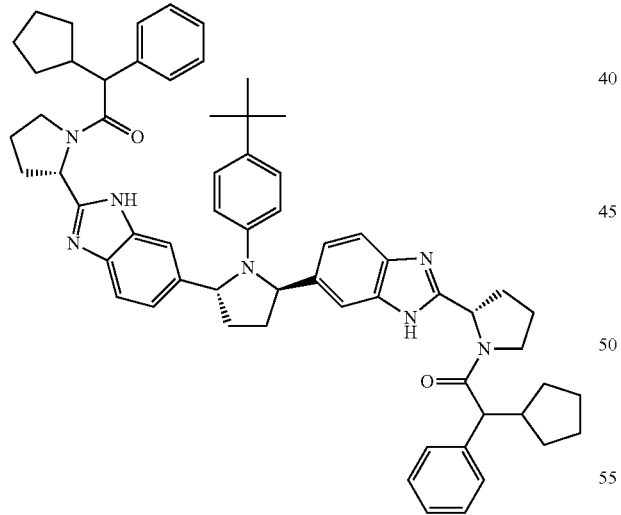

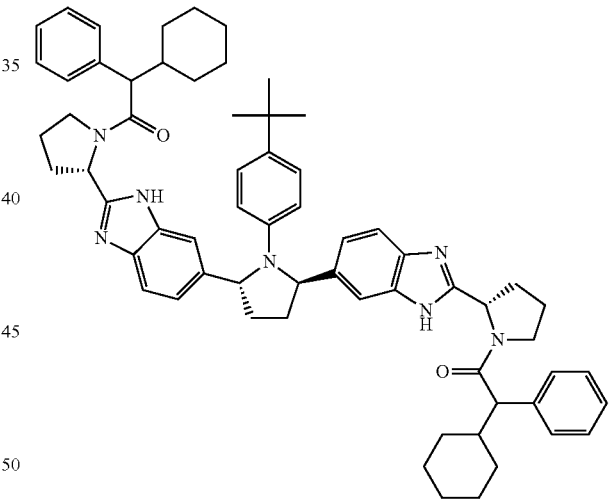

Example 288

1,1'-{[(2R,5R)-1-(4-tert-butylphenyl)pyrrolidine-2,5-diyl]bis[1H-benzimidazole-6,2-diyl(2S)pyrrolidine-2,1-diyl]}bis(2-cyclopentyl-2-phenylethanone)

MS (ESI) positive ion 946 (M+H)$^+$.

Example 289

1,1'-{[(2R,5R)-1-(4-tert-butylphenyl)pyrrolidine-2,5-diyl]bis[1H-benzimidazole-6,2-diyl(2S)pyrrolidine-2,1-diyl]}bis(2-cyclohexyl-2-phenylethanone)

MS (ESI) positive ion 974 (M+H)$^+$.

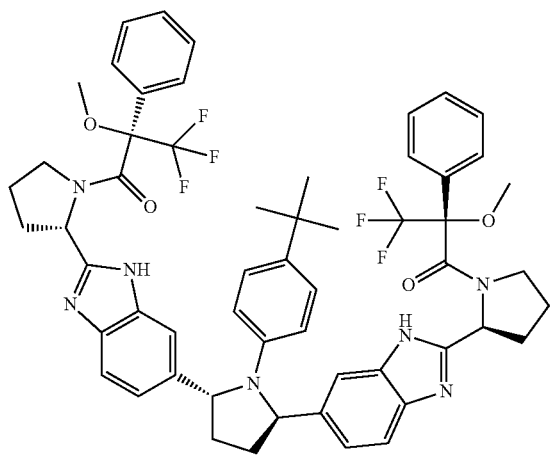 [SMILES: CO[C@@](C(=O)N1CCC[C@H]1c1nc2ccc([C@H]3CC[C@H](c4ccc5nc([C@@H]6CCCN6C(=O)[C@](OC)(c6ccccc6)C(F)(F)F)[nH]c5c4)N3c3ccc(C(C)(C)C)cc3)cc2[nH]1)(c1ccccc1)C(F)(F)F]

Example 290

(2R,2'R)-1,1'-({[(2R,5R)-1-(4-tert-butylphenyl)pyrrolidine-2,5-diyl]bis[1H-benzimidazole-6,2-diyl(2S)pyrrolidine-2,1-diyl]}bis(3,3,3-trifluoro-2-methoxy-2-phenylpropan-1-one)

MS (ESI) positive ion 1006 (M+H)+.

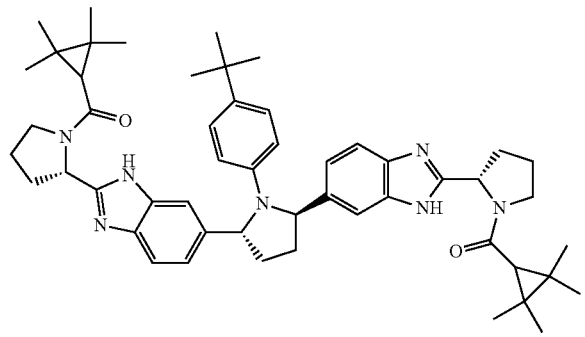 [SMILES: CC(C)(C)c1ccc(N2[C@@H](c3ccc4nc([C@@H]5CCCN5C(=O)C5C(C)(C)C5(C)C)[nH]c4c3)CC[C@@H]2c2ccc3nc([C@@H]4CCCN4C(=O)C4C(C)(C)C4(C)C)[nH]c3c2)cc1]

Example 291

{[(2R,5R)-1-(4-tert-butylphenyl)pyrrolidine-2,5-diyl]bis[1H-benzimidazole-6,2-diyl(2S)pyrrolidine-2,1-diyl]}bis[(2,2,3,3-tetramethylcyclopropyl)methanone]

MS (ESI) positive ion 822 (M+H)+.

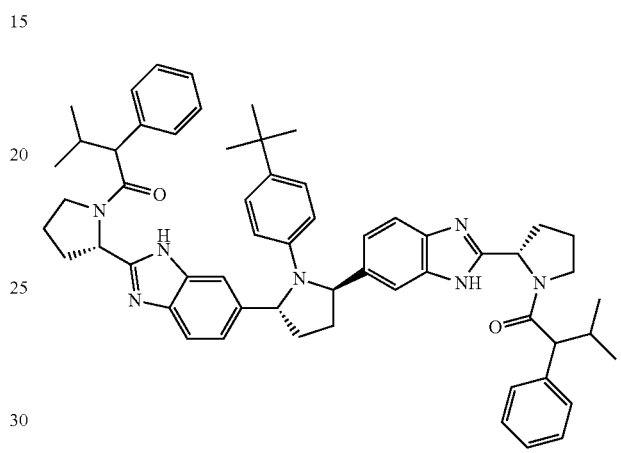

Example 292

1,1'-{[(2R,5R)-1-(4-tert-butylphenyl)pyrrolidine-2,5-diyl]bis[1H-benzimidazole-6,2-diyl(2S)pyrrolidine-2,1-diyl]}bis(3-methyl-2-phenylbutan-1-one)

MS (ESI) positive ion 893 (M+NH$_4$—H$_2$O)+.

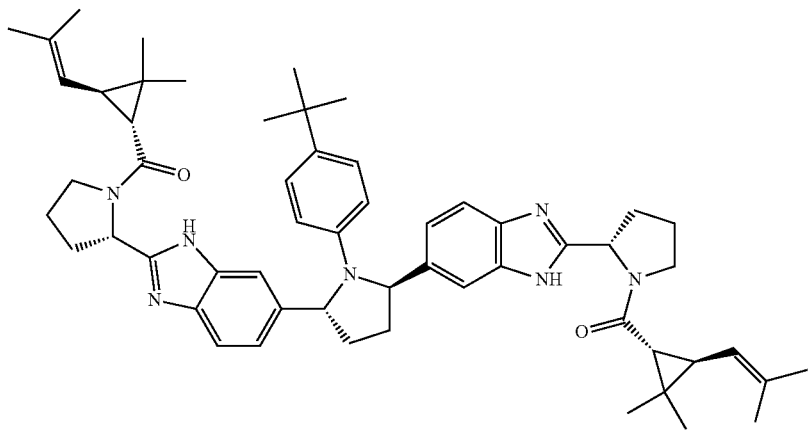 [SMILES: CC(C)=C[C@@H]1[C@@H](C(=O)N2CCC[C@H]2c2nc3ccc([C@H]4CC[C@H](c5ccc6nc([C@@H]7CCCN7C(=O)[C@@H]7[C@@H](C=C(C)C)C7(C)C)[nH]c6c5)N4c4ccc(C(C)(C)C)cc4)cc3[nH]2)C1(C)C]

Example 293

[(2R,5R)-1-(4-tert-butylphenyl)pyrrolidine-2,5-diyl]
bis[1H-benzimidazole-6,2-diyl(2S)pyrrolidine-2,1-
diyl]}bis{[(1R,3R)-2,2-dimethyl-3-(2-methylprop-1-
en-1-yl)cyclopropyl]methanone MS (ESI) positive ion 874 (M+H)+.

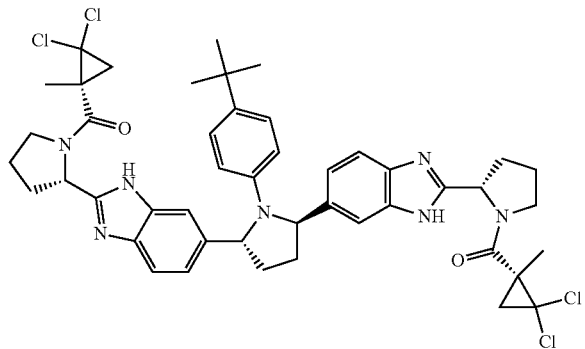 [SMILES: CC(C)(C)c1ccc(N2[C@@H](c3ccc4nc([C@@H]5CCCN5C(=O)[C@@]5(C)CC5(Cl)Cl)[nH]c4c3)CC[C@@H]2c2ccc3nc([C@@H]4CCCN4C(=O)[C@@]4(C)CC4(Cl)Cl)[nH]c3c2)cc1]

Example 294

{[(2R,5R)-1-(4-tert-butylphenyl)pyrrolidine-2,5-
diyl]bis[1H-benzimidazole-6,2-diyl(2S)pyrrolidine-
2,1-diyl]}bis[(2,2-dichloro-1-methylcyclopropyl)
methanone]

MS (ESI) positive ion 874 (M+H)+.

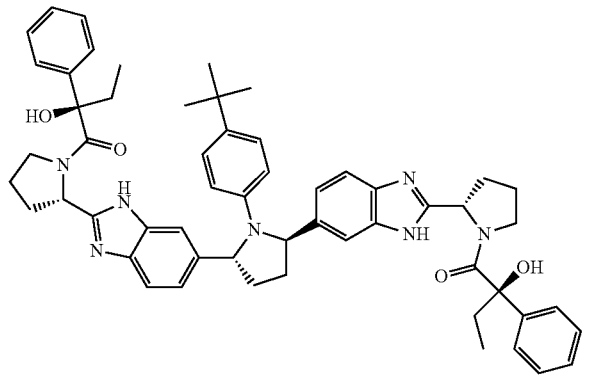 [SMILES: CC[C@](O)(C(=O)N1CCC[C@H]1c1nc2ccc([C@H]3CC[C@H](c4ccc5nc([C@@H]6CCCN6C(=O)[C@@](O)(CC)c6ccccc6)[nH]c5c4)N3c3ccc(C(C)(C)C)cc3)cc2[nH]1)c1ccccc1]

Example 295

(2R,2'R)-1,1'-{[(2R,5R)-1-(4-tert-butylphenyl)pyrro-
lidine-2,5-diyl]bis[1H-benzimidazole-6,2-diyl(2S)
pyrrolidine-2,1-diyl]}bis(2-hydroxy-2-phenylbutan-
1-one)

MS (ESI) positive ion (M+H)+.

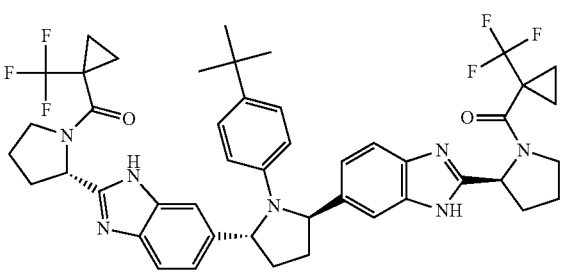 [SMILES: CC(C)(C)c1ccc(N2[C@@H](c3ccc4nc([C@@H]5CCCN5C(=O)C5(C(F)(F)F)CC5)[nH]c4c3)CC[C@@H]2c2ccc3nc([C@@H]4CCCN4C(=O)C4(C(F)(F)F)CC4)[nH]c3c2)cc1]

Example 296

[(2R,5R)-1-(4-tert-butylphenyl)pyrrolidine-2,5-diyl]
bis[1H-benzimidazole-6,2-diyl(2S)pyrrolidine-2,1-
diyl]}bis{[1-(trifluoromethyl)cyclopropyl]metha-
none MS (ESI) positive ion 846 (M+H)+.

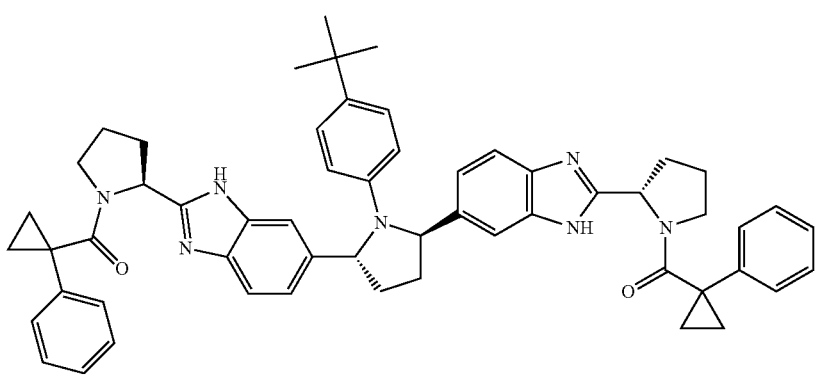 [SMILES: CC(C)(C)c1ccc(N2[C@@H](c3ccc4nc([C@@H]5CCCN5C(=O)C5(c6ccccc6)CC5)[nH]c4c3)CC[C@@H]2c2ccc3nc([C@@H]4CCCN4C(=O)C4(c5ccccc5)CC4)[nH]c3c2)cc1]

521

Example 297

{[(2R,5R)-1-(4-tert-butylphenyl)pyrrolidine-2,5-diyl]bis[1H-benzimidazole-6,2-diyl(2S)pyrrolidine-2,1-diyl]}bis[(1-phenylcyclopropyl)methanone]

MS (ESI) positive ion 862.5 (M+H)+.

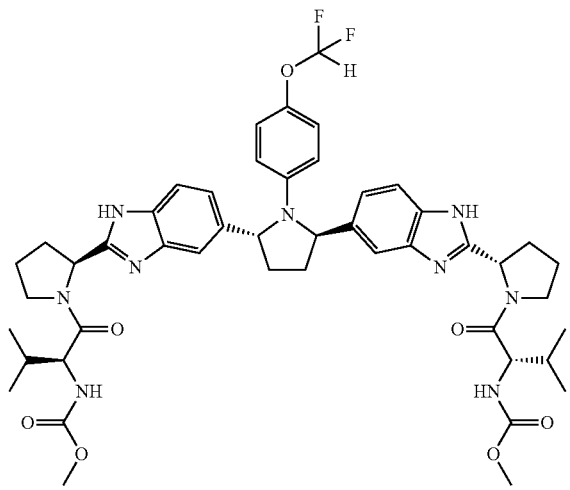 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(OC(F)F)cc3)ccc2[nH]1)C(C)C]

Example 298 methyl {(2S)-1-[(2S)-2-{5-[(2R,5R)-1-[4-(difluoromethoxy)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (ESI+) m/z 898.4 (M+H)+

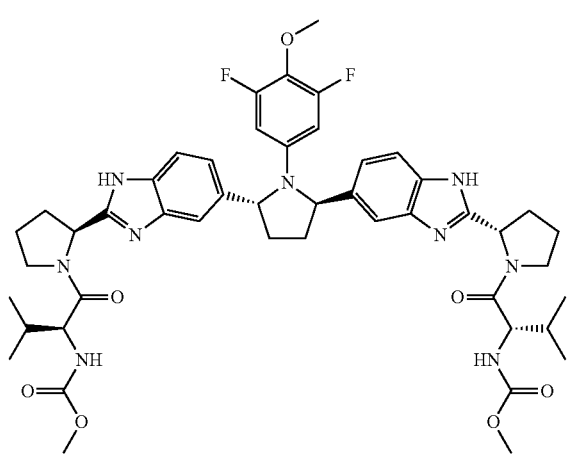 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3cc(F)c(OC)c(F)c3)ccc2[nH]1)C(C)C]

522

Example 299 methyl {(2S)-1-[(2S)-2-{5-[(2R,5R)-1-(3,5-difluoro-4-methoxyphenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (ESI+) m/z 898.4 (M+H)+

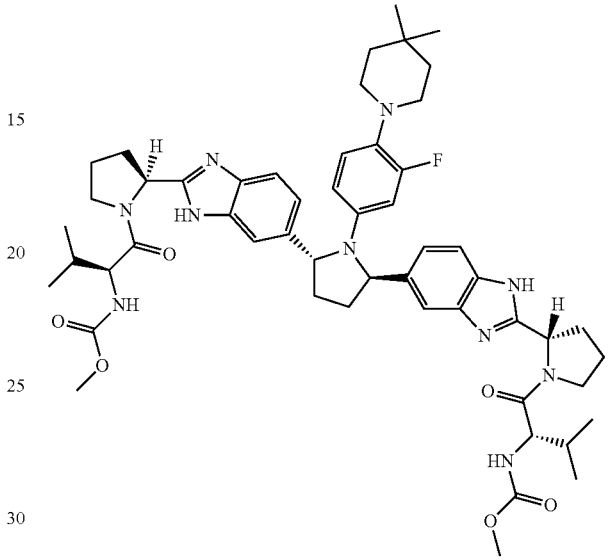

Example 300 methyl {(2S)-1-[(2S)-2-{5-[(2R,5R)-1-[4-(4,4-dimethylpiperidin-1-yl)-3-fluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate MS+ESI m/z (rel abundance) 962 (100, M+H); $^1$H NMR (400 MHz, DMSO-$d_6$) δ 7.52 (d, J=8.2, 1H), 7.44 (d, J=8.1, 1H), 7.35 (d, J=8.1, 3H), 7.26 (s, 1H), 7.14 (m, 2H), 6.75 (s, 1H), 6.12 (m, 2H), 5.40 (s, 2H), 5.19 (s, 2H), 4.12 (t, J=8.4, 2H), 3.88 (s, 4H), 3.60 (s, 6H), 2.70 (m, 5H), 2.24 (s, 4H), 1.99 (m, 7H), 1.75 (s, 2H), 1.46 (s, 3H), 1.39 (s, 8H), 0.89 (m, 20H).

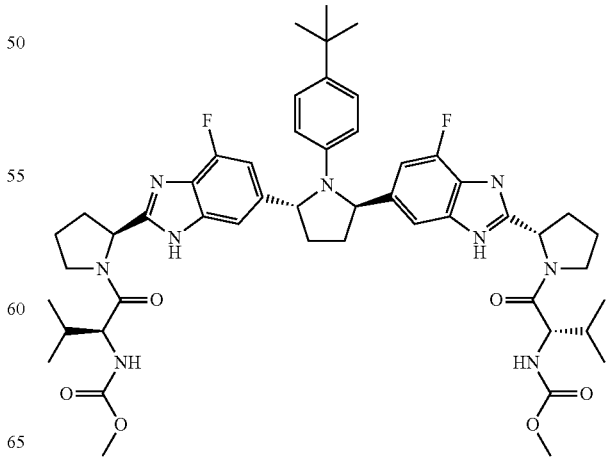

Example 301 methyl {(2S)-1-[(2S)-2-{6-[1-(4-tert-butylphenyl)-5-{4-fluoro-2-[(2S)-1-{(2S)-2-[(methoxycarbonyl)amino]-3-methylbutanoyl}pyrrolidin-2-yl]-1H-benzimidazol-6-yl}pyrrolidin-2-yl]-4-fluoro-1H-benzimidazol-2-yl}pyrrolidin-1-yl]-3-methyl-1-oxobutan-2-yl}carbamate MS (ESI) m/z 924 (M+H)⁺

Example 303 methyl {(2S)-1-[(2S)-2-{6-[(2R,5R)-5-{2-[(2S)-1-{(2S)-2-[(methoxycarbonyl)amino]-3-methylbutanoyl}pyrrolidin-2-yl]-1H-benzimidazol-6-yl}-1-{4-[2-(2-methoxyethoxy)ethoxy]phenyl}pyrrolidin-2-yl]-1H-benzimidazol-2-yl}pyrrolidin-1-yl]-3-methyl-1-oxobutan-2-yl}carbamate MS (ESI) m/z 950 (M+H)⁺, 948 (M−H)⁺.

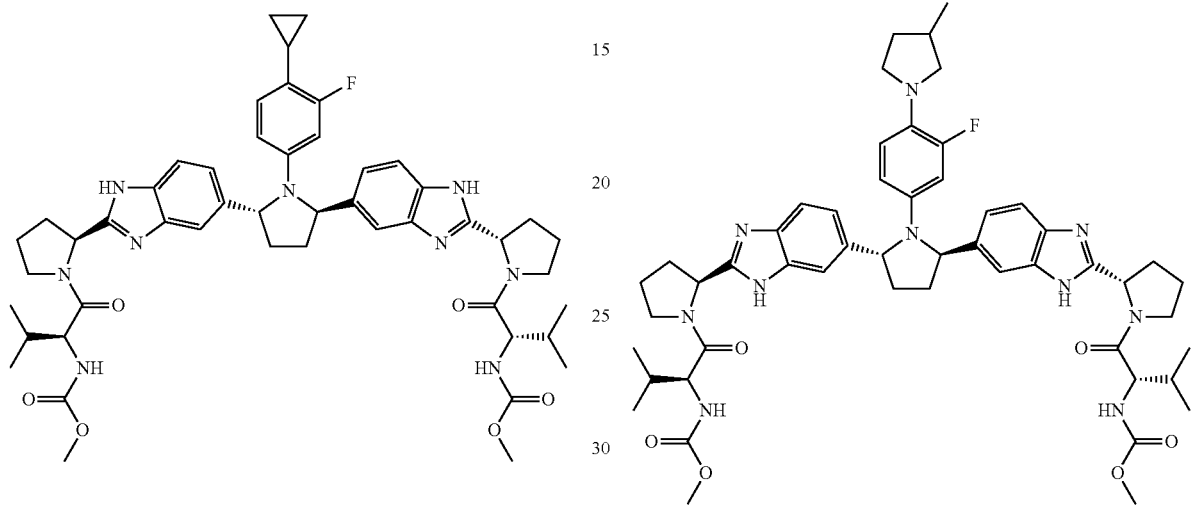

Example 302 methyl {(2S)-1-[(2S)-2-{5-[(2R,5R)-1-(4-cyclopropyl-3-fluorophenyl)-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbmate MS (ESI) m/z 891 (M+H)⁺

Example 304 methyl {(2S)-1-[(2S)-2-{6-[(2R,5R)-1-[3-fluoro-4-(3-methylpyrrolidin-1-yl)phenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate 1H NMR (400 MHz, DMSO-D6) δ ppm 0.76-0.89 (m, 12H) 0.95 (d, J=6.72 Hz, 3H) 1.62-1.72 (m, 2H) 1.83-2.06

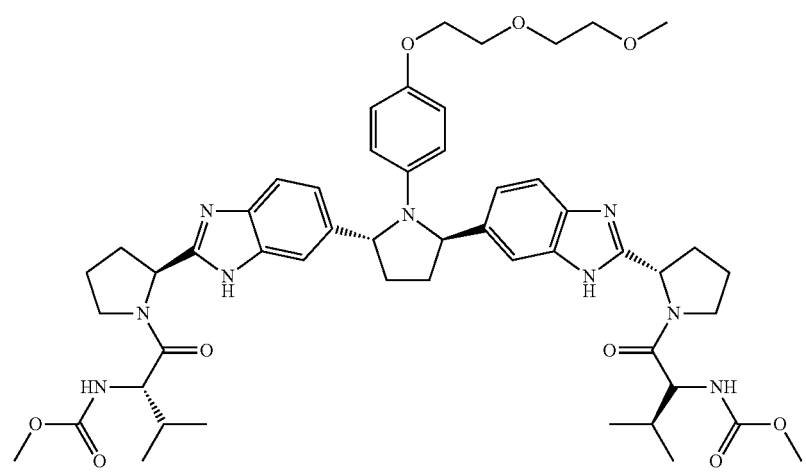

(m, 9H) 2.09-2.24 (m, 6H) 2.52-2.61 (m, 2H) 2.91-3.15 (m, 4H) 3.52 (s, 6H) 3.74-3.86 (m, 4H) 4.05 (t, J=8.35 Hz, 2H) 5.08-5.17 (m, 2H) 5.26-5.38 (m, 2H) 5.97-6.10 (m, 2H) 6.35-6.45 (m, 1H) 7.01-7.08 (m, 2H) 7.19 (s, 1H) 7.25-7.32 (m, 3H) 7.36 (d, J=8.24 Hz, 1H) 7.44 (d, J=7.92 Hz, 1H) 12.01 (s, 2H).

1.73-1.83 (m, 2H) 1.86-2.02 (m, 6H) 2.14-2.23 (m, 4H) 2.59-2.72 (m, 6H) 3.53 (s, 6H) 3.77-3.84 (m, 4H) 3.97-4.10 (m, 2H) 5.06-5.18 (m, 2H) 5.46-5.56 (m, 2H) 6.36-6.47 (m, 2H) 7.03-7.11 (m, 2H) 7.23-7.45 (m, 6H) 11.95-12.10 (m, 2H)

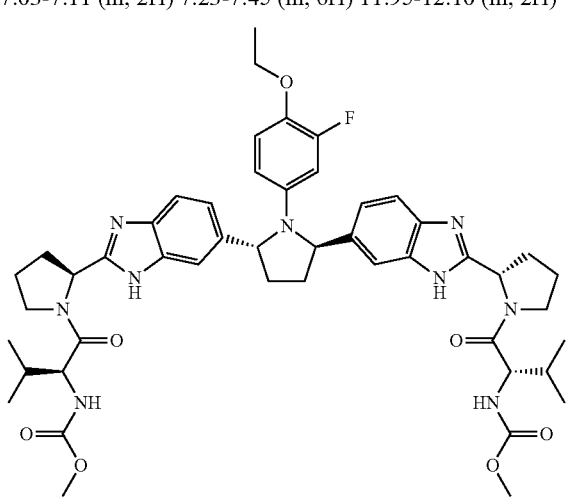

Example 306 methyl {(2S)-1-[(2S)-2-{6-[(2R,5R)-1-(4-ethoxy-3-fluorophenyl)-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+ (m/z): 894.4

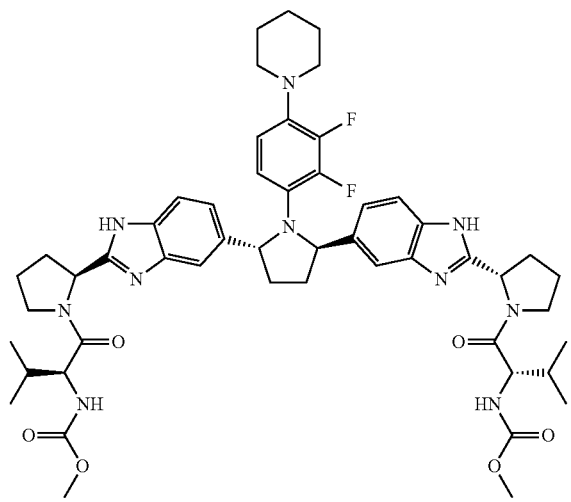 [SMILES: COC(=O)N[C@H](C(=O)N1CCC[C@H]1c1nc2cc([C@H]3CC[C@H](c4ccc5[nH]c([C@@H]6CCCN6C(=O)[C@@H](NC(=O)OC)C(C)C)nc5c4)N3c3ccc(N4CCCCC4)c(F)c3F)ccc2[nH]1)C(C)C]

Example 305 methyl {(2S)-1-[(2S)-2-{5-[(2R,5R)-1-[2,3-difluoro-4-(piperidin-1-yl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate ESI+ (m/z): 951.5; 1H NMR (400 MHz, DMSO-D6) δ ppm 0.74-0.90 (m, 12H) 1.35-1.41 (m, 2H) 1.44-1.51 (m, 4H)

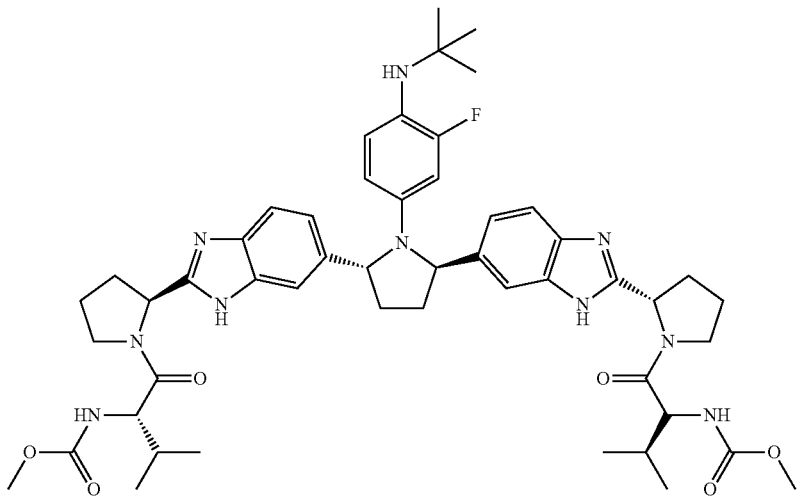

Example 307 methyl {(2S)-1-[(2S)-2-{6-[(2R,5R)-1-[4-(tert-butylamino)-3-fluorophenyl]-5-{2-[(2S)-1-{(2S)-2-[(methoxycarbonyl)amino]-3-methylbutanoyl}pyrrolidin-2-yl]-1H-benzimidazol-6-yl}pyrrolidin-2-yl]-1H-benzimidazol-2-yl}pyrrolidin-1-yl]-3-methyl-1-oxobutan-2-yl}carbamate ESI+ (m/z): 922; 1H NMR (400 MHz, DMSO-D6) δ ppm 0.75-0.90 (m, 12H) 0.97 (s, 9H) 1.61-1.71 (m, 2H) 1.83-2.04

(m, 6H) 2.12-2.23 (m, 4H) 3.52 (s, 6H) 3.76-3.86 (m, 4H) 4.01-4.08 (m, 2H) 5.09-5.17 (m, 2H) 5.27-5.37 (m, 2H) 5.98-6.07 (m, 2H) 6.56-6.66 (m, 1H) 7.06 (t, J=7.92 Hz, 2H) 7.19 (s, 1H) 7.27 (d, J=9.00 Hz, 3H) 7.38 (d, J=8.24 Hz, 1H) 7.46 (d, J=8.13 Hz, 1H) 12.00 (s, 1H) 12.08 (s, 1H)

1.65-1.77 (m, 2H) 1.81-2.13 (m, 8H) 2.20-2.28 (m, 2H) 2.55-2.62 (m, 2H) 3.53 (d, J=4.23 Hz, 6H) 3.80-3.92 (m, 4H) 4.04-4.13 (m, 2H) 4.41-4.59 (m, 4H) 5.38-5.49 (m, 2H) 5.66-5.76 (m, 2H) 6.17-6.33 (m, 2H) 6.82-7.00 (m, 3H) 7.18-7.56 (m, 5H) 7.75-7.91 (m, 2H)

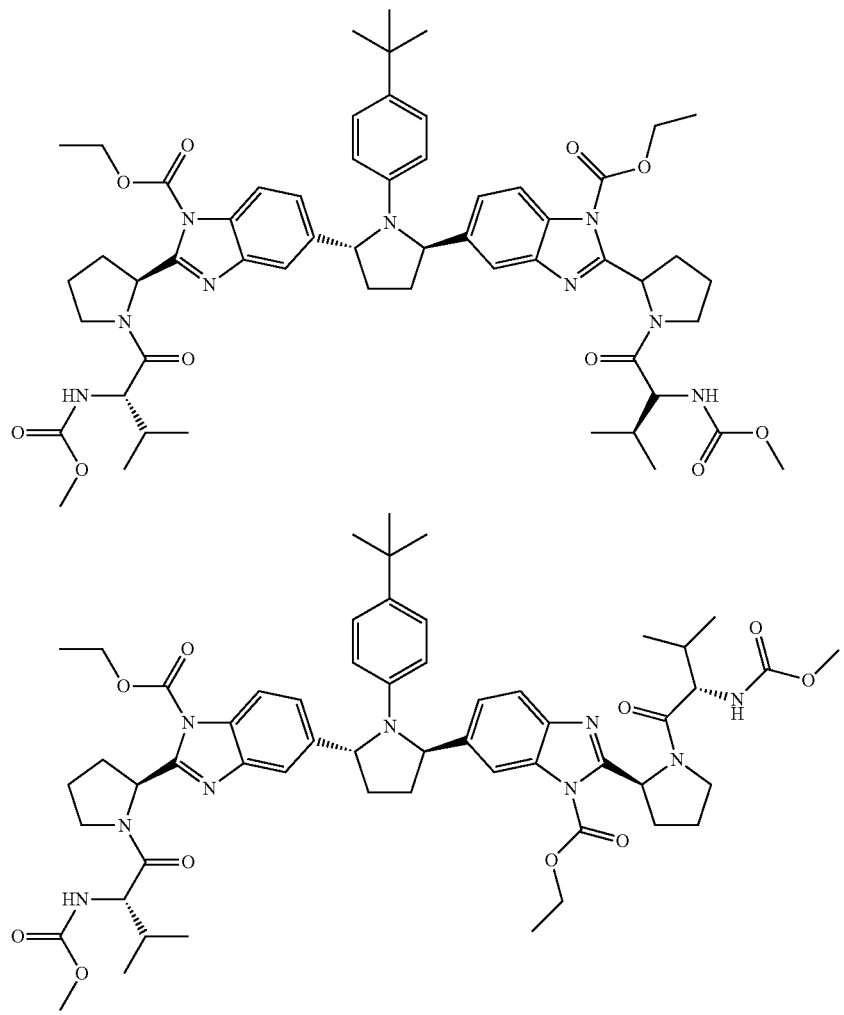

Example 308 ethyl 5-{(2R,5R)-1-(4-tert-butylphenyl)-5-[1-(ethoxycarbonyl)-2-{(2S)-1-[N-(methoxycarbonyl)-L-valyl]pyrrolidin-2-yl}-1H-benzimidazol-5-yl]pyrrolidin-2-yl}-2-{1-[N-(methoxycarbonyl)-L-valyl]pyrrolidin-2-yl}-1H-benzimidazole-1-carboxylate and ethyl 5-{(2R,5R)-1-(4-tert-butylphenyl)-5-[1-(ethoxycarbonyl)-2-{(2S)-1-[N-(methoxycarbonyl)-L-valyl]pyrrolidin-2-yl}-1H-benzimidazol-6-yl]pyrrolidin-2-yl}-2-{(2S)-1-[N-(methoxycarbonyl)-L-valyl]pyrrolidin-2-yl}-1H-benzimidazole-1-carboxylate ESI+ (m/z): 1032.5; 1H NMR (400 MHz, DMSO-D6) δ ppm 0.70-1.04 (m, 12H) 1.08 (s, 9H) 1.33-1.46 (m, 6H)

The title compounds of Examples 52, 53, 54, 58, 59, 60, 61, 62, 63, 64, 65, 66, 67, 68, 69, 74, 75, 76, 77, 79, 80, 81, 82, 83, 84, 85, 86, 87, 88, 89, 90, 91, 93, 94, 95, 96, 97, 99, 101, 102, 103, 109, 110, 111, 112, 113, 117, 121, 122, 123, 125, 126, 127, 128, 129, 130, 131, 132, 135, 136, 137, 138, 139, 140, 141, 144, 145, 146, 148, 149, 150, 151, 152, 153, 154, 155, 156, 157, 159, 160, 161, 162, 163, 166, 167, 168, 169, 170, 171, 173, 176, 178, 179, 180, 181, 183, 184, 185, 186, 188, 189, 191, 192, 194, 195, 197, 198, 199, 200, 201, 202, 203, 205, 207, 208, 209, 210, 211, 212, 214, 215, 216, 217, 218, 219, 220, 221, 224, 226, 227, 228, 229, 230, 231, 233, 234, 235, 236, 237, 238, 240, 241, 242, 245, 247, 248, 250, 251, 252, 254, 256, 257, 258, 262, 263, 264, 266, 267, 268, 270, 271, 272, 273, 274, 275, 276, 277, 278, 282, 294, 295, 296, 297, 298, 299, 300, 301, 302, 305, and 306 showed an $EC_{50}$ value of less than about 0.1 nM in HCV 1b-Con1 replicon assays in the presence of 5% FBS. The title compounds of Examples 51, 55, 56, 57, 70, 71, 72, 73, 78, 98, 100, 108, 114, 115, 116, 119, 120, 133, 134, 142, 143, 147, 164, 172, 174, 182, 196, 204, 206, 222, 223, 225, 239, 244, 249, 253, 259, 261, 265, 281, 287, 288, 292, 303, 304, 307, and 308 showed an $EC_{50}$ value of from about 0.1 to about 1 nM in HCV 1b-Con1 replicon assays in the presence of 5% FBS. The title compounds of Examples 92, 105, 106, 107, 118, 124, 158, 165, 175, 177, 187, 190, 193, 213, 232, 243, 246, 255, 260, 269, 279, 280, 283, 284, 285, 286, 289, 290, 291, and 293 showed an $EC_{50}$ value of from about 1 to about 100 nM in HCV 1b-Con11 replicon assays in the presence of 5% FBS.

The present invention also contemplates pharmaceutically acceptable salts of each compound in Examples 1-308, as well as pharmaceutically acceptable salts of each compound described hereinbelow.

The following compounds were similarly prepared according to the procedures described above:

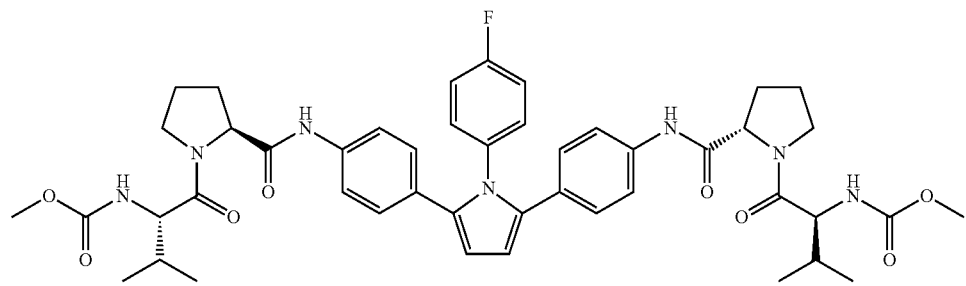

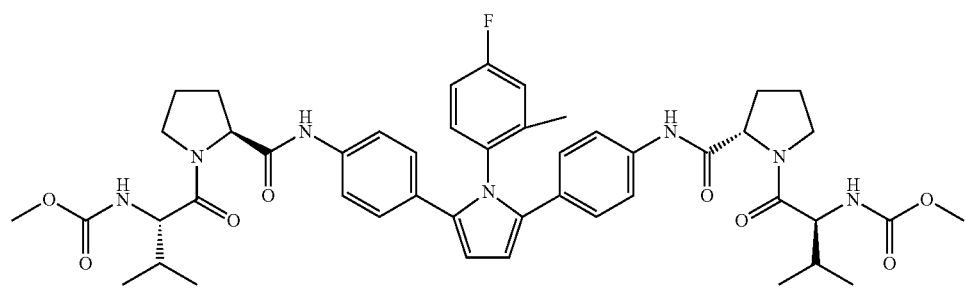

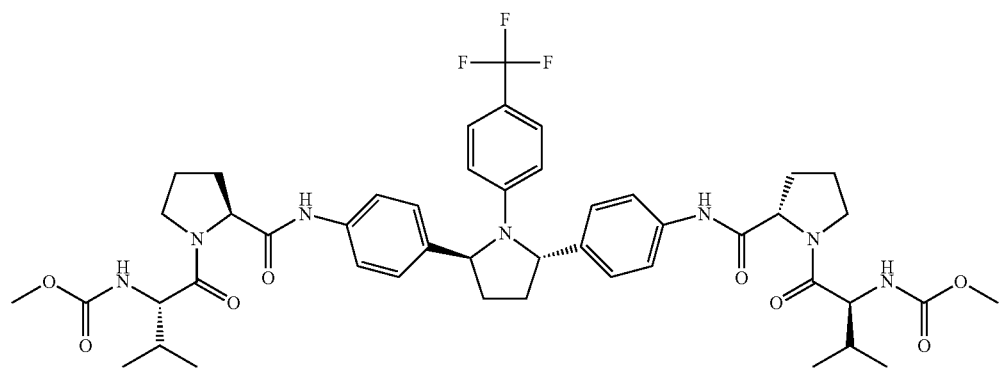

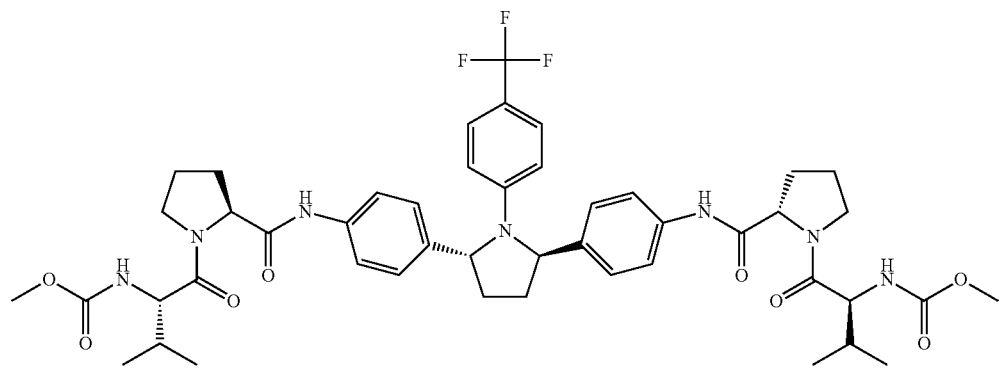

-continued
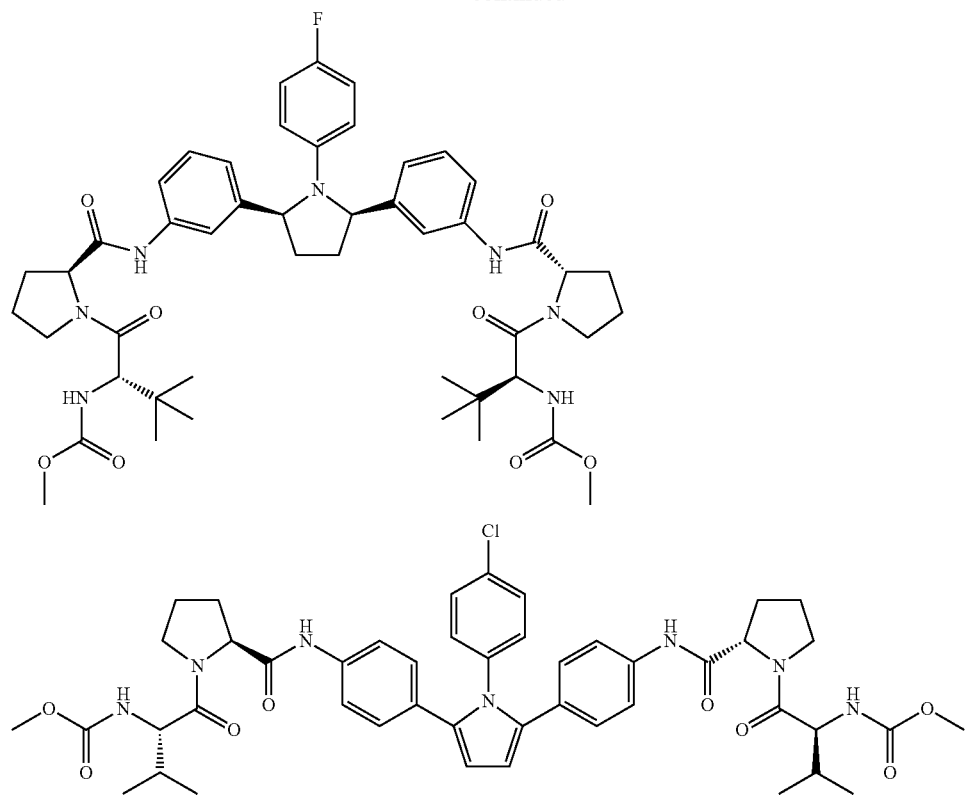
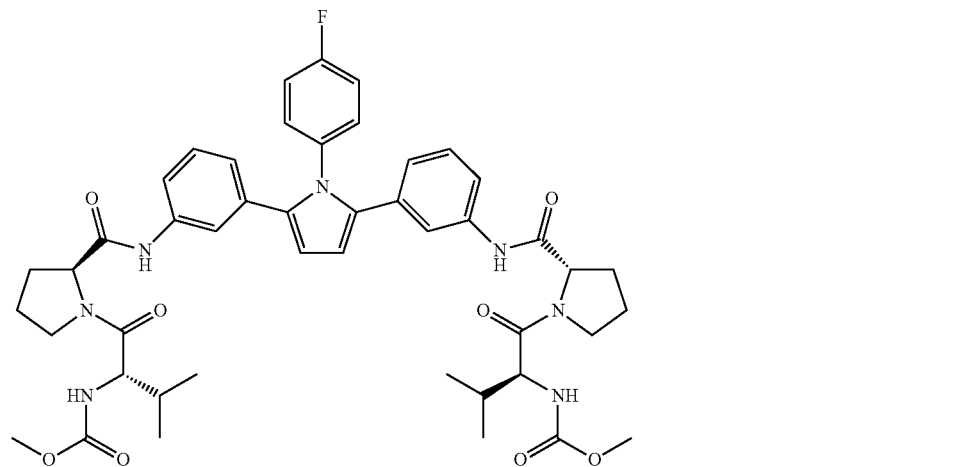
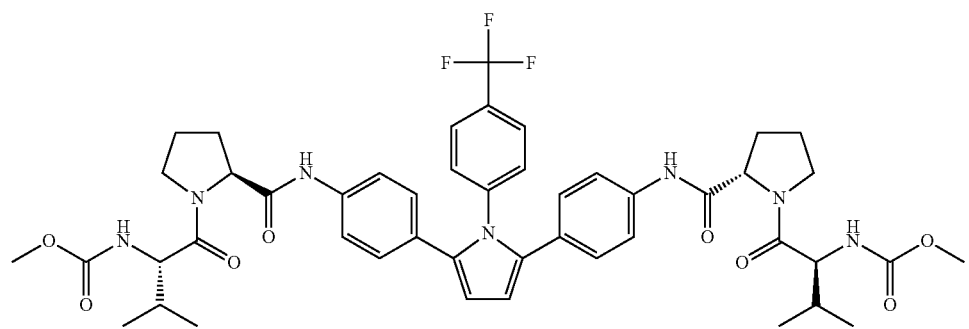

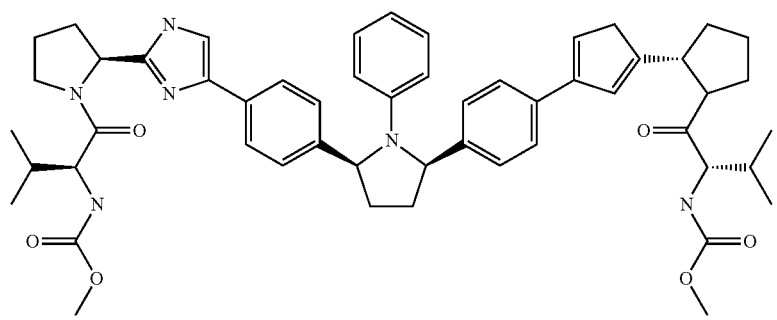
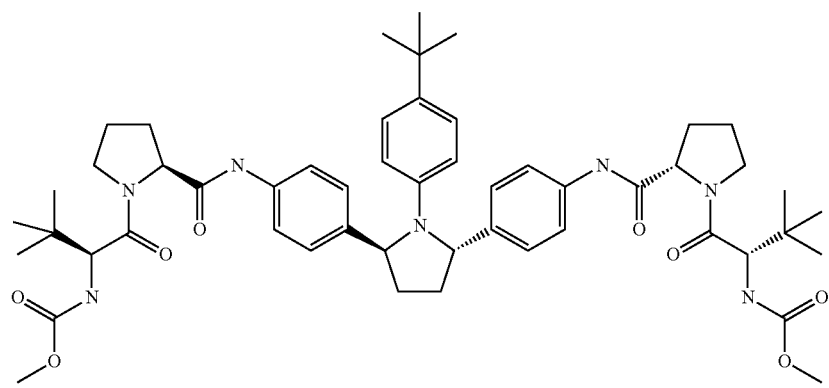
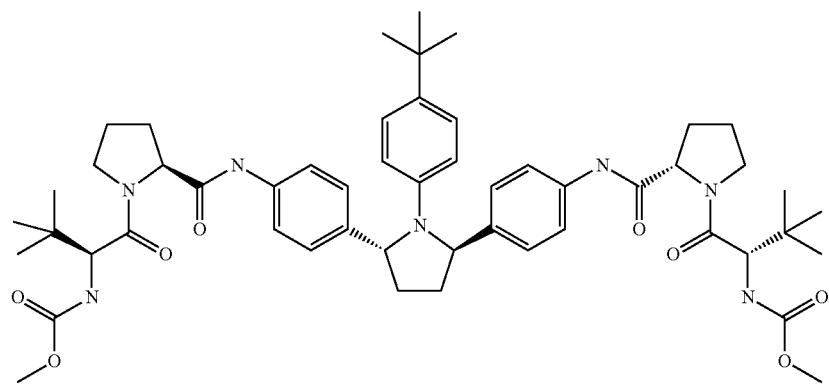
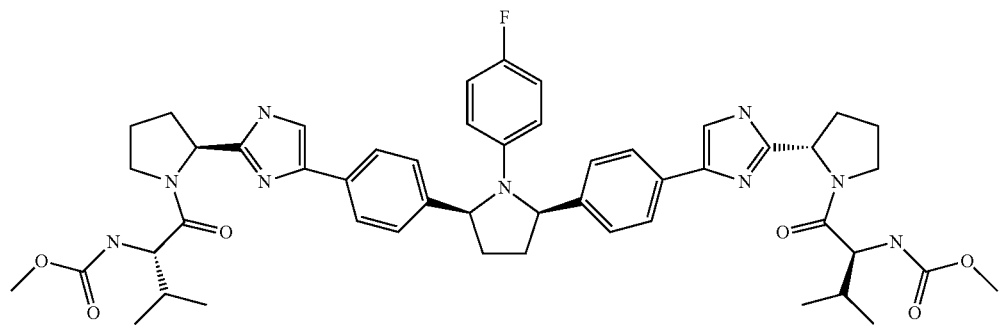

-continued
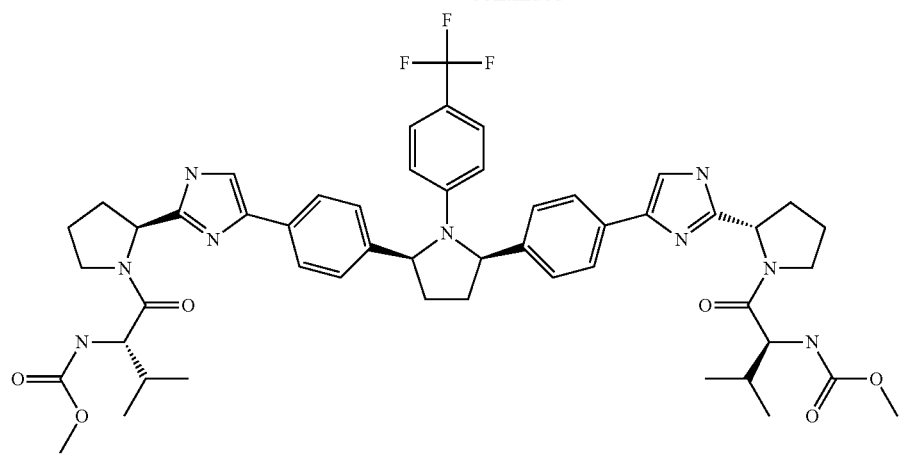
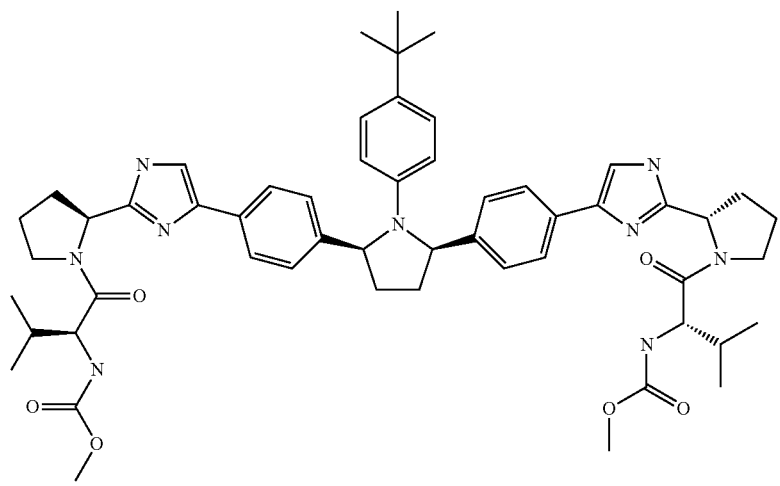
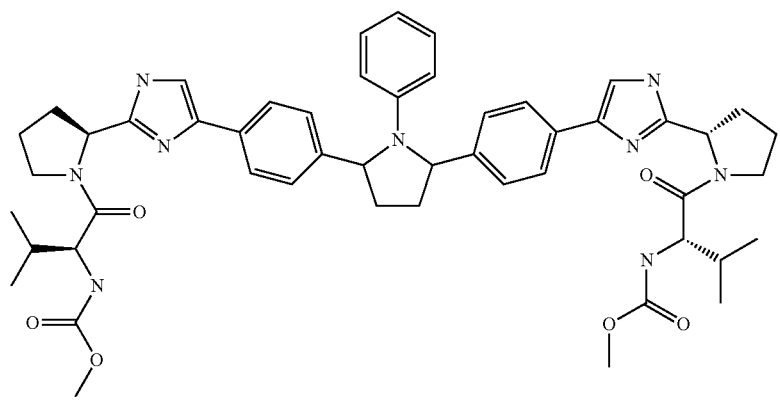

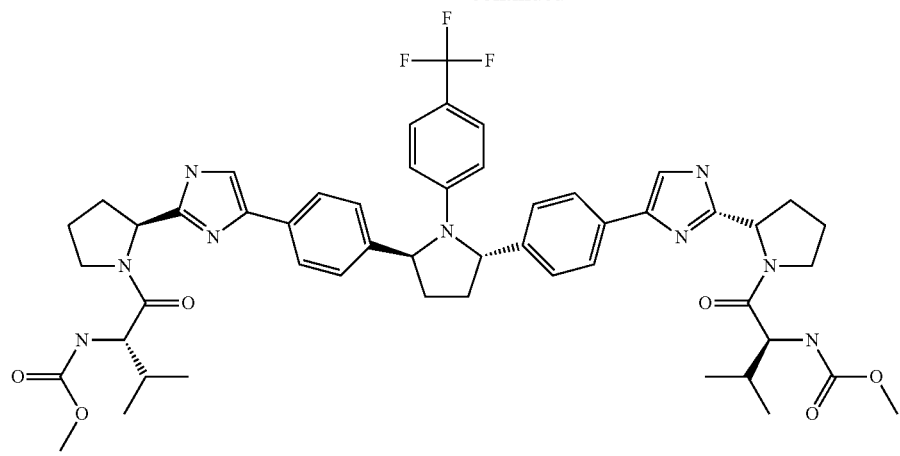
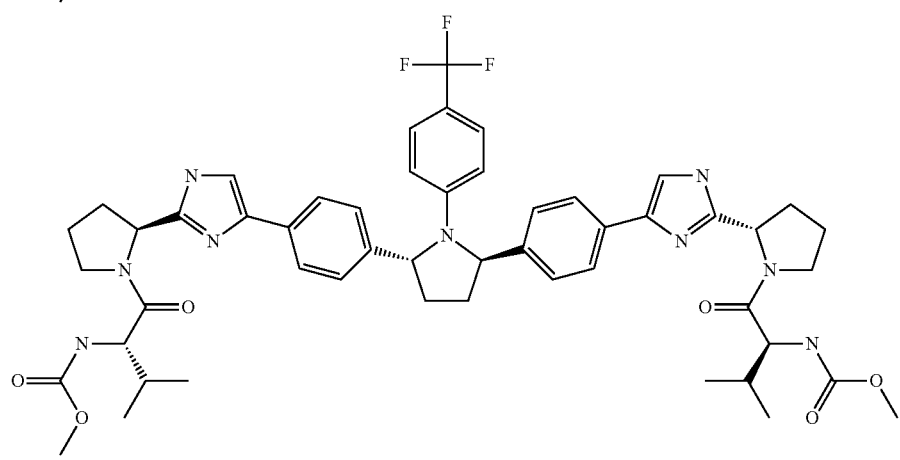
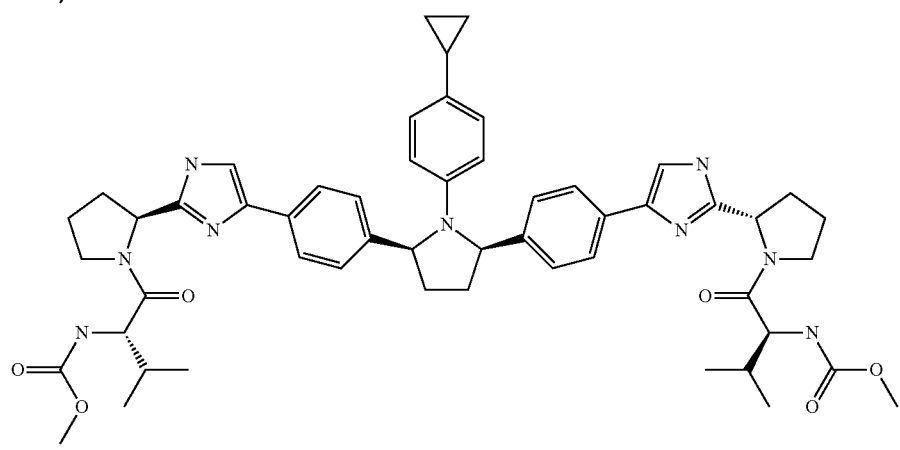
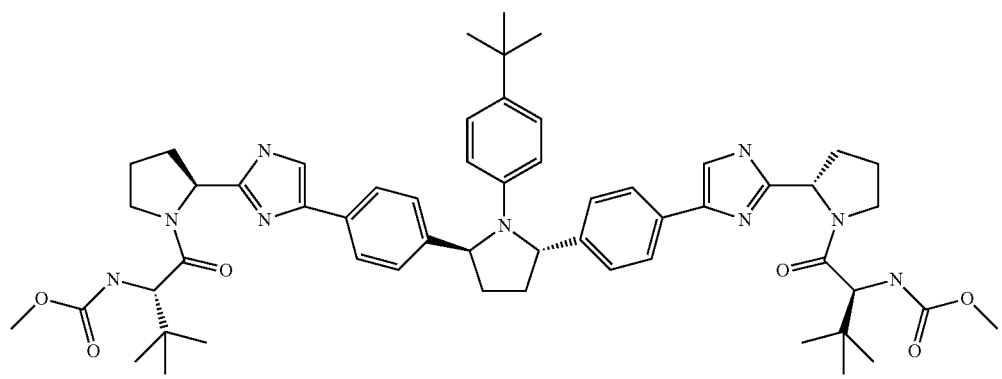

-continued
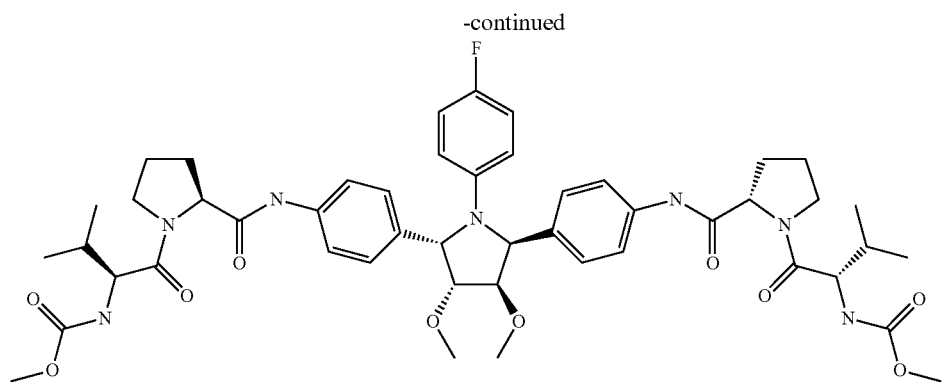
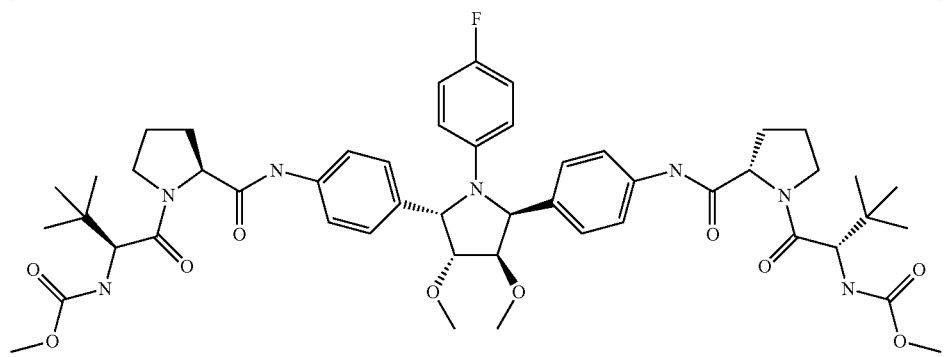
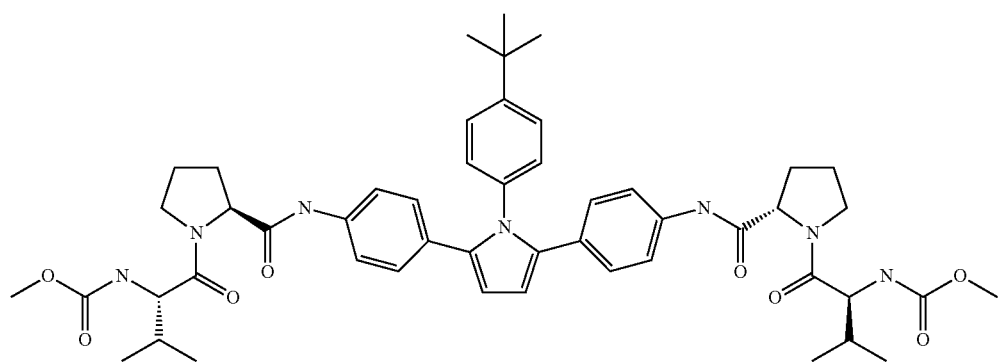
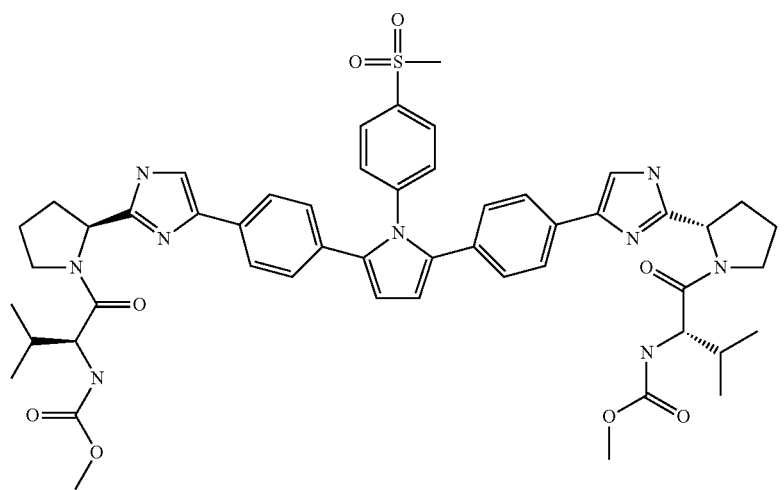

-continued
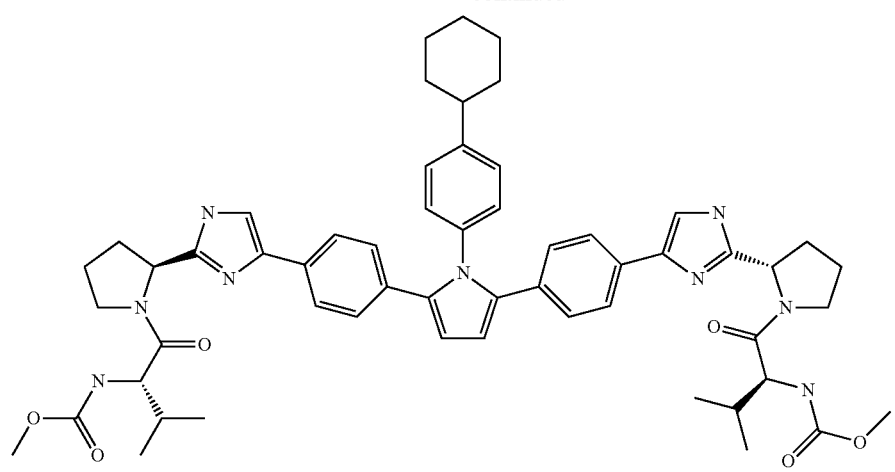
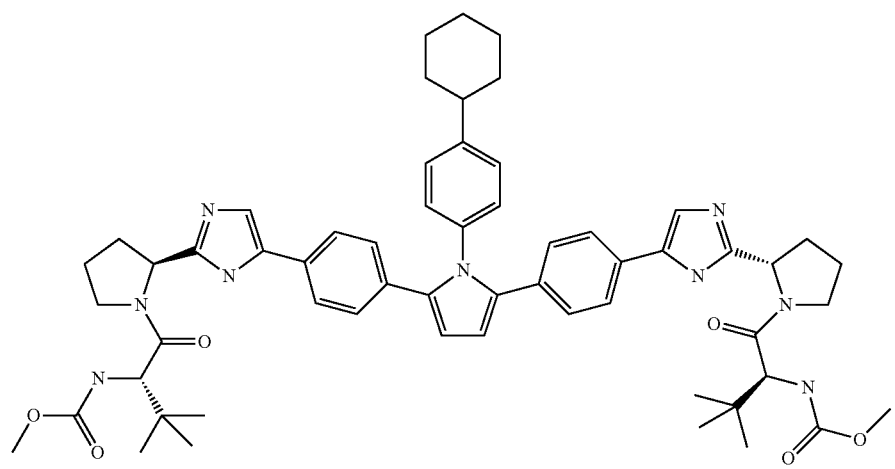
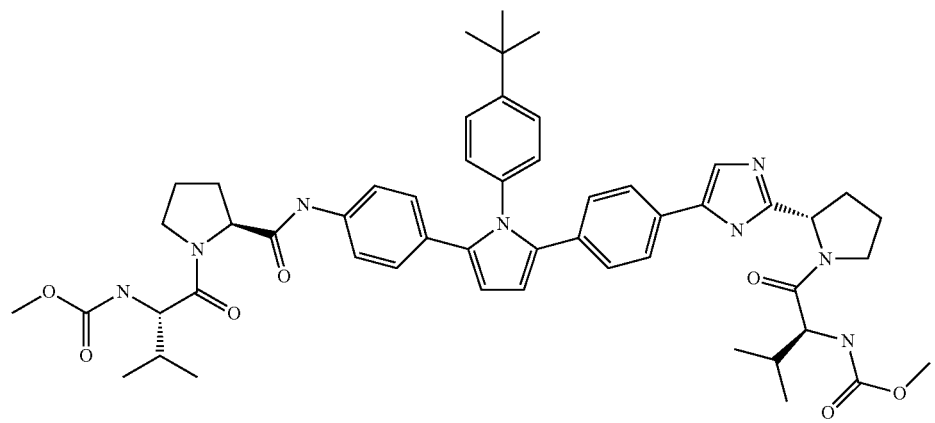

-continued
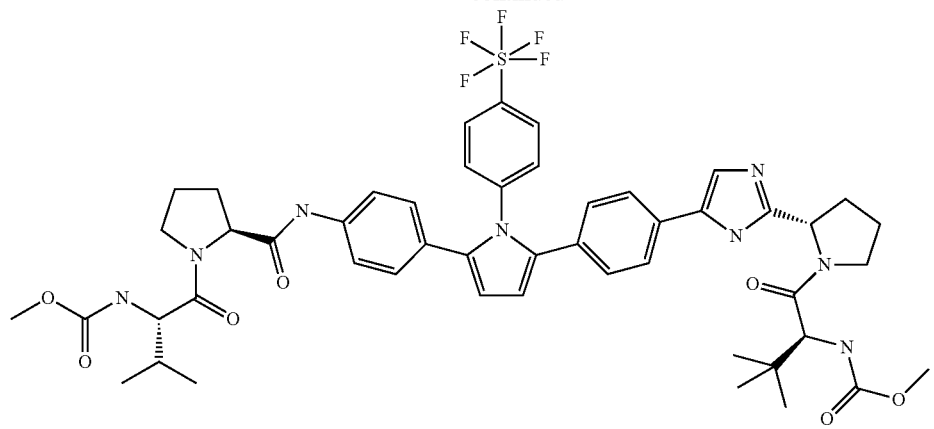
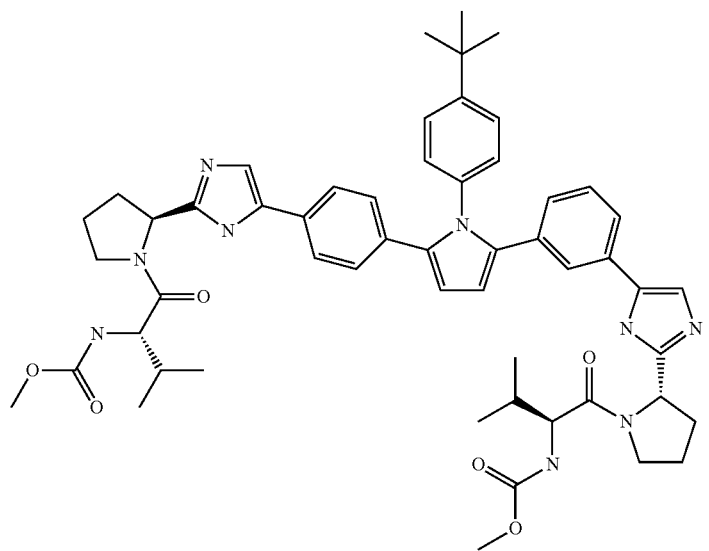
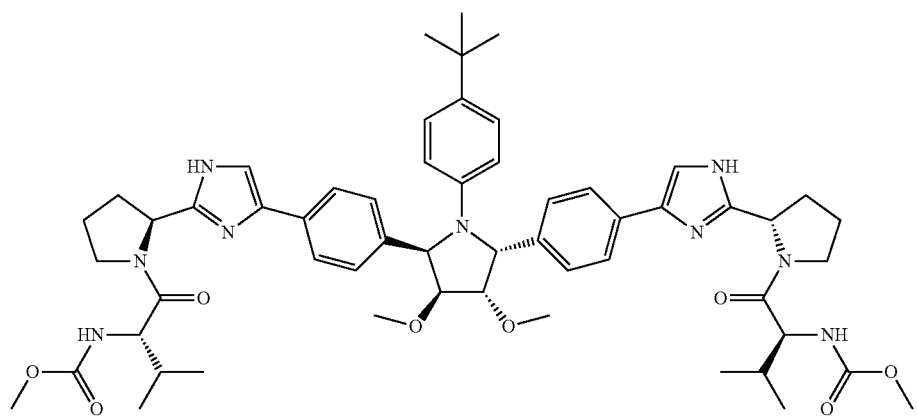

-continued

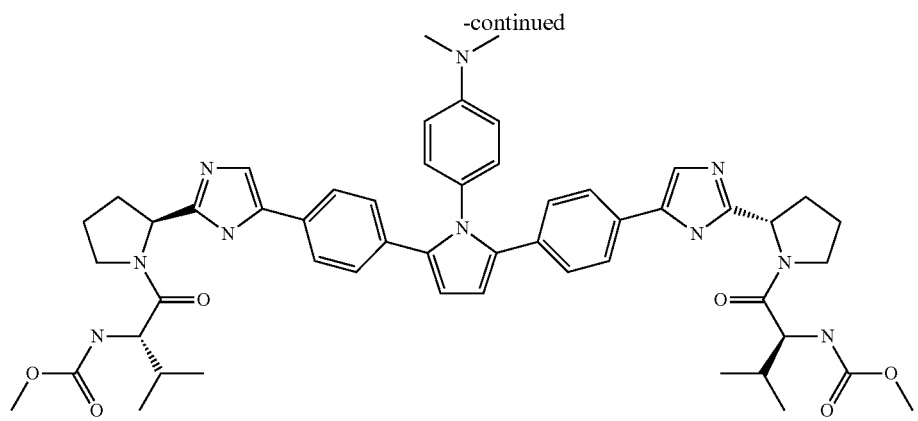

When tested using HCV 1b-Con1 replicon assays in the presence of 5% FBS, each of the above compounds showed an $EC_{50}$ value of less than 1 nM.

In addition, the following mixtures of stereoisomers were prepared according to procedures similar to those described above, where each compound in each stereoisomer mixture can be readily isolated using chiral chromatography or other suitable methods as appreciated by those skilled in the art and, therefore, the present invention also features each compound in these stereoisomer mixtures:

mixture 1

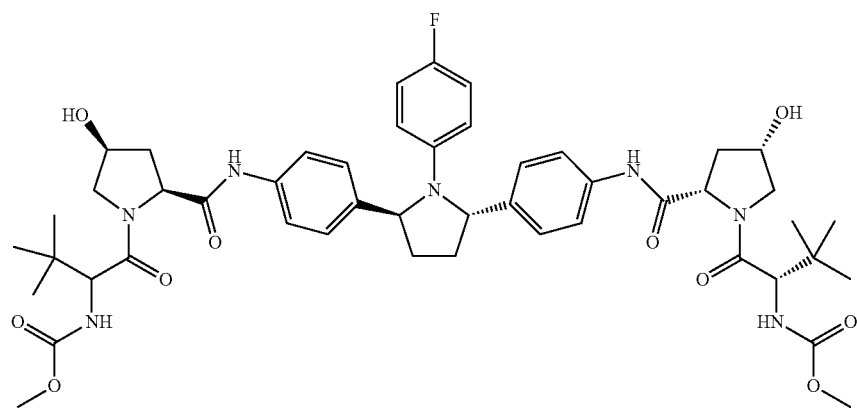

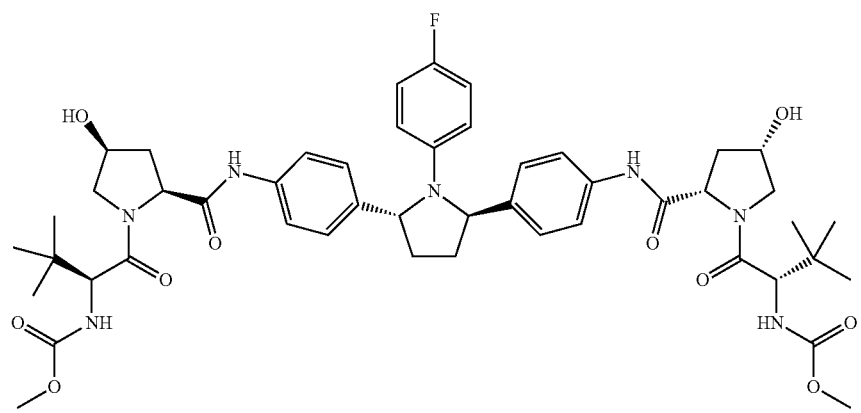

-continued
mixture 2
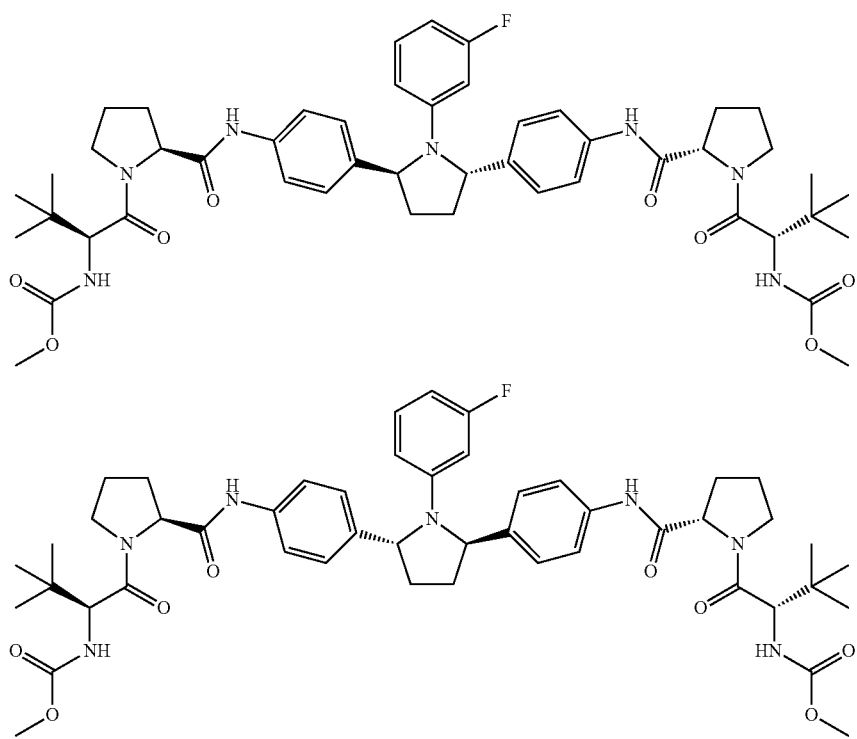
mixture 3
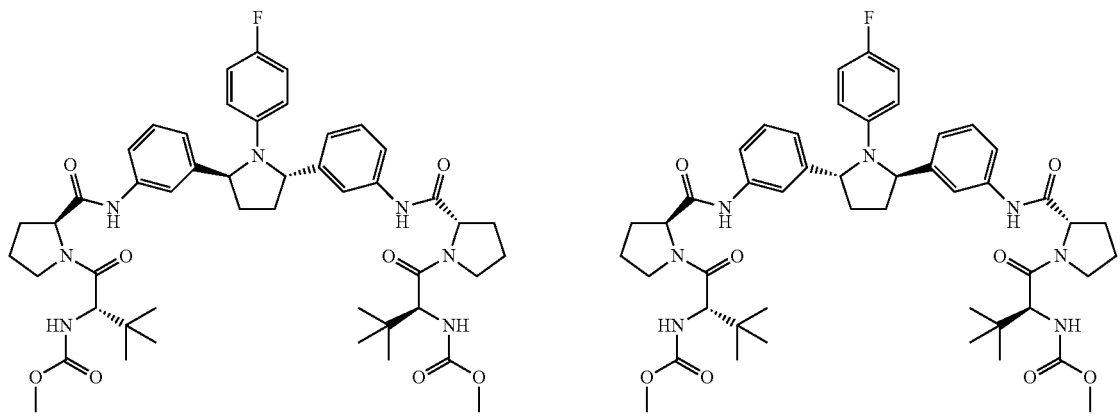
mixture 4
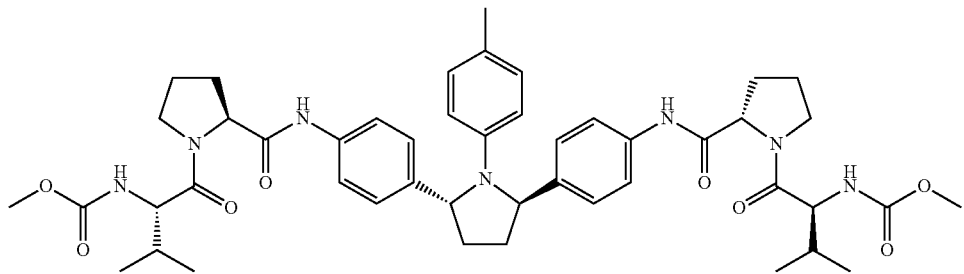

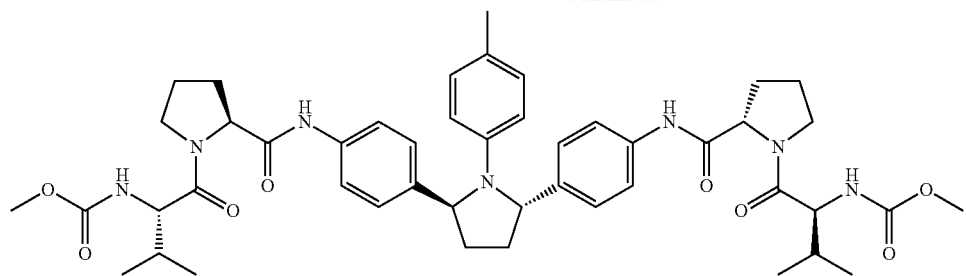
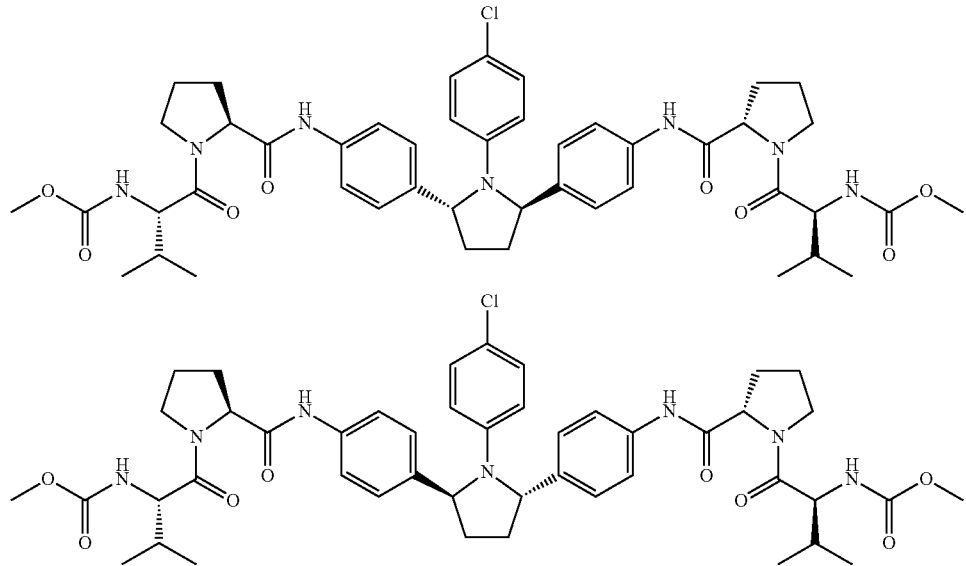
mixture 5
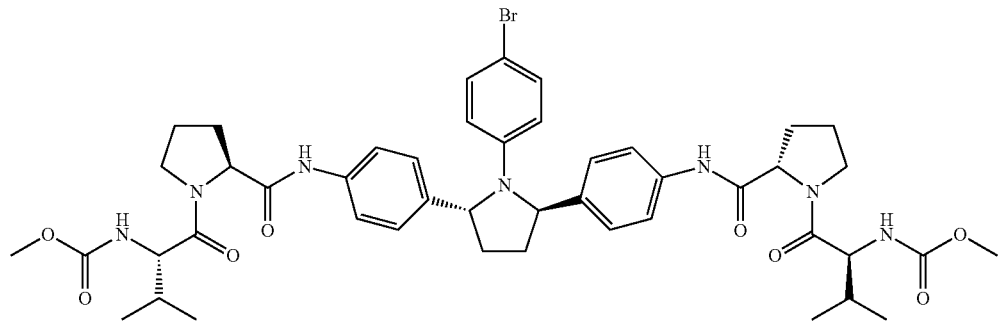
mixture 6
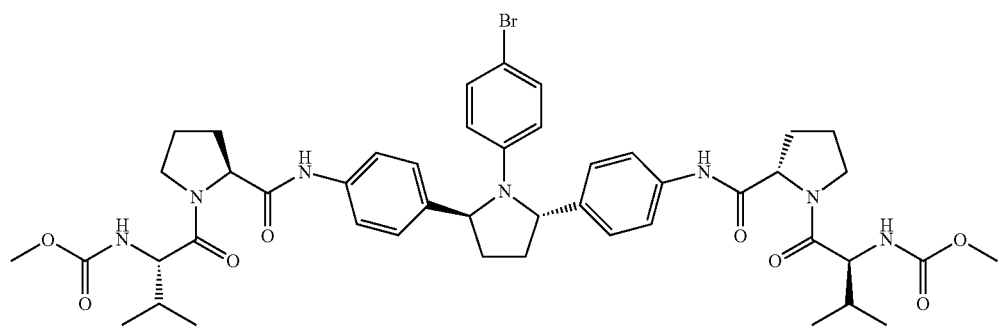

mixture 7
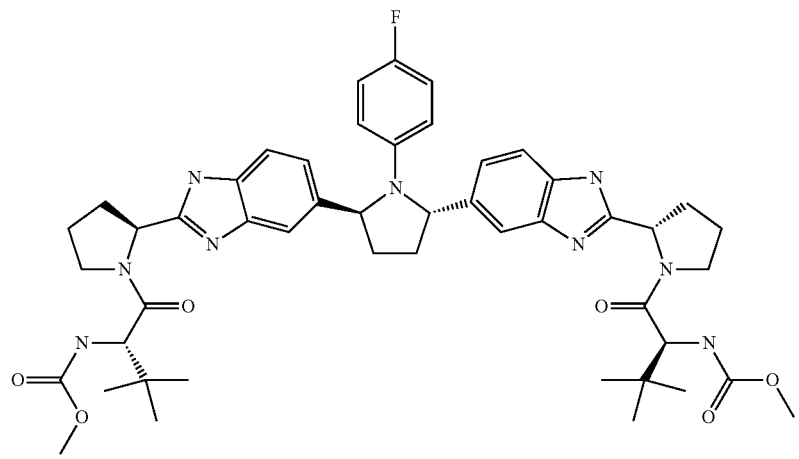
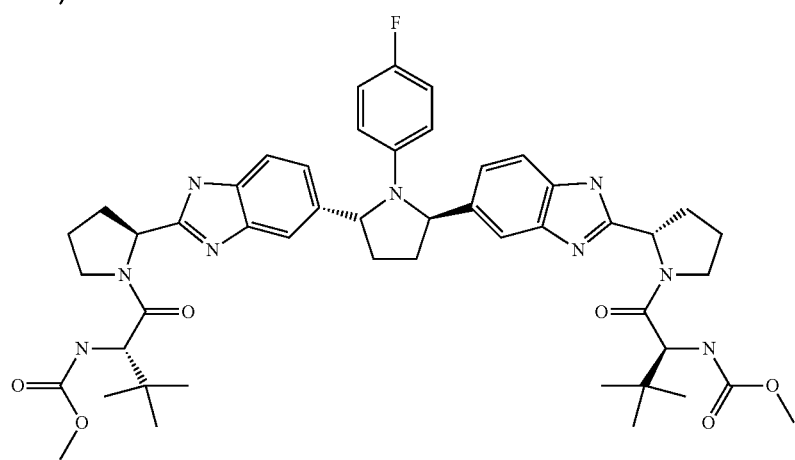
mixture 8
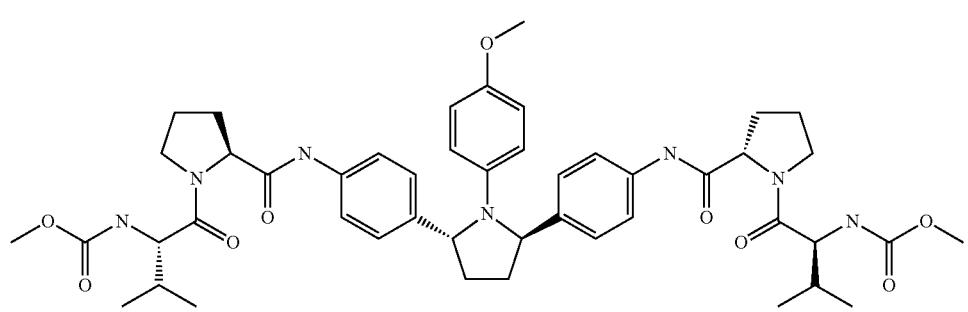
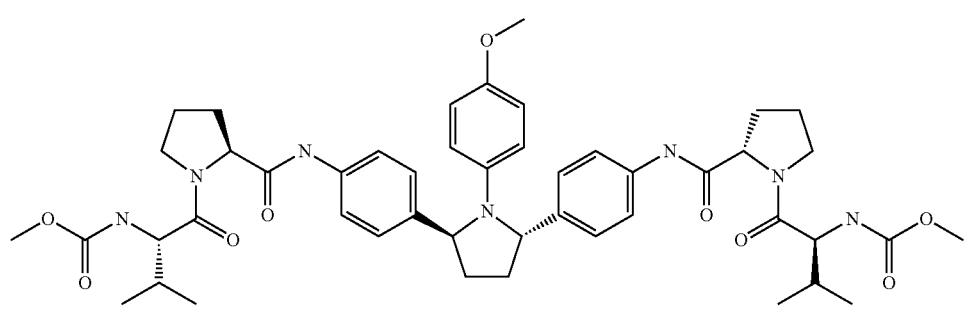

mixture 9
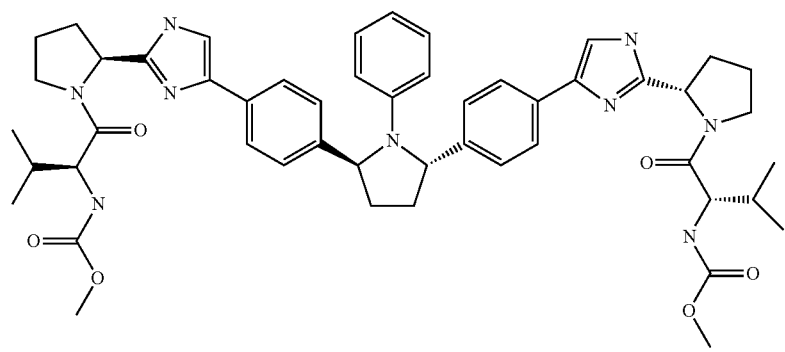
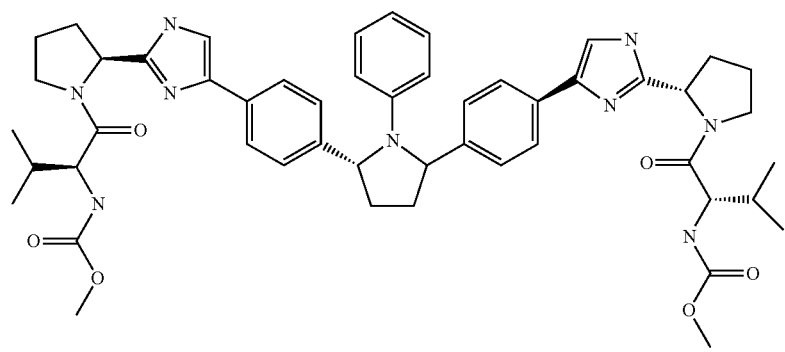
mixture 10
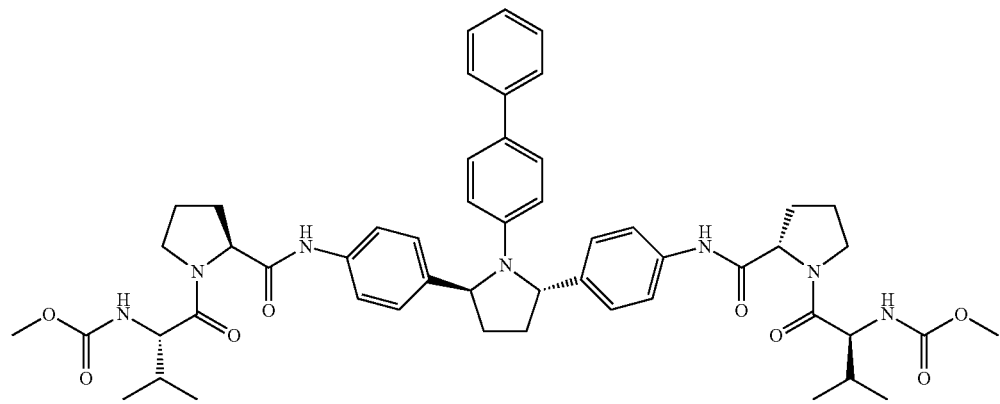
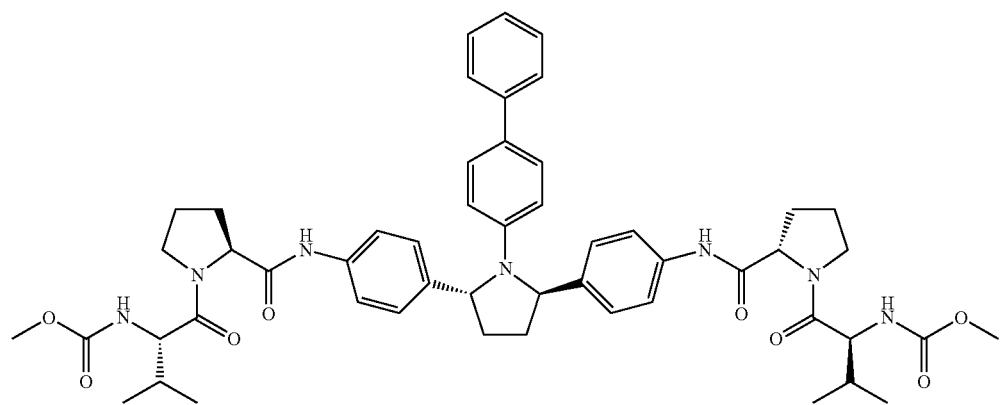

mixture 11
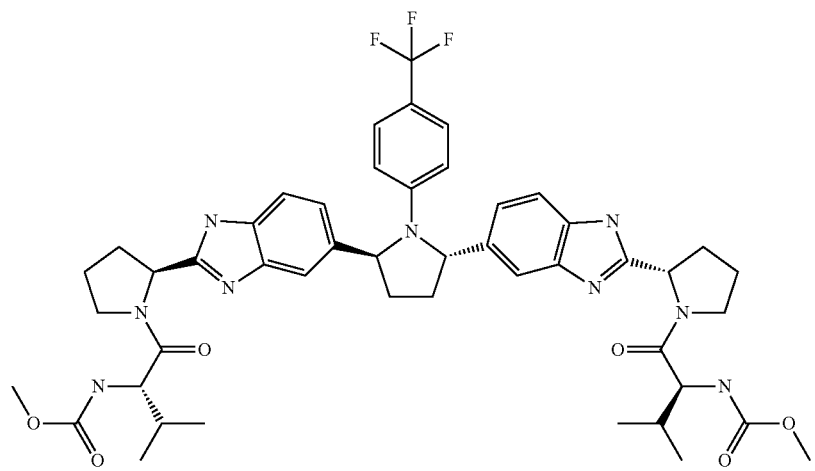
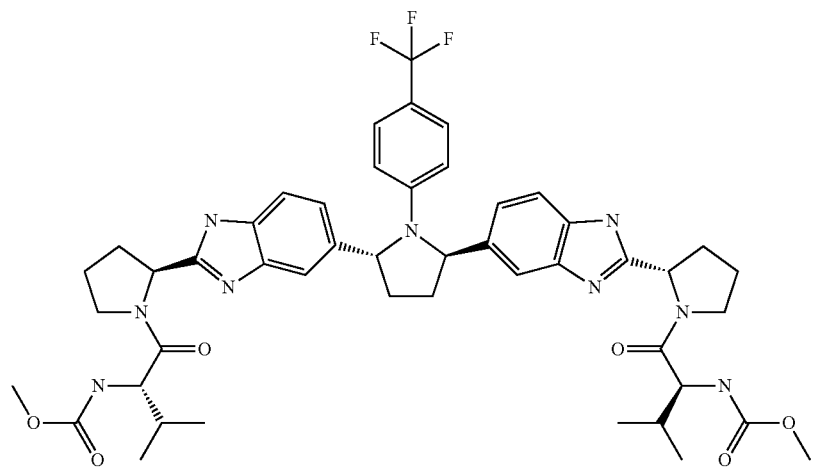
mixture 12
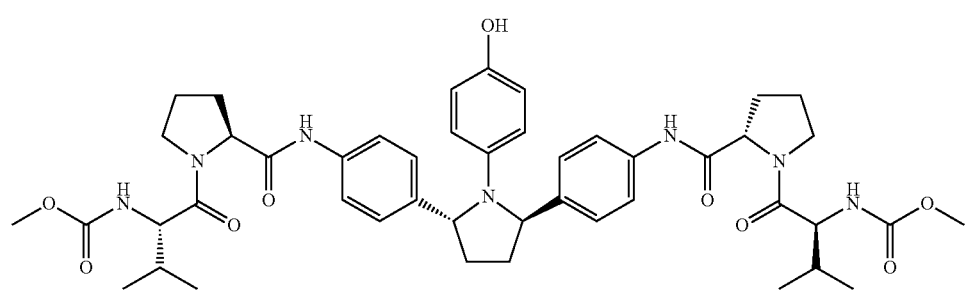
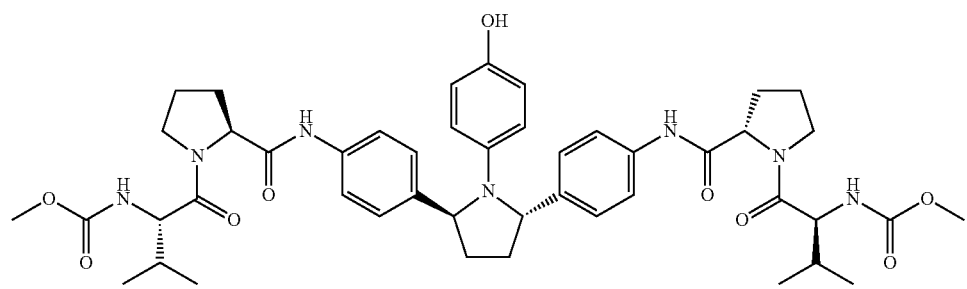

mixture 13
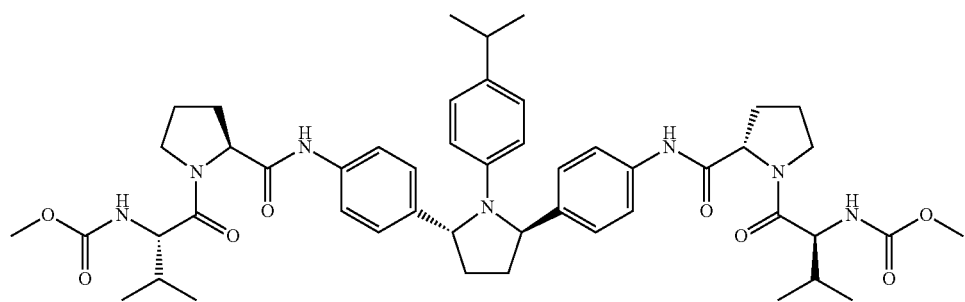
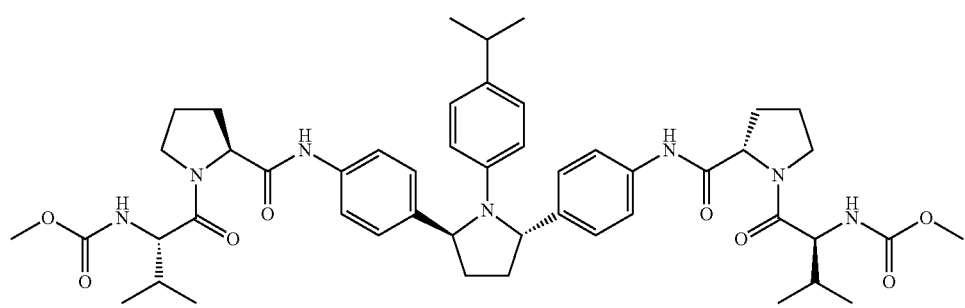
mixture 14
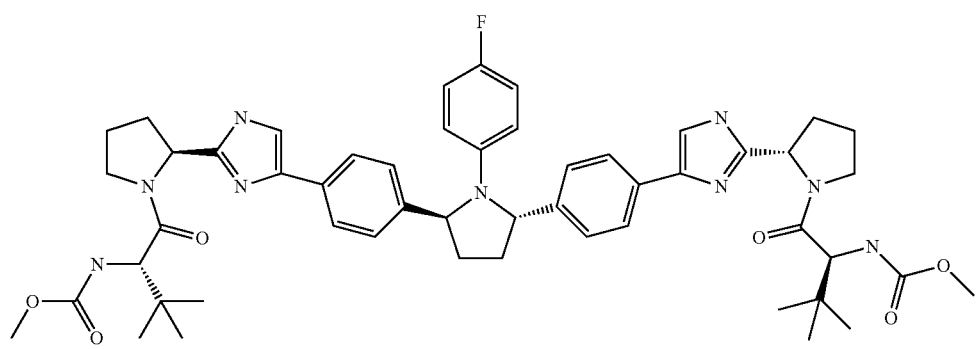
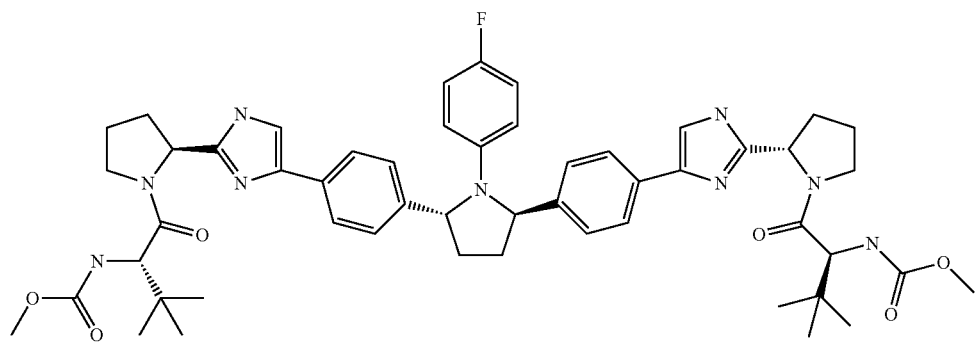

-continued
mixture 15
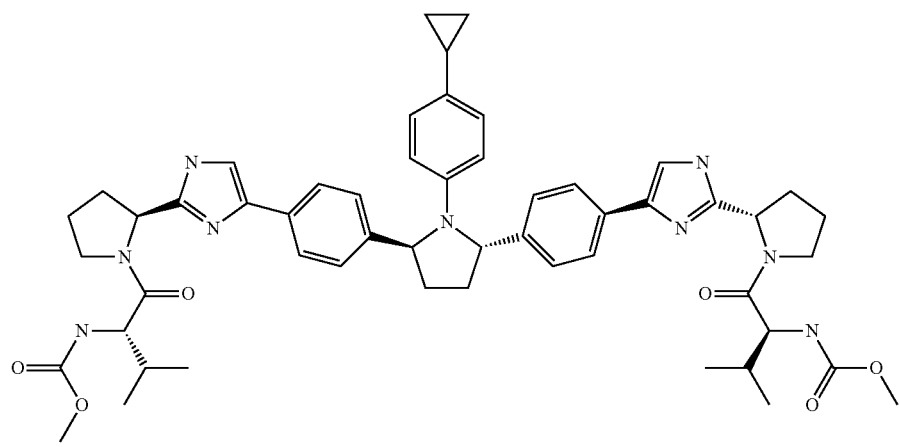
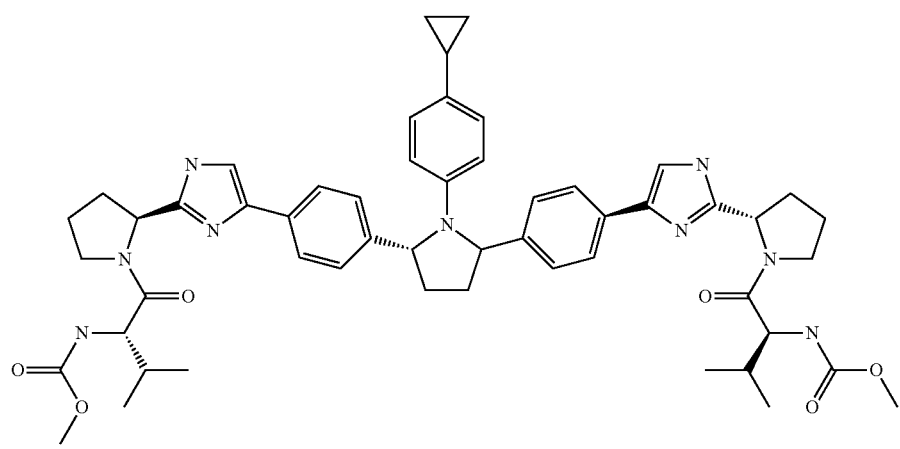
mixture 16
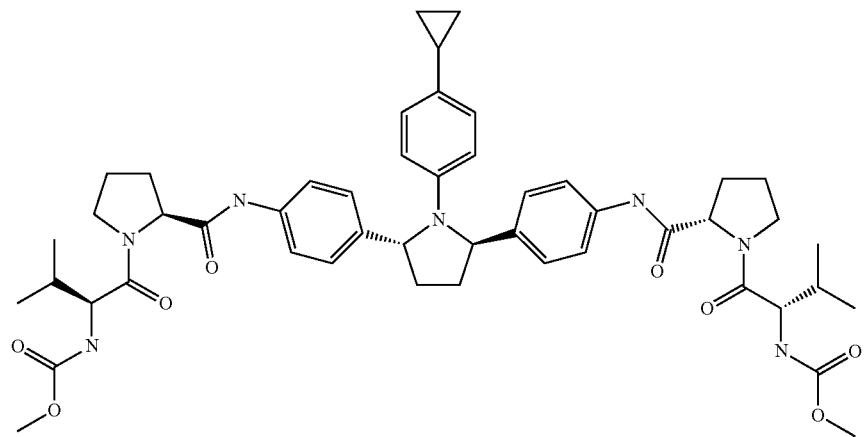

-continued
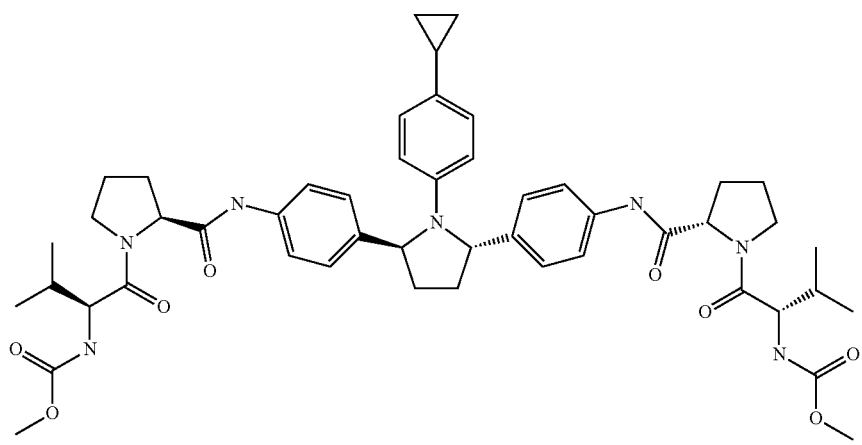
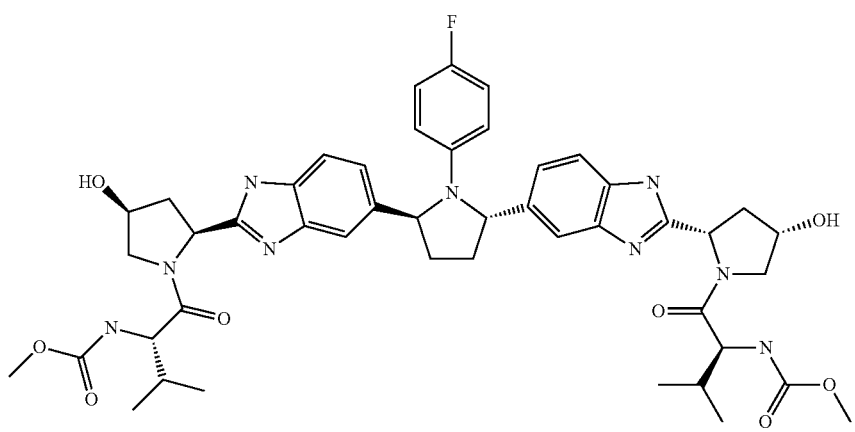
mixture 17
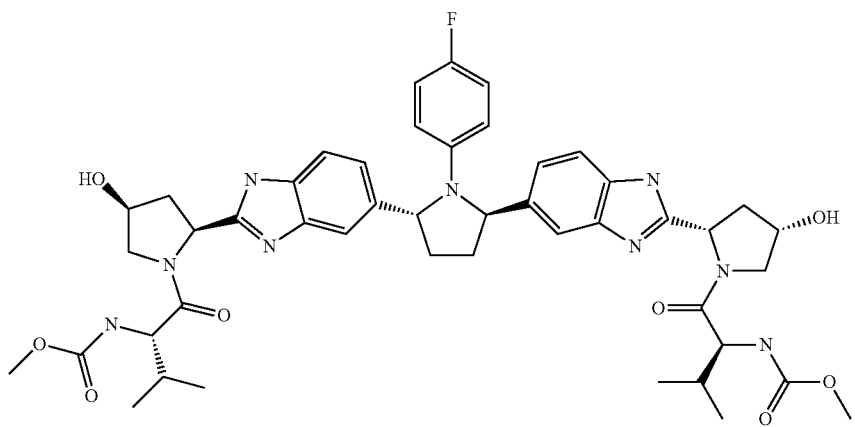

-continued
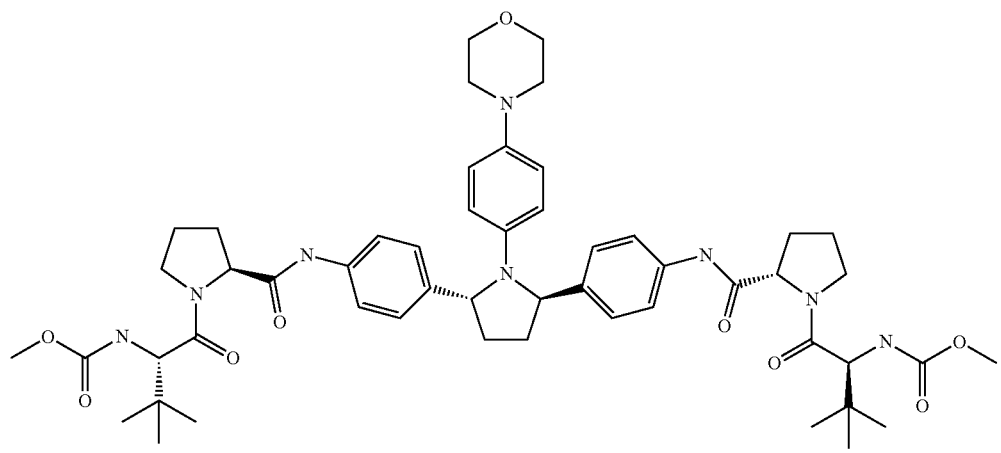
mixture 18
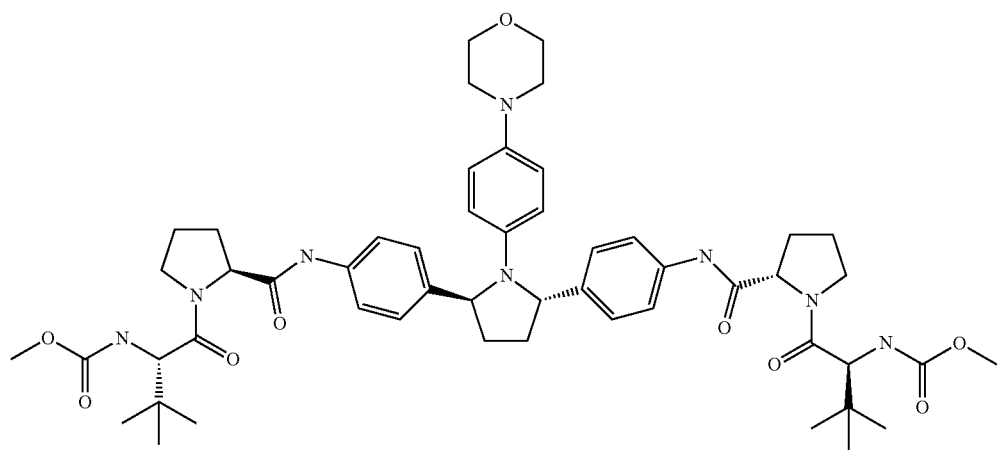
mixture 19
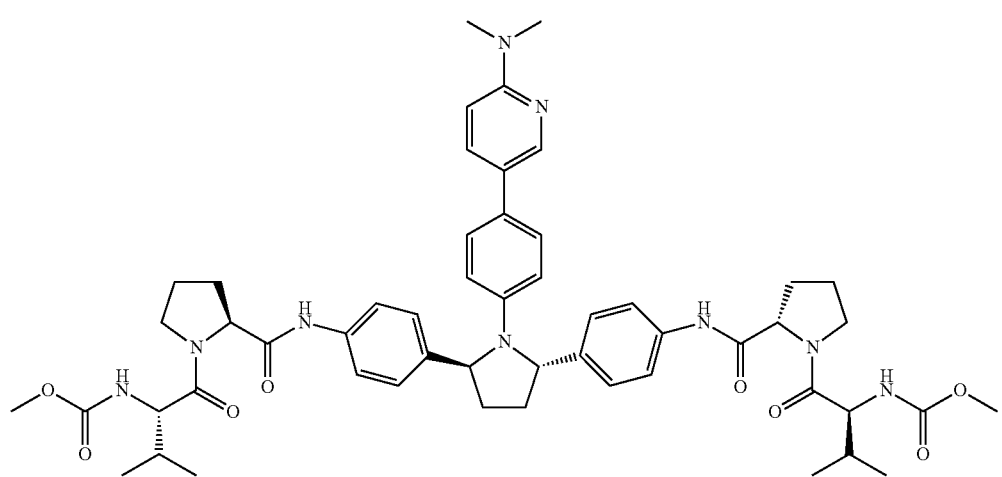

-continued
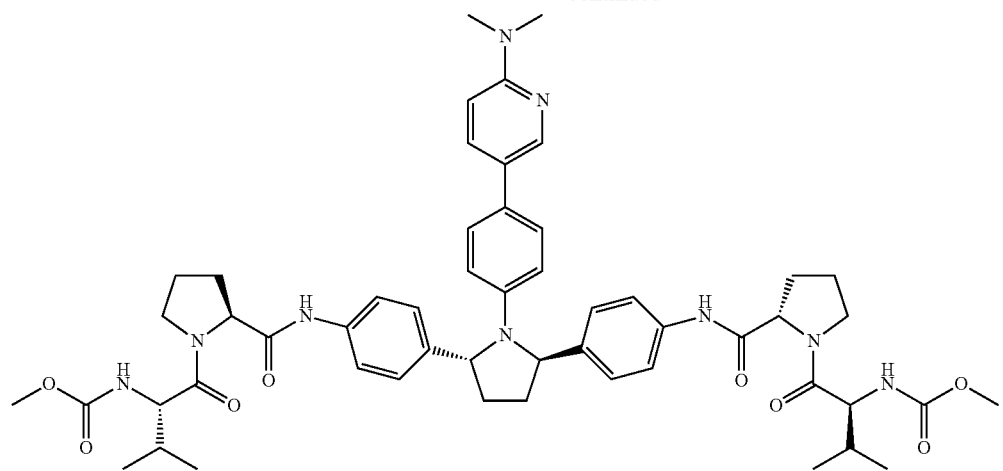
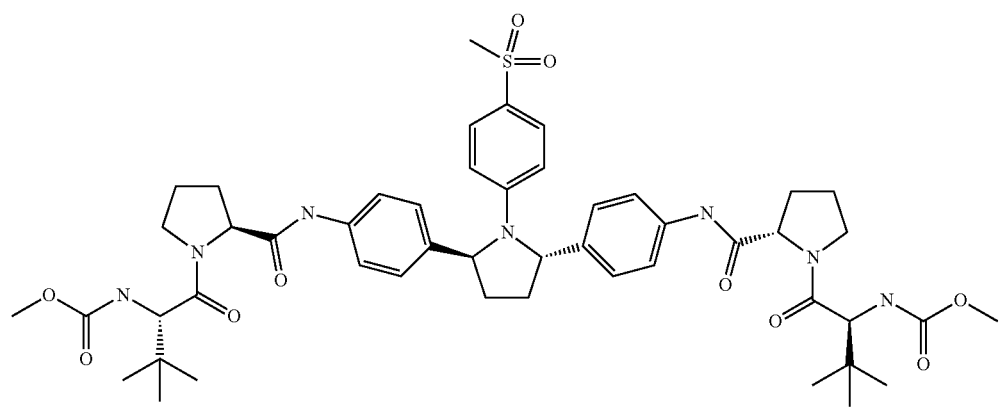
mixture 20
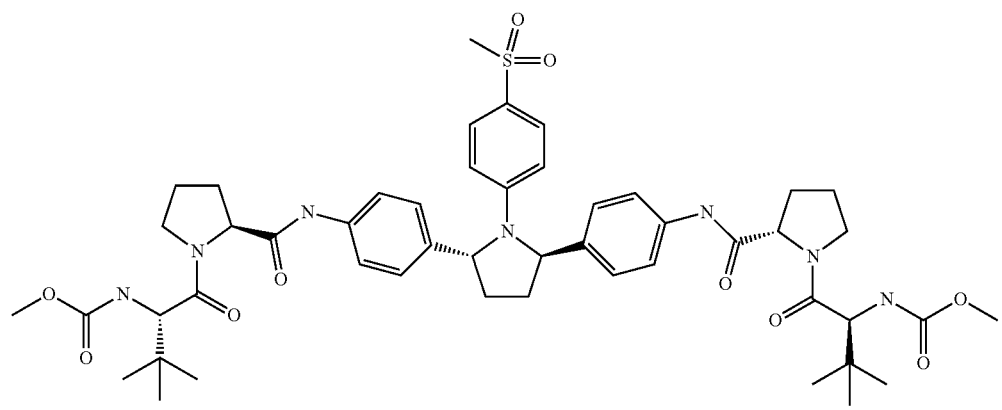

mixture 21
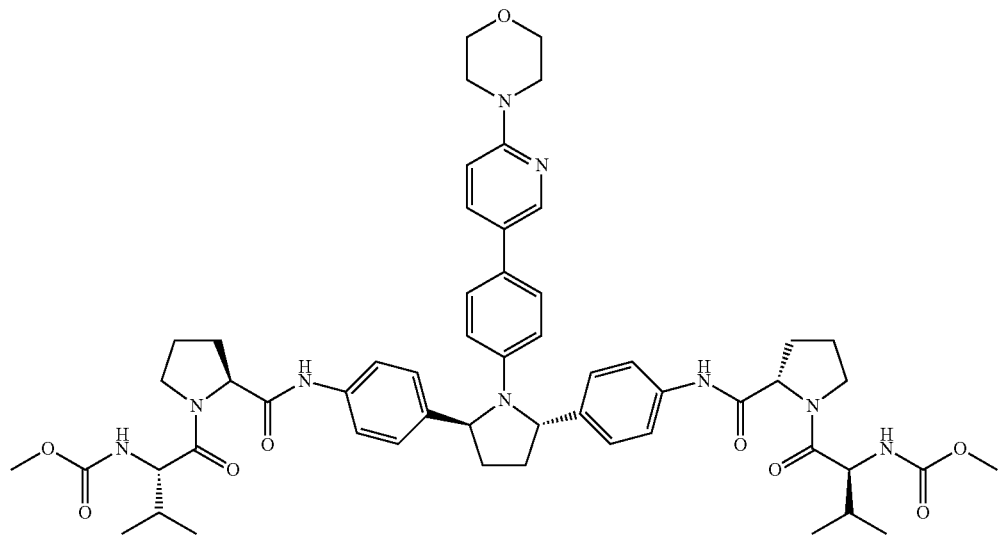
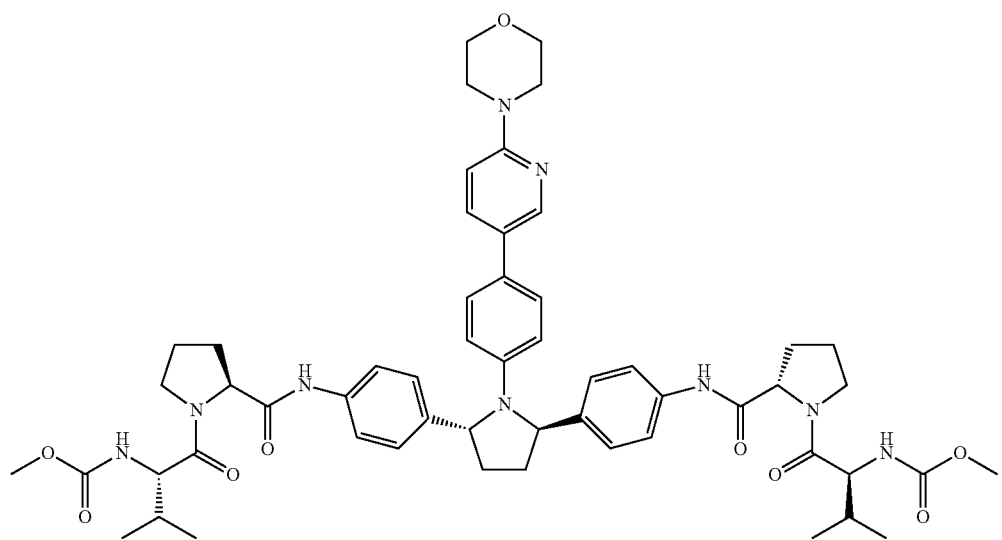
mixture 22
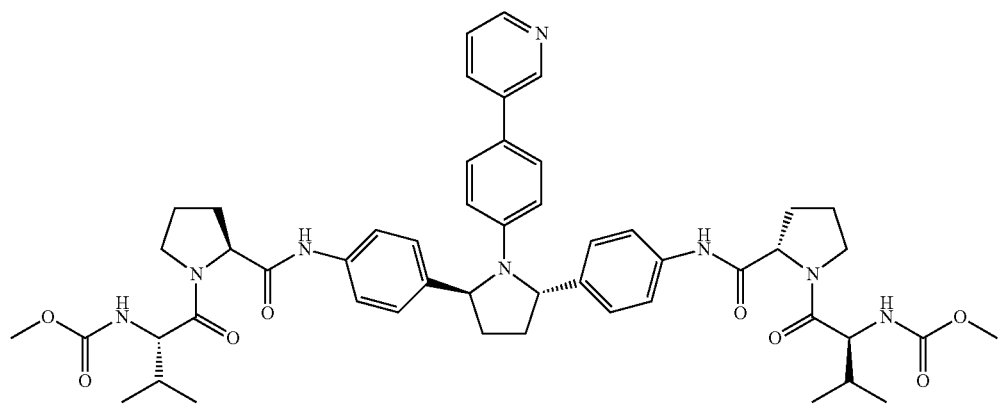

-continued
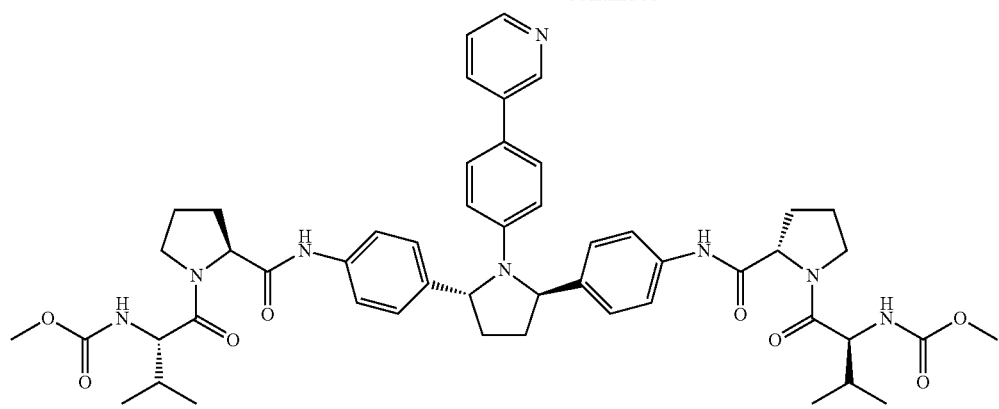
mixture 23
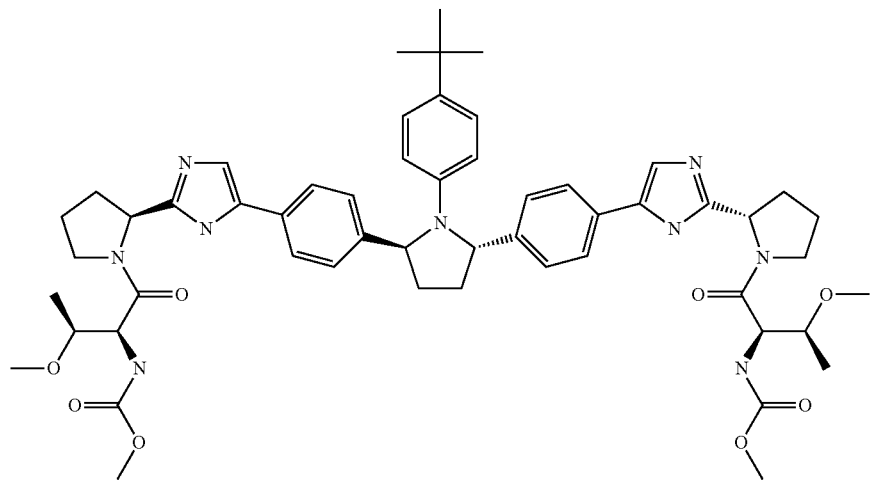
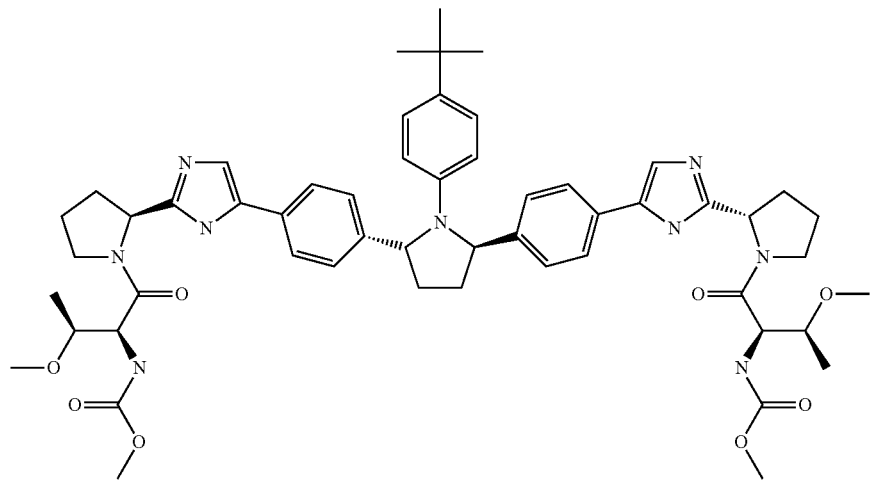

-continued mixture 24

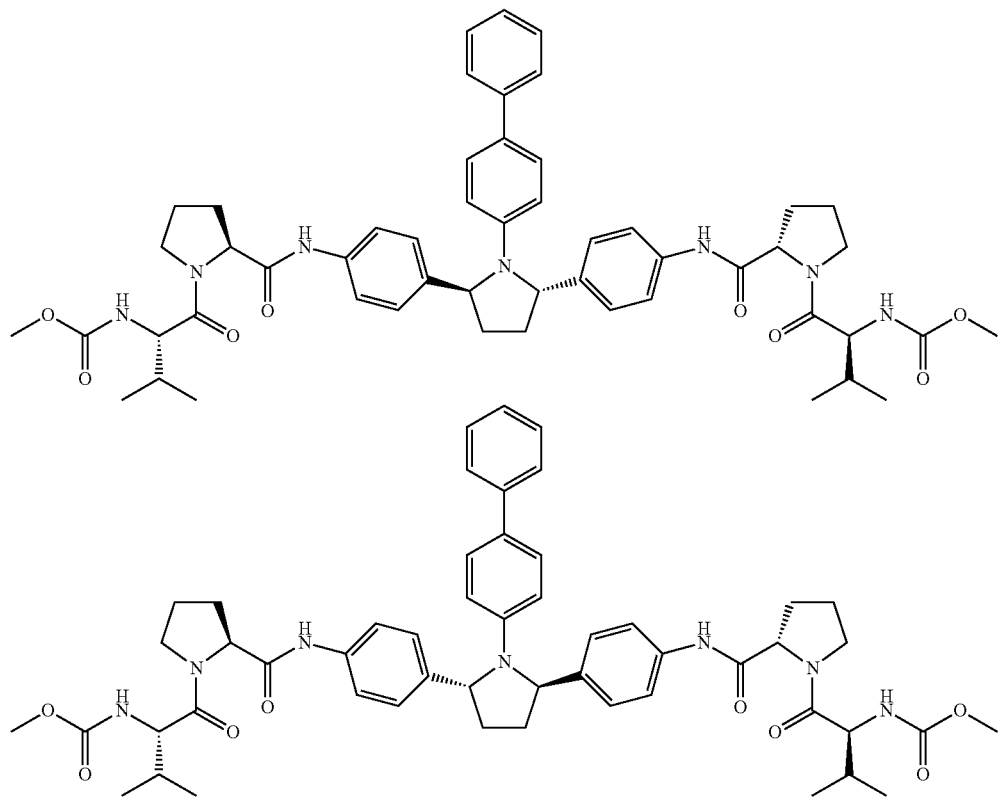

When tested using HCV 1b-Con1 replicon assays in the presence of 5% FBS, each of the above mixtures (except mixture 12) showed an $EC_{50}$ value of less than 1 nM. Mixture 12 showed an $EC_{50}$ value of from about 1 to 10 nM in HCV 1b-Con1 replicon assays in the presence of 5% FBS.

Likewise, the following compounds of Formula I or pharmaceutically acceptable salts thereof can be similarly prepared according to the schemes and procedures described above,

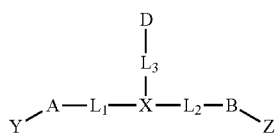

I wherein A is selected from Table 1a, B is selected from Table 1b, D is selected from Table 2, Y and Z are each independently selected from Table 3, and

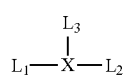

is selected from Table 4, and A, B, D and X are each independently optionally substituted with one or more $R_4$, and wherein $L_1, L_2, L_3$ and $R_4$ are as described above. Preferably, $L_1, L_2$ and $L_3$ are bond.

TABLE 1a

A

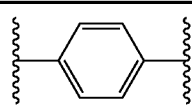

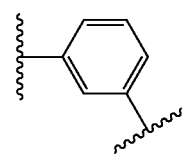

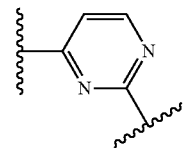 [SMILES: *c1ccnc(*)n1]

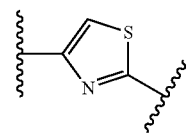 [SMILES: *c1csc(*)n1]

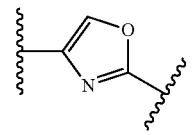

TABLE 1a-continued
A
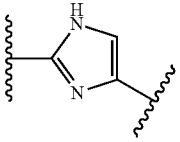 [SMILES: *c1c[nH]c(*)n1]
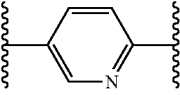
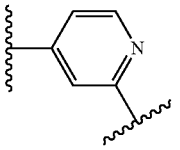 [SMILES: *c1ccnc(*)c1]
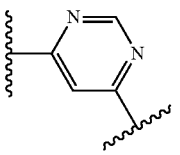 [SMILES: *c1cc(*)ncn1]
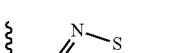
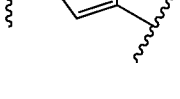
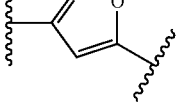
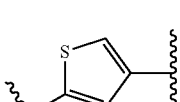
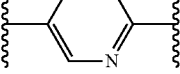
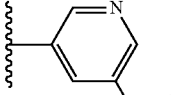
TABLE 1a-continued
A
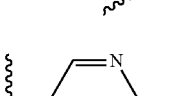
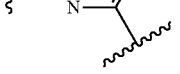
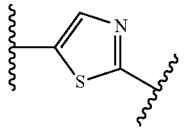 [SMILES: *c1cnc(*)s1]
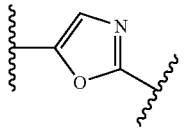 [SMILES: *c1cnc(*)o1]
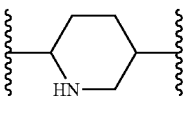
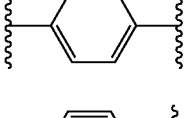
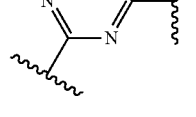
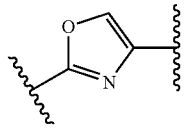
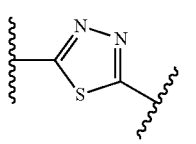 [SMILES: *c1nnc(*)s1]
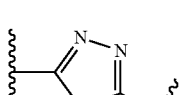
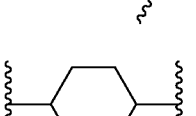
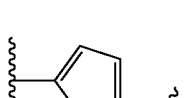

TABLE 1a-continued
A
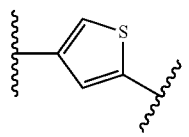 [SMILES: *c1csc(*)c1]
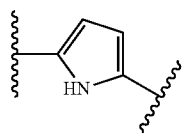 [SMILES: *c1ccc(*)s1]
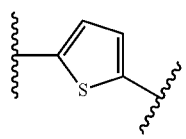
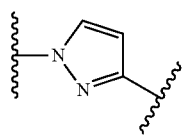
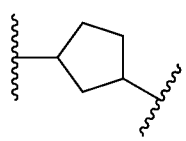 [SMILES: *C1CCC(*)C1]
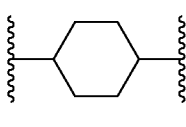
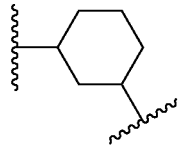 [SMILES: *C1CCCC(*)C1]
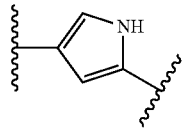
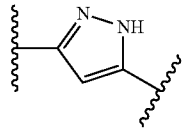
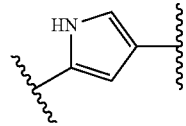 [SMILES: *c1c[nH]c(*)c1]
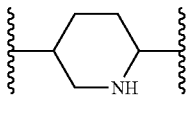
TABLE 1a-continued
A
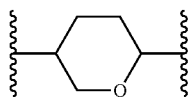
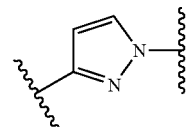 [SMILES: *c1ccn(*)n1]
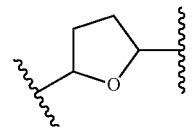
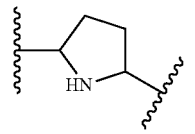 [SMILES: *C1CCC(*)N1]
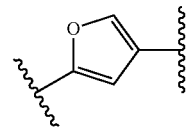 [SMILES: *c1coc(*)c1]
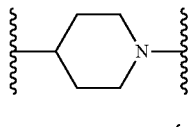
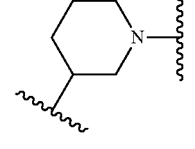
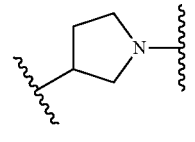
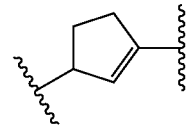 [SMILES: *C1=CC(*)CC1]
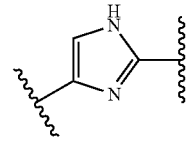 [SMILES: *c1c[nH]c(*)n1]

TABLE 1a-continued

TABLE 1a-continued
A
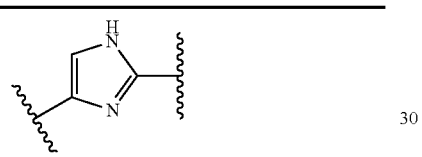
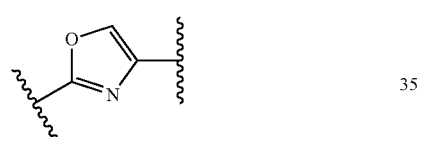
TABLE 1b
B
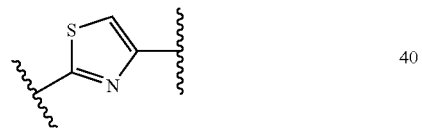
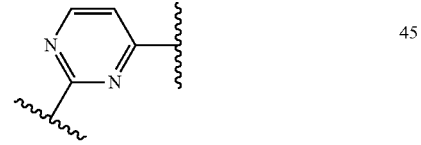
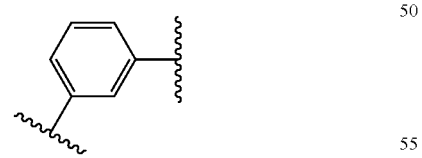
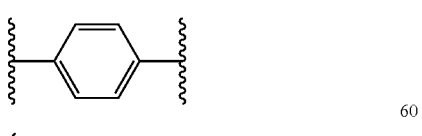
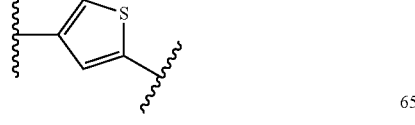
TABLE 1b-continued
B
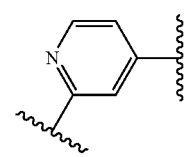 [SMILES: *c1ccnc(*)c1]
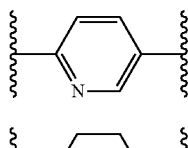
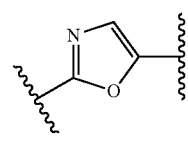
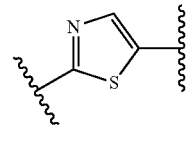
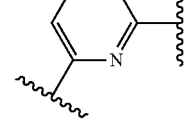
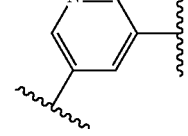
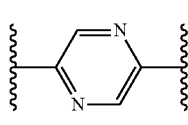

US 9,006,387 B2
| 581 | | 582 | |
|---|---|---|---|
| TABLE 1b-continued | | TABLE 1b-continued | |
| B | | B | |
| 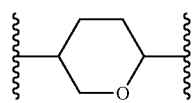 | 5 | 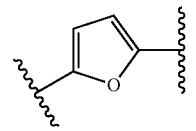 | |
| 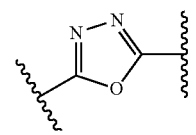 [SMILES: *c1nnc(*)o1] | 10 | 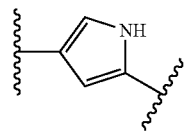 | |
| 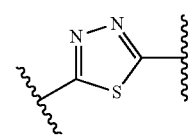 [SMILES: *c1nnc(*)s1] | 15 | 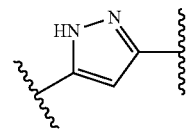 | |
| 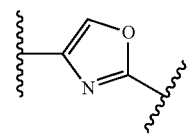 [SMILES: *c1coc(*)n1] | 20 | 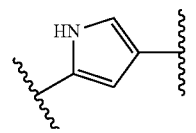 | |
| 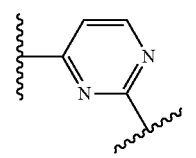 [SMILES: *c1ccnc(*)n1] | 25 | 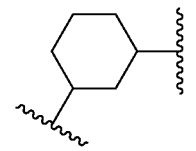 [SMILES: *C1CCCC(*)C1] | |
| 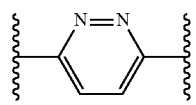 | 30 | 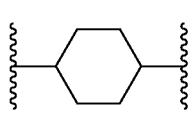 | |
| 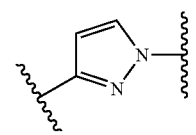 | 35 | 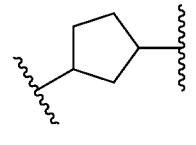 [SMILES: *C1CCC(*)C1] | |
| 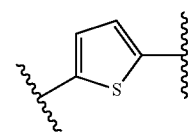 | 40 | 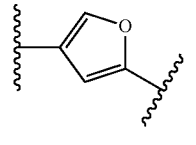 [SMILES: *c1coc(*)c1] | |
| 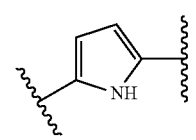 | 45 | 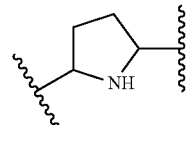 [SMILES: *C1CCC(*)N1] | |
| 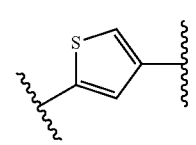 | 50 | 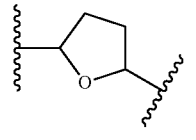 [SMILES: *C1CCC(*)O1] | |
| 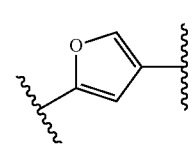 | 55 | 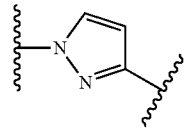 [SMILES: *c1ccn(*)n1] | |
| | 60 | | |
| | 65 | | |

TABLE 1b-continued

TABLE 1b-continued
B
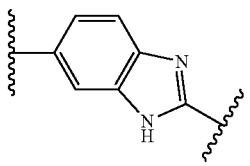 [SMILES: *c1ccc2nc(*)[nH]c2c1]
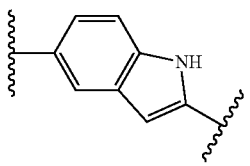 [SMILES: *c1ccc2[nH]c(*)cc2c1]
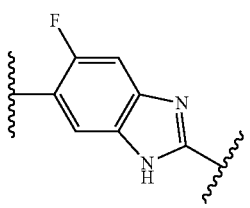 [SMILES: *c1nc2cc(F)c(*)cc2[nH]1]
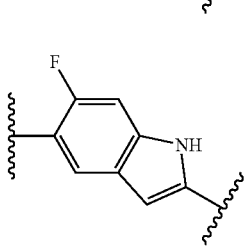
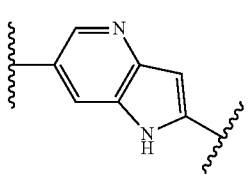 [SMILES: *c1cnc2cc(*)[nH]c2c1]
TABLE 1b-continued
B
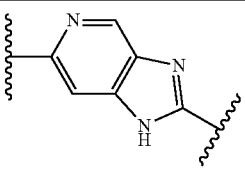
TABLE 2
D
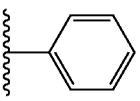 [SMILES: *c1ccccc1]
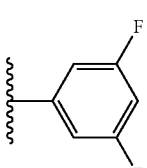
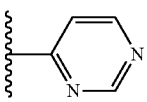
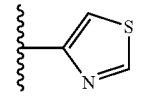
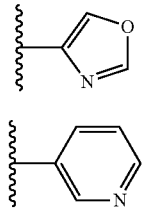
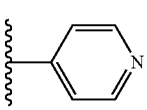 [SMILES: *c1ccncc1]
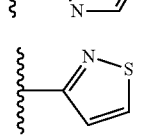
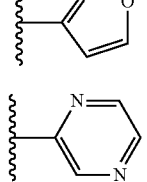
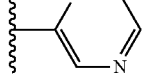

TABLE 2-continued
| D |
|---|
| 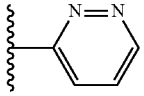 |
| 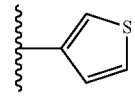 |
| 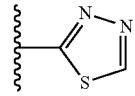 |
| 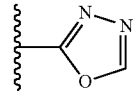 |
| 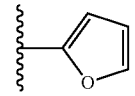 [SMILES: *c1ccco1] |
| 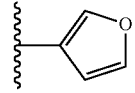 |
| 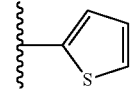 |
| 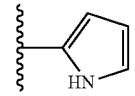 |
| 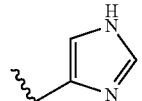 |
|  |
| 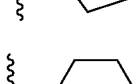 |
| 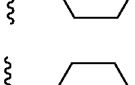 |
| 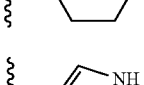 |
| 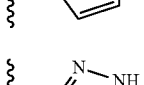 |
TABLE 2-continued
| D |
|---|
| 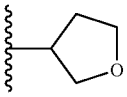 |
| 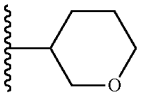 |
| 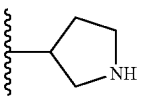 |
| 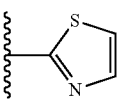 |
| 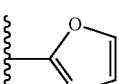 |
| 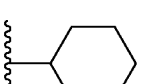 |
| 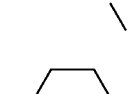 |
| 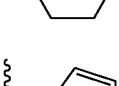 |
| 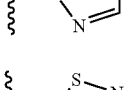 |
| 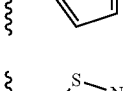 |
| 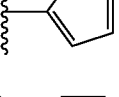 |
| 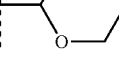 |
| 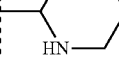 |

TABLE 2-continued
D
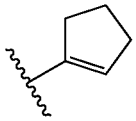 [SMILES: *C1=CCCC1]
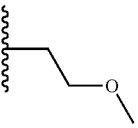 [SMILES: *CCOC]
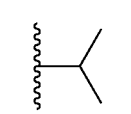
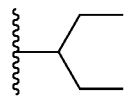
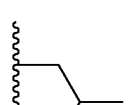
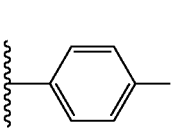
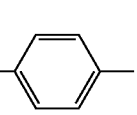
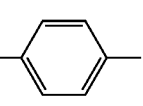
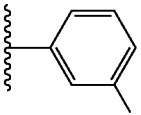
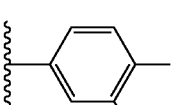
TABLE 3
Y and Z
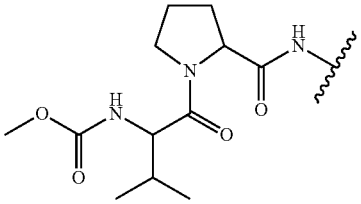 [SMILES: *NC(=O)C1CCCN1C(=O)C(NC(=O)OC)C(C)C]
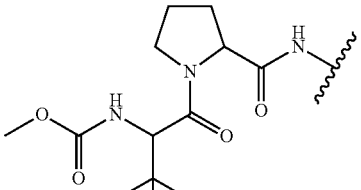
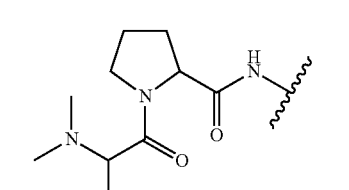
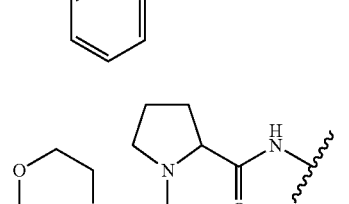
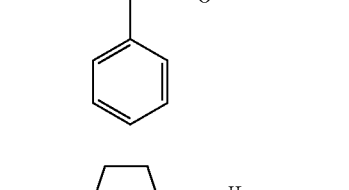
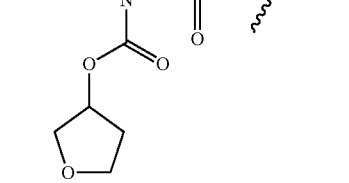
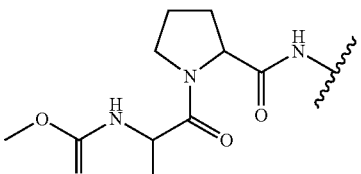
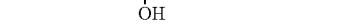

TABLE 3-continued
Y and Z
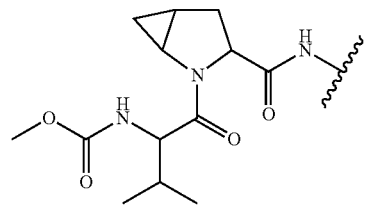 [SMILES: *NC(=O)C1CC2CC2N1C(=O)C(NC(=O)OC)C(C)C]
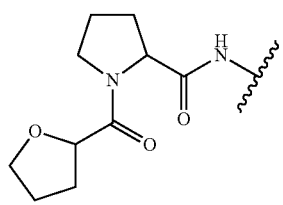 [SMILES: *NC(=O)C1CCCN1C(=O)C1CCCO1]
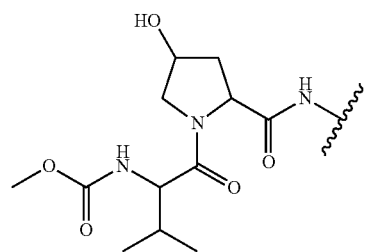 [SMILES: *NC(=O)C1CC(O)CN1C(=O)C(NC(=O)OC)C(C)C]
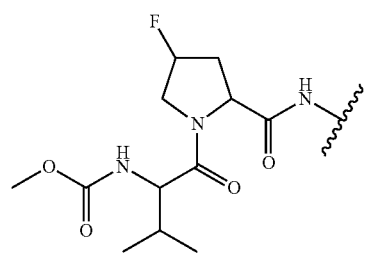 [SMILES: *NC(=O)C1CC(F)CN1C(=O)C(NC(=O)OC)C(C)C]
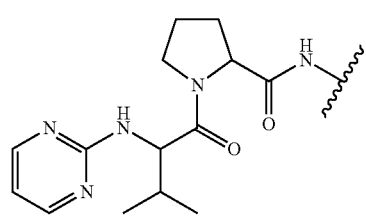 [SMILES: *NC(=O)C1CCCN1C(=O)C(Nc1ncccn1)C(C)C]
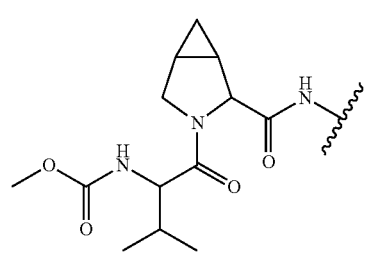 [SMILES: *NC(=O)C1C2CC2CN1C(=O)C(NC(=O)OC)C(C)C]
TABLE 3-continued
Y and Z
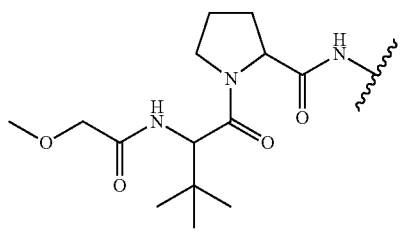 [SMILES: *NC(=O)C1CCCN1C(=O)C(NC(=O)COC)C(C)(C)C]
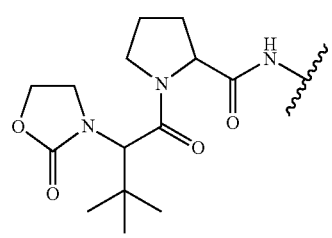 [SMILES: *NC(=O)C1CCCN1C(=O)C(N1CCOC1=O)C(C)(C)C]
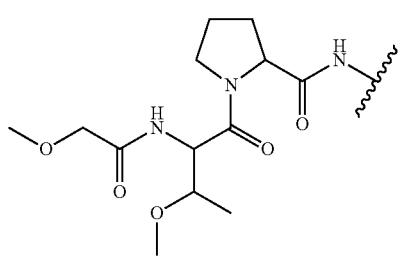 [SMILES: *NC(=O)C1CCCN1C(=O)C(NC(=O)COC)C(C)OC]
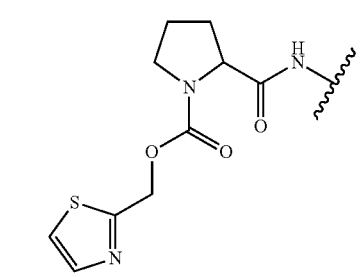 [SMILES: *NC(=O)C1CCCN1C(=O)OCc1nccs1]
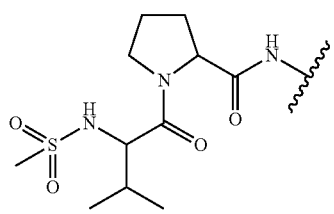 [SMILES: *NC(=O)C1CCCN1C(=O)C(NS(C)(=O)=O)C(C)C]
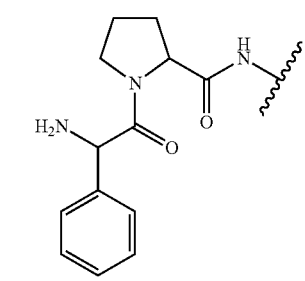 [SMILES: *NC(=O)C1CCCN1C(=O)C(N)c1ccccc1]

593
TABLE 3-continued
Y and Z
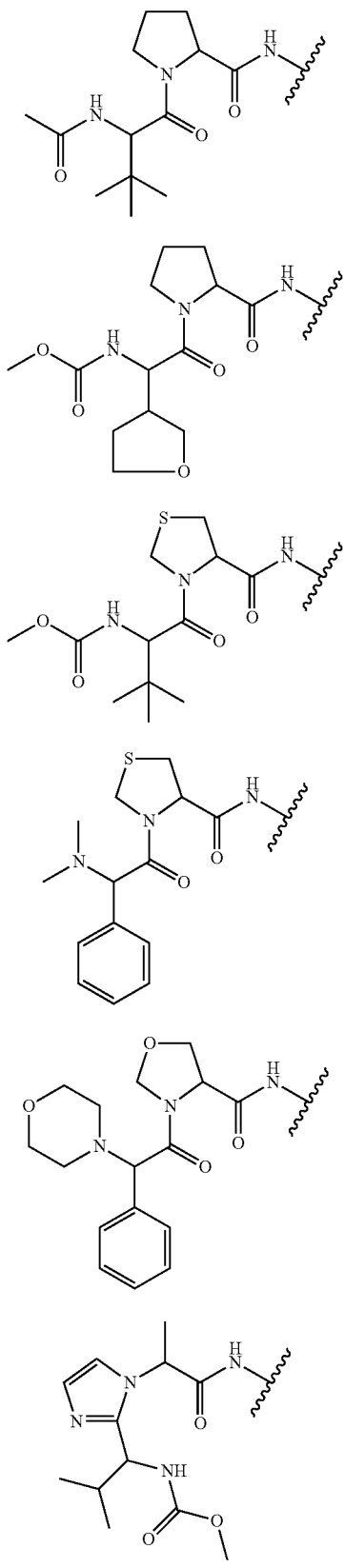
594
TABLE 3-continued
Y and Z
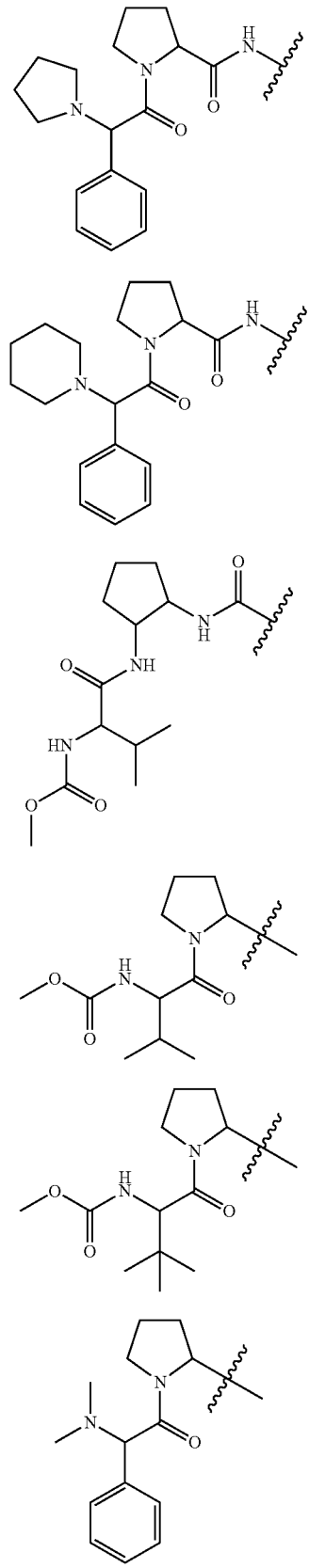

TABLE 3-continued

Y and Z

TABLE 3-continued

Y and Z

TABLE 3-continued
Y and Z
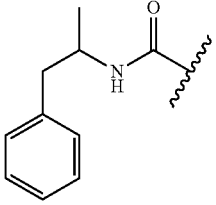 [SMILES: *C(=O)NC(C)Cc1ccccc1]
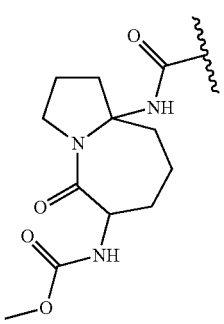 [SMILES: *C(=O)NC12CCCC(NC(=O)OC)C(=O)N1CCC2]
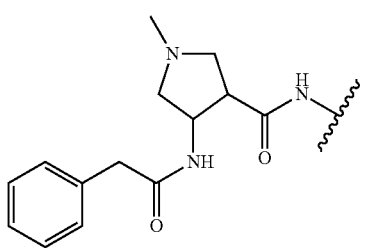 [SMILES: *NC(=O)C1CN(C)CC1NC(=O)Cc1ccccc1]
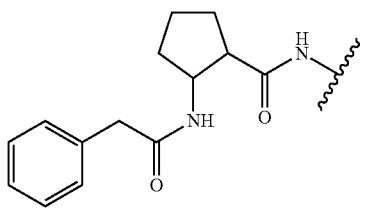 [SMILES: *NC(=O)C1CCCC1NC(=O)Cc1ccccc1]
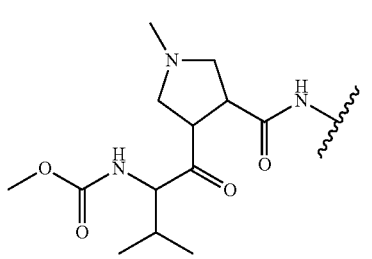 [SMILES: *NC(=O)C1CN(C)CC1C(=O)C(NC(=O)OC)C(C)C]
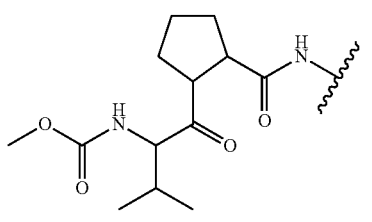 [SMILES: *NC(=O)C1CCCC1C(=O)C(NC(=O)OC)C(C)C]
TABLE 3-continued
Y and Z
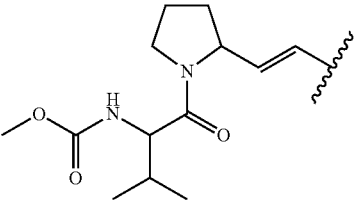 [SMILES: */C=C/C1CCCN1C(=O)C(NC(=O)OC)C(C)C]
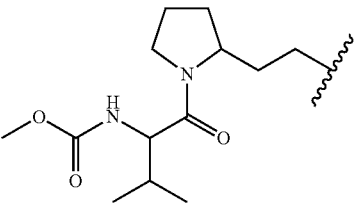 [SMILES: *CCC1CCCN1C(=O)C(NC(=O)OC)C(C)C]
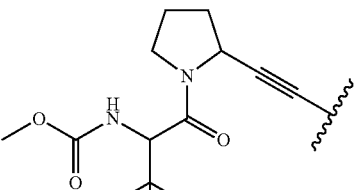
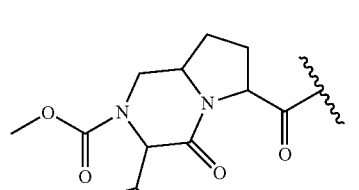
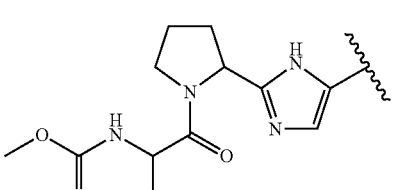
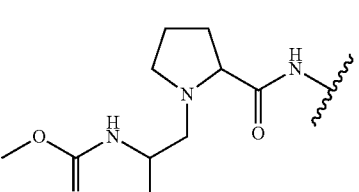
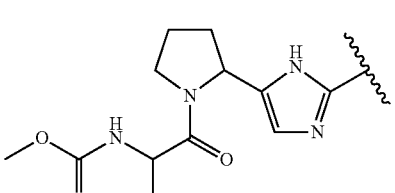

TABLE 4
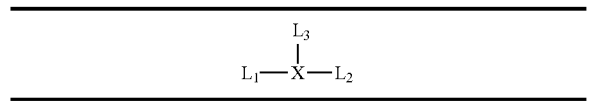
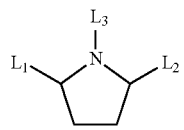
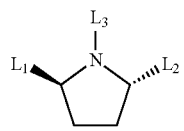
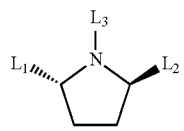
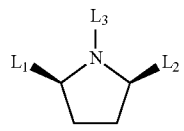
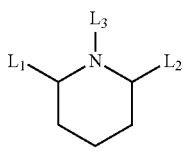
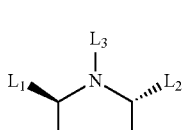
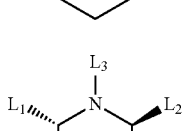
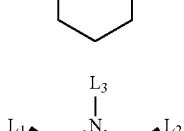
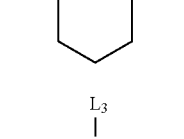
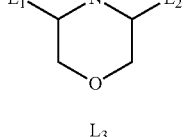
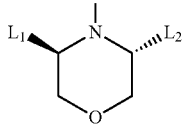
TABLE 4-continued
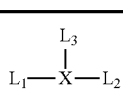
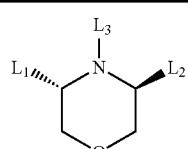
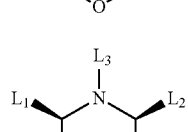
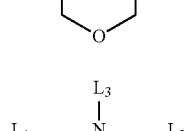
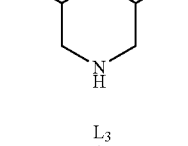
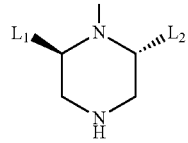
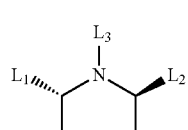
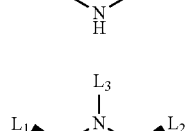
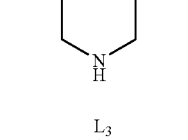
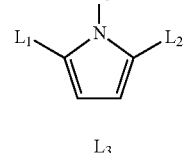
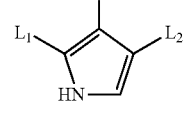
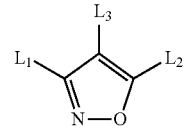

603
TABLE 4-continued
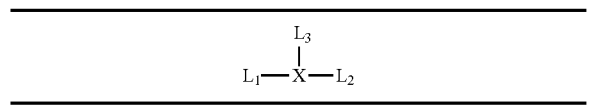
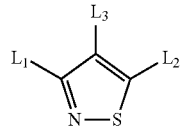
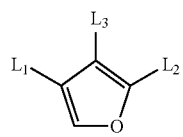
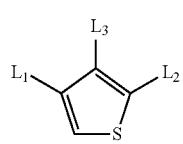
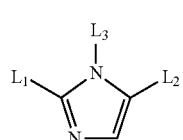
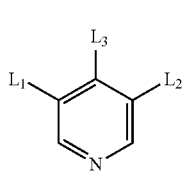
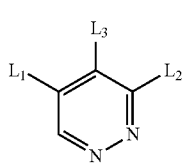
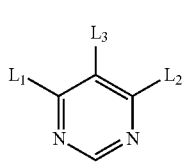
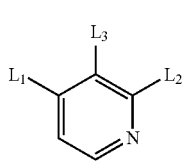
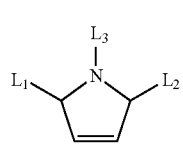
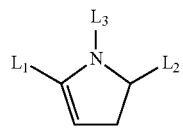
604
TABLE 4-continued
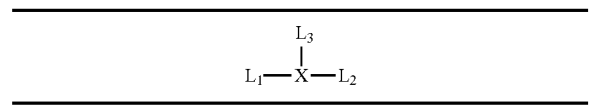
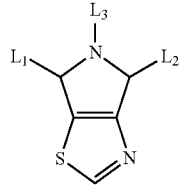
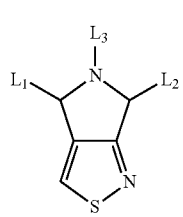
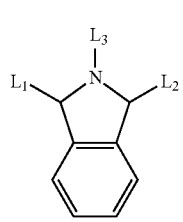
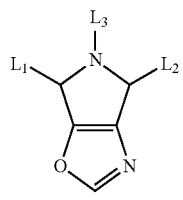
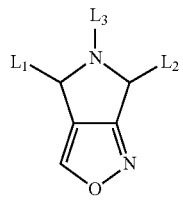
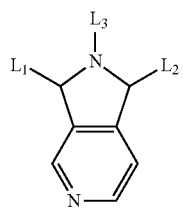
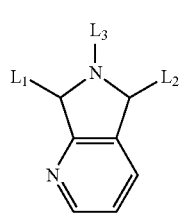
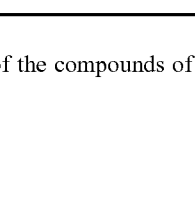
Other examples of the compounds of Formula I are provided in Table 5.

TABLE 5
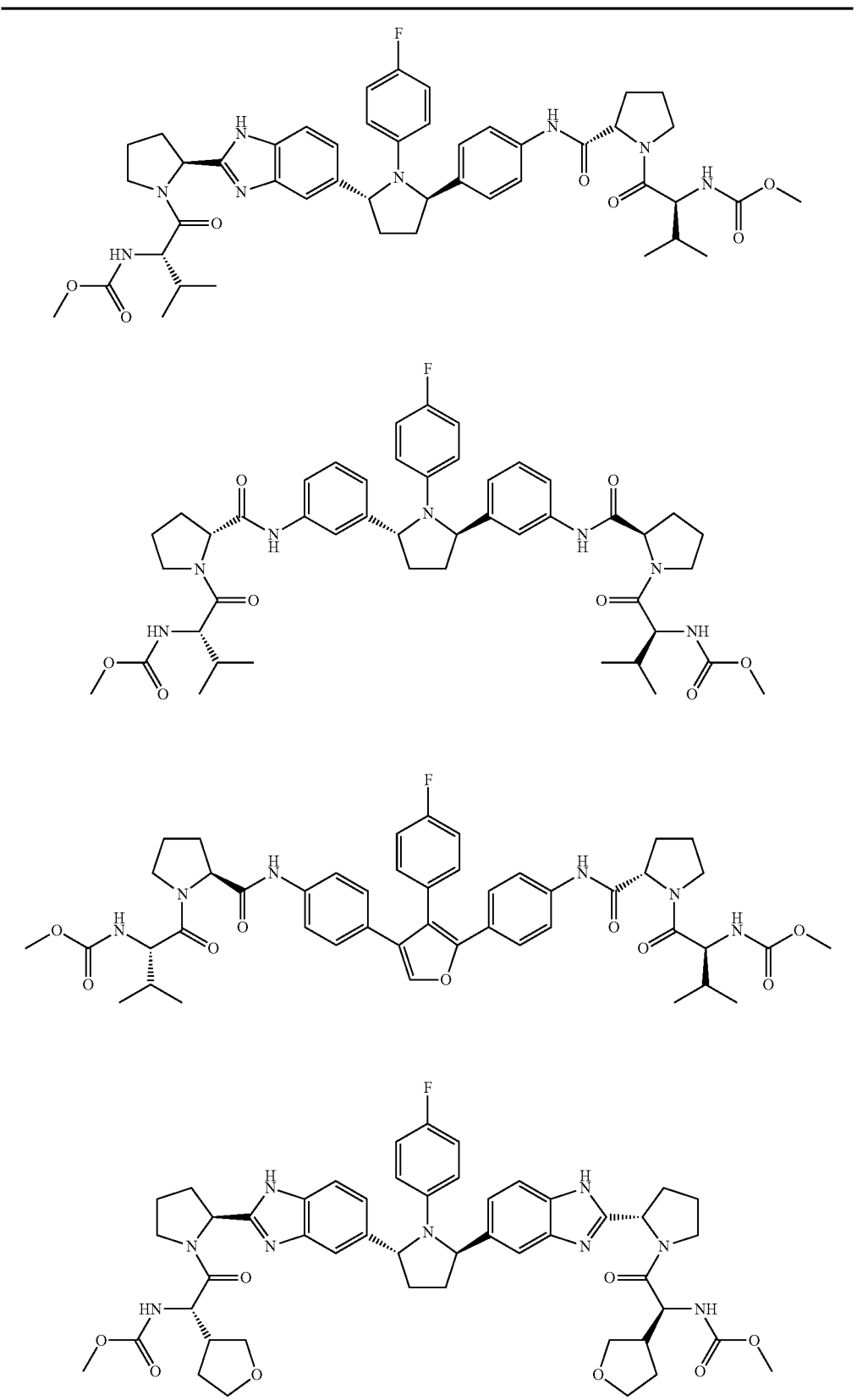

TABLE 5-continued
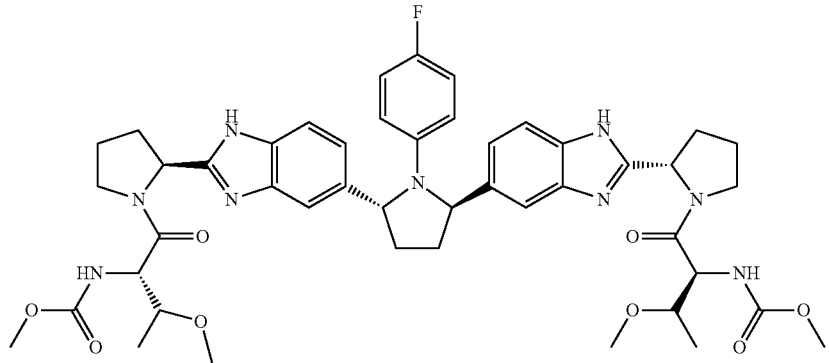
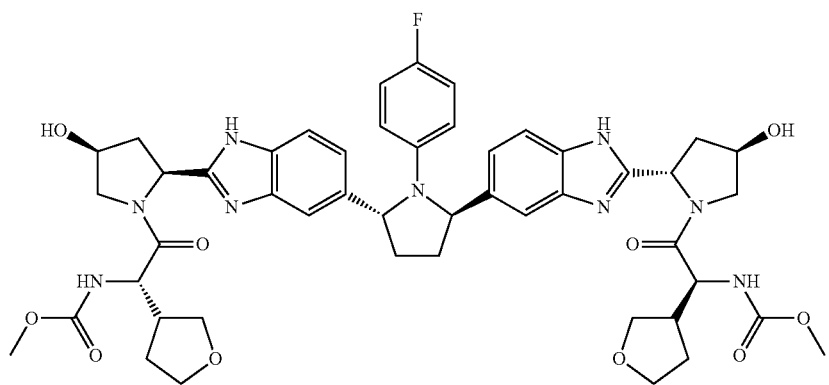
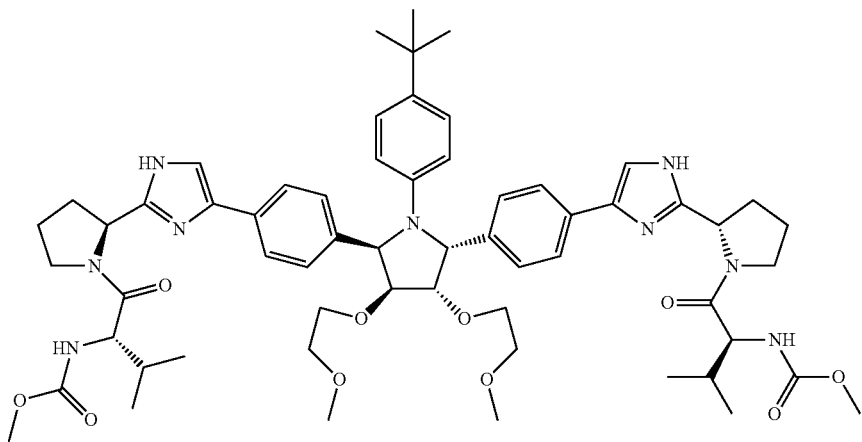

TABLE 5-continued
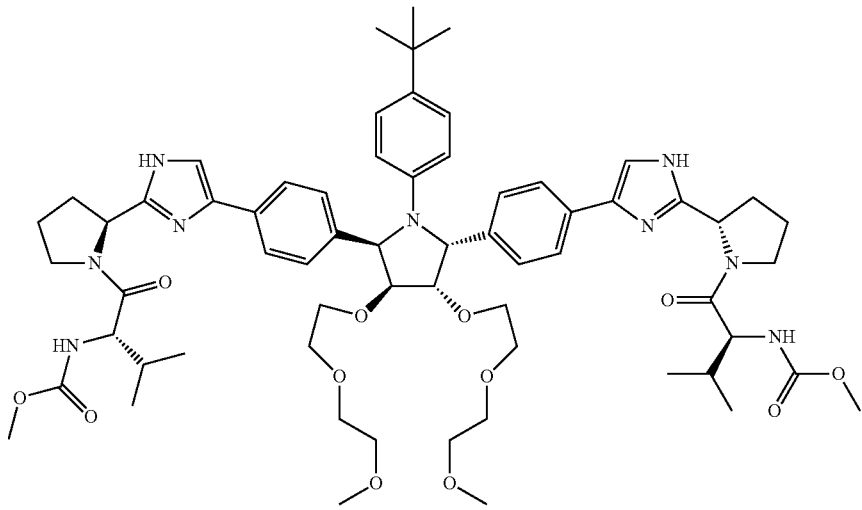
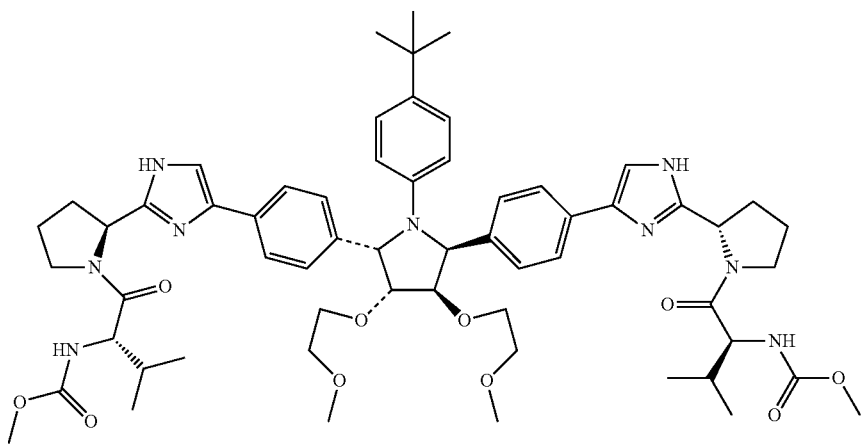
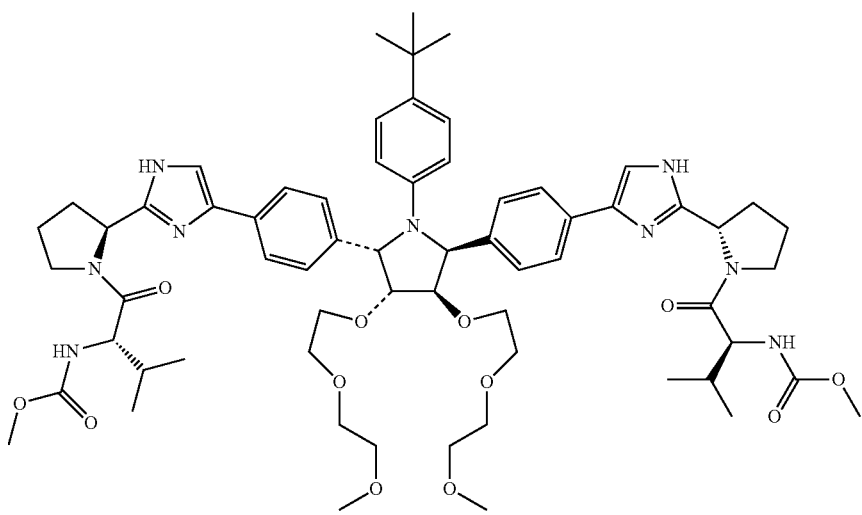

TABLE 5-continued
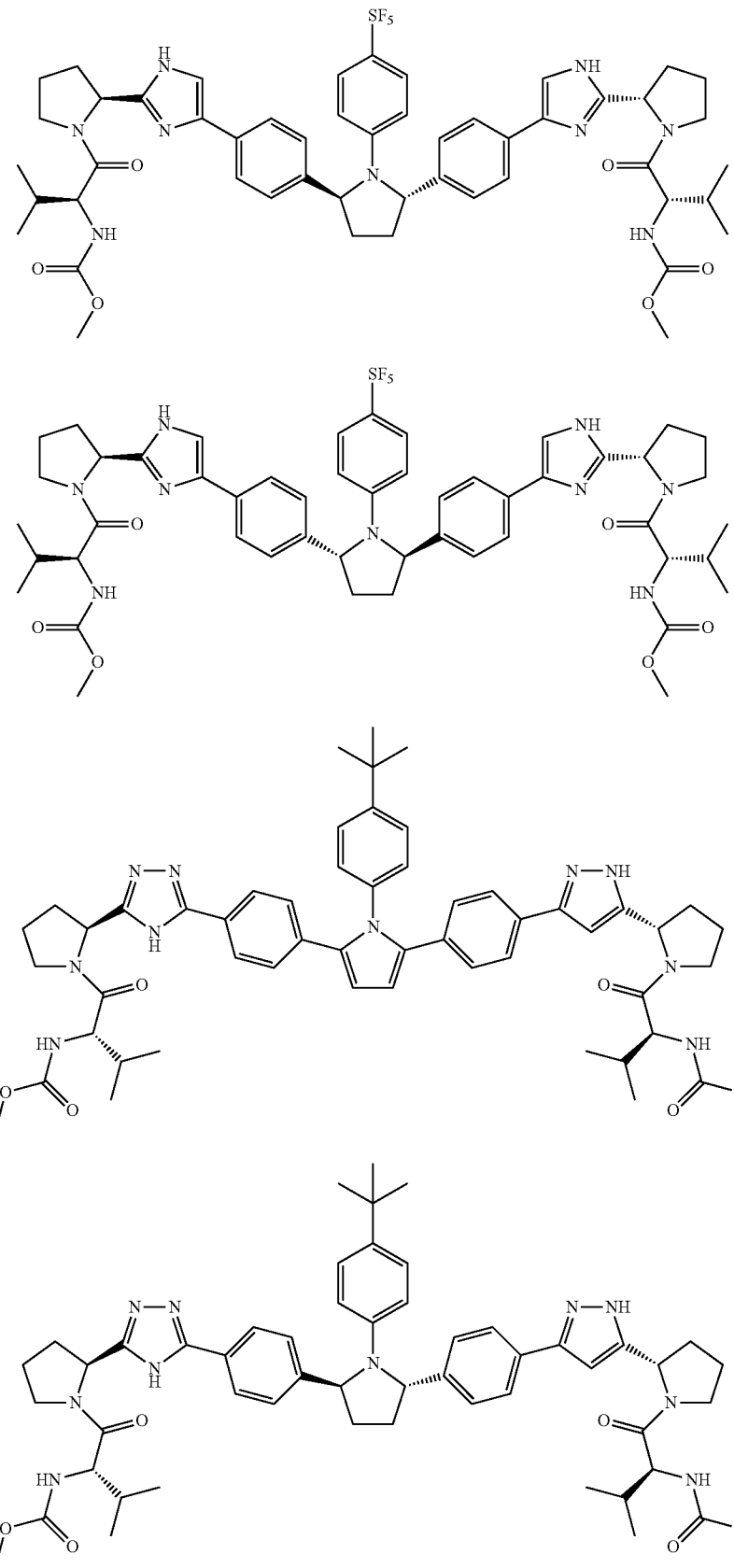

TABLE 5-continued
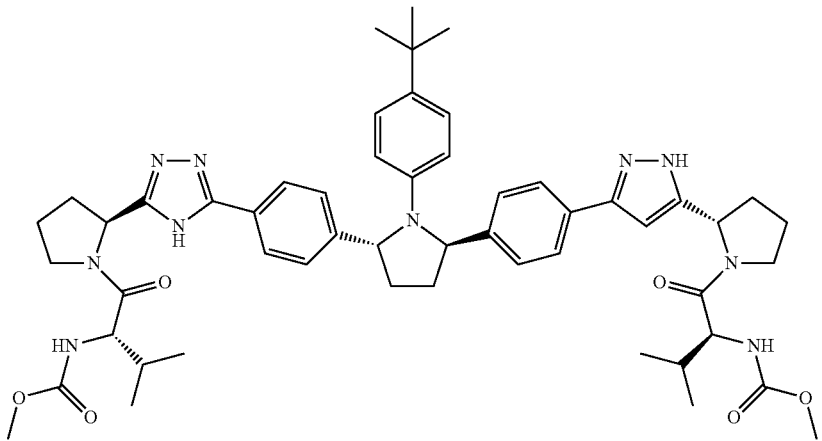
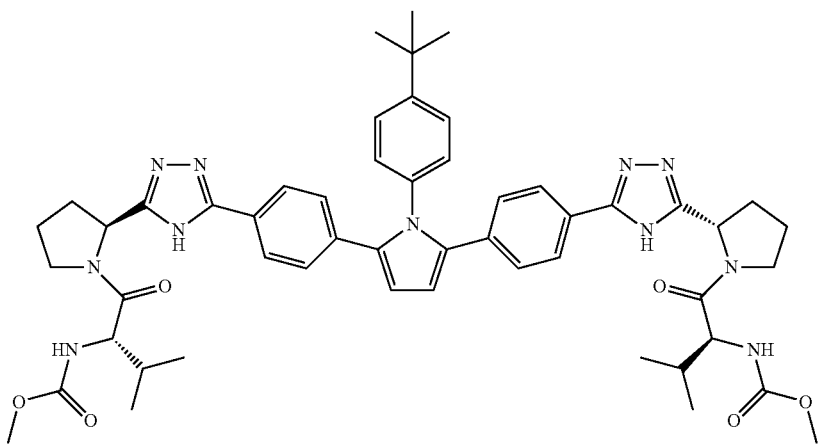
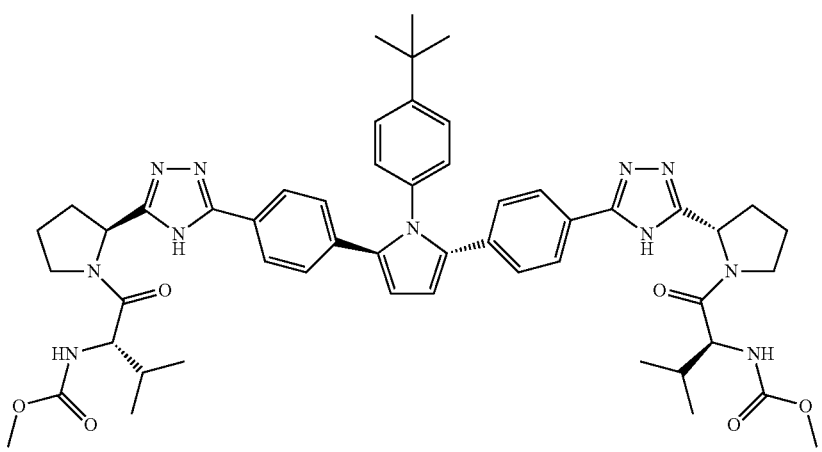

TABLE 5-continued
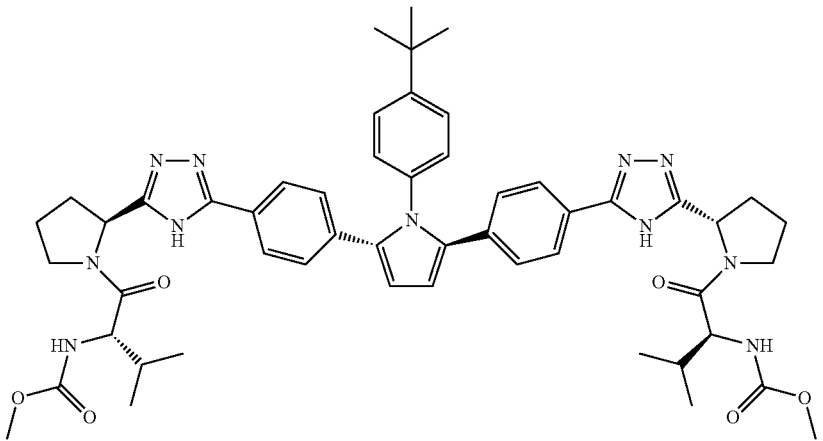
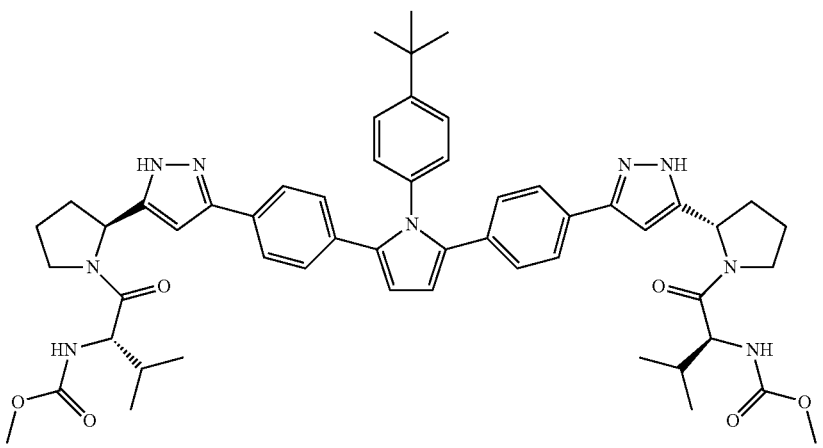
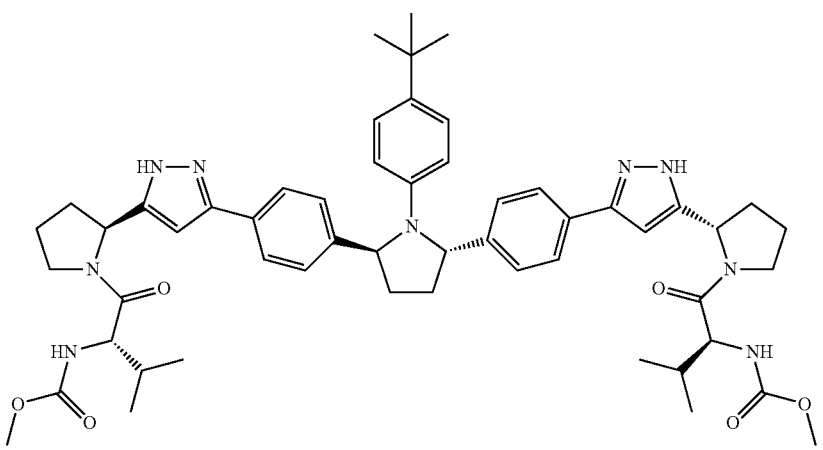

TABLE 5-continued
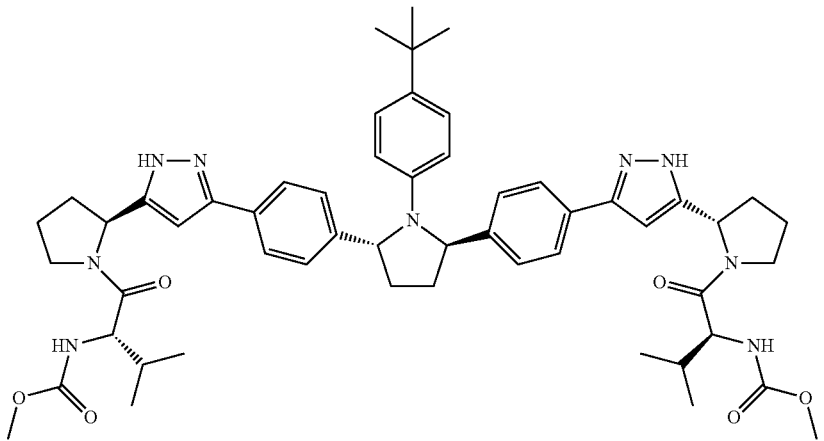
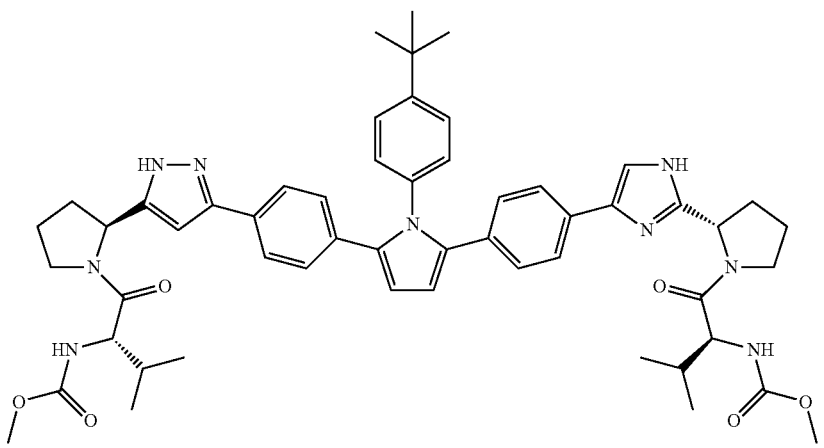
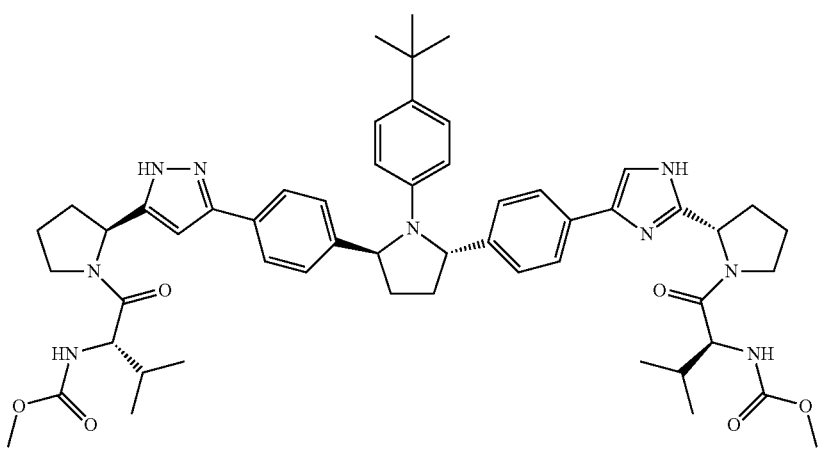

TABLE 5-continued
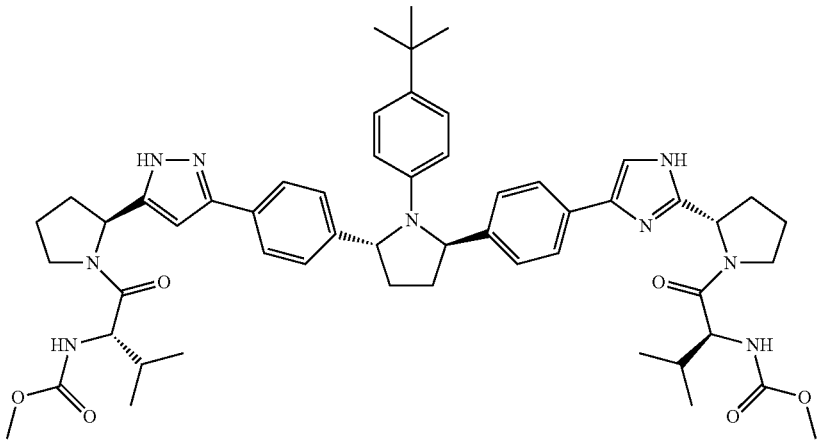
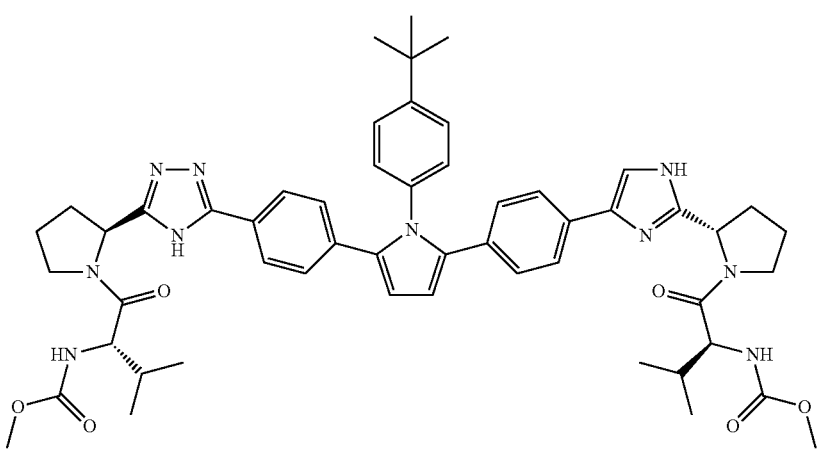
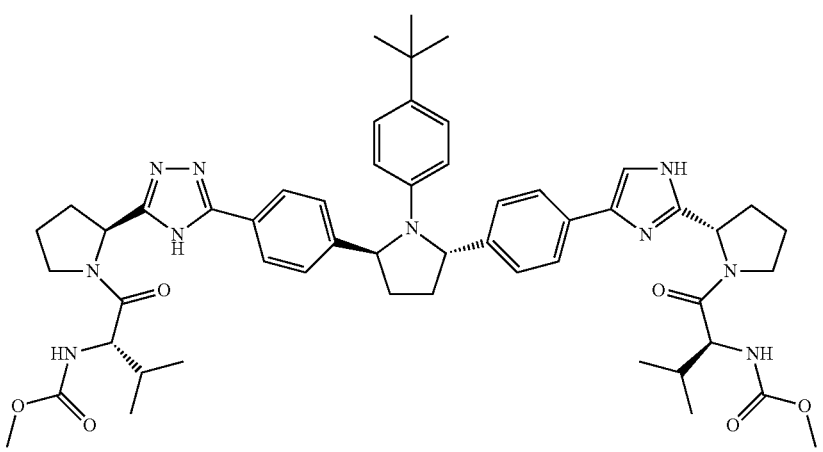

TABLE 5-continued

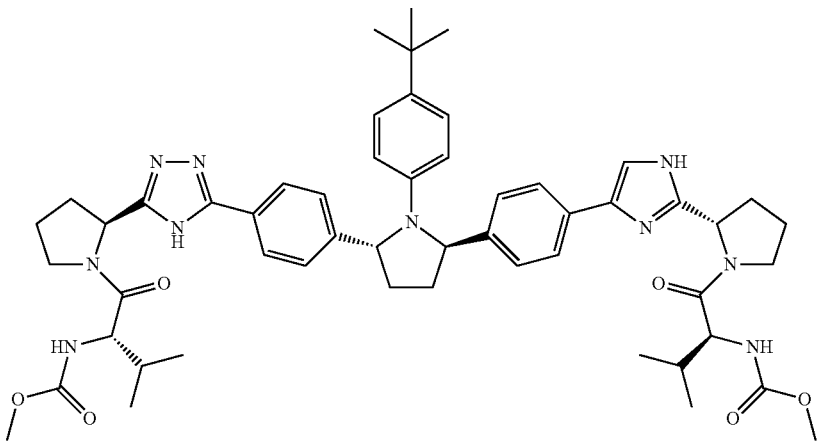

Each compound's anti-HCV activity can be determined by measuring the activity of the luciferase reporter gene in the replicon in the presence of 5% FBS. The luciferase reporter gene is placed under the translational control of the poliovirus IRES instead of the HCV IRES, and HuH-7 cells are used to support the replication of the replicon.

The inhibitory activities of the compounds of the present invention can be evaluated using a variety of assays known in the art. For instance, two stable subgenomic replicon cell lines can be used for compound characterization in cell culture: one derived from genotype 1a-H77 and the other derived from genotype 1b-Con1, obtained from University of Texas Medical Branch, Galveston, Tex. or Apath, LLC, St. Louis, Mo., respectively. The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the HCV 5' UTR, 3' UTR, and NS3-NS5B coding region are derived from the 1b-Con1 strain, and the adaptive mutations are K1609E, K1846T and Y3005C. In addition, the 1b-Con1 replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 µl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 µl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators after which time 30 µl of Passive Lysis buffer (Promega) can be added to each well, and then the plates are incubated for 15 minutes with rocking to lyse the cells. Luciferin solution (100 µl, Promega) can be added to each well, and luciferase activity can be measured with a Victor II luminometer (Perkin-Elmer). The percent inhibition of HCV RNA replication can be calculated for each compound concentration and the $EC_{50}$ value can be calculated using nonlinear regression curve fitting to the 4-parameter logistic equation and GraphPad Prism 4 software. Using the above-described assays or similar cell-based replicon assays, representative compounds of the present invention showed significantly inhibitory activities against HCV replication.

The present invention also features pharmaceutical compositions comprising the compounds of the invention. A pharmaceutical composition of the present invention can comprise one or more compounds of the invention, each of which has Formula I (or $I_A$, $I_B$, $I_C$ or $I_D$).

In addition, the present invention features pharmaceutical compositions comprising pharmaceutically acceptable salts, solvates, or prodrugs of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt, solvate or prodrug thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immunomodulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio-025, NIM-811, R7128, R1626, R4048, T-1106, PSI-7851 (Pharmasset) (nucleoside polymerase inhibitor), PSI-938 (Pharmasset) (nucleoside polymerase inhibitor), PF-00868554, ANA-598, IDX184 (nucleoside polymerase inhibitor), IDX102, IDX375 (non-nucleoside polymerase inhibitor), GS-9190 (non-nucleoside polymerase inhibitor), VCH-759, VCH-916, MK-3281, BCX-4678, MK-3281, VBY708, ANA598, GL59728, GL60667, BMS-790052 (NS5A inhibitor), BMS-791325 (protease Inhibitor), BMS-650032, BMS-824393, GS-9132, ACH-1095 (protease inhibitor), AP-H005, A-831 (Arrow Therapeutics) (NS5A inhibitor), A-689 (Arrow Therapeutics) (NS5A inhibitor), INX08189 (Inhibitex) (polymerase inhibitor), AZD2836, telaprevir (protease Inhibitor), boceprevir (protease Inhibitor), ITMN-191 (Intermune/Roche), BI-201335 (protease Inhibitor), VBY-376, VX-500 (Vertex) (protease Inhibitor), PHX-B, ACH-1625, IDX136, IDX316, VX-813 (Vertex) (protease Inhibitor), SCH 900518 (Schering-Plough), TMC-435 (Tibotec) (protease Inhibitor), ITMN-191 (Intermune, Roche) (protease Inhibitor), MK-7009 (Merck) (protease Inhibitor), IDX-PI (Novartis), BI-201335 (Boehringer Ingelheim), R7128 (Roche) (nucleoside polymerase inhibitor), MK-3281 (Merck), MK-0608 (Merck) (nucleoside polymerase inhibitor), PF-868554 (Pfizer) (non-nucleoside polymerase inhibitor), PF-4878691 (Pfizer), IDX-184 (Novartis), IDX-375 (Pharmasset), PPI-461 (Presidio) (NS5A inhibitor), BILB-1941 (Boehringer Ingelheim), GS-9190 (Gilead), BMS-790052 (BMS), Albuferon (Novartis), ABT-450 (Abbott/Enanta) (protease Inhibitor), ABT-333 (Abbott) (non-nucleoside polymerase inhibitor), ABT-072 (Abbott) (non-nucleoside polymerase inhibitor), ritonavir, another cytochrome P450 monooxygenase inhibitor, or any combination thereof.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. For example, a pharmaceutical composition of the present invention can comprise a compound(s) of the present invention having Formula I, $I_A$, $I_B$, $I_C$, or $I_D$ (or a salt, solvate or prodrug thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NSSA inhibitors.

In yet another embodiment, a pharmaceutical composition of the present invention comprises one or more compounds of the present invention (or salts, solvates or prodrugs thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art.

In a preferred embodiment, a pharmaceutical composition of the invention comprises a compound of the invention (e.g., a compound of Formula I, $I_A$, $I_B$, $I_C$, or $I_D$, or preferably a compound selected from Examples 1-308, or a salt, solvate or prodrug thereof), and a HCV protease inhibitor. In another preferred embodiment, a pharmaceutical composition of the invention comprises a compound of the invention (e.g., a compound of Formula I, $I_A$, $I_B$, $I_C$, or $I_D$, or preferably a compound selected from Examples 1-308, or a salt, solvate or prodrug thereof), and a HCV polymerase inhibitor (e.g., a non-nucleoside polymerase inhibitor, or preferably a nucleoside polymerase inhibitor). In yet another preferred embodiment, a pharmaceutical composition of the present invention comprises (1) a compound of the invention (e.g., a compound of Formula I, $I_A$, $I_B$, $I_C$, or $I_D$, or preferably a compound selected from Examples 1-308, or a salt, solvate or prodrug thereof), (2) a HCV protease inhibitor, and (3) a HCV polymerase inhibitor (e.g., a non-nucleoside polymerase inhibitor, or preferably a nucleoside polymerase inhibitor). Non-limiting examples of protease and polymerase inhibitors are described above.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHAR- MACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

In a preferred embodiment, a compound of the invention (e.g., a compound of Formula I, $I_A$, $I_B$, $I_C$, or $I_D$, or preferably a compound selected from Examples 1-308, or a salt, solvate or prodrug thereof) is formulated in a solid dispersion, where the compound of the invention can be molecularly dispersed in an amorphous matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt-extrusion, spray-drying, co-precipitation, freeze drying, or other solvent evaporation techniques, with melt-extrusion and spray-drying being preferred. In one example, a compound of the invention is formulated in a solid dispersion comprising copovidone and vitamin E TPGS. In another example, a compound of the invention is formulated in a solid dispersion comprising copovidone and Span 20.

A solid dispersion described herein may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion described herein may also contain at least 1% by weight of a pharmaceutically acceptable surfactant or a combination of such surfactants. Preferably, the solid dispersion contains at least 2% by weight of a pharmaceutically acceptable surfactant or a combination of such surfactants. More preferably, the solid dispersion contains from 4% to 20% by weight of the surfactant(s), such as from 5% to 10% by weight of the surfactant(s). In addition, a solid dispersion described herein may contain at least 1% by weight of a compound of the invention, preferably at least 5%, including, e.g., at least 10%. In one example, the solid dispersion comprises 5% of a compound of the invention (e.g., a compound of Formula I, $I_A$, $I_B$, $I_C$, or $I_D$, or preferably a compound selected from Examples 1-308, or a salt, solvate or prodrug thereof), which is molecularly dispersed in a an amorphous matrix comprising 7% Vitamin E-TPGS and 88% copovidone; the solid dispersion can also be mixed with other excipients such as mannitol/aerosil (99:1), and the weight ratio of the solid dispersion over the other excipients can range from 5:1 to 1:5 with 1:1 being preferred. In another example, the solid dispersion comprises 5% of a compound of the invention (e.g., a compound of Formula I, $I_A$, $I_B$, $I_C$, or $I_D$, or preferably a compound selected from Examples 1-308, or a salt, solvate or prodrug thereof), which is molecularly dispersed in a an amorphous matrix comprising 5% Span 20 and 90% copovidone; the solid dispersion can also be mixed with other excipients such as mannitol/aerosil (99:1), the solid dispersion can also be mixed with other excipients such as mannitol/aerosil (99:1), and the weight ratio of the solid dispersion over the other excipients can range from 5:1 to 1:5 with 1:1 being preferred.

Various additives can also be included in or mixed with the solid dispersion. For instance, at least one additive selected from flow regulators, binders, lubricants, fillers, disintegrants, plasticizers, colorants, or stabilizers may be used in compressing the solid dispersion to tablets. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like. Non-limiting examples of stabilizers include antioxidants, light stabilizers, radical scavengers, or stabilizers against microbial attack.

The present invention further features methods of using the compounds of the present invention (or salts, solvates or prodrugs thereof) to inhibit HCV replication. The methods comprise contacting cells infected with HCV virus with an effective amount of a compound of the present invention (or a salt, solvate or prodrug thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may inhibit one or more HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c, 3a or 4a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. The methods typically comprise administering a therapeutic effective amount of a compound of the present invention (or a salt, solvate or prodrug thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof), or a pharmaceutical composition comprising the same, to an HCV patient, thereby reducing the HCV viral level in the blood or liver of the patient.

A compound of the present invention (or a salt, solvate or prodrug thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention. In one embodiment, the present invention features methods of treating HCV infection, wherein said methods comprise administering a compound of the invention (e.g., a compound of Formula I, $I_A$, $I_B$, $I_C$, or $I_D$, or preferably a compound selected from Examples 1-308, or a salt, solvate or prodrug thereof), interferon and ribavirin to an HCV patient. The interferon preferably is α-interferon, and more preferably, pegylated interferon-α such as PEGASYS (peginterferon alfa-2a).

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The present invention further features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

The compounds of the present invention can also be isotopically substituted. Preferred isotopic substitution include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 5 mol % (e.g., at least 10 mol %) of hydrogen in a compound of the present invention is substituted with deuterium. In another example, at least 25 mole % of hydrogen in a compound of the present invention is substituted with deuterium. In a further example, at least 50, 60, 70, 80 or 90 mole % of hydrogen in a compound of the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A method of treating HCV infection, comprising administering to an HCV patient a compound of Formula I or a pharmaceutically acceptable salt thereof,

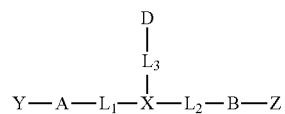

wherein:
X is

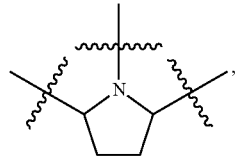 [SMILES: *C1CCC(*)N1*]

wherein the nitrogen ring atom is directly linked to -$L_3$-D, and wherein X is optionally substituted with one or more $R_4$;
$L_1$, $L_2$ and $L_3$ are bond;
A and B are each independently

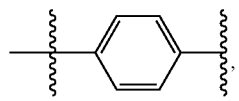

and are each independently optionally substituted with one or more $R_4$;
D is $C_3$-$C_{12}$carbocycle or 3- to 12-membered heterocycle, and is optionally substituted with one or more $R_4$;
Y is —N($R_B$)C(O)C($R_1R_2$)N($R_5$)-T-$R_D$ or —N($R_B$)C(O)C($R_3R_4$)C($R_6R_7$)-T-$R_D$;
Z is —N($R_B$)C(O)C($R_8R_9$)N($R_{12}$)-T-$R_D$ or —N($R_B$)C(O)C($R_{10}R_{11}$)C($R_{13}R_{14}$)-T-$R_D$;
$R_1$ is $R_C$, and $R_2$ and $R_5$, taken together with the atoms to which they are attached, form a 3- to 12-membered heterocycle which is optionally substituted with one or more $R_4$;
$R_3$ and $R_6$ are each independently $R_C$, and $R_4$ and $R_7$, taken together with the atoms to which they are attached, form a 3- to 12-membered carbocycle or heterocycle which is optionally substituted with one or more $R_4$;
$R_8$ is $R_C$, and $R_9$ and $R_{12}$, taken together with the atoms to which they are attached, form a 3- to 12-membered heterocycle which is optionally substituted with one or more $R_4$;
$R_{10}$ and $R_{13}$ are each independently $R_C$, and $R_{11}$ and $R_{14}$, taken together with the atoms to which they are attached, form a 3- to 12-membered carbocycle or heterocycle which is optionally substituted with one or more $R_A$;

T is each independently selected at each occurrence from bond, $-L_S-$, $-L_S-M-L_S'-$, or $-L_S-M-L_S'-M'-L_S''-$, wherein M and M' are each independently selected at each occurrence from bond, $-O-$, $-S-$, $-N(R_B)-$, $-C(O)-$, $-S(O)_2-$, $-S(O)-$, $-OS(O)-$, $-OS(O)_2-$, $-S(O)_2O-$, $-S(O)O-$, $-C(O)O-$, $-OC(O)-$, $-OC(O)O-$, $-C(O)N(R_B)-$, $-N(R_B)C(O)-$, $-N(R_B)C(O)O-$, $-OC(O)N(R_B)-$, $-N(R_B)S(O)-$, $-N(R_B)S(O)_2-$, $-S(O)N(R_B)-$, $-S(O)_2N(R_B)-$, $-C(O)N(R_B)C(O)-$, $-N(R_B)C(O)N(R_B')-$, $-N(R_B)SO_2N(R_B')-$, $-N(R_B)S(O)N(R_B')-$, $C_3-C_{12}$carbocycle or 3- to 12-membered heterocycle, and wherein said $C_3-C_{12}$carbocycle and 3- to 12-membered heterocycle are each independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or $-L_S-R_E$;

$R_B$ and $R_B'$ are each independently selected at each occurrence from hydrogen; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_B$ or $R_B'$ is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl;

$R_C$ is independently selected at each occurrence from hydrogen, halogen, hydroxy, mercapto, amino, carboxy, nitro, oxo, phosphonoxy, phosphono, thioxo, formyl or cyano; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_C$ is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl;

$R_E$ is independently selected at each occurrence from $-O-R_S$, $-S-R_S$, $-C(O)R_S$, $-OC(O)R_S$, $-C(O)OR_S$, $-N(R_SR_S')$, $-S(O)R_S$, $-SO_2R_S$, $-C(O)N(R_SR_S')$, $-N(R_S)C(O)R_S'$, $-N(R_S)C(O)N(R_S'R_S'')$, $-N(R_S)SO_2R_S'$, $-SO_2N(R_SR_S')$, $-N(R_S)SO_2N(R_S'R_S'')$, $-N(R_S)S(O)N(R_S'R_S'')$, $-OS(O)-R_S$, $-OS(O)_2-R_S$, $-S(O)_2OR_S$, $-S(O)OR_S$, $-OC(O)OR_S$, $-OC(O)N(R_SR_S')$, $-N(R_S)S(O)C(O)OR_S'$, $-S(O)N(R_SR_S')$ or $-C(O)N(R_S)C(O)-R_S'$; or $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3-C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl;

$R_L$ is independently selected at each occurrence from halogen, nitro, oxo, phosphonoxy, phosphono, thioxo, cyano, $-O-R_S$, $-S-R_S$, $-C(O)R_S$, $-OC(O)R_S$, $-C(O)OR_S$, $-N(R_SR_S')$, $-S(O)R_S$, $-SO_2R_S$, $-C(O)N(R_SR_S')$ or $-N(R_S)C(O)R_S'$; or $C_3-C_6$carbocycle 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl;

$L_S$, $L_S'$ and $L_S''$ are each independently selected at each occurrence from bond; or $C_1-C_6$alkylene, $C_2-C_6$alkenylene or $C_2-C_6$alkynylene, each of which is independently optionally substituted at each occurrence with one or more $R_L$; and $R_S$, $R_S'$ and $R_S''$ are each independently selected at each occurrence from hydrogen; $C_1-C_6$alkyl, $C_2-C_6$alkenyl or $C_2-C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_S$, $R_S'$ or $R_S'$ is independently optionally substituted at each occurrence with one or more substituents selected from halogen, hydroxy, mercapto, amino, carboxy, nitro, oxo, phosphonoxy, phosphono, thioxo, formyl, cyano, $C_1-C_6$alkyl, $C_2-C_6$alkenyl, $C_2-C_6$alkynyl, $C_1-C_6$haloalkyl, $C_2-C_6$haloalkenyl or $C_2-C_6$haloalkynyl.

2. The method of claim 1, wherein:

T is independently selected at each occurrence from $-C(O)-L_S'-M'-L_S''-$ or $-N(R_B)C(O)-L_S'-M'-L_S''-$; and $L_S'$ is each independently $C_1-C_6$alkylene, and is independently optionally substituted at each occurrence with one or more $R_L$.

3. The method of claim 1, wherein:

Y is $-N(R_B)C(O)C(R_1R_2)N(R_5)-T-R_D$;

Z is $-N(R_B)C(O)C(R_8R_9)N(R_{12})-T-R_D$;

T is independently selected at each occurrence from $-C(O)-L_S'-M'-L_S''-$; and

D is $C_5-C_6$carbocycle, 5- to 6-membered heterocycle, or 6- to 10-membered bicycles, and is substituted with one or more $R_A$.

4. The method of claim 3, wherein T is independently selected at each occurrence from $-C(O)-L_S'-N(R_B)C(O)-L_S''-$ or $-C(O)-L_S'-N(R_B)C(O)O-L_S''-$; and $R_2$ and $R_5$, taken together with the atoms to which they are attached, form

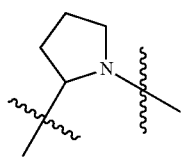 [SMILES: *C1CCCN1*]

which is optionally substituted with one or more $R_4$; and $R_9$ and $R_{12}$, taken together with the atoms to which they are attached, form

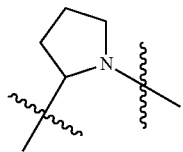 [SMILES: *C1CCCN1*]

which is optionally substituted with one or more $R_4$.

5. The method of claim 1, wherein $R_4$ is independently selected at each occurrence from halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

6. The method of claim 5, wherein $L_S$, $L_S'$ and $L_S''$ are each independently selected at each occurrence from bond; or $C_1$-$C_6$alkylene, $C_2$-$C_6$alkenylene or $C_2$-$C_6$alkynylene.

7. The method of claim 4, wherein $R_4$ is independently selected at each occurrence from halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

8. The method of claim 7, wherein $L_S$, $L_S'$ and $L_S''$ are each independently selected at each occurrence from bond; or $C_1$-$C_6$alkylene, $C_2$-$C_6$alkenylene or $C_2$-$C_6$alkynylene.

9. A method of claim 1, wherein said compound is dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl))bis(3-methyl-1-oxobutane-2,1-diyl)dicarbamate.

* * * * *